US011993774B2

(12) United States Patent
Soundarapandian et al.

(10) Patent No.: US 11,993,774 B2
(45) Date of Patent: May 28, 2024

(54) HUNTINGTIN (HTT) iRNA AGENT COMPOSITIONS AND METHODS OF USE THEREOF

(71) Applicant: Alnylam Pharmaceuticals, Inc., Cambridge, MA (US)

(72) Inventors: Mangala Meenakshi Soundarapandian, Cambridge, MA (US); James D. McIninch, Burlington, MA (US); Mark K. Schlegel, Boston, MA (US); Adam Castoreno, Framingham, MA (US)

(73) Assignee: Alnylam Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 18/327,139

(22) Filed: Jun. 1, 2023

(65) Prior Publication Data

US 2023/0392152 A1 Dec. 7, 2023

Related U.S. Application Data

(63) Continuation of application No. PCT/US2022/022093, filed on Mar. 28, 2022.

(60) Provisional application No. 63/167,140, filed on Mar. 29, 2021.

(51) Int. Cl.
*C07H 21/04* (2006.01)
*C12N 15/113* (2010.01)

(52) U.S. Cl.
CPC ........ *C12N 15/113* (2013.01); *C12N 2310/14* (2013.01); *C12N 2310/315* (2013.01); *C12N 2310/321* (2013.01); *C12N 2310/322* (2013.01)

(58) Field of Classification Search
None
See application file for complete search history.

(56) References Cited

U.S. PATENT DOCUMENTS

| | | | |
|---|---|---|---|
| 7,902,352 B2 | 3/2011 | Kaemmerer et al. | |
| 7,947,658 B2 | 5/2011 | Aronin et al. | |
| 7,951,934 B2 | 5/2011 | Freier | |
| 8,183,219 B2 | 5/2012 | Burright | |
| 8,258,112 B2 | 9/2012 | Kaemmerer et al. | |
| 8,258,286 B2 * | 9/2012 | Davidson | C12N 15/111 435/320.1 |
| 8,415,465 B2 | 4/2013 | Freier | |
| 8,557,975 B2 | 10/2013 | Kaemmerer et al. | |
| 8,680,063 B2 | 3/2014 | Aronin et al. | |
| 8,779,116 B2 | 7/2014 | Davidson et al. | |
| 8,952,145 B2 | 2/2015 | Freier | |
| 8,987,222 B2 | 3/2015 | Aronin et al. | |
| 9,057,066 B2 | 6/2015 | Hung et al. | |
| 9,340,785 B2 | 5/2016 | Corey et al. | |
| 9,353,372 B2 | 5/2016 | Freier | |
| 9,434,943 B2 | 9/2016 | Aronin et al. | |
| 9,809,817 B2 | 11/2017 | Khvorova et al. | |
| 9,914,924 B2 | 3/2018 | Aronin et al. | |
| 9,920,321 B2 | 3/2018 | Freier | |
| 10,174,321 B2 | 1/2019 | Konstantinova et al. | |
| 10,344,277 B2 | 7/2019 | Aronin et al. | |
| 10,435,688 B2 | 10/2019 | Khvorova et al. | |
| 10,533,172 B2 | 1/2020 | Southwell et al. | |
| 10,655,129 B2 | 5/2020 | Freier | |
| 10,738,307 B2 | 8/2020 | Hung et al. | |
| 10,767,180 B2 | 9/2020 | Konstantinova et al. | |
| 10,774,327 B2 | 9/2020 | Khvorova et al. | |
| 11,072,794 B2 | 7/2021 | Freier | |
| 11,230,713 B2 | 1/2022 | Khvorova et al. | |
| 11,299,734 B2 | 4/2022 | Aronin et al. | |
| 11,371,044 B2 | 6/2022 | Konstantinova et al. | |
| 2020/0123543 A1 | 4/2020 | Khvorova et al. | |
| 2020/0339992 A1 | 10/2020 | Konstantinova et al. | |
| 2020/0385740 A1 | 12/2020 | Khvorova et al. | |
| 2021/0017522 A1 | 1/2021 | Hung et al. | |
| 2021/0071177 A1 | 3/2021 | Khvorova et al. | |
| 2022/0010309 A1 | 1/2022 | Khvorova et al. | |
| 2022/0042013 A1 | 2/2022 | Freier | |
| 2022/0090069 A1 | 3/2022 | Khvorova et al. | |
| 2022/0098585 A1 | 3/2022 | Brown et al. | |
| 2022/0251554 A1 | 8/2022 | Khvorova et al. | |

FOREIGN PATENT DOCUMENTS

| | | |
|---|---|---|
| WO | WO-2004094595 A2 | 11/2004 |
| WO | WO-2005105995 A2 | 11/2005 |
| WO | WO-2007/022506 A2 | 2/2007 |
| WO | WO-2007022470 A2 | 2/2007 |
| WO | WO-2007051045 A2 | 5/2007 |
| WO | WO-2007089584 A2 | 8/2007 |
| WO | WO-2008150897 A2 | 12/2008 |

(Continued)

OTHER PUBLICATIONS

U.S. Appl. No. 17/731,317, filed Apr. 28, 2022, US 20220380762, Published/Pending.
PCT/US2020/057849, Oct. 29, 2020, WO 2021/087036, Published.
PCT/US2022/022093, Mar. 28, 2022, WO 2022/212231, Published.
PCT/US2022/047986, Oct. 27, 2022, Pending.
DiFiglia et al. "Therapeutic silencing of mutant huntingtin with siRNA attenuates striatal and cortical neuropathology and behavioral deficits", PNAS, 104(43), 2007, pp. 17205-1709.
Peel et al., "Conjugation and Evaluation of Small Hydrophobic Molecules to Triazole-Linked siRNAs", ACS Med. Chem. Lett. 2015, 6, 117?122.

(Continued)

*Primary Examiner* — Kimberly Chong
(74) *Attorney, Agent, or Firm* — McCarter & English, LLP; Maria Laccotripe Zacharakis; Deborah L. Nagle

(57) ABSTRACT

The disclosure relates to double stranded ribonucleic acid (dsRNAi) agents and compositions targeting a Huntingtin (HTT) gene, as well as methods of inhibiting expression of an HTT gene and methods of treating subjects having an HTT-associated disease or disorder, e.g., Huntington's disease, using such dsRNAi agents and compositions.

30 Claims, 43 Drawing Sheets

Specification includes a Sequence Listing.

(56) References Cited

FOREIGN PATENT DOCUMENTS

| | | | |
|---|---|---|---|
| WO | WO-2013/074974 | A2 | 5/2013 |
| WO | WO-2016028649 | A1 | 2/2016 |
| WO | WO-2016161374 | A1 | 10/2016 |
| WO | WO-2018098328 | A1 | 5/2018 |
| WO | WO-2019217459 | A1 | 11/2019 |
| WO | WO-2019222479 | A1 | 11/2019 |
| WO | WO-2020097044 | A1 | 5/2020 |
| WO | WO-2020160336 | A1 | 8/2020 |
| WO | WO-2020198509 | A2 | 10/2020 |
| WO | WO-2021053018 | A1 | 3/2021 |
| WO | WO-2021087036 | A1 | 5/2021 |
| WO | WO-2021115141 | A1 | 6/2021 |
| WO | WO-2021216556 | A2 | 10/2021 |
| WO | WO-2022031591 | A2 | 2/2022 |
| WO | WO-2022061378 | A2 | 3/2022 |
| WO | WO-2022077024 | A1 | 4/2022 |

OTHER PUBLICATIONS

Neueder et al., "The pathogenic exon 1 HTT protein is produced by incomplete splicing in Huntington's disease patients", Scientific Reports vol. 7, Article No. 1307 (2017).

Romo et al., A Fresh Look at Huntingtin mRNA Processing in Huntington's Disease, J. Huntington;s Dis. 2018 7 101-108.

Sathasivam et al, Aberrant splicing of HTT generates the pathogenic exon 1 protein in Huntington disease, PNAS 2013 110:2366-70.

Gipson et al., "Aberrantly spliced HTT, a new player in Huntington's disease pathogenesis", RNA Biology, vol. 10, No. 11, Nov. 1, 2013 (Nov. 1, 2013), pp. 1647-1652.

Miniarikova et al., "Design, Characterization, and Lead Selection of Therapeutic miRNAs Targeting Huntingtin for Development of Gene Therapy for Huntington's Disease", Molecular Therapy—Nucleic Acids vol. 5, No. 3, Mar. 22, 2016 (Mar. 22, 2016), p. e297.

Tabrizi et al., "Huntingtin Lowering Strategies for Disease Modification in Huntington's Disease", Neuron, vol. 101, No. 5, Mar. 6, 2019 (Mar. 6, 2019), pp. 801-819.

Aguiar et al., "RNAi mechanisms in Huntington's disease therapy: siRNA versus shRNA", Translational Neurodegeneration, Biomed Central Ltd, London, UK, vol. 6, No. 1, Nov. 27, 2017 (Nov. 27, 2017), pp. 1-10.

Yamada et al., Versatile Site-Specific Conjugation of Small Molecules to siRNA Using Click Chemistry, vol. 76, No. 5, Feb. 7, 2011 (Feb. 7, 2011), pp. 1198-1211.

Haraszti et al., "5'-Vinylphosphonate improves tissue accumulation and efficacy of conjugated siRNAs in vivo", Nucleic Acids Research, vol. 45, No. 13, Jun. 7, 2017 (Jun. 7, 2017), pp. 7581-7592.

* cited by examiner

| | | | | | | | | | | | |
|---|---|---|---|---|---|---|---|---|---|---|---|
| ACSF | Mean | 1.00 | 1.00 | 1.00 | 1.00 | 1.00 | 1.00 | 1.00 | 1.00 | 1.00 | 1.00 |
| | SD | 0.08 | 0.26 | 0.13 | 0.18 | 0.16 | 0.31 | 0.18 | 0.11 | 0.24 | 0.33 |
| AD-1019465 | Mean | 0.86 | 0.63 | 0.44 | 0.77 | 0.78 | 0.76 | 0.80 | 0.74 | 0.87 | 0.57 |
| | SD | 0.16 | 0.32 | 0.13 | 0.35 | 0.22 | 0.16 | 0.15 | 0.13 | 0.27 | 0.02 |
| AD-1271082 | Mean | 0.80 | 0.47 | 0.48 | 0.52 | 0.83 | 0.69 | 0.95 | 0.61 | 0.78 | 0.55 |
| | SD | 0.08 | 0.02 | 0.11 | 0.14 | 0.19 | 0.10 | 0.24 | 0.04 | 0.09 | 0.11 |
| AD-1271085 | Mean | 0.56 | 0.20 | 0.18 | 0.23 | 0.38 | 0.36 | 0.36 | 0.40 | 0.44 | 0.31 |
| | SD | 0.10 | 0.02 | 0.01 | 0.04 | 0.05 | 0.09 | 0.04 | 0.07 | 0.17 | 0.10 |

FIG. 2

| | | Brain-Prefrontal | | | Brain-Hippocampus | | | Brain-Striatum Caudate | | | Spine-Lumbar | | | Spine-Thoracic | | |
|---|---|---|---|---|---|---|---|---|---|---|---|---|---|---|---|---|
| Treatment | Study dose (mg) | Mean HTT (ng/mg) | % K/D | SD | Mean HTT (ng/mg) | % K/D | SD | Mean HTT (ng/mg) | % K/D | SD | Mean HTT (ng/mg) | % K/D | SD | Mean HTT (ng/mg) | % K/D | SD |
| aCSF | 0 | 35.91 | 0.000 | 44.96 | 39.13 | 0.000 | 60.01 | 50.85 | 0.000 | 47.02 | 19.61 | 0.000 | 26.53 | 27.85 | 0.000 | 8.20 |
| AD-1019465 | 60 | 9.36 | 73.935 | 14.10 | 6.56 | 83.241 | 1.27 | 46.35 | 8.862 | 60.69 | 19.17 | 2.246 | 17.31 | 15.81 | 43.223 | 7.52 |
| AD-1271082 | 60 | 25.25 | 29.687 | 14.38 | 10.25 | 73.800 | 8.68 | 194.83 | -283.104 | 39.25 | 17.23 | 12.167 | 7.59 | 16.68 | 40.108 | 10.50 |
| AD-1271085 | 60 | 0.97 | 97.307 | 0.93 | 2.04 | 94.774 | 3.99 | 29.01 | 42.964 | 30.91 | 6.18 | 68.483 | 2.40 | 4.69 | 83.147 | 2.04 |

*Q175 Het Si-Control vs treatments*: One-way ANOVA followed by Dunnett's multiple comparisons test compared at the respective timepoint

*p ≤0.05 ***p <0.001 p <0.01 **p<0.0001

HUNTINGTIN (HTT) iRNA AGENT COMPOSITIONS AND METHODS OF USE THEREOF

RELATED APPLICATIONS

This application is a 35 § U.S.C. 111(a) continuation application which claims the benefit of priority to PCT/US2022/022093, filed on Mar. 28, 2022, which, in turn, claims the benefit of priority to U.S. Provisional Application No. 63/167,140, filed on Mar. 29, 2021. The entire contents of each of the foregoing application are incorporated herein by reference.

SEQUENCE LISTING

The instant application contains a Sequence Listing which has been submitted electronically in XML file format and is hereby incorporated by reference in its entirety. Said XML copy, created on May 30, 2023, is named 121301-14402_SL.xml and is 884,042 bytes in size.

BACKGROUND OF THE INVENTION

Huntington's disease is a progressive neurodegenerative disorder characterized by motor disturbance, cognitive loss and psychiatric manifestations (Martin and Gusella (1986) *N. Engl. J. Med.* 315:1267-1276). It is inherited in an autosomal dominant fashion, and affects about 1/10,000 individuals in most populations of European origin (Harper, P. S. et al., in *Huntington's Disease, W.* B. Saunders, Philadelphia, 1991). The hallmark of Huntington's disease is a distinctive choreic movement disorder that typically has a subtle, insidious onset in the fourth to fifth decade of life and gradually worsens over a course of 10 to 20 years until death. Occasionally, Huntington's disease is expressed in juveniles typically manifesting with more severe symptoms including rigidity and a more rapid course. Juvenile onset of Huntington's disease is associated with a preponderance of paternal transmission of the disease allele. The neuropathology of Huntington's disease also displays a distinctive pattern, with selective loss of neurons that is most severe in the caudate and putamen regions of the brain.

Huntington's disease has been shown to be caused by an expanding glutamine repeat in exon 1 of a gene termed IT15 or Huntingtin (HTT). Although this gene is widely expressed and is required for normal development, the pathology of Huntington's disease is restricted to the brain, for reasons that remain poorly understood. In patients having HD (an autosomal dominant disease), the expansion of the polyglutamine repeat results in a wild-type transcript, a full-length mutant transcript having the expanded polyglutamine repeat, as well as a truncated mutant transcript having the expanded polyglutamine repeat. It has been shown that, although the Huntingtin gene product is expressed at similar levels in patients and controls, it is the expansion of the polyglutamine repeat and the presence of the full-length mutant transcript and the truncated mutant transcript that induces toxicity.

Effective treatment for Huntington's disease is currently not available. The choreic movements and agitated behaviors may be suppressed, usually only partially, by antipsychotics (e.g., chlorpromazine) or reserpine until adverse effects of lethargy, hypotension, or parkinsonism occur. In addition, despite significant advances in the field of RNAi and Huntington's disease treatment, there remains a need for an agent that can selectively and efficiently silence the HD gene using the cell's own RNAi machinery that has both high biological activity and in vivo stability, and that can effectively inhibit expression of a target Huntingtin gene.

BRIEF SUMMARY OF THE INVENTION

The present disclosure provides RNAi agent compositions which effect the RNA-induced silencing complex (RISC)-mediated cleavage of RNA transcripts of a huntingin (HTT) gene. The HTT gene may be within a cell, e.g., a cell within a subject, such as a human. The present disclosure also provides methods of using the RNAi agent compositions of the disclosure for inhibiting the expression of an HTT gene or for treating a subject who would benefit from inhibiting or reducing the expression of an HTT gene, e.g., a subject suffering or prone to suffering from an HTT-associated disease.

In one aspect, the present invention provides a double stranded ribonucleic acid (dsRNA) agent for inhibiting expression of Huntingtin (HTT), in a cell, wherein the dsRNA comprises a sense strand and an antisense strand forming a double stranded region, wherein the antisense strand comprises a region of complementarity to an mRNA encoding HTT, and wherein the region of complementarity comprises at least 15 contiguous nucleotides differing by no more than 3, e.g., 3, 2, 1, or 0. nucleotides from any one of the antisense nucleotide sequences in any one of Tables 2-5.

In another aspect, the present invention provides a double stranded ribonucleic acid (dsRNA) agent for inhibiting expression of Huntingtin (HTT), in a cell, wherein the dsRNA comprises a sense strand and an antisense strand forming a double stranded region, wherein the sense strand comprises at least 15, e.g., 15, 16, 17, 18, 19, 20, or 21, contiguous nucleotides differing by no more than three, e.g., 3, 2, 1, or 0, nucleotides from any one of the nucleotide sequence of nucleotides 4391-4669; 6500-6540; or 6009-6037 of SEQ ID NO:1, and the antisense strand comprises at least 15 contiguous nucleotides from the corresponding nucleotide sequence of SEQ ID NO:6.

In one embodiment, the sense strand comprises at least 15, e.g., 15, 16, 17, 18, 19, 20, or 21, contiguous nucleotides differing by no more than three nucleotides from any one of the nucleotide sequence of nucleotides 4398-4420; 4403-4425; or 6512-6534 of SEQ ID NO:1.

In one embodiment, the sense strand comprises at least 15, e.g., 15, 16, 17, 18, 19, 20, or 21, contiguous nucleotides differing by no more than three nucleotides from nucleotides 4398-4420 of SEQ ID NO:1.

In one embodiment, the antisense strand comprises at least 15, e.g., 15, 16, 17, 18, 19, 20, 21, 22, or 23, contiguous nucleotides differing by no more that three nucleotides from any one of the antisense strand nucleotide sequences of a duplex selected from the group consisting of AD-1271085, AD-1271083, or AD-1271084.

In one embodiment, the antisense strand comprises at least 15, e.g., 15, 16, 17, 18, 19, 20, 21, 22, or 23, contiguous nucleotides differing by no more that three nucleotides from the antisense strand nucleotide sequence of AD-1271085.

In one embodiment, the sense strand comprises the nucleotide sequence 5'-GCUAUUCAUAAUCA-CAUUCGA-3' (SEQ ID NO: 15).

In one embodiment, the sense strand consists of the nucleotide sequence 5'-GCUAUUCAUAAUCA-CAUUCGA-3'(SEQ ID NO: 15).

In one embodiment, the antisense strand comprises the nucleotide sequence 5'-UCGAAUGUGAUUAUGAAUAG-CAU-3' (SEQ ID NO: 16).

In one embodiment, the antisense strand consists of the nucleotide sequence 5'-UCGAAUGUGAUUAUGAAUAGCAU-3' (SEQ ID NO: 15).

In one embodiment, the sense strand comprises the nucleotide sequence 5'-GCUAUUCAUAAUCACAUUCGA-3' (SEQ ID NO: 15) and the antisense strand comprises the nucleotide sequence 5'-UCGAAUGUGAUUAUGAAUAGCAU-3' (SEQ ID NO: 16).

In one embodiment, the sense strand consists of the nucleotide sequence 5'-GCUAUUCAUAAUCACAUUCGA-3' (SEQ ID NO: 15) and the antisense strand consists of the nucleotide sequence 5'-UCGAAUGUGAUUAUGAAUAGCAU-3' (SEQ ID NO: 16).

In one aspect, the present invention provides a double stranded ribonucleic acid (dsRNA) agent for inhibiting expression of Huntingtin (HTT) in a cell, wherein said dsRNA comprises a sense strand and an antisense strand forming a double stranded region, wherein the sense strand comprises at least 15 contiguous nucleotides differing by no more than three nucleotides from nucleotides 26-77; or 142-202 of SEQ ID NO: 1, and the antisense strand comprises at least 15 contiguous nucleotides from the corresponding nucleotide sequence of SEQ ID NO:6.

In one embodiment, the sense strand comprises at least 15 contiguous nucleotides differing by no more than three nucleotides from the nucleotide sequence of nucleotides 27-49; 55-77; 147-169; or 173-195 of SEQ ID NO:1.

In one embodiment, the sense strand comprises at least 15 contiguous nucleotides differing by no more than three nucleotides from nucleotides 147-169 of SEQ ID NO:1.

In one embodiment, the antisense strand comprises at least 15 contiguous nucleotides differing by no more that three nucleotides from the antisense strand nucleotide sequence of a duplex selected from the group consisting of AD-1019448, AD-1498524, AD-1498526, or AD-1498528.

In one embodiment, the antisense strand comprises at least 15 contiguous nucleotides differing by no more that three nucleotides from the antisense strand nucleotide sequence of AD-1498524.

The sense strand, the antisense strand, or both the sense strand and the antisense strand may be conjugated to one or more lipophilic moieties. In some embodiments, the lipophilic moiety is conjugated to one or more internal positions in the double stranded region of the dsRNA agent, e.g., the one or more lipophilic moieties may be conjugated to one or more internal positions on the antisense strand. In some embodiments, the one or more lipophilic moieties are conjugated to one or more internal positions on at least one strand via a linker or carrier.

In some embodiments, lipophilicity of the lipophilic moiety, measured by log Kow, exceeds 0.

In some embodiments, the hydrophobicity of the dsRNA agent, measured by the unbound fraction in a plasma protein binding assay of the dsRNA agent, exceeds 0.2. In some embodiments, the plasma protein binding assay is an electrophoretic mobility shift assay using human serum albumin protein.

In some embodiments, the internal positions include all positions except the terminal two positions from each end of the sense strand or the antisense strand. In other embodiments, the internal positions include all positions except the terminal three positions from each end of the sense strand or the antisense strand.

In some embodiments, the internal positions exclude a cleavage site region of the sense strand, such as the internal positions include all positions except positions 9-12, counting from the 5'-end of the sense strand or the internal positions include all positions except positions 11-13, counting from the 3'-end of the sense strand.

In some embodiments, the internal positions exclude a cleavage site region of the antisense strand. In other embodiments, the internal positions include all positions except positions 12-14, counting from the 5'-end of the antisense strand. In some embodiments, the internal positions include all positions except positions 11-13 on the sense strand, counting from the 3'-end, and positions 12-14 on the antisense strand, counting from the 5'-end.

In some embodiments, the one or more lipophilic moieties are conjugated to one or more of the internal positions selected from the group consisting of positions 4-8 and 13-18 on the sense strand, and positions 6-10 and 15-18 on the antisense strand, counting from the 5'end of each strand.

In some embodiments, the one or more lipophilic moieties are conjugated to one or more of the internal positions selected from the group consisting of positions 5, 6, 7, 15, and 17 on the sense strand, and positions 15 and 17 on the antisense strand, counting from the 5'-end of each strand.

In some embodiments, the positions in the double stranded region exclude a cleavage site region of the sense strand.

In some embodiments, the sense strand is 21 nucleotides in length, the antisense strand is 23 nucleotides in length, and the lipophilic moiety is conjugated to position 20, position 15, position 1, position 7, position 6, or position 2 of the sense strand or position 16 of the antisense strand.

In other embodiments, the sense strand is 21 nucleotides in length, the antisense strand is 23 nucleotides in length, and the lipophilic moiety is conjugated to position 21, position 20, position 15, position 1, position 7, position 6, or position 2 of the sense strand or position 16 of the antisense strand.

In some embodiments, the lipophilic moiety is an aliphatic, alicyclic, or polyalicyclic compound.

In some embodiments, the lipophilic moiety is selected from the group consisting of lipid, cholesterol, retinoic acid, cholic acid, adamantane acetic acid, 1-pyrene butyric acid, dihydrotestosterone, 1,3-bis-O(hexadecyl)glycerol, geranyloxyhexyanol, hexadecylglycerol, borneol, menthol, 1,3-propanediol, heptadecyl group, palmitic acid, myristic acid, O3-(oleoyl)lithocholic acid, O3-(oleoyl)cholenic acid, dimethoxytrityl, or phenoxazine.

In some embodiments, the lipophilic moiety contains a saturated or unsaturated C4-C30 hydrocarbon chain, and an optional functional group selected from the group consisting of hydroxyl, amine, carboxylic acid, sulfonate, phosphate, thiol, azide, and alkyne.

In some embodiments, the lipophilic moiety contains a saturated or unsaturated C6-C18 hydrocarbon chain.

In some embodiments, the lipophilic moiety contains a saturated or unsaturated C16 hydrocarbon chain. In some embodiments, the saturated or unsaturated C16 hydrocarbon chain is conjugated to position 6, counting from the 5'-end of the strand.

In some embodiments, the lipophilic moiety is conjugated via a carrier that replaces one or more nucleotide(s) in the internal position(s) or the double stranded region. In some embodiments, the carrier is a cyclic group selected from the group consisting of pyrrolidinyl, pyrazolinyl, pyrazolidinyl, imidazolinyl, imidazolidinyl, piperidinyl, piperazinyl, [1,3]dioxolanyl, oxazolidinyl, isoxazolidinyl, morpholinyl, thiazolidinyl, isothiazolidinyl, quinoxalinyl, pyridazinonyl, tetrahydrofuranyl, and decalinyl; or is an acyclic moiety based on a serinol backbone or a diethanolamine backbone.

In some embodiments, the lipophilic moiety is conjugated to the dsRNA agent via a linker containing an ether, thioether, urea, carbonate, amine, amide, maleimide-thioether, disulfide, phosphodiester, sulfonamide linkage, a product of a click reaction, or carbamate.

In some embodiments, the lipophilic moiety is conjugated to a nucleobase, sugar moiety, or internucleosidic linkage.

In some embodiments, the dsRNA agent comprises at least one modified nucleotide. In some embodiments, no more than five of the sense strand nucleotides and no more than five of the nucleotides of the antisense strand are unmodified nucleotides. In other embodiments, all of the nucleotides of the sense strand and all of the nucleotides of the antisense strand comprise a modification.

In some embodiments, at least one of the modified nucleotides is selected from the group a deoxy-nucleotide, a 3'-terminal deoxy-thymine (dT) nucleotide, a 2'-O-methyl modified nucleotide, a 2'-fluoro modified nucleotide, a 2'-deoxy-modified nucleotide, a locked nucleotide, an unlocked nucleotide, a conformationally restricted nucleotide, a constrained ethyl nucleotide, an abasic nucleotide, a 2'-amino-modified nucleotide, a 2'-O-allyl-modified nucleotide, 2'-C-alkyl-modified nucleotide, 2'-hydroxly-modified nucleotide, a 2'-methoxyethyl modified nucleotide, a 2'-O-alkyl-modified nucleotide, a morpholino nucleotide, a phosphoramidate, a non-natural base comprising nucleotide, a tetrahydropyran modified nucleotide, a 1,5-anhydrohexitol modified nucleotide, a cyclohexenyl modified nucleotide, a nucleotide comprising a 5'-phosphorothioate group, a nucleotide comprising a 5'-methylphosphonate group, a nucleotide comprising a 5' phosphate or 5' phosphate mimic, a nucleotide comprising vinyl phosphonate, a nucleotide comprising adenosine-glycol nucleic acid (GNA), a nucleotide comprising thymidine-glycol nucleic acid (GNA)S-Isomer, a nucleotide comprising 2-hydroxymethyl-tetrahydrofurane-5-phosphate, a nucleotide comprising 2'-deoxythymidine-3' phosphate, a nucleotide comprising 2'-deoxyguanosine-3'-phosphate, and a terminal nucleotide linked to a cholesteryl derivative and a dodecanoic acid bisdecylamide group; and combinations thereof.

In other embodiments, the modified nucleotide is selected from the group consisting of a 2'-deoxy-2'-fluoro modified nucleotide, a 2'-deoxy-modified nucleotide, 3'-terminal deoxy-thymine nucleotides (dT), a locked nucleotide, an abasic nucleotide, a 2'-amino-modified nucleotide, a 2'-alkyl-modified nucleotide, a morpholino nucleotide, a phosphoramidate, and a non-natural base comprising nucleotide.

In some embodiments, at least one of the modified nucleotides is selected from the group consisting of a deoxy-nucleotide, a 2'-O-methyl modified nucleotide, a 2'-fluoro modified nucleotide, a 2'-deoxy-modified nucleotide, a glycol modified nucleotide (GNA), and, a vinyl-phosphonate nucleotide; and combinations thereof.

In some embodiments, at least one of the modifications on the nucleotides is a thermally destabilizing nucleotide modification. In some embodiments, the thermally destabilizing nucleotide modification is selected from the group consisting of an abasic modification; a mismatch with the opposing nucleotide in the duplex; and destabilizing sugar modification, a 2'-deoxy modification, an acyclic nucleotide, an unlocked nucleic acids (UNA), and a glycerol nucleic acid (GNA) In some embodiments, the modified nucleotide comprises a short sequence of 3'-terminal deoxy-thymine nucleotides (dT).

In some embodiments, the modifications on the nucleotides are 2'-O-methyl, GNA and 2'fluoro modifications.

In some embodiments, the dsRNA agent further comprises at least one phosphorothioate internucleotide linkage. In some embodiments, the dsRNA agent comprises 6-8 phosphorothioate internucleotide linkages. In one embodiment, the phosphorothioate or methylphosphonate internucleotide linkage is at the 3'-terminus of one strand. Optionally, the strand is the antisense strand. In another embodiment, the strand is the sense strand. In a related embodiment, the phosphorothioate or methylphosphonate internucleotide linkage is at the 5'-terminus of one strand. Optionally, the strand is the antisense strand. In another embodiment, the strand is the sense strand. In another embodiment, the phosphorothioate or methylphosphonate internucleotide linkage is at the both the 5'- and 3'-terminus of one strand. Optionally, the strand is the antisense strand. In another embodiment, the strand is the sense strand.

In some embodiments, each strand is no more than 30 nucleotides in length.

In some embodiments, at least one strand comprises a 3' overhang of at least 1 nucleotide or a 3' overhang of at least 2 nucleotides.

The double stranded region may be 15-30 nucleotide pairs in length; 17-23 nucleotide pairs in length; 17-25 nucleotide pairs in length; 23-27 nucleotide pairs in length; 19-21 nucleotide pairs in length; or 21-23 nucleotide pairs in length.

Each strand may be 19-30 nucleotides; 19-23 nucleotides; or 21-23 nucleotides.

In some embodiments, the dsRNA agent further comprises a targeting ligand that targets a liver tissue. In some embodiments, the targeting ligand is a GalNAc conjugate. In other embodiments, the dsRNA agent does not comprise a targeting ligand that targets a liver tissue, such as a GalNAc conjugate.

In certain embodiments, the double-stranded RNAi agent further includes a targeting ligand that targets a receptor which mediates delivery to a CNS tissue, e.g., a hydrophilic ligand.

In certain embodiments, the targeting ligand is a C16 ligand. In one embodiment, the ligand is

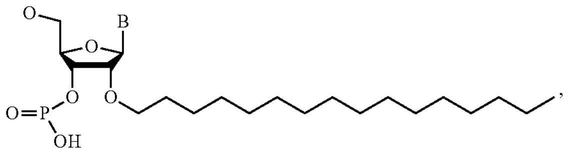

where B is a nucleotide base or a nucleotide base analog, optionally where B is adenine, guanine, cytosine, thymine or uracil.

In some embodiments, the dsRNA agent further includes a targeting ligand that targets a receptor which mediates delivery to a CNS tissue, e.g., a hydrophilic ligand, such as a C16 ligand, e.g.,

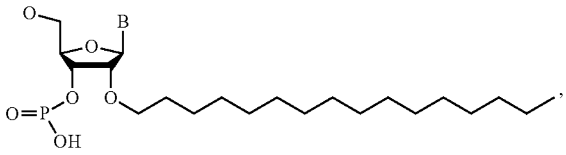

where B is a nucleotide base or a nucleotide base analog, optionally where B is adenine, guanine, cytosine, thymine or uracil and does not comprise a targeting ligand that targets a liver tissue, such as a GalNAc conjugate.

In some embodiments, the lipophilic moeity or targeting ligand is conjugated via a bio-clevable linker selected from the group consisting of DNA, RNA, disulfide, amide, funtionalized monosaccharides or oligosaccharides of galactosamine, glucosamine, glucose, galactose, mannose, and combinations thereof.

In some embodiments, the 3' end of the sense strand is protected via an end cap which is a cyclic group having an amine, said cyclic group being selected from the group consisting of pyrrolidinyl, pyrazolinyl, pyrazolidinyl, imidazolinyl, imidazolidinyl, piperidinyl, piperazinyl, [1,3]dioxolanyl, oxazolidinyl, isoxazolidinyl, morpholinyl, thiazolidinyl, isothiazolidinyl, quinoxalinyl, pyridazinonyl, tetrahydrofuranyl, and decalinyl.

In some embodiments, the dsRNA agent further comprises a terminal, chiral modification occurring at the first internucleotide linkage at the 3' end of the antisense strand, having the linkage phosphorus atom in Sp configuration, a terminal, chiral modification occurring at the first internucleotide linkage at the 5' end of the antisense strand, having the linkage phosphorus atom in Rp configuration, and a terminal, chiral modification occurring at the first internucleotide linkage at the 5' end of the sense strand, having the linkage phosphorus atom in either Rp configuration or Sp configuration.

In some embodiments, the dsRNA agent further comprises a terminal, chiral modification occurring at the first and second internucleotide linkages at the 3' end of the antisense strand, having the linkage phosphorus atom in Sp configuration, a terminal, chiral modification occurring at the first internucleotide linkage at the 5' end of the antisense strand, having the linkage phosphorus atom in Rp configuration, and a terminal, chiral modification occurring at the first internucleotide linkage at the 5' end of the sense strand, having the linkage phosphorus atom in either Rp or Sp configuration.

In some embodiments, the dsRNA agent further comprises a terminal, chiral modification occurring at the first, second and third internucleotide linkages at the 3' end of the antisense strand, having the linkage phosphorus atom in Sp configuration, a terminal, chiral modification occurring at the first internucleotide linkage at the 5' end of the antisense strand, having the linkage phosphorus atom in Rp configuration, and a terminal, chiral modification occurring at the first internucleotide linkage at the 5' end of the sense strand, having the linkage phosphorus atom in either Rp or Sp configuration.

In some embodiments, the dsRNA agent further comprises a terminal, chiral modification occurring at the first, and second internucleotide linkages at the 3' end of the antisense strand, having the linkage phosphorus atom in Sp configuration, a terminal, chiral modification occurring at the third internucleotide linkages at the 3' end of the antisense strand, having the linkage phosphorus atom in Rp configuration, a terminal, chiral modification occurring at the first internucleotide linkage at the 5' end of the antisense strand, having the linkage phosphorus atom in Rp configuration, and a terminal, chiral modification occurring at the first internucleotide linkage at the 5' end of the sense strand, having the linkage phosphorus atom in either Rp or Sp configuration.

In some embodiments, the dsRNA agent further comprises a terminal, chiral modification occurring at the first, and second internucleotide linkages at the 3' end of the antisense strand, having the linkage phosphorus atom in Sp configuration, a terminal, chiral modification occurring at the first, and second internucleotide linkages at the 5' end of the antisense strand, having the linkage phosphorus atom in Rp configuration, and a terminal, chiral modification occurring at the first internucleotide linkage at the 5' end of the sense strand, having the linkage phosphorus atom in either Rp or Sp configuration.

In some embodiments, the dsRNA agent further comprises a phosphate or phosphate mimic at the 5'-end of the antisense strand. In some embodiments, the phosphate mimic is a 5'-vinyl phosphonate (VP).

In some embodiments, the base pair at the 1 position of the 5'-end of the antisense strand of the duplex is an AU base pair.

In some embodiments, the sense strand has a total of 21 nucleotides and the antisense strand has a total of 23 nucleotides.

In one embodiment, the antisense strand comprises the nucleotide sequence 5'-UAUCAGCUUUUCCAGGGUCGCCG-3' (SEQ ID NO: 53).

In one embodiment, the sense strand comprises the nucleotide sequence 5'-GCGACCCUGGAAAAGCUGAUA-3' (SEQ ID NO: 40).

In one embodiment, the sense strand comprises the nucleotide sequence 5'-GCGACCCUGGAAAAGCUGAUA-3' (SEQ ID NO: 40) and the antisense strand comprises the nucleotide sequence 5'-UAUCAGCUUUUCCAGGGUCGCCG-3' (SEQ ID NO: 53).

In one embodiment, the antisense strand comprises the nucleotide sequence 5'-UAGGACTUGAGGGACUCGAAGGC-3' (SEQ ID NO: 57).

In one embodiment, the sense strand comprises the nucleotide sequence 5'-CUUCGAGUCCCUCAAGUCCUA-3' (SEQ ID NO: 44).

In one embodiment, the sense strand comprises the nucleotide sequence 5'-CUUCGAGUCCCUCAAGUCCUA-3' (SEQ ID NO: 44) and the antisense strand comprises the nucleotide sequence 5'-UAGGACTUGAGGGACUCGAAGGC-3'(SEQ ID NO: 57).

In one embodiment, the antisense strand comprises the nucleotide sequence 5'-UUAAAAGCAGAACCUGACCGGCC-3' (SEQ ID NO: 59).

In one embodiment, the sense strand comprises the nucleotide sequence 5'-CCGGUCAGGUUCUGCUUUUAA-3' (SEQ ID NO: 46).

In one embodiment, the sense strand comprises the nucleotide sequence 5'-CCGGUCAGGUUCUGCUUUUAA-3' (SEQ ID NO: 46) and the antisense strand comprises the nucleotide sequence 5'-UUAAAAGCAGAACCUGACCGGCC-3' (SEQ ID NO: 59).

In one aspect, the present invention provides a double stranded ribonucleic acid (dsRNA) agent for inhibiting expression of Huntingtin (HTT) in a cell, wherein the dsRNA agent comprises a sense strand and an antisense strand forming a double stranded region, wherein the sense strand comprises at least 15 contiguous nucleotides differing by no more than 4 nucleotides from the nucleotide sequence 5'-gscsgac(Chd)CfuGfGfAfaaagcugasusa-3' (SEQ ID NO:65) and the antisense strand comprises at least 15 contiguous nucleotides differing by no more than 4 nucleotides from the nucleotide sequence 5'-VPusAfsucdAg(C2p)uuuudCcAfgdGgucgcscsg-3' (SEQ ID NO:79), wherein a, g, c and u are 2'-O-methyl (2'-OMe) A, G, C, and U; s is a phosphorothioate linkage; Af, Cf, Gf, Uf are 2'-fluoro A, C, G, and U; (Chd) is 2'-O-hexadecyl-cytosine-3'-phosphate; C2p is cytidine-2'-phosphate; and VP is 5'-vinyl phosphonate.

In one embodiment, the sense strand comprises at least 15 contiguous nucleotides differing by no more than 3 nucleotides from the nucleotide sequence 5'-gscsgac(Chd)CfuGfGfAfaaagcugasusa-3' (SEQ ID NO:65) and the antisense strand comprises at least 15 contiguous nucleotides differing by no more than 3 nucleotides from the nucleotide sequence 5'-VPusAfsucdAg(C2p)uuuudCcAfgdGgucgcscsg-3' (SEQ ID NO:79).

In one embodiment, the sense strand comprises at least 15 contiguous nucleotides differing by no more than 2 nucleotides from the nucleotide sequence 5'-gscsgac(Chd)CfuGfGfAfaaagcugasusa-3' (SEQ ID NO:65) and the antisense strand comprises at least 15 contiguous nucleotides differing by no more than 2 nucleotides from the nucleotide sequence 5'-VPusAfsucdAg(C2p)uuuudCcAfgdGgucgcscsg-3' (SEQ ID NO:79).

In one embodiment, the sense strand comprises at least 15 contiguous nucleotides differing by no more than 1 nucleotide from the nucleotide sequence 5'-gscsgac(Chd)CfuGfGfAfaaagcugasusa-3' (SEQ ID NO:65) and the antisense strand comprises at least 15 contiguous nucleotides differing by no more than 1 nucleotide from the nucleotide sequence 5'-VPusAfsucdAg(C2p)uuuudCcAfgdGgucgcscsg-3' (SEQ ID NO:79).

In one embodiment, the sense strand comprises the nucleotide sequence 5'-gscsgac(Chd)CfuGfGfAfaaagcugasusa-3' (SEQ ID NO:65) and the antisense strand comprises the nucleotide sequence 5'-VPusAfsucdAg(C2p)uuuudCcAfgdGgucgcscsg-3' (SEQ ID NO:79).

In one embodiment, the sense strand consists of the nucleotide sequence 5'-gscsgac(Chd)CfuGfGfAfaaagcugasusa-3' (SEQ ID NO:65) and the antisense strand consists of the nucleotide sequence 5'-VPusAfsucdAg(C2p)uuuudCcAfgdGgucgcscsg-3' (SEQ ID NO:79).

In another aspect, the present invention provides a double stranded ribonucleic acid (dsRNA) agent for inhibiting expression of Huntingtin (HTT) in a cell, wherein the dsRNA agent comprises a sense strand and an antisense strand forming a double stranded region, wherein the sense strand comprises at least 15 contiguous nucleotides differing by no more than 4 nucleotides from the nucleotide sequence 5'-csusucg(Ahd)GfuCfCfCfucaaguccsusa-3' (SEQ ID NO:70) and the antisense strand comprises at least 15 contiguous nucleotides differing by no more than 4 nucleotides from the nucleotide sequence 5'-VPusAfsggac(Tgn)ugagggAfcUfcgaagsgsc-3' (SEQ ID NO:83), wherein a, g, c and u are 2'-O-methyl (2'-OMe) A, G, C, and U; s is a phosphorothioate linkage; Af, Cf, Gf, Uf are 2'-fluoro A, C, G, and U; (Ahd) is 2'-O-hexadecyl-adenosine-3'-phosphate; Tgn is thymidine-glycol nucleic acid (GNA)S-isomer; and VP is 5'-vinyl phosphonate.

In one embodiment, the sense strand comprises at least 15 contiguous nucleotides differing by no more than 3 nucleotides from the nucleotide sequence 5'-csusucg(Ahd)GfuCfCfCfucaaguccsusa-3' (SEQ ID NO:70) and the antisense strand comprises at least 15 contiguous nucleotides differing by no more than 3 nucleotides from the nucleotide sequence 5'-VPusAfsggac(Tgn)ugagggAfcUfcgaagsgsc-3' (SEQ ID NO:83).

In one embodiment, the sense strand comprises at least 15 contiguous nucleotides differing by no more than 2 nucleotides from the nucleotide sequence 5'-csusucg(Ahd)GfuCfCfCfucaaguccsusa-3' (SEQ ID NO:70) and the antisense strand comprises at least 15 contiguous nucleotides differing by no more than 2 nucleotides from the nucleotide sequence 5'-VPusAfsggac(Tgn)ugagggAfcUfcgaagsgsc-3' (SEQ ID NO:83).

In one embodiment, the sense strand comprises at least 15 contiguous nucleotides differing by no more than 1 nucleotide from the nucleotide sequence 5'-csusucg(Ahd)GfuCfCfCfucaaguccsusa-3' (SEQ ID NO:70) and the antisense strand comprises at least 15 contiguous nucleotides differing by no more than 1 nucleotide from the nucleotide sequence 5'-VPusAfsggac(Tgn)ugagggAfcUfcgaagsgsc-3' (SEQ ID NO:83).

In one embodiment, the sense strand comprises the nucleotide sequence 5'-csusucg(Ahd)GfuCfCfCfucaaguccsusa-3' (SEQ ID NO:70) and the antisense strand comprises the nucleotide sequence 5'-VPusAfsggac(Tgn)ugagggAfcUfcgaagsgsc-3' (SEQ ID NO:83).

In one embodiment, the sense strand consists of the nucleotide sequence 5'-csusucg(Ahd)GfuCfCfCfucaaguccsusa-3' (SEQ ID NO:70) and the antisense strand consists of the nucleotide sequence 5'-VPusAfsggac(Tgn)ugagggAfcUfcgaagsgsc-3' (SEQ ID NO:83).

In one aspect, the present invention provides a double stranded ribonucleic acid (dsRNA) agent for inhibiting expression of Huntingtin (HTT) in a cell, wherein the dsRNA agent comprises a sense strand and an antisense strand forming a double stranded region, wherein the sense strand comprises at least 15 contiguous nucleotides differing by no more than 4 nucleotides from the nucleotide sequence 5'-cscsggu(Chd)AfgGfUfUfcugcuuuusasa-3' (SEQ ID NO:72) and the antisense strand comprises at least 15 contiguous nucleotides differing by no more than 4 nucleotides from the nucleotide sequence 5'-VPusUfsaadAadGcagaacCfudGaccggscsc-3' (SEQ ID NO:85), wherein a, g, c and u are 2'-O-methyl (2'-OMe) A, G, C, and U; s is a phosphorothioate linkage; Af, Cf, Gf, Uf are 2'-fluoro A, C, G, and U; (Chd) is 2'-O-hexadecyl-cytosine-3'-phosphate; and VP is 5'-vinyl phosphonate.

In one embodiment, the sense strand comprises at least 15 contiguous nucleotides differing by no more than 3 nucleotides from the nucleotide sequence 5'-cscsggu(Chd)AfgGfUfUfcugcuuuusasa-3' (SEQ ID NO:72) and the antisense strand comprises at least 15 contiguous nucleotides differing by no more than 3 nucleotides from the nucleotide sequence 5'-VPusUfsaadAadGcagaacCfudGaccggscsc-3' (SEQ ID NO:85).

In one embodiment, the sense strand comprises at least 15 contiguous nucleotides differing by no more than 2 nucleotides from the nucleotide sequence 5'-cscsggu(Chd)AfgGfUfUfcugcuuuusasa-3' (SEQ ID NO:72) and the antisense strand comprises at least 15 contiguous nucleotides differing by no more than 2 nucleotides from the nucleotide sequence 5'-VPusUfsaadAadGcagaacCfudGaccggscsc-3' (SEQ ID NO:85).

In one embodiment, the sense strand comprises at least 15 contiguous nucleotides differing by no more than 1 nucleotide from the nucleotide sequence 5'-cscsggu(Chd)AfgGfUfUfcugcuuuusasa-3' (SEQ ID NO:72) and the antisense strand comprises at least 15 contiguous nucleotides differing by no more than 1 nucleotide from the nucleotide sequence 5'-VPusUfsaadAadGcagaacCfudGaccggscsc-3' (SEQ ID NO:85).

In one embodiment, the sense strand comprises the nucleotide sequence 5'-cscsggu(Chd)AfgGfUfUfcugcuuuusasa-3' (SEQ ID NO:72) and the antisense strand comprises the nucleotide sequence 5'-VPusUfsaadAadGcagaacCfudGaccggscsc-3' (SEQ ID NO:85).

In one embodiment, the sense strand consists of the nucleotide sequence 5'-cscsggu(Chd)AfgGfUfUfcugcuuuusasa-3' (SEQ ID NO:72) and the antisense strand consists of the nucleotide sequence 5'-VPusUfsaadAadGcagaacCfudGaccggscsc-3' (SEQ ID NO:85).

In another aspect, the present invention provides a double stranded RNAi agent for inhibiting expression of a huntingtin (HTT) gene in a cell, where the double stranded RNAi agent comprises a sense strand and an antisense strand forming a double stranded region, where the sense strand comprises at least 15, e.g., 15, 16, 17, 18, 19, 20, or 21 contiguous nucleotides differing by no more than 3 nucleotides (i.e., differing by 3, 2, 1, or 0 nucleotides) from the nucleotide sequence 5'-GCUAUUCAUAAUCACAUUCGA-3' (SEQ ID NO: 15) and the antisense strand comprises at least 15, e.g., 15, 16, 17, 18, 19, 20, 21, 22, or 23 contiguous nucleotides differing by no more than 3 nucleotides (i.e., differing by 3, 2, 1, or 0 nucleotides) from the nucleotide sequence 5'-UCGAAUGUGAUUAUGAAUAGCAU-3' (SEQ ID NO: 16), wherein substantially all, e.g., no less than 18, 19, 20, or 21, of the nucleotides of the sense stand and substantially all, e.g., no less than 20, 21, 22, or 23, of the nucleotides of the antisense strand comprise a nucleotide modification selected from the group consisting of a 2'-O-methyl modification, a 2'-fluoro modification, and a 2'-O-hexadecyl modification, wherein the dsRNA agent comprises six to eight phosphorothioate internucleotide linkages, wherein the sense strand comprises one or more a vinyl phosphonate (VP) modifications, e.g., a single VP modification at the 5'-terminus of the antisense strand, and wherein the dsRNA agent does not comprise a ligand targeting a liver tissue, e.g., a GalNAc ligand. In one embodiment, the dsRNA agent comprises eight phosphorothioate internucleotide linkages.

In another aspect, the present invention provides a double stranded RNAi agent for inhibiting expression of a huntingtin (HTT) gene in a cell, where the double stranded RNAi agent comprises a sense strand and an antisense strand forming a double stranded region, where the sense strand comprises at least 15, e.g., 15, 16, 17, 18, 19, 20, or 21 contiguous nucleotides differing by no more than 3 nucleotides (i.e., differing by 3, 2, 1, or 0 nucleotides) from the nucleotide sequence 5'-GCUAUUCAUAAUCACAUUCGA-3' (SEQ ID NO: 15) and the antisense strand comprises at least 15, e.g., 15, 16, 17, 18, 19, 20, 21, 22, or 23 contiguous nucleotides differing by no more than 3 nucleotides (i.e., differing by 3, 2, 1, or 0 nucleotides) from the nucleotide sequence 5'-UCGAAUGUGAUUAUGAAUAGCAU-3' (SEQ ID NO: 16), wherein substantially all, e.g., no less than 18, 19, 20, or 21, of the nucleotides of the sense stand and substantially all, e.g., no less than 20, 21, 22, or 23, of the nucleotides of the antisense strand comprise a nucleotide modification selected from the group consisting of a 2'-O-methyl modification, a 2'-fluoro modification, and a 2'-O-hexadecyl modification, wherein the sense strand comprises four phosphorothioate internucleotide linkages, e.g., two phosphorothioate internucleotide linkages at the 5'-terminus and two phosphorothioate internucleotide linkages at the 3'-terminus, and wherein the antisense strand comprises four phosphorothioate internucleotide linkages, e.g., two phosphorothioate internucleotide linkages at the 5'-terminus and two phosphorothioate internucleotide linkages at the 3'-terminus, and wherein the sense strand comprises one or more a vinyl phosphonate (VP) modifications, e.g., a single VP modification at the 5'-terminus of the antisense strand.

In another embodiment, the sense strand comprises the nucleotide sequence 5'-gscsuau(Uhd)CfaUfAfAfucacauucsgsa-3' (SEQ ID NO: 17) and the antisense strand comprises the nucleotide sequence 5'-VPusCfsgaaUfgUfGfauuaUfgAfauagcsasu-3' (SEQ ID NO: 18), wherein a, c, g, and u are 2'-O-methyl (2'-OMe) modified A, C, G, and U, respectively; Af, Cf, Gf, and Uf are 2'-fluoro modified A, C, G, and U, respectively; s is a phosphorothioate linkage; and VP is a vinyl phosphonate. In one embodiment, the dsRNA agent further comprises a ligand, such as N-[tris(GalNAc-alkyl)-amidodecanoyl)]-4-hydroxyprolinol.

In one embodiment, the sense strand consists of the nucleotide sequence 5'-gscsuau(Uhd)CfaUfAfAfucacauucsgsa-3' (SEQ ID NO: 17) and the antisense strand consists of the nucleotide sequence 5'-VPusCfsgaaUfgUfGfauuaUfgAfauagcsasu-3' (SEQ ID NO: 18), wherein a, c, g, and u are 2'-O-methyl (2'-OMe) modified A, C, G, and U, respectively; Af, Cf, Gf, and Uf are 2'-fluoro modified A, C, G, and U, respectively; s is a phosphorothioate linkage; and VP is a vinyl phosphonate. In one embodiment, the dsRNA agent further comprises a ligand, such as N-[tris(GalNAc-alkyl)-amidodecanoyl)]-4-hydroxyprolinol.

In another embodiment, the sense strand comprises the nucleotide sequence 5'-gscsuau(Uhd)CfaUfAfAfucacauucsgsa-3' (SEQ ID NO: 17) and the antisense strand comprises the nucleotide sequence 5'-VPusCfsgaaUfgUfGfauuaUfgAfauagcsasu-3' (SEQ ID NO: 18), wherein a, c, g, and u are 2'-O-methyl (2'-OMe) modified A, C, G, and U, respectively; Af, Cf, Gf, and Uf are 2'-fluoro modified A, C, G, and U, respectively; s is a phosphorothioate linkage; and VP is a vinyl phosphonate, and wherein a ligand is conjugated to the 3' end of the sense strand as shown in the following schematic:

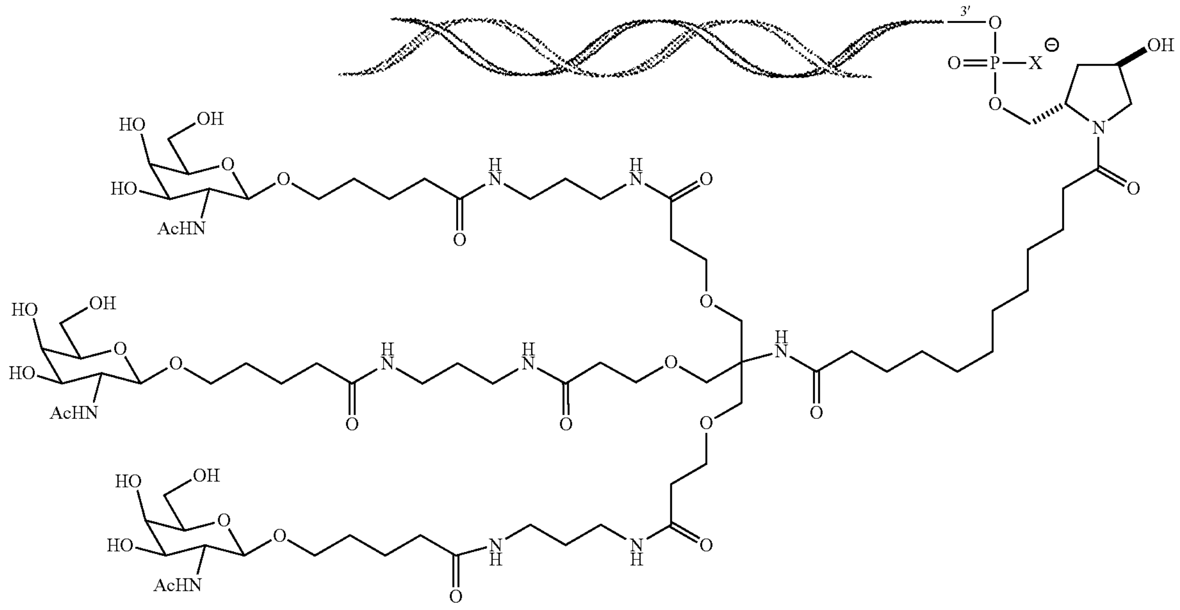

wherein X is O.

In one embodiment, the sense strand consists of the nucleotide sequence 5'-gscsuau(Uhd)CfaUfAfAfuca-cauucsgsa-3' (SEQ ID NO: 17) and the antisense strand consists of the nucleotide sequence 5'-VPus-CfsgaaUfgUfGfauuaUfgAfauagcsasu-3' (SEQ ID NO: 18), wherein a, c, g, and u are 2'-O-methyl (2'-OMe) modified A, C, G, and U, respectively; Af, Cf, Gf, and Uf are 2'-fluoro modified A, C, G, and U, respectively; s is a phosphorothioate linkage; and VP is a vinyl phosphonate, and wherein a ligand is conjugated to the 3' end of the sense strand as shown in the following schematic:

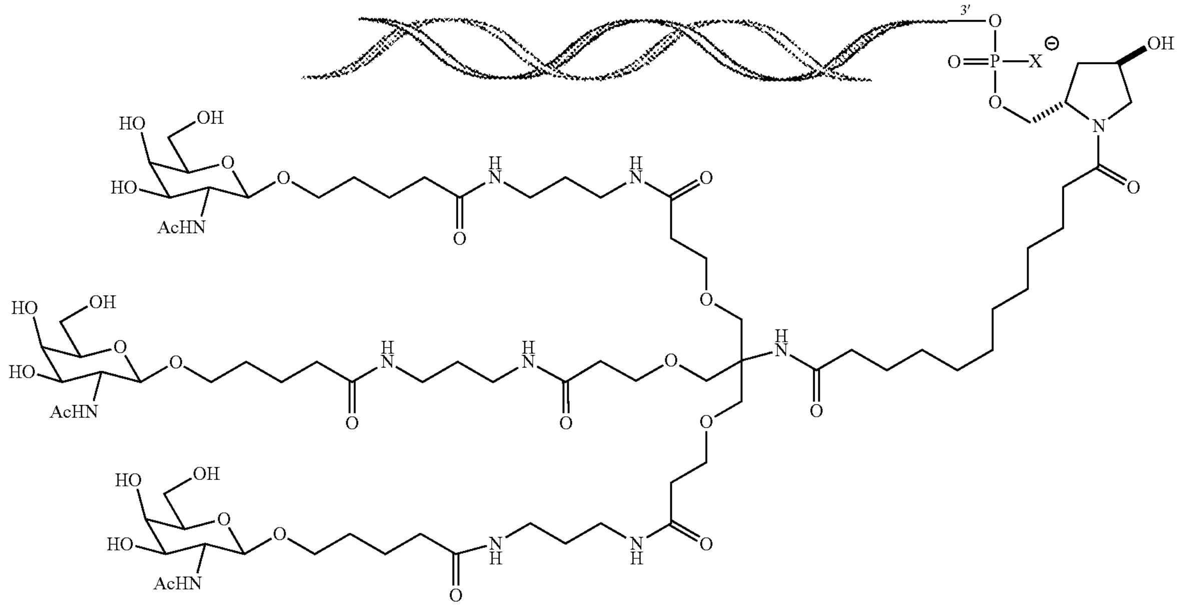

In one aspect, the present invention provides a double stranded ribonucleic acid (dsRNA) agent for inhibiting expression of Huntingtin (HTT) in a cell, wherein the dsRNA agent comprises a sense strand and an antisense strand forming a double stranded region, wherein the sense strand comprises the modified nucleotide sequence 5'-uscsaua(Ahd)UfcAfCfAfuucguuugsusa-3' (SEQ ID NO:19) and the antisense strand comprises the modified nucleotide sequence 5'-VPusAfscaaAfcGfAfauguGfaUfuaugasasu-3' (SEQ ID NO:20), wherein a, g, c and u are 2'-O-methyl (2'-OMe) A, G, C, and U; s is a phosphorothioate linkage; Af, Cf, Gf, Uf are 2'-fluoro A, C, G, and U; (Ahd) is 2'-O-hexadecyl-adenosine-3'-phosphate; and VP is 5'-vinyl phosphonate.

In one aspect, the present invention provides a double stranded ribonucleic acid (dsRNA) agent for inhibiting expression of Huntingtin (HTT) in a cell, wherein the dsRNA agent comprises a sense strand and an antisense strand forming a double stranded region, wherein the sense strand comprises the modified nucleotide sequence 5'-gscsugg(Uhd)GfaAfUfCfggauuccusgsa-3'(SEQ ID NO:21) and the antisense strand comprises the modified nucleotide sequence 5'-VPusCfsaggAfaUfCfcgauUfcAfccagcsusc-3' (SEQ ID NO:22), wherein a, g, c and u are 2'-O-methyl (2'-OMe) A, G, C, and U, respectively; s is a phosphorothioate linkage; Af, Cf, Gf, Uf are 2'-fluoro A, C, G, and U, respectively; (Uhd) is 2'-O-hexadecyl-uridine-3'-phosphate; and VP is 5'-vinyl phosphonate.

In one aspect, the present invention provides a double stranded ribonucleic acid (dsRNA) agent for inhibiting expression of Huntingtin (HTT) in a cell, wherein the dsRNA agent comprises a sense strand and an antisense strand forming a double stranded region, wherein the sense strand comprises the modified nucleotide sequence 5'-gscsuau(Uhd)CfaUfAfAfucacauucsgsa-3' (SEQ ID NO:17) and the antisense strand comprises the modified nucleotide sequence 5'-VPusCfsgaaUfgUfGfauuaUfgAfauagcsasu-3' (SEQ ID NO:18), wherein a, g, c and u are 2'-O-methyl (2'-OMe) A, G, C, and U, respectively; s is a phosphorothioate linkage; Af, Cf, Uf are 2'-fluoro A, C, and U, respectively; dG and dT are 2'-deoxy G and T, respectively; (Uhd) is 2'-O-hexadecyl-uridine-3'-phosphate; and VP is 5'-vinyl phosphonate.

In one aspect, the present invention provides a double stranded ribonucleic acid (dsRNA) agent for inhibiting expression of Huntingtin (HTT) in a cell, wherein the dsRNA agent comprises a sense strand and an antisense strand forming a double stranded region, wherein the sense strand comprises the modified nucleotide sequence 5'-usgsgaa(Ahd)AfgCfUfGfaugaaggcscsa-3' (SEQ ID NO:23) and the antisense strand comprises the modified nucleotide sequence 5'-VPusGfsgccu(Tgn)caucagCfuUfuuccasgsg-3' (SEQ ID NO:24), wherein a, g, c and u are 2'-O-methyl (2'-OMe) A, G, C, and U, respectively; s is a phosphorothioate linkage; Af, Cf, Gf, Uf are 2'-fluoro A, C, G, and U, respectively; (Ahd) is 2'-O-hexadecyl-adenosine-3'-phosphate; (Tgn) is thymidine-glycol nucleic acid (GNA) S-Isomer; and VP is 5'-vinyl phosphonate.

In one aspect, the present invention provides a double stranded ribonucleic acid (dsRNA) agent for inhibiting expression of Huntingtin (HTT) in a cell, wherein the dsRNA agent comprises a sense strand and an antisense strand forming a double stranded region, wherein the sense strand consists of the modified nucleotide sequence 5'-uscsaua(Ahd)UfcAfCfAfuucguuugsusa-3' (SEQ ID NO:19) and the antisense strand consists of the modified nucleotide sequence 5'-VPusAfscaaAfcGfAfauguGfaUfuaugasasu-3' (SEQ ID NO:20), wherein a, g, c and u are 2'-O-methyl (2'-OMe) A, G, C, and U, respectively; s is a phosphorothioate linkage; Af, Cf, Gf, Uf are 2'-fluoro A, C, G, and U, respectively; (Ahd) is 2'-O-hexadecyl-adenosine-3'-phosphate; and VP is 5'-vinyl phosphonate.

In one aspect, the present invention provides a double stranded ribonucleic acid (dsRNA) agent for inhibiting expression of Huntingtin (HTT) in a cell, wherein the dsRNA agent comprises a sense strand and an antisense strand forming a double stranded region, wherein the sense strand consists of the modified nucleotide sequence 5'-gscsugg(Uhd)GfaAfUfCfggauuccusgsa-3'(SEQ ID NO:21) and the antisense strand consists of the modified nucleotide sequence 5'-VPusCfsaggAfaUfCfcgauUfcAfccagcsusc-3' (SEQ ID NO:22), wherein a, g, c and u are 2'-O-methyl (2'-OMe) A, G, C, and U, respectively; s is a phosphorothioate linkage; Af, Cf, Gf, Uf are 2'-fluoro A, C, G, and U, respectively; (Uhd) is 2'-O-hexadecyl-uridine-3'-phosphate; and VP is 5'-vinyl phosphonate.

In one aspect, the present invention provides a double stranded ribonucleic acid (dsRNA) agent for inhibiting expression of Huntingtin (HTT) in a cell, wherein the dsRNA agent comprises a sense strand and an antisense strand forming a double stranded region, wherein the sense strand consists of the modified nucleotide sequence 5'-gscsuau(Uhd)CfaUfAfAfucacauucsgsa-3' (SEQ ID NO:17) and the antisense strand consists of the modified nucleotide sequence 5'-VPusCfsgaaUfgUfGfauuaUfgAfauagcsasu-3' (SEQ ID NO:18), wherein a, g, c and u are 2'-O-methyl (2'-OMe) A, G, C, and U, respectively; s is a phosphorothioate linkage; Af, Cf, Uf are 2'-fluoro A, C, and U, respectively; dG and dT are 2'-deoxy G and T, respectively; (Uhd) is 2'-O-hexadecyl-uridine-3'-phosphate; and VP is 5'-vinyl phosphonate.

In one aspect, the present invention provides a double stranded ribonucleic acid (dsRNA) agent for inhibiting expression of Huntingtin (HTT) in a cell, wherein the dsRNA agent comprises a sense strand and an antisense strand forming a double stranded region, wherein the sense strand consists of the modified nucleotide sequence 5'-usgsgaa(Ahd)AfgCfUfGfaugaaggcscsa-3' (SEQ ID NO:23) and the antisense strand consists of the modified nucleotide sequence 5'-VPusGfsgccu(Tgn)caucagCfuUfuuccasgsg-3' (SEQ ID NO:24), wherein a, g, c and u are 2'-O-methyl (2'-OMe) A, G, C, and U, respectively; s is a phosphorothioate linkage; Af, Cf, Gf, Uf are 2'-fluoro A, C, G, and U; (Ahd) is 2'-O-hexadecyl-adenosine-3'-phosphate; (Tgn) is thymidine-glycol nucleic acid (GNA)S-Isomer; and VP is 5'-vinyl phosphonate.

The present invention further provides cells containing any of the dsRNA agents of the invention and pharmaceutical compositions for inhibiting expression of a gene encoding HTT, comprising any of the dsRNA agents of the invention.

In one embodiment, the double stranded RNAi agent is in an unbuffered solution. Optionally, the unbuffered solution is saline or water. In another embodiment, the double stranded RNAi agent is in a buffer solution. Optionally, the buffer solution includes acetate, citrate, prolamine, carbonate, or phosphate or any combination thereof. In another embodiment, the buffer solution is phosphate buffered saline (PBS). Another aspect of the disclosure provides a pharmaceutical composition that includes a double stranded RNAi agent of the instant disclosure and a lipid formulation. In one embodiment, the lipid formulation includes a lipid nanoparticle (LNP).

The present invention provides a composition comprising two or more dsRNA agents for inhibiting expression of Huntingtin (HTT) in a cell, such as a first dsRNA agent targeting exon 1 of human HTT and a second dsRNA agent targeting full-length human HTT.

In one aspect, the present invention provides a composition comprising two or more dsRNA agents for inhibiting expression of Huntingtin (HTT) in a cell, wherein each dsRNA agent independently comprises a sense strand and an antisense strand forming a double stranded region, wherein each of the antisense strands independently comprises a region of complementarity to an mRNA encoding HTT, and wherein the each of the regions of complementarity independently comprises at least 15 contiguous nucleotides differing by no more than 3 nucleotides from any one of the antisense nucleotide sequences in any one of Tables 2-5.

In another aspect, the present invention provides a composition comprising two or more dsRNA agents for inhibiting expression of Huntingtin (HTT) in a cell, wherein each dsRNA agent independently comprises a sense strand and an antisense strand forming a double stranded region, wherein each of the sense strands independently comprises a nucleotide sequence comprising at least 15 contiguous nucleotides differing by no more than three nucleotides from any one of the nucleotide sequence of nucleotides 4391-4669; 6500-6540; or 6009-6037 of SEQ ID NO: 1, and each of the antisense strands independently comprises a nucleotide sequence comprising at least 15 contiguous nucleotides from the corresponding nucleotide sequence of SEQ ID NO:6.

In one embodiment, each of the sense strand independently comprises at least 15 contiguous nucleotides differing by no more than three nucleotides from any one of the nucleotide sequence of nucleotides 4398-4420; 4403-4425; or 6512-6534 of SEQ ID NO:1.

In one embodiment, one of the sense strand comprises at least 15 contiguous nucleotides differing by no more than three nucleotides from nucleotides 4398-4420 of SEQ ID NO:1.

In one embodiment, each of the antisense strand comprises independently at least 15 contiguous nucleotides differing by no more that three nucleotides from any one of the antisense strand nucleotide sequences of a duplex selected from the group consisting of AD-1271085, AD-1271083, or AD-1271084.

In one embodiment, one of the antisense strand comprises at least 15 contiguous nucleotides differing by no more that three nucleotides from the antisense strand nucleotide sequence of AD-1271085.

In one aspect, the present invention provides a composition comprising two or more dsRNA agents for inhibiting expression of Huntingtin (HTT) in a cell, wherein each dsRNA agent independently comprises a sense strand and an antisense strand forming a double stranded region, wherein each of the sense strands independently comprises a nucleotide sequence comprising at least 15 contiguous nucleotides differing by no more than three nucleotides from any one of the nucleotide sequence of nucleotides 26-77; or 142-202 of SEQ ID NO: 1, and each of the antisense strands independently comprises a nucleotide sequence comprising at least 15 contiguous nucleotides from the corresponding nucleotide sequence of SEQ ID NO:6.

In one embodiment, each of the sense strand independently comprises at least 15 contiguous nucleotides differing by no more than three nucleotides from any one of the nucleotide sequence of nucleotides 27-49; 55-77; 147-169; or 173-195 of SEQ ID NO:1.

In one embodiment, one of the sense strand comprises at least 15 contiguous nucleotides differing by no more than three nucleotides from nucleotides 147-169 of SEQ ID NO:1.

In one embodiment, each of the antisense strand comprises independently at least 15 contiguous nucleotides differing by no more that three nucleotides from any one of the antisense strand nucleotide sequences of a duplex selected from the group consisting of AD-1019448; AD-1498524, AD-1498526, or AD-1498528.

In one embodiment, one of the antisense strand comprises at least 15 contiguous nucleotides differing by no more that three nucleotides from the antisense strand nucleotide sequence of AD-1498524.

In one embodiment, at least one of said sense strands or at least one of said antisense strands is independently conjugated to one or more lipophilic moieties.

In one embodiment, all of the sense strands or all of the antisense strand of each of the dsRNA agents are independently conjugated to one or more lipophilic moieties.

In one embodiment, each lipophilic moiety is independently conjugated to one or more positions in the double stranded region of the dsRNA agent.

In one embodiment, each lipophilic moiety is independently conjugated via a linker or a carrier.

In one embodiment, the lipophilicity of each lipophilic moiety, measured by log Kow, independently exceeds 0.

In one embodiment, the hydrophobicity of each double-stranded RNAi agent, measured by the unbound fraction in a plasma protein binding assay of the double-stranded RNAi agent, independently exceeds 0.2.

In one embodiment, the plasma protein binding assay is an electrophoretic mobility shift assay using human serum albumin protein.

In one embodiment, each of the dsRNA agents independently comprises at least one modified nucleotide.

In one embodiment, each sense strand and each antisense strand of each dsRNA agent independently comprises no more than five unmodified nucleotides.

In one embodiment, all of the nucleotides of each sense strand and all of the nucleotides of each antisense strand independently comprise a modification.

In one embodiment, at least one of the modified nucleotides is selected from the group consisting of a deoxy-nucleotide, a 3'-terminal deoxy-thymine (dT) nucleotide, a 2'-O-methyl modified nucleotide, a 2'-fluoro modified nucleotide, a 2'-deoxy-modified nucleotide, a locked nucleotide, an unlocked nucleotide, a conformationally restricted nucleotide, a constrained ethyl nucleotide, an abasic nucleotide, a 2'-amino-modified nucleotide, a 2'-O-allyl-modified nucleotide, 2'-C-alkyl-modified nucleotide, a 2'-methoxyethyl modified nucleotide, a 2'-O-alkyl-modified nucleotide, a morpholino nucleotide, a phosphoramidate, a non-natural base comprising nucleotide, a tetrahydropyran modified nucleotide, a 1,5-anhydrohexitol modified nucleotide, a cyclohexenyl modified nucleotide, a nucleotide comprising a 5'-phosphorothioate group, a nucleotide comprising a 5'-methylphosphonate group, a nucleotide comprising a 5' phosphate or 5' phosphate mimic, a nucleotide comprising vinyl phosphonate, a nucleotide comprising adenosine-glycol nucleic acid (GNA), a nucleotide comprising thymidine-glycol nucleic acid (GNA)S-Isomer, a nucleotide comprising 2-hydroxymethyl-tetrahydrofurane-5-phosphate, a nucleotide comprising 2'-deoxythymidine-3'phosphate, a nucleotide comprising 2'-deoxyguanosine-3'-phosphate, a 2'-O-hexadecyl nucleotide, a nucleotide comprising a 2'-phosphate, a cytidine-2'-phosphate nucleotide, a guanosine-2'-phosphate nucleotide, a 2'-O-hexadecyl-cytidine-3'-phosphate nucleotide, a 2'-O-hexadecyl-adenosine-3'-phosphate nucleotide, a 2'-O-hexadecyl-guanosine-3'-phosphate nucleotide, a 2'-O-hexadecyl-uridine-3'-phosphate nucleotide, a 5'-vinyl phosphonate (VP), a 2'-deoxyadenosine-3'-phosphate nucleotide, a 2'-deoxycytidine-3'-phosphate nucleotide, a 2'-deoxyguanosine-3'-phosphate nucleotide, a 2'-deoxythymidine-3'-phosphate nucleotide, a 2'-deoxyuridine nucleotide, and a terminal nucleotide linked to a cholesteryl derivative and a dodecanoic acid bisdecylamide group; and combinations thereof.

In one embodiment, the modified nucleotide is independently selected from the group consisting of a 2'-deoxy-2'-fluoro modified nucleotide, a 2'-deoxy-modified nucleotide, 3'-terminal deoxy-thymine nucleotides (dT), a locked nucleotide, an abasic nucleotide, a 2'-amino-modified nucleotide, a 2'-alkyl-modified nucleotide, a morpholino nucleotide, a phosphoramidate, and a non-natural base comprising nucleotide.

In another embodiment, the modified nucleotide comprises a short sequence of 3'-terminal deoxy-thymine nucleotides (dT).

In one embodiment, the modifications on the nucleotides are each independently selected from the group consisting of 2'-O-methyl modifications, 2'-deoxy-modifications, or 2'fluoro modifications.

In one embodiment, at least one of the dsRNA agents further comprises at least one phosphorothioate internucleotide linkage.

In one embodiment, at least one of the dsRNA agents comprises 6-8 phosphorothioate internucleotide linkages.

In one embodiment, each strand of each dsRNA agent is independently no more than 30 nucleotides in length.

In one embodiment, wherein at least one strand of at least one dsRNA agent independently comprises a 3' overhang of at least 1 nucleotide.

In another embodiment, at least one strand of at least one dsRNA agent independently comprises a 3' overhang of at least 2 nucleotides.

The double stranded region of each dsRNA agent may be independently 15-30 nucleotide pairs in length; 17-23 nucleotide pairs in length; 17-25 nucleotide pairs in length; 23-27 nucleotide pairs in length; 19-21 nucleotide pairs in length1 or 21-23 nucleotide pairs in length.

Each strand of each dsRNA agent may be independently has 19-30 nucleotides; 19-23 nucleotides in length; or 21-23 nucleotides in length.

In one embodiment, each dsRNA agent comprises one or more lipophilic moieties independently conjugated to one or more internal positions on at least one strand.

In one embodiment, the one or more lipophilic moieties are each independently conjugated to one or more internal positions on at least one strand via a linker or carrier.

In one embodiment, each of the internal positions independently include all positions except the terminal two positions from each end of the at least one strand.

In one embodiment, each of the internal positions independently include all positions except the terminal three positions from each end of the at least one strand.

In one embodiment, each of the internal positions independently exclude a cleavage site region of the sense strand.

In one embodiment, each of the internal positions independently include all positions except positions 9-12, counting from the 5'-end of the sense strand.

In one embodiment, each of the internal positions independently include all positions except positions 11-13, counting from the 3'-end of the sense strand.

In one embodiment, each of the internal positions independently exclude a cleavage site region of the antisense strand.

In one embodiment, each of the internal positions independently include all positions except positions 12-14, counting from the 5'-end of the antisense strand.

In one embodiment, each of the internal positions independently include all positions except positions 11-13 on the sense strand, counting from the 3'-end, and positions 12-14 on the antisense strand, counting from the 5'-end.

In one embodiment, each of the one or more lipophilic moieties are independently conjugated to one or more of the internal positions selected from the group consisting of positions 4-8 and 13-18 on the sense strand, and positions 6-10 and 15-18 on the antisense strand, counting from the 5'end of each strand.

In one embodiment, the one or more lipophilic moieties are each independently conjugated to one or more of the internal positions selected from the group consisting of positions 5, 6, 7, 15, and 17 on the sense strand, and positions 15 and 17 on the antisense strand, counting from the 5'-end of each strand.

In one embodiment, each of the positions in the double stranded region independently exclude a cleavage site region of the sense strand.

In one embodiment, each of the sense strands is independently 21 nucleotides in length, each of the antisense strands is independently 23 nucleotides in length, and each of the lipophilic moieties is independently conjugated to position 21, position 20, position 15, position 1, position 7, position 6, or position 2 of the sense strand or position 16 of the antisense strand.

In one embodiment, each of the lipophilic moieties is independently conjugated to position 21, position 20, position 15, position 1, or position 7 of the sense strand.

In one embodiment, each of the lipophilic moieties is independently conjugated to position 21, position 20, or position 15 of the sense strand.

In one embodiment, each of the lipophilic moieties is independently conjugated to position 20 or position 15 of the sense strand.

In one embodiment, each of the lipophilic moieties is independently conjugated to position 16 of the antisense strand.

In one embodiment, each of the lipophilic moieties is independently an aliphatic, alicyclic, or polyalicyclic compound.

In one embodiment, each of the lipophilic moieties is independently selected from the group consisting of lipid, cholesterol, retinoic acid, cholic acid, adamantane acetic acid, 1-pyrene butyric acid, dihydrotestosterone, 1,3-bis-O (hexadecyl)glycerol, geranyloxyhexyanol, hexadecylglycerol, borneol, menthol, 1,3-propanediol, heptadecyl group, palmitic acid, myristic acid, O3-(oleoyl)lithocholic acid, O3-(oleoyl)cholenic acid, dimethoxytrityl, or phenoxazine.

In one embodiment, each of the lipophilic moieties independently contains a saturated or unsaturated C4-C30 hydrocarbon chain, and an optional functional group selected from the group consisting of hydroxyl, amine, carboxylic acid, sulfonate, phosphate, thiol, azide, and alkyne.

In one embodiment, each of the lipophilic moieties independently contains a saturated or unsaturated C6-C18 hydrocarbon chain.

In one embodiment, each of the lipophilic moieties independently contains a saturated or unsaturated C16 hydrocarbon chain.

In one embodiment, each of the saturated or unsaturated C16 hydrocarbon chain is independently conjugated to position 6, counting from the 5'-end of the strand.

In one embodiment, each of the lipophilic moieties is independently conjugated via a carrier that replaces one or more nucleotide(s) in the internal position(s) or the double stranded region.

In one embodiment, each of the carriers is independently a cyclic group selected from the group consisting of pyrrolidinyl, pyrazolinyl, pyrazolidinyl, imidazolinyl, imidazolidinyl, piperidinyl, piperazinyl, [1,3]dioxolanyl, oxazolidinyl, isoxazolidinyl, morpholinyl, thiazolidinyl, isothiazolidinyl, quinoxalinyl, pyridazinonyl, tetrahydrofuranyl, and decalinyl; or is an acyclic moiety based on a serinol backbone or a diethanolamine backbone.

In one embodiment, each of the lipophilic moieties is independently conjugated to the double-stranded iRNA agent via a linker containing an ether, thioether, urea, carbonate, amine, amide, maleimide-thioether, disulfide, phosphodiester, sulfonamide linkage, a product of a click reaction, or carbamate.

In one embodiment, each of the lipophilic moieties is independently conjugated to a nucleobase, sugar moiety, or internucleosidic linkage.

In one embodiment, each of the lipophilic moieties or one or more targeting ligands is independently conjugated via a bio-clevable linker selected from the group consisting of DNA, RNA, disulfide, amide, funtionalized monosaccharides or oligosaccharides of galactosamine, glucosamine, glucose, galactose, mannose, and combinations thereof.

In one embodiment, the 3' end of at least one of the sense strands is independently protected via an end cap which is a cyclic group having an amine, said cyclic group being selected from the group consisting of pyrrolidinyl, pyrazolinyl, pyrazolidinyl, imidazolinyl, imidazolidinyl, piperidinyl, piperazinyl, [1,3]dioxolanyl, oxazolidinyl, isoxazolidinyl, morpholinyl, thiazolidinyl, isothiazolidinyl, quinoxalinyl, pyridazinonyl, tetrahydrofuranyl, and decalinyl.

In one embodiment, at least one of the dsRNA agents further comprises a phosphate or phosphate mimic at the 5'-end of the antisense strand.

In one embodiment, each of the phosphate mimic is independently a 5'-vinyl phosphonate (VP).

In one embodiment, each of the sense strands independently has a total of 21 nucleotides and each of the antisense strands independently has a total of 23 nucleotides.

In another embodiment, the RNAi agent is a pharmaceutically acceptable salt thereof. "Pharmaceutically acceptable salts" of each of RNAi agents herein include, but are not limited to, a sodium salt, a calcium salt, a lithium salt, a potassium salt, an ammonium salt, a magnesium salt, an mixtures thereof. One skilled in the art will appreciate that the RNAi agent, when provided as a polycationic salt having one cation per free acid group of the optionally modified phosphodiester backbone and/or any other acidic modifications (e.g., 5'-terminal phosphonate groups). For example, an oligonucleotide of "n" nucleotides in length contains n-1 optionally modified phosphodiesters, so that an oligonucleotide of 21 nt in length may be provided as a salt having up to 20 cations (e.g., 20 sodium cations). Similarly, an RNAi agents having a sense strand of 21 nt in length and an antisense strand of 23 nt in length may be provided as a salt having up to 42 cations (e.g., 42 sodium cations). In the preceding example, where the RNAi agent also includes a 5'-terminal phosphate or a 5'-terminal vinylphosphonate group, the RNAi agent may be provided as a salt having up to 44 cations (e.g., 44 sodium cations).

The present invention also provides cells and pharmaceutical compostions comprising the compositions of the invention, e.g., comprising a lipid formulation.

An additional aspect of the disclosure provides a method of inhibiting expression of an HTT gene in a cell, the method including (a) contacting the cell with a double stranded RNAi agent of the instant disclosure, a composition of the invention, or a pharmaceutical composition of the instant disclosure; and (b) maintaining the cell produced in step (a) for a time sufficient to obtain degradation of the mRNA transcript of an HTT gene, thereby inhibiting expression of the HTT gene in the cell.

In one embodiment, the cell is contacted with two or more, e.g., 2, 3, or 4, of the dsRNA agents of the invention (or compositions of the invention), such as a first dsRNA agent targeting exon 1 of human HTT nd a second dsRNA agent targeting full-length human HTT.

In one embodiment, the cell is within a subject. Optionally, the subject is a human.

In certain embodiments, the subject is a rhesus monkey, a cynomolgous monkey, a mouse, or a rat. In certain embodiments HTT expression is inhibited by at least about 50% by the RNAi agent.

In certain embodiments, the human subject has been diagnosed with an HTT-associated disease, e.g., Huntington's disease.

Another aspect of the disclosure provides a method of treating a subject diagnosed with an HTT-associated disease, e.g., Huntington's disease, the method including administering to the subject a therapeutically effective amount of a double stranded RNAi agent of the disclosure, a composition of the invention, or a pharmaceutical composition of the disclosure, thereby treating the subject.

In one embodiment, the subject is administered two or more, e.g., 2, 3, or 4, dsRNA agents of the invention (or compositions of the invention), such as a first dsRNA agent targeting exon 1 of human HTT nd a second dsRNA agent targeting full-length human HTT.

The first and second dsRNA agents may be present in the same or separate compositions.

The first and second dsRNA agents may be administered to the subject in the same time or different times.

In one embodiment, treating comprises amelioration of at least on sign or symptom of the disease. In another embodiment, treating comprises prevention of progression of the disease.

In some embodiments, the dsRNA agent is administered to the subject at a dose of about 0.01 mg/kg to about 50 mg/kg.

In some embodiments, the dsRNA agent is administered to the subject intrathecally. In one embodiment, the method reduces the expression of an HTT gene in a brain (e.g., striatum) or spine tissue. Optionally, the brain or spine tissue is striatum, cortex, cerebellum, cervical spine, lumbar spine, or thoracic spine.

In some embodiments, the method further comprises measuring a level of HTT in a sample obtained from the subject.

Another aspect of the instant disclosure provides a method of inhibiting the expression of huntingtin (HTT) in a subject, the method involving: administering to the subject a therapeutically effective amount of a double stranded RNAi agent of the disclosure or a pharmaceutical composition of the disclosure, thereby inhibiting the expression of HTT in the subject.

In some embodiment, the method further comprises administering to the subject an additional agent suitable for treatment or prevention of an HTT-associated disorder.

BRIEF DESCRIPTIONS OF THE FIGURES

FIG. 2 is a table depicting the inhibition of HTT mRNA expression in the indicated regions of the brain and spine of non-human primates (n=5 per group) at 24 hours post intrathecal administration of a single 60 mg dose of the indicated duplexes.

Figure 6B:
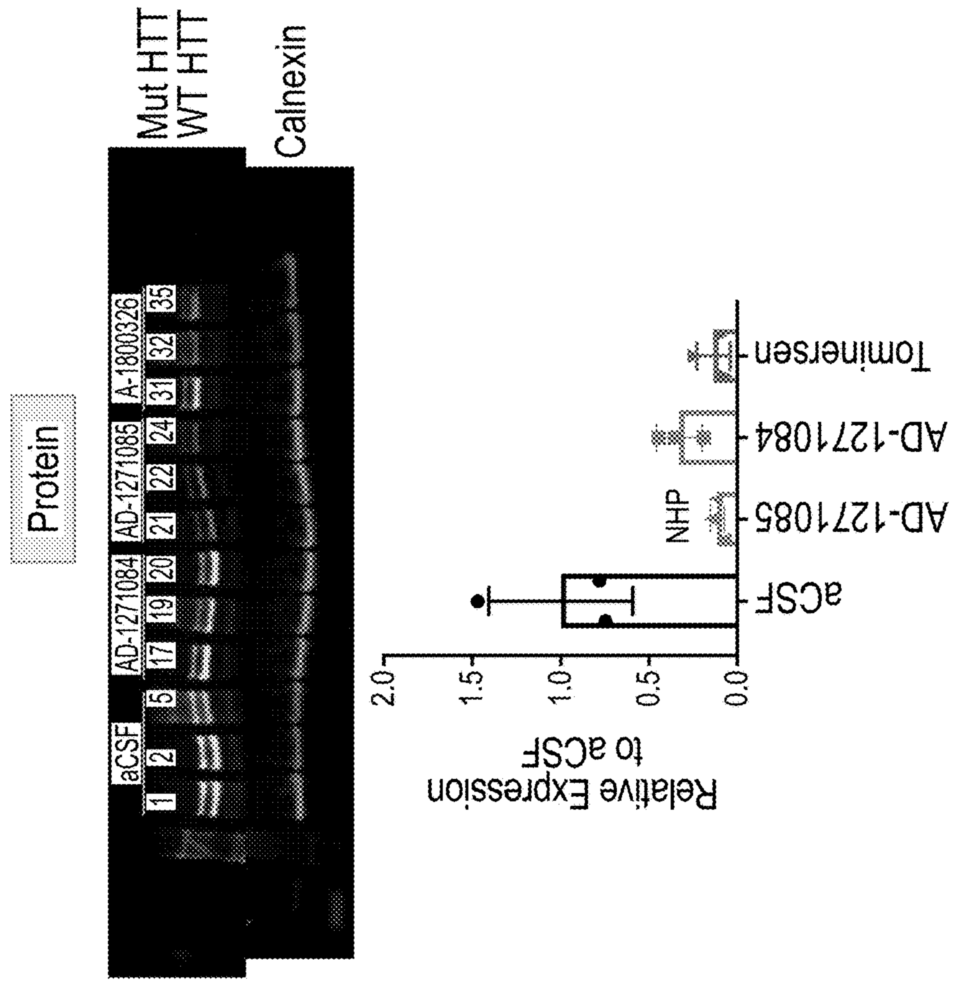
FIG. 6A is a graph depicting the level of knockdown of mutant human HTT mRNA in the frontal cortex of YAC128 administered a single 300 μg/kg dose of the indicated duplexes or artificial CSF (aCSF) control by intracerebroventricular injection (ICV). For comparison purposes the effect of the antisense oligonucleotide, Tominersen (Roche, also known as IONIS-HTTRx and RG6042) is also shown.

FIG. 6B is a Western blot and a graph depicting the level of mutant human HTT protein and mouse wild type protein knock down in in the frontal cortex of YAC128 administered a single 300 μg/kg dose of the indicated duplexes or artificial CSF (aCSF) control by intracerebroventricular injection (ICV). The human protein levels are quantified in the graph below. For comparison purposes the effect of the antisense oligonucleotide, Tominersen (Roche, also known as IONIS-HTTRx and RG6042) is also shown in the graph.

Figure 7:
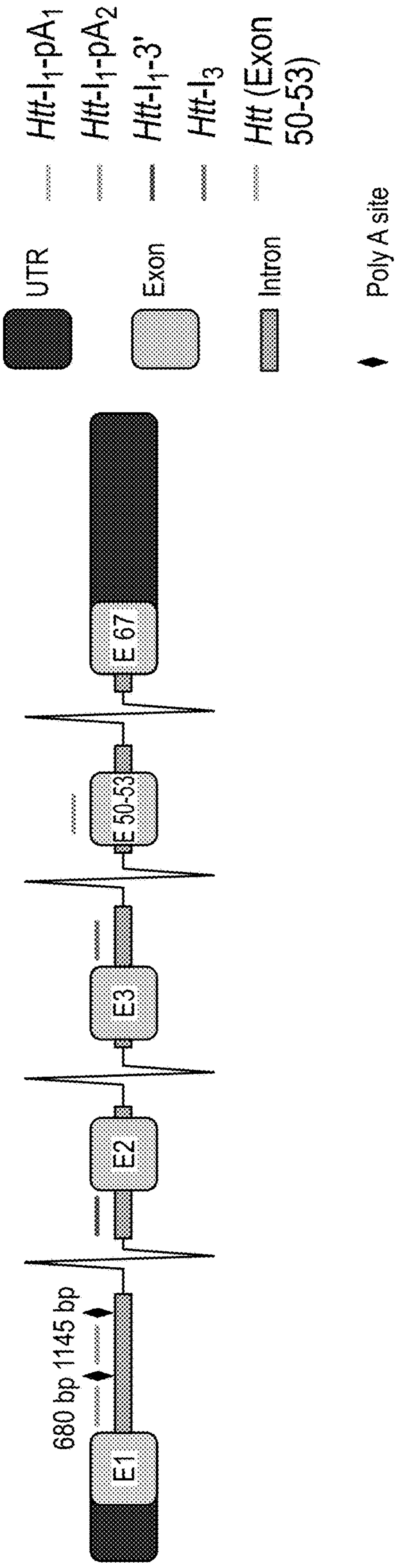

FIG. 7 schematically depicts the portion of the Htt transcript assessed by each assay of the QuantiGene panel. From Papadopoulou, et al. (2019) *Scientific Reports* volume 9, Article number 16137.

Figure 8A:
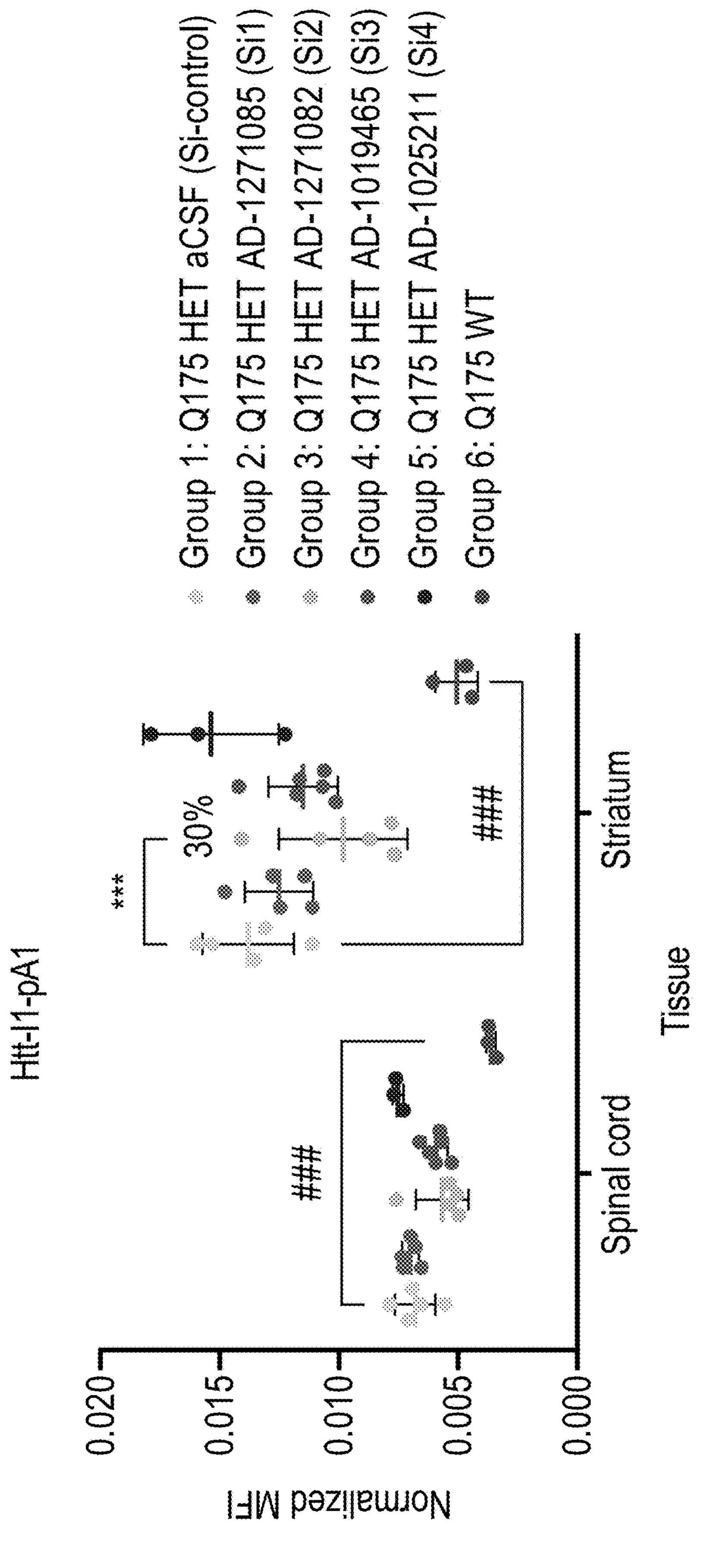

FIG. 8A is a graph depicting the mean fluorescent intensity (MFI) of Htt (mouse endogenous), intron 1 with the polyA-site 1 (the 680 bp variant) expression in the spinal cord and striatum of Q175 KI mice following a single intracerebroventricular injection of 300 μg of the indicated agents or aCSF control, and the level of Htt (mouse endogenous), intron 1 with the polyA-site 1 (the 680 bp variant) expression in the spinal cord and striatum of wild-type mice. Mean+/−SD, ***p<0.001 (ANOVA with Dunnett's multiple comparisons test) and ###p<0.001 (unpaired t-test with Si-control against WT). Normalized to geomean of 3 reference genes.

Figure 8B:
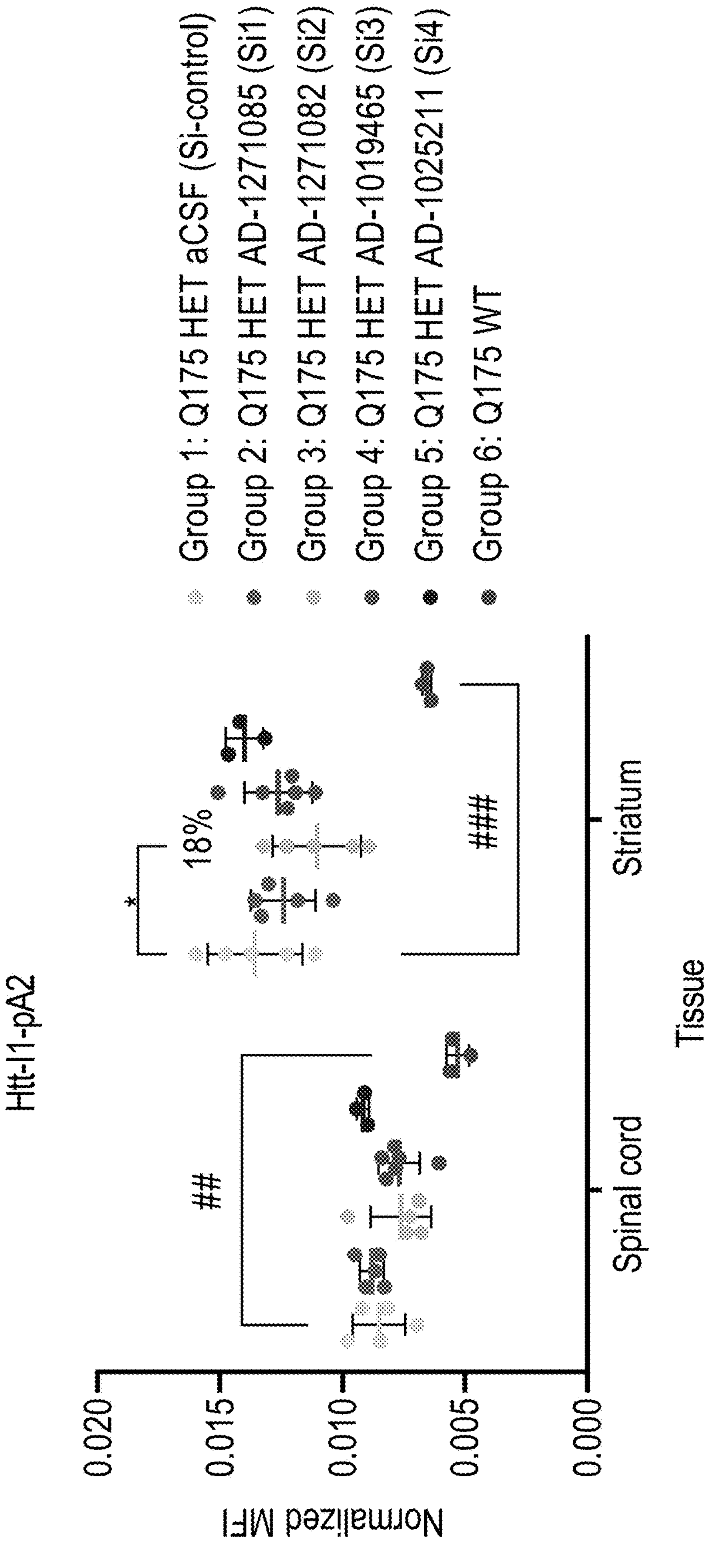

FIG. 8B is a graph depicting the mean fluorescent intensity (MFI) of Htt (mouse endogenous), intron 1 with the polyA-site 2 (the 1145 bp variant) expression in the spinal cord and striatum of Q175 KI mice following a single intracerebroventricular injection of 300 μg of the indicated agents or aCSF control, and the level of Htt (mouse endogenous), intron 1 with the polyA-site 1 (the 680 bp variant) expression in the spinal cord and striatum of wild-type mice. Mean+/−SD, *p<0.05 (ANOVA with Dunnett's multiple comparisons test) and ##p<0.01; ###p<0.001 (unpaired t-test with Si-control against WT). Normalized to geomean of 3 reference genes.

Figure 8C:
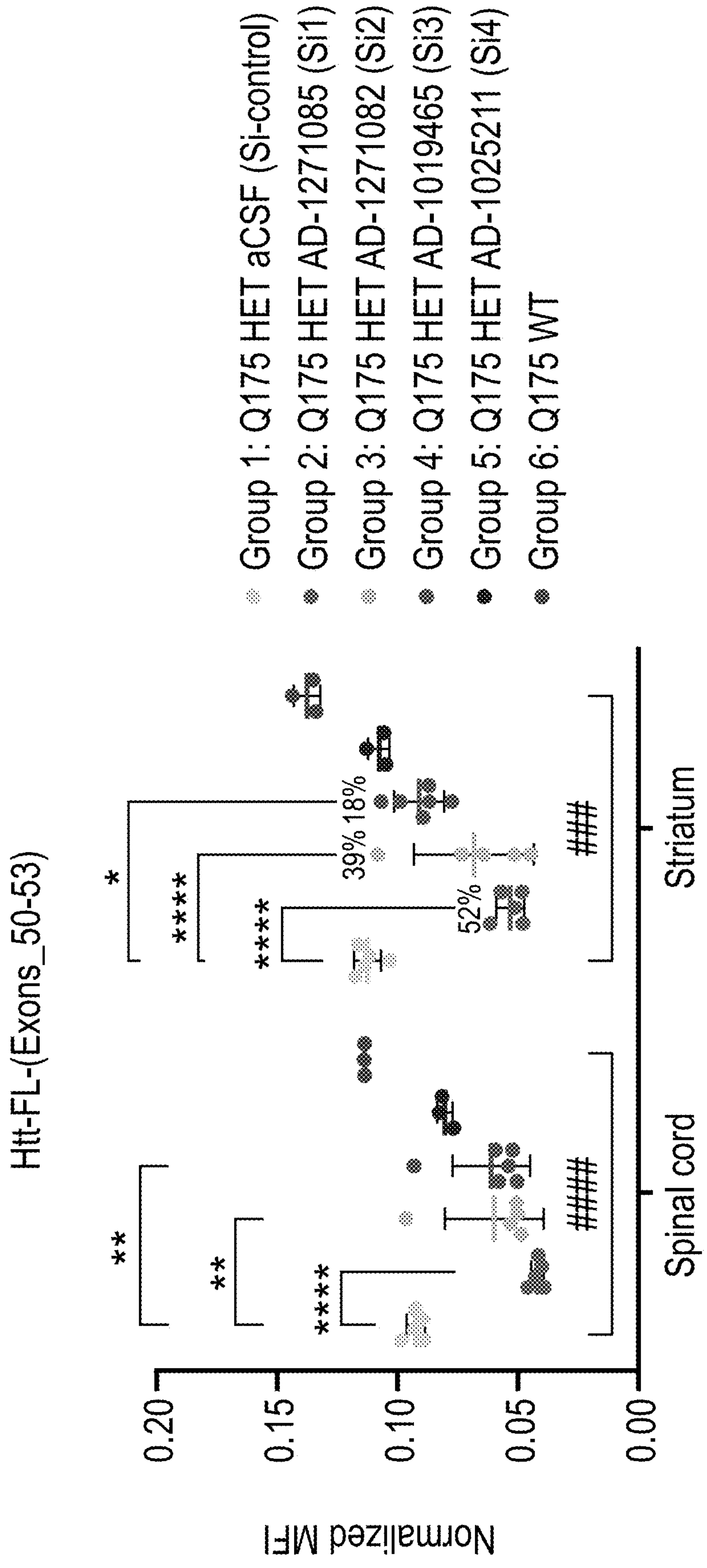

FIG. 8C is a graph depicting the mean fluorescent intensity (MFI) of Huntingtin, full-length (total) expression in the spinal cord and striatum of Q175 KI mice following a single intracerebroventricular injection of 300 μg of the indicated agents or aCSF control, and the level of Huntingtin, full-length (total) expression in the spinal cord and striatum of wild-type mice. Data is presented as mean with SD, n=3-6 per group. Pairwise comparisons as indicated: *p<0.05; p<0.01; **p<0.0001 (ANOVA with Dunnett's multiple comparisons test) and ###p<0.001; ####p<0.0001 (unpaired t-test with Si-control against WT). The comparison between group 1 and group 6 serves as a control for the model (genotype) effect. Normalized to geomean of 3 reference genes.

Figure 8D:
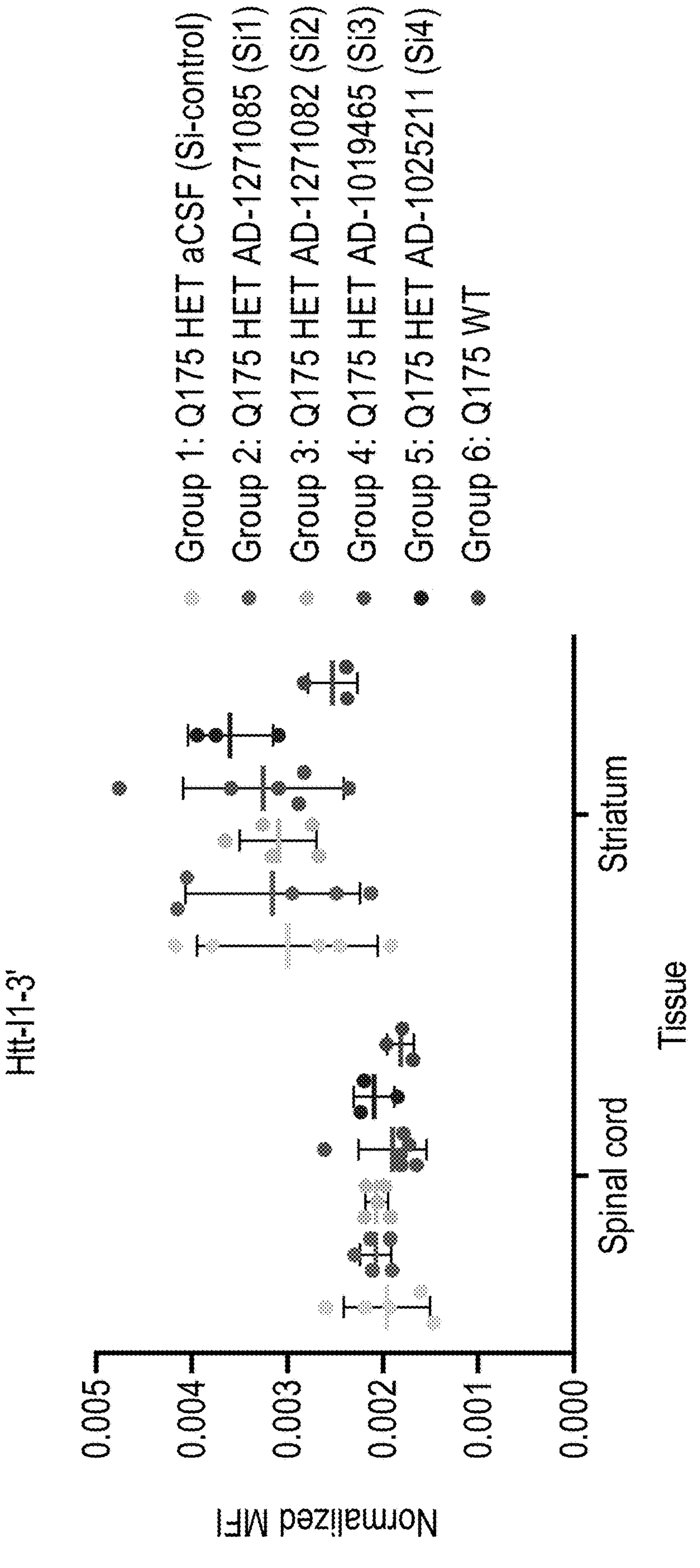

FIG. 8D is a graph depicting the mean fluorescent intensity (MFI) of Htt (mouse endogenous), intron 1 at its 3' end expression (as a negative control for detection of retained intronic region expression) in the spinal cord and striatum of Q175 KI mice following a single intracerebroventricular injection of 300 μg of the indicated agents or aCSF control, and the level of Huntingtin, full-length (total) expression in the spinal cord and striatum of wild-type mice. Normalized to geomean of 3 reference genes.

Figure 8E:
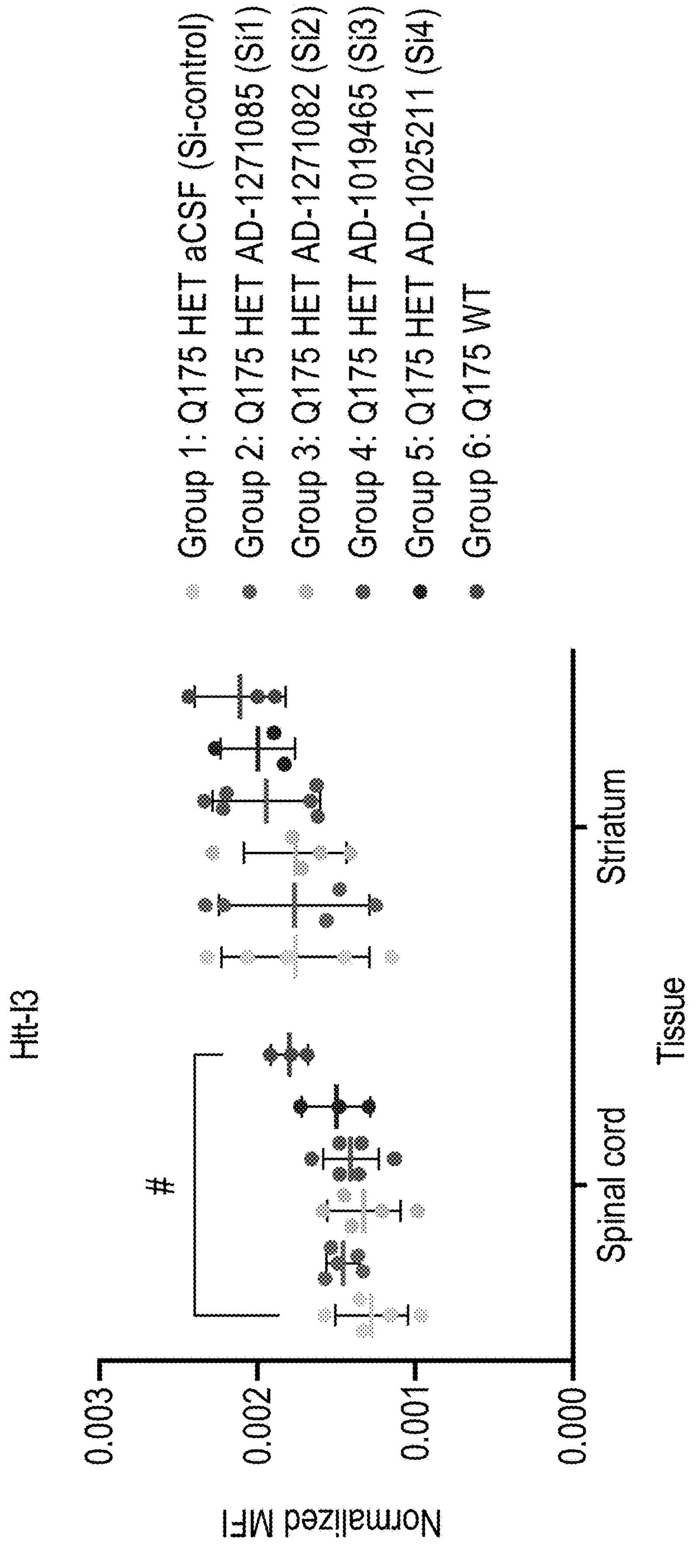

FIG. 8E is a graph depicting the mean fluorescent intensity (MFI) of Htt (mouse endogenous), intron 3 expression (as a negative control for detection of retained intronic region expression) in the spinal cord and striatum of Q175 KI mice following a single intracerebroventricular injection of 300 μg of the indicated agents or aCSF control, and the level of Huntingtin, full-length (total) expression in the spinal cord and striatum of wild-type mice. Normalized to geomean of 3 reference genes.

Figure 8F:
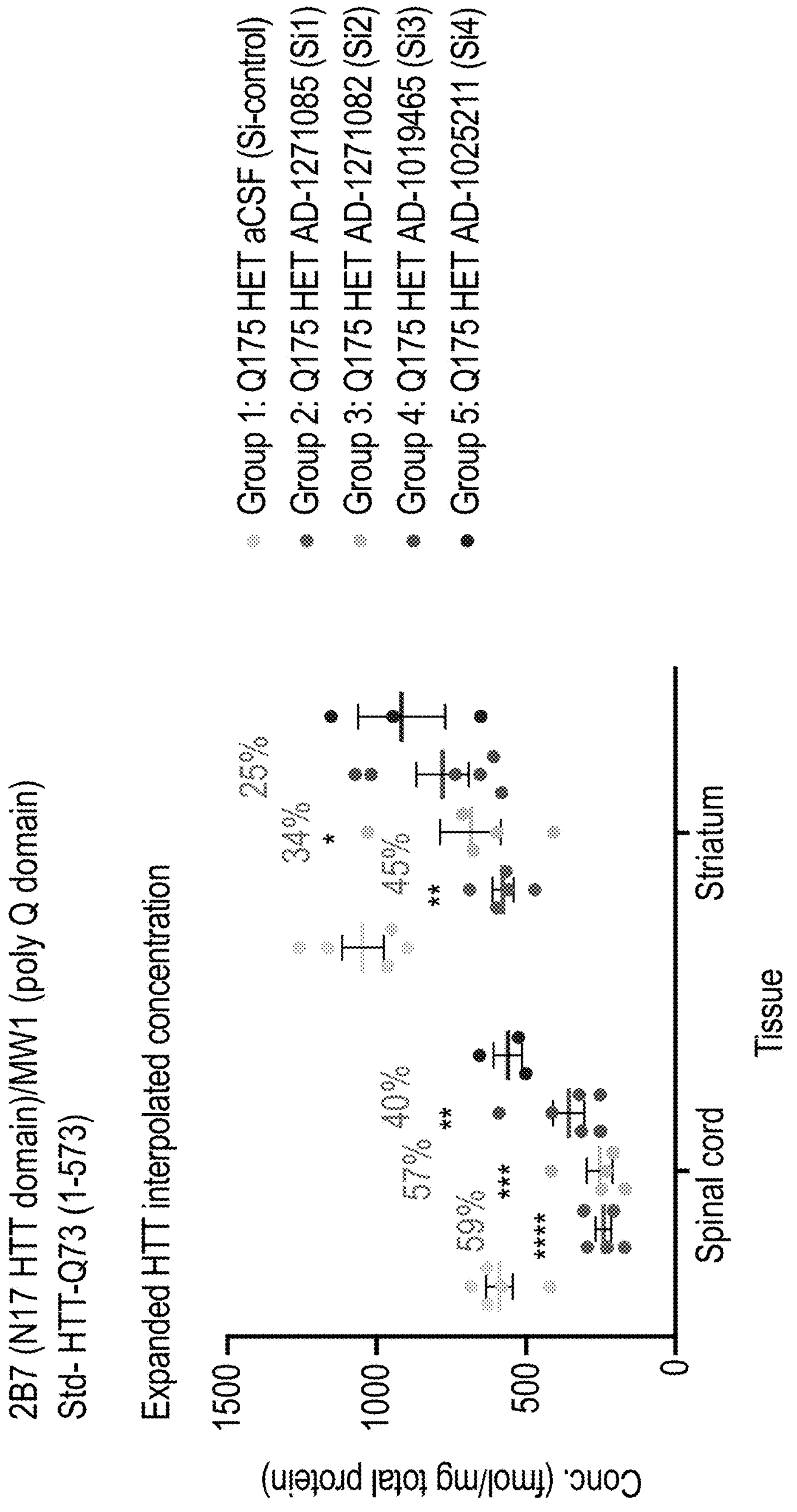

FIG. 8F is a graph depicting the concentration of mutant Huntingtin protein in the spinal cord and striatum of heterozygous Q175 KI mice following a single intracerebroventricular injection of 300 μg of the indicated agents, a non-targeting control agent, or aCSF control. The concentration of mutant Huntingtin protein is shown as femtomoles of mutant Huntingtin protein per milligram of total protein.

Figure 8G:
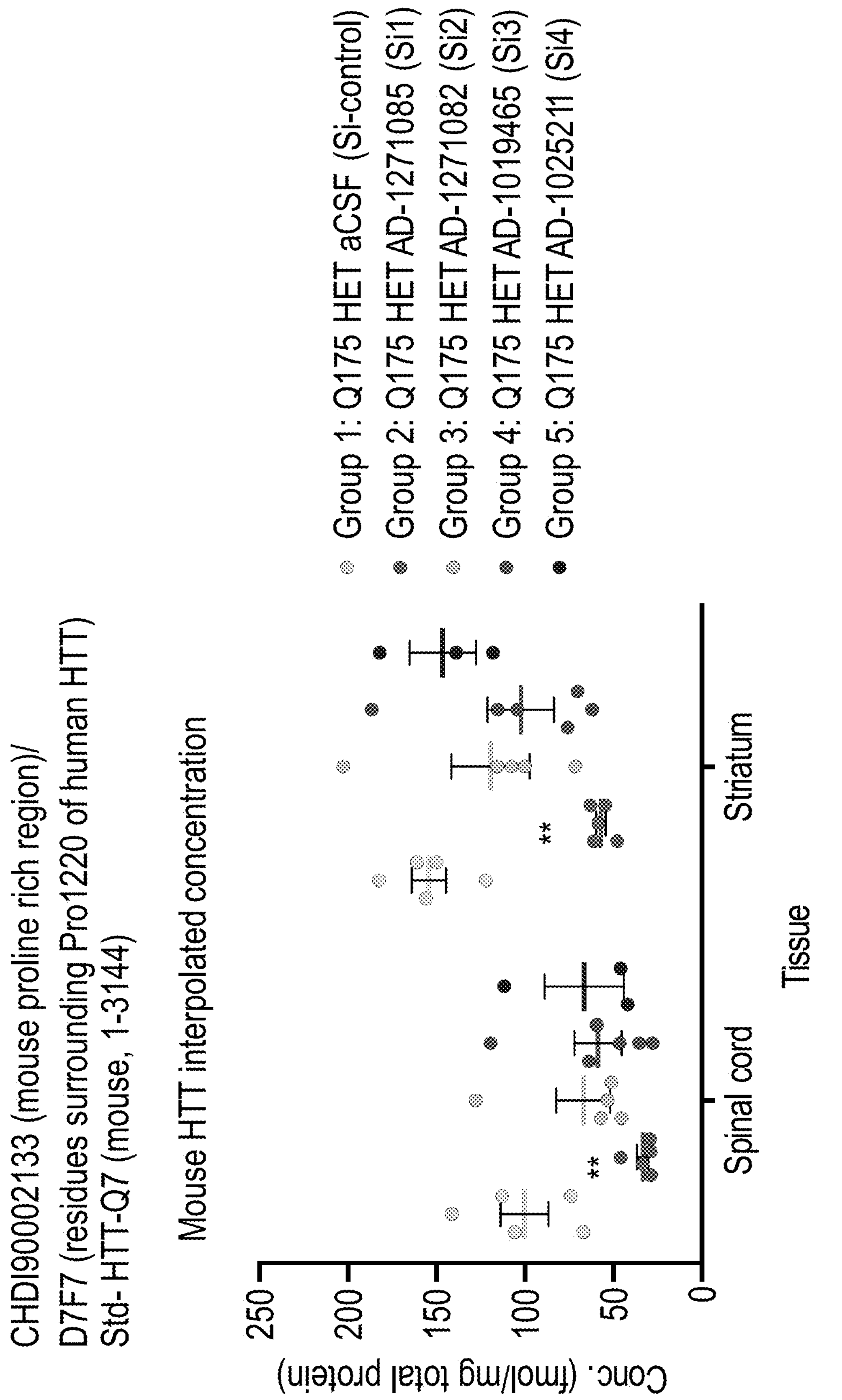

FIG. 8G is a graph depicting the concentration of wild-type Huntingtin protein in the spinal cord and striatum of heterozygous Q175 KI mice following a single intracerebroventricular injection of 300 μg of the indicated agents, a non-targeting control agent, or aCSF control. The concentration of wild-type Huntingtin protein is shown as femtomoles of wild-type Huntingtin protein per milligram of total protein.

Figure 9:
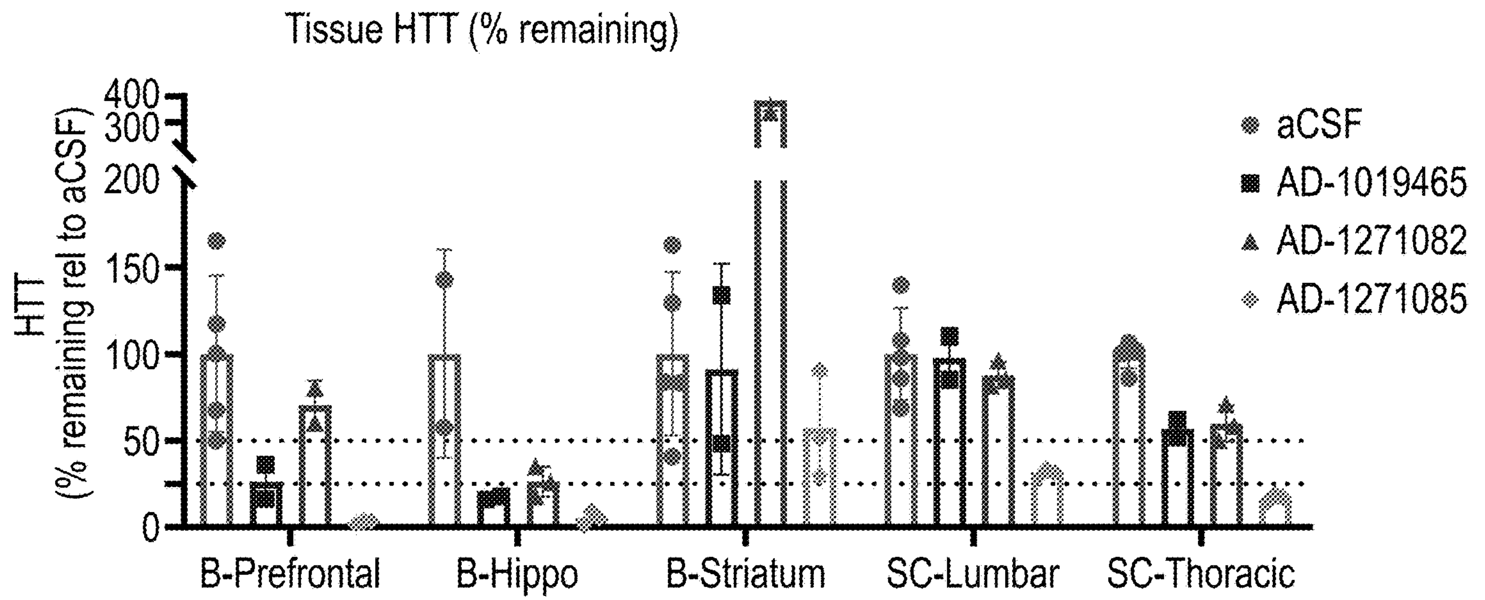

FIG. 9 depicts the percent HTT protein remaining in prefrontal cortex, hippocampus, striatum caudate, lumbar spine, and thoracic spine tissues of non-human primates intrathecally administered a single 60 mg dose of AD-1019465 (n=5), AD-1271082 (n=5), or AD-1271085 (n=5) at Day 45 post-dose. The percent of HTT protein remaining is relative to the level of HTT protein in the corresponding tissues of non-human primates administered artificial CSF (aCSF).

Figure 10A:
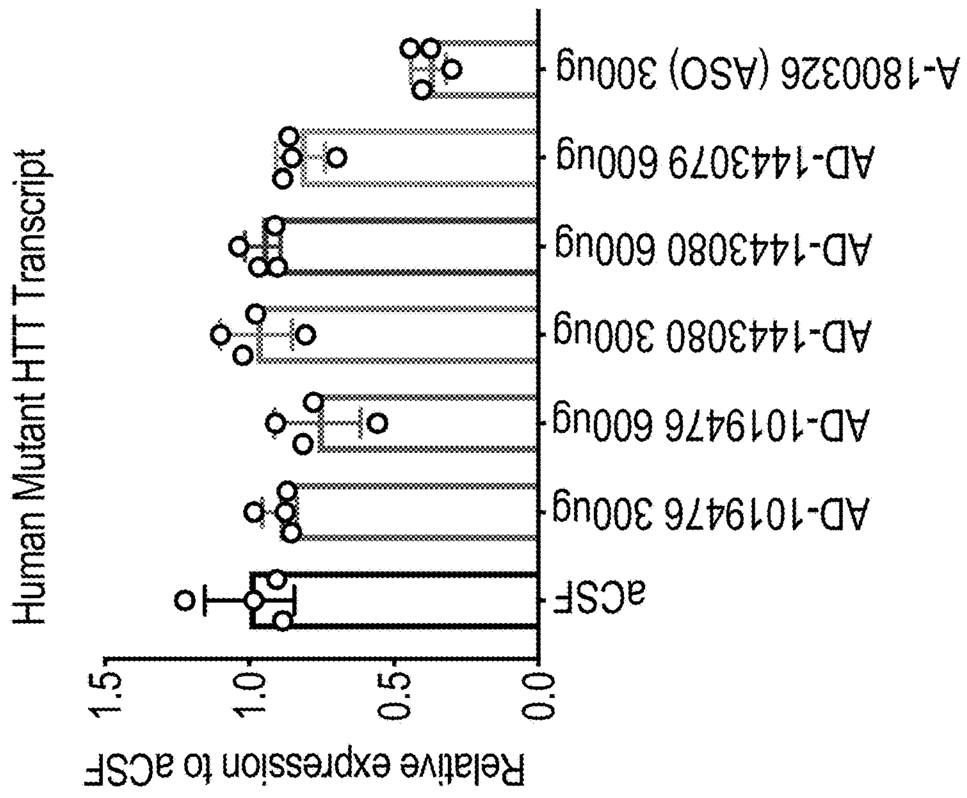

FIG. 10A is a graph depicting the level of knockdown of mutant human HTT mRNA in the frontal cortex of YAC128 administered a single 300 μg or 600 μg dose of the indicated duplexes or artificial CSF (aCSF) control by intracerebroventricular injection (ICV). For comparison purposes the effect of the antisense oligonucleotide, A-1800326 (Tominersen; Roche, also known as IONIS-HTTRx and RG6042) is also shown.

Figure 10B:
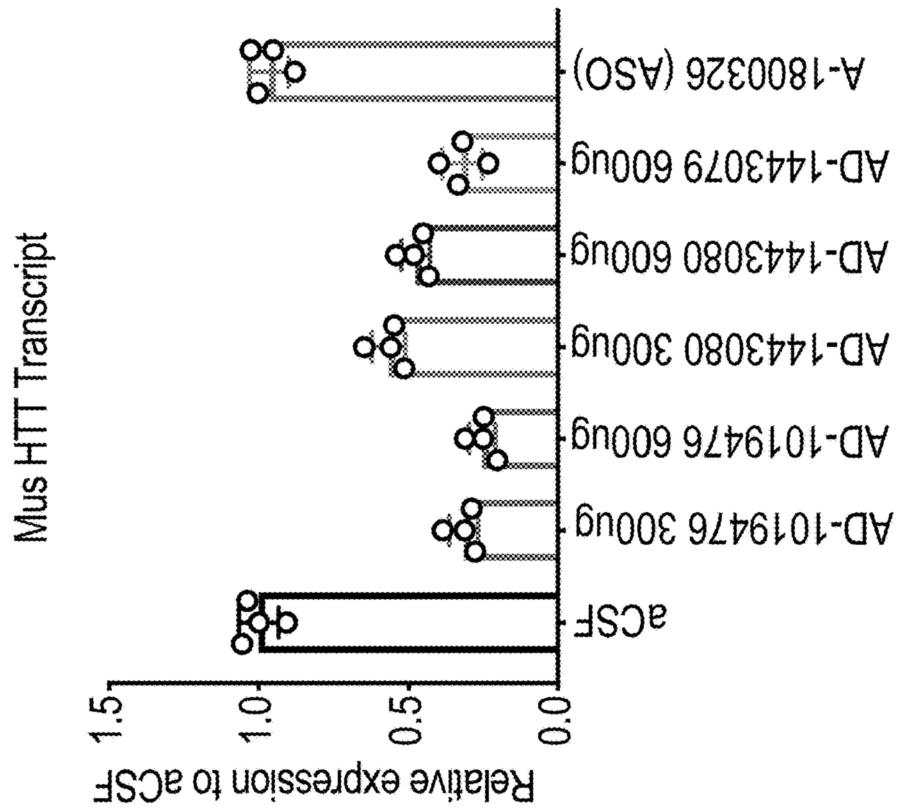

FIG. 10B is a graph depicting the level of knockdown of wild-type mouse HTT mRNA in the frontal cortex of YAC128 administered a single 300 μg or 600 μg dose of the indicated duplexes or artificial CSF (aCSF) control by intracerebroventricular injection (ICV). For comparison purposes the effect of the antisense oligonucleotide, A-1800326 (Tominersen; Roche, also known as IONIS-HTTRx and RG6042) is also shown.

Figure 10C:
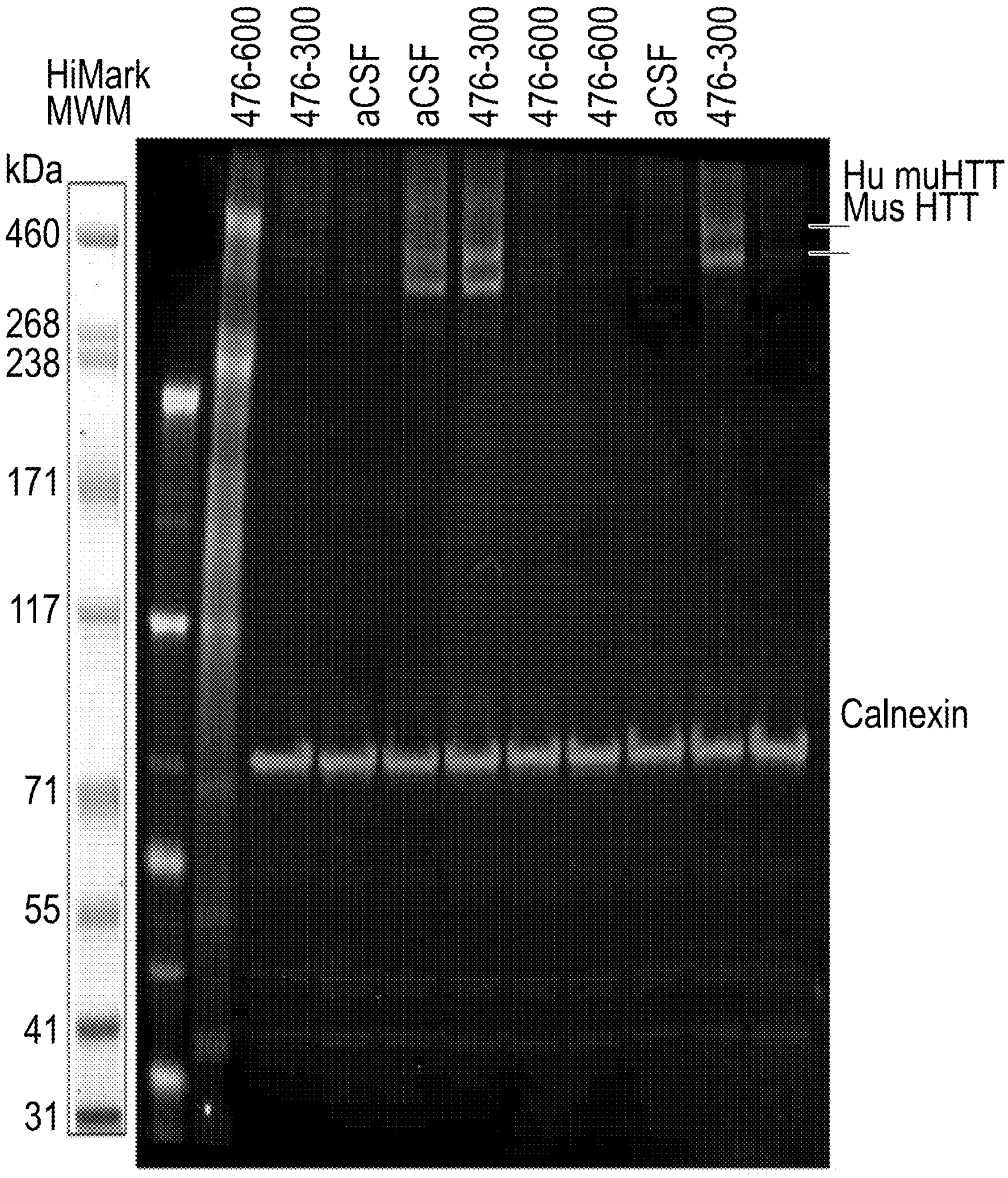

FIG. 10C is a Western blot depicting the level of mutant human HTT protein and mouse wild type protein knock down in the frontal cortex of YAC128 mice administered a single 300 μg or 600 μg dose of the indicated duplexes or artificial CSF (aCSF) control by intracerebroventricular injection (ICV). "a-CSF" refers to artificial CSF; "476-600" refers to a 600 μg/kg dose of AD-1019476; and "476-300" refers to a 300 μg/kg dose of AD-1019476. MAB2166 (EMD Millipore) was used for protein detection.

Figure 10D:
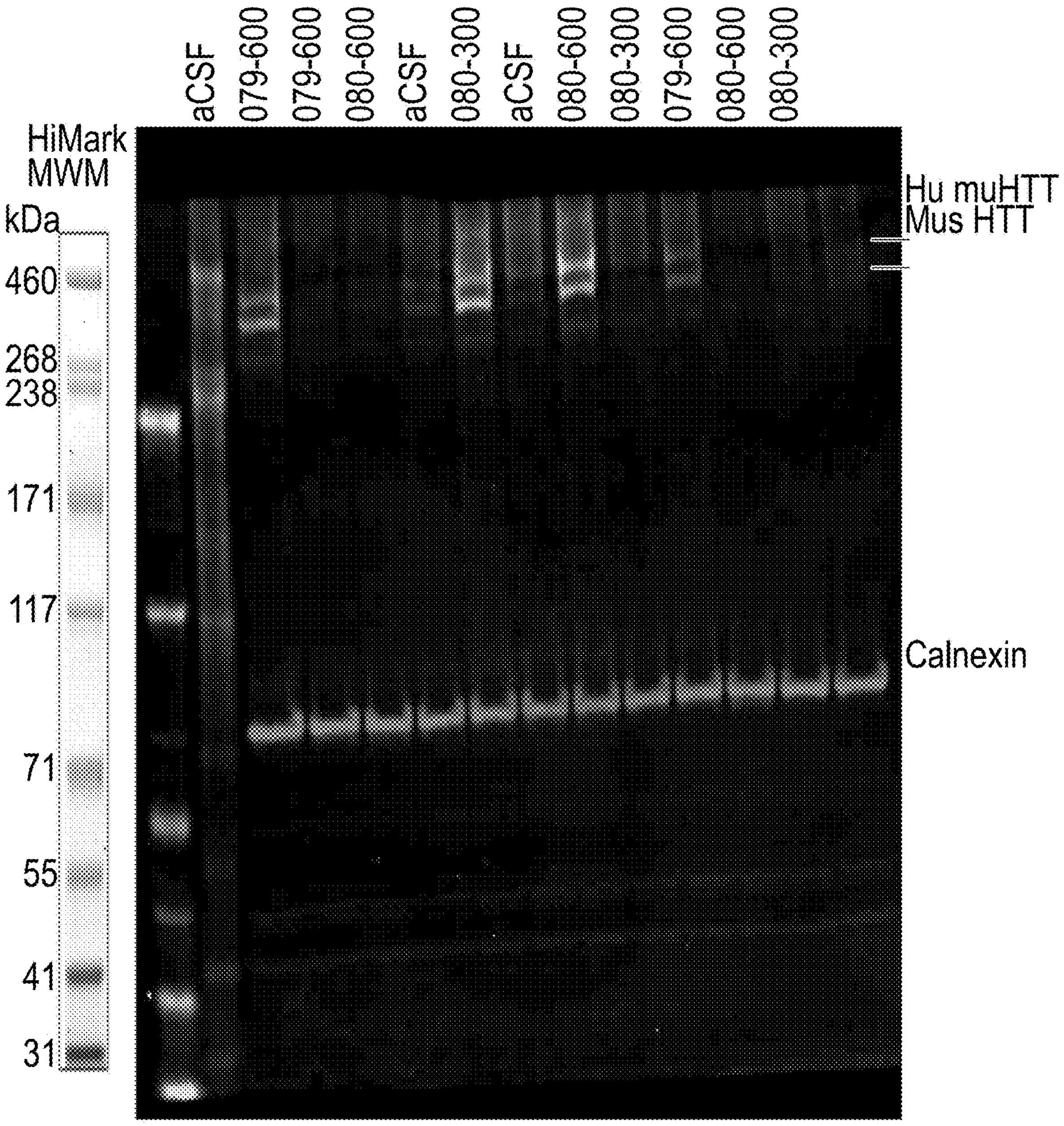

FIG. 10D is a Western blot depicting the level of mutant human HTT protein and mouse wild type protein knock down in the frontal cortex of YAC128 mice administered a single 300 μg or 600 μg dose of the indicated duplexes or artificial CSF (aCSF) control by intracerebroventricular injection (ICV). "a-CSF" refers to artificial CSF; "079-600" refers to a 600 μg/kg dose of AD-1443079; "079-300" refers to a 300 μg/kg dose of AD-1443079; "080-600" refers to a 600 μg/kg dose of AD-1443080; and "080-300" refers to a 300 μg/kg dose of AD-1443080. MAB2166 (EMD Millipore) was used for protein detection.

Figure 10E:
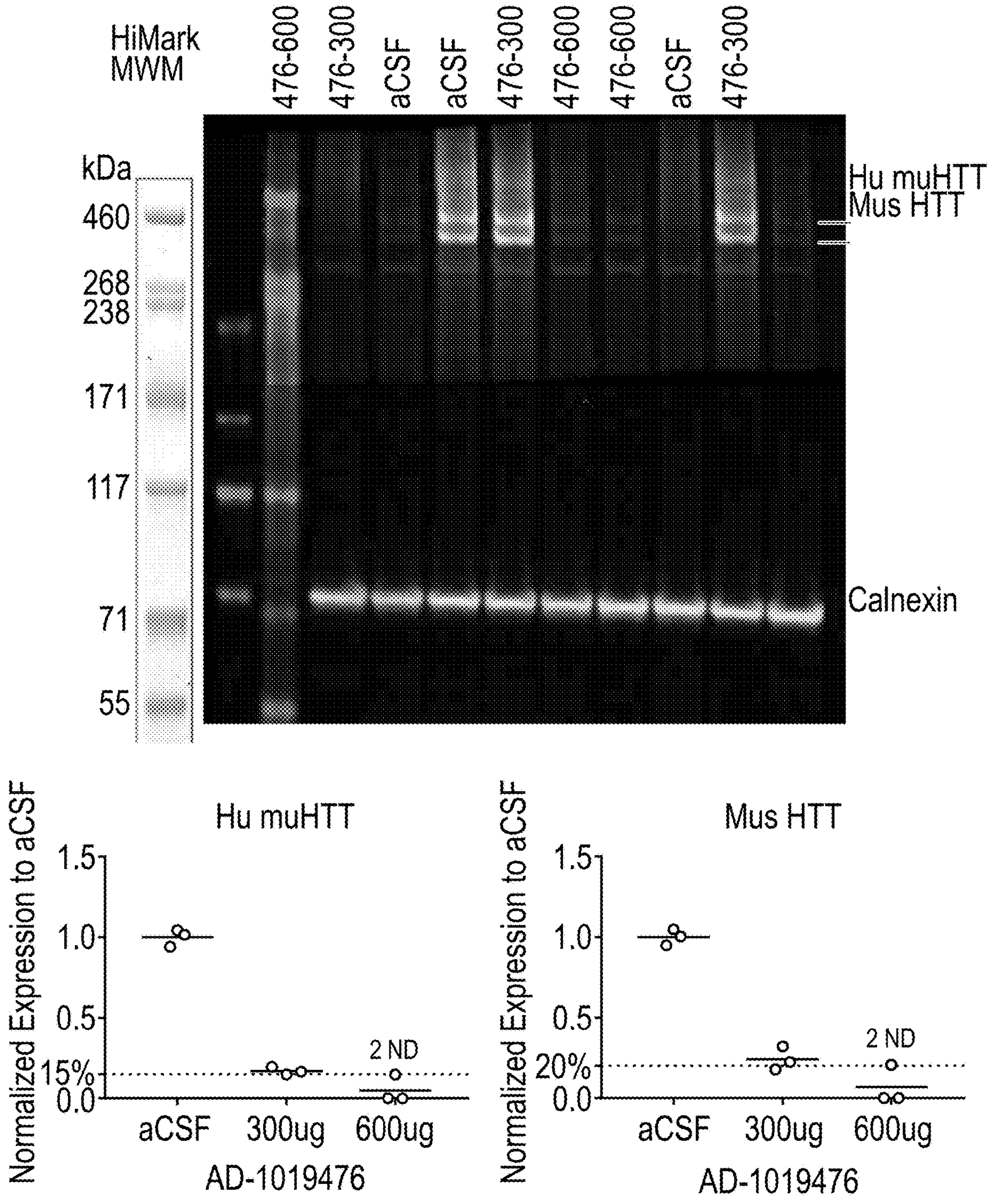

FIG. 10E is a Western blot and graphs depicting the level of mutant human HTT protein and mouse wild type protein knock down in the frontal cortex of YAC128 administered a single 300 μg or 600 μg dose of the indicated duplexes or artificial CSF (aCSF) control by intracerebroventricular injection (ICV). Lysates from FIG. 10C were re-analyzed with D7F7 antibody to confirm observed HTT protein knockdown. The mutant human HTT protein and mouse wild type protein levels are quantified in the graphs below. "a-CSF" refers to artificial CSF; "476-600" refers to a 600 μg/kg dose of AD-1019476; and "476-300" refers to a 300 μg/kg dose of AD-1019476.

Figure 10F:
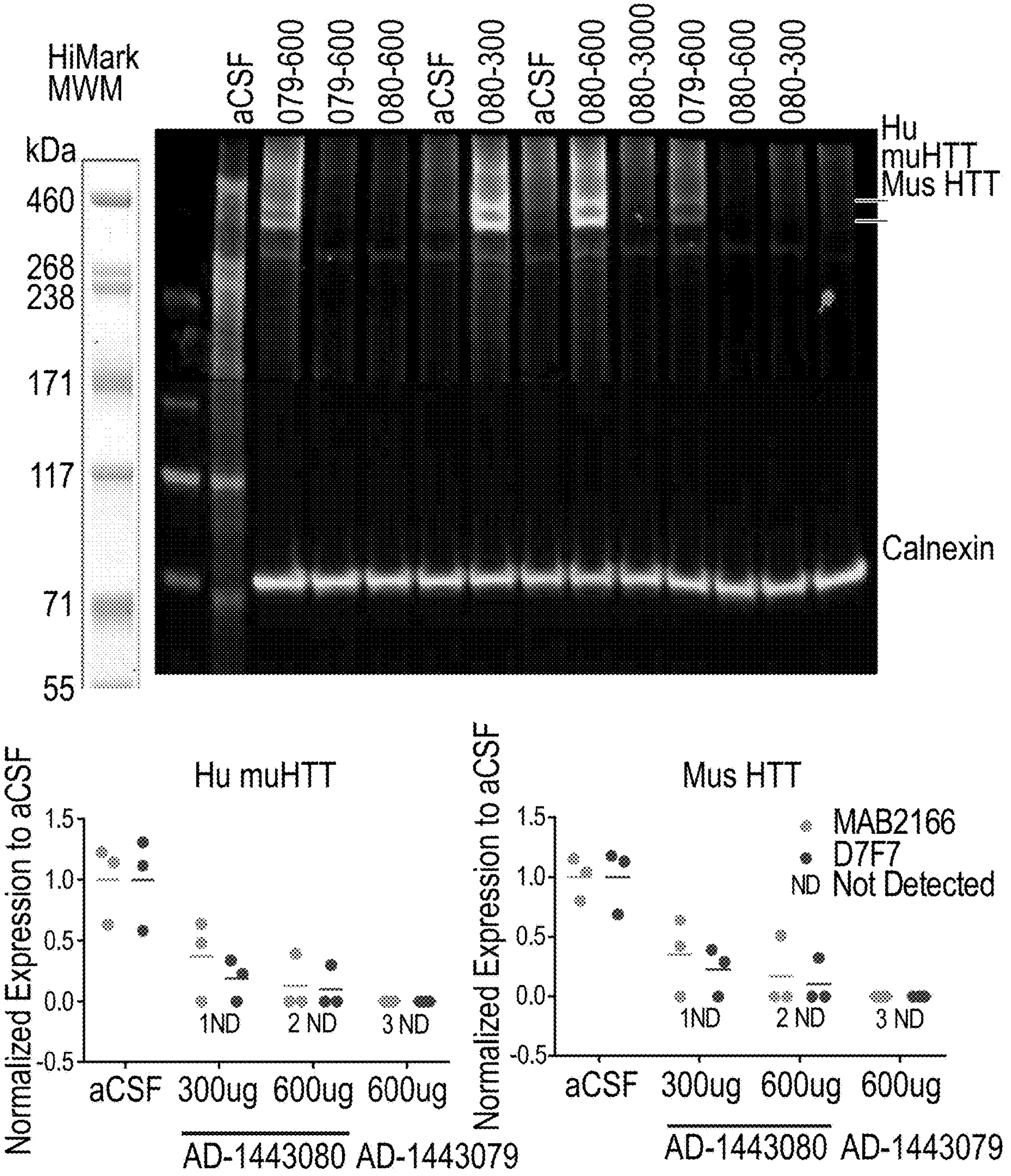

FIG. 10F is a Western blot and graphs depicting the level of mutant human HTT protein and mouse wild type protein knock down in in the frontal cortex of YAC128 administered a single 300 μg or 600 μg dose of the indicated duplexes or artificial CSF (aCSF) control by intracerebroventricular injection (ICV). Lysates from FIG. 10D were re-analyzed with D7F7 antibody to confirm observed HTT protein knockdown. The mutant human HTT protein and mouse wild type protein levels are quantified in the graphs below. Quantification from both blots (FIG. 10E and FIG. 10F blots) are shown side by side for comparison. "a-CSF" refers to artificial CSF; "079-600" refers to a 600 μg/kg dose of AD-1443079; "079-300" refers to a 300 μg/kg dose of AD-1443079; "080-600" refers to a 600 μg/kg dose of AD-1443080; and "080-300" refers to a 300 μg/kg dose of AD-1443080.

Figure 11B:
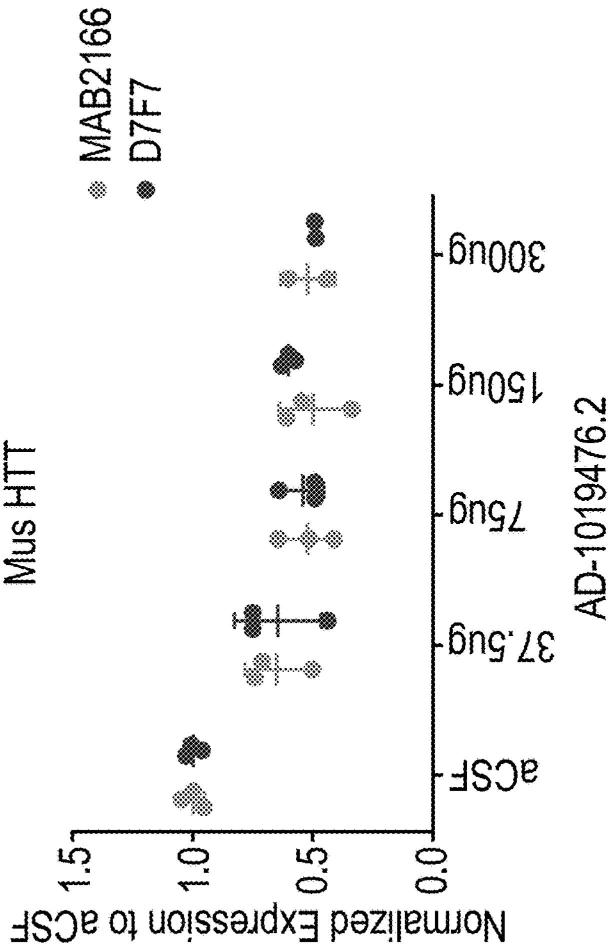
Figure 11A:
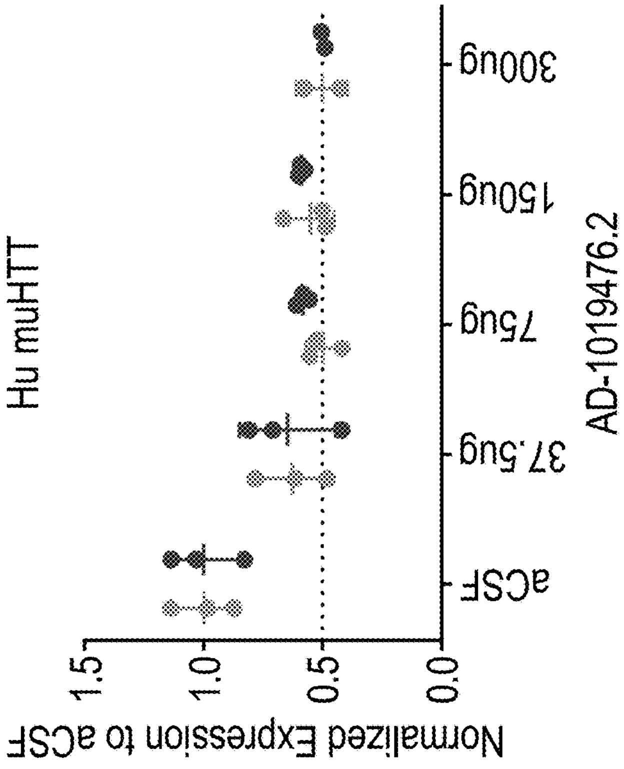

FIG. 11A is a graph depicting the level of mutant human HTT protein in the frontal cortex of YAC128 administered a single 37.5 μg, 75 μg, 150 μg or 300 μg dose of AD-1019476, or artificial CSF (aCSF) control by intracerebroventricular injection (ICV). Two different antibodies were used, MAB2166 (EMD Millipore) and D7F7 (Cell Signaling), and the results from both antibodies demonstrated similar knockdown of HTT protein.

FIG. 11B is a graph depicting the level of mouse wild type protein in the frontal cortex of YAC128 administered a single 37.5 μg, 75 μg, 150 μg or 300 μg dose of AD-1019476, or artificial CSF (aCSF) control by intracerebroventricular injection (ICV). Two different antibodies were used, MAB2166 (EMD Millipore) and D7F7 (Cell Signaling), and the results from both antibodies demonstrated similar knockdown of HTT protein.

Figure 12A:
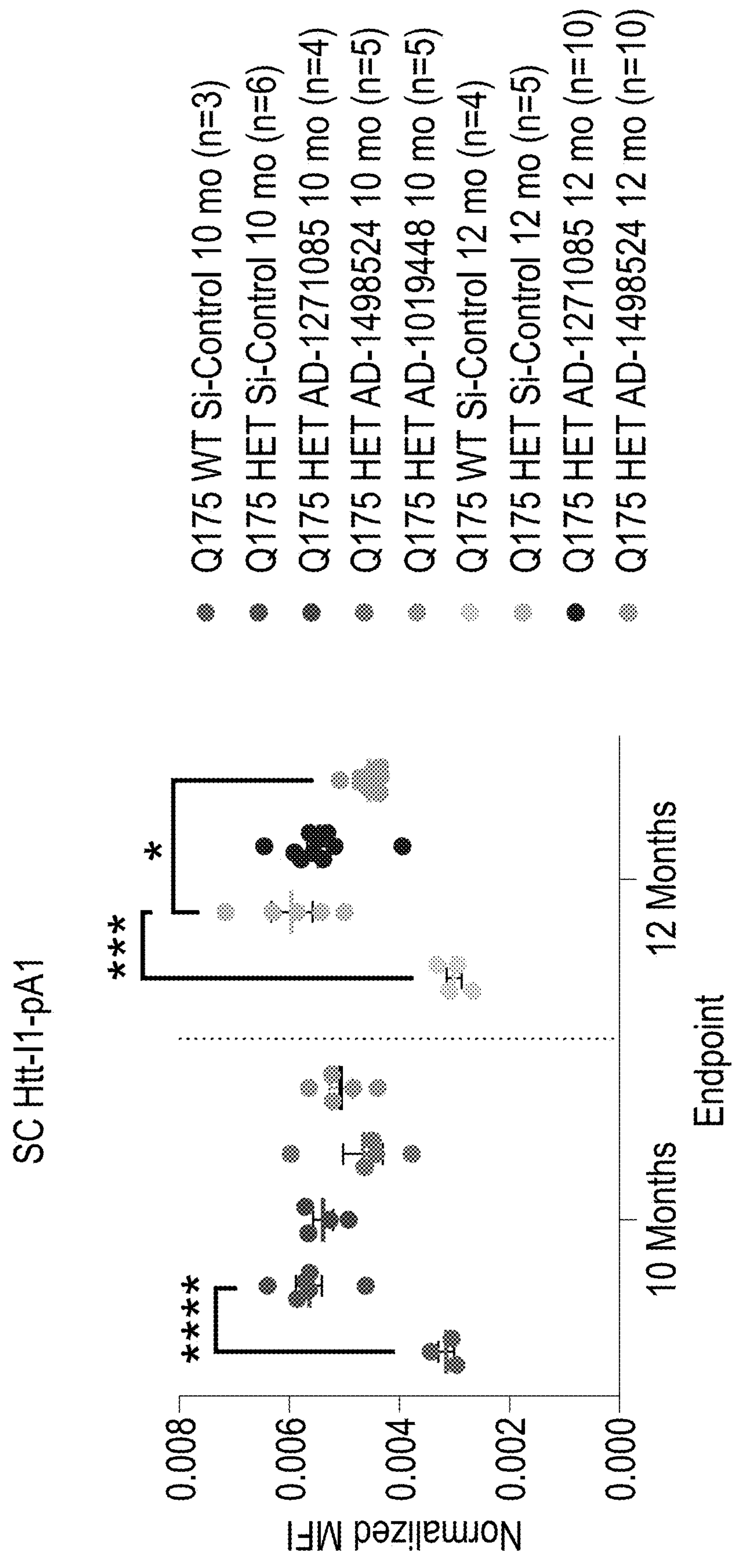

FIG. 12A is a graph depicting the mean fluorescent intensity (MFI) of Htt (mouse endogenous), intron 1 with the polyA-site 1 (the 680 bp variant) expression in the spinal cord of Q175 WT and HET mice 10 months and 12 months following a single intracerebroventricular injection of 300 μg of the indicated agents or aCSF control (Si-Control). Data is presented as mean with SD, n=3-10 per group. Statistical significances: ****$p<0.0001$, Q175 HET Si-Control 10 mo vs. Q175 WT Si-Control 10 mo; *$p<0.05$, ***$p<0.001$, Q175 WT Si-Control 12 mo & Q175 HET AD-1498524 12 mo vs. Q175 HET Si-Control 12 mo (Unpaired t test with Welch correction/Welch's ANOVA test, Dunnett's T3 multiple comparisons test). Normalized to geomean of 3 reference genes.

Figure 12B:
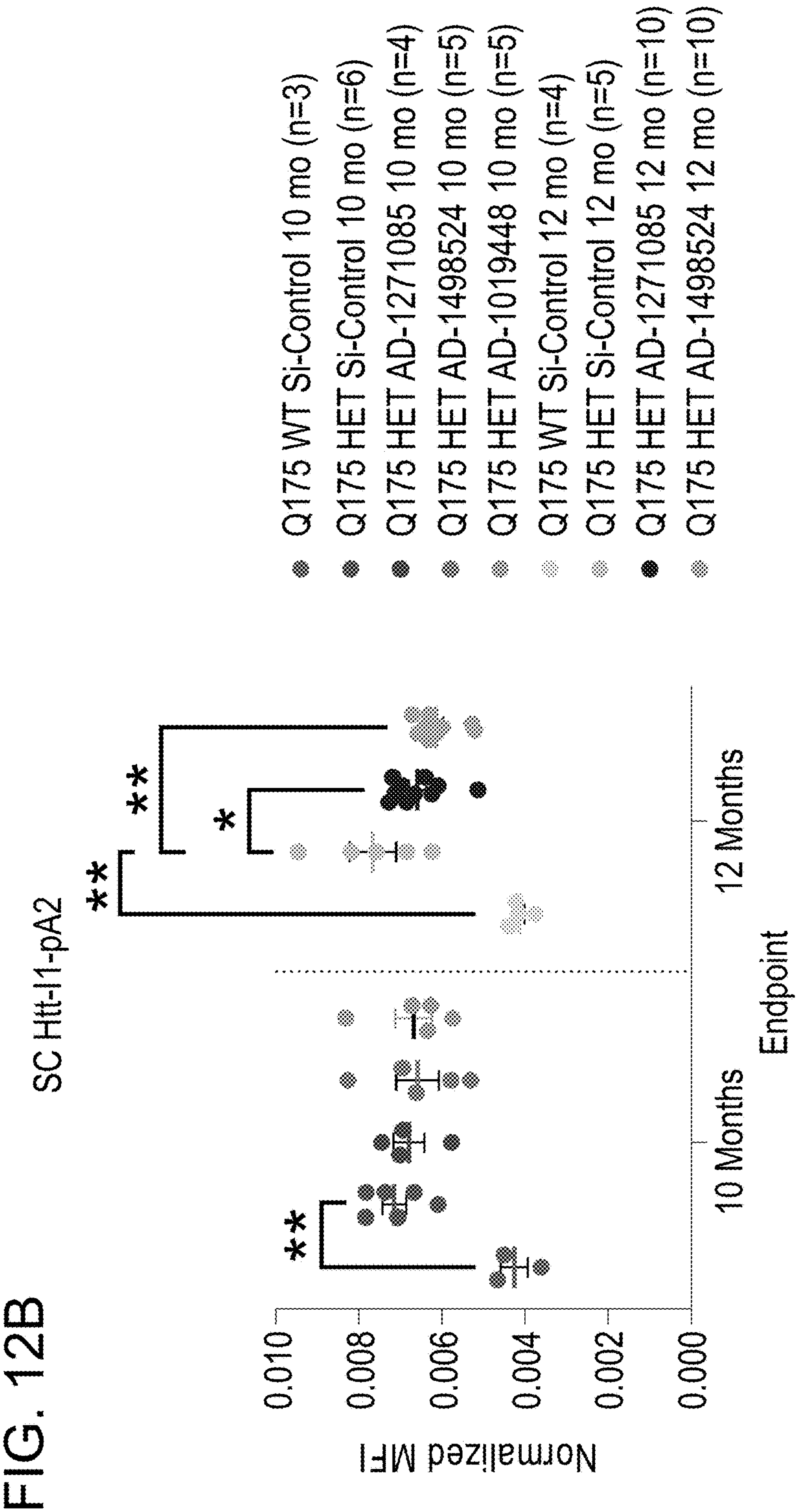

FIG. 12B is a graph depicting the mean fluorescent intensity (MFI) of Htt (mouse endogenous), intron 1 with the polyA-site 2 (the 1145 bp variant) expression in the spinal cord of Q175 WT and HET mice 10 months and 12 months following a single intracerebroventricular injection of 300 μg of the indicated agents or aCSF control (Si-Control). Data is presented as mean with SD, n=3-10 per group. Statistical significances: **$p<0.01$, Q175 HET Si-Control 10 mo vs. Q175 WT Si-Control 10 mo; *$p<0.05$, **$p<0.001$, Q175 WT Si-Control 12 mo, Q175 HET AD-1498524 12 mo & Q175 HET AD-1271085 12 mo vs. Q175 HET Si-Control 12 mo (Unpaired t test with Welch correction/Ordinary one-way ANOVA, Dunnett's multiple comparisons test). Normalized to geomean of 3 reference genes.

Figure 12C:
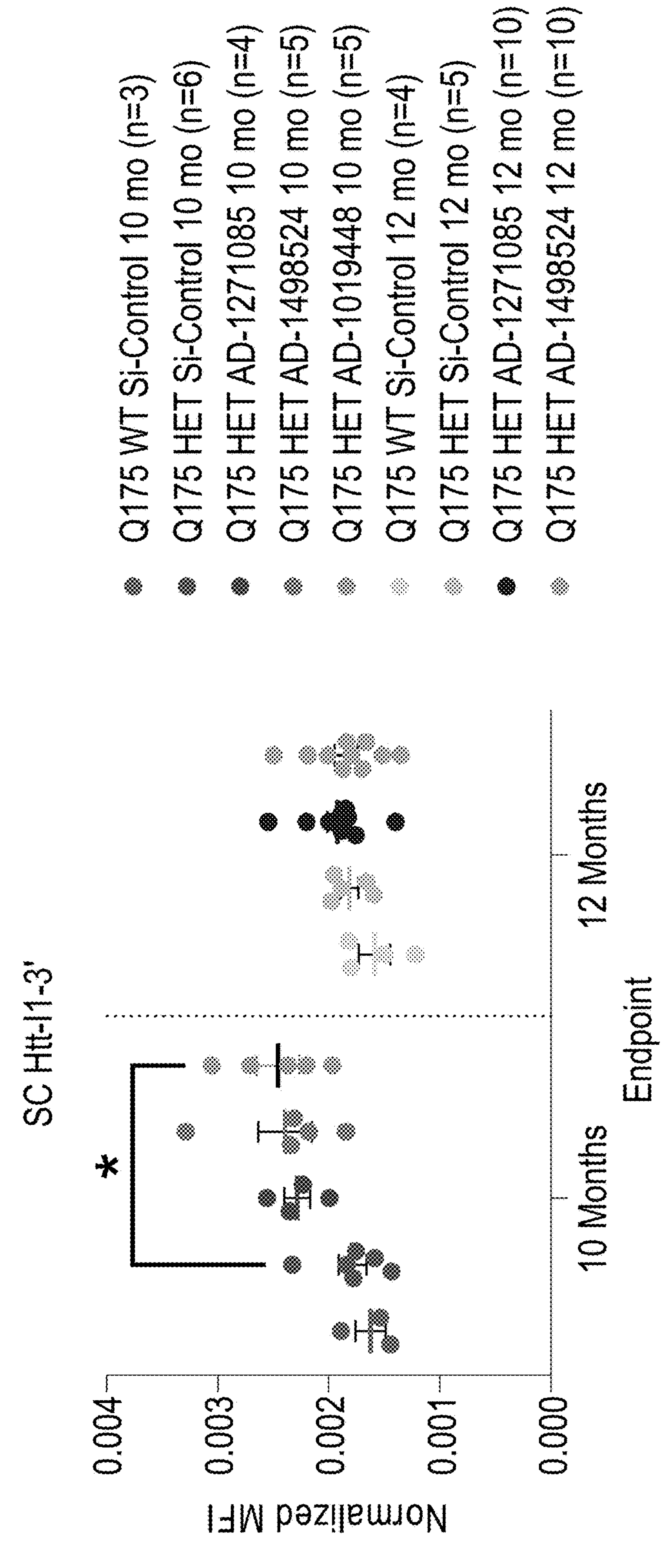

FIG. 12C is a graph depicting the mean fluorescent intensity (MFI) of Htt (mouse endogenous), intron 1 at its 3' end expression (as a negtive control for detection of retained intronic region expression) in the spinal cord of Q175 WT and HET mice 10 months and 12 months following a single intracerebroventricular injection of 300 μg of the indicated agents or aCSF control (Si-Control). Data is presented as mean with SD, n=3-10 per group. Statistical significances: *p<0.05, Q175 HET AD-1019448 10 mo vs. Q175 HET Si-Control 10 mo (Ordinary one-way ANOVA, Dunnett's multiple comparisons test). Normalized to geomean of 3 reference genes.

Figure 12D:
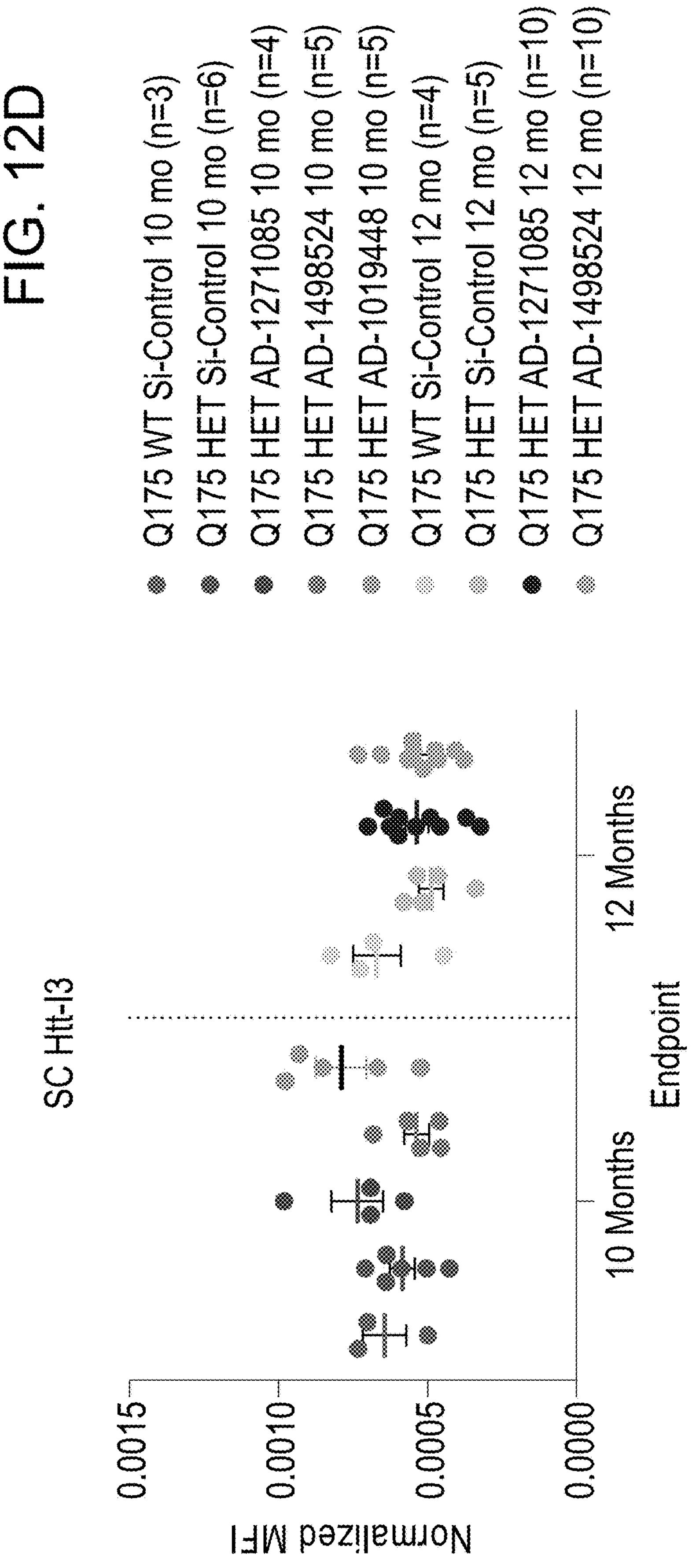

FIG. 12D is a graph depicting the mean fluorescent intensity (MFI) of Htt (mouse endogenous), intron 3 expression (as a negative control for detection of retained intronic region expression) in the spinal cord of Q175 WT and HET mice 10 months and 12 months following a single intracerebroventricular injection of 300 μg of the indicated agents or aCSF control (Si-Control). Data is presented as mean with SD, n=3-10 per group. No statistical significances: p>0.05, (Unpaired t test with Welch correction/Ordinary One-way ANOVA). Normalized to geomean of 3 reference genes.

Figure 12E:
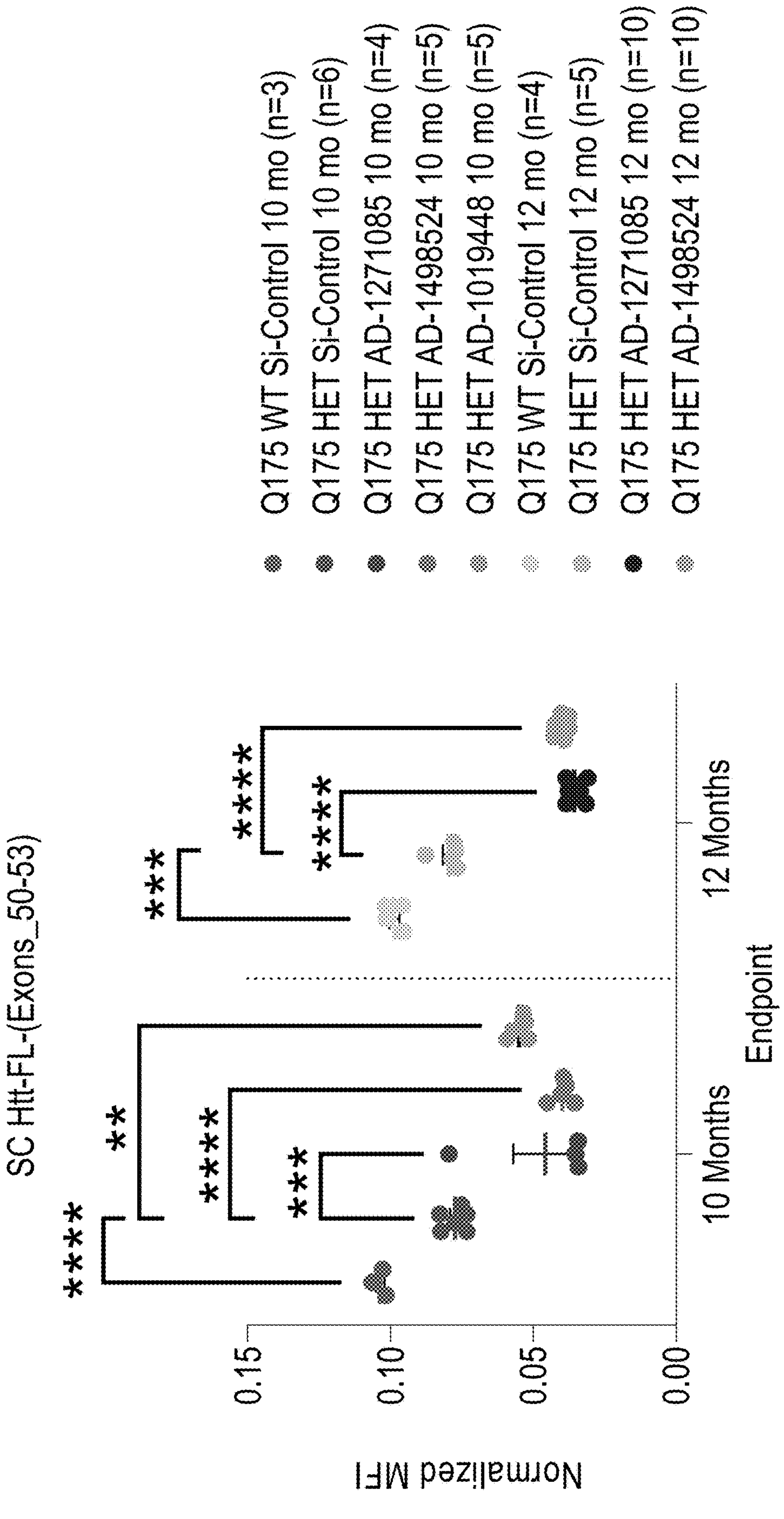

FIG. 12E is a graph depicting the mean fluorescent intensity (MFI) of Huntingtin, full-length (total) expression in the spinal cord of Q175 WT and HET mice 10 months and 12 months following a single intracerebroventricular injection of 300 μg of the indicated agents or aCSF control (Si-Control). Data is presented as mean with SD, n=3-10 per group. Statistical significances: p<0.01, *p<0.001, **p<0.0001, Q175 WT Si-Control 10 mo, Q175 HET AD-1271085 10 mo, Q175 HET AD-1498524 10 mo, Q175 HET AD-1019448 10 mo vs. Q175 HET Si-Control 10 mo; *p<0.001, ****p<0.0001, Q175 WT Si-Control 12 mo, Q175 HET AD-1271085 12 mo & Q175 HET AD-1498524 12 mo vs. Q175 HET Si-Control 12 mo (Unpaired t test with Welch correction/Ordinary one-way ANOVA, Dunnett's multiple comparisons test). Normalized to geomean of 3 reference genes.

Figure 12F:
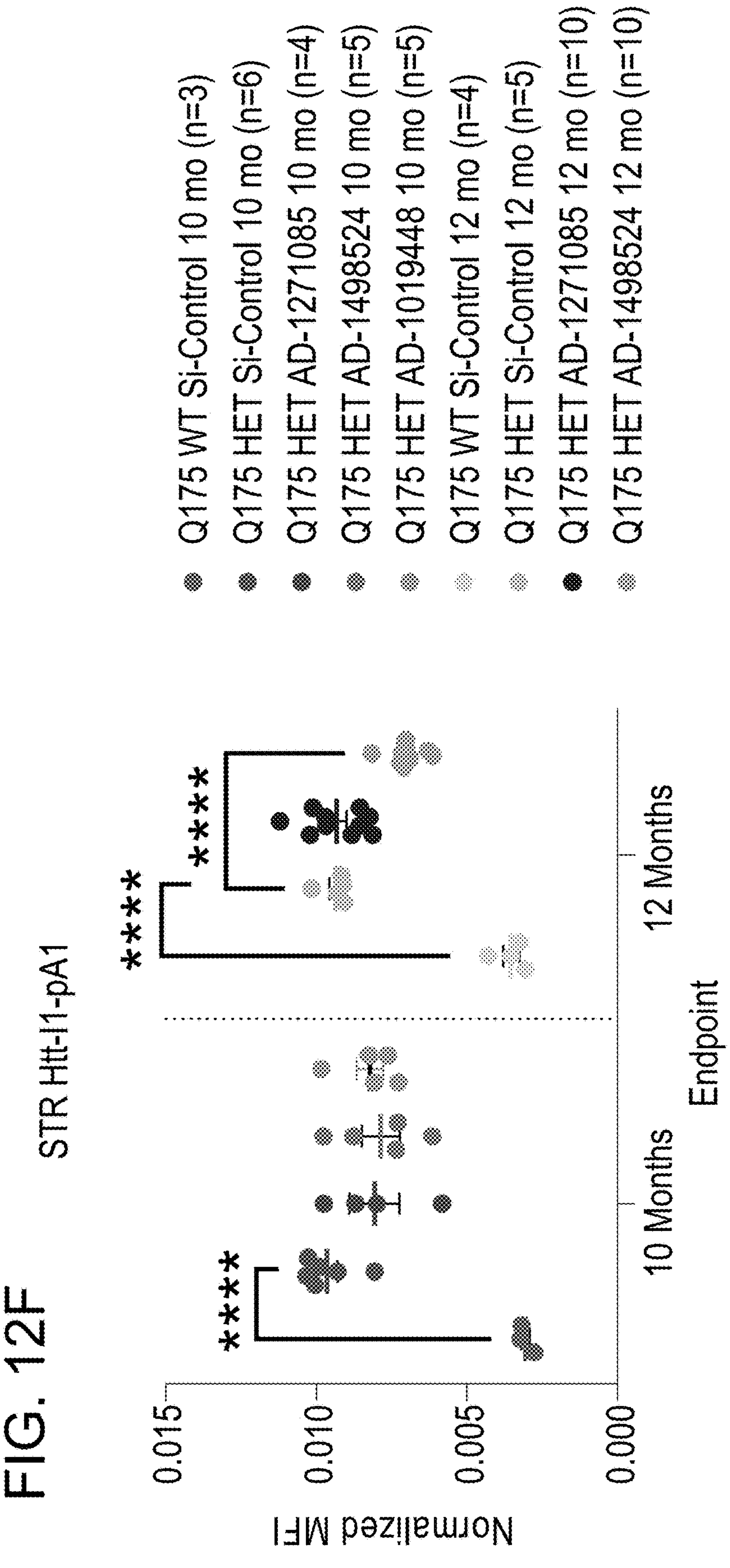

FIG. 12F is a graph depicting the mean fluorescent intensity (MFI) of Htt (mouse endogenous), intron 1 with the polyA-site 1 (the 680 bp variant) expression in the striatum of Q175 WT and HET mice 10 months and 12 months following a single intracerebroventricular injection of 300 μg of the indicated agents or aCSF control (Si-Control). Data is presented as mean with SD, n=3-10 per group. Statistical significances: **p<0.0001, Q175 HET Si-Control 10 mo vs. Q175 WT Si-Control 10 mo; **p<0.0001, Q175 WT Si-Control 12 mo & Q175 HET AD-1498524 12 mo vs. Q175 HET Si-Control 12 mo (Unpaired t test with Welch correction/Welch's ANOVA test, Dunnett's T3 multiple comparisons test). Normalized to geomean of 3 reference genes.

Figure 12G:
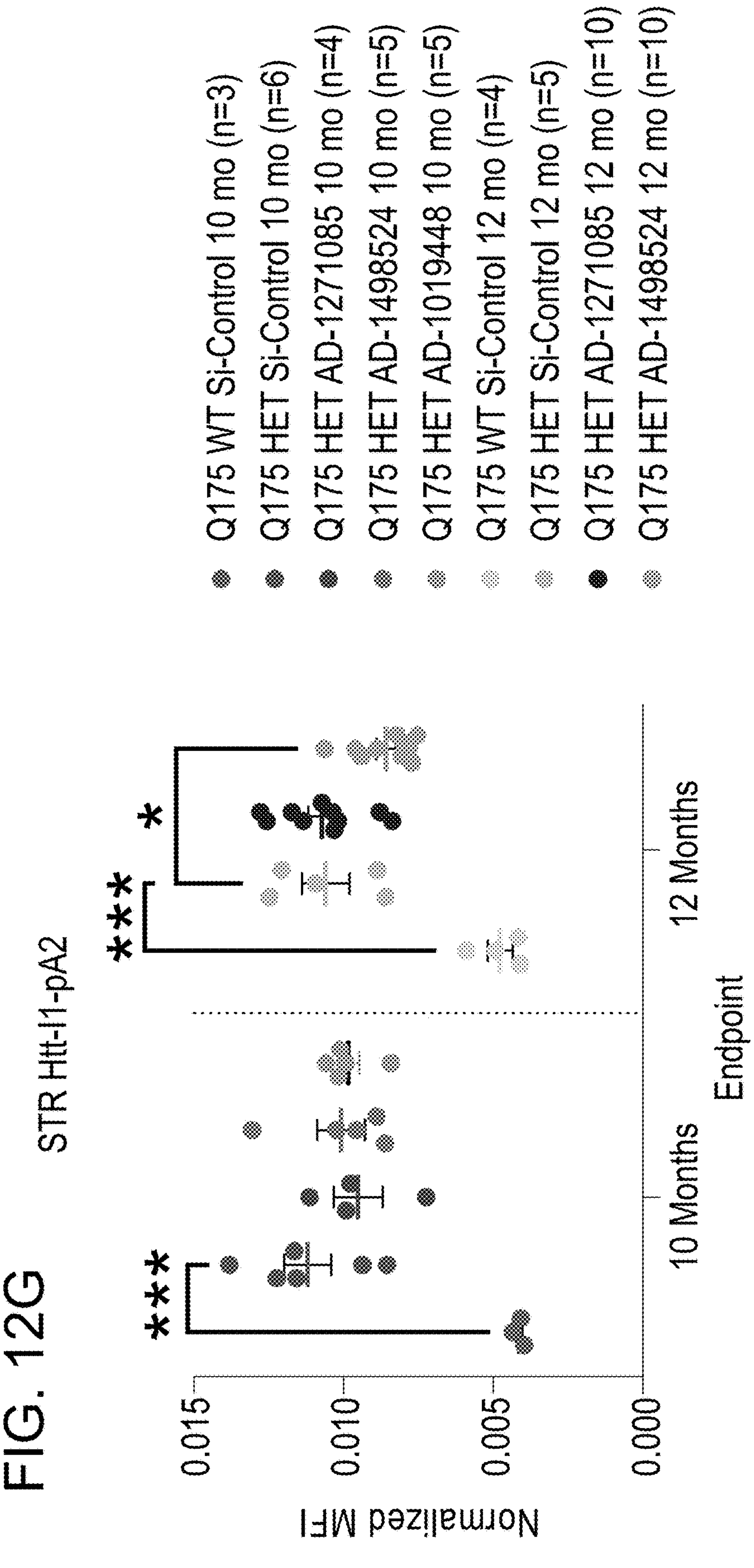

FIG. 12G is a graph depicting the mean fluorescent intensity (MFI) of Htt (mouse endogenous), intron 1 with the polyA-site 2 (the 1145 bp variant) expression in the striatum of Q175 WT and HET mice 10 months and 12 months following a single intracerebroventricular injection of 300 μg of the indicated agents or aCSF control (Si-Control). Data is presented as mean with SD, n=3-10 per group. Statistical significances: ***p<0.001, Q175 HET Si-Control 10 mo vs. Q175 WT Si-Control 10 mo; *p<0.05, ***p<0.001, Q175 WT Si-Control 12 mo & Q175 HET AD-1498524 12 mo vs. Q175 HET Si-Control 12 mo (Unpaired t test with Welch correction/Ordinary one-way ANOVA, Dunnett's multiple comparisons test). Normalized to geomean of 3 reference genes.

Figure 12H:
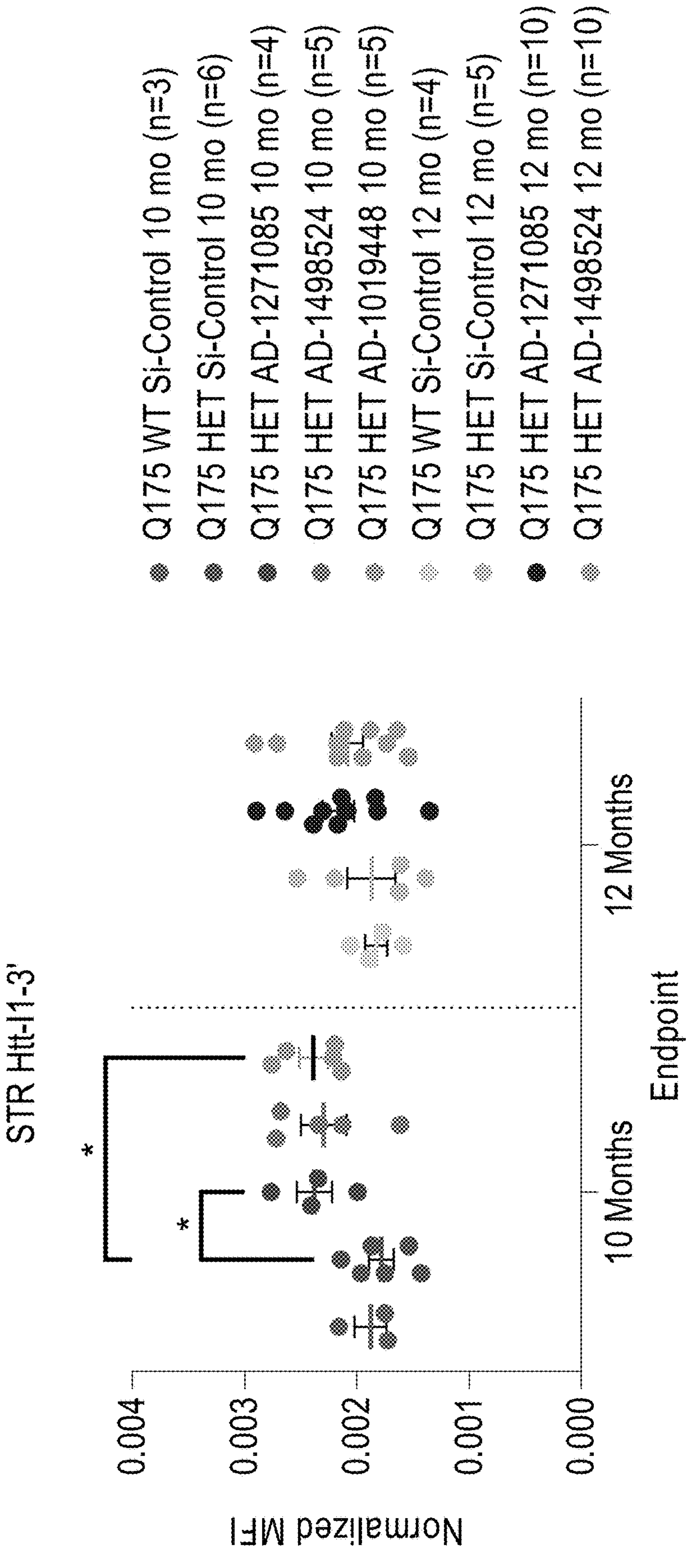

FIG. 12H is a graph depicting the mean fluorescent intensity (MFI) of Htt (mouse endogenous), intron 1 at its 3' end expression (as a negtive control for detection of retained intronic region expression) in the striatum of Q175 WT and HET mice 10 months and 12 months following a single intracerebroventricular injection of 300 μg of the indicated agents or aCSF control (Si-Control). Data is presented as mean with SD, n=3-10 per group. Statistical significances: *p<0.05, Q175 HET AD-1271085 10 mo & Q175 HET AD-1019448 10 mo vs. Q175 HET Si-Control 10 mo (Ordinary one-way ANOVA, Dunnett's multiple comparisons test). Normalized to geomean of 3 reference genes.

Figure 12I:
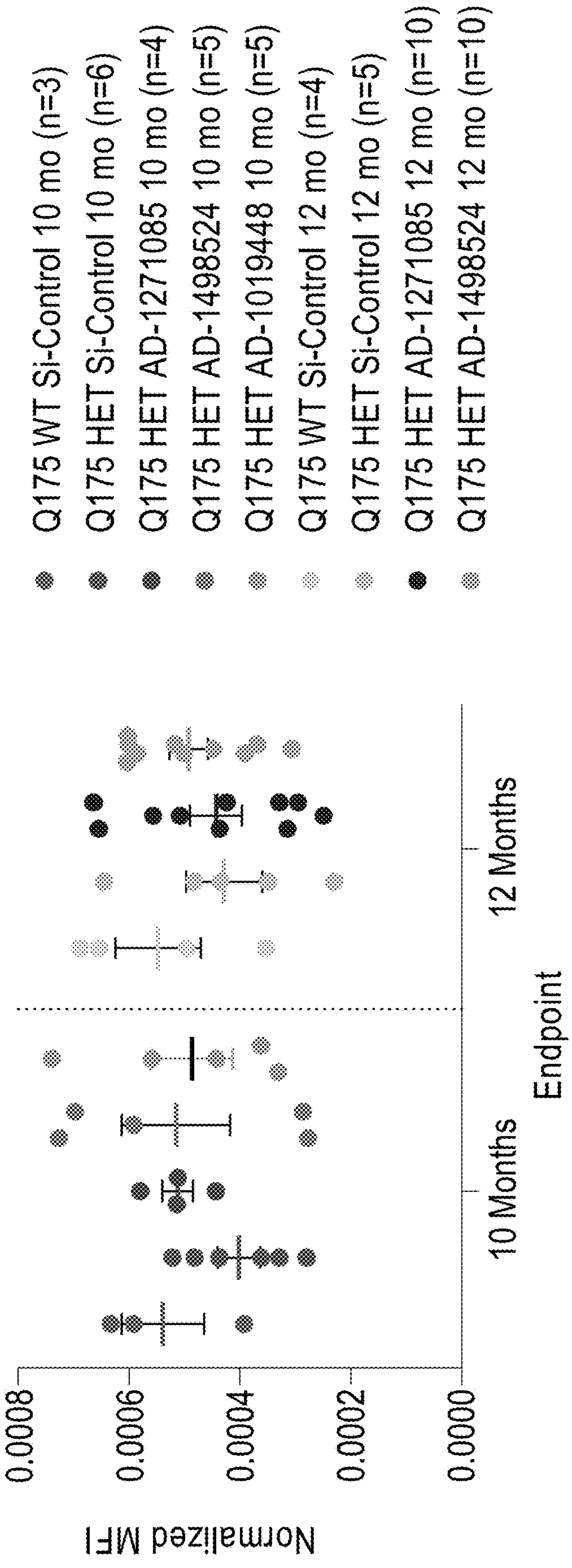

FIG. 12I is a graph depicting the mean fluorescent intensity (MFI) of Htt (mouse endogenous), intron 3 expression (as a negative control for detection of retained intronic region expression) in the striatum of Q175 WT and HET mice 10 months and 12 months following a single intracerebroventricular injection of 300 μg of the indicated agents or aCSF control (Si-Control). Data is presented as mean with SD, n=3-10 per group. No statistical significances: p>0.05, (Unpaired t test with Welch correction/Ordinary One-way ANOVA). Normalized to geomean of 3 reference genes.

Figure 12J:
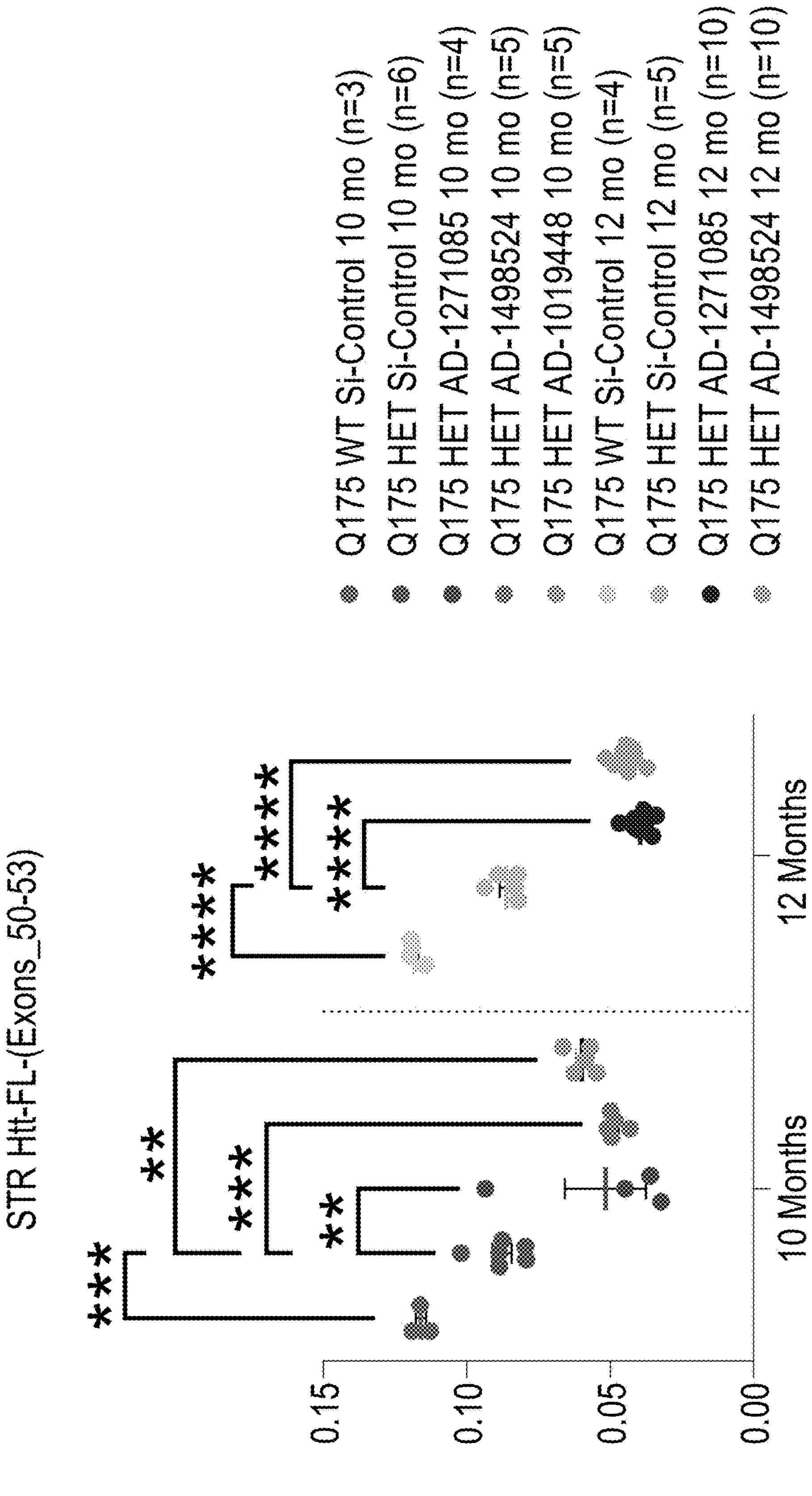

FIG. 12J is a graph depicting the mean fluorescent intensity (MFI) of Huntingtin, full-length (total) expression in the striatum of Q175 WT and HET mice 10 months and 12 months following a single intracerebroventricular injection of 300 μg of the indicated agents or aCSF control (Si-Control). Data is presented as mean with SD, n=3-10 per group. Statistical significances: p<0.01, *p<0.001, Q175 WT Si-Control 10 mo, Q175 HET AD-1271085 10 mo, Q175 HET AD-1498524 10 mo, Q175 HET AD-1019448 10 mo vs. Q175 HET Si-Control 10 mo; ****p<0.0001, Q175 WT Si-Control 12 mo, Q175 HET AD-1271085 12 mo & Q175 HET AD-1498524 12 mo vs. Q175 HET Si-Control 12 mo (Unpaired t test with Welch correction/Ordinary one-way ANOVA, Dunnett's multiple comparisons test). Normalized to geomean of 3 reference genes.

Figure 12K:
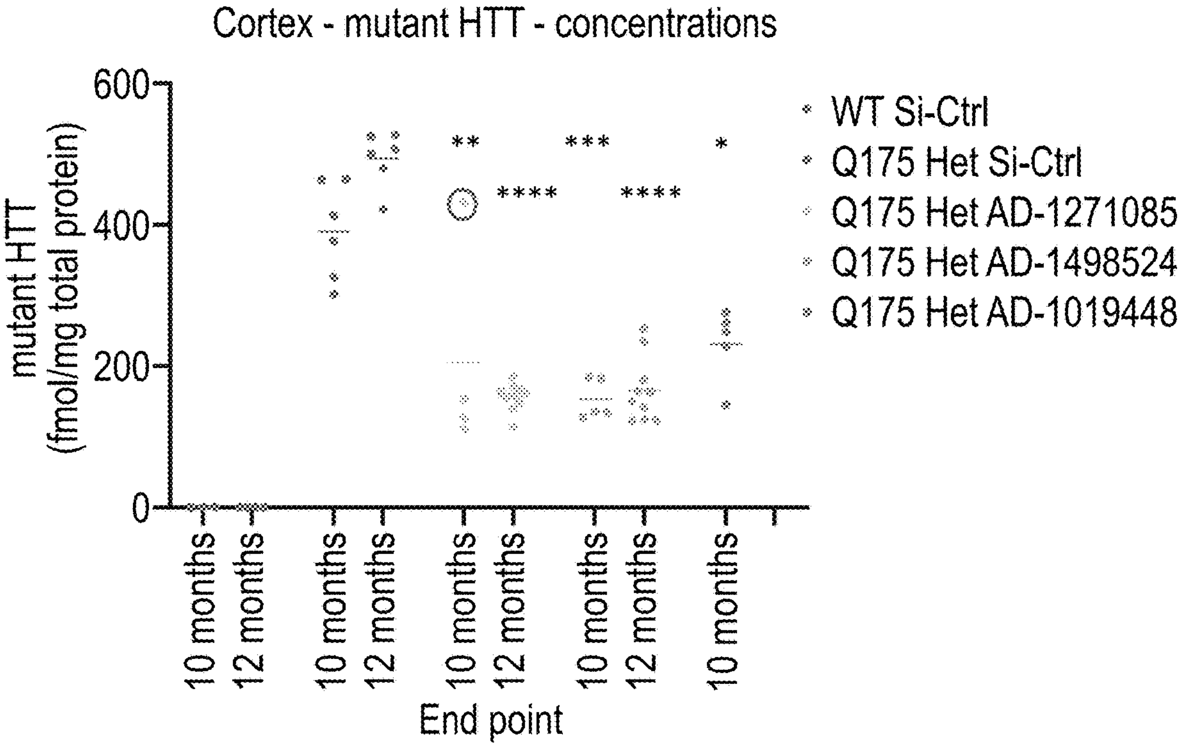
Figure 12K:
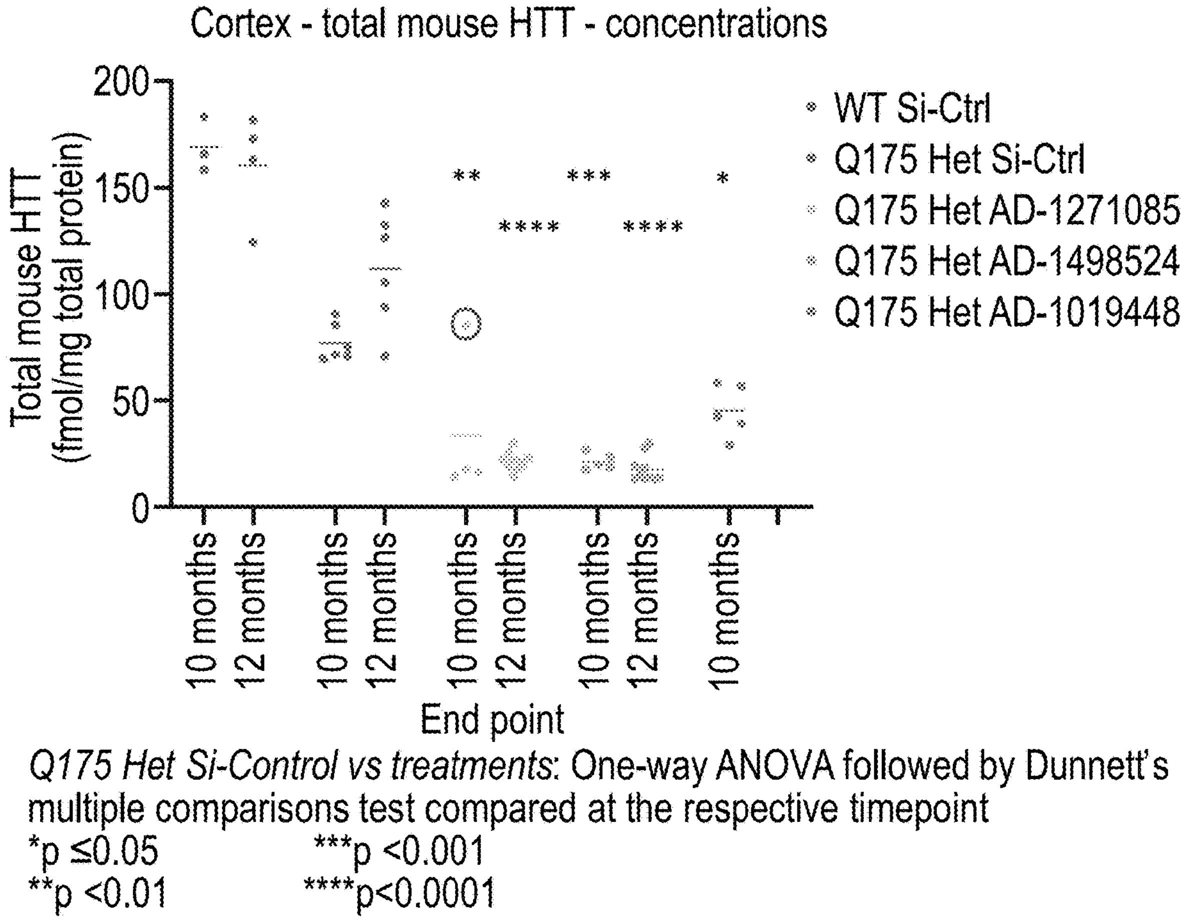

FIG. 12K is a graph depicting the concentration of mutant Huntingtin protein (top) and the concentration of the total HTT protein (bottom) in the striatum of WT and Q175 HET mice following a single intracerebroventricular injection of 300 μg of the indicated agents, or a CSF control (Si-Control). The concentration of mutant and total Huntingtin protein is shown as femtomoles of mutant Huntingtin protein per milligram of total protein. Statistical significances: Q175 Het Si-Control vs treatments: One-way ANOVA followed by Dunnett's multiple comparisons test compared at the respective timepoint. *p<0.05, *p<0.001, p<0.01, ****p<0.0001.

Figure 12L:
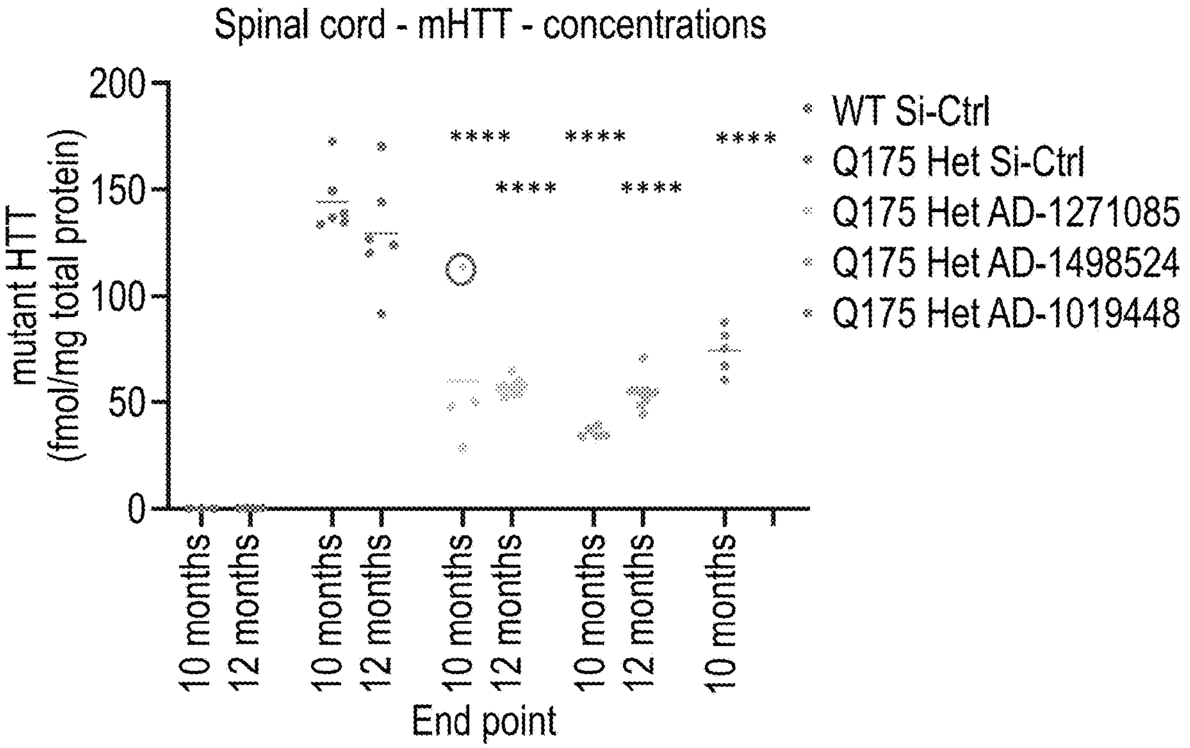
Figure 12L:
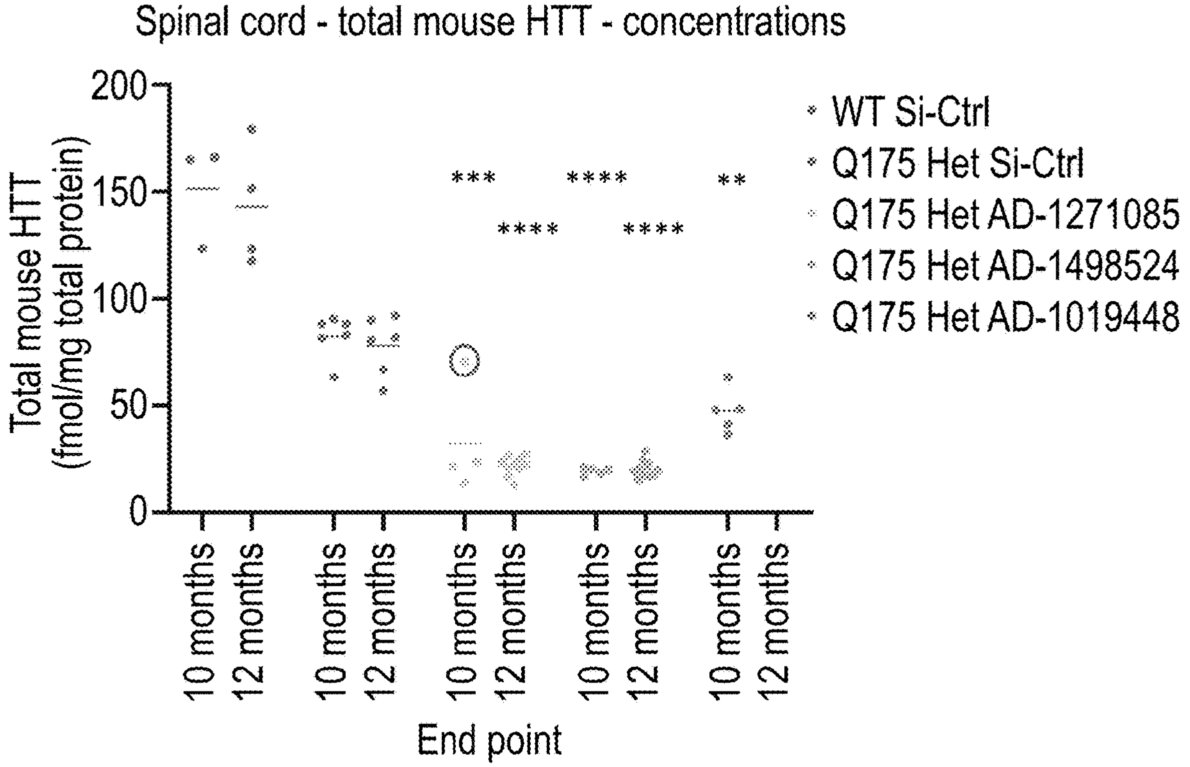

FIG. 12L is a graph depicting the concentration of mutant Huntingtin protein (top) and the concentration of the total HTT protein (bottom) in the spinal cord of WT and Q175 HET mice following a single intracerebroventricular injection of 300 μg of the indicated agents, or aCSF control (Si-Control). The concentration of mutant and total Huntingtin protein is shown as femtomoles of mutant Huntingtin protein per milligram of total protein. Statistical significances: Q175 Het Si-Control vs treatments: One-way ANOVA followed by Dunnett's multiple comparisons test compared at the respective timepoint. *p<0.001, p<0.01, ****p<0.0001.

Figure 13A:
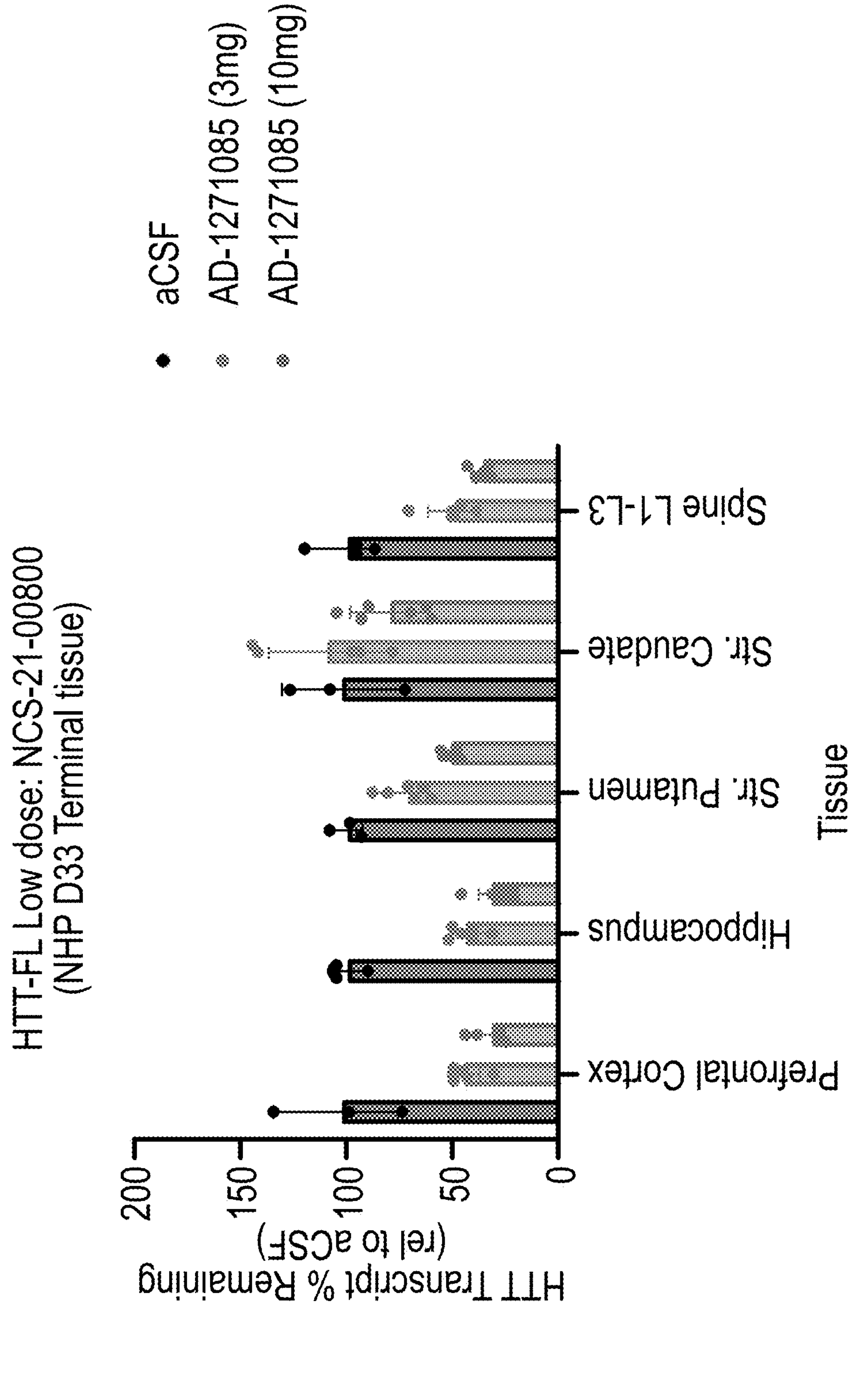

FIG. 13A is a graph depicting the percent HTT transcript remaining in prefrontal cortex, hippocampus, striatum putamen, striatum caudate, and lumbar spine (spine L1-L3) tissues of non-human primates intrathecally administered a single 3 mg or 10 mg dose of AD-1271085 (n=8) at Day 33 post-dose. The percent of HTT transcript remaining is relative to the level of HTT transcript in the corresponding tissues of non-human primates administered artificial CSF (aCSF).

Figure 13B:
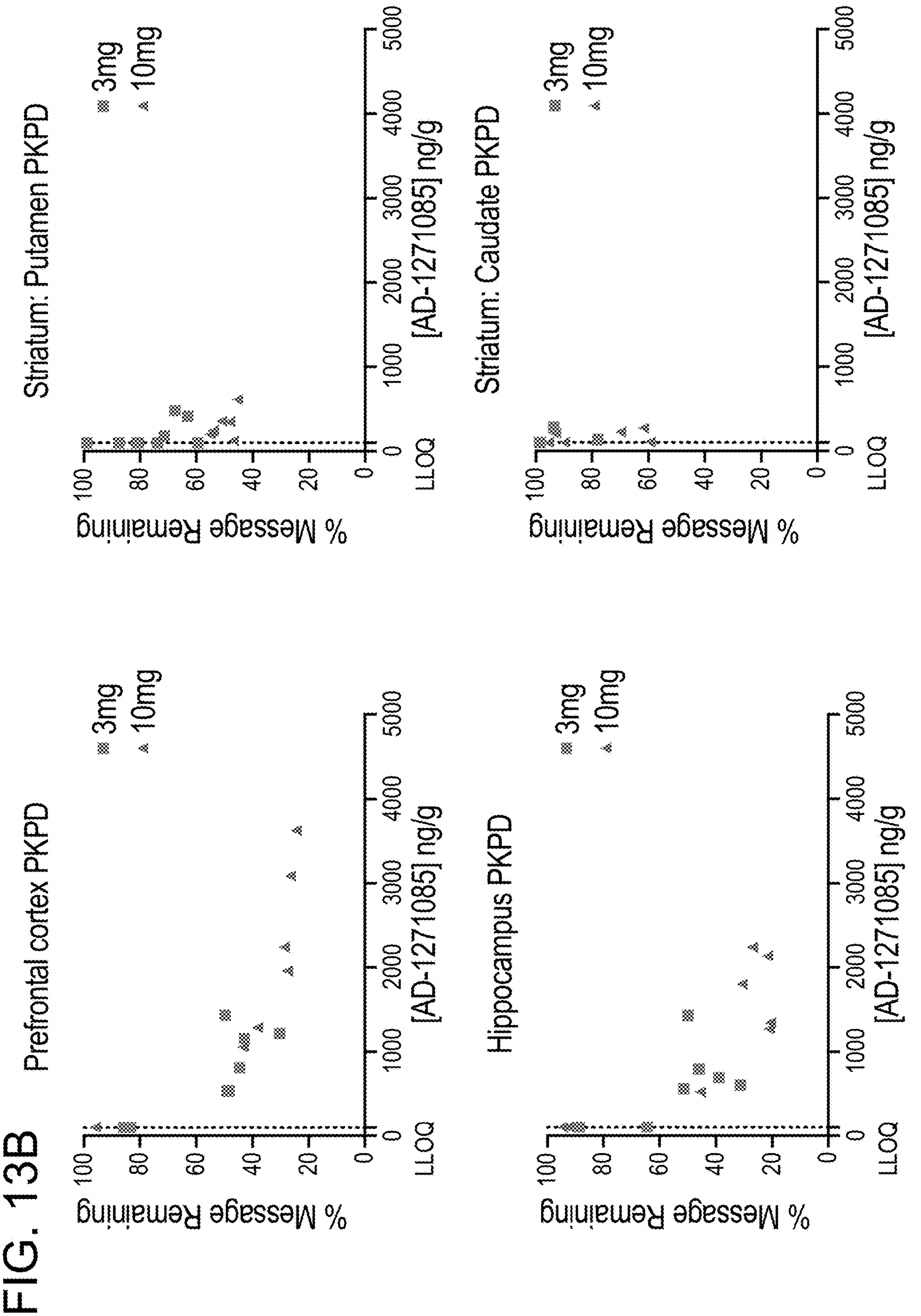

FIG. 13B is a graph depicting the percent HTT transcript remaining in prefrontal cortex, hippocampus, striatum putamen, and striatum caudate tissues of non-human primates intrathecally administered a single 3 mg or 10 mg dose of AD-1271085 (n=8) at Day 33 post-dose. The percent of HTT transcript remaining is relative to the level of HTT transcript in the corresponding tissues of non-human primates administered artificial CSF (aCSF).

Figure 13C:
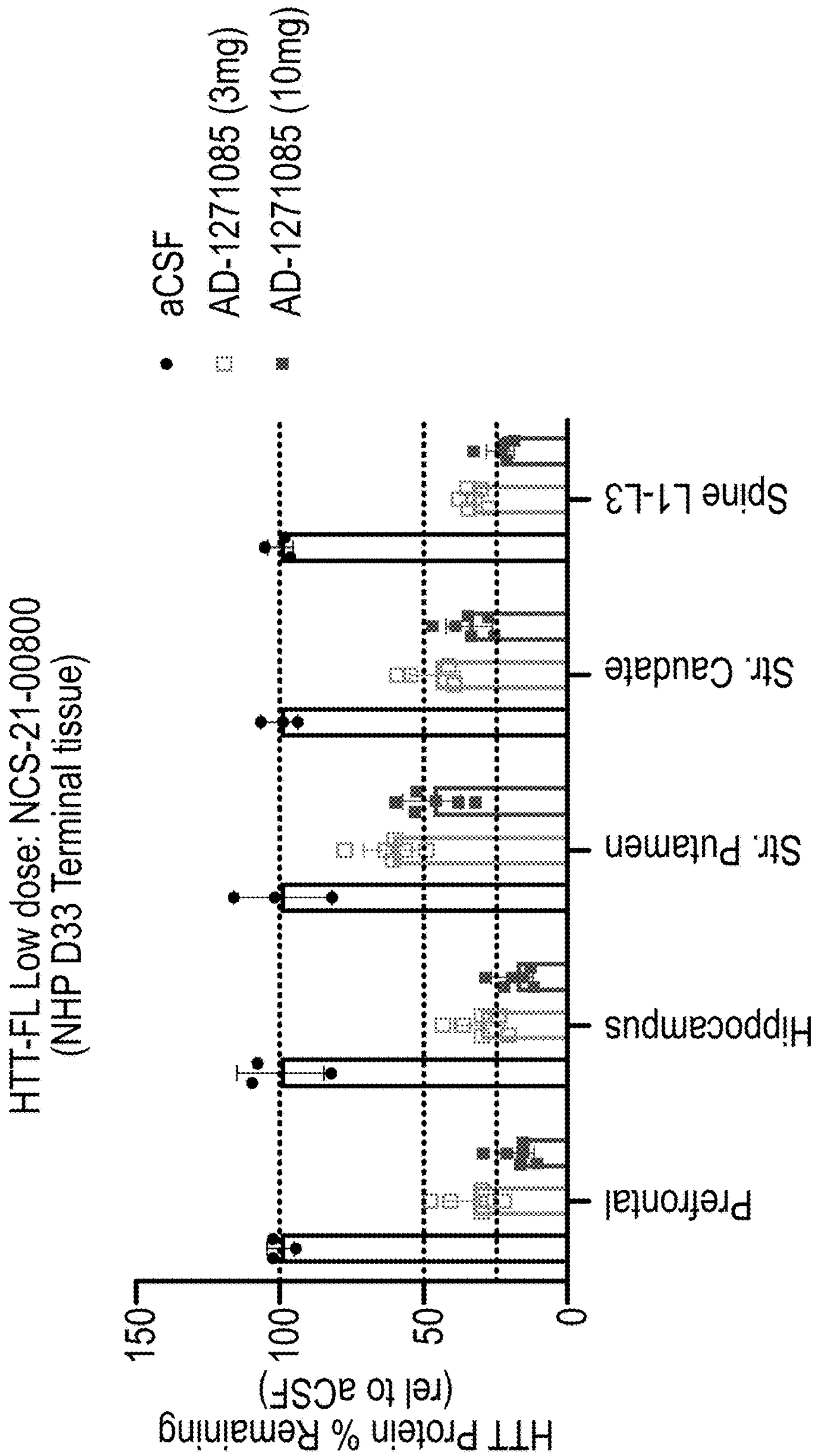

FIG. 13C is a graph depicting the percent HTT protein remaining in prefrontal cortex, hippocampus, striatum putamen, striatum caudate, and lumbar spine (spine L1-L3) tissues of non-human primates intrathecally administered a single 3 mg or 10 mg dose of AD-1271085 (n=8) at Day 33 post-dose. The percent of HTT protein remaining is relative to the level of HTT protein in the corresponding tissues of non-human primates administered artificial CSF (aCSF).

Figure 13D:
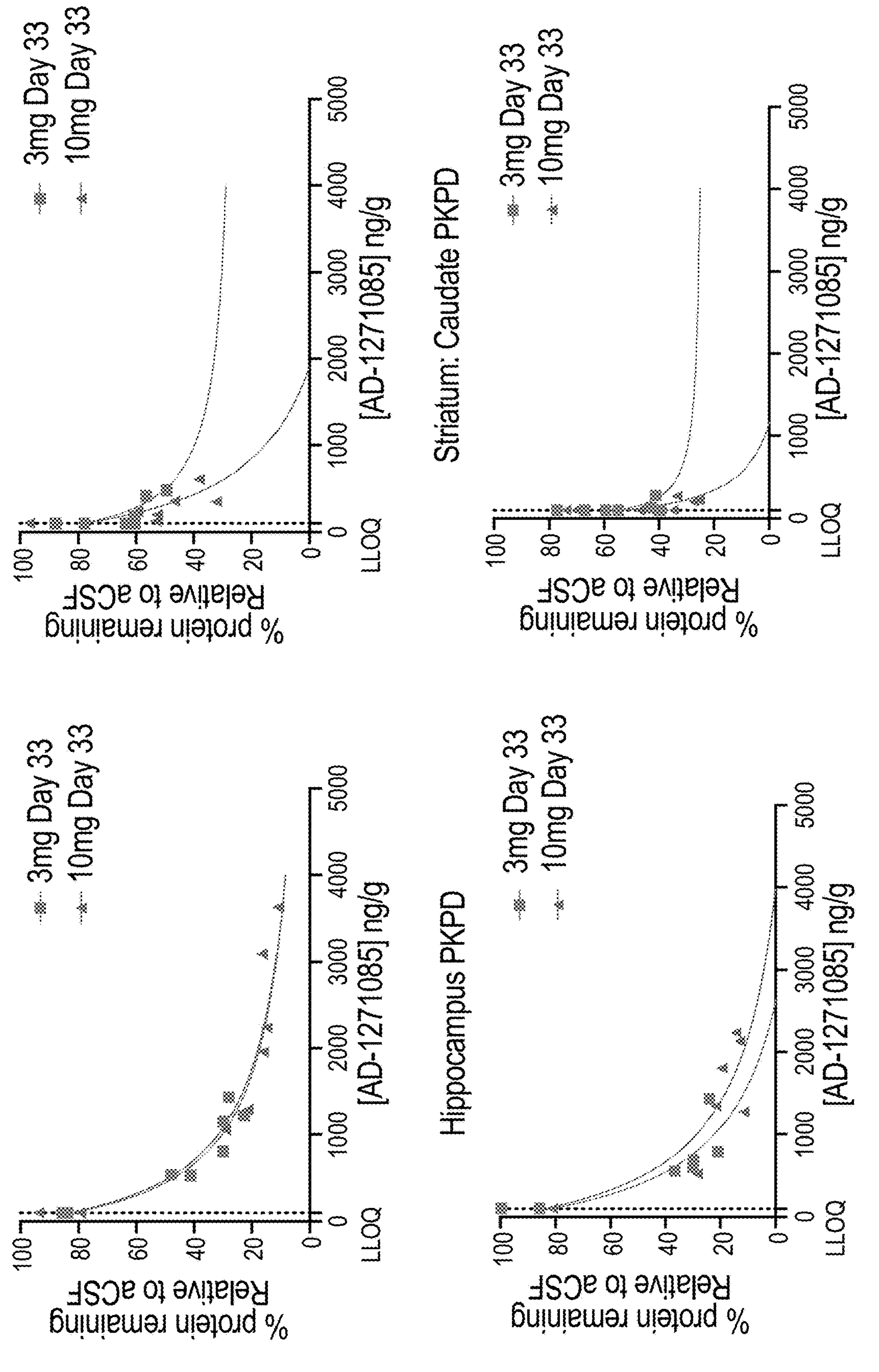

FIG. 13D is a graph depicting the percent HTT protein remaining in prefrontal cortex, hippocampus, striatum putamen, and striatum caudate tissues of non-human primates intrathecally administered a single 3 mg or 10 mg dose of AD-1271085 (n=8) at Day 33 post-dose. The percent of HTT protein remaining is relative to the level of HTT protein in the corresponding tissues of non-human primates administered artificial CSF (aCSF).

Figure 13E:
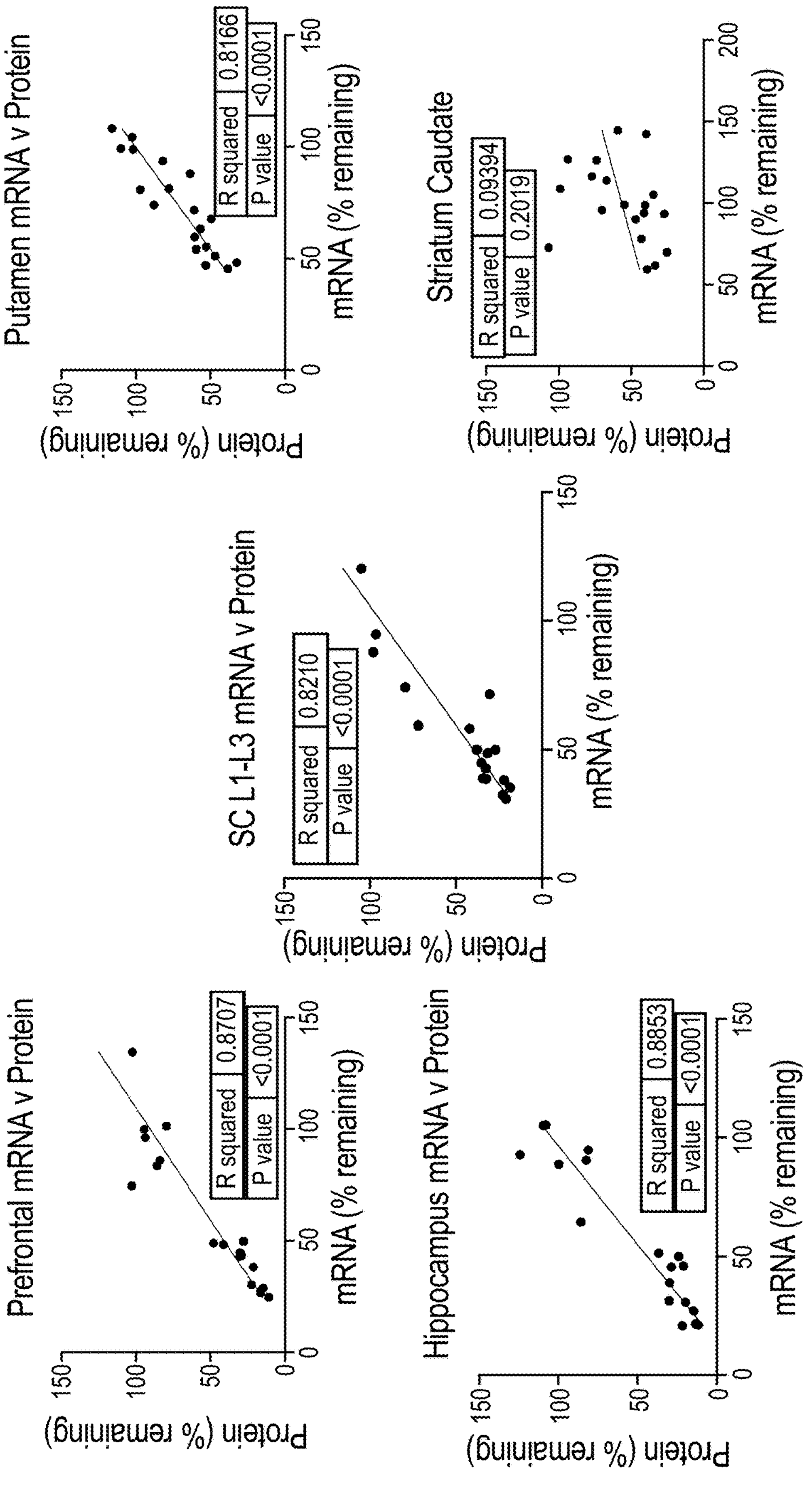

FIG. 13E is a graph depicting the correlation of the effect of intrathecal administration of a single 3 mg or 10 mg dose of AD-1271085 (n=8) at Day 33 post-dose on the percent HTT transcript and protein remaining in prefrontal cortex, hippocampus, striatum putamen, striatum caudate, and lumbar spine (spine L1-L3) tissues of non-human primates. The percent of HTT protein and transcript remaining is relative to the level of HTT protein and transcript in the corresponding tissues of non-human primates administered artificial CSF (aCSF).

Figure 14A:
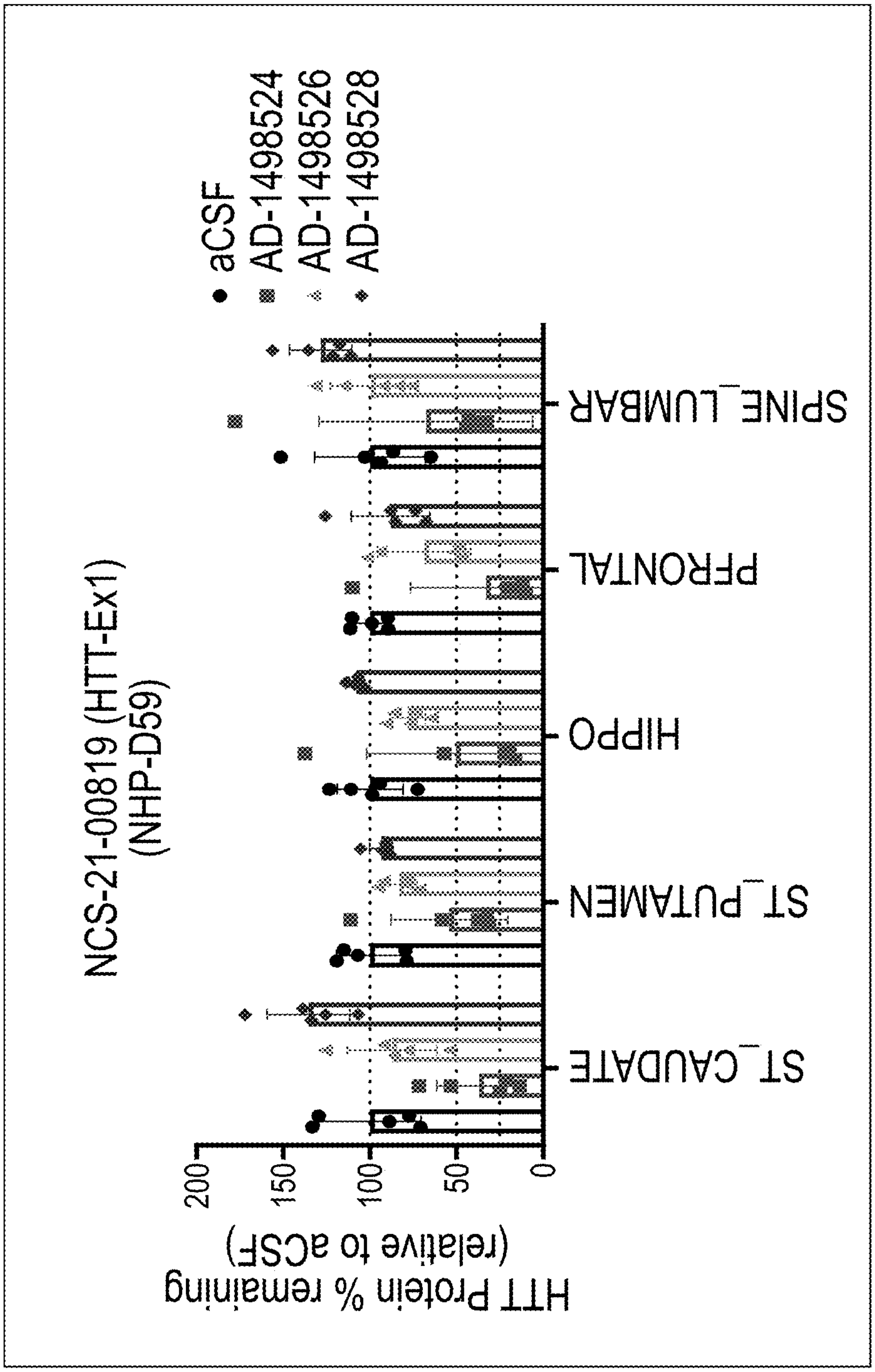

FIG. 14A is a graph depicting the percent HTT protein remaining in striatum caudate, striatum putamen, hippocampus, prefrontal cortex, and lumbar spine tissues of non-human primates intrathecally administered a single 60 mg dose of AD-1498524, AD-1498526 or AD-1498528 (n=5) at Day 59 post-dose. The percent of HTT protein remaining is relative to the level of HTT protein in the corresponding tissues of non-human primates administered artificial CSF (aCSF).

Figure 14B:
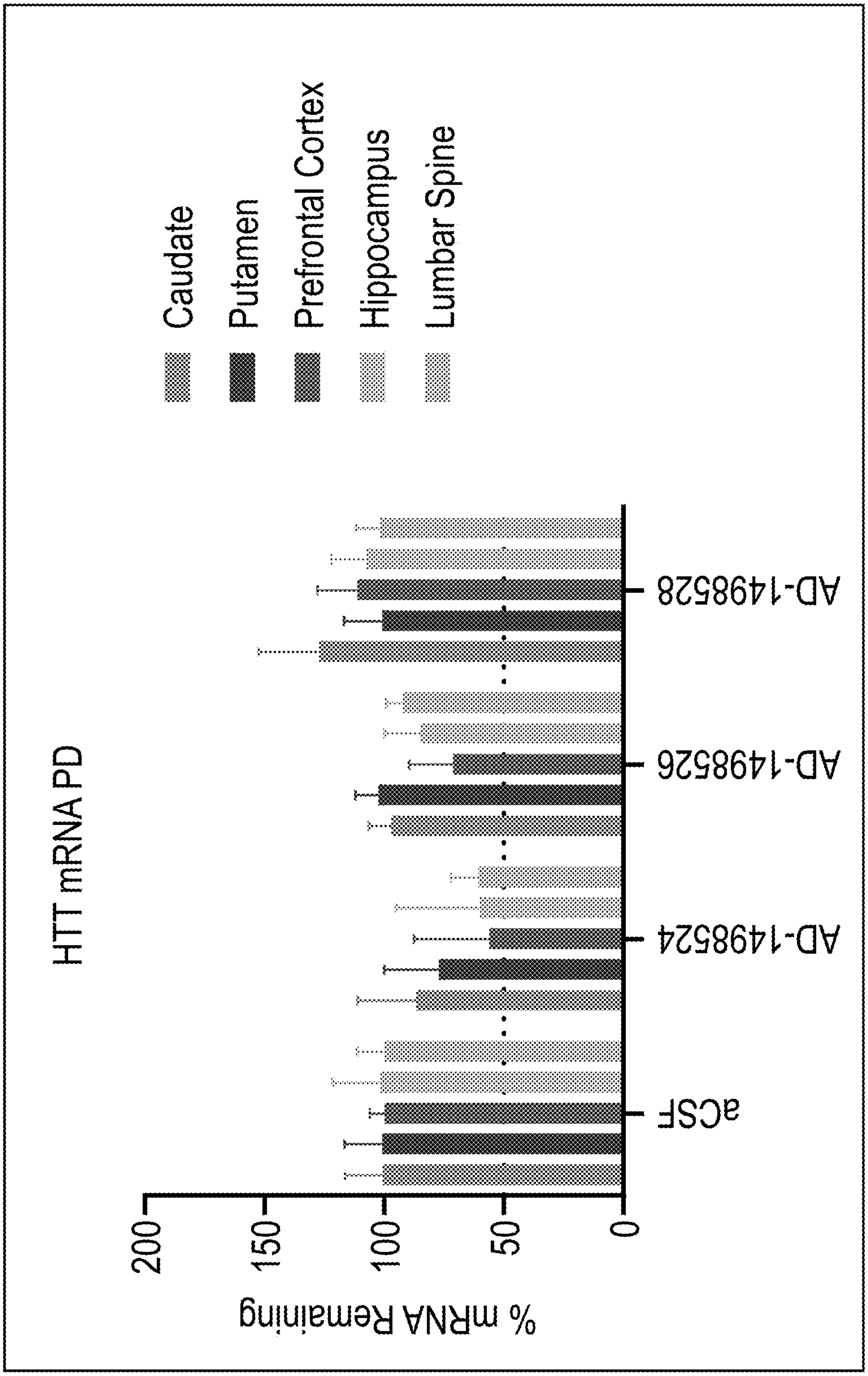

FIG. 14B is a graph depicting the percent HTT transcript remaining in striatum caudate, striatum putamen, hippocampus, prefrontal cortex, and lumbar spine tissues of non-human primates intrathecally administered a single 60 mg dose of AD-1498524, AD-1498526 or AD-1498528 (n=5) at Day 59 post-dose. The percent of HTT transcript remaining is relative to the level of HTT transcript in the corresponding tissues of non-human primates administered artificial CSF (aCSF).

Figure 14C:
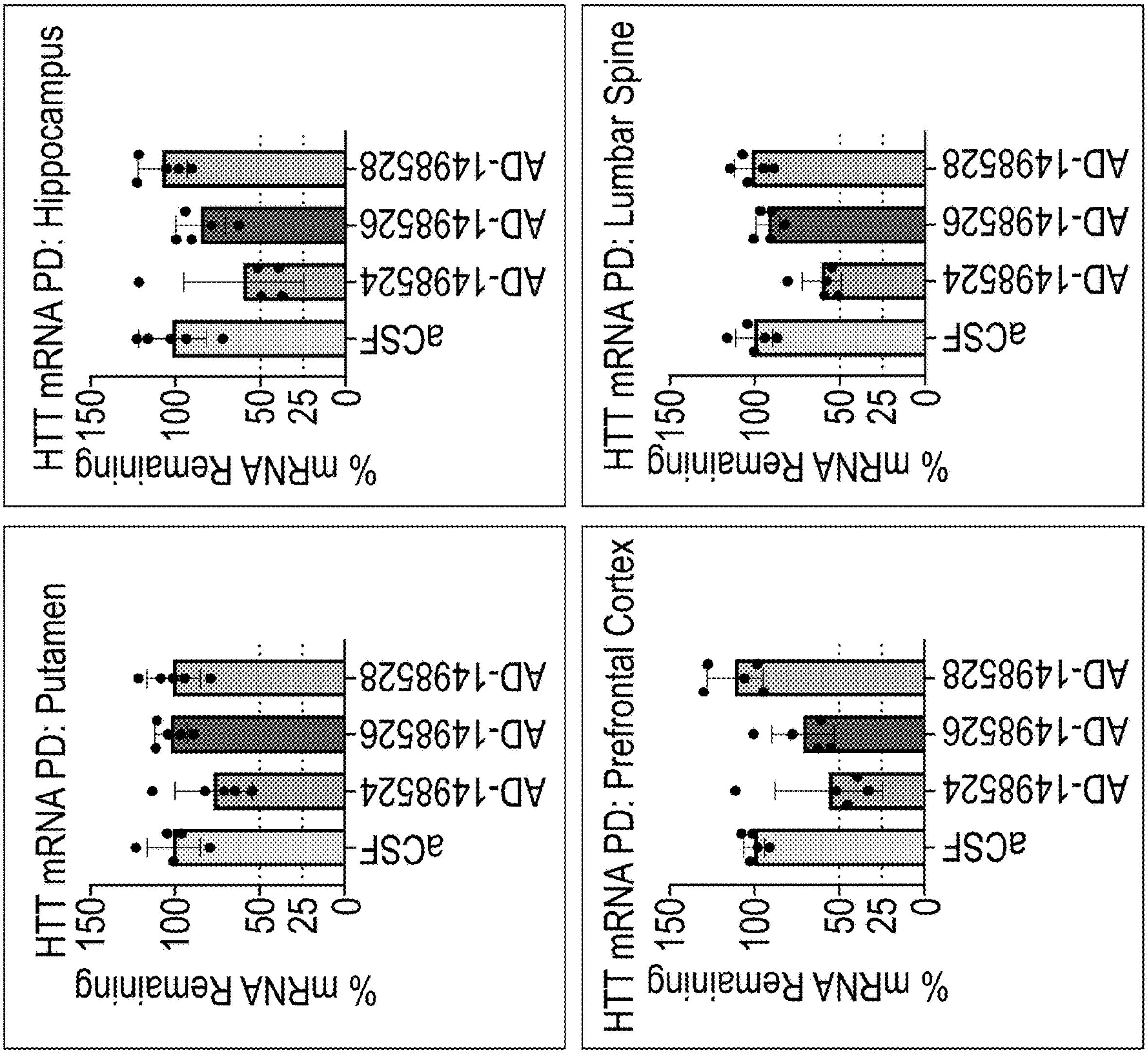

FIG. 14C is a graph depicting the percent HTT transcript remaining in prefrontal cortex, hippocampus, striatum putamen, and lumbar spine tissues of non-human primates intrathecally administered a single 60 mg dose of AD-1498524, AD-1498526 or AD-1498528 (n=5) at Day 59 post-dose. The percent of HTT transcript remaining is relative to the level of HTT transcript in the corresponding tissues of non-human primates administered artificial CSF (aCSF).

Figure 14D:
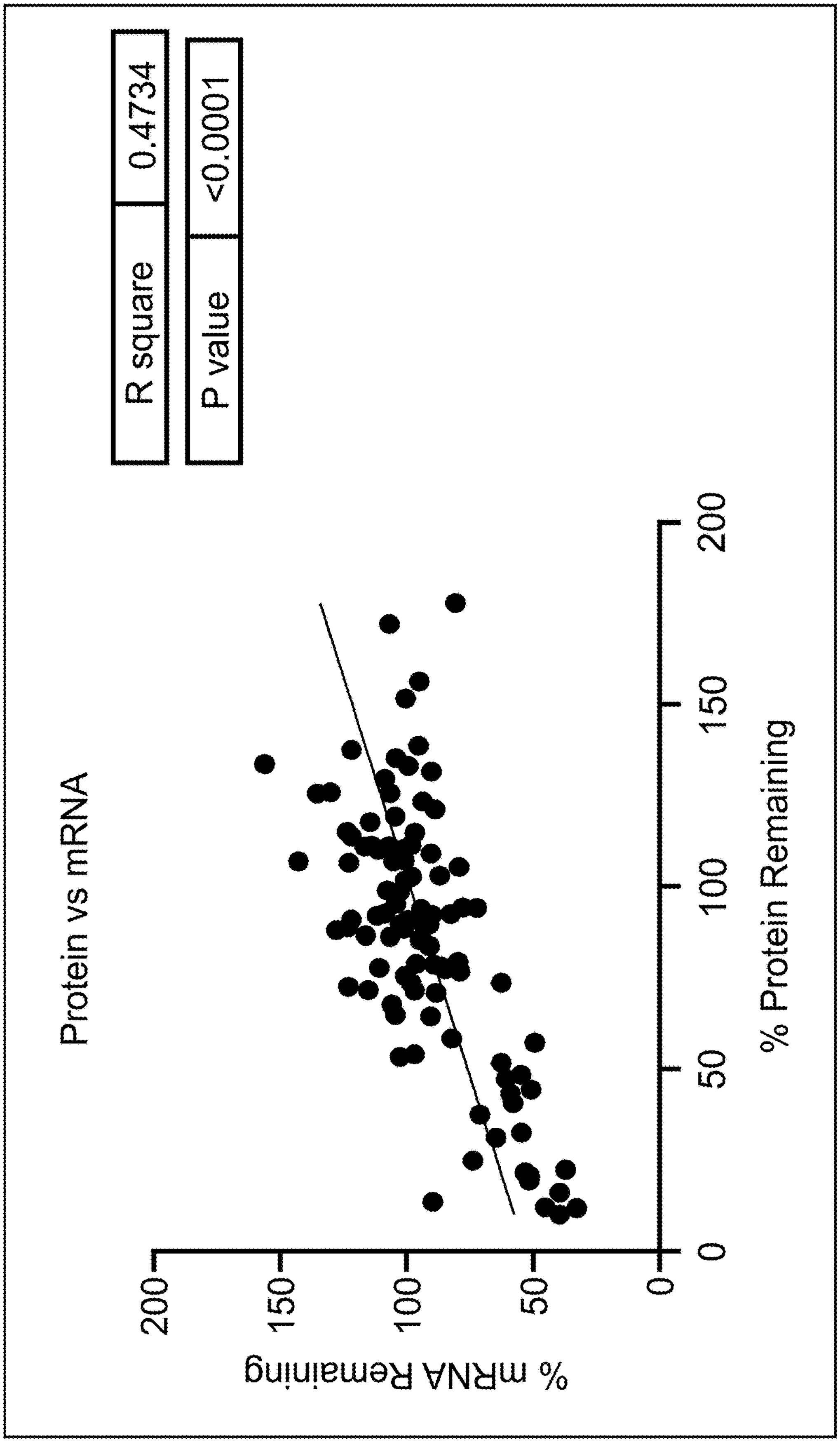

FIG. 14D is a graph depicting the correlation of the effect of intrathecal administration of a single 60 mg dose of AD-1498524, AD-1498526 or AD-1498528 (n=5) at Day 59 post-dose on the percent HTT transcript and protein remaining in tissues of non-human primates. The percent of HTT protein and transcript remaining is relative to the level of HTT protein and transcript in the corresponding tissues of non-human primates administered artificial CSF (aCSF).

Figure 15:
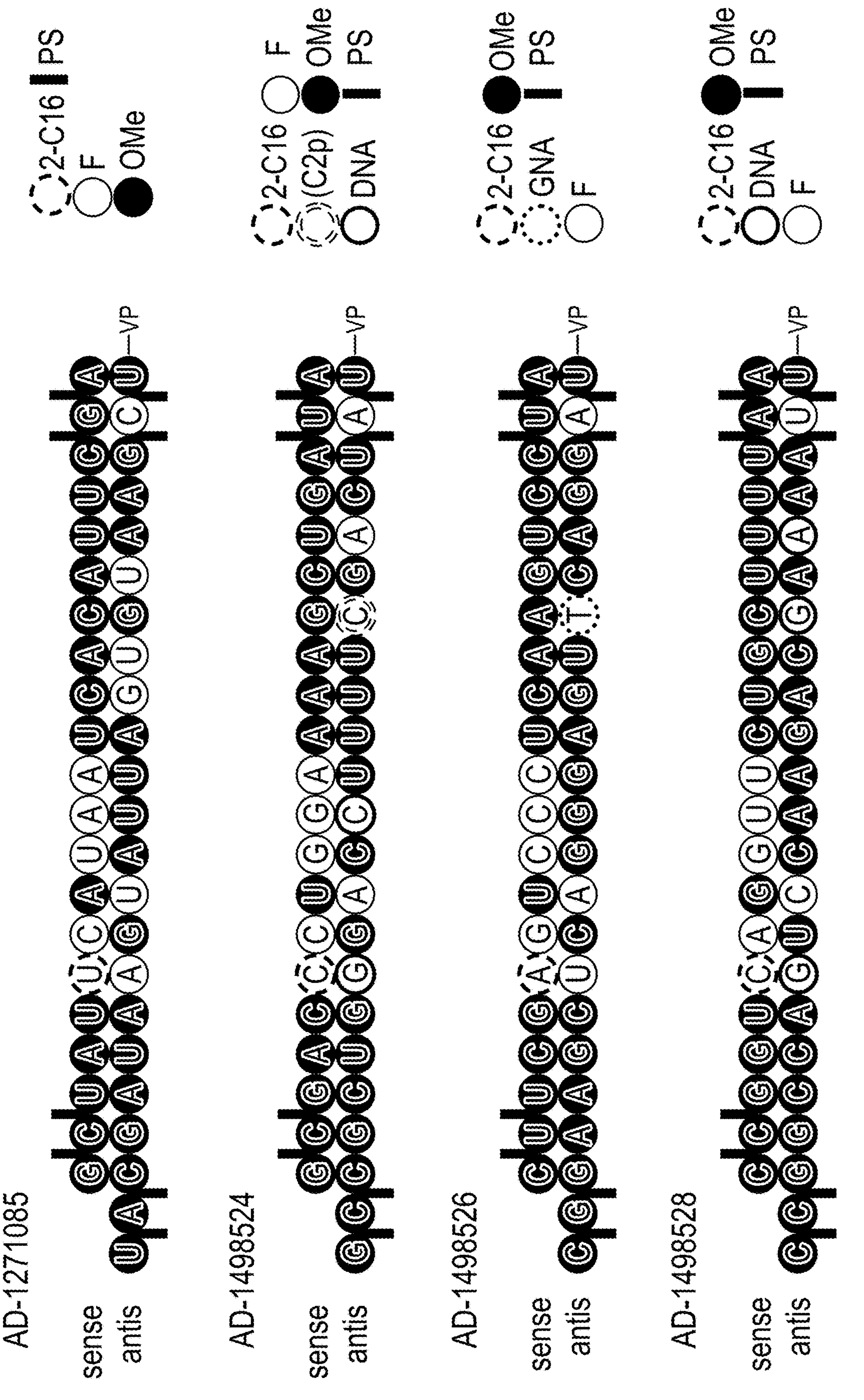

FIG. 15 are schematics of the structures of the indicated duplexes. The sequences disclosed in the Figure, in order of appearance, are SEQ ID NOs:17, 18, 65, 79, 70, 83, 72, and 85.

DETAILED DESCRIPTION OF THE INVENTION

The present disclosure provides RNAi compositions, which effect the RNA-induced silencing complex (RISC)-mediated cleavage of RNA transcripts of a huntingtin (HTT) gene. The HTT gene may be within a cell, e.g., a cell within a subject, such as a human. The use of these iRNAs enables the targeted degradation of mRNAs of the corresponding gene (HTT gene) in mammals.

The iRNAs of the invention have been designed to target a full-length HTT gene, including portions of the gene that are conserved in the HTT orthologs of other mammalian species, e.g., thereby targeting the full-length wild-type transcript and the full-length mutant transcript. Without intending to be limited by theory, it is believed that a combination or sub-combination of the foregoing properties and the specific target sites, or the specific modifications in these iRNAs confer to the iRNAs of the invention improved efficacy, stability, potency, durability, and safety.

Accordingly, the present disclosure also provides methods of using the RNAi compositions of the disclosure, including, compositions comprising one or more, e.g., 2, 3, or 4, dsRNA agents of the invention, for inhibiting the expression of an HTT gene or for treating a subject having a disorder that would benefit from inhibiting or reducing the expression of an HTT gene, e.g., an HTT-associated disease, for example, Huntington's disease (HD).

The RNAi agents of the disclosure include an RNA strand (the antisense strand) having a region which is about 30 nucleotides or less in length, e.g., 15-30, 15-29, 15-28, 15-27, 15-26, 15-25, 15-24, 15-23, 15-22, 15-21, 15-20, 15-19, 15-18, 15-17, 18-30, 18-29, 18-28, 18-27, 18-26, 18-25, 18-24, 18-23, 18-22, 18-21, 18-20, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24,20-23, 20-22, 20-21, 21-30, 21-29, 21-28, 21-27, 21-26, 21-25, 21-24, 21-23, or 21-22 nucleotides in length, which region is substantially complementary to at least part of an mRNA transcript of an HTT gene. In certain embodiments, the RNAi agents of the disclosure include an RNA strand (the antisense strand) having a region which is about 21-23 nucleotides in length, which region is substantially complementary to at least part of an mRNA transcript of an HTT gene.

In certain embodiments, the RNAi agents of the disclosure include an RNA strand (the antisense strand) which can include longer lengths, for example up to 66 nucleotides, e.g., 36-66, 26-36, 25-36, 31-60, 22-43, 27-53 nucleotides in length with a region of at least 19 contiguous nucleotides that is substantially complementary to at least a part of an mRNA transcript of an HTT gene. These RNAi agents with the longer length antisense strands preferably include a second RNA strand (the sense strand) of 20-60 nucleotides in length wherein the sense and antisense strands form a duplex of 18-30 contiguous nucleotides.

The use of these RNAi agents enables the targeted degradation of mRNAs of an HTT gene in mammals. Thus, methods and compositions including these RNAi agents are useful for treating a subject who would benefit by a reduction in the levels or activity of an HTT protein, such as a subject having an HTT-associated disease, such as Huntington's disease (HD).

The following detailed description discloses how to make and use compositions containing RNAi agents to inhibit the expression of an HTT gene, as well as compositions and methods for treating subjects having diseases and disorders that would benefit from inhibition or reduction of the expression of the genes.

I. Definitions

In order that the present disclosure may be more readily understood, certain terms are first defined. In addition, it should be noted that whenever a value or range of values of a parameter are recited, it is intended that values and ranges intermediate to the recited values are also intended to be part of this disclosure.

The articles "a" and "an" are used herein to refer to one or to more than one (i.e., to at least one) of the grammatical object of the article. By way of example, "an element" means one element or more than one element, e.g., a plurality of elements.

The term "including" is used herein to mean, and is used interchangeably with, the phrase "including but not limited to". The term "or" is used herein to mean, and is used interchangeably with, the term "and/or," unless context clearly indicates otherwise.

The term "about" is used herein to mean within the typical ranges of tolerances in the art. For example, "about" can be understood as about 2 standard deviations from the mean. In certain embodiments, about means±10%. In certain embodiments, about means±5%. When about is present before a series of numbers or a range, it is understood that "about" can modify each of the numbers in the series or range.

The term "at least", "no less than", or "or more" prior to a number or series of numbers is understood to include the number adjacent to the term "at least", and all subsequent numbers or integers that could logically be included, as clear from context. For example, the number of nucleotides in a nucleic acid molecule must be an integer. For example, "at least 18 nucleotides of a 21 nucleotide nucleic acid molecule" means that 18, 19, 20, or 21 nucleotides have the indicated property. When at least is present before a series of numbers or a range, it is understood that "at least" can modify each of the numbers in the series or range.

As used herein, "no more than" or "less than" is understood as the value adjacent to the phrase and logical lower values or integers, as logical from context, to zero. For example, a duplex with an overhang of "no more than 2 nucleotides" has a 2, 1, or 0 nucleotide overhang. When "no more than" is present before a series of numbers or a range, it is understood that "no more than" can modify each of the numbers in the series or range.

As used herein, methods of detection can include determination that the amount of analyte present is below the level of detection of the method.

In the event of a conflict between an indicated target site and the nucleotide sequence for a sense or antisense strand, the indicated sequence takes precedence.

In the event of a conflict between a chemical structure and a chemical name, the chemical structure takes precedence.

The term "HTT" or "huntingtin", also known as "Huntingtin," "Huntington Disease Protein," "IT15," "HD," "HD Protein," or "LOMARS," refers to the well-known gene that encodes the protein, HTT, that is widely expressed, required for normal development and the disease gene linked to Huntington's disease, a neurodegenerative disorder characterized by loss of striatal neurons caused by an expanded, unstable trinucleotide (CAG) repeat in the huntingtin gene, which translates as a polyglutamine repeat in the protein product.

Exemplary nucleotide and amino acid sequences of HTT can be found, for example, at GenBank Accession No. NM_002111.8 (*Homo sapiens* HTT, SEQ ID NO: 1, reverse complement, SEQ ID NO: 6); GenBank Accession No. NM_010414.3 (*Mus musculus* HTT, SEQ ID NO: 2;

reverse complement, SEQ ID NO: 7); GenBank Accession No.: NM_024357.3 (*Rattus norvegicus* HTT, SEQ ID NO: 3, reverse complement, SEQ ID NO: 8); GenBank Accession No.: XM_015449989.1 (*Macaca fascicularis* HTT, SEQ ID NO: 4, reverse complement, SEQ ID NO: 9); and GenBank Accession No.: XM_028848247.1 (*Macaca* mulatta HTT, SEQ ID NO: 5, reverse complement, SEQ ID NO: 10).

Additional examples of HTT sequences can be found in publically available databases, for example, GenBank, OMIM, and UniProt.

Further information on HTT can be found, for example, at www.ncbi.nlm.nih.gov/gene/3064.

The entire contents of each of the foregoing GenBank Accession numbers and the Gene database numbers are incorporated herein by reference as of the date of filing this application.

The term HTT, as used herein, also refers to variations of the HTT gene including variants provided in the SNP database. Numerous seuqnce variations within the HTT gene have been identified and may be found at, for example, NCBI dbSNP and UniProt (see, e.g., www.ncbi.nlm.nih.gov/snp/?LinkName=gene_snp&from_uid=3064, the entire contents of which is incorporated herein by reference as of the date of filing this application.

As used herein, "target sequence" refers to a contiguous portion of the nucleotide sequence of an mRNA molecule formed during the transcription of an HTT gene, including mRNA that is a product of RNA processing of a primary transcription product. In one embodiment, the target portion of the sequence will be at least long enough to serve as a substrate for RNAi-directed cleavage at or near that portion of the nucleotide sequence of an mRNA molecule formed during the transcription of an HTT gene.

The target sequence is about 15-30 nucleotides in length. For example, the target sequence can be from about 15-30 nucleotides, 15-29, 15-28, 15-27, 15-26, 15-25, 15-24, 15-23, 15-22, 15-21, 15-20, 15-19, 15-18, 15-17, 18-30, 18-29, 18-28, 18-27, 18-26, 18-25, 18-24, 18-23, 18-22, 18-21, 18-20, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24,20-23, 20-22, 20-21, 21-30, 21-29, 21-28, 21-27, 21-26, 21-25, 21-24, 21-23, or 21-22 nucleotides in length. In certain embodiments, the target sequence is 19-23 nucleotides in length, optionally 21-23 nucleotides in length. Ranges and lengths intermediate to the above recited ranges and lengths are also contemplated to be part of the disclosure.

As used herein, the term "strand comprising a sequence" refers to an oligonucleotide comprising a chain of nucleotides that is described by the sequence referred to using the standard nucleotide nomenclature.

"G," "C," "A," "T", and "U" each generally stand for a nucleotide that contains guanine, cytosine, adenine, thymidine, and uracil as a base, respectively in the context of a modified or unmodified nucleotide. However, it will be understood that the term "ribonucleotide" or "nucleotide" can also refer to a modified nucleotide, as further detailed below, or a surrogate replacement moiety (see, e.g., Table 1). The skilled person is well aware that guanine, cytosine, adenine, thymidine, and uracil can be replaced by other moieties without substantially altering the base pairing properties of an oligonucleotide comprising a nucleotide bearing such replacement moiety. For example, without limitation, a nucleotide comprising inosine as its base can base pair with nucleotides containing adenine, cytosine, or uracil. Hence, nucleotides containing uracil, guanine, or adenine can be replaced in the nucleotide sequences of dsRNA featured in the disclosure by a nucleotide containing, for example, inosine. In another example, adenine and cytosine anywhere in the oligonucleotide can be replaced with guanine and uracil, respectively to form G-U Wobble base pairing with the target mRNA. Sequences containing such replacement moieties are suitable for the compositions and methods featured in the disclosure.

The terms "iRNA", "RNAi agent," "iRNA agent," "RNA interference agent" as used interchangeably herein, refer to an agent that contains RNA as that term is defined herein, and which mediates the targeted cleavage of an RNA transcript via an RNA-induced silencing complex (RISC) pathway. RNA interference (RNAi) is a process that directs the sequence-specific degradation of mRNA. RNAi modulates, e.g., inhibits, the expression of HTT in a cell, e.g., a cell within a subject, such as a mammalian subject.

In one embodiment, an RNAi agent of the disclosure includes a single stranded RNAi that interacts with a target RNA sequence, e.g., an HTT target mRNA sequence, to direct the cleavage of the target RNA. Without wishing to be bound by theory it is believed that long double stranded RNA introduced into cells is broken down into double-stranded short interfering RNAs (siRNAs) comprising a sense strand and an antisense strand by a Type III endonuclease known as Dicer (Sharp et al. (2001) *Genes Dev.* 15:485). Dicer, a ribonuclease-III-like enzyme, processes these dsRNA into 19-23 base pair short interfering RNAs with characteristic two base 3' overhangs (Bernstein, et al., (2001) *Nature* 409:363). These siRNAs are then incorporated into an RNA-induced silencing complex (RISC) where one or more helicases unwind the siRNA duplex, enabling the complementary antisense strand to guide target recognition (Nykanen, et al., (2001) *Cell* 107:309). Upon binding to the appropriate target mRNA, one or more endonucleases within the RISC cleave the target to induce silencing (Elbashir, et al., (2001) *Genes Dev.* 15:188). Thus, in one aspect the disclosure relates to a single stranded RNA (ssRNA) (the antisense strand of a siRNA duplex) generated within a cell and which promotes the formation of a RISC complex to effect silencing of the target gene, i.e., an HTT gene. Accordingly, the term "siRNA" is also used herein to refer to an RNAi as described above.

In another embodiment, the RNAi agent may be a single-stranded RNA that is introduced into a cell or organism to inhibit a target mRNA. Single-stranded RNAi agents bind to the RISC endonuclease, Argonaute 2, which then cleaves the target mRNA. The single-stranded siRNAs are generally 15-30 nucleotides and are chemically modified. The design and testing of single-stranded RNAs are described in U.S. Pat. No. 8,101,348 and in Lima et al., (2012) *Cell* 150:883-894, the entire contents of each of which are hereby incorporated herein by reference. Any of the antisense nucleotide sequences described herein may be used as a single-stranded siRNA as described herein or as chemically modified by the methods described in Lima et al., (2012) *Cell* 150:883-894.

In another embodiment, a "RNAi agent" for use in the compositions and methods of the disclosure is a double stranded RNA and is referred to herein as a "double stranded RNAi agent," "double stranded RNA (dsRNA) molecule," "dsRNA agent," or "dsRNA". The term "dsRNA" refers to a complex of ribonucleic acid molecules, having a duplex structure comprising two anti-parallel and substantially complementary nucleic acid strands, referred to as having "sense" and "antisense" orientations with respect to a target RNA, i.e., an HTT gene. In some embodiments of the disclosure, a double stranded RNA (dsRNA) triggers the degradation of a target RNA, e.g., an mRNA, through a post-transcriptional gene-silencing mechanism referred to herein as RNA interference or RNAi.

In general, a dsRNA molecule can include ribonucleotides, but as described in detail herein, each or both strands can also include one or more non-ribonucleotides, e.g., a deoxyribonucleotide, a modified nucleotide. In addition, as used in this specification, an "RNAi agent" may include ribonucleotides with chemical modifications; an RNAi agent may include substantial modifications at multiple nucleotides. As used herein, the term "modified nucleotide" refers to a nucleotide having, independently, a modified sugar moiety, a modified internucleotide linkage, or a modified nucleobase. Thus, the term modified nucleotide encompasses substitutions, additions or removal of, e.g., a functional group or atom, to internucleoside linkages, sugar moieties, or nucleobases. The modifications suitable for use in the agents of the disclosure include all types of modifications disclosed herein or known in the art. Any such modifications, as used in a siRNA type molecule, are encompassed by "RNAi agent" for the purposes of this specification and claims.

In certain embodiments of the instant disclosure, inclusion of a deoxy-nucleotide if present within an RNAi agent can be considered to constitute a modified nucleotide.

The duplex region may be of any length that permits specific degradation of a desired target RNA through a RISC pathway, and may range from about 15-36 base pairs in length, for example, about 15, 16, 17, 18, 19, 20, 21, 22, 23, 24, 25, 26, 27, 28, 29, 30, 31, 32, 33, 34, 35, or 36 base pairs in length, such as about 15-30, 15-29, 15-28, 15-27, 15-26, 15-25, 15-24, 15-23, 15-22, 15-21, 15-20, 15-19, 15-18, 15-17, 18-30, 18-29, 18-28, 18-27, 18-26, 18-25, 18-24, 18-23, 18-22, 18-21, 18-20, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24,20-23, 20-22, 20-21, 21-30, 21-29, 21-28, 21-27, 21-26, 21-25, 21-24, 21-23, or 21-22 base pairs in length. In certain embodiments, the duplex region is 19-21 base pairs in length, e.g., 21 base pairs in length. Ranges and lengths intermediate to the above recited ranges and lengths are also contemplated to be part of the disclosure.

The two strands forming the duplex structure may be different portions of one larger RNA molecule, or they may be separate RNA molecules. Where the two strands are part of one larger molecule, and therefore are connected by an uninterrupted chain of nucleotides between the 3'-end of one strand and the 5'-end of the respective other strand forming the duplex structure, the connecting RNA chain is referred to as a "hairpin loop." A hairpin loop can comprise at least one unpaired nucleotide. In some embodiments, the hairpin loop can comprise at at least 4, at least 5, at least 6, at least 7, at least 8, at least 9, at least 10, at least 20, at least 23 or more unpaired nucleotides or nucleotides not directed to the target site of the dsRNA. In some embodiments, the hairpin loop can be 10 or fewer nucleotides. In some embodiments, the hairpin loop can be 8 or fewer unpaired nucleotides. In some embodiments, the hairpin loop can be 4-10 unpaired nucleotides. In some embodiments, the hairpin loop can be 4-8 nucleotides.

Where the two substantially complementary strands of a dsRNA are comprised by separate RNA molecules, those molecules need not, but can be covalently connected. In certain embodiments where the two strands are connected covalently by means other than an uninterrupted chain of nucleotides between the 3'-end of one strand and the 5'-end of the respective other strand forming the duplex structure, the connecting structure is referred to as a "linker" (though it is noted that certain other structures defined elsewhere herein can also be referred to as a "linker"). The RNA strands may have the same or a different number of nucleotides. The maximum number of base pairs is the number of nucleotides in the shortest strand of the dsRNA minus any overhangs that are present in the duplex. In addition to the duplex structure, an RNAi may comprise one or more nucleotide overhangs. In one embodiment of the RNAi agent, at least one strand comprises a 3' overhang of at least 1 nucleotide. In another embodiment, at least one strand comprises a 3' overhang of at least 2 nucleotides, e.g., 2, 3, 4, 5, 6, 7, 9, 10, 11, 12, 13, 14, or 15 nucleotides. In other embodiments, at least one strand of the RNAi agent comprises a 5' overhang of at least 1 nucleotide. In certain embodiments, at least one strand comprises a 5' overhang of at least 2 nucleotides, e.g., 2, 3, 4, 5, 6, 7, 9, 10, 11, 12, 13, 14, or 15 nucleotides. In still other embodiments, both the 3' and the 5' end of one strand of the RNAi agent comprise an overhang of at least 1 nucleotide.

In one embodiment, an RNAi agent of the disclosure is a dsRNA, each strand of which independently comprises 19-23 nucleotides, that interacts with a target RNA sequence, e.g., an HTT target mRNA sequence, to direct the cleavage of the target RNA.

As used herein, the term "nucleotide overhang" refers to at least one unpaired nucleotide that protrudes from the duplex structure of an RNAi agent, e.g., a dsRNA. For example, when a 3-end of one strand of a dsRNA extends beyond the 5-end of the other strand, or vice versa, there is a nucleotide overhang. A dsRNA can comprise an overhang of at least one nucleotide; alternatively, the overhang can comprise at least two nucleotides, at least three nucleotides, at least four nucleotides, at least five nucleotides or more. A nucleotide overhang can comprise or consist of a nucleotide/nucleoside analog, including a deoxynucleotide/nucleoside. The overhang(s) can be on the sense strand, the antisense strand or any combination thereof. Furthermore, the nucleotide(s) of an overhang can be present on the 5-end, 3-end or both ends of either an antisense or sense strand of a dsRNA.

In one embodiment, the antisense strand of a dsRNA has a 1-10 nucleotide, e.g., a 1, 2, 3, 4, 5, 6, 7, 8, 9, or 10 nucleotide, overhang at the 3'-end or the 5'-end. In one embodiment, the sense strand of a dsRNA has a 1-10 nucleotide, e.g., a 1, 2, 3, 4, 5, 6, 7, 8, 9, or 10 nucleotide, overhang at the 3'-end or the 5'-end. In another embodiment, one or more of the nucleotides in the overhang is replaced with a nucleoside thiophosphate.

In certain embodiments, the antisense strand of a dsRNA has a 1-10 nucleotide, e.g., 0-3, 1-3, 2-4, 2-5, 4-10, 5-10, e.g., a 1, 2, 3, 4, 5, 6, 7, 8, 9, or 10 nucleotide, overhang at the 3'-end or the 5'-end. In one embodiment, the sense strand of a dsRNA has a 1-10 nucleotide, e.g., a 1, 2, 3, 4, 5, 6, 7, 8, 9, or 10 nucleotide, overhang at the 3'-end or the 5'-end. In another embodiment, one or more of the nucleotides in the overhang is replaced with a nucleoside thiophosphate.

In certain embodiments, the overhang on the sense strand or the antisense strand, can include extended lengths longer than 10 nucleotides, e.g., 1-30 nucleotides, 2-30 nucleotides, 10-30 nucleotides, or 10-15 nucleotides in length. In certain embodiments, an extended overhang is on the sense strand of the duplex. In certain embodiments, an extended overhang is present on the 3'end of the sense strand of the duplex. In certain embodiments, an extended overhang is present on the 5'end of the sense strand of the duplex. In certain embodiments, an extended overhang is on the antisense strand of the duplex. In certain embodiments, an extended overhang is present on the 3'end of the antisense strand of the duplex. In certain embodiments, an extended overhang is present on the 5'end of the antisense strand of the duplex. In certain embodiments, one or more of the nucleotides in the overhang is replaced with a nucleoside thiophosphate. In certain embodiments, the overhang includes a self-complementary portion such that the overhang is capable of forming a hairpin structure that is stable under physiological conditions.

In certain embodiments, at least one end of at least one strand is extended beyond a duplex targeting region, including structures where one of the strands includes a thermodynamically-stabilizing tetraloop structure (see, e.g., U.S. Pat. Nos. 8,513,207 and 8,927,705, as well as WO2010033225, the entire contents of each of which are incorporated by reference herein). Such structures may include single-stranded extensions (on one or both sides of the molecule) as well as double-stranded extensions.

In certain embodiments, the 3' end of the sense strand and the 5' end of the antisense strand are joined by a polynucleotide sequence comprising ribonucleotides, deoxyribonucleotides or both, optionally wherein the polynucleotide sequence comprises a tetraloop sequence. In certain embodiments, the sense strand is 25-35 nucleotides in length.

A tetraloop may contain ribonucleotides, deoxyribonucleotides, modified nucleotides, and combinations thereof. Typically, a tetraloop has 4 to 5 nucleotides. In some embodiments, the loop comprises a sequence set forth as GAAA. In some embodiments, at least one of the nucleotide of the loop (GAAA) comprises a nucleotide modification. In some embodiments, the modified nucleotide comprises a 2'-modification. In some embodiments, the 2'-modification is a modification selected from the group consisting of 2'-aminoethyl, 2'-fluoro, 2-O-methyl, 2'-O-methoxyethyl, 2'-aminodiethoxymethanol, 2'-adem, and 2'-deoxy-2'-fhioro-d-arabinonucleic acid. In some embodiments, all of the nucleotides of the loop are modified. In some embodiments, the G in the GAAA sequence comprises a 2-OH. In some embodiments, each of the nucleotides in the GAAA sequence comprises a 2'-O-methyl modification. In some embodiments, each of the A in the GAAA sequence comprises a 2'-OH and the G in the GAAA sequence comprises a 2'-O-methyl modification. In preferred embodiments, In some embodiments, each of the A in the GAAA sequence comprises a 2'-O-methoxyethyl (MOE) modification and the G in the GAAA sequence comprises a 2'-O-methyl modification; or each of the A in the GAAA sequence comprises a 2'-adem modification and the G in the GAAA sequence comprises a 2'-O-methyl modification. See, e.g., PCT Publication No. WO 2020/206350, the entire contents of which are incorporated herein by reference.

An exemplary 2'adem modified nucleotide is shown below:

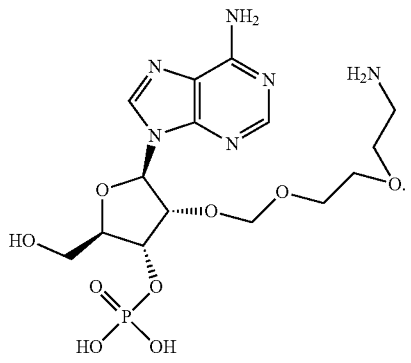 [SMILES: NCCOCCOCO[C@@H]1[C@H](OP(=O)(O)O)[C@@H](CO)O[C@H]1n1cnc2c(N)ncnc21]

The terms "blunt" or "blunt ended" as used herein in reference to a dsRNA mean that there are no unpaired nucleotides or nucleotide analogs at a given terminal end of a dsRNA, i.e., no nucleotide overhang. One or both ends of a dsRNA can be blunt. Where both ends of a dsRNA are blunt, the dsRNA is said to be blunt ended. To be clear, a "blunt ended" dsRNA is a dsRNA that is blunt at both ends, i.e., no nucleotide overhang at either end of the molecule. Most often such a molecule will be double stranded over its entire length.

The term "antisense strand" or "guide strand" refers to the strand of an RNAi agent, e.g., a dsRNA, which includes a region that is substantially complementary to a target sequence, e.g., an HTT mRNA.

As used herein, the term "region of complementarity" refers to the region on the antisense strand that is substantially complementary to a sequence, for example a target sequence, e.g., an HTT nucleotide sequence, as defined herein. Where the region of complementarity is not fully complementary to the target sequence, the mismatches can be in the internal or terminal regions of the molecule. Generally, the most tolerated mismatches are in the terminal regions, e.g., within 5, 4, 3, or 2 nucleotides of the 5'- or 3'-terminus of the RNAi agent. In some embodiments, a double stranded RNA agent of the invention includes a nucleotide mismatch in the antisense strand. In some embodiments, the antisense strand of the double stranded RNA agent of the invention includes no more than 4 mismatches with the target mRNA, e.g., the antisense strand includes 4, 3, 2, 1, or 0 mismatches with the target mRNA. In some embodiments, the antisense strand double stranded RNA agent of the invention includes no more than 4 mismatches with the sense strand, e.g., the antisense strand includes 4, 3, 2, 1, or 0 mismatches with the sense strand. In some embodiments, a double stranded RNA agent of the invention includes a nucleotide mismatch in the sense strand. In some embodiments, the sense strand of the double stranded RNA agent of the invention includes no more than 4 mismatches with the antisense strand, e.g., the sense strand includes 4, 3, 2, 1, or 0 mismatches with the antisense strand. In some embodiments, the nucleotide mismatch is, for example, within 5, 4, 3 nucleotides from the 3'-end of the iRNA. In another embodiment, the nucleotide mismatch is, for example, in the 3'-terminal nucleotide of the iRNA agent. In some embodiments, the mismatch(s) is not in the seed region.

Thus, an RNAi agent as described herein can contain one or more mismatches to the target sequence. In one embodiment, an RNAi agent as described herein contains no more than 3 mismatches (i.e., 3, 2, 1, or 0 mismatches). In one embodiment, an RNAi agent as described herein contains no more than 2 mismatches. In one embodiment, an RNAi agent as described herein contains no more than 1 mismatch. In one embodiment, an RNAi agent as described herein contains 0 mismatches. In certain embodiments, if the antisense strand of the RNAi agent contains mismatches to the target sequence, the mismatch can optionally be restricted to be within the last 5 nucleotides from either the 5'- or 3'-end of the region of complementarity. For example, in such embodiments, for a 23 nucleotide RNAi agent, the strand which is complementary to a region of an HTT gene, generally does not contain any mismatch within the central 13 nucleotides. The methods described herein or methods known in the art can be used to determine whether an RNAi agent containing a mismatch to a target sequence is effective in inhibiting the expression of an HTT gene. Consideration of the efficacy of RNAi agents with mismatches in inhibiting expression of an HTT gene is important, especially if the particular region of complementarity in an HTT gene is known to have polymorphic sequence variation within the population.

The term "sense strand" or "passenger strand" as used herein, refers to the strand of an RNAi agent that includes a region that is substantially complementary to a region of the antisense strand as that term is defined herein.

As used herein, the term "cleavage region" refers to a region that is located immediately adjacent to the cleavage site. The cleavage site is the site on the target at which cleavage occurs. In some embodiments, the cleavage region comprises three bases on either end of, and immediately adjacent to, the cleavage site. In some embodiments, the cleavage region comprises two bases on either end of, and immediately adjacent to, the cleavage site. In some embodiments, the cleavage site specifically occurs at the site bound by nucleotides 10 and 11 of the antisense strand, and the cleavage region comprises nucleotides 11, 12 and 13.

As used herein, and unless otherwise indicated, the term "complementary," when used to describe a first nucleotide sequence in relation to a second nucleotide sequence, refers to the ability of an oligonucleotide or polynucleotide comprising the first nucleotide sequence to hybridize and form a duplex structure under certain conditions with an oligonucleotide or polynucleotide comprising the second nucleotide sequence, as will be understood by the skilled person.

Complementary sequences within an RNAi agent, e.g., within a dsRNA as described herein, include base-pairing of the oligonucleotide or polynucleotide comprising a first nucleotide sequence to an oligonucleotide or polynucleotide comprising a second nucleotide sequence over the entire length of one or both nucleotide sequences. Such sequences can be referred to as "fully complementary" with respect to each other herein. However, where a first sequence is referred to as "substantially complementary" with respect to a second sequence herein, the two sequences can be fully complementary, or they can form one or more, but generally not more than 5, 4, 3 or 2 mismatched base pairs upon hybridization for a duplex up to 30 base pairs, while retaining the ability to hybridize under the conditions most relevant to their ultimate application, e.g., inhibition of gene expression via a RISC pathway. However, where two oligonucleotides are designed to form, upon hybridization, one or more single stranded overhangs, such overhangs shall not be regarded as mismatches with regard to the determination of complementarity. For example, a dsRNA comprising one oligonucleotide 21 nucleotides in length and another oligonucleotide 23 nucleotides in length, wherein the longer oligonucleotide comprises a sequence of 21 nucleotides that is fully complementary to the shorter oligonucleotide, can yet be referred to as "fully complementary" for the purposes described herein.

"Complementary" sequences, as used herein, can also include, or be formed entirely from, non-Watson-Crick base pairs or base pairs formed from non-natural and modified nucleotides, in so far as the above requirements with respect to their ability to hybridize are fulfilled. Such non-Watson-Crick base pairs include, but are not limited to, G:U Wobble or Hoogstein base pairing.

The terms "complementary," "fully complementary" and "substantially complementary" herein can be used with respect to the base matching between the sense strand and the antisense strand of a dsRNA, or between the antisense strand of an RNAi agent and a target sequence, as will be understood from the context of their use.

As used herein, a polynucleotide that is "substantially complementary to at least part of" a messenger RNA (mRNA) refers to a polynucleotide that is substantially complementary to a contiguous portion of the mRNA of interest (e.g., an mRNA encoding HTT). For example, a polynucleotide is complementary to at least a part of an HTT mRNA if the sequence is substantially complementary to a non-interrupted portion of an mRNA encoding HTT.

Accordingly, in some embodiments, the antisense polynucleotides disclosed herein are fully complementary to the target HTT sequence. In other embodiments, the antisense polynucleotides disclosed herein are substantially complementary to the target complement component HTT sequence and comprise a contiguous nucleotide sequence which is at least 80% complementary over its entire length to the equivalent region of the nucleotide sequence of any one of SEQ ID NOs:1-5, or a fragment of any one of SEQ ID NOs:1-5, such as about 85%, about 90%, about 91%, about 92%, about 93%, about 94%, about 95%, about 96%, about 97%, about 98%, or about 99% complementary.

In other embodiments, the antisense polynucleotides disclosed herein are substantially complementary to the target HTT sequence and comprise a contiguous nucleotide sequence which is at least about 80% complementary over its entire length to any one of the sense strand nucleotide sequences in any one of any one of Tables 2-5, or a fragment of any one of the sense strand nucleotide sequences in any one of Tables 2-5, such as about 85%, about 90%, about 91%, about 92%, about 93%, about 94%, about 95%, about 96%, about 97%, about 98%, about 99%, or 100% complementary.

In one embodiment, an RNAi agent of the disclosure includes a sense strand that is substantially complementary to an antisense polynucleotide which, in turn, is the same as a target HTT sequence, and wherein the sense strand polynucleotide comprises a contiguous nucleotide sequence which is at least about 80% complementary over its entire length to the equivalent region of the nucleotide sequence of SEQ ID NOs: 6-10, or a fragment of any one of SEQ ID NOs:6-10, such as about 85%, about 90%, about 91%, about 92%, about 93%, about 94%, about 95%, about 96%, about 97%, about 98%, about 99%, or 100% complementary.

In some embodiments, an iRNA of the invention includes a sense strand that is substantially complementary to an antisense polynucleotide which, in turn, is complementary to a target HTT sequence, and wherein the sense strand polynucleotide comprises a contiguous nucleotide sequence which is at least about 80% complementary over its entire length to any one of the antisense strand nucleotide sequences in any one of any one of Tables 2-5, or a fragment of any one of the antisense strand nucleotide sequences in any one of Tables 2-5, such as about 85%, about 90%, about 91%, about 92%, about 93%, about 94%, about 95%, about 96%, about 97%, about 98%, about 99%, or 100% complementary.

In one embodiment, at least partial suppression of the expression of an HTT gene, is assessed by a reduction of the amount of HTT mRNA which can be isolated from or detected in a first cell or group of cells in which an HTT gene is transcribed and which has or have been treated such that the expression of an HTT gene is inhibited, as compared to a second cell or group of cells substantially identical to the first cell or group of cells but which has or have not been so treated (control cells). The degree of inhibition may be expressed in terms of:

$$\frac{(\text{mRNA in control cells}) - (\text{mRNA in treated cells})}{(\text{mRNA in control cells})} \cdot 100\%$$

The phrase "contacting a cell with an RNAi agent," such as a dsRNA, as used herein, includes contacting a cell by any possible means. Contacting a cell with an RNAi agent includes contacting a cell in vitro with the RNAi agent or contacting a cell in vivo with the RNAi agent. The contacting may be done directly or indirectly. Thus, for example, the RNAi agent may be put into physical contact with the cell by the individual performing the method, or alternatively, the RNAi agent may be put into a situation that will permit or cause it to subsequently come into contact with the cell.

Contacting a cell in vitro may be done, for example, by incubating the cell with the RNAi agent. Contacting a cell in vivo may be done, for example, by injecting the RNAi agent into or near the tissue where the cell is located, or by injecting the RNAi agent into another area, e.g., the central nervous system (CNS), optionally via intrathecal, intravitreal or other injection, or to the bloodstream or the subcutaneous space, such that the agent will subsequently reach the tissue where the cell to be contacted is located. For example, the RNAi agent may contain or be coupled to a ligand, e.g., a lipophilic moiety or moieties as described below and further detailed, e.g., in PCT/US2019/031170, which is incorporated herein by reference, that directs or otherwise stabilizes the RNAi agent at a site of interest, e.g., the CNS. Combinations of in vitro and in vivo methods of contacting are also possible. For example, a cell may also be contacted in vitro with an RNAi agent and subsequently transplanted into a subject.

In one embodiment, contacting a cell with an RNAi agent includes "introducing" or "delivering the RNAi agent into the cell" by facilitating or effecting uptake or absorption into the cell. Absorption or uptake of an RNAi agent can occur through unaided diffusive or active cellular processes, or by auxiliary agents or devices. Introducing an RNAi agent into a cell may be in vitro or in vivo. For example, for in vivo introduction, an RNAi agent can be injected into a tissue site or administered systemically. In vitro introduction into a cell includes methods known in the art such as electroporation and lipofection. Further approaches are described herein below or are known in the art.

The term "lipophile" or "lipophilic moiety" broadly refers to any compound or chemical moiety having an affinity for lipids. One way to characterize the lipophilicity of the lipophilic moiety is by the octanol-water partition coefficient, log $K_{ow}$, where $K_{ow}$ is the ratio of a chemical's concentration in the octanol-phase to its concentration in the aqueous phase of a two-phase system at equilibrium. The octanol-water partition coefficient is a laboratory-measured property of a substance. However, it may also be predicted by using coefficients attributed to the structural components of a chemical which are calculated using first-principle or empirical methods (see, for example, Tetko et al., *J. Chem. Inf. Comput. Sci.* 41:1407-21 (2001), which is incorporated herein by reference in its entirety). It provides a thermodynamic measure of the tendency of the substance to prefer a non-aqueous or oily milieu rather than water (i.e. its hydrophilic/lipophilic balance). In principle, a chemical substance is lipophilic in character when its log $K_{ow}$ exceeds 0. Typically, the lipophilic moiety possesses a log $K_{ow}$ exceeding 1, exceeding 1.5, exceeding 2, exceeding 3, exceeding 4, exceeding 5, or exceeding 10. For instance, the log $K_{ow}$ of 6-amino hexanol, for instance, is predicted to be approximately 0.7. Using the same method, the log $K_{ow}$ of cholesteryl N-(hexan-6-ol) carbamate is predicted to be 10.7.

The lipophilicity of a molecule can change with respect to the functional group it carries. For instance, adding a hydroxyl group or amine group to the end of a lipophilic moiety can increase or decrease the partition coefficient (e.g., log $K_{ow}$) value of the lipophilic moiety.

Alternatively, the hydrophobicity of the double-stranded RNAi agent, conjugated to one or more lipophilic moieties, can be measured by its protein binding characteristics. For instance, in certain embodiments, the unbound fraction in the plasma protein binding assay of the double-stranded RNAi agent could be determined to positively correlate to the relative hydrophobicity of the double-stranded RNAi agent, which could then positively correlate to the silencing activity of the double-stranded RNAi agent.

In one embodiment, the plasma protein binding assay determined is an electrophoretic mobility shift assay (EMSA) using human serum albumin protein. An exemplary protocol of this binding assay is illustrated in detail in, e.g., PCT/US2019/031170. The hydrophobicity of the double-stranded RNAi agent, measured by fraction of unbound siRNA in the binding assay, exceeds 0.15, exceeds 0.2, exceeds 0.25, exceeds 0.3, exceeds 0.35, exceeds 0.4, exceeds 0.45, or exceeds 0.5 for an enhanced in vivo delivery of siRNA.

Accordingly, conjugating the lipophilic moieties to the internal position(s) of the double-stranded RNAi agent provides optimal hydrophobicity for the enhanced in vivo delivery of siRNA.

The term "lipid nanoparticle" or "LNP" is a vesicle comprising a lipid layer encapsulating a pharmaceutically active molecule, such as a nucleic acid molecule, e.g., a rNAi agent or a plasmid from which an RNAi agent is transcribed. LNPs are described in, for example, U.S. Pat. Nos. 6,858,225, 6,815,432, 8,158,601, and 8,058,069, the entire contents of which are hereby incorporated herein by reference.

As used herein, a "subject" is an animal, such as a mammal, including a primate (such as a human, a non-human primate, e.g., a monkey, and a chimpanzee), or a non-primate (such as a rat, or a mouse). In a preferred embodiment, the subject is a human, such as a human being treated or assessed for a disease, disorder, or condition that would benefit from reduction in HTT expression; a human at risk for a disease, disorder, or condition that would benefit from reduction in HTT expression; a human having a disease, disorder, or condition that would benefit from reduction in HTT expression; or human being treated for a disease, disorder, or condition that would benefit from reduction in HTT expression as described herein. In some embodiments, the subject is a female human. In other embodiments, the subject is a male human. In one embodiment, the subject is an adult subject. In one embodiment, the subject is a pediatric subject. In another embodiment, the subject is a juvenile subject, i.e., a subject below 20 years of age.

As used herein, the terms "treating" or "treatment" refer to a beneficial or desired result including, but not limited to, alleviation or amelioration of one or more signs or symptoms associated with HTT gene expression or HTT protein production, e.g., HTT-associated diseases, such as Huntington's disease. "Treatment" can also mean prolonging survival as compared to expected survival in the absence of treatment.

The term "lower" in the context of the level of HTT in a subject or a disease marker or symptom refers to a statistically significant decrease in such level. The decrease can be, for example, at least 10%, 15%, 20%, 25%, 30%, %, 40%, 45%, 50%, 55%, 60%, 65%, 70%, 75%, 80%, 85%, 90%, 95%, or more. In certain embodiments, a decrease is at least 20%. In certain embodiments, the decrease is at least 50% in a disease marker, e.g., protein or gene expression level. "Lower" in the context of the level of HTT in a subject is preferably down to a level accepted as within the range of normal for an individual without such disorder. In certain embodiments, "lower" is the decrease in the difference between the level of a marker or symptom for a subject suffering from a disease and a level accepted within the range of normal for an individual, e.g., the level of decrease in bodyweight between an obese individual and an individual having a weight accepted within the range of normal.

As used herein, "prevention" or "preventing," when used in reference to a disease, disorder, or condition thereof, that would benefit from a reduction in expression of an HTT gene or production of an HTT protein, refers to a reduction in the likelihood that a subject will develop a symptom associated with such a disease, disorder, or condition, e.g., a symptom of an HTT-associated disease. The failure to develop a disease, disorder, or condition, or the reduction in the development of a symptom associated with such a disease, disorder, or condition (e.g., by at least about 10% on a clinically accepted scale for that disease or disorder), or the exhibition of delayed symptoms delayed (e.g., by days, weeks, months or years) is considered effective prevention.

As used herein, the term "HTT-associated disease" or "HTT-associated disorder" is understood as any disease or disorder that would benefit from reduction in the expression and/or activity of HTT. Exemplary HTT-associated diseases include Huntington's disease.

"Huntington's disease," also known as HD, Huntington's Chorea, Chorea Maior, Chronic Progressive Chorea, and Hereditary Chorea, is an autosomal dominant genetic disorder characterized by choreiform movements and progressive intellectual deterioration, usually beginning in middle age (35 to 50 yr). The disease affects both sexes equally. The caudate nucleus atrophies, the small-cell population degenerates, and levels of the neurotransmitters gamma-aminobutyric acid (GABA) and substance P decrease. This degeneration results in characteristic "boxcar ventricles" seen on CT scans.

Symptoms and signs of HD develop insidiously. HD's most obvious symptoms are abnormal body movements called chorea and lack of coordination, but it also affects a number of mental abilities and some aspects of personality. These physical symptoms commonly become noticeable in a person's forties, but can occur at any age. If the age of onset is below 20 years then it is known as Juvenile HD.

Dementia or psychiatric disturbances, ranging from apathy and irritability to full-blown bipolar or schizophreniform disorder, may precede the movement disorder or develop during its course. Anhedonia or asocial behavior may be the first behavioral manifestation. Motor manifestations include flicking movements of the extremities, a lilting gait, motor impersistence (inability to sustain a motor act, such as tongue protrusion), facial grimacing, ataxia, and dystonia.

HD is caused by a trinucleotide repeat expansion in the Huntingtin (HTT) gene, and is one of several polyglutamine expansion (or PolyQ expansion) diseases. This produces an extended form of the mutant Huntingtin protein (mHtt), which causes cell death in selective areas of the brain.

"Therapeutically effective amount," as used herein, is intended to include the amount of an RNAi agent that, when administered to a subject having an HTT-associated disease, is sufficient to effect treatment of the disease (e.g., by diminishing, ameliorating, or maintaining the existing disease or one or more symptoms of disease). The "therapeutically effective amount" may vary depending on the RNAi agent, how the agent is administered, the disease and its severity and the history, age, weight, family history, genetic makeup, the types of preceding or concomitant treatments, if any, and other individual characteristics of the subject to be treated.

"Prophylactically effective amount," as used herein, is intended to include the amount of an RNAi agent that, when administered to a subject having an HTT-associated disorder, is sufficient to prevent or ameliorate the disease or one or more symptoms of the disease. Ameliorating the disease includes slowing the course of the disease or reducing the severity of later-developing disease. The "prophylactically effective amount" may vary depending on the RNAi agent, how the agent is administered, the degree of risk of disease, and the history, age, weight, family history, genetic makeup, the types of preceding or concomitant treatments, if any, and other individual characteristics of the patient to be treated.

A "therapeutically-effective amount" or "prophylactically effective amount" also includes an amount of an RNAi agent that produces some desired local or systemic effect at a reasonable benefit/risk ratio applicable to any treatment. An RNAi agent employed in the methods of the present disclosure may be administered in a sufficient amount to produce a reasonable benefit/risk ratio applicable to such treatment.

The phrase "pharmaceutically acceptable" is employed herein to refer to those compounds, materials (including salts), compositions, or dosage forms which are, within the scope of sound medical judgment, suitable for use in contact with the tissues of human subjects and animal subjects without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the subject being treated. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) lubricating agents, such as magnesium state, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates or polyanhydrides; (22) bulking agents, such as polypeptides and amino acids (23) serum component, such as serum albumin, HDL and LDL; and (22) other non-toxic compatible substances employed in pharmaceutical formulations.

The term "sample," as used herein, includes a collection of similar fluids, cells, or tissues isolated from a subject, as well as fluids, cells, or tissues present within a subject. Examples of biological fluids include blood, serum and serosal fluids, plasma, cerebrospinal fluid, ocular fluids, lymph, urine, saliva, and the like. Tissue samples may include samples from tissues, organs or localized regions. For example, samples may be derived from particular organs, parts of organs, or fluids or cells within those organs. In certain embodiments, samples may be derived from the brain (e.g., whole brain or certain segments of brain, e.g., striatum, or certain types of cells in the brain, such as, e.g., neurons and glial cells (astrocytes, oligodendrocytes, microglial cells)). In some embodiments, a "sample derived from a subject" refers to blood drawn from the subject or plasma or serum derived therefrom. In further embodiments, a "sample derived from a subject" refers to brain tissue (or subcomponents thereof) or retinal tissue (or subcomponents thereof) derived from the subject.

II. RNAi Agents of the Disclosure

Described herein are RNAi agents which inhibit the expression of an HTT gene. In one embodiment, the RNAi agent includes double stranded ribonucleic acid (dsRNA) molecules for inhibiting the expression of an HTT gene in a cell, such as a cell within a subject, e.g., a mammal, such as a human having an HTT-associated disease, e.g., Huntington's disease. The dsRNA includes an antisense strand having a region of complementarity which is complementary to at least a part of an mRNA formed in the expression of an HTT gene. The region of complementarity is about 15-30 nucleotides or less in length. Upon contact with a cell expressing the HTT gene, the RNAi agent inhibits the expression of the HTT gene (e.g., a human gene, a primate gene, a non-primate gene) by at least 50% as assayed by, for example, a PCR or branched DNA (bDNA)-based method, or by a protein-based method, such as by immunofluorescence analysis, using, for example, western blotting or flow cytometric techniques. In one, the level of knockdown is assayed in Cos 7 cells using a Dual-Luciferase assay method.

A dsRNA includes two RNA strands that are complementary and hybridize to form a duplex structure under conditions in which the dsRNA will be used. One strand of a dsRNA (the antisense strand) includes a region of complementarity that is substantially complementary, and generally fully complementary, to a target sequence. The target sequence can be derived from the sequence of an mRNA formed during the expression of an HTT gene. The other strand (the sense strand) includes a region that is complementary to the antisense strand, such that the two strands hybridize and form a duplex structure when combined under suitable conditions. As described elsewhere herein and as known in the art, the complementary sequences of a dsRNA can also be contained as self-complementary regions of a single nucleic acid molecule, as opposed to being on separate oligonucleotides.

Generally, the duplex structure is 15 to 30 base pairs in length, e.g., 15-29, 15-28, 15-27, 15-26, 15-25, 15-24, 15-23, 15-22, 15-21, 15-20, 15-19, 15-18, 15-17, 18-30, 18-29, 18-28, 18-27, 18-26, 18-25, 18-24, 18-23, 18-22, 18-21, 18-20, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24,20-23, 20-22, 20-21, 21-30, 21-29, 21-28, 21-27, 21-26, 21-25, 21-24, 21-23, or 21-22 base pairs in length. In certain preferred embodiments, the duplex structure is 18 to 25 base pairs in length, e.g., 18-25, 18-24, 18-23, 18-22, 18-21, 18-20, 19-25, 19-24, 19-23, 19-22, 19-21, 19-20, 20-25, 20-24,20-23, 20-22, 20-21, 21-25, 21-24, 21-23, 21-22, 22-25, 22-24, 22-23, 23-25, 23-24 or 24-25 base pairs in length, for example, 19-21 basepairs in length. Ranges and lengths intermediate to the above recited ranges and lengths are also contemplated to be part of the disclosure.

Similarly, the region of complementarity to the target sequence is 15 to 30 nucleotides in length, e.g., 15-29, 15-28, 15-27, 15-26, 15-25, 15-24, 15-23, 15-22, 15-21, 15-20, 15-19, 15-18, 15-17, 18-30, 18-29, 18-28, 18-27, 18-26, 18-25, 18-24, 18-23, 18-22, 18-21, 18-20, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24,20-23, 20-22, 20-21, 21-30, 21-29, 21-28, 21-27, 21-26, 21-25, 21-24, 21-23, or 21-22 nucleotides in length, for example 19-23 nucleotides in length or 21-23 nucleotides in length. Ranges and lengths intermediate to the above recited ranges and lengths are also contemplated to be part of the disclosure.

In some embodiments, the duplex structure is 19 to 30 base pairs in length. Similarly, the region of complementarity to the target sequence is 19 to 30 nucleotides in length.

In some embodiments, the dsRNA is 15 to 23 nucleotides in length, 19 to 23 nucleotides in length, or 25 to 30 nucleotides in length. In general, the dsRNA is long enough to serve as a substrate for the Dicer enzyme. For example, it is well known in the art that dsRNAs longer than about 21-23 nucleotides can serve as substrates for Dicer. As the ordinarily skilled person will also recognize, the region of an RNA targeted for cleavage will most often be part of a larger RNA molecule, often an mRNA molecule. Where relevant, a "part" of an mRNA target is a contiguous sequence of an mRNA target of sufficient length to allow it to be a substrate for RNAi-directed cleavage (i.e., cleavage through a RISC pathway).

One of skill in the art will also recognize that the duplex region is a primary functional portion of a dsRNA, e.g., a duplex region of about 15 to 36 base pairs, e.g., 15-36, 15-35, 15-34, 15-33, 15-32, 15-31, 15-30, 15-29, 15-28, 15-27, 15-26, 15-25, 15-24, 15-23, 15-22, 15-21, 15-20, 15-19, 15-18, 15-17, 18-30, 18-29, 18-28, 18-27, 18-26, 18-25, 18-24, 18-23, 18-22, 18-21, 18-20, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24,20-23, 20-22, 20-21, 21-30, 21-29, 21-28, 21-27, 21-26, 21-25, 21-24, 21-23, or 21-22 base pairs, for example, 19-21 base pairs. Thus, in one embodiment, to the extent that it becomes processed to a functional duplex, of e.g., 15-30 base pairs, that targets a desired RNA for cleavage, an RNA molecule or complex of RNA molecules having a duplex region greater than 30 base pairs is a dsRNA. Thus, an ordinarily skilled artisan will recognize that in one embodiment, a miRNA is a dsRNA. In another embodiment, a dsRNA is not a naturally occurring miRNA. In another embodiment, an RNAi agent useful to target HTT expression is not generated in the target cell by cleavage of a larger dsRNA.

A dsRNA as described herein can further include one or more single-stranded nucleotide overhangs e.g., 1, 2, 3, or 4 nucleotides. A nucleotide overhang can comprise or consist of a nucleotide/nucleoside analog, including a deoxynucleotide/nucleoside. The overhang(s) can be on the sense strand, the antisense strand or any combination thereof. Furthermore, the nucleotide(s) of an overhang can be present on the 5-end, 3-end or both ends of either an antisense or sense strand of a dsRNA.

A dsRNA can be synthesized by standard methods known in the art. Double stranded RNAi compounds of the invention may be prepared using a two-step procedure. First, the individual strands of the double stranded RNA molecule are prepared separately. Then, the component strands are annealed. The individual strands of the siRNA compound can be prepared using solution-phase or solid-phase organic synthesis or both. Organic synthesis offers the advantage that the oligonucleotide strands comprising unnatural or modified nucleotides can be easily prepared. Similarly, single-stranded oligonucleotides of the invention can be prepared using solution-phase or solid-phase organic synthesis or both.

In one aspect, a dsRNA of the disclosure includes at least two nucleotide sequences, a sense sequence and an antisense sequence. The sense strand sequence for HTT may be selected from the group of sequences provided in any one of Tables 2-5, and the corresponding nucleotide sequence of the antisense strand of the sense strand may be selected from the group of sequences of any one of Tables 2-5. In this aspect, one of the two sequences is complementary to the other of the two sequences, with one of the sequences being substantially complementary to a sequence of an mRNA generated in the expression of an HTT gene. As such, in this aspect, a dsRNA will include two oligonucleotides, where one oligonucleotide is described as the sense strand (passenger strand) in any one of Tables 2-5, and the second oligonucleotide is described as the corresponding antisense strand (guide strand) of the sense strand in any one of Tables 2-5.

In one embodiment, the substantially complementary sequences of the dsRNA are contained on separate oligonucleotides. In another embodiment, the substantially complementary sequences of the dsRNA are contained on a single oligonucleotide.

It will be understood that, although some of the sequences in Tables 2-5 are described as modified or conjugated sequences, the RNA of the RNAi agent of the disclosure e.g., a dsRNA of the disclosure, may comprise any one of the sequences set forth in any one of Tables 2-5 that is un-modified, un-conjugated, or modified or conjugated differently than described therein. For example, although the sense strands of the agents of the invention shown in Table 3 are conjugated to a C16 ligand, these agents may be conjugated to a moiety that directs delivery to the liver, e.g., a GalNAc ligand, as described herein. A lipophilic ligand can be included in any of the positions provided in the instant application.

The skilled person is well aware that dsRNAs having a duplex structure of about 20 to 23 base pairs, e.g., 21, base pairs have been hailed as particularly effective in inducing RNA interference (Elbashir et al., (2001) *EMBO J.,* 20:6877-6888). However, others have found that shorter or longer RNA duplex structures can also be effective (Chu and Rana (2007) *RNA* 14:1714-1719; Kim et al. (2005) *Nat Biotech* 23:222-226). In the embodiments described above, by virtue of the nature of the oligonucleotide sequences provided herein, dsRNAs described herein can include at least one strand of a length of minimally 21 nucleotides. It can be reasonably expected that shorter duplexes minus only a few nucleotides on one or both ends can be similarly effective as compared to the dsRNAs described above. Hence, dsRNAs having a sequence of at least 15, 16, 17, 18, 19, 20, or more contiguous nucleotides derived from one of the sequences provided herein, and differing in their ability to inhibit the expression of an HTT gene by not more than 10, 15, 20, 25, or 30% inhibition from a dsRNA comprising the full sequence using the in vitro assay with Cos 7 and a 10 nM concentration of the RNA agent and the PCR assay as provided in the examples herein, are contemplated to be within the scope of the present disclosure.

In addition, the RNAs described herein identify a site(s) in an HTT transcript that is susceptible to RISC-mediated cleavage. As such, the present disclosure further features RNAi agents that target within this site(s). As used herein, an RNAi agent is said to target within a particular site of an RNA transcript if the RNAi agent promotes cleavage of the transcript anywhere within that particular site. Such an RNAi agent will generally include at least about 15 contiguous nucleotides, preferably at least 19 nucleotides, from one of the sequences provided herein coupled to additional nucleotide sequences taken from the region contiguous to the selected sequence in an HTT gene.

III. Modified RNAi Agents of the Disclosure

In one embodiment, the RNA of the RNAi agent of the disclosure e.g., a dsRNA, is un-modified, and does not comprise, e.g., chemical modifications or conjugations known in the art and described herein. In preferred embodiments, the RNA of an RNAi agent of the disclosure, e.g., a dsRNA, is chemically modified to enhance stability or other beneficial characteristics. In certain embodiments of the disclosure, substantially all of the nucleotides of an RNAi agent of the disclosure are modified. In other embodiments of the disclosure, all of the nucleotides of an RNAi agent of the disclosure are modified. RNAi agents of the disclosure in which "substantially all of the nucleotides are modified" are largely but not wholly modified and can include not more than 5, 4, 3, 2, or unmodified nucleotides. In still other embodiments of the disclosure, RNAi agents of the disclosure can include not more than 5, 4, 3, 2 or 1 modified nucleotides.

The nucleic acids featured in the disclosure can be synthesized or modified by methods well established in the art, such as those described in "Current protocols in nucleic acid chemistry," Beaucage, S. L. et al. (Edrs.), John Wiley & Sons, Inc., New York, NY, USA, which is hereby incorporated herein by reference. Modifications include, for example, end modifications, e.g., 5'-end modifications (phosphorylation, conjugation, inverted linkages) or 3'-end modifications (conjugation, DNA nucleotides, inverted linkages, etc.); base modifications, e.g., replacement with stabilizing bases, destabilizing bases, or bases that base pair with an expanded repertoire of partners, removal of bases (abasic nucleotides), or conjugated bases; sugar modifications (e.g., at the 2'-position or 4'-position) or replacement of the sugar; or backbone modifications, including modification or replacement of the phosphodiester linkages. Specific examples of RNAi agents useful in the embodiments described herein include, but are not limited to, RNAs containing modified backbones or no natural internucleoside linkages. RNAs having modified backbones include, among others, those that do not have a phosphorus atom in the backbone. For the purposes of this specification, and as sometimes referenced in the art, modified RNAs that do not have a phosphorus atom in their internucleoside backbone can also be considered to be oligonucleosides. In some embodiments, a modified RNAi agent will have a phosphorus atom in its internucleoside backbone.

Modified RNA backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5'-linked analogs of these, and those having inverted polarity wherein the adjacent pairs of nucleoside units are linked 3'-5' to 5'-3' or 2'-5' to 5'-2'. Various salts, mixed salts and free acid forms are also included. In some embodiments of the invention, the dsRNA agents of the invention are in a free acid form. In other embodiments of the invention, the dsRNA agents of the invention are in a salt form. In one embodiment, the dsRNA agents of the invention are in a sodium salt form. In certain embodiments, when the dsRNA agents of the invention are in the sodium salt form, sodium ions are present in the agent as counterions for substantially all of the phosphodiester and/or phosphorothioate groups present in the agent. Agents in which substantially all of the phosphodiester and/or phosphorothioate linkages have a sodium counterion include not more than 5, 4, 3, 2, or 1 phosphodiester and/or phosphorothioate linkages without a sodium counterion. In some embodiments, when the dsRNA agents of the invention are in the sodium salt form, sodium ions are present in the agent as counterions for all of the phosphodiester and/or phosphorothioate groups present in the agent.

Representative U.S. patents that teach the preparation of the above phosphorus-containing linkages include, but are not limited to, U.S. Pat. Nos. 3,687,808; 4,469,863; 4,476,301; 5,023,243; 5,177,195; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,316; 5,550,111; 5,563,253; 5,571,799; 5,587,361; 5,625,050; 6,028,188; 6,124,445; 6,160,109; 6,169,170; 6,172,209; 6,239,265; 6,277,603; 6,326,199; 6,346,614; 6,444,423; 6,531,590; 6,534,639; 6,608,035; 6,683,167; 6,858,715; 6,867,294; 6,878,805; 7,015,315; 7,041,816; 7,273,933; 7,321,029; and U.S. Pat. RE39464, the entire contents of each of which are hereby incorporated herein by reference.

Modified RNA backbones that do not include a phosphorus atom therein have backbones that are formed by short chain alkyl or cycloalkyl internucleoside linkages, mixed heteroatoms and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative U.S. patents that teach the preparation of the above oligonucleosides include, but are not limited to, U.S. Pat. Nos. 5,034,506; 5,166,315; 5,185,444; 5,214,134; 5,216,141; 5,235,033; 5,64,562; 5,264,564; 5,405,938; 5,434,257; 5,466,677; 5,470,967; 5,489,677; 5,541,307; 5,561,225; 5,596,086; 5,602,240; 5,608,046; 5,610,289; 5,618,704; 5,623,070; 5,663,312; 5,633,360; 5,677,437; and, 5,677,439, the entire contents of each of which are hereby incorporated herein by reference.

In other embodiments, suitable RNA mimetics are contemplated for use in RNAi agents, in which both the sugar and the internucleoside linkage, i.e., the backbone, of the nucleotide units are replaced with novel groups. The base units are maintained for hybridization with an appropriate nucleic acid target compound. One such oligomeric compound, a RNA mimetic that has been shown to have excellent hybridization properties, is referred to as a peptide nucleic acid (PNA). In PNA compounds, the sugar backbone of an RNA is replaced with an amide containing backbone, in particular an aminoethylglycine backbone. The nucleobases are retained and are bound directly or indirectly to aza nitrogen atoms of the amide portion of the backbone. Representative U.S. patents that teach the preparation of PNA compounds include, but are not limited to, U.S. Pat. Nos. 5,539,082; 5,714,331; and 5,719,262, the entire contents of each of which are hereby incorporated herein by reference. Additional PNA compounds suitable for use in the RNAi agents of the disclosure are described in, for example, in Nielsen et al., *Science,* 1991, 254, 1497-1500.

Some embodiments featured in the disclosure include RNAs with phosphorothioate backbones and oligonucleosides with heteroatom backbones, and in particular $—CH_2—NH—CH_2—$, $—CH_2—N(CH_3)—O—CH_2—$[known as a methylene (methylimino) or MMI backbone], $—CH_2—O—N(CH_3)—CH_2—$, $—CH_2—N(CH_3)—N(CH_3)—CH_2—$ and $—N(CH_3)—CH_2—CH_2—$[wherein the native phosphodiester backbone is represented as $—O—P—O—CH_2—$] of the above-referenced U.S. Pat. No. 5,489,677, and the amide backbones of the above-referenced U.S. Pat. No. 5,602,240. In some embodiments, the RNAs featured herein have morpholino backbone structures of the above-referenced U.S. Pat. No. 5,034,506.

Modified RNAs can also contain one or more substituted sugar moieties. The RNAi agents, e.g., dsRNAs, featured herein can include one of the following at the 2'-position: OH; F; O-, S-, or N-alkyl; O-, S-, or N-alkenyl; O—, S- or N-alkynyl; or O-alkyl-O-alkyl, wherein the alkyl, alkenyl and alkynyl can be substituted or unsubstituted $C_1$ to $C_{10}$ alkyl or $C_2$ to $C_{10}$ alkenyl and alkynyl. Exemplary suitable modifications include $O[(CH_2)_nO]_mCH_3$, $O(CH_2)—OCH_3$, $O(CH_2)_nNH_2$, $O(CH_2)—CH_3$, $O(CH_2)_nONH_2$, and $O(CH_2)_nON[(CH_2)·CH_3)]_2$, where n and m are from 1 to about 10. In other embodiments, dsRNAs include one of the following at the 2' position: $C_1$ to $C_{10}$ lower alkyl, substituted lower alkyl, alkaryl, aralkyl, O-alkaryl or O-aralkyl, SH, $SCH_3$, OCN, $C_1$, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an RNAi agent, or a group for improving the pharmacodynamic properties of an RNAi agent, and other substituents having similar properties. In some embodiments, the modification includes a 2'-methoxyethoxy (2'-$O—CH_2CH_2OCH_3$, also known as 2'-O-(2-methoxyethyl) or 2'-MOE) (Martin et al., *Helv. Chim. Acta,* 1995, 78:486-504) i.e., an alkoxy-alkoxy group. Another exemplary modification is 2'-dimethylaminooxyethoxy, i.e., a $O(CH_2)_2ON(CH_3)_2$ group, also known as 2'-DMAOE, as described in examples herein below, and 2'-dimethylaminoethoxyethoxy (also known in the art as 2'-O-dimethylaminoethoxyethyl or 2'-DMAEOE), i.e., 2'-$O—CH_2—O—CH_2—N(CH_2)_2$. Further exemplary modifications include: 5'-Me-2'-F nucleotides, 5'-Me-2'-OMe nucleotides, 5'-Me-2'-deoxynucleotides, (both R and S isomers in these three families); 2'-alkoxyalkyl; and 2'-NMA (N-methylacetamide).

Other modifications include 2'-methoxy (2'-$OCH_3$), 2'-aminopropoxy (2'-$OCH_2CH_2CH_2NH_2$), 2'-O-hexadecyl, and 2'-fluoro (2'-F). Similar modifications can also be made at other positions on the RNA of an RNAi agent, particularly the 3' position of the sugar on the 3' terminal nucleotide or in 2'-5' linked dsRNAs and the 5' position of 5' terminal nucleotide. RNAi agents can also have sugar mimetics such as cyclobutyl moieties in place of the pentofuranosyl sugar. Representative U.S. patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, certain of which are commonly owned with the instant application. The entire contents of each of the foregoing are hereby incorporated herein by reference.

An RNAi agent of the disclosure can also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl anal other 8-substituted adenines and guanines, 5-halo, particularly 5-bromo, 5-trifluoromethyl and other 5-substituted uracils and cytosines, 7-methylguanine and 7-methyladenine, 8-azaguanine and 8-azaadenine, 7-deazaguanine and 7-daazaadenine and 3-deazaguanine and 3-deazaadenine. Further nucleobases include those disclosed in U.S. Pat. No. 3,687,808, those disclosed in Modified Nucleosides in Biochemistry, Biotechnology and Medicine, Herdewijn, P. ed. Wiley-VCH, 2008; those disclosed in The Concise Encyclopedia Of Polymer Science And Engineering, pages 858-859, Kroschwitz, J. L, ed. John Wiley & Sons, 1990, these disclosed by Englisch et al., (1991) *Angewandte Chemie, Interna-*

*tional Edition,* 30:613, and those disclosed by Sanghvi, Y S., Chapter 15, dsRNA Research and Applications, pages 289-302, Crooke, S. T. and Lebleu, B., Ed., CRC Press, 1993. Certain of these nucleobases are particularly useful for increasing the binding affinity of the oligomeric compounds featured in the disclosure. These include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., Eds., dsRNA Research and Applications, CRC Press, Boca Raton, 1993, pp. 276-278) and are exemplary base substitutions, even more particularly when combined with 2'-O-methoxyethyl sugar modifications.

Representative U.S. patents that teach the preparation of certain of the above noted modified nucleobases as well as other modified nucleobases include, but are not limited to, the above noted U.S. Pat. Nos. 3,687,808, 4,845,205; 5,130, 30; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,681,941; 5,750,692; 6,015,886; 6,147,200; 6,166,197; 6,222,025; 6,235,887; 6,380,368; 6,528,640; 6,639,062; 6,617,438; 7,045,610; 7,427,672; and 7,495,088, the entire contents of each of which are hereby incorporated herein by reference.

In some embodiments, an RNAi agent of the disclosure can also be modified to include one or more bicyclic sugar moieties. A "bicyclic sugar" is a furanosyl ring modified by a ring formed by the bridging of two carbons, whether adjacent or non-adjacent. A "bicyclic nucleoside" ("BNA") is a nucleoside having a sugar moiety comprising a ring formed by bridging two carbons, whether adjacent or non-adjacent, of the sugar ring, thereby forming a bicyclic ring system. In certain embodiments, the bridge connects the 4'-carbon and the 2'-carbon of the sugar ring, optionally, via the 2'-acyclic oxygen atom. Thus, in some embodiments an agent of the invention may include one or more locked nucleic acids (LNA). A locked nucleic acid is a nucleotide having a modified ribose moiety in which the ribose moiety comprises an extra bridge connecting the 2' and 4' carbons. In other words, an LNA is a nucleotide comprising a bicyclic sugar moiety comprising a 4'-$CH_2$—O-2' bridge. This structure effectively "locks" the ribose in the 3'-endo structural conformation. The addition of locked nucleic acids to siRNAs has been shown to increase siRNA stability in serum, and to reduce off-target effects (Elmen, J. et al., (2005) *Nucleic Acids Research* 33(1):439-447; Mook, O R. et al., (2007) *Mol Canc Ther* 6(3):833-843; Grunweller, A. et al., (2003) *Nucleic Acids Research* 31(12):3185-3193). Examples of bicyclic nucleosides for use in the polynucleotides of the invention include without limitation nucleosides comprising a bridge between the 4' and the 2' ribosyl ring atoms. In certain embodiments, the antisense polynucleotide agents of the invention include one or more bicyclic nucleosides comprising a 4' to 2' bridge.

A locked nucleoside can be represented by the structure (omitting stereochemistry),

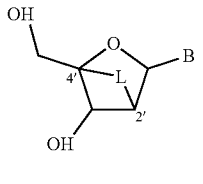

wherein B is a nucleobase or modified nucleobase and L is the linking group that joins the 2'-carbon to the 4'-carbon of the ribose ring. Examples of such 4' to 2' bridged bicyclic nucleosides, include but are not limited to 4'-($CH_2$)—O-2' (LNA); 4'-($CH_2$)—S-2'; 4'-$(CH_2)_2$-O-2' (ENA); 4'-CH($CH_3$)—O-2' (also referred to as "constrained ethyl" or "cEt") and 4'-CH($CH_2OCH_3$)—O-2' (and analogs thereof; see, e.g., U.S. Pat. No. 7,399,845); 4'-C($CH_3$)($CH_3$)—O-2' (and analogs thereof; see e.g., U.S. Pat. No. 8,278,283); 4'-$CH_2$—N($OCH_3$)-2' (and analogs thereof; see e.g., U.S. Pat. No. 8,278,425); 4'-$CH_2$—O—N($CH_3$)-2' (see, e.g., U.S. Patent Publication No. 2004/0171570); 4'-$CH_2$—N(R)—O-2', wherein R is H, $C_1$-$C_{12}$ alkyl, or a nitrogen protecting group (see, e.g., U.S. Pat. No. 7,427,672); 4'-$CH_2$—C(H)($CH_3$)-2' (see, e.g., Chattopadhyaya et al., *J. Org. Chem.,* 2009, 74, 118-134); and 4'-$CH_2$—C(=$CH_2$)-2' (and analogs thereof; see, e.g., U.S. Pat. No. 8,278,426). The entire contents of each of the foregoing are hereby incorporated herein by reference.

Additional representative U.S. Patents and U.S. Patent Publications that teach the preparation of locked nucleic acid nucleotides include, but are not limited to, the following: U.S. Pat. Nos. 6,268,490; 6,525,191; 6,670,461; 6,770,748; 6,794,499; 6,998,484; 7,053,207; 7,034,133; 7,084,125; 7,399,845; 7,427,672; 7,569,686; 7,741,457; 8,022,193; 8,030,467; 8,278,425; 8,278,426; 8,278,283; US 2008/0039618; and US 2009/0012281, the entire contents of each of which are hereby incorporated herein by reference.

Any of the foregoing bicyclic nucleosides can be prepared having one or more stereochemical sugar configurations including for example α-L-ribofuranose and β-D-ribofuranose (see WO 99/14226).

The RNA of an iRNA can also be modified to include one or more constrained ethyl nucleotides. As used herein, a "constrained ethyl nucleotide" or "cEt" is a locked nucleic acid comprising a bicyclic sugar moiety comprising a 4'-CH($CH_3$)—O-2' bridge (i.e., L in the preceding structure). In one embodiment, a constrained ethyl nucleotide is in the S conformation referred to herein as "S-cEt."

An iRNA of the invention may also include one or more "conformationally restricted nucleotides" ("CRN"). CRN are nucleotide analogs with a linker connecting the C2' and C4' carbons of ribose or the C3 and —C5' carbons of ribose. CRN lock the ribose ring into a stable conformation and increase the hybridization affinity to mRNA. The linker is of sufficient length to place the oxygen in an optimal position for stability and affinity resulting in less ribose ring puckering.

Representative publications that teach the preparation of certain of the above noted CRN include, but are not limited to, U.S. Patent Publication No. 2013/0190383; and PCT publication WO 2013/036868, the entire contents of each of which are hereby incorporated herein by reference.

In some embodiments, an iRNA of the invention comprises one or more monomers that are UNA (unlocked nucleic acid) nucleotides. UNA is unlocked acyclic nucleic acid, wherein any of the bonds of the sugar has been removed, forming an unlocked "sugar" residue. In one example, UNA also encompasses monomer with bonds between C1'-C4' have been removed (i.e. the covalent carbon-oxygen-carbon bond between the C1' and C4' carbons). In another example, the C2'-C3' bond (i.e. the covalent carbon-carbon bond between the C2' and C3' carbons) of the sugar has been removed (see *Nuc. Acids Symp. Series,* 52, 133-134 (2008) and Fluiter et al., *Mol. Biosyst.,* 2009, 10, 1039 hereby incorporated by reference).

Representative U.S. publications that teach the preparation of UNA include, but are not limited to, U.S. Pat. No. 8,314,227; and U.S. Patent Publication Nos. 2013/0096289; 2013/0011922; and 2011/0313020, the entire contents of each of which are hereby incorporated herein by reference.

Potentially stabilizing modifications to the ends of RNA molecules can include N-(acetylaminocaproyl)-4-hydroxyprolinol (Hyp-C6-NHAc), N-(caproyl-4-hydroxyprolinol (Hyp-C6), N-(acetyl-4-hydroxyprolinol (Hyp-NHAc), thymidine-2'-O-deoxythymidine (ether), N-(aminocaproyl)-4-hydroxyprolinol (Hyp-C6-amino), 2-docosanoyl-uridine-3'-phosphate, inverted 2'-deoxy-modified ribonucleotide, such as inverted dT(idT), inverted dA (idA), and inverted abasic 2'-deoxyribonucleotide (iAb) and others. Disclosure of this modification can be found in WO 2011/005861.

In one example, the 3' or 5' terminal end of a oligonucleotide is linked to an inverted 2'-deoxy-modified ribonucleotide, such as inverted dT(idT), inverted dA (idA), or a inverted abasic 2'-deoxyribonucleotide (iAb). In one particular example, the inverted 2'-deoxy-modified ribonucleotide is linked to the 3'end of an oligonucleotide, such as the 3'-end of a sense strand described herein, where the linking is via a 3'-3' phosphodiester linkage or a 3'-3'-phosphorothioate linkage.

In another example, the 3'-end of a sense strand is linked via a 3'-3'-phosphorothioate linkage to an inverted abasic ribonucleotide (iAb). In another example, the 3'-end of a sense strand is linked via a 3'-3'-phosphorothioate linkage to an inverted dA (idA).

In one particular example, the inverted 2'-deoxy-modified ribonucleotide is linked to the 3'end of an oligonucleotide, such as the 3'-end of a sense strand described herein, where the linking is via a 3'-3' phosphodiester linkage or a 3'-3'-phosphorothioate linkage.

In another example, the 3'-terminal nucleotides of a sense strand is an inverted dA (idA) and is linked to the preceding nucleotide via a 3'-3'-linkage (e.g., 3'-3'-phosphorothioate linkage).

Other modifications of the nucleotides of an iRNA of the invention include a 5'phosphate or 5' phosphate mimic, e.g., a 5'-terminal phosphate or phosphate mimic on the antisense strand of an iRNA. Suitable phosphate mimics are disclosed in, for example U.S. Patent Publication No. 2012/0157511, the entire contents of which are incorporated herein by reference.

A. Modified RNAi Agents Comprising Motifs of the Disclosure

In certain aspects of the disclosure, the double-stranded RNAi agents of the disclosure include agents with chemical modifications as disclosed, for example, in WO 2013/075035, the entire contents of which are incorporated herein by reference. As shown herein and in WO 2013/075035, a superior result may be obtained by introducing one or more motifs of three identical modifications on three consecutive nucleotides into a sense strand or antisense strand of an RNAi agent, particularly at or near the cleavage site. In some embodiments, the sense strand and antisense strand of the RNAi agent may otherwise be completely modified. The introduction of these motifs interrupts the modification pattern, if present, of the sense or antisense strand. The RNAi agent may be optionally conjugated with a lipophilic ligand, e.g., a C16 ligand, for instance on the sense strand. The RNAi agent may be optionally modified with a (S)-glycol nucleic acid (GNA) modification, for instance on one or more residues of the antisense strand. The resulting RNAi agents present superior gene silencing activity.

Accordingly, the disclosure provides double stranded RNAi agents capable of inhibiting the expression of a target gene (i.e., an HTT gene) in vivo. The RNAi agent comprises a sense strand and an antisense strand. Each strand of the RNAi agent may be 15-30 nucleotides in length. For example, each strand may be 16-30 nucleotides in length, 17-30 nucleotides in length, 25-30 nucleotides in length, 27-30 nucleotides in length, 17-23 nucleotides in length, 17-21 nucleotides in length, 17-19 nucleotides in length, 19-25 nucleotides in length, 19-23 nucleotides in length, 19-21 nucleotides in length, 21-25 nucleotides in length, or 21-23 nucleotides in length. In certain embodiments, each strand is 19-23 nucleotides in length.

The sense strand and antisense strand typically form a duplex double stranded RNA ("dsRNA"), also referred to herein as an "RNAi agent." The duplex region of an RNAi agent may be 15-30 nucleotide pairs in length. For example, the duplex region can be 16-30 nucleotide pairs in length, 17-30 nucleotide pairs in length, 27-30 nucleotide pairs in length, 17-23 nucleotide pairs in length, 17-21 nucleotide pairs in length, 17-19 nucleotide pairs in length, 19-25 nucleotide pairs in length, 19-23 nucleotide pairs in length, 19-21 nucleotide pairs in length, 21-25 nucleotide pairs in length, or 21-23 nucleotide pairs in length. In another example, the duplex region is selected from 15, 16, 17, 18, 19, 20, 21, 22, 23, 24, 25, 26, and 27 nucleotides in length. In preferred embodiments, the duplex region is 19-21 nucleotide pairs in length.

In one embodiment, the RNAi agent may contain one or more overhang regions or capping groups at the 3'-end, 5'-end, or both ends of one or both strands. The overhang can be 1-6 nucleotides in length, for instance 2-6 nucleotides in length, 1-5 nucleotides in length, 2-5 nucleotides in length, 1-4 nucleotides in length, 2-4 nucleotides in length, 1-3 nucleotides in length, 2-3 nucleotides in length, or 1-2 nucleotides in length. In preferred embodiments, the nucleotide overhang region is 2 nucleotides in length. The overhangs can be the result of one strand being longer than the other, or the result of two strands of the same length being staggered. The overhang can form a mismatch with the target mRNA or it can be complementary to the gene sequences being targeted or can be another sequence. The first and second strands can also be joined, e.g., by additional bases to form a hairpin, or by other non-base linkers.

In one embodiment, the nucleotides in the overhang region of the RNAi agent can each independently be a modified or unmodified nucleotide including, but no limited to 2'-sugar modified, such as, 2-F, 2'-O-methyl, thymidine (T), and any combinations thereof.

For example, TT can be an overhang sequence for either end on either strand. The overhang can form a mismatch with the target mRNA or it can be complementary to the gene sequences being targeted or can be another sequence.

The 5'- or 3'-overhangs at the sense strand, antisense strand or both strands of the RNAi agent may be phosphorylated. In some embodiments, the overhang region(s) contains two nucleotides having a phosphorothioate between the two nucleotides, where the two nucleotides can be the same or different. In one embodiment, the overhang is present at the 3'-end of the sense strand, antisense strand, or both strands. In one embodiment, this 3'-overhang is present in the antisense strand. In one embodiment, this 3'-overhang is present in the sense strand.

The RNAi agent may contain only a single overhang, which can strengthen the interference activity of the RNAi, without affecting its overall stability. For example, the single-stranded overhang may be located at the 3-terminal end of the sense strand or, alternatively, at the 3-terminal end of the antisense strand. The RNAi may also have a blunt end, located at the 5'-end of the antisense strand (or the 3'-end of the sense strand) or vice versa. Generally, the antisense strand of the RNAi has a nucleotide overhang at the 3'-end, and the 5'-end is blunt. While not wishing to be bound by theory, the asymmetric blunt end at the 5'-end of the antisense strand and 3'-end overhang of the antisense strand favor the guide strand loading into RISC process.

In one embodiment, the RNAi agent is a double ended bluntmer of 19 nucleotides in length, wherein the sense strand contains at least one motif of three 2'-F modifications on three consecutive nucleotides at positions 7, 8, 9 from the 5'end. The antisense strand contains at least one motif of three 2'-O-methyl modifications on three consecutive nucleotides at positions 11, 12, 13 from the 5'end.

In another embodiment, the RNAi agent is a double ended bluntmer of 20 nucleotides in length, wherein the sense strand contains at least one motif of three 2'-F modifications on three consecutive nucleotides at positions 8, 9, 10 from the 5'end. The antisense strand contains at least one motif of three 2'-O-methyl modifications on three consecutive nucleotides at positions 11, 12, 13 from the 5'end.

In yet another embodiment, the RNAi agent is a double ended bluntmer of 21 nucleotides in length, wherein the sense strand contains at least one motif of three 2'-F modifications on three consecutive nucleotides at positions 9, 10, 11 from the 5'end. The antisense strand contains at least one motif of three 2'-O-methyl modifications on three consecutive nucleotides at positions 11, 12, 13 from the 5'end.

In one embodiment, the RNAi agent comprises a 21 nucleotide sense strand and a 23 nucleotide antisense strand, wherein the sense strand contains at least one motif of three 2'-F modifications on three consecutive nucleotides at positions 9, 10, 11 from the 5'end; the antisense strand contains at least one motif of three 2'-O-methyl modifications on three consecutive nucleotides at positions 11, 12, 13 from the 5'end, wherein one end of the RNAi agent is blunt, while the other end comprises a 2 nucleotide overhang. Preferably, the 2 nucleotide overhang is at the 3'-end of the antisense strand. When the 2 nucleotide overhang is at the 3'-end of the antisense strand, there may be two phosphorothioate internucleotide linkages between the terminal three nucleotides, wherein two of the three nucleotides are the overhang nucleotides, and the third nucleotide is a paired nucleotide next to the overhang nucleotide. In one embodiment, the RNAi agent additionally has two phosphorothioate internucleotide linkages between the terminal three nucleotides at both the 5'-end of the sense strand and at the 5'-end of the antisense strand. In one embodiment, every nucleotide in the sense strand and the antisense strand of the RNAi agent, including the nucleotides that are part of the motifs are modified nucleotides. In one embodiment each residue is independently modified with a 2'-O-methyl or 3'-fluoro, e.g., in an alternating motif. Optionally, the RNAi agent further comprises a ligand (e.g., a lipophilic ligand, optionally a C16 ligand).

In one embodiment, the RNAi agent comprises a sense and an antisense strand, wherein the sense strand is 25-30 nucleotide residues in length, wherein starting from the 5' terminal nucleotide (position 1) positions 1 to 23 of the first strand comprise at least 8 ribonucleotides; the antisense strand is 36-66 nucleotide residues in length and, starting from the 3' terminal nucleotide, comprises at least 8 ribonucleotides in the positions paired with positions 1-23 of sense strand to form a duplex; wherein at least the 3' terminal nucleotide of antisense strand is unpaired with sense strand, and up to 6 consecutive 3' terminal nucleotides are unpaired with sense strand, thereby forming a 3' single stranded overhang of 1-6 nucleotides; wherein the 5' terminus of antisense strand comprises from 10-30 consecutive nucleotides which are unpaired with sense strand, thereby forming a 10-30 nucleotide single stranded 5' overhang; wherein at least the sense strand 5' terminal and 3' terminal nucleotides are base paired with nucleotides of antisense strand when sense and antisense strands are aligned for maximum complementarity, thereby forming a substantially duplexed region between sense and antisense strands; and antisense strand is sufficiently complementary to a target RNA along at least 19 ribonucleotides of antisense strand length to reduce target gene expression when the double stranded nucleic acid is introduced into a mammalian cell; and wherein the sense strand contains at least one motif of three 2'-F modifications on three consecutive nucleotides, where at least one of the motifs occurs at or near the cleavage site. The antisense strand contains at least one motif of three 2'-O-methyl modifications on three consecutive nucleotides at or near the cleavage site.

In one embodiment, the RNAi agent comprises sense and antisense strands, wherein the RNAi agent comprises a first strand having a length which is at least 25 and at most 29 nucleotides and a second strand having a length which is at most 30 nucleotides with at least one motif of three 2'-O-methyl modifications on three consecutive nucleotides at position 11, 12, 13 from the 5' end; wherein the 3' end of the first strand and the 5' end of the second strand form a blunt end and the second strand is 1-4 nucleotides longer at its 3' end than the first strand, wherein the duplex region region which is at least 25 nucleotides in length, and the second strand is sufficiently complementary to a target mRNA along at least 19 nucleotide of the second strand length to reduce target gene expression when the RNAi agent is introduced into a mammalian cell, and wherein dicer cleavage of the RNAi agent preferentially results in an siRNA comprising the 3' end of the second strand, thereby reducing expression of the target gene in the mammal. Optionally, the RNAi agent further comprises a ligand.

In one embodiment, the sense strand of the RNAi agent contains at least one motif of three identical modifications on three consecutive nucleotides, where one of the motifs occurs at the cleavage site in the sense strand.

In one embodiment, the antisense strand of the RNAi agent can also contain at least one motif of three identical modifications on three consecutive nucleotides, where one of the motifs occurs at or near the cleavage site in the antisense strand.

For an RNAi agent having a duplex region of 17-23 nucleotide in length, the cleavage site of the antisense strand is typically around the 10, 11 and 12 positions from the 5'-end. Thus the motifs of three identical modifications may occur at the 9, 10, 11 positions; 10, 11, 12 positions; 11, 12, 13 positions; 12, 13, 14 positions; or 13, 14, 15 positions of the antisense strand, the count starting from the $1^{st}$ nucleotide from the 5'-end of the antisense strand, or, the count starting from the 1V paired nucleotide within the duplex region from the 5'-end of the antisense strand. The cleavage site in the antisense strand may also change according to the length of the duplex region of the RNAi from the 5'-end.

The sense strand of the RNAi agent may contain at least one motif of three identical modifications on three consecutive nucleotides at the cleavage site of the strand; and the antisense strand may have at least one motif of three identical modifications on three consecutive nucleotides at or near the cleavage site of the strand. When the sense strand and the antisense strand form a dsRNA duplex, the sense strand and the antisense strand can be so aligned that one motif of the three nucleotides on the sense strand and one motif of the three nucleotides on the antisense strand have at least one nucleotide overlap, i.e., at least one of the three nucleotides of the motif in the sense strand forms a base pair with at least one of the three nucleotides of the motif in the antisense strand. Alternatively, at least two nucleotides may overlap, or all three nucleotides may overlap.

In one embodiment, the sense strand of the RNAi agent may contain more than one motif of three identical modifications on three consecutive nucleotides. The first motif may occur at or near the cleavage site of the strand and the other motifs may be a wing modification. The term "wing modification" herein refers to a motif occurring at another portion of the strand that is separated from the motif at or near the cleavage site of the same strand. The wing modification is either adjacent to the first motif or is separated by at least one or more nucleotides. When the motifs are immediately adjacent to each other then the chemistry of the motifs are distinct from each other and when the motifs are separated by one or more nucleotide than the chemistries can be the same or different. Two or more wing modifications may be present. For instance, when two wing modifications are present, each wing modification may occur at one end relative to the first motif which is at or near cleavage site or on either side of the lead motif.

Like the sense strand, the antisense strand of the RNAi agent may contain more than one motif of three identical modifications on three consecutive nucleotides, with at least one of the motifs occurring at or near the cleavage site of the strand. This antisense strand may also contain one or more wing modifications in an alignment similar to the wing modifications that may be present on the sense strand.

In one embodiment, the wing modification on the sense strand or antisense strand of the RNAi agent typically does not include the first one or two terminal nucleotides at the 3'-end, 5'-end or both ends of the strand.

In another embodiment, the wing modification on the sense strand or antisense strand of the RNAi agent typically does not include the first one or two paired nucleotides within the duplex region at the 3'-end, 5'-end or both ends of the strand.

When the sense strand and the antisense strand of the RNAi agent each contain at least one wing modification, the wing modifications may fall on the same end of the duplex region, and have an overlap of one, two or three nucleotides.

When the sense strand and the antisense strand of the RNAi agent each contain at least two wing modifications, the sense strand and the antisense strand can be so aligned that two modifications each from one strand fall on one end of the duplex region, having an overlap of one, two or three nucleotides; two modifications each from one strand fall on the other end of the duplex region, having an overlap of one, two or three nucleotides; two modifications one strand fall on each side of the lead motif, having an overlap of one, two, or three nucleotides in the duplex region.

In one embodiment, the RNAi agent comprises mismatch(es) with the target, within the duplex, or combinations thereof. The mistmatch may occur in the overhang region or the duplex region. The base pair may be ranked on the basis of their propensity to promote dissociation or melting (e.g., on the free energy of association or dissociation of a particular pairing, the simplest approach is to examine the pairs on an individual pair basis, though next neighbor or similar analysis can also be used). In terms of promoting dissociation: A:U is preferred over G:C; G:U is preferred over G:C; and J:C is preferred over G:C (I=inosine). Mismatches, e.g., non-canonical or other than canonical pairings (as described elsewhere herein) are preferred over canonical (A:T, A:U, G:C) pairings; and pairings which include a universal base are preferred over canonical pairings.

In one embodiment, the RNAi agent comprises at least one of the first 1, 2, 3, 4, or 5 base pairs within the duplex regions from the 5'-end of the antisense strand independently selected from the group of: A:U, G:U, J:C, and mismatched pairs, e.g., non-canonical or other than canonical pairings or pairings which include a universal base, to promote the dissociation of the antisense strand at the 5'-end of the duplex.

In one embodiment, the nucleotide at the 1 position within the duplex region from the 5'-end in the antisense strand is selected from the group consisting of A, dA, dU, U, and dT. Alternatively, at least one of the first 1, 2 or 3 base pair within the duplex region from the 5'-end of the antisense strand is an AU base pair. For example, the first base pair within the duplex region from the 5'-end of the antisense strand is an AU base pair.

In another embodiment, the nucleotide at the 3'-end of the sense strand is deoxy-thymine (dT). In another embodiment, the nucleotide at the 3'-end of the antisense strand is deoxy-thymine (dT). In one embodiment, there is a short sequence of deoxy-thymine nucleotides, for example, two dT nucleotides on the 3'-end of the sense or antisense strand.

In one embodiment, the sense strand sequence may be represented by formula (I):

$$5'\ n_p\text{-}N_a\text{-}(X\ X\ X)_i\text{-}N_b\text{-}Y\ Y\ Y\text{-}N_b\text{-}(Z\ Z\ Z)_j\text{-}N_a\text{-}n_q\ 3' \quad (I)$$

wherein:

i and j are each independently 0 or 1;

p and q are each independently 0-6;

each $N_a$ independently represents an oligonucleotide sequence comprising 0-25 modified nucleotides, each sequence comprising at least two differently modified nucleotides;

each $N_b$ independently represents an oligonucleotide sequence comprising 0-10 modified nucleotides;

each $n_p$ and $n_q$ independently represent an overhang nucleotide;

wherein Nb and Y do not have the same modification; and

XXX, YYY and ZZZ each independently represent one motif of three identical modifications on three consecutive nucleotides. Preferably YYY is all 2'-F modified nucleotides.

In one embodiment, the $N_a$ or $N_b$ comprise modifications of alternating pattern.

In one embodiment, the YYY motif occurs at or near the cleavage site of the sense strand. For example, when the RNAi agent has a duplex region of 17-23 nucleotides in length, the YYY motif can occur at or the vicinity of the cleavage site (e.g.: can occur at positions 6, 7, 8, 7, 8, 9, 8, 9, 10, 9, 10, 11, 10, 11, 12 or 11, 12, 13) of—the sense strand, the count starting from the $1^{st}$ nucleotide, from the 5'-end; or optionally, the count starting at the $1^{st}$ paired nucleotide within the duplex region, from the 5'-end.

In one embodiment, i is 1 and j is 0, or i is 0 and j is 1, or both i and j are 1. The sense strand can therefore be represented by the following formulas:

$$5'\ n_p\text{-}N_a\text{-YYY-}N_b\text{-ZZZ-}N_a\text{-}n_q\ 3'; \quad \text{(Ib)}$$

$$5'\ n_p\text{-}N_a\text{-XXX-}N_b\text{-YYY-}N_a\text{-}n_q\ 3'; \quad \text{(Ic)}$$

or $$5'\ n_p\text{-}N_a\text{-XXX-}N_b\text{-YYY-}N_b\text{-ZZZ-}N_a\text{-}n_q\ 3'. \quad \text{(Id)}$$

When the sense strand is represented by formula (Ib), $N_b$ represents an oligonucleotide sequence comprising 0-10, 0-7, 0-5, 0-4, 0-2 or 0 modified nucleotides.

Each $N_a$ independently can represent an oligonucleotide sequence comprising 2-20, 2-15, or 2-10 modified nucleotides.

When the sense strand is represented as formula (Ic), $N_b$ represents an oligonucleotide sequence comprising 0-10, 0-7, 0-10, 0-7, 0-5, 0-4, 0-2 or 0 modified nucleotides. Each $N_a$ can independently represent an oligonucleotide sequence comprising 2-20, 2-15, or 2-10 modified nucleotides.

When the sense strand is represented as formula (Id), each $N_b$ independently represents an oligonucleotide sequence comprising 0-10, 0-7, 0-5, 0-4, 0-2 or 0 modified nucleotides. Preferably, $N_b$ is 0, 1, 2, 3, 4, 5 or 6. Each $N_a$ can independently represent an oligonucleotide sequence comprising 2-20, 2-15, or 2-10 modified nucleotides.

Each of X, Y and Z may be the same or different from each other.

In other embodiments, i is 0 and j is 0, and the sense strand may be represented by the formula:

$$5'\ n_p\text{-}N_a\text{-YYY-}N_a\text{-}n_q\ 3'. \quad \text{(Ia)}$$

When the sense strand is represented by formula (Ia), each $N_a$ independently can represent an oligonucleotide sequence comprising 2-20, 2-15, or 2-10 modified nucleotides.

In one embodiment, the antisense strand sequence of the RNAi may be represented by formula (II):

$$5'\ n_q'\text{-}N_a'\text{-(Z'Z'Z')}_k\text{-}N_b'\text{-Y'Y'Y'-}N_b'\text{-(X'X'X')}_l\text{-}N'_a\text{-}n_p'\ 3' \quad \text{(II)}$$

wherein:

k and 1 are each independently 0 or 1;

p' and q' are each independently 0-6;

each $N_a'$ independently represents an oligonucleotide sequence comprising 0-25 modified nucleotides, each sequence comprising at least two differently modified nucleotides;

each $N_b'$ independently represents an oligonucleotide sequence comprising 0-10 modified nucleotides;

each $n_p'$ and $n_q'$ independently represent an overhang nucleotide;

wherein $N_b'$ and Y' do not have the same modification; and

X'X'X', Y'Y'Y' and Z'Z'Z' each independently represent one motif of three identical modifications on three consecutive nucleotides.

In one embodiment, the $N_a'$ or $N_b'$ comprise modifications of alternating pattern.

The Y'Y'Y' motif occurs at or near the cleavage site of the antisense strand. For example, when the RNAi agent has a duplex region of 17-23 nucleotide in length, the Y'Y'Y' motif can occur at positions 9, 10, 11; 10, 11, 12; 11, 12, 13; 12, 13, 14; or 13, 14, 15 of the antisense strand, with the count starting from the 1$^{st}$ nucleotide, from the 5'-end; or optionally, the count starting at the 1 paired nucleotide within the duplex region, from the 5'-end. Preferably, the Y'Y'Y' motif occurs at positions 11, 12, 13.

In one embodiment, Y'Y'Y' motif is all 2'-OMe modified nucleotides.

In one embodiment, k is 1 and 1 is 0, or k is 0 and 1 is 1, or both k and 1 are 1.

The antisense strand can therefore be represented by the following formulas:

$$5'\ n_q'\text{-}N_a'\text{-Z'Z'Z'-}N_b'\text{-Y'Y'Y'-}N_a'\text{-}n_p'\ 3'; \quad \text{(IIb)}$$

$$5'\ n_q'\text{-}N_a'\text{-Y'Y'Y'-}N_b'\text{-X'X'X'-}n_p\ 3'; \quad \text{(IIc)}$$

or $$5'\ n_q'\text{-}N_a'\text{-Z'Z'Z'-}N_b'\text{-Y'Y'Y'-}N_b'\text{-X'X'X'-}N_a'\text{-}n_p\ 3'. \quad \text{(IId)}$$

When the antisense strand is represented by formula (IIb), $N_b'$ represents an oligonucleotide sequence comprising 0-10, 0-7, 0-10, 0-7, 0-5, 0-4, 0-2 or 0 modified nucleotides. Each $N_a'$ independently represents an oligonucleotide sequence comprising 2-20, 2-15, or 2-10 modified nucleotides.

When the antisense strand is represented as formula (IIc), $N_b'$ represents an oligonucleotide sequence comprising 0-10, 0-7, 0-10, 0-7, 0-5, 0-4, 0-2 or 0 modified nucleotides. Each $N_a'$ independently represents an oligonucleotide sequence comprising 2-20, 2-15, or 2-10 modified nucleotides.

When the antisense strand is represented as formula (IId), each $N_b'$ independently represents an oligonucleotide sequence comprising 0-10, 0-7, 0-10, 0-7, 0-5, 0-4, 0-2 or 0 modified nucleotides. Each $N_a'$ independently represents an oligonucleotide sequence comprising 2-20, 2-15, or 2-10 modified nucleotides. Preferably, $N_b$ is 0, 1, 2, 3, 4, 5 or 6.

In other embodiments, k is 0 and 1 is 0 and the antisense strand may be represented by the formula:

$$5'\ n_p'\text{-}N_a'\text{-Y'Y'Y'-}N_a'\text{-}n_q'\ 3'. \quad \text{(Ia)}$$

When the antisense strand is represented as formula (IIa), each $N_a'$ independently represents an oligonucleotide sequence comprising 2-20, 2-15, or 2-10 modified nucleotides.

Each of X', Y' and Z' may be the same or different from each other.

Each nucleotide of the sense strand and antisense strand may be independently modified with LNA, HNA, CeNA, 2'-methoxyethyl, 2'-O-methyl, 2'-O-allyl, 2'-C-allyl, 2'-hydroxyl, or 2'-fluoro. For example, each nucleotide of the sense strand and antisense strand is independently modified with 2'-O-methyl or 2'-fluoro. Each X, Y, Z, X', Y' and Z', in particular, may represent a 2'-O-methyl modification or a 2'-fluoro modification.

In one embodiment, the sense strand of the RNAi agent may contain YYY motif occurring at 9, 10 and 11 positions of the strand when the duplex region is 21 nt, the count starting from the 1V nucleotide from the 5'-end, or optionally, the count starting at the 1st paired nucleotide within the duplex region, from the 5'-end; and Y represents 2'-F modification. The sense strand may additionally contain XXX motif or ZZZ motifs as wing modifications at the opposite end of the duplex region; and XXX and ZZZ each independently represents a 2'-OMe modification or 2'-F modification.

In one embodiment the antisense strand may contain Y'Y'Y' motif occurring at positions 11, 12, 13 of the strand, the count starting from the 1st nucleotide from the 5'-end, or optionally, the count starting at the 1st paired nucleotide within the duplex region, from the 5'-end; and Y' represents 2'-O-methyl modification. The antisense strand may additionally contain X'X'X' motif or Z'Z'Z' motifs as wing modifications at the opposite end of the duplex region; and X'X'X' and Z'Z'Z' each independently represents a 2'-OMe modification or 2'-F modification.

The sense strand represented by any one of the above formulas (Ia), (Ib), (Ic), and (Id) forms a duplex with a antisense strand being represented by any one of formulas (IIa), (IIb), (IIc), and (IId), respectively.

Accordingly, the RNAi agents for use in the methods of the disclosure may comprise a sense strand and an antisense strand, each strand having 14 to 30 nucleotides, the RNAi duplex represented by formula (III):

(III)

sense:

$$5'\ n_p\text{-}N_a\text{-}(X\ X\ X)_i\text{-}N_b\text{-}Y\ Y\ Y\text{-}N_b\text{-}(Z\ Z\ Z)_j\text{-}N_a\text{-}n_q\ 3'$$

antisense:

$$3'\ n_p'\text{-}N_a\text{-}(X'X'X')_k\text{-}N_b'\text{-}Y'Y'Y'\text{-}N_b'\text{-}(Z'Z'Z')_l\text{-}N_a'\text{-}n_q'\ 5'$$

wherein:

i, j, k, and 1 are each independently 0 or 1;

p, p', q, and q' are each independently 0-6;

each $N_a$ and $N_a$ independently represents an oligonucleotide sequence comprising 0-25 modified nucleotides, each sequence comprising at least two differently modified nucleotides;

each $N_b$ and $N_b$ independently represents an oligonucleotide sequence comprising 0-10 modified nucleotides;

wherein each $n_p'$, $n_p$, $n_q'$, and $n_q$, each of which may or may not be present, independently represents an overhang nucleotide; and XXX, YYY, ZZZ, X'X'X', Y'Y'Y', and Z'Z'Z' each independently represent one motif of three identical modifications on three consecutive nucleotides.

In one embodiment, i is 0 and j is 0; or i is 1 and j is 0; or i is 0 and j is 1; or both i and j are 0; or both i and j are 1. In another embodiment, k is 0 and 1 is 0; or k is 1 and 1 is 0; k is 0 and 1 is 1; or both k and 1 are 0; or both k and 1 are 1.

Exemplary combinations of the sense strand and antisense strand forming an RNAi duplex include the formulas below:

(IIIa)

$$5'\ n_p\text{-}N_a\text{-}Y\ Y\ Y\text{-}N_a\text{-}n_q\ 3'$$

$$3'\ n_p'\text{-}N_a'\text{-}Y'Y'Y'\text{-}N_a'n_q'\ 5'$$

(IIIb)

$$5'\ n_p\text{-}N_a\text{-}Y\ Y\ Y\text{-}N_b\text{-}ZZZ\text{-}N_a\text{-}n_q\ 3'$$

$$3'\ n_p'\text{-}N_a'\text{-}Y'Y'Y'\text{-}N_b'\text{-}Z'Z'Z'\text{-}N_a'n_q'\ 5'$$

(IIIc)

$$5'\ n_p\text{-}N_a\text{-}X\ X\ X\text{-}N_b\text{-}Y\ Y\ Y\text{-}N_a\text{-}n_q\ 3'$$

$$3'\ n_p'\text{-}N_a'\text{-}X'X'X'\text{-}N_b'\text{-}Y'Y'Y'\text{-}N_a'\text{-}n_q'\ 5'$$

(IIId)

$$5'\ n_p\text{-}N_a\text{-}X\ X\ X\text{-}N_b\text{-}Y\ Y\ Y\text{-}N_b\text{-}ZZZ\text{-}N_a\text{-}n_q\ 3'$$

$$3'\ n_p'\text{-}N_a'\text{-}X'X'X'\text{-}N_b'\text{-}Y'Y'Y'\text{-}N_b'\text{-}Z'Z'Z'\text{-}N_b\text{-}n_q'\ 5'$$

When the RNAi agent is represented by formula (IIIa), each $N_a$ independently represents an oligonucleotide sequence comprising 2-20, 2-15, or 2-10 modified nucleotides.

When the RNAi agent is represented by formula (IIIb), each $N_b$ independently represents an oligonucleotide sequence comprising 1-10, 1-7, 1-5 or 1-4 modified nucleotides. Each $N_a$ independently represents an oligonucleotide sequence comprising 2-20, 2-15, or 2-10 modified nucleotides.

When the RNAi agent is represented as formula (IIIc), each $N_b$, $N_b'$ independently represents an oligonucleotide sequence comprising 0-10, 0-7, 0-10, 0-7, 0-5, 0-4, 0-2 or 0 modified nucleotides. Each $N_a$ independently represents an oligonucleotide sequence comprising 2-20, 2-15, or 2-10 modified nucleotides.

When the RNAi agent is represented as formula (IIId), each $N_b$, $N_b'$ independently represents an oligonucleotide sequence comprising 0-10, 0-7, 0-10, 0-7, 0-5, 0-4, 0-2 or 0 modified nucleotides. Each $N_a$, $N_a$ independently represents an oligonucleotide sequence comprising 2-20, 2-15, or 2-10 modified nucleotides. Each of $N_a$, $N_a'$, $N_b$ and $N_b'$ independently comprises modifications of alternating pattern.

In one embodiment, when the RNAi agent is represented by formula (IIId), the $N_a$ modifications are 2'-O-methyl or 2'-fluoro modifications. In another embodiment, when the RNAi agent is represented by formula (IIId), the $N_a$ modifications are 2'-O-methyl or 2'-fluoro modifications and $n_p'>0$ and at least one $n_p'$ is linked to a neighboring nucleotide a via phosphorothioate linkage. In yet another embodiment, when the RNAi agent is represented by formula (IIId), the $N_a$ modifications are 2'-O-methyl or 2'-fluoro modifications, $n_p'>0$ and at least one $n_p'$ is linked to a neighboring nucleotide via phosphorothioate linkage, and the sense strand is conjugated to one or more C16 (or related) moieties attached through a bivalent or trivalent branched linker (described below). In another embodiment, when the RNAi agent is represented by formula (IIId), the $N_a$ modifications are 2'-O-methyl or 2'-fluoro modifications, $n_p'>0$ and at least one $n_p'$ is linked to a neighboring nucleotide via phosphorothioate linkage, the sense strand comprises at least one phosphorothioate linkage, and the sense strand is conjugated to one or more lipophilic, e.g., C16 (or related) moieties, optionally attached through a bivalent or trivalent branched linker.

In one embodiment, when the RNAi agent is represented by formula (IIIa), the $N_a$ modifications are 2'-O-methyl or 2'-fluoro modifications, $n_p$'>0 and at least one $n_p$' is linked to a neighboring nucleotide via phosphorothioate linkage, the sense strand comprises at least one phosphorothioate linkage, and the sense strand is conjugated to one or more lipophilic, e.g., C16 (or related) moieties attached through a bivalent or trivalent branched linker.

In one embodiment, the RNAi agent is a multimer containing at least two duplexes represented by formula (III), (IIIa), (IIIb), (IIIc), and (IIId), wherein the duplexes are connected by a linker. The linker can be cleavable or non-cleavable. Optionally, the multimer further comprises a ligand. Each of the duplexes can target the same gene or two different genes; or each of the duplexes can target same gene at two different target sites.

In one embodiment, the RNAi agent is a multimer containing three, four, five, six or more duplexes represented by formula (III), (IIIa), (IIIb), (IIIc), and (IIId), wherein the duplexes are connected by a linker. The linker can be cleavable or non-cleavable. Optionally, the multimer further comprises a ligand. Each of the duplexes can target the same gene or two different genes; or each of the duplexes can target same gene at two different target sites.

In one embodiment, two RNAi agents represented by formula (III), (IIIa), (IIIb), (IIIc), and (IIId) are linked to each other at the 5' end, and one or both of the 3' ends and are optionally conjugated to a ligand. Each of the agents can target the same gene or two different genes; or each of the agents can target same gene at two different target sites.

Various publications describe multimeric RNAi agents that can be used in the methods of the disclosure. Such publications include WO2007/091269, WO2010/141511, WO2007/117686, WO2009/014887, and WO2011/031520; and U.S. Pat. No. 7,858,769, the entire contents of each of which are hereby incorporated herein by reference.

In certain embodiments, the compositions and methods of the disclosure include a vinyl phosphonate (VP) modification of an RNAi agent as described herein. In exemplary embodiments, a 5' vinyl phosphonate modified nucleotide of the disclosure has the structure:

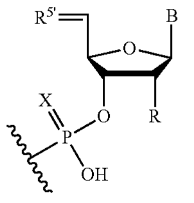

wherein X is O or S;

R is hydrogen, hydroxy, fluoro, or $C_{1-20}$ alkoxy (e.g., methoxy or n-hexadecyloxy);

$R^{5'}$ is $=C(H)-P(O)(OH)_2$ and the double bond between the C5' carbon and $R^{5'}$ is in the E or Z orientation (e.g., E orientation); and B is a nucleobase or a modified nucleobase, optionally where B is adenine, guanine, cytosine, thymine, or uracil.

In one embodiment, $R^{5'}$ is $=C(H)-P(O)(OH)_2$ and the double bond between the C5' carbon and R5' is in the E orientation. In another embodiment, R is methoxy and $R^{5'}$ is $=C(H)-P(O)(OH)_2$ and the double bond between the C5' carbon and R5' is in the E orientation. In another embodiment, X is S, R is methoxy, and $R^{5'}$ is $=C(H)-P(O)(OH)_2$ and the double bond between the C5' carbon and R5' is in the E orientation.

A vinyl phosphonate of the instant disclosure may be attached to either the antisense or the sense strand of a dsRNA of the disclosure. In certain embodiments, a vinyl phosphonate of the instant disclosure is attached to the antisense strand of a dsRNA, optionally at the 5' end of the antisense strand of the dsRNA.

Vinyl phosphate modifications are also contemplated for the compositions and methods of the instant disclosure. An exemplary vinyl phosphate structure includes the preceding structure, where R5' is $=C(H)-OP(O)(OH)_2$ and the double bond between the C5' carbon and R5' is in the E or Z orientation (e.g., E orientation).

i. Thermally Destabilizing Modifications

In certain embodiments, a dsRNA molecule can be optimized for RNA interference by incorporating thermally destabilizing modifications in the seed region of the antisense strand (i.e., at positions 2-9 of the 5'-end of the antisense strand) to reduce or inhibit off-target gene silencing. It has been discovered that dsRNAs with an antisense strand comprising at least one thermally destabilizing modification of the duplex within the first 9 nucleotide positions, counting from the 5' end, of the antisense strand have reduced off-target gene silencing activity. Accordingly, in some embodiments, the antisense strand comprises at least one (e.g., one, two, three, four, five or more) thermally destabilizing modification of the duplex within the first 9 nucleotide positions of the 5' region of the antisense strand. In some embodiments, one or more thermally destabilizing modification(s) of the duplex is/are located in positions 2-9, or preferably positions 4-8, from the 5'-end of the antisense strand. In some further embodiments, the thermally destabilizing modification(s) of the duplex is/are located at position 6, 7 or 8 from the 5'-end of the antisense strand. In still some further embodiments, the thermally destabilizing modification of the duplex is located at position 7 from the 5'-end of the antisense strand. The term "thermally destabilizing modification(s)" includes modification(s) that would result with a dsRNA with a lower overall melting temperature (Tm) (preferably a Tm with one, two, three or four degrees lower than the Tm of the dsRNA without having such modification(s). In some embodiments, the thermally destabilizing modification of the duplex is located at position 2, 3, 4, 5 or 9 from the 5'-end of the antisense strand.

The thermally destabilizing modifications can include, but are not limited to, abasic modification; mismatch with the opposing nucleotide in the opposing strand; and sugar modification such as 2'-deoxy modification, acyclic nucleotide, e.g., unlocked nucleic acids (UNA) or glycol nucleic acid (GNA); and 2'-5'-linked ribonucleotides ("3'-RNA").

Exemplified abasic modifications include, but are not limited to the following:

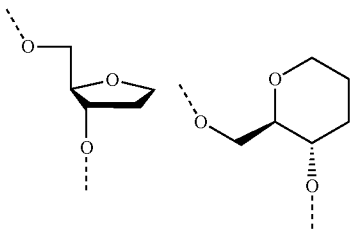

-continued

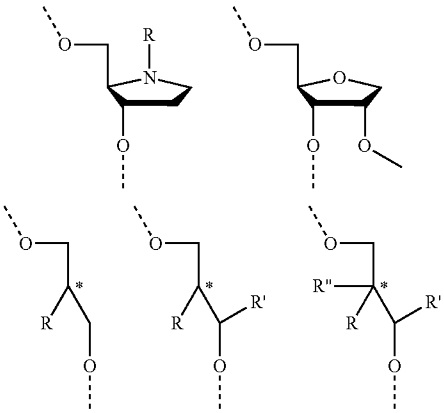

Wherein R=H, Me, Et or OMe; R'=H, Me, Et or OMe; R"=H, Me, Et or OMe

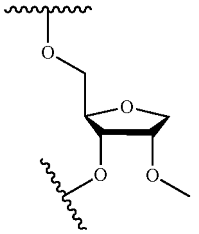

Mod2
(2'-OMe Abasic Spacer)

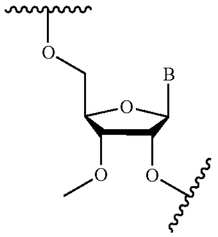

Mod3
(3'-OMe)

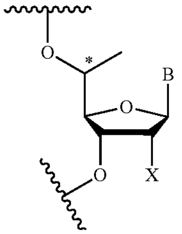

Mod4
(5'-Me)
X = OMe, F

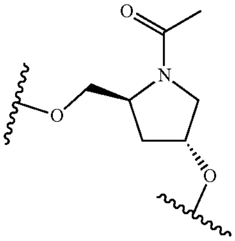

Mod5
(Hyp-spacer)

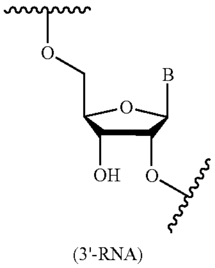

(3'-RNA)

wherein B is a modified or unmodified nucleobase.

Exemplified sugar modifications include, but are not limited to the following:

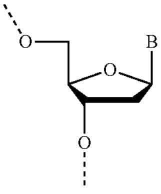

2'-deoxy

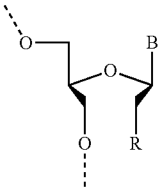

unlocked nucleic acid
R = H, OH, O-alkyl

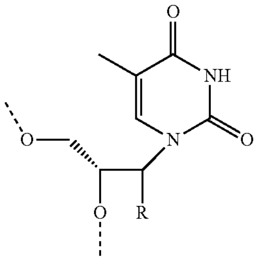

glycol nucleic acid
R = H, OH, O-alkyl

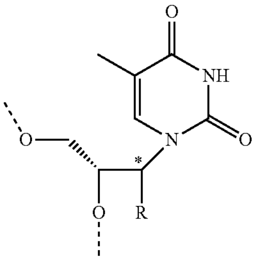

glycol nucleic acid
R = H, OH, O-alkyl

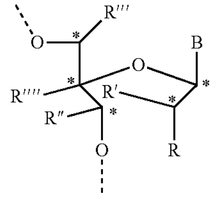

unlocked nucleic acid
R = H, OH, $CH_3$, $CH_2CH_3$, O-alkyl, $NH_2$, NHMe, $NMe_2$
R' = H, OH, $CH_3$, $CH_2CH_3$, O-alkyl, $NH_2$, NHMe, $NMe_2$
R'' = H, OH, $CH_3$, $CH_2CH_3$, O-alkyl, $NH_2$, NHMe, $NMe_2$
R''' = H, OH, $CH_3$, $CH_2CH_3$, O-alkyl, $NH_2$, NHMe, $NMe_2$
R'''' = H, OH, $CH_3$, $CH_2CH_3$, O-alkyl, $NH_2$, NHMe, $NMe_2$

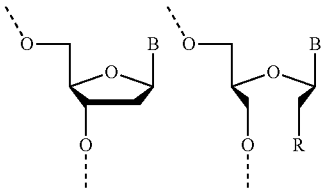

R = H, methyl, ethyl wherein B is a modified or unmodified nucleobase.

In some embodiments the thermally destabilizing modification of the duplex is selected from the group consisting of:

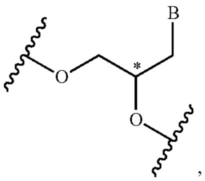

,

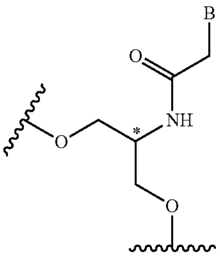

,

-continued

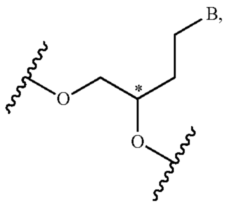
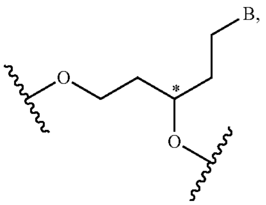

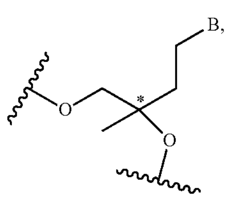
and
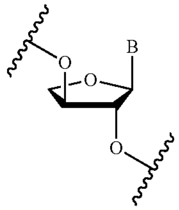
and

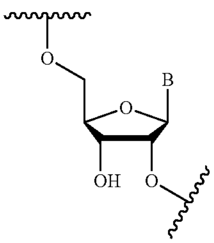

wherein B is a modified or unmodified nucleobase and the asterisk on each structure represents either R, S or racemic.

In some embodiments the thermally destabilizing modification of the duplex is selected from the group consisting of:

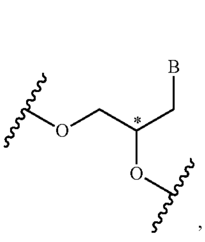
,
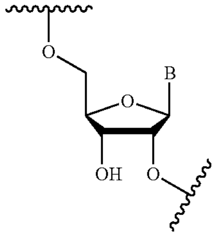

wherein B is a modified or unmodified nucleobase and the asterisk represents either R, S or racemic (e.g., S).

The term "acyclic nucleotide" refers to any nucleotide having an acyclic ribose sugar, for example, where any of bonds between the ribose carbons (e.g., C1'-C2', C2'-C3', C3'-C4', C4'-C4', or C1'-C4') is absent or at least one of ribose carbons or oxygen (e.g., C1', C2', C3', C4' or 04') are independently or in combination absent from the nucleotide. In some embodiments, acyclic nucleotide is

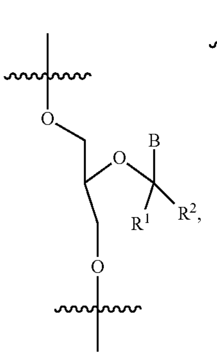
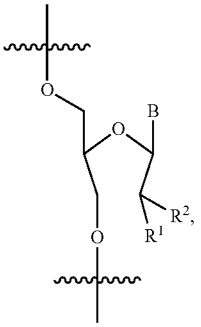

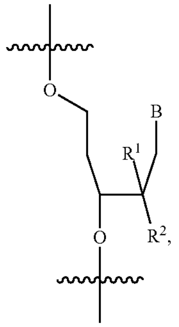
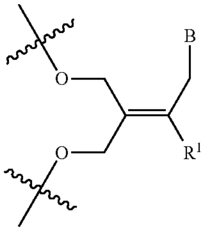
or

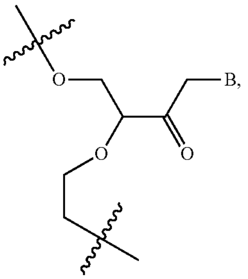

when B is a modified or unmodified nucleobase, $R^1$ and $R^2$ independently are H, halogen, $OR_3$, or alkyl; and $R_3$ is H, alkyl, cycloalkyl, aryl, aralkyl, heteroaryl or sugar). The term "UNA" refers to unlocked acyclic nucleic acid, wherein any of the bonds of the sugar has been removed, forming an unlocked "sugar" residue. In one example, UNA also encompasses monomers with bonds between C1'-C4' being removed (i.e. the covalent carbon-oxygen-carbon bond between the C1' and C4' carbons). In another example, the C2'-C3' bond (i.e. the covalent carbon-carbon bond between the C2' and C3' carbons) of the sugar is removed (see Mikhailov et. al., Tetrahedron Letters, 26 (17): 2059 (1985); and Fluiter et al., Mol. Biosyst., 10: 1039 (2009), which are hereby incorporated by reference in their entirety). The acyclic derivative provides greater backbone flexibility without affecting the Watson-Crick pairings. The acyclic nucleotide can be linked via 2'-5' or 3'-5' linkage.

The term 'GNA' refers to glycol nucleic acid which is a polymer similar to DNA or RNA but differing in the composition of its "backbone" in that is composed of repeating glycerol units linked by phosphodiester bonds:

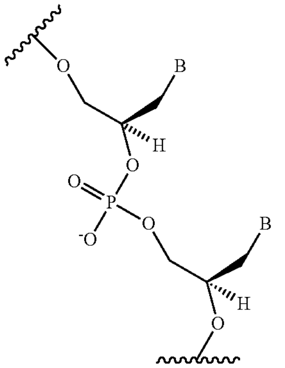

(R)-GNA

The thermally destabilizing modification of the duplex can be mismatches (i.e., noncomplementary base pairs) between the thermally destabilizing nucleotide and the opposing nucleotide in the opposite strand within the dsRNA duplex. Exemplary mismatch base pairs include G:G, G:A, G:U, G:T, A:A, A:C, C:C, C:U, C:T, U:U, T:T, U:T, or a combination thereof. Other mismatch base pairings known in the art are also amenable to the present invention. A mismatch can occur between nucleotides that are either naturally occurring nucleotides or modified nucleotides, i.e., the mismatch base pairing can occur between the nucleobases from respective nucleotides independent of the modifications on the ribose sugars of the nucleotides. In certain embodiments, the dsRNA molecule contains at least one nucleobase in the mismatch pairing that is a 2'-deoxy nucleobase; e.g., the 2'-deoxy nucleobase is in the sense strand.

In some embodiments, the thermally destabilizing modification of the duplex in the seed region of the antisense strand includes nucleotides with impaired W—C H-bonding to complementary base on the target mRNA, such as:

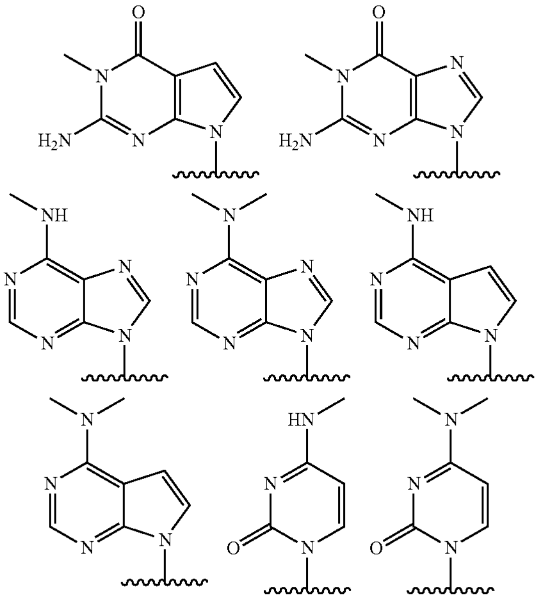

-continued

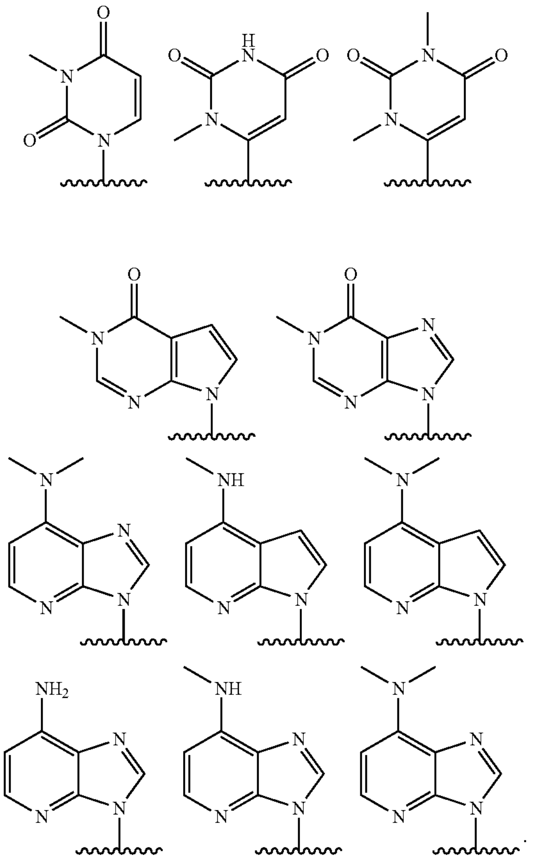

More examples of abasic nucleotide, acyclic nucleotide modifications (including UNA and GNA), and mismatch modifications have been described in detail in WO 2011/133876, which is herein incorporated by reference in its entirety.

The thermally destabilizing modifications may also include universal base with reduced or abolished capability to form hydrogen bonds with the opposing bases, and phosphate modifications.

In some embodiments, the thermally destabilizing modification of the duplex includes nucleotides with non-canonical bases such as, but not limited to, nucleobase modifications with impaired or completely abolished capability to form hydrogen bonds with bases in the opposite strand. These nucleobase modifications have been evaluated for destabilization of the central region of the dsRNA duplex as described in WO 2010/0011895, which is herein incorporated by reference in its entirety. Exemplary nucleobase modifications are:

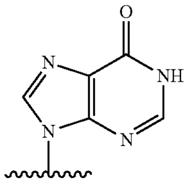

inosine

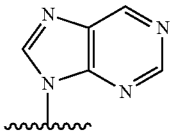

nebularine

-continued

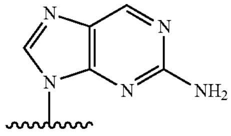

2-aminopurine

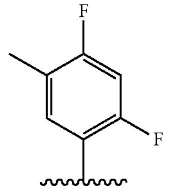

2,4-difluorotoluene

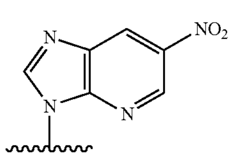

5-nitroindole

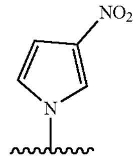

3-nitropyrrole

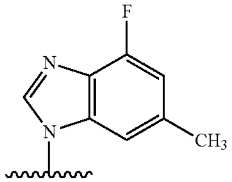

4-Fluoro-6-methylbenzimidazole

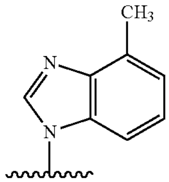

4-Methylbenzimidazole

In some embodiments, the thermally destabilizing modification of the duplex in the seed region of the antisense strand includes one or more α-nucleotide complementary to the base on the target mRNA, such as:

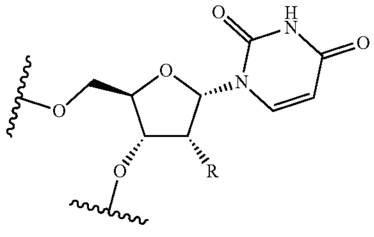

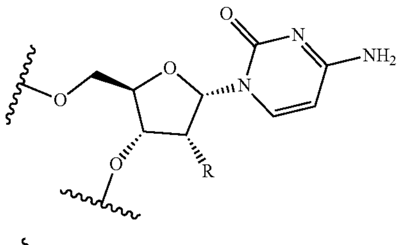

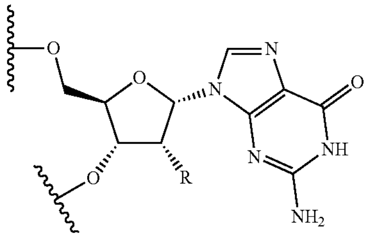

-continued

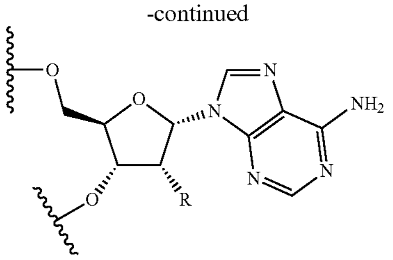

wherein R is H, OH, $OCH_3$, F, $NH_2$, NHMe, $NMe_2$ or O-alkyl.

Exemplary phosphate modifications known to decrease the thermal stability of dsRNA duplexes compared to natural phosphodiester linkages are:

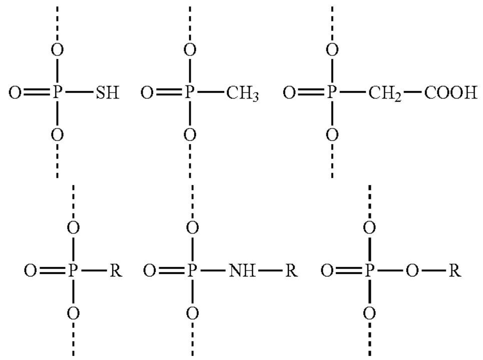

R = alkyl

The alkyl for the R group can be a C1-C6alkyl. Specific alkyls for the R group include, but are not limited to methyl, ethyl, propyl, isopropyl, butyl, pentyl and hexyl.

As the skilled artisan will recognize, in view of the functional role of nucleobases is defining specificity of an RNAi agent of the disclosure, while nucleobase modifications can be performed in the various manners as described herein, e.g., to introduce destabilizing modifications into an RNAi agent of the disclosure, e.g., for purpose of enhancing on-target effect relative to off-target effect, the range of modifications available and, in general, present upon RNAi agents of the disclosure tends to be much greater for non-nucleobase modifications, e.g., modifications to sugar groups or phosphate backbones of polyribonucleotides. Such modifications are described in greater detail in other sections of the instant disclosure and are expressly contemplated for RNAi agents of the disclosure, either possessing native nucleobases or modified nucleobases as described above or elsewhere herein.

In addition to the antisense strand comprising a thermally destabilizing modification, the dsRNA can also comprise one or more stabilizing modifications. For example, the dsRNA can comprise at least two (e.g., two, three, four, five, six, seven, eight, nine, ten or more) stabilizing modifications. Without limitations, the stabilizing modifications all can be present in one strand. In some embodiments, both the sense and the antisense strands comprise at least two stabilizing modifications. The stabilizing modification can occur on any nucleotide of the sense strand or antisense strand. For instance, the stabilizing modification can occur on every nucleotide on the sense strand or antisense strand; each stabilizing modification can occur in an alternating pattern on the sense strand or antisense strand; or the sense strand or antisense strand comprises both stabilizing modification in an alternating pattern. The alternating pattern of the stabilizing modifications on the sense strand may be the same or different from the antisense strand, and the alternating pattern of the stabilizing modifications on the sense strand can have a shift relative to the alternating pattern of the stabilizing modifications on the antisense strand.

In some embodiments, the antisense strand comprises at least two (e.g., two, three, four, five, six, seven, eight, nine, ten or more) stabilizing modifications. Without limitations, a stabilizing modification in the antisense strand can be present at any positions. In some embodiments, the antisense comprises stabilizing modifications at positions 2, 6, 8, 9, 14, and 16 from the 5'-end. In some other embodiments, the antisense comprises stabilizing modifications at positions 2, 6, 14, and 16 from the 5'-end. In still some other embodiments, the antisense comprises stabilizing modifications at positions 2, 14, and 16 from the 5'-end.

In some embodiments, the antisense strand comprises at least one stabilizing modification adjacent to the destabilizing modification. For example, the stabilizing modification can be the nucleotide at the 5'-end or the 3'-end of the destabilizing modification, i.e., at position −1 or +1 from the position of the destabilizing modification. In some embodiments, the antisense strand comprises a stabilizing modification at each of the 5'-end and the 3'-end of the destabilizing modification, i.e., positions −1 and +1 from the position of the destabilizing modification.

In some embodiments, the antisense strand comprises at least two stabilizing modifications at the 3'-end of the destabilizing modification, i.e., at positions+1 and +2 from the position of the destabilizing modification.

In some embodiments, the sense strand comprises at least two (e.g., two, three, four, five, six, seven, eight, nine, ten or more) stabilizing modifications. Without limitations, a stabilizing modification in the sense strand can be present at any positions. In some embodiments, the sense strand comprises stabilizing modifications at positions 7, 10, and 11 from the 5'-end. In some other embodiments, the sense strand comprises stabilizing modifications at positions 7, 9, 10, and 11 from the 5'-end. In some embodiments, the sense strand comprises stabilizing modifications at positions opposite or complimentary to positions 11, 12, and 15 of the antisense strand, counting from the 5'-end of the antisense strand. In some other embodiments, the sense strand comprises stabilizing modifications at positions opposite or complimentary to positions 11, 12, 13, and 15 of the antisense strand, counting from the 5'-end of the antisense strand. In some embodiments, the sense strand comprises a block of two, three, or four stabilizing modifications.

In some embodiments, the sense strand does not comprise a stabilizing modification in position opposite or complimentary to the thermally destabilizing modification of the duplex in the antisense strand.

Exemplary thermally stabilizing modifications include, but are not limited to, 2'-fluoro modifications. Other thermally stabilizing modifications include, but are not limited to, LNA.

In some embodiments, the dsRNA of the disclosure comprises at least four (e.g., four, five, six, seven, eight, nine, ten, or more) 2'-fluoro nucleotides. Without limitations, the 2'-fluoro nucleotides all can be present in one strand. In some embodiments, both the sense and the antisense strands comprise at least two 2'-fluoro nucleotides. The 2'-fluoro modification can occur on any nucleotide of the sense strand or antisense strand. For instance, the 2'-fluoro modification can occur on every nucleotide on the sense strand or antisense strand; each 2'-fluoro modification can occur in an alternating pattern on the sense strand or antisense strand; or the sense strand or antisense strand comprises both 2'-fluoro modifications in an alternating pattern. The alternating pattern of the 2'-fluoro modifications on the sense strand may be the same or different from the antisense strand, and the alternating pattern of the 2'-fluoro modifications on the sense strand can have a shift relative to the alternating pattern of the 2'-fluoro modifications on the antisense strand.

In some embodiments, the antisense strand comprises at least two (e.g., two, three, four, five, six, seven, eight, nine, ten, or more) 2'-fluoro nucleotides. Without limitations, a 2'-fluoro modification in the antisense strand can be present at any positions. In some embodiments, the antisense comprises 2'-fluoro nucleotides at positions 2, 6, 8, 9, 14, and 16 from the 5'-end. In some other embodiments, the antisense comprises 2'-fluoro nucleotides at positions 2, 6, 14, and 16 from the 5'-end. In still some other embodiments, the antisense comprises 2'-fluoro nucleotides at positions 2, 14, and 16 from the 5'-end.

In some embodiments, the antisense strand comprises at least one 2'-fluoro nucleotide adjacent to the destabilizing modification. For example, the 2'-fluoro nucleotide can be the nucleotide at the 5'-end or the 3'-end of the destabilizing modification, i.e., at position −1 or +1 from the position of the destabilizing modification. In some embodiments, the antisense strand comprises a 2'-fluoro nucleotide at each of the 5'-end and the 3'-end of the destabilizing modification, i.e., positions −1 and +1 from the position of the destabilizing modification.

In some embodiments, the antisense strand comprises at least two 2'-fluoro nucleotides at the 3'-end of the destabilizing modification, i.e., at positions+1 and +2 from the position of the destabilizing modification.

In some embodiments, the sense strand comprises at least two (e.g., two, three, four, five, six, seven, eight, nine, ten or more) 2'-fluoro nucleotides. Without limitations, a 2'-fluoro modification in the sense strand can be present at any positions. In some embodiments, the antisense comprises 2'-fluoro nucleotides at positions 7, 10, and 11 from the 5'-end. In some other embodiments, the sense strand comprises 2'-fluoro nucleotides at positions 7, 9, 10, and 11 from the 5'-end. In some embodiments, the sense strand comprises 2'-fluoro nucleotides at positions opposite or complimentary to positions 11, 12, and 15 of the antisense strand, counting from the 5'-end of the antisense strand. In some other embodiments, the sense strand comprises 2'-fluoro nucleotides at positions opposite or complimentary to positions 11, 12, 13, and 15 of the antisense strand, counting from the 5'-end of the antisense strand. In some embodiments, the sense strand comprises a block of two, three or four 2'-fluoro nucleotides.

In some embodiments, the sense strand does not comprise a 2'-fluoro nucleotide in position opposite or complimentary to the thermally destabilizing modification of the duplex in the antisense strand.

In some embodiments, the dsRNA molecule of the disclosure comprises a 21 nucleotides (nt) sense strand and a 23 nucleotides (nt) antisense, wherein the antisense strand contains at least one thermally destabilizing nucleotide, where the at least one thermally destabilizing nucleotide occurs in the seed region of the antisense strand (i.e., at position 2-9 of the 5'-end of the antisense strand), wherein one end of the dsRNA is blunt, while the other end is comprises a 2 nt overhang, and wherein the dsRNA optionally further has at least one (e.g., one, two, three, four, five, six or all seven) of the following characteristics: (i) the antisense comprises 2, 3, 4, 5 or 6 2'-fluoro modifications; (ii) the antisense comprises 1, 2, 3, 4 or 5 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3, 4 or 5 phosphorothioate internucleotide linkages; (vi) the dsRNA comprises at least four 2'-fluoro modifications; and (vii) the dsRNA comprises a blunt end at 5'-end of the antisense strand. Preferably, the 2 nt overhang is at the 3'-end of the antisense.

In some embodiments, the dsRNA molecule of the disclosure comprise a sense and antisense strands, wherein: the sense strand is 25-30 nucleotide residues in length, wherein starting from the 5' terminal nucleotide (position 1), positions 1 to 23 of said sense strand comprise at least 8 ribonucleotides; antisense strand is 36-66 nucleotide residues in length and, starting from the 3' terminal nucleotide, at least 8 ribonucleotides in the positions paired with positions 1-23 of sense strand to form a duplex; wherein at least the 3' terminal nucleotide of antisense strand is unpaired with sense strand, and up to 6 consecutive 3' terminal nucleotides are unpaired with sense strand, thereby forming a 3' single stranded overhang of 1-6 nucleotides; wherein the 5' terminus of antisense strand comprises from 10-30 consecutive nucleotides which are unpaired with sense strand, thereby forming a 10-30 nucleotide single stranded 5' overhang; wherein at least the sense strand 5' terminal and 3' terminal nucleotides are base paired with nucleotides of antisense strand when sense and antisense strands are aligned for maximum complementarity, thereby forming a substantially duplexed region between sense and antisense strands; and antisense strand is sufficiently complementary to a target RNA along at least 19 ribonucleotides of antisense strand length to reduce target gene expression when said double stranded nucleic acid is introduced into a mammalian cell; and wherein the antisense strand contains at least one thermally destabilizing nucleotide, where at least one thermally destabilizing nucleotide is in the seed region of the antisense strand (i.e. at position 2-9 of the 5'-end of the antisense strand). For example, the thermally destabilizing nucleotide occurs between positions opposite or complimentary to positions 14-17 of the 5'-end of the sense strand, and wherein the dsRNA optionally further has at least one (e.g., one, two, three, four, five, six or all seven) of the following characteristics: (i) the antisense comprises 2, 3, 4, 5, or 6 2'-fluoro modifications; (ii) the antisense comprises 1, 2, 3, 4, or 5 phosphorothioate internucleotide linkages; (iii) the sense strand is conjugated with a ligand; (iv) the sense strand comprises 2, 3, 4, or 5 2'-fluoro modifications; (v) the sense strand comprises 1, 2, 3, 4, or 5 phosphorothioate internucleotide linkages; and (vi) the dsRNA comprises at least four 2'-fluoro modifications; and (vii) the dsRNA comprises a duplex region of 12-30 nucleotide pairs in length.

In some embodiments, the dsRNA molecule of the disclosure comprises a sense and antisense strands, wherein said dsRNA molecule comprises a sense strand having a length which is at least 25 and at most 29 nucleotides and an antisense strand having a length which is at most 30 nucleotides with the sense strand comprises a modified nucleotide that is susceptible to enzymatic degradation at position 11 from the 5'end, wherein the 3' end of said sense strand and the 5' end of said antisense strand form a blunt end and said antisense strand is 1-4 nucleotides longer at its 3' end than the sense strand, wherein the duplex region which is at least 25 nucleotides in length, and said antisense strand is sufficiently complementary to a target mRNA along at least 19 nt of said antisense strand length to reduce target gene expression when said dsRNA molecule is introduced into a mammalian cell, and wherein dicer cleavage of said dsRNA preferentially results in an siRNA comprising said 3' end of said antisense strand, thereby reducing expression of the target gene in the mammal, wherein the antisense strand contains at least one thermally destabilizing nucleotide, where the at least one thermally destabilizing nucleotide is in the seed region of the antisense strand (i.e. at position 2-9 of the 5'-end of the antisense strand), and wherein the dsRNA optionally further has at least one (e.g., one, two, three, four, five, six or all seven) of the following characteristics: (i) the antisense comprises 2, 3, 4, 5, or 6 2'-fluoro modifications; (ii) the antisense comprises 1, 2, 3, 4, or 5 phosphorothioate internucleotide linkages; (iii) the sense strand is conjugated with a ligand; (iv) the sense strand comprises 2, 3, 4, or 5 2'-fluoro modifications; (v) the sense strand comprises 1, 2, 3, 4, or 5 phosphorothioate internucleotide linkages; and (vi) the dsRNA comprises at least four 2'-fluoro modifications; and (vii) the dsRNA has a duplex region of 12-29 nucleotide pairs in length.

In some embodiments, every nucleotide in the sense strand and antisense strand of the dsRNA molecule may be modified. Each nucleotide may be modified with the same or different modification which can include one or more alteration of one or both of the non-linking phosphate oxygens or of one or more of the linking phosphate oxygens; alteration of a constituent of the ribose sugar, e.g., of the 2' hydroxyl on the ribose sugar; wholesale replacement of the phosphate moiety with "dephospho" linkers; modification or replacement of a naturally occurring base; and replacement or modification of the ribose-phosphate backbone.

As nucleic acids are polymers of subunits, many of the modifications occur at a position which is repeated within a nucleic acid, e.g., a modification of a base, or a phosphate moiety, or a non-linking O of a phosphate moiety. In some cases, the modification will occur at all of the subject positions in the nucleic acid but in many cases it will not. By way of example, a modification may only occur at a 3' or 5' terminal position, may only occur in a terminal region, e.g., at a position on a terminal nucleotide or in the last 2, 3, 4, 5, or 10 nucleotides of a strand. A modification may occur in a double strand region, a single strand region, or in both. A modification may occur only in the double strand region of an RNA or may only occur in a single strand region of an RNA. E.g., a phosphorothioate modification at a non-linking O position may only occur at one or both termini, may only occur in a terminal region, e.g., at a position on a terminal nucleotide or in the last 2, 3, 4, 5, or 10 nucleotides of a strand, or may occur in double strand and single strand regions, particularly at termini. The 5' end or ends can be phosphorylated.

It may be possible, e.g., to enhance stability, to include particular bases in overhangs, or to include modified nucleotides or nucleotide surrogates, in single strand overhangs, e.g., in a 5' or 3' overhang, or in both. E.g., it can be desirable to include purine nucleotides in overhangs. In some embodiments all or some of the bases in a 3' or 5' overhang may be modified, e.g., with a modification described herein. Modifications can include, e.g., the use of modifications at the 2' position of the ribose sugar with modifications that are known in the art, e.g., the use of deoxyribonucleotides, 2'-deoxy-2'-fluoro (2'-F) or 2'-O-methyl modified instead of the ribosugar of the nucleobase, and modifications in the phosphate group, e.g., phosphorothioate modifications. Overhangs need not be homologous with the target sequence.

In some embodiments, each residue of the sense strand and antisense strand is independently modified with LNA, HNA, CeNA, 2'-methoxyethyl, 2'-O-methyl, 2'-O-allyl, 2'-C-allyl, 2'-deoxy, or 2'-fluoro. The strands can contain more than one modification. In some embodiments, each residue of the sense strand and antisense strand is independently modified with 2'-O-methyl or 2'-fluoro. It is to be understood that these modifications are in addition to the at least one thermally destabilizing modification of the duplex present in the antisense strand.

At least two different modifications are typically present on the sense strand and antisense strand. Those two modifications may be the 2'-deoxy, 2'-O-methyl or 2'-fluoro modifications, acyclic nucleotides or others. In some embodiments, the sense strand and antisense strand each comprises two differently modified nucleotides selected from 2'-O-methyl or 2'-deoxy. In some embodiments, each residue of the sense strand and antisense strand is independently modified with 2'-O-methyl nucleotide, 2'-deoxy nucleotide, 2'-deoxy-2'-fluoro nucleotide, 2'-O—N-methylacetamido (2'-O-NMA) nucleotide, a 2'-O-dimethylaminoethoxyethyl (2'-O-DMAEOE) nucleotide, 2'-O-aminopropyl (2'-O-AP) nucleotide, or 2'-ara-F nucleotide. Again, it is to be understood that these modifications are in addition to the at least one thermally destabilizing modification of the duplex present in the antisense strand.

In some embodiments, the dsRNA molecule of the disclosure comprises modifications of an alternating pattern, particular in the B1, B2, B3, B1', B2', B3', B4' regions. The term "alternating motif" or "alternative pattern" as used herein refers to a motif having one or more modifications, each modification occurring on alternating nucleotides of one strand. The alternating nucleotide may refer to one per every other nucleotide or one per every three nucleotides, or a similar pattern. For example, if A, B and C each represent one type of modification to the nucleotide, the alternating motif can be "ABABABABABAB . . . ," "AABBAABBAABB . . . ," "AABAABAABAAB . . . ," "AAABAAABAAAB . . . ," "AAABBBAAABBB . . . ," or "ABCABCABCABC . . . ," etc. The type of modifications contained in the alternating motif may be the same or different. For example, if A, B, C, D each represent one type of modification on the nucleotide, the alternating pattern, i.e., modifications on every other nucleotide, may be the same, but each of the sense strand or antisense strand can be selected from several possibilities of modifications within the alternating motif such as "ABABAB . . . ", "ACACAC . . . " "BDBDBD . . . " or "CDCDCD . . . ," etc.

In some embodiments, the dsRNA molecule of the disclosure comprises the modification pattern for the alternating motif on the sense strand relative to the modification pattern for the alternating motif on the antisense strand is shifted. The shift may be such that the modified group of nucleotides of the sense strand corresponds to a differently modified group of nucleotides of the antisense strand and vice versa. For example, the sense strand when paired with the antisense strand in the dsRNA duplex, the alternating motif in the sense strand may start with "ABABAB" from 5'-3' of the strand and the alternating motif in the antisense strand may start with "BABABA" from 3'-5' of the strand within the duplex region. As another example, the alternating motif in the sense strand may start with "AABBAABB" from 5'-3' of the strand and the alternating motif in the antisense strand may start with "BBAABBAA" from 3'-5' of the strand within the duplex region, so that there is a complete or partial shift of the modification patterns between the sense strand and the antisense strand.

In one particular example, the alternating motif in the sense strand is "ABABAB" from 5'-3' of the strand, where each A is an unmodified ribonucleotide and each B is a 2'-Omethyl modified nucleotide.

In one particular example, the alternating motif in the sense strand is "ABABAB" from 5'-3' of the strand, where each A is an 2'-deoxy-2'-fluoro modified nucleotide and each B is a 2'-Omethyl modified nucleotide.

In another particular example, the alternating motif in the antisense strand is "BABABA" from 3'-5' of the strand, where each A is a 2'-deoxy-2'-fluoro modified nucleotide and each B is a 2'-Omethyl modified nucleotide.

In one particular example, the alternating motif in the sense strand is "ABABAB" from 5'-3' of the strand and the alternating motif in the antisense strand is "BABABA" from 3'-5' of the strand, where each A is an unmodified ribonucleotide and each B is a 2'-Omethyl modified nucleotide.

In one particular example, the alternating motif in the sense strand is "ABABAB" from 5'-3' of the strand and the alternating motif in the antisense strand is "BABABA" from 3'-5' of the strand, where each A is a 2'-deoxy-2'-fluoro modified nucleotide and each B is a 2'-Omethyl modified nucleotide.

The dsRNA molecule of the disclosure may further comprise at least one phosphorothioate or methylphosphonate internucleotide linkage. The phosphorothioate or methylphosphonate internucleotide linkage modification may occur on any nucleotide of the sense strand or antisense strand or both in any position of the strand. For instance, the internucleotide linkage modification may occur on every nucleotide on the sense strand or antisense strand; each internucleotide linkage modification may occur in an alternating pattern on the sense strand or antisense strand; or the sense strand or antisense strand comprises both internucleotide linkage modifications in an alternating pattern. The alternating pattern of the internucleotide linkage modification on the sense strand may be the same or different from the antisense strand, and the alternating pattern of the internucleotide linkage modification on the sense strand may have a shift relative to the alternating pattern of the internucleotide linkage modification on the antisense strand.

In some embodiments, the dsRNA molecule comprises the phosphorothioate or methylphosphonate internucleotide linkage modification in the overhang region. For example, the overhang region comprises two nucleotides having a phosphorothioate or methylphosphonate internucleotide linkage between the two nucleotides. Internucleotide linkage modifications also may be made to link the overhang nucleotides with the terminal paired nucleotides within duplex region. For example, at least 2, 3, 4, or all the overhang nucleotides may be linked through phosphorothioate or methylphosphonate internucleotide linkage, and optionally, there may be additional phosphorothioate or methylphosphonate internucleotide linkages linking the overhang nucleotide with a paired nucleotide that is next to the overhang nucleotide. For instance, there may be at least two phosphorothioate internucleotide linkages between the terminal three nucleotides, in which two of the three nucleotides are overhang nucleotides, and the third is a paired nucleotide next to the overhang nucleotide. Preferably, these terminal three nucleotides may be at the 3'-end of the antisense strand.

In some embodiments, the sense strand of the dsRNA molecule comprises 1-10 blocks of two to ten phosphorothioate or methylphosphonate internucleotide linkages separated by 1, 2, 3, 4, 5, 6, 7, 8, 9, 10, 11, 12, 13, 14, 15, or 16 phosphate internucleotide linkages, wherein one of the phosphorothioate or methylphosphonate internucleotide linkages is placed at any position in the oligonucleotide sequence and the said sense strand is paired with an antisense strand comprising any combination of phosphorothioate, methylphosphonate and phosphate internucleotide linkages or an antisense strand comprising either phosphorothioate or methylphosphonate or phosphate linkage.

In some embodiments, the antisense strand of the dsRNA molecule comprises two blocks of two phosphorothioate or methylphosphonate internucleotide linkages separated by 1, 2, 3, 4, 5, 6, 7, 8, 9, 10, 11, 12, 13, 14, 15, 16, 17, or 18 phosphate internucleotide linkages, wherein one of the phosphorothioate or methylphosphonate internucleotide linkages is placed at any position in the oligonucleotide sequence and the said antisense strand is paired with a sense strand comprising any combination of phosphorothioate, methylphosphonate and phosphate internucleotide linkages or an antisense strand comprising either phosphorothioate or methylphosphonate or phosphate linkage.

In some embodiments, the antisense strand of the dsRNA molecule comprises two blocks of three phosphorothioate or methylphosphonate internucleotide linkages separated by 1, 2, 3, 4, 5, 6, 7, 8, 9, 10, 11, 12, 13, 14, 15, or 16 phosphate internucleotide linkages, wherein one of the phosphorothioate or methylphosphonate internucleotide linkages is placed at any position in the oligonucleotide sequence and the said antisense strand is paired with a sense strand comprising any combination of phosphorothioate, methylphosphonate and phosphate internucleotide linkages or an antisense strand comprising either phosphorothioate or methylphosphonate or phosphate linkage.

In some embodiments, the antisense strand of the dsRNA molecule comprises two blocks of four phosphorothioate or methylphosphonate internucleotide linkages separated by 1, 2, 3, 4, 5, 6, 7, 8, 9, 10, 11, 12, 13, or 14 phosphate internucleotide linkages, wherein one of the phosphorothioate or methylphosphonate internucleotide linkages is placed at any position in the oligonucleotide sequence and the said antisense strand is paired with a sense strand comprising any combination of phosphorothioate, methylphosphonate and phosphate internucleotide linkages or an antisense strand comprising either phosphorothioate or methylphosphonate or phosphate linkage.

In some embodiments, the antisense strand of the dsRNA molecule comprises two blocks of five phosphorothioate or methylphosphonate internucleotide linkages separated by 1, 2, 3, 4, 5, 6, 7, 8, 9, 10, 11, or 12 phosphate internucleotide linkages, wherein one of the phosphorothioate or methylphosphonate internucleotide linkages is placed at any position in the oligonucleotide sequence and the said antisense strand is paired with a sense strand comprising any combination of phosphorothioate, methylphosphonate and phosphate internucleotide linkages or an antisense strand comprising either phosphorothioate or methylphosphonate or phosphate linkage.

In some embodiments, the antisense strand of the dsRNA molecule comprises two blocks of six phosphorothioate or methylphosphonate internucleotide linkages separated by 1, 2, 3, 4, 5, 6, 7, 8, 9, or 10 phosphate internucleotide linkages, wherein one of the phosphorothioate or methylphosphonate internucleotide linkages is placed at any position in the oligonucleotide sequence and the said antisense strand is paired with a sense strand comprising any combination of phosphorothioate, methylphosphonate and phosphate internucleotide linkages or an antisense strand comprising either phosphorothioate or methylphosphonate or phosphate linkage.

In some embodiments, the antisense strand of the dsRNA molecule comprises two blocks of seven phosphorothioate or methylphosphonate internucleotide linkages separated by 1, 2, 3, 4, 5, 6, 7, or 8 phosphate internucleotide linkages, wherein one of the phosphorothioate or methylphosphonate internucleotide linkages is placed at any position in the oligonucleotide sequence and the said antisense strand is paired with a sense strand comprising any combination of phosphorothioate, methylphosphonate and phosphate internucleotide linkages or an antisense strand comprising either phosphorothioate or methylphosphonate or phosphate linkage.

In some embodiments, the antisense strand of the dsRNA molecule comprises two blocks of eight phosphorothioate or methylphosphonate internucleotide linkages separated by 1, 2, 3, 4, 5, or 6 phosphate internucleotide linkages, wherein one of the phosphorothioate or methylphosphonate internucleotide linkages is placed at any position in the oligonucleotide sequence and the said antisense strand is paired with a sense strand comprising any combination of phosphorothioate, methylphosphonate and phosphate internucleotide linkages or an antisense strand comprising either phosphorothioate or methylphosphonate or phosphate linkage.

In some embodiments, the antisense strand of the dsRNA molecule comprises two blocks of nine phosphorothioate or methylphosphonate internucleotide linkages separated by 1, 2, 3, or 4 phosphate internucleotide linkages, wherein one of the phosphorothioate or methylphosphonate internucleotide linkages is placed at any position in the oligonucleotide sequence and the said antisense strand is paired with a sense strand comprising any combination of phosphorothioate, methylphosphonate and phosphate internucleotide linkages or an antisense strand comprising either phosphorothioate or methylphosphonate or phosphate linkage.

In some embodiments, the dsRNA molecule of the disclosure further comprises one or more phosphorothioate or methylphosphonate internucleotide linkage modification within 1-10 of the termini position(s) of the sense or antisense strand. For example, at least 2, 3, 4, 5, 6, 7, 8, 9, or 10 nucleotides may be linked through phosphorothioate or methylphosphonate internucleotide linkage at one end or both ends of the sense or antisense strand.

In some embodiments, the dsRNA molecule of the disclosure further comprises one or more phosphorothioate or methylphosphonate internucleotide linkage modification within 1-10 of the internal region of the duplex of each of the sense or antisense strand. For example, at least 2, 3, 4, 5, 6, 7, 8, 9, or 10 nucleotides may be linked through phosphorothioate methylphosphonate internucleotide linkage at position 8-16 of the duplex region counting from the 5'-end of the sense strand; the dsRNA molecule can optionally further comprise one or more phosphorothioate or methylphosphonate internucleotide linkage modification within 1-10 of the termini position(s).

In some embodiments, the dsRNA molecule of the disclosure further comprises one to five phosphorothioate or methylphosphonate internucleotide linkage modification(s) within position 1-5 and one to five phosphorothioate or methylphosphonate internucleotide linkage modification(s) within position 18-23 of the sense strand (counting from the 5'-end), and one to five phosphorothioate or methylphosphonate internucleotide linkage modification at positions 1 and 2 and one to five within positions 18-23 of the antisense strand (counting from the 5'-end).

In some embodiments, the dsRNA molecule of the disclosure further comprises one phosphorothioate internucleotide linkage modification within position 1-5 and one phosphorothioate or methylphosphonate internucleotide linkage modification within position 18-23 of the sense strand (counting from the 5'-end), and one phosphorothioate internucleotide linkage modification at positions 1 and 2 and two phosphorothioate or methylphosphonate internucleotide linkage modifications within positions 18-23 of the antisense strand (counting from the 5'-end).

In some embodiments, the dsRNA molecule of the disclosure further comprises two phosphorothioate internucleotide linkage modifications within position 1-5 and one phosphorothioate internucleotide linkage modification within position 18-23 of the sense strand (counting from the 5'-end), and one phosphorothioate internucleotide linkage modification at positions 1 and 2 and two phosphorothioate internucleotide linkage modifications within positions 18-23 of the antisense strand (counting from the 5'-end).

In some embodiments, the dsRNA molecule of the disclosure further comprises two phosphorothioate internucleotide linkage modifications within position 1-5 and two phosphorothioate internucleotide linkage modifications within position 18-23 of the sense strand (counting from the 5'-end), and one phosphorothioate internucleotide linkage modification at positions 1 and 2 and two phosphorothioate internucleotide linkage modifications within positions 18-23 of the antisense strand (counting from the 5'-end).

In some embodiments, the dsRNA molecule of the disclosure further comprises two phosphorothioate internucleotide linkage modifications within position 1-5 and two phosphorothioate internucleotide linkage modifications within position 18-23 of the sense strand (counting from the 5'-end), and one phosphorothioate internucleotide linkage modification at positions 1 and 2 and one phosphorothioate internucleotide linkage modification within positions 18-23 of the antisense strand (counting from the 5'-end).

In some embodiments, the dsRNA molecule of the disclosure further comprises one phosphorothioate internucleotide linkage modification within position 1-5 and one phosphorothioate internucleotide linkage modification within position 18-23 of the sense strand (counting from the 5'-end), and two phosphorothioate internucleotide linkage modifications at positions 1 and 2 and two phosphorothioate internucleotide linkage modifications within positions 18-23 of the antisense strand (counting from the 5'-end).

In some embodiments, the dsRNA molecule of the disclosure further comprises one phosphorothioate internucleotide linkage modification within position 1-5 and one within position 18-23 of the sense strand (counting from the 5'-end), and two phosphorothioate internucleotide linkage modification at positions 1 and 2 and one phosphorothioate internucleotide linkage modification within positions 18-23 of the antisense strand (counting from the 5'-end).

In some embodiments, the dsRNA molecule of the disclosure further comprises one phosphorothioate internucleotide linkage modification within position 1-5 (counting from the 5'-end) of the sense strand, and two phosphorothioate internucleotide linkage modifications at positions 1 and 2 and one phosphorothioate internucleotide linkage modification within positions 18-23 of the antisense strand (counting from the 5'-end).

In some embodiments, the dsRNA molecule of the disclosure further comprises two phosphorothioate internucleotide linkage modifications within position 1-5 (counting from the 5'-end) of the sense strand, and one phosphorothioate internucleotide linkage modification at positions 1 and 2 and two phosphorothioate internucleotide linkage modifications within positions 18-23 of the antisense strand (counting from the 5'-end).

In some embodiments, the dsRNA molecule of the disclosure further comprises two phosphorothioate internucleotide linkage modifications within position 1-5 and one within position 18-23 of the sense strand (counting from the 5'-end), and two phosphorothioate internucleotide linkage modifications at positions 1 and 2 and one phosphorothioate internucleotide linkage modification within positions 18-23 of the antisense strand (counting from the 5'-end).

In some embodiments, the dsRNA molecule of the disclosure further comprises two phosphorothioate internucleotide linkage modifications within position 1-5 and one phosphorothioate internucleotide linkage modification within position 18-23 of the sense strand (counting from the 5'-end), and two phosphorothioate internucleotide linkage modifications at positions 1 and 2 and two phosphorothioate internucleotide linkage modifications within positions 18-23 of the antisense strand (counting from the 5'-end).

In some embodiments, the dsRNA molecule of the disclosure further comprises two phosphorothioate internucleotide linkage modifications within position 1-5 and one phosphorothioate internucleotide linkage modification within position 18-23 of the sense strand (counting from the 5'-end), and one phosphorothioate internucleotide linkage modification at positions 1 and 2 and two phosphorothioate internucleotide linkage modifications within positions 18-23 of the antisense strand (counting from the 5'-end).

In some embodiments, the dsRNA molecule of the disclosure further comprises two phosphorothioate internucleotide linkage modifications at position 1 and 2, and two phosphorothioate internucleotide linkage modifications at position 20 and 21 of the sense strand (counting from the 5'-end), and one phosphorothioate internucleotide linkage modification at positions 1 and one at position 21 of the antisense strand (counting from the 5'-end).

In some embodiments, the dsRNA molecule of the disclosure further comprises one phosphorothioate internucleotide linkage modification at position 1, and one phosphorothioate internucleotide linkage modification at position 21 of the sense strand (counting from the 5'-end), and two phosphorothioate internucleotide linkage modifications at positions 1 and 2 and two phosphorothioate internucleotide linkage modifications at positions 20 and 21 of the antisense strand (counting from the 5'-end).

In some embodiments, the dsRNA molecule of the disclosure further comprises two phosphorothioate internucleotide linkage modifications at position 1 and 2, and two phosphorothioate internucleotide linkage modifications at position 21 and 22 of the sense strand (counting from the 5'-end), and one phosphorothioate internucleotide linkage modification at position 1 and one phosphorothioate internucleotide linkage modification at position 21 of the antisense strand (counting from the 5'-end).

In some embodiments, the dsRNA molecule of the disclosure further comprises one phosphorothioate internucleotide linkage modification at position 1, and one phosphorothioate internucleotide linkage modification at position 21 of the sense strand (counting from the 5'-end), and two phosphorothioate internucleotide linkage modifications at positions 1 and 2 and two phosphorothioate internucleotide linkage modifications at positions 21 and 22 of the antisense strand (counting from the 5'-end).

In some embodiments, the dsRNA molecule of the disclosure further comprises two phosphorothioate internucleotide linkage modifications at position 1 and 2, and two phosphorothioate internucleotide linkage modifications at position 22 and 23 of the sense strand (counting from the 5'-end), and one phosphorothioate internucleotide linkage modification at position 1 and one phosphorothioate internucleotide linkage modification at position 21 of the antisense strand (counting from the 5'-end).

In some embodiments, the dsRNA molecule of the disclosure further comprises one phosphorothioate internucleotide linkage modification at position 1, and one phosphorothioate internucleotide linkage modification at position 21 of the sense strand (counting from the 5'-end), and two phosphorothioate internucleotide linkage modifications at positions 1 and 2 and two phosphorothioate internucleotide linkage modifications at positions 23 and 23 of the antisense strand (counting from the 5'-end).

In some embodiments, compound of the disclosure comprises a pattern of backbone chiral centers. In some embodiments, a common pattern of backbone chiral centers comprises at least 5 internucleotidic linkages in the Sp configuration. In some embodiments, a common pattern of backbone chiral centers comprises at least 6 internucleotidic linkages in the Sp configuration. In some embodiments, a common pattern of backbone chiral centers comprises at least 7 internucleotidic linkages in the Sp configuration. In some embodiments, a common pattern of backbone chiral centers comprises at least 8 internucleotidic linkages in the Sp configuration. In some embodiments, a common pattern of backbone chiral centers comprises at least 9 internucleotidic linkages in the Sp configuration. In some embodiments, a common pattern of backbone chiral centers comprises at least 10 internucleotidic linkages in the Sp configuration. In some embodiments, a common pattern of backbone chiral centers comprises at least 11 internucleotidic linkages in the Sp configuration. In some embodiments, a common pattern of backbone chiral centers comprises at least 12 internucleotidic linkages in the Sp configuration. In some embodiments, a common pattern of backbone chiral centers comprises at least 13 internucleotidic linkages in the Sp configuration. In some embodiments, a common pattern of backbone chiral centers comprises at least 14 internucleotidic linkages in the Sp configuration. In some embodiments, a common pattern of backbone chiral centers comprises at least 15 internucleotidic linkages in the Sp configuration. In some embodiments, a common pattern of backbone chiral centers comprises at least 16 internucleotidic linkages in the Sp configuration. In some embodiments, a common pattern of backbone chiral centers comprises at least 17 internucleotidic linkages in the Sp configuration. In some embodiments, a common pattern of backbone chiral centers comprises at least 18 internucleotidic linkages in the Sp configuration. In some embodiments, a common pattern of backbone chiral centers comprises at least 19 internucleotidic linkages in the Sp configuration. In some embodiments, a common pattern of backbone chiral centers comprises no more than 8 internucleotidic linkages in the Rp configuration. In some embodiments, a common pattern of backbone chiral centers comprises no more than 7 internucleotidic linkages in the Rp configuration. In some embodiments, a common pattern of backbone chiral centers comprises no more than 6 internucleotidic linkages in the Rp configuration. In some embodiments, a common pattern of backbone chiral centers comprises no more than 5 internucleotidic linkages in the Rp configuration. In some embodiments, a common pattern of backbone chiral centers comprises no more than 4 internucleotidic linkages in the Rp configuration. In some embodiments, a common pattern of backbone chiral centers comprises no more than 3 internucleotidic linkages in the Rp configuration. In some embodiments, a common pattern of backbone chiral centers comprises no more than 2 internucleotidic linkages in the Rp configuration. In some embodiments, a common pattern of backbone chiral centers comprises no more than 1 internucleotidic linkages in the Rp configuration. In some embodiments, a common pattern of backbone chiral centers comprises no more than 8 internucleotidic linkages which are not chiral (as a non-limiting example, a phosphodiester). In some embodiments, a common pattern of backbone chiral centers comprises no more than 7 internucleotidic linkages which are not chiral. In some embodiments, a common pattern of backbone chiral centers comprises no more than 6 internucleotidic linkages which are not chiral. In some embodiments, a common pattern of backbone chiral centers comprises no more than 5 internucleotidic linkages which are not chiral. In some embodiments, a common pattern of backbone chiral centers comprises no more than 4 internucleotidic linkages which are not chiral. In some embodiments, a common pattern of backbone chiral centers comprises no more than 3 internucleotidic linkages which are not chiral. In some embodiments, a common pattern of backbone chiral centers comprises no more than 2 internucleotidic linkages which are not chiral. In some embodiments, a common pattern of backbone chiral centers comprises no more than 1 internucleotidic linkages which are not chiral. In some embodiments, a common pattern of backbone chiral centers comprises at least 10 internucleotidic linkages in the Sp configuration, and no more than 8 internucleotidic linkages which are not chiral. In some embodiments, a common pattern of backbone chiral centers comprises at least 11 internucleotidic linkages in the Sp configuration, and no more than 7 internucleotidic linkages which are not chiral. In some embodiments, a common pattern of backbone chiral centers comprises at least 12 internucleotidic linkages in the Sp configuration, and no more than 6 internucleotidic linkages which are not chiral. In some embodiments, a common pattern of backbone chiral centers comprises at least 13 internucleotidic linkages in the Sp configuration, and no more than 6 internucleotidic linkages which are not chiral. In some embodiments, a common pattern of backbone chiral centers comprises at least 14 internucleotidic linkages in the Sp configuration, and no more than 5 internucleotidic linkages which are not chiral. In some embodiments, a common pattern of backbone chiral centers comprises at least 15 internucleotidic linkages in the Sp configuration, and no more than 4 internucleotidic linkages which are not chiral. In some embodiments, the internucleotidic linkages in the Sp configuration are optionally contiguous or not contiguous. In some embodiments, the internucleotidic linkages in the Rp configuration are optionally contiguous or not contiguous. In some embodiments, the internucleotidic linkages which are not chiral are optionally contiguous or not contiguous.

In some embodiments, compound of the disclosure comprises a block is a stereochemistry block. In some embodiments, a block is an Rp block in that each internucleotidic linkage of the block is Rp. In some embodiments, a 5'-block is an Rp block. In some embodiments, a 3'-block is an Rp block. In some embodiments, a block is an Sp block in that each internucleotidic linkage of the block is Sp. In some embodiments, a 5'-block is an Sp block. In some embodiments, a 3'-block is an Sp block. In some embodiments, provided oligonucleotides comprise both Rp and Sp blocks. In some embodiments, provided oligonucleotides comprise one or more Rp but no Sp blocks. In some embodiments, provided oligonucleotides comprise one or more Sp but no Rp blocks. In some embodiments, provided oligonucleotides comprise one or more PO blocks wherein each internucleotidic linkage in a natural phosphate linkage.

In some embodiments, compound of the disclosure comprises a 5'-block is an Sp block wherein each sugar moiety comprises a 2'-F modification. In some embodiments, a 5'-block is an Sp block wherein each of internucleotidic linkage is a modified internucleotidic linkage and each sugar moiety comprises a 2'-F modification. In some embodiments, a 5'-block is an Sp block wherein each of internucleotidic linkage is a phosphorothioate linkage and each sugar moiety comprises a 2'-F modification. In some embodiments, a 5'-block comprises 4 or more nucleoside units. In some embodiments, a 5'-block comprises 5 or more nucleoside units. In some embodiments, a 5'-block comprises 6 or more nucleoside units. In some embodiments, a 5'-block comprises 7 or more nucleoside units. In some embodiments, a 3'-block is an Sp block wherein each sugar moiety comprises a 2'-F modification. In some embodiments, a 3'-block is an Sp block wherein each of internucleotidic linkage is a modified internucleotidic linkage and each sugar moiety comprises a 2'-F modification. In some embodiments, a 3'-block is an Sp block wherein each of internucleotidic linkage is a phosphorothioate linkage and each sugar moiety comprises a 2'-F modification. In some embodiments, a 3'-block comprises 4 or more nucleoside units. In some embodiments, a 3'-block comprises 5 or more nucleoside units. In some embodiments, a 3'-block comprises 6 or more nucleoside units. In some embodiments, a 3'-block comprises 7 or more nucleoside units.

In some embodiments, compound of the disclosure comprises a type of nucleoside in a region or an oligonucleotide is followed by a specific type of internucleotidic linkage, e.g., natural phosphate linkage, modified internucleotidic linkage, Rp chiral internucleotidic linkage, Sp chiral internucleotidic linkage, etc. In some embodiments, A is followed by Sp. In some embodiments, A is followed by Rp. In some embodiments, A is followed by natural phosphate linkage (PO). In some embodiments, U is followed by Sp. In some embodiments, U is followed by Rp. In some embodiments, U is followed by natural phosphate linkage (PO). In some embodiments, C is followed by Sp. In some embodiments, C is followed by Rp. In some embodiments, C is followed by natural phosphate linkage (PO). In some embodiments, G is followed by Sp. In some embodiments, G is followed by Rp. In some embodiments, G is followed by natural phosphate linkage (PO). In some embodiments, C and U are followed by Sp. In some embodiments, C and U are followed by Rp. In some embodiments, C and U are followed by natural phosphate linkage (PO). In some embodiments, A and G are followed by Sp. In some embodiments, A and G are followed by Rp.

In some embodiments, the antisense strand comprises phosphorothioate internucleotide linkages between nucleotide positions 21 and 22, and between nucleotide positions 22 and 23, wherein the antisense strand contains at least one thermally destabilizing modification of the duplex located in the seed region of the antisense strand (i.e., at position 2-9 of the 5'-end of the antisense strand), and wherein the dsRNA optionally further has at least one (e.g., one, two, three, four, five, six, seven or all eight) of the following characteristics: (i) the antisense comprises 2, 3, 4, 5 or 6 2'-fluoro modifications; (ii) the antisense comprises 3, 4 or 5 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3, 4 or 5 phosphorothioate internucleotide linkages; (vi) the dsRNA comprises at least four 2'-fluoro modifications; (vii) the dsRNA comprises a duplex region of 12-40 nucleotide pairs in length; and (viii) the dsRNA has a blunt end at 5'-end of the antisense strand.

In some embodiments, the antisense strand comprises phosphorothioate internucleotide linkages between nucleotide positions 1 and 2, between nucleotide positions 2 and 3, between nucleotide positions 21 and 22, and between nucleotide positions 22 and 23, wherein the antisense strand contains at least one thermally destabilizing modification of the duplex located in the seed region of the antisense strand (i.e., at position 2-9 of the 5'-end of the antisense strand), and wherein the dsRNA optionally further has at least one (e.g., one, two, three, four, five, six, seven or all eight) of the following characteristics: (i) the antisense comprises 2, 3, 4, 5 or 6 2'-fluoro modifications; (ii) the sense strand is conjugated with a ligand; (iii) the sense strand comprises 2, 3, 4 or 5 2'-fluoro modifications; (iv) the sense strand comprises 1, 2, 3, 4 or 5 phosphorothioate internucleotide linkages; (v) the dsRNA comprises at least four 2'-fluoro modifications; (vi) the dsRNA comprises a duplex region of 12-40 nucleotide pairs in length; (vii) the dsRNA comprises a duplex region of 12-40 nucleotide pairs in length; and (viii) the dsRNA has a blunt end at 5'-end of the antisense strand.

In some embodiments, the sense strand comprises phosphorothioate internucleotide linkages between nucleotide positions 1 and 2, and between nucleotide positions 2 and 3, wherein the antisense strand contains at least one thermally destabilizing modification of the duplex located in the seed region of the antisense strand (i.e., at position 2-9 of the 5'-end of the antisense strand), and wherein the dsRNA optionally further has at least one (e.g., one, two, three, four, five, six, seven or all eight) of the following characteristics: (i) the antisense comprises 2, 3, 4, 5 or 6 2'-fluoro modifications; (ii) the antisense comprises 1, 2, 3, 4 or 5 phosphorothioate internucleotide linkages; (iii) the sense strand is conjugated with a ligand; (iv) the sense strand comprises 2, 3, 4 or 5 2'-fluoro modifications; (v) the sense strand comprises 3, 4 or 5 phosphorothioate internucleotide linkages; (vi) the dsRNA comprises at least four 2'-fluoro modifications; (vii) the dsRNA comprises a duplex region of 12-40 nucleotide pairs in length; and (viii) the dsRNA has a blunt end at 5'-end of the antisense strand.

In some embodiments, the sense strand comprises phosphorothioate internucleotide linkages between nucleotide positions 1 and 2, and between nucleotide positions 2 and 3, the antisense strand comprises phosphorothioate internucleotide linkages between nucleotide positions 1 and 2, between nucleotide positions 2 and 3, between nucleotide positions 21 and 22, and between nucleotide positions 22 and 23, wherein the antisense strand contains at least one thermally destabilizing modification of the duplex located in the seed region of the antisense strand (i.e., at position 2-9 of the 5'-end of the antisense strand), and wherein the dsRNA optionally further has at least one (e.g., one, two, three, four, five, six or all seven) of the following characteristics: (i) the antisense comprises 2, 3, 4, 5 or 6 2'-fluoro modifications; (ii) the sense strand is conjugated with a ligand; (iii) the sense strand comprises 2, 3, 4 or 5 2'-fluoro modifications; (iv) the sense strand comprises 3, 4 or 5 phosphorothioate internucleotide linkages; (v) the dsRNA comprises at least four 2'-fluoro modifications; (vi) the dsRNA comprises a duplex region of 12-40 nucleotide pairs in length; and (vii) the dsRNA has a blunt end at 5'-end of the antisense strand.

In some embodiments, the dsRNA molecule of the disclosure comprises mismatch(es) with the target, within the duplex, or combinations thereof. The mismatch can occur in the overhang region or the duplex region. The base pair can be ranked on the basis of their propensity to promote dissociation or melting (e.g., on the free energy of association or dissociation of a particular pairing, the simplest approach is to examine the pairs on an individual pair basis, though next neighbor or similar analysis can also be used). In terms of promoting dissociation: A:U is preferred over G:C; G:U is preferred over G:C; and J:C is preferred over G:C (I=inosine). Mismatches, e.g., non-canonical or other than canonical pairings (as described elsewhere herein) are preferred over canonical (A:T, A:U, G:C) pairings; and pairings which include a universal base are preferred over canonical pairings.

In some embodiments, the dsRNA molecule of the disclosure comprises at least one of the first 1, 2, 3, 4, or 5 base pairs within the duplex regions from the 5'-end of the antisense strand can be chosen independently from the group of: A:U, G:U, J:C, and mismatched pairs, e.g., non-canonical or other than canonical pairings or pairings which include a universal base, to promote the dissociation of the antisense strand at the 5'-end of the duplex.

In some embodiments, the nucleotide at the 1 position within the duplex region from the 5'-end in the antisense strand is selected from the group consisting of A, dA, dU, U, and dT.

Alternatively, at least one of the first 1, 2 or 3 base pair within the duplex region from the 5'-end of the antisense strand is an AU base pair. For example, the first base pair within the duplex region from the 5'-end of the antisense strand is an AU base pair.

It was found that introducing 4'-modified or 5'-modified nucleotide to the 3'-end of a phosphodiester (PO), phosphorothioate (PS), or phosphorodithioate (PS2) linkage of a dinucleotide at any position of single stranded or double stranded oligonucleotide can exert steric effect to the internucleotide linkage and, hence, protecting or stabilizing it against nucleases.

In some embodiments, 5'-modified nucleoside is introduced at the 3'-end of a dinucleotide at any position of single stranded or double stranded siRNA. For instance, a 5'-alkylated nucleoside may be introduced at the 3'-end of a dinucleotide at any position of single stranded or double stranded siRNA. The alkyl group at the 5' position of the ribose sugar can be racemic or chirally pure R or S isomer. An exemplary 5'-alkylated nucleoside is 5'-methyl nucleoside. The 5'-methyl can be either racemic or chirally pure R or S isomer.

In some embodiments, 4'-modified nucleoside is introduced at the 3'-end of a dinucleotide at any position of single stranded or double stranded siRNA. For instance, a 4'-alkylated nucleoside may be introduced at the 3'-end of a dinucleotide at any position of single stranded or double stranded siRNA. The alkyl group at the 4' position of the ribose sugar can be racemic or chirally pure R or S isomer. An exemplary 4'-alkylated nucleoside is 4'-methyl nucleoside. The 4'-methyl can be either racemic or chirally pure R or S isomer. Alternatively, a 4'-O-alkylated nucleoside may be introduced at the 3'-end of a dinucleotide at any position of single stranded or double stranded siRNA. The 4'-O-alkyl of the ribose sugar can be racemic or chirally pure R or S isomer. An exemplary 4'-O-alkylated nucleoside is 4'-O-methyl nucleoside. The 4'-O-methyl can be either racemic or chirally pure R or S isomer.

In some embodiments, 5'-alkylated nucleoside is introduced at any position on the sense strand or antisense strand of a dsRNA, and such modification maintains or improves potency of the dsRNA. The 5'-alkyl can be either racemic or chirally pure R or S isomer. An exemplary 5'-alkylated nucleoside is 5'-methyl nucleoside. The 5'-methyl can be either racemic or chirally pure R or S isomer.

In some embodiments, 4'-alkylated nucleoside is introduced at any position on the sense strand or antisense strand of a dsRNA, and such modification maintains or improves potency of the dsRNA. The 4'-alkyl can be either racemic or chirally pure R or S isomer. An exemplary 4'-alkylated nucleoside is 4'-methyl nucleoside. The 4'-methyl can be either racemic or chirally pure R or S isomer.

In some embodiments, 4'-O-alkylated nucleoside is introduced at any position on the sense strand or antisense strand of a dsRNA, and such modification maintains or improves potency of the dsRNA. The 5'-alkyl can be either racemic or chirally pure R or S isomer. An exemplary 4'-O-alkylated nucleoside is 4'-O-methyl nucleoside. The 4'-O-methyl can be either racemic or chirally pure R or S isomer.

In some embodiments, the dsRNA molecule of the disclosure can comprise 2'-5' linkages (with 2'-H, 2'-OH and 2'-OMe and with P═O or P═S). For example, the 2'-5' linkages modifications can be used to promote nuclease resistance or to inhibit binding of the sense to the antisense strand, or can be used at the 5' end of the sense strand to avoid sense strand activation by RISC.

In another embodiment, the dsRNA molecule of the disclosure can comprise L sugars (e.g., L ribose, L-arabinose with 2'-H, 2'-OH and 2'-OMe). For example, these L sugars modifications can be used to promote nuclease resistance or to inhibit binding of the sense to the antisense strand, or can be used at the 5' end of the sense strand to avoid sense strand activation by RISC.

Various publications describe multimeric siRNA which can all be used with the dsRNA of the disclosure. Such publications include WO2007/091269, U.S. Pat. No. 7,858,769, WO2010/141511, WO2007/117686, WO2009/014887, and WO2011/031520 which are hereby incorporated by their entirely.

As described in more detail below, the RNAi agent that contains conjugations of one or more carbohydrate moieties to an RNAi agent can optimize one or more properties of the RNAi agent. In many cases, the carbohydrate moiety will be attached to a modified subunit of the RNAi agent. For example, the ribose sugar of one or more ribonucleotide subunits of a dsRNA agent can be replaced with another moiety, e.g., a non-carbohydrate (preferably cyclic) carrier to which is attached a carbohydrate ligand. A ribonucleotide subunit in which the ribose sugar of the subunit has been so replaced is referred to herein as a ribose replacement modification subunit (RRMS). A cyclic carrier may be a carbocyclic ring system, i.e., all ring atoms are carbon atoms, or a heterocyclic ring system, i.e., one or more ring atoms may be a heteroatom, e.g., nitrogen, oxygen, sulfur. The cyclic carrier may be a monocyclic ring system, or may contain two or more rings, e.g. fused rings. The cyclic carrier may be a fully saturated ring system, or it may contain one or more double bonds.

The ligand may be attached to the polynucleotide via a carrier. The carriers include (i) at least one "backbone attachment point," preferably two "backbone attachment points" and (ii) at least one "tethering attachment point." A "backbone attachment point" as used herein refers to a functional group, e.g. a hydroxyl group, or generally, a bond available for, and that is suitable for incorporation of the carrier into the backbone, e.g., the phosphate, or modified phosphate, e.g., sulfur containing, backbone, of a ribonucleic acid. A "tethering attachment point" (TAP) in some embodiments refers to a constituent ring atom of the cyclic carrier, e.g., a carbon atom or a heteroatom (distinct from an atom which provides a backbone attachment point), that connects a selected moiety. The moiety can be, e.g., a carbohydrate, e.g. monosaccharide, disaccharide, trisaccharide, tetrasaccharide, oligosaccharide and polysaccharide. Optionally, the selected moiety is connected by an intervening tether to the cyclic carrier. Thus, the cyclic carrier will often include a functional group, e.g., an amino group, or generally, provide a bond, that is suitable for incorporation or tethering of another chemical entity, e.g., a ligand to the constituent ring.

The RNAi agents may be conjugated to a ligand via a carrier, wherein the carrier can be cyclic group or acyclic group; preferably, the cyclic group is selected from pyrrolidinyl, pyrazolinyl, pyrazolidinyl, imidazolinyl, imidazolidinyl, piperidinyl, piperazinyl, [1,3]dioxolane, oxazolidinyl, isoxazolidinyl, morpholinyl, thiazolidinyl, isothiazolidinyl, quinoxalinyl, pyridazinonyl, tetrahydrofuryl and decalin; preferably, the acyclic group is selected from serinol backbone or diethanolamine backbone.

In certain specific embodiments, the RNAi agent for use in the methods of the disclosure is an agent selected from the group of agents listed in any one of Tables 2-5. These agents may further comprise a ligand.

IV. iRNAs Conjugated to Ligands

Another modification of the RNA of an iRNA of the invention involves chemically linking to the iRNA one or more ligands, moieties or conjugates that enhance the activity, cellular distribution or cellular uptake of the iRNA, e.g., into a cell. Such moieties include but are not limited to lipid moieties such as a cholesterol moiety (Letsinger et al., *Proc. Natl. Acid. Sci. USA,* 1989, 86: 6553-6556), cholic acid (Manoharan et al., *Biorg. Med. Chem. Let.,* 1994, 4:1053-1060), a thioether, e.g., beryl-S-tritylthiol (Manoharan et al., *Ann. N.Y. Acad. Sci.,* 1992, 660:306-309; Manoharan et al., *Biorg. Med. Chem. Let.,* 1993, 3:2765-2770), a thiocholesterol (Oberhauser et al., *Nucl. Acids Res.,* 1992, 20:533-538), an aliphatic chain, e.g., dodecandiol or undecyl residues (Saison-Behmoaras et al., *EMBO J,* 1991, 10:1111-1118; Kabanov et al., *FEBS Lett.,* 1990, 259:327-330; Svinarchuk et al., *Biochimie,* 1993, 75:49-54), a phospholipid, e.g., di-hexadecyl-rac-glycerol or triethylammonium 1,2-di-O-hexadecyl-rac-glycero-3-phosphonate (Manoharan et al., *Tetrahedron Lett.,* 1995, 36:3651-3654; Shea et al., *Nucl. Acids Res.,* 1990, 18:3777-3783), a polyamine or a polyethylene glycol chain (Manoharan et al., *Nucleosides & Nucleotides,* 1995, 14:969-973), or adamantane acetic acid (Manoharan et al., *Tetrahedron Lett.,* 1995, 36:3651-3654), a palmityl moiety (Mishra et al., *Biochim. Biophys. Acta,* 1995, 1264:229-237), or an octadecylamine or hexylamino-carbonyloxycholesterol moiety (Crooke et al., *J. Pharmacol. Exp. Ther.,* 1996, 277:923-937).

In certain embodiments, a ligand alters the distribution, targeting or lifetime of an iRNA agent into which it is incorporated. In some embodiments, a ligand provides an enhanced affinity for a selected target, e.g., molecule, cell or cell type, compartment, e.g., a cellular or organ compartment, tissue, organ or region of the body, as, e.g., compared to a species absent such a ligand. Typical ligands will not take part in duplex pairing in a duplexed nucleic acid.

Ligands can include a naturally occurring substance, such as a protein (e.g., human serum albumin (HSA), low-density lipoprotein (LDL), or globulin); carbohydrate (e.g., a dextran, pullulan, chitin, chitosan, inulin, cyclodextrin or hyaluronic acid); or a lipid. The ligand may also be a recombinant or synthetic molecule, such as a synthetic polymer, e.g., a synthetic polyamino acid. Examples of polyamino acids include polyamino acid is a polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacryllic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an α helical peptide.

Ligands can also include targeting groups, e.g., a cell or tissue targeting agent, e.g., a lectin, glycoprotein, lipid or protein, e.g., an antibody, that binds to a specified cell type such as a kidney cell. A targeting group can be a thyrotropin, melanotropin, lectin, glycoprotein, surfactant protein A, Mucin carbohydrate, multivalent lactose, multivalent galactose, N-acetyl-galactosamine, N-acetyl-glucosamine multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, biotin, or an RGD peptide or RGD peptide mimetic. In certain embodiments, the ligand is a multivalent galactose, e.g., an N-acetyl-galactosamine.

Other examples of ligands include dyes, intercalating agents (e.g. acridines), cross-linkers (e.g. psoralene, mitomycin C), porphyrins (TPPC4, texaphyrin, Sapphyrin), polycyclic aromatic hydrocarbons (e.g., phenazine, dihydrophenazine), artificial endonucleases (e.g. EDTA), lipophilic molecules, e.g., cholesterol, cholic acid, adamantane acetic acid, 1-pyrene butyric acid, dihydrotestosterone, 1,3-Bis-O (hexadecyl)glycerol, geranyloxyhexyl group, hexadecylglycerol, borneol, menthol, 1,3-propanediol, heptadecyl group, palmitic acid, myristic acid, O3-(oleoyl) lithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, $[MPEG]_2$, polyamino, alkyl, substituted alkyl, radiolabeled markers, enzymes, haptens (e.g. biotin), transport/absorption facilitators (e.g., aspirin, vitamin E, folic acid), synthetic ribonucleases (e.g., imidazole, bisimidazole, histamine, imidazole clusters, acridine-imidazole conjugates, Eu3+ complexes of tetraazamacrocycles), dinitrophenyl, HRP, or AP.

Ligands can be proteins, e.g., glycoproteins, or peptides, e.g., molecules having a specific affinity for a co-ligand, or antibodies e.g., an antibody, that binds to a specified cell type such as a cancer cell, endothelial cell, or bone cell. Ligands may also include hormones and hormone receptors. They can also include non-peptidic species, such as lipids, lectins, carbohydrates, vitamins, cofactors, multivalent lactose, multivalent galactose, N-acetyl-galactosamine, N-acetyl-glucosamine multivalent mannose, or multivalent fucose. The ligand can be, for example, a lipopolysaccharide, an activator of p38 MAP kinase, or an activator of NF-κB.

The ligand can be a substance, e.g., a drug, which can increase the uptake of the iRNA agent into the cell, for example, by disrupting the cell's cytoskeleton, e.g., by disrupting the cell's microtubules, microfilaments, or intermediate filaments. The drug can be, for example, taxon, vincristine, vinblastine, cytochalasin, nocodazole, japlakinolide, latrunculin A, phalloidin, swinholide A, indanocine, or myoservin.

In some embodiments, a ligand attached to an iRNA as described herein acts as a pharmacokinetic modulator (PK modulator). PK modulators include lipophiles, bile acids, steroids, phospholipid analogues, peptides, protein binding agents, PEG, vitamins etc. Exemplary PK modulators include, but are not limited to, cholesterol, fatty acids, cholic acid, lithocholic acid, dialkylglycerides, diacylglyceride, phospholipids, sphingolipids, naproxen, ibuprofen, vitamin E, biotin etc. Oligonucleotides that comprise a number of phosphorothioate linkages are also known to bind to serum protein, thus short oligonucleotides, e.g., oligonucleotides of about 5 bases, 10 bases, 15 bases or 20 bases, comprising multiple of phosphorothioate linkages in the backbone are also amenable to the present invention as ligands (e.g. as PK modulating ligands). In addition, aptamers that bind serum components (e.g. serum proteins) are also suitable for use as PK modulating ligands in the embodiments described herein.

Ligand-conjugated iRNAs of the invention may be synthesized by the use of an oligonucleotide that bears a pendant reactive functionality, such as that derived from the attachment of a linking molecule onto the oligonucleotide (described below). This reactive oligonucleotide may be reacted directly with commercially-available ligands, ligands that are synthesized bearing any of a variety of protecting groups, or ligands that have a linking moiety attached thereto.

The oligonucleotides used in the conjugates of the present invention may be conveniently and routinely made through the well-known technique of solid-phase synthesis. Equipment for such synthesis is sold by several vendors including, for example, Applied Biosystems® (Foster City, Calif.). Any other means for such synthesis known in the art may additionally or alternatively be employed. It is also known to use similar techniques to prepare other oligonucleotides, such as the phosphorothioates and alkylated derivatives.

In the ligand-conjugated oligonucleotides and ligand-molecule bearing sequence-specific linked nucleosides of the present invention, the oligonucleotides and oligonucleosides may be assembled on a suitable DNA synthesizer utilizing standard nucleotide or nucleoside precursors, or nucleotide or nucleoside conjugate precursors that already bear the linking moiety, ligand-nucleotide or nucleoside-conjugate precursors that already bear the ligand molecule, or non-nucleoside ligand-bearing building blocks.

When using nucleotide-conjugate precursors that already bear a linking moiety, the synthesis of the sequence-specific linked nucleosides is typically completed, and the ligand molecule is then reacted with the linking moiety to form the ligand-conjugated oligonucleotide. In some embodiments, the oligonucleotides or linked nucleosides of the present invention are synthesized by an automated synthesizer using phosphoramidites derived from ligand-nucleoside conjugates in addition to the standard phosphoramidites and non-standard phosphoramidites that are commercially available and routinely used in oligonucleotide synthesis.

A. Lipid Conjugates

In certain embodiments, the ligand or conjugate is a lipid or lipid-based molecule. Such a lipid or lipid-based molecule can typically bind a serum protein, such as human serum albumin (HSA). An HSA binding ligand allows for distribution of the conjugate to a target tissue, e.g., a non-kidney target tissue of the body. For example, the target tissue can be the liver, including parenchymal cells of the liver. Other molecules that can bind HSA can also be used as ligands. For example, naproxen or aspirin can be used. A lipid or lipid-based ligand can (a) increase resistance to degradation of the conjugate, (b) increase targeting or transport into a target cell or cell membrane, or (c) can be used to adjust binding to a serum protein, e.g., HSA.

A lipid-based ligand can be used to modulate, e.g., control (e.g., inhibit) the binding of the conjugate to a target tissue. For example, a lipid or lipid-based ligand that binds to HSA more strongly will be less likely to be targeted to the kidney and therefore less likely to be cleared from the body. A lipid or lipid-based ligand that binds to HSA less strongly can be used to target the conjugate to the kidney.

In certain embodiments, the lipid-based ligand binds HSA. For example, the ligand can bind HSA with a sufficient affinity such that distribution of the conjugate to a non-kidney tissue is enhanced. However, the affinity is typically not so strong that the HSA-ligand binding cannot be reversed.

In certain embodiments, the lipid-based ligand binds HSA weakly or not at all, such that distribution of the conjugate to the kidney is enhanced. Other moieties that target to kidney cells can also be used in place of or in addition to the lipid-based ligand.

In another aspect, the ligand is a moiety, e.g., a vitamin, which is taken up by a target cell, e.g., a proliferating cell. These are particularly useful for treating disorders characterized by unwanted cell proliferation, e.g., of the malignant or non-malignant type, e.g., cancer cells. Exemplary vitamins include vitamin A, E, and K. Other exemplary vitamins include are B vitamin, e.g., folic acid, B12, riboflavin, biotin, pyridoxal or other vitamins or nutrients taken up by cancer cells. Also included are HSA and low density lipoprotein (LDL).

B. Cell Permeation Agents

In another aspect, the ligand is a cell-permeation agent, such as a helical cell-permeation agent. In certain embodiments, the agent is amphipathic. An exemplary agent is a peptide such as tat or antennopedia. If the agent is a peptide, it can be modified, including a peptidylmimetic, invertomers, non-peptide or pseudo-peptide linkages, and use of D-amino acids. The helical agent is typically an α-helical agent and can have a lipophilic and a lipophobic phase.

The ligand can be a peptide or peptidomimetic. A peptidomimetic (also referred to herein as an oligopeptidomimetic) is a molecule capable of folding into a defined three-dimensional structure similar to a natural peptide. The attachment of peptide and peptidomimetics to iRNA agents can affect pharmacokinetic distribution of the iRNA, such as by enhancing cellular recognition and absorption. The peptide or peptidomimetic moiety can be about 5-50 amino acids long, e.g., about 5, 10, 15, 20, 25, 30, 35, 40, 45, or 50 amino acids long.

A peptide or peptidomimetic can be, for example, a cell permeation peptide, cationic peptide, amphipathic peptide, or hydrophobic peptide (e.g., consisting primarily of Tyr, Trp, or Phe). The peptide moiety can be a dendrimer peptide, constrained peptide or crosslinked peptide. In another alternative, the peptide moiety can include a hydrophobic membrane translocation sequence (MTS). An exemplary hydrophobic MTS-containing peptide is RFGF having the amino acid sequence AAVALLPAVLLALLAP (SEQ ID NO: 11). An RFGF analogue (e.g., amino acid sequence AALLPVLLAAP (SEQ ID NO: 12)) containing a hydrophobic MTS can also be a targeting moiety. The peptide moiety can be a "delivery" peptide, which can carry large polar molecules including peptides, oligonucleotides, and protein across cell membranes. For example, sequences from the HIV Tat protein (GRKKRRQRRRPPQ (SEQ ID NO: 13)) and the Drosophila Antennapedia protein (RQIKIWFQNRRMKWKK (SEQ ID NO: 14)) have been found to be capable of functioning as delivery peptides. A peptide or peptidomimetic can be encoded by a random sequence of DNA, such as a peptide identified from a phage-display library, or one-bead-one-compound (OBOC) combinatorial library (Lam et al., *Nature,* 354:82-84, 1991). Typically, the peptide or peptidomimetic tethered to a dsRNA agent via an incorporated monomer unit is a cell targeting peptide such as an arginine-glycine-aspartic acid (RGD)-peptide, or RGD mimic. A peptide moiety can range in length from about 5 amino acids to about 40 amino acids. The peptide moieties can have a structural modification, such as to increase stability or direct conformational properties. Any of the structural modifications described below can be utilized.

An RGD peptide for use in the compositions and methods of the invention may be linear or cyclic, and may be modified, e.g., glycosylated or methylated, to facilitate targeting to a specific tissue(s). RGD-containing peptides and peptidiomimemtics may include D-amino acids, as well as synthetic RGD mimics. In addition to RGD, one can use other moieties that target the integrin ligand. Preferred conjugates of this ligand target PECAM-1 or VEGF.

An RGD peptide moiety can be used to target a particular cell type, e.g., a tumor cell, such as an endothelial tumor cell or a breast cancer tumor cell (Zitzmann et al., *Cancer Res.,* 62:5139-43, 2002). An RGD peptide can facilitate targeting of an dsRNA agent to tumors of a variety of other tissues, including the lung, kidney, spleen, or liver (Aoki et al., *Cancer Gene Therapy* 8:783-787, 2001). Typically, the RGD peptide will facilitate targeting of an iRNA agent to the kidney. The RGD peptide can be linear or cyclic, and can be modified, e.g., glycosylated or methylated to facilitate targeting to specific tissues. For example, a glycosylated RGD peptide can deliver an iRNA agent to a tumor cell expressing $\alpha v \beta_3$ (Haubner et al., *Jour. Nucl. Med.,* 42:326-336, 2001).

A "cell permeation peptide" is capable of permeating a cell, e.g., a microbial cell, such as a bacterial or fungal cell, or a mammalian cell, such as a human cell. A microbial cell-permeating peptide can be, for example, an α-helical linear peptide (e.g., LL-37 or Ceropin P1), a disulfide bond-containing peptide (e.g., α-defensin, β-defensin or bactenecin), or a peptide containing only one or two dominating amino acids (e.g., PR-39 or indolicidin). A cell permeation peptide can also include a nuclear localization signal (NLS). For example, a cell permeation peptide can be a bipartite amphipathic peptide, such as MPG, which is derived from the fusion peptide domain of HIV-1 gp41 and the NLS of SV40 large T antigen (Simeoni et al., *Nucl. Acids Res.* 31:2717-2724, 2003).

C. Carbohydrate Conjugates

In some embodiments of the compositions and methods of the invention, an iRNA further comprises a carbohydrate. The carbohydrate conjugated iRNA are advantageous for the in vivo delivery of nucleic acids, as well as compositions suitable for in vivo therapeutic use, as described herein. As used herein, "carbohydrate" refers to a compound which is either a carbohydrate per se made up of one or more monosaccharide units having at least 6 carbon atoms (which can be linear, branched or cyclic) with an oxygen, nitrogen or sulfur atom bonded to each carbon atom; or a compound having as a part thereof a carbohydrate moiety made up of one or more monosaccharide units each having at least six carbon atoms (which can be linear, branched or cyclic), with an oxygen, nitrogen or sulfur atom bonded to each carbon atom. Representative carbohydrates include the sugars (mono-, di-, tri- and oligosaccharides containing from about 4, 5, 6, 7, 8, or 9 monosaccharide units), and polysaccharides such as starches, glycogen, cellulose and polysaccharide gums. Specific monosaccharides include C5 and above (e.g., C5, C6, C7, or C8) sugars; di- and tri-saccharides include sugars having two or three monosaccharide units (e.g., C5, C6, C7, or C8).

In certain embodiments, a carbohydrate conjugate comprises a monosaccharide.

In certain embodiments, the monosaccharide is an N-acetylgalactosamine (GalNAc). GalNAc conjugates, which comprise one or more N-acetylgalactosamine (GalNAc) derivatives, are described, for example, in U.S. Pat. No. 8,106,022, the entire content of which is hereby incorporated herein by reference. In some embodiments, the GalNAc conjugate serves as a ligand that targets the iRNA to particular cells. In some embodiments, the GalNAc conjugate targets the iRNA to liver cells, e.g., by serving as a ligand for the asialoglycoprotein receptor of liver cells (e.g., hepatocytes).

In some embodiments, the carbohydrate conjugate comprises one or more GalNAc derivatives. The GalNAc derivatives may be attached via a linker, e.g., a bivalent or trivalent branched linker. In some embodiments the GalNAc conjugate is conjugated to the 3' end of the sense strand. In some embodiments, the GalNAc conjugate is conjugated to the iRNA agent (e.g., to the 3' end of the sense strand) via a linker, e.g., a linker as described herein. In some embodiments the GalNAc conjugate is conjugated to the 5' end of the sense strand. In some embodiments, the GalNAc conjugate is conjugated to the iRNA agent (e.g., to the 5' end of the sense strand) via a linker, e.g., a linker as described herein.

In certain embodiments of the invention, the GalNAc or GalNAc derivative is attached to an iRNA agent of the invention via a monovalent linker. In some embodiments, the GalNAc or GalNAc derivative is attached to an iRNA agent of the invention via a bivalent linker. In yet other embodiments of the invention, the GalNAc or GalNAc derivative is attached to an iRNA agent of the invention via a trivalent linker. In other embodiments of the invention, the GalNAc or GalNAc derivative is attached to an iRNA agent of the invention via a tetravalent linker.

In certain embodiments, the double stranded RNAi agents of the invention comprise one GalNAc or GalNAc derivative attached to the iRNA agent. In certain embodiments, the double stranded RNAi agents of the invention comprise a plurality (e.g., 2, 3, 4, 5, or 6) GalNAc or GalNAc derivatives, each independently attached to a plurality of nucleotides of the double stranded RNAi agent through a plurality of monovalent linkers.

In some embodiments, for example, when the two strands of an iRNA agent of the invention are part of one larger molecule connected by an uninterrupted chain of nucleotides between the 3'-end of one strand and the 5'-end of the respective other strand forming a hairpin loop comprising, a plurality of unpaired nucleotides, each unpaired nucleotide within the hairpin loop may independently comprise a GalNAc or GalNAc derivative attached via a monovalent linker. The hairpin loop may also be formed by an extended overhang in one strand of the duplex.

In some embodiments, for example, when the two strands of an iRNA agent of the invention are part of one larger molecule connected by an uninterrupted chain of nucleotides between the 3'-end of one strand and the 5'-end of the respective other strand forming a hairpin loop comprising, a plurality of unpaired nucleotides, each unpaired nucleotide within the hairpin loop may independently comprise a GalNAc or GalNAc derivative attached via a monovalent linker. The hairpin loop may also be formed by an extended overhang in one strand of the duplex.

In some embodiments, the GalNAc conjugate is

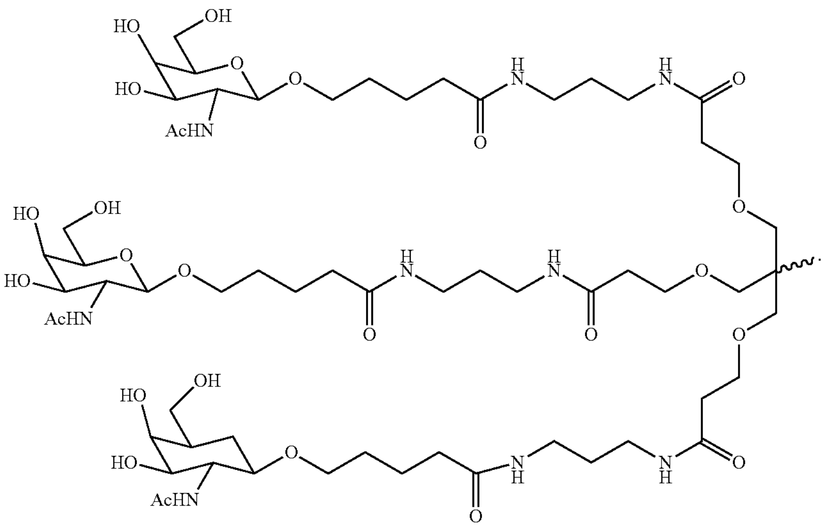

Formula II.

In some embodiments, the RNAi agent is attached to the carbohydrate conjugate via a linker as shown in the following schematic wherein X is O or S

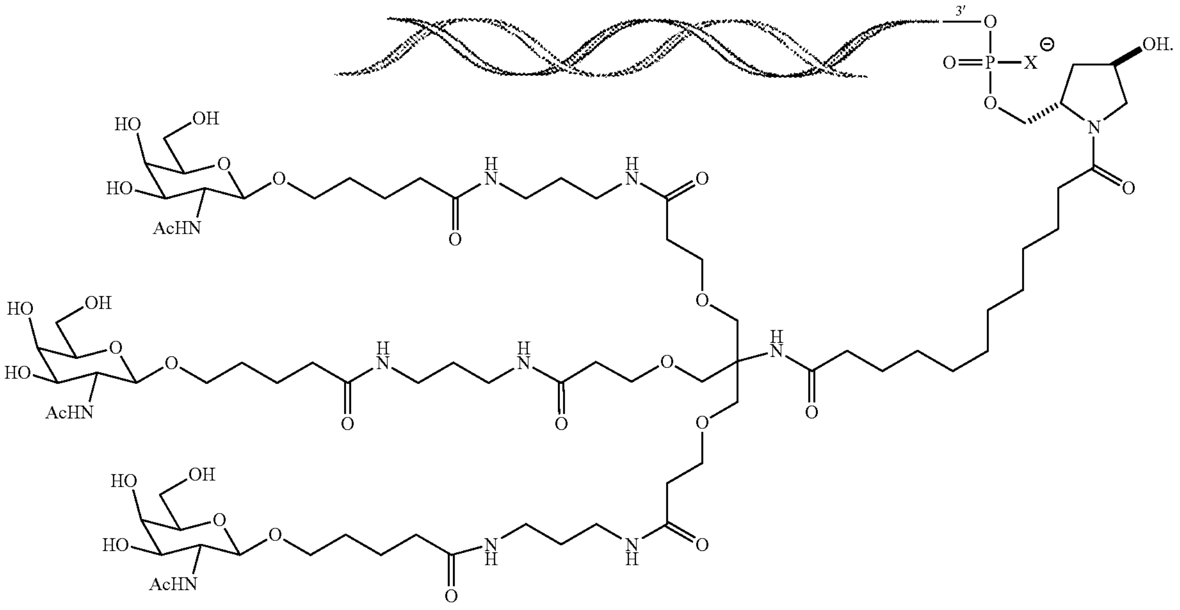

In some embodiments, the RNAi agent is conjugated to L96 as defined in Table 1 and shown below:
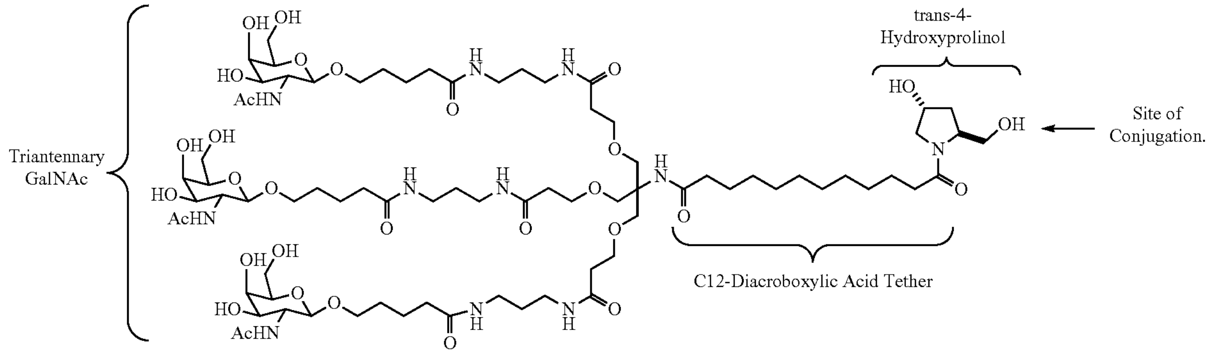
In certain embodiments, a carbohydrate conjugate for use in the compositions and methods of the invention is selected from the group consisting of:
Formula II
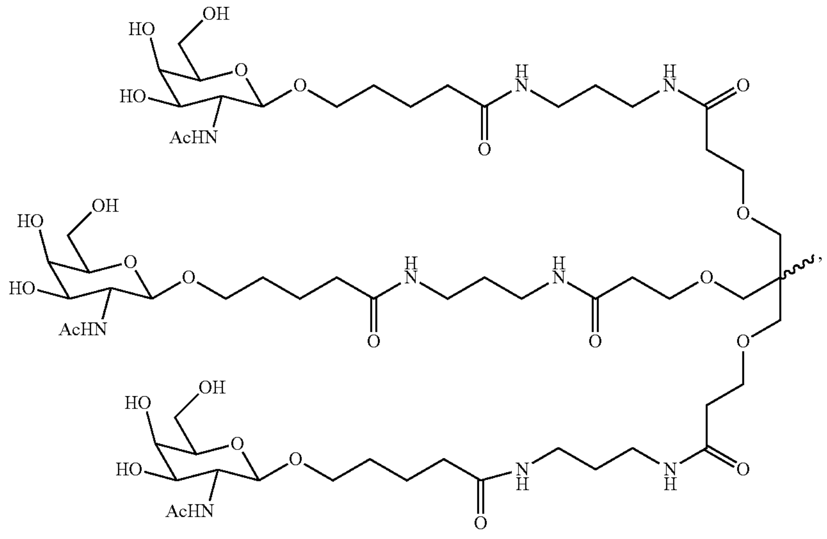
Formula III
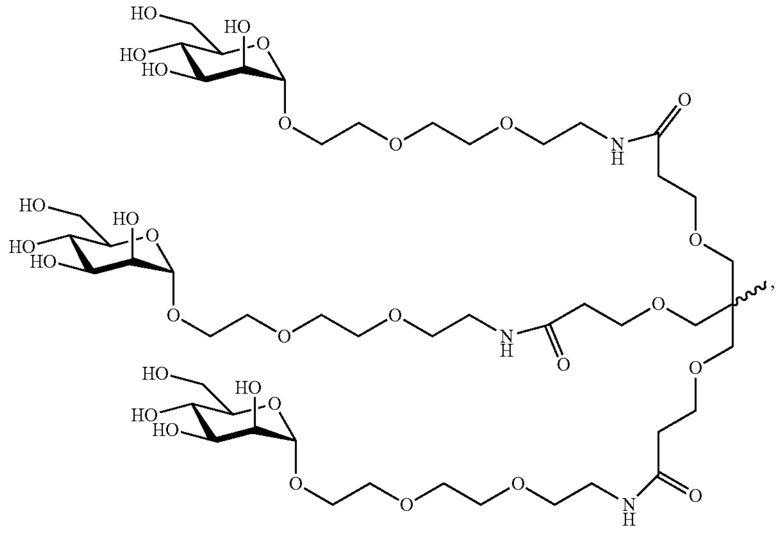

-continued
Formula IV
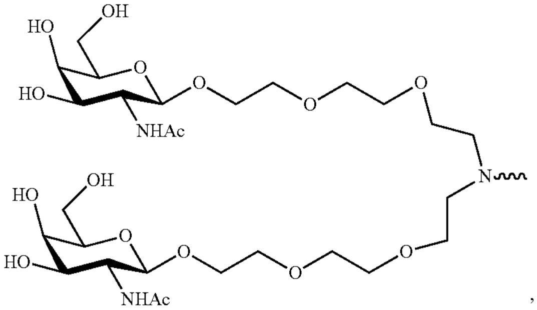
,
Formula V
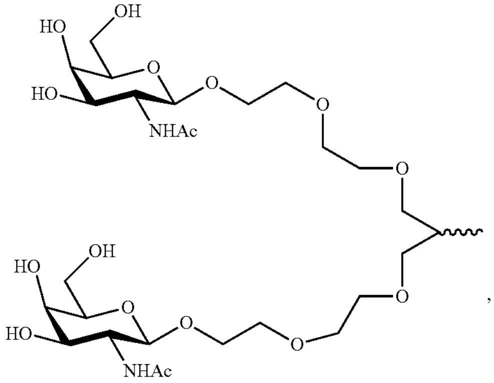
,
Formula VI
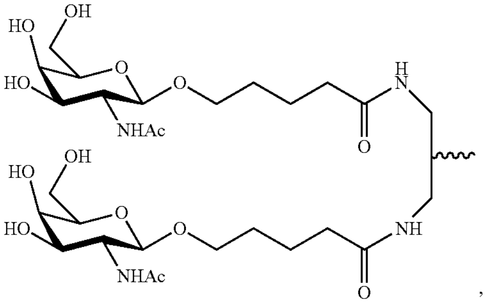
,
Formula VII
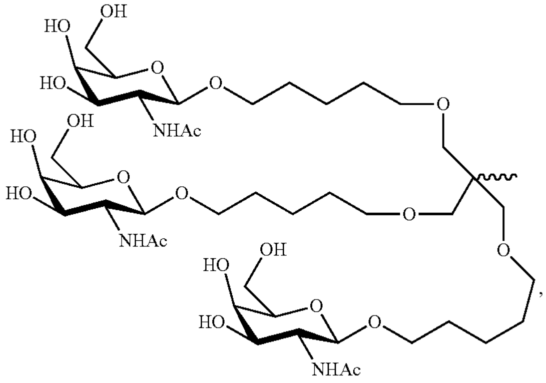
,
Formula VIII
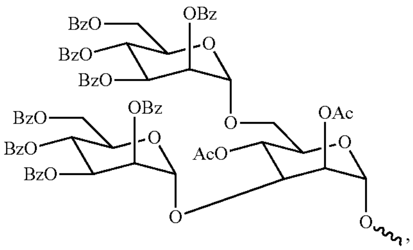
,
Formula IX
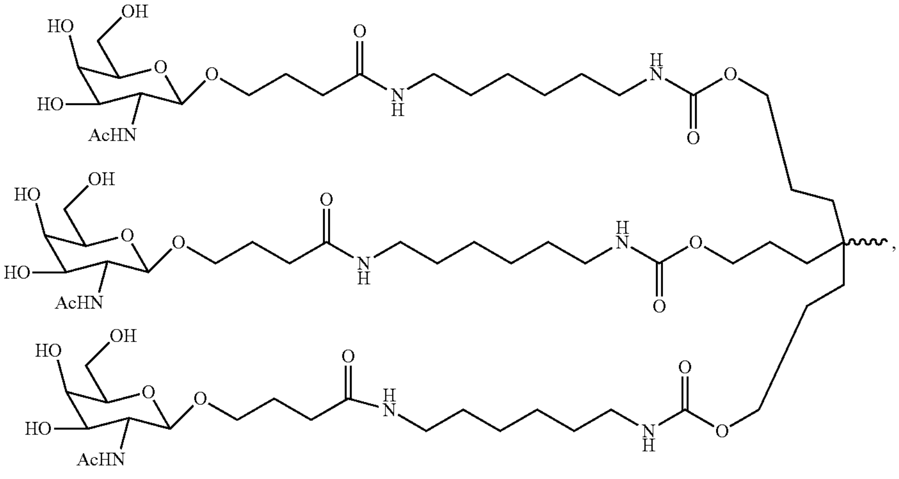
, -continued
Formula X
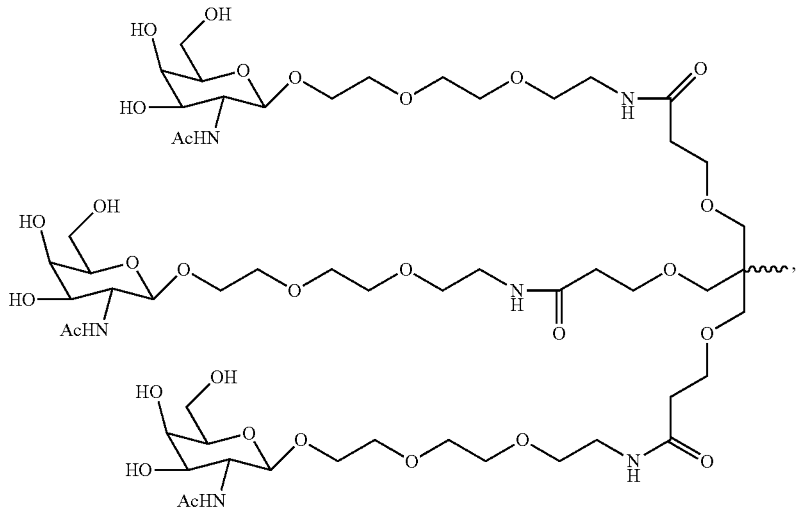
Formula XI
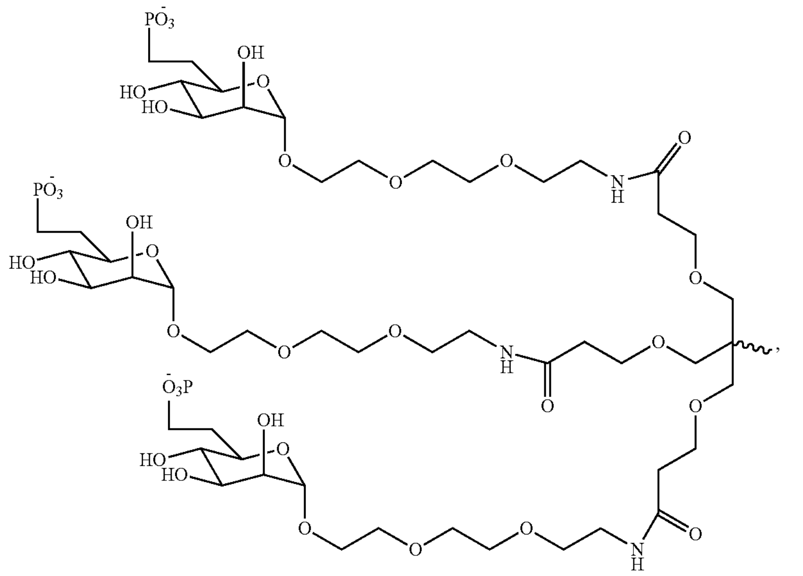

-continued
Formula XII
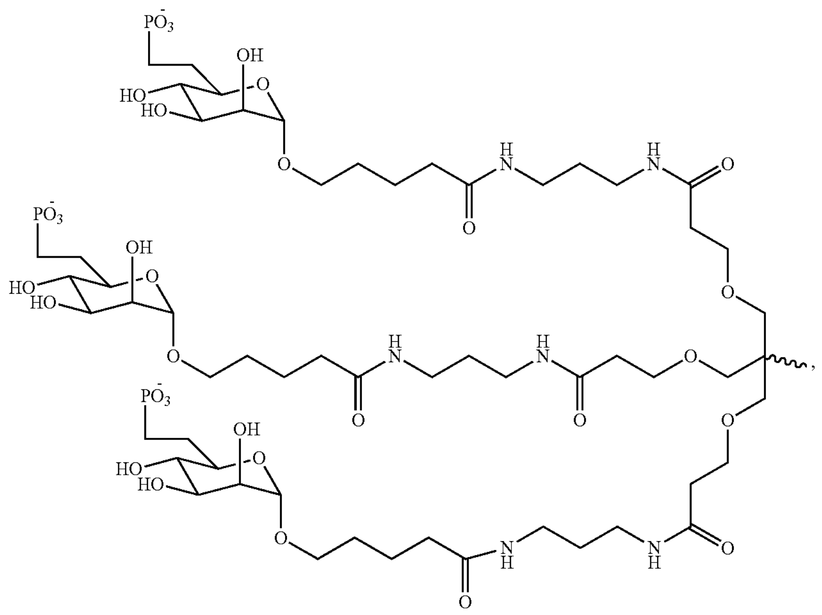
Formula XIII
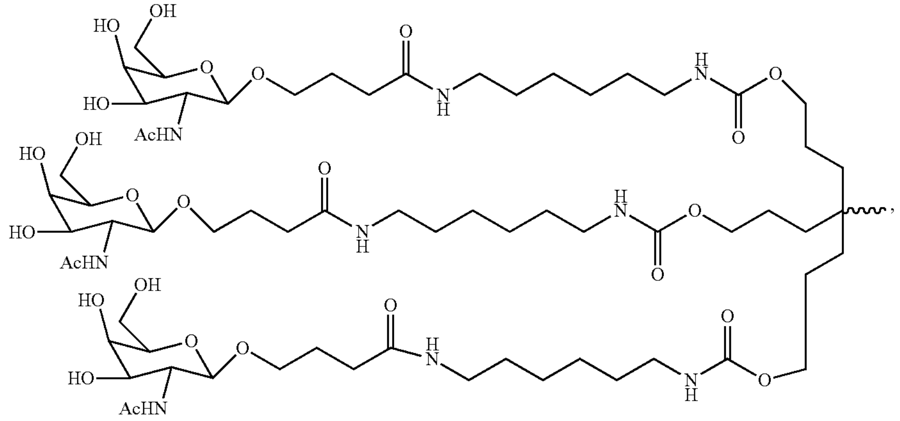
Formula XIV
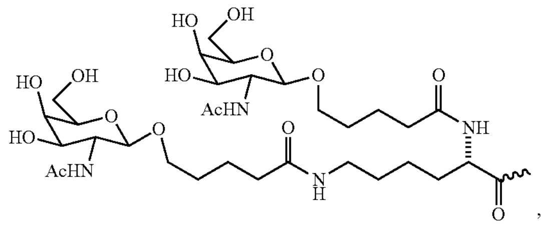
Formula XV
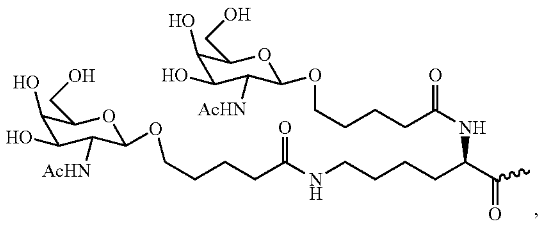
Formula XVI
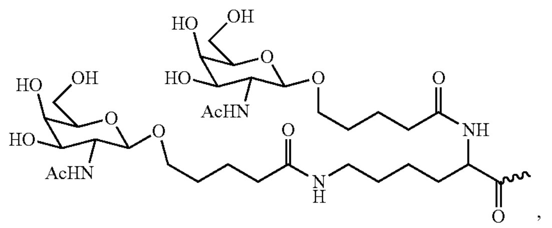
Formula XVII
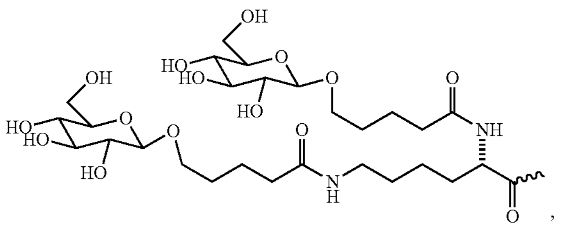

-continued
Formula XVIII
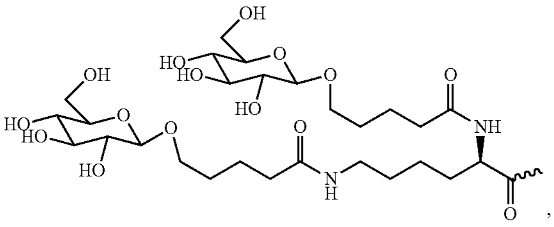
,
Formula XIX
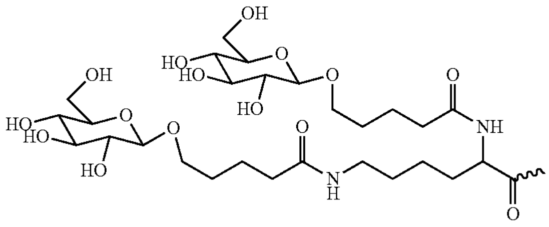
,
Formula XX
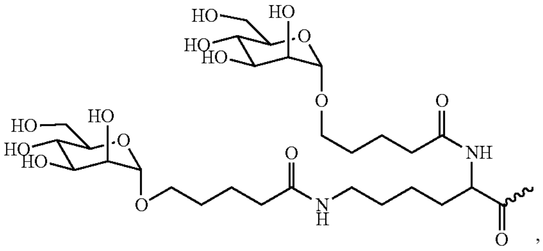
,
Formula XXI
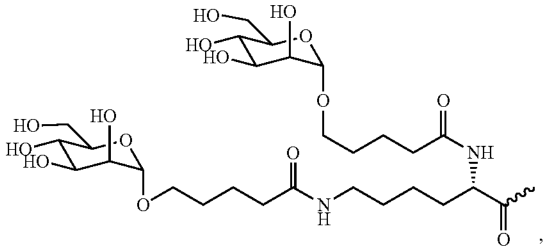
,
Formula XXII
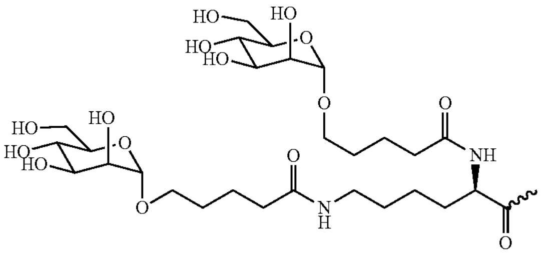
,
Formula XXIII
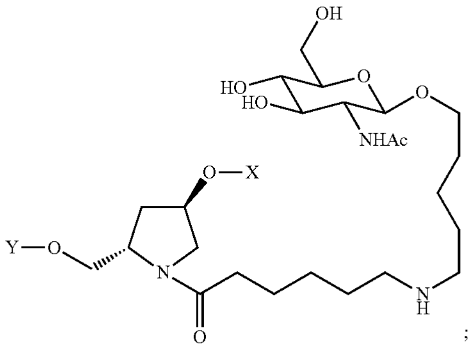
;
(Formula XXIV)
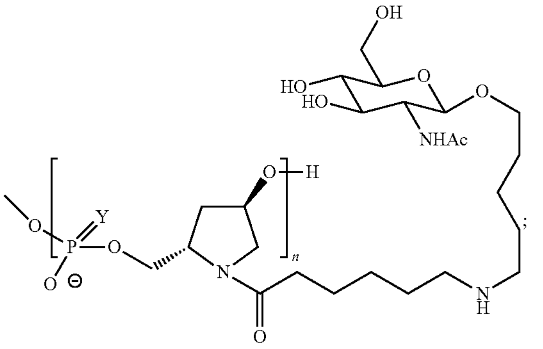
wherein Y is O or S and n is 3-6
(Formula XXV)
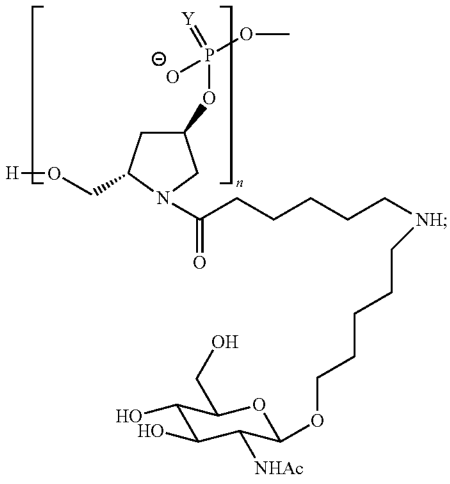
wherein Y is O or S and n is 3-6

-continued
Formula XXVI
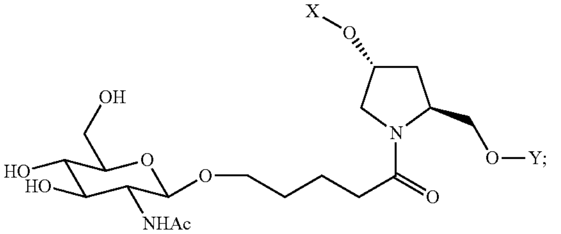
(Formula XXVII)
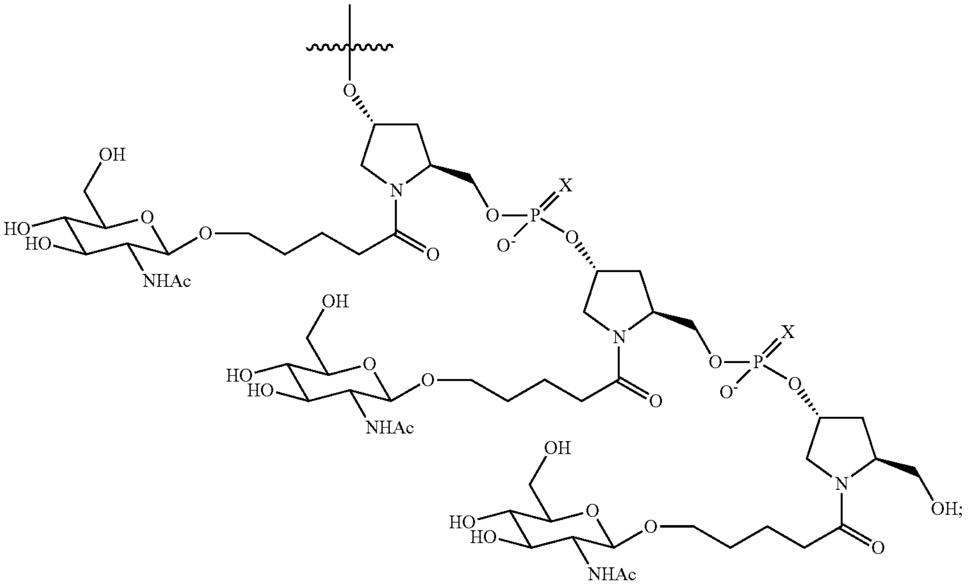
wherein X is O or S
Formula XXVII
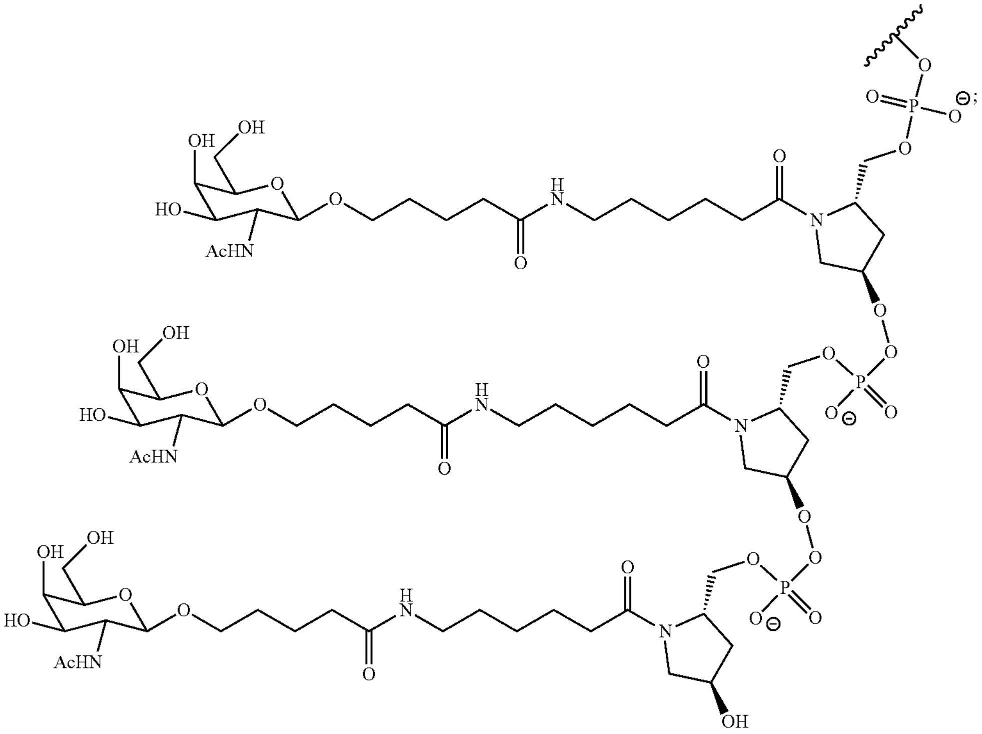

-continued
Formula XXIX
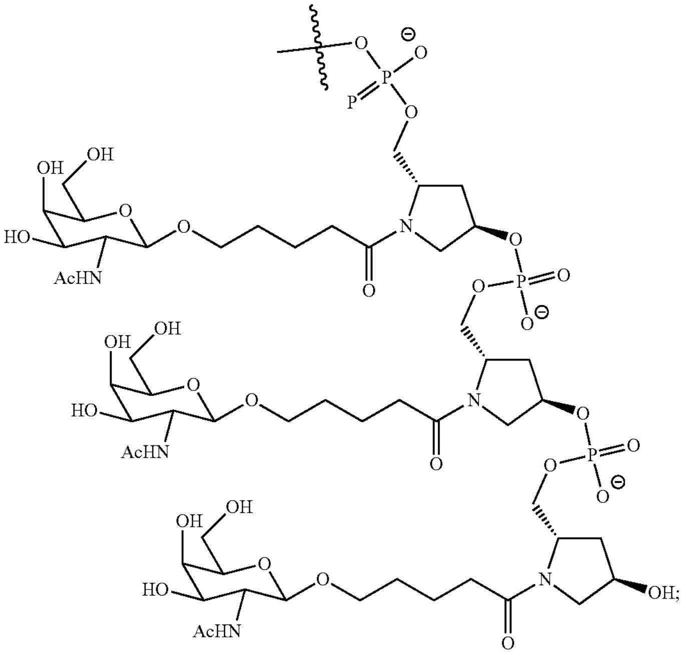
Formula XXX
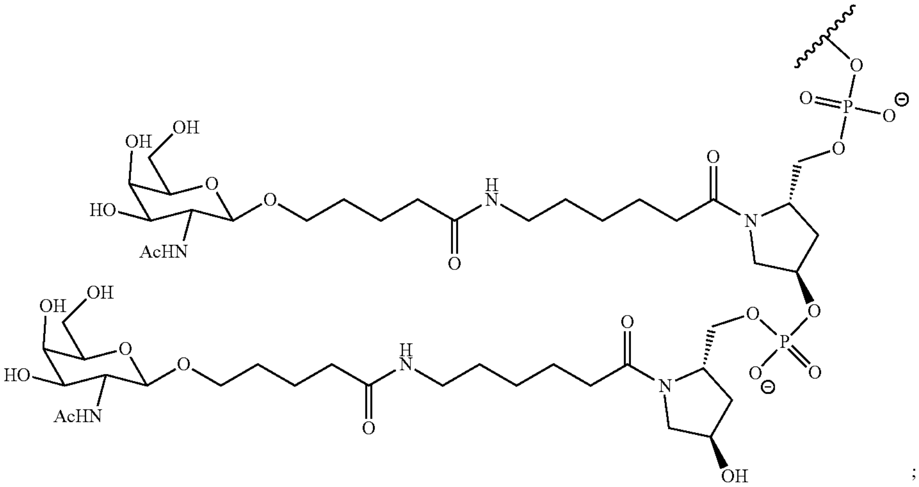
;
Formula XXXI
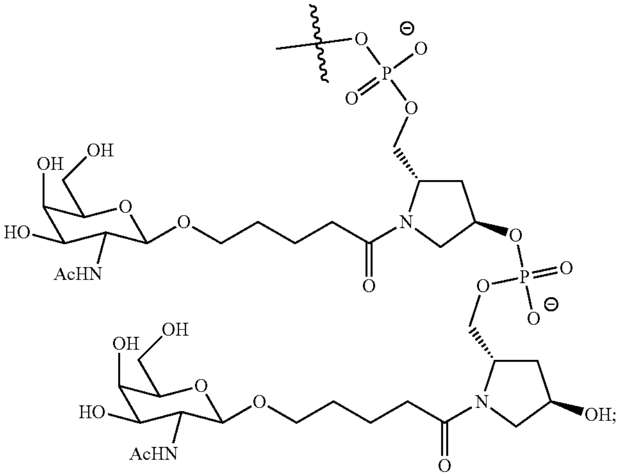

-continued
Formula XXXII
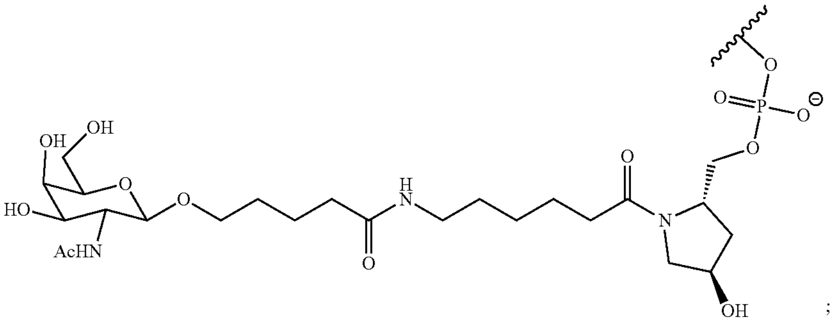
; and
Formula XXXIII
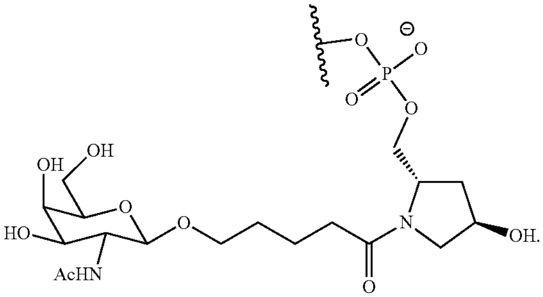
Formula XXXIV
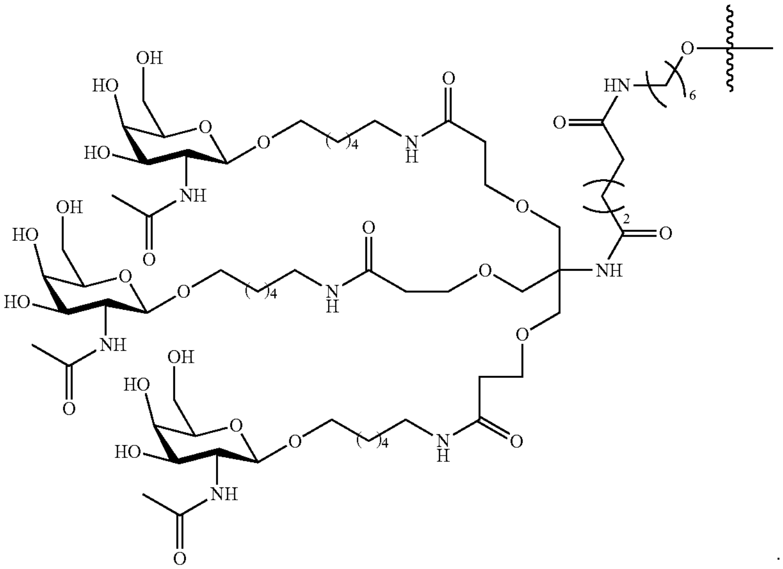

In certain embodiments, a carbohydrate conjugate for use in the compositions and methods of the invention is a monosaccharide. In certain embodiments, the monosaccharide is an N-acetylgalactosamine, such as

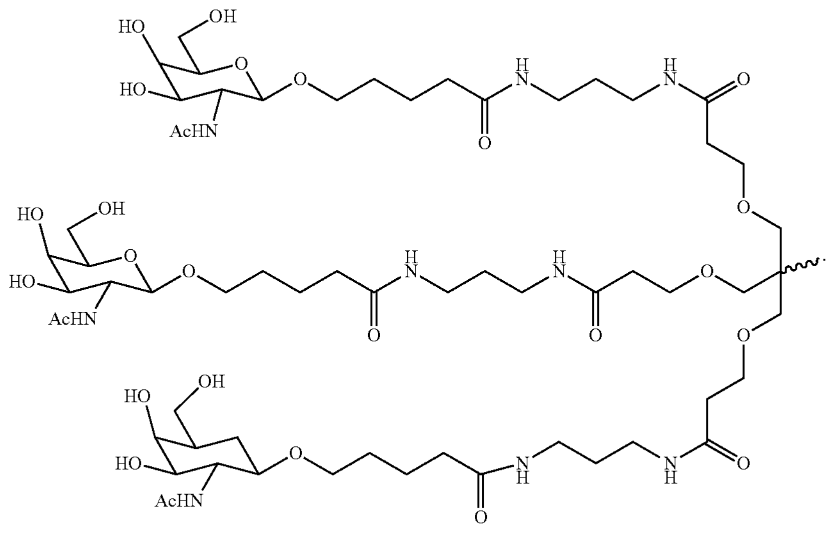

Formula II.

In some embodiments, the RNAi agent is attached to the carbohydrate conjugate via a linker as shown in the following schematic, wherein X is O or S

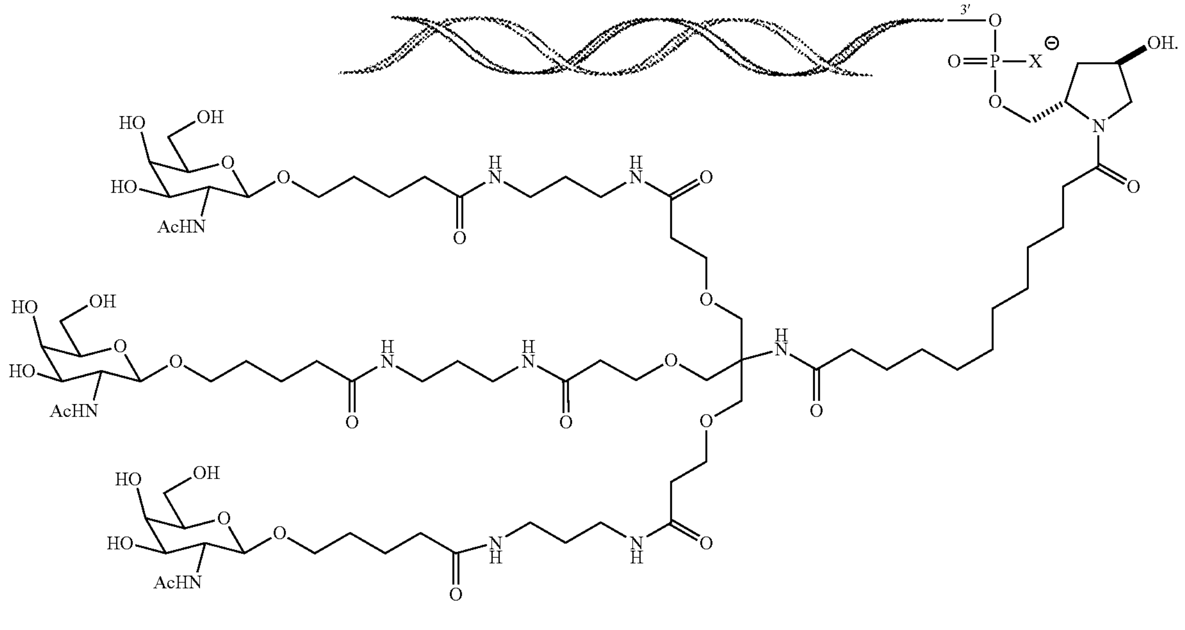

In some embodiments, the RNAi agent is conjugated to L96 as defined in Table 1 and shown below:
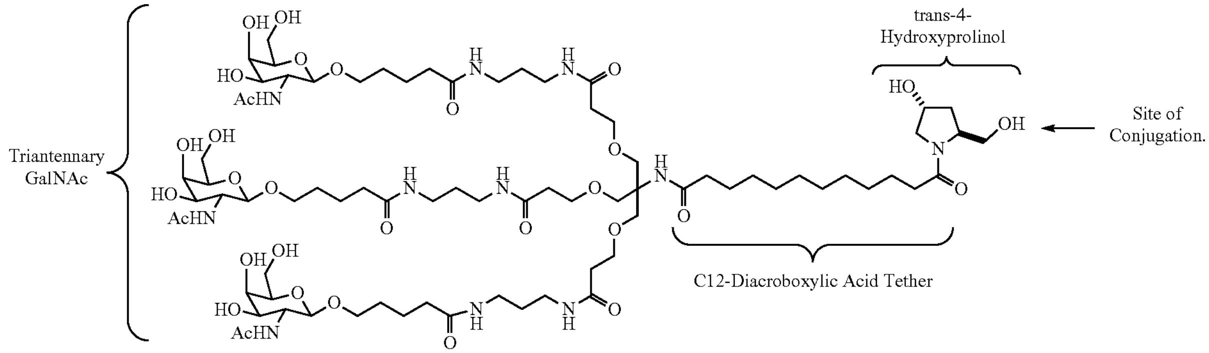
Another representative carbohydrate conjugate for use in the embodiments described herein includes, but is not limited to,
(Formula XXXVI)
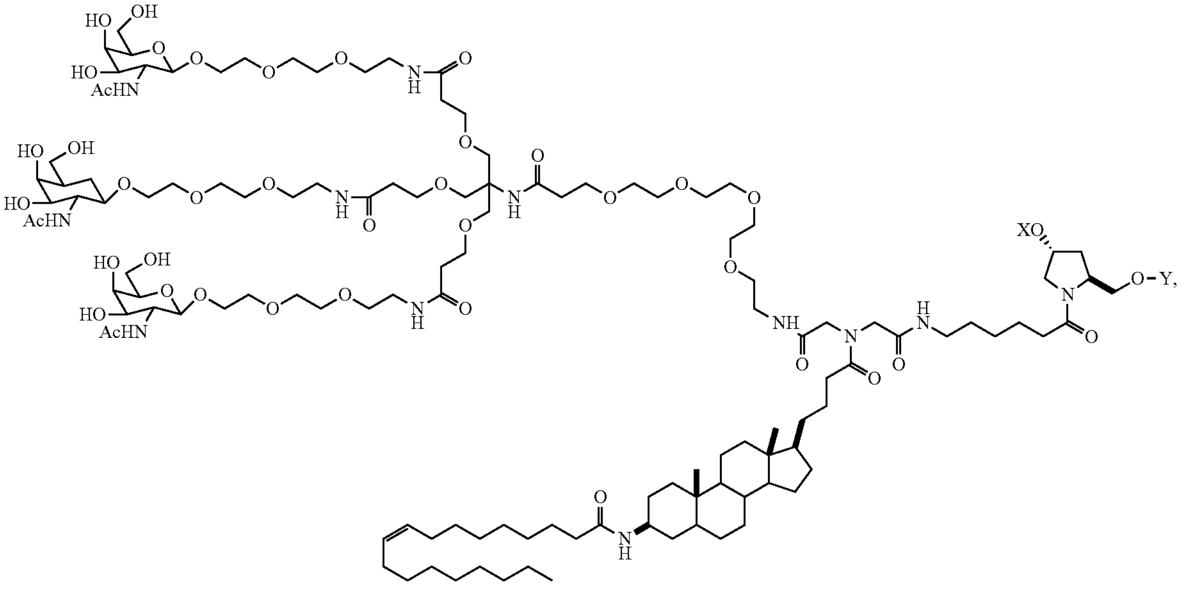

when one of X or Y is an oligonucleotide, the other is a hydrogen.

In some embodiments, a suitable ligand is a ligand disclosed in WO 2019/055633, the entire contents of which are incorporated herein by reference. In one embodiment the ligand comprises the structure below:

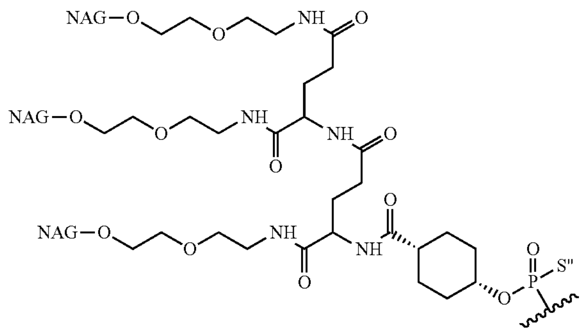

(NAG37)s

In certain embodiments, the RNAi agents of the disclosure may include GalNAc ligands, even if such GalNAc ligands are currently projected to be of limited value for the preferred intrathecal/CNS delivery route(s) of the instant disclosure.

In certain embodiments of the invention, the GalNAc or GalNAc derivative is attached to an iRNA agent of the invention via a monovalent linker. In some embodiments, the GalNAc or GalNAc derivative is attached to an iRNA agent of the invention via a bivalent linker. In yet other embodiments of the invention, the GalNAc or GalNAc derivative is attached to an iRNA agent of the invention via a trivalent linker.

In one embodiment, the double stranded RNAi agents of the invention comprise one or more GalNAc or GalNAc derivative attached to the iRNA agent. The GalNAc may be attached to any nucleotide via a linker on the sense strand or antsisense strand. The GalNac may be attached to the 5'-end of the sense strand, the 3' end of the sense strand, the 5'-end of the antisense strand, or the 3'-end of the antisense strand. In one embodiment, the GalNAc is attached to the 3' end of the sense strand, e.g., via a trivalent linker.

In other embodiments, the double stranded RNAi agents of the invention comprise a plurality (e.g., 2, 3, 4, 5, or 6) GalNAc or GalNAc derivatives, each independently attached to a plurality of nucleotides of the double stranded RNAi agent through a plurality of linkers, e.g., monovalent linkers.

In some embodiments, for example, when the two strands of an iRNA agent of the invention is part of one larger molecule connected by an uninterrupted chain of nucleotides between the 3'-end of one strand and the 5'-end of the respective other strand forming a hairpin loop comprising, a plurality of unpaired nucleotides, each unpaired nucleotide within the hairpin loop may independently comprise a GalNAc or GalNAc derivative attached via a monovalent linker.

In some embodiments, the carbohydrate conjugate further comprises one or more additional ligands as described above, such as, but not limited to, a PK modulator or a cell permeation peptide.

Additional carbohydrate conjugates and linkers suitable for use in the present invention include those described in WO 2014/179620 and WO 2014/179627, the entire contents of each of which are incorporated herein by reference.

D. Linkers

In some embodiments, the conjugate or ligand described herein can be attached to an iRNA oligonucleotide with various linkers that can be cleavable or non-cleavable.

The term "linker" or "linking group" means an organic moiety that connects two parts of a compound, e.g., covalently attaches two parts of a compound. Linkers typically comprise a direct bond or an atom such as oxygen or sulfur, a unit such as NR8, C(O), C(O)NH, SO, $SO_2$, $SO_2NH$ or a chain of atoms, such as, but not limited to, substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylhereroaryl, which one or more methylenes can be interrupted or terminated by O, S, S(O), $SO_2$, N(R8), C(O), substituted or unsubstituted aryl, substituted or unsubstituted heteroaryl, substituted or unsubstituted heterocyclic; where R8 is hydrogen, acyl, aliphatic or substituted aliphatic. In certain embodiments, the linker is between about 1-24 atoms, 2-24, 3-24, 4-24, 5-24, 6-24, 6-18, 7-18, 8-18 atoms, 7-17, 8-17, 6-16, 7-16, or 8-16 atoms.

A cleavable linking group is one which is sufficiently stable outside the cell, but which upon entry into a target cell is cleaved to release the two parts the linker is holding together. In a preferred embodiment, the cleavable linking group is cleaved at least about 10 times, 20, times, 30 times, 40 times, 50 times, 60 times, 70 times, 80 times, 90 times or more, or at least about 100 times faster in a target cell or under a first reference condition (which can, e.g., be selected to mimic or represent intracellular conditions) than in the blood of a subject, or under a second reference condition (which can, e.g., be selected to mimic or represent conditions found in the blood or serum).

Cleavable linking groups are susceptible to cleavage agents, e.g., pH, redox potential or the presence of degradative molecules. Generally, cleavage agents are more prevalent or found at higher levels or activities inside cells than in serum or blood. Examples of such degradative agents include: redox agents which are selected for particular substrates or which have no substrate specificity, including, e.g., oxidative or reductive enzymes or reductive agents such as mercaptans, present in cells, that can degrade a redox cleavable linking group by reduction; esterases; endosomes or agents that can create an acidic environment, e.g., those that result in a pH of five or lower; enzymes that can hydrolyze or degrade an acid cleavable linking group by acting as a general acid, peptidases (which can be substrate specific), and phosphatases.

A cleavable linkage group, such as a disulfide bond can be susceptible to pH. The pH of human serum is 7.4, while the average intracellular pH is slightly lower, ranging from about 7.1-7.3. Endosomes have a more acidic pH, in the range of 5.5-6.0, and lysosomes have an even more acidic pH at around 5.0. Some linkers will have a cleavable linking group that is cleaved at a preferred pH, thereby releasing a cationic lipid from the ligand inside the cell, or into the desired compartment of the cell.

A linker can include a cleavable linking group that is cleavable by a particular enzyme. The type of cleavable linking group incorporated into a linker can depend on the cell to be targeted. For example, a liver-targeting ligand can be linked to a cationic lipid through a linker that includes an ester group. Liver cells are rich in esterases, and therefore the linker will be cleaved more efficiently in liver cells than in cell types that are not esterase-rich. Other cell-types rich in esterases include cells of the lung, renal cortex, and testis.

Linkers that contain peptide bonds can be used when targeting cell types rich in peptidases, such as liver cells and synoviocytes.

In general, the suitability of a candidate cleavable linking group can be evaluated by testing the ability of a degradative agent (or condition) to cleave the candidate linking group. It will also be desirable to also test the candidate cleavable linking group for the ability to resist cleavage in the blood or when in contact with other non-target tissue. Thus, one can determine the relative susceptibility to cleavage between a first and a second condition, where the first is selected to be indicative of cleavage in a target cell and the second is selected to be indicative of cleavage in other tissues or biological fluids, e.g., blood or serum. The evaluations can be carried out in cell free systems, in cells, in cell culture, in organ or tissue culture, or in whole animals. It can be useful to make initial evaluations in cell-free or culture conditions and to confirm by further evaluations in whole animals. In preferred embodiments, useful candidate compounds are cleaved at least about 2, 4, 10, 20, 30, 40, 50, 60, 70, 80, 90, or about 100 times faster in the cell (or under in vitro conditions selected to mimic intracellular conditions) as compared to blood or serum (or under in vitro conditions selected to mimic extracellular conditions).

i. Redox Cleavable Linking Groups

In certain embodiments, a cleavable linking group is a redox cleavable linking group that is cleaved upon reduction or oxidation. An example of reductively cleavable linking group is a disulphide linking group (—S—S—). To determine if a candidate cleavable linking group is a suitable "reductively cleavable linking group," or for example is suitable for use with a particular iRNA moiety and particular targeting agent one can look to methods described herein. For example, a candidate can be evaluated by incubation with dithiothreitol (DTT), or other reducing agent using reagents know in the art, which mimic the rate of cleavage which would be observed in a cell, e.g., a target cell. The candidates can also be evaluated under conditions which are selected to mimic blood or serum conditions. In one, candidate compounds are cleaved by at most about 10% in the blood. In other embodiments, useful candidate compounds are degraded at least about 2, 4, 10, 20, 30, 40, 50, 60, 70, 80, 90, or about 100 times faster in the cell (or under in vitro conditions selected to mimic intracellular conditions) as compared to blood (or under in vitro conditions selected to mimic extracellular conditions). The rate of cleavage of candidate compounds can be determined using standard enzyme kinetics assays under conditions chosen to mimic intracellular media and compared to conditions chosen to mimic extracellular media.

ii. Phosphate-Based Cleavable Linking Groups

In certain embodiments, a cleavable linker comprises a phosphate-based cleavable linking group. A phosphate-based cleavable linking group is cleaved by agents that degrade or hydrolyze the phosphate group. An example of an agent that cleaves phosphate groups in cells are enzymes such as phosphatases in cells. Examples of phosphate-based linking groups are —O—P(O)(ORk)-O—, —O—P(S)(ORk)—O—, —O—P(S)(SRk)—O—, —S—P(O)(ORk)—O—, —O—P(O)(ORk)-S—, —S—P(O)(ORk)-S—, —O—P(S)(ORk)-S—, —S—P(S)(ORk)—O—, —O—P(O)(Rk)—O—, —O—P(S)(Rk)—O—, —S—P(O)(Rk)—O—, —S—P(S)(Rk)—O—, —S—P(O)(Rk)-S—, —O—P(S)(Rk)-S—. Preferred embodiments are —O—P(O)(OH)—O—, —O—P(S)(OH)—O—, —O—P(S)(SH)—O—, —S—P(O)(OH)—O—, —O—P(O)(OH)—S—, —S—P(O)(OH)—S—, —O—P(S)(OH)—S—, —S—P(S)(OH)—O—, —O—P(O)(H)—O—, —O—P(S)(H)—O—, —S—P(O)(H)—O, —S—P(S)(H)—O—, —S—P(O)(H)—S—, —O—P(S)(H)—S—. A preferred embodiment is —O—P(O)(OH)—O—. These candidates can be evaluated using methods analogous to those described above.

iii. Acid Cleavable Linking Groups

In certain embodiments, a cleavable linker comprises an acid cleavable linking group. An acid cleavable linking group is a linking group that is cleaved under acidic conditions. In preferred embodiments acid cleavable linking groups are cleaved in an acidic environment with a pH of about 6.5 or lower (e.g., about 6.0, 5.75, 5.5, 5.25, 5.0, or lower), or by agents such as enzymes that can act as a general acid. In a cell, specific low pH organelles, such as endosomes and lysosomes can provide a cleaving environment for acid cleavable linking groups. Examples of acid cleavable linking groups include but are not limited to hydrazones, esters, and esters of amino acids. Acid cleavable groups can have the general formula —C═NN—, C(O)O, or —OC(O). A preferred embodiment is when the carbon attached to the oxygen of the ester (the alkoxy group) is an aryl group, substituted alkyl group, or tertiary alkyl group such as dimethyl pentyl or t-butyl. These candidates can be evaluated using methods analogous to those described above.

iv. Ester-Based Cleavable Linking Groups

In certain embodiments, a cleavable linker comprises an ester-based cleavable linking group. An ester-based cleavable linking group is cleaved by enzymes such as esterases and amidases in cells. Examples of ester-based cleavable linking groups include but are not limited to esters of alkylene, alkenylene and alkynylene groups. Ester cleavable linking groups have the general formula —C(O)O—, or —OC(O)—. These candidates can be evaluated using methods analogous to those described above.

v. Peptide-Based Cleavable Linking Groups

In yet another embodiment, a cleavable linker comprises a peptide-based cleavable linking group. A peptide-based cleavable linking group is cleaved by enzymes such as peptidases and proteases in cells. Peptide-based cleavable linking groups are peptide bonds formed between amino acids to yield oligopeptides (e.g., dipeptides, tripeptides etc.) and polypeptides. Peptide-based cleavable groups do not include the amide group (—C(O)NH—). The amide group can be formed between any alkylene, alkenylene or alkynelene. A peptide bond is a special type of amide bond formed between amino acids to yield peptides and proteins. The peptide based cleavage group is generally limited to the peptide bond (i.e., the amide bond) formed between amino acids yielding peptides and proteins and does not include the entire amide functional group. Peptide-based cleavable linking groups have the general formula —NHCHRAC(O)NHCHRBC(O)—, where RA and RB are the R groups of the two adjacent amino acids. These candidates can be evaluated using methods analogous to those described above.

In some embodiments, an iRNA of the invention is conjugated to a carbohydrate through a linker. Non-limiting examples of iRNA carbohydrate conjugates with linkers of the compositions and methods of the invention include, but are not limited to, (Formula XXXVII)

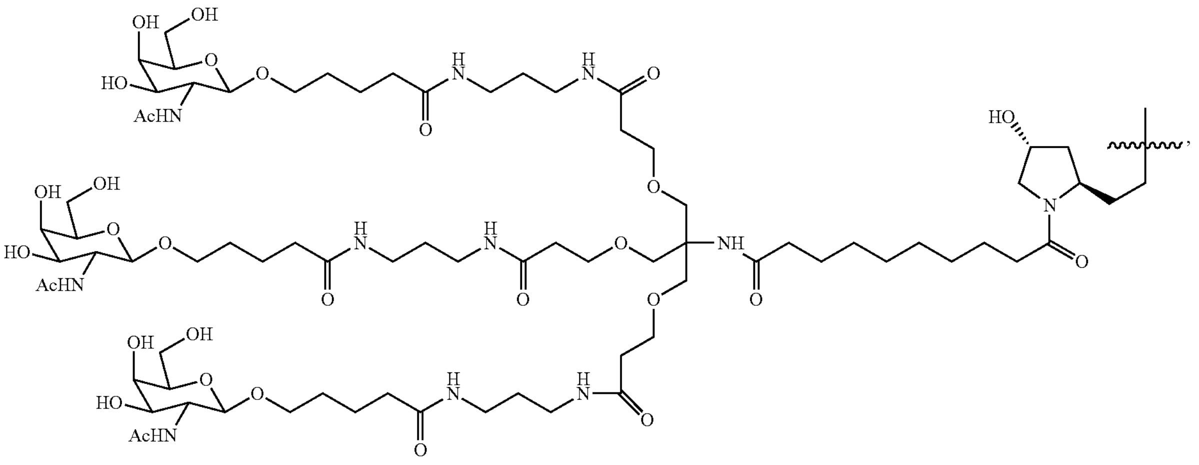

(Formula XXXVIII)

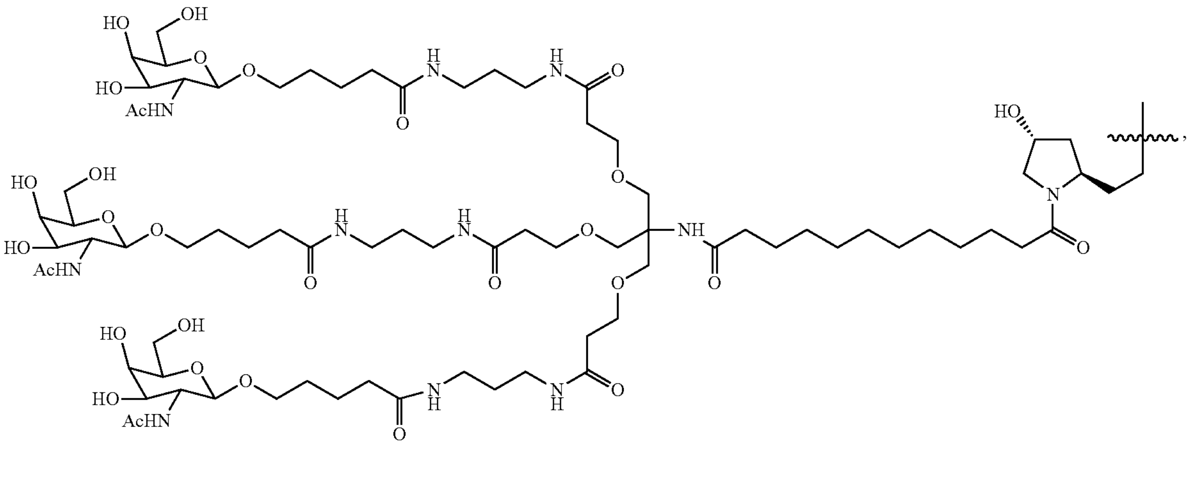

-continued
(Formula XXXIX)
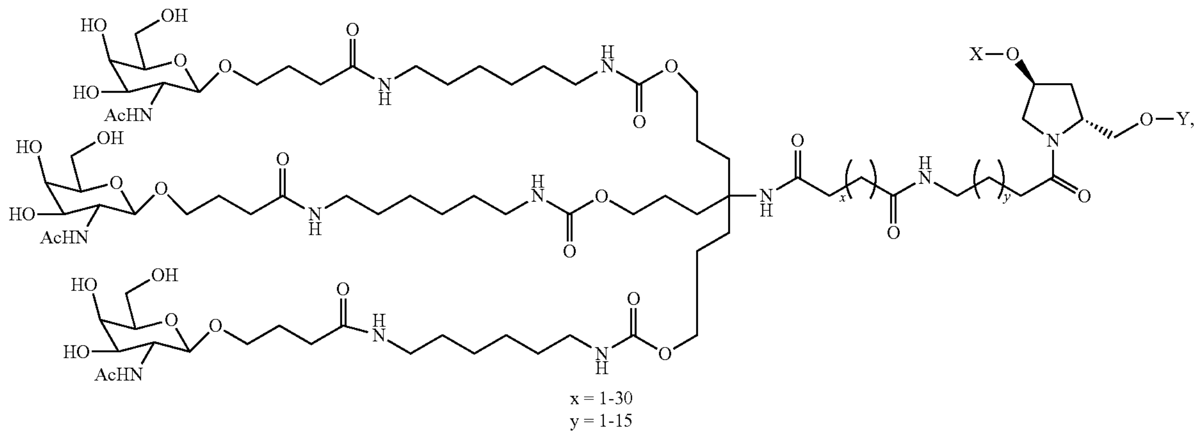
x = 1-30
y = 1-15
(Formula XL)
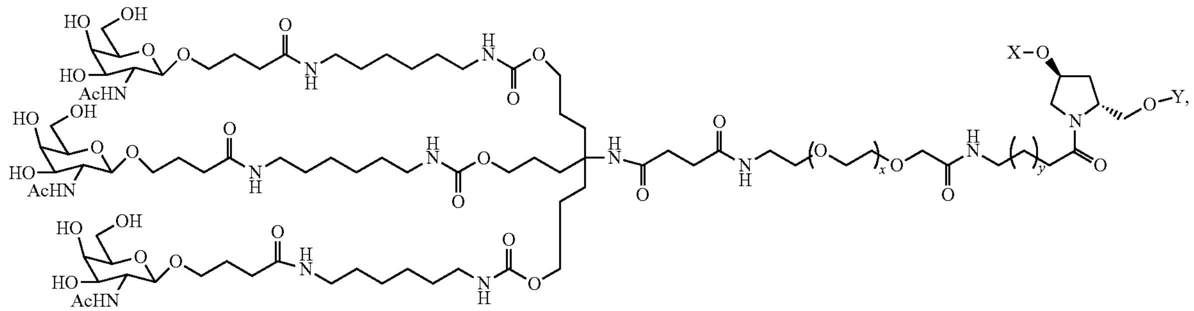
x = 1-30
y = 1-15
(Formula XLI)
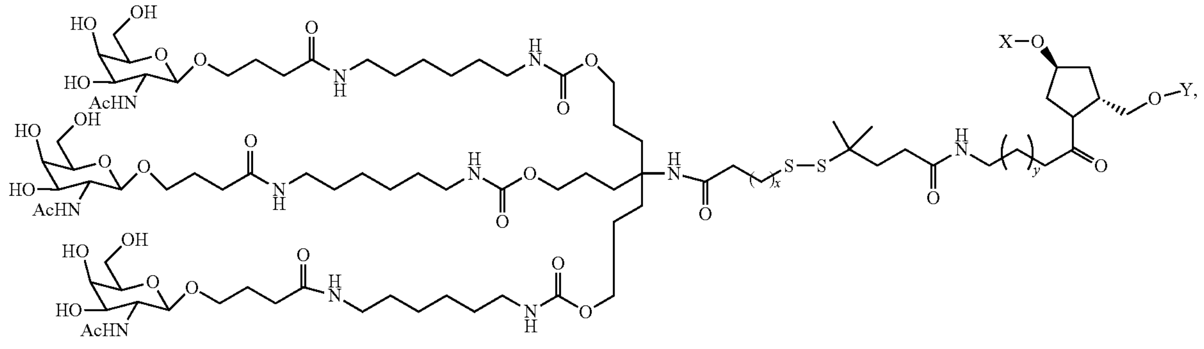
x = 0-30
y = 1-15

-continued
(Formula XLII)
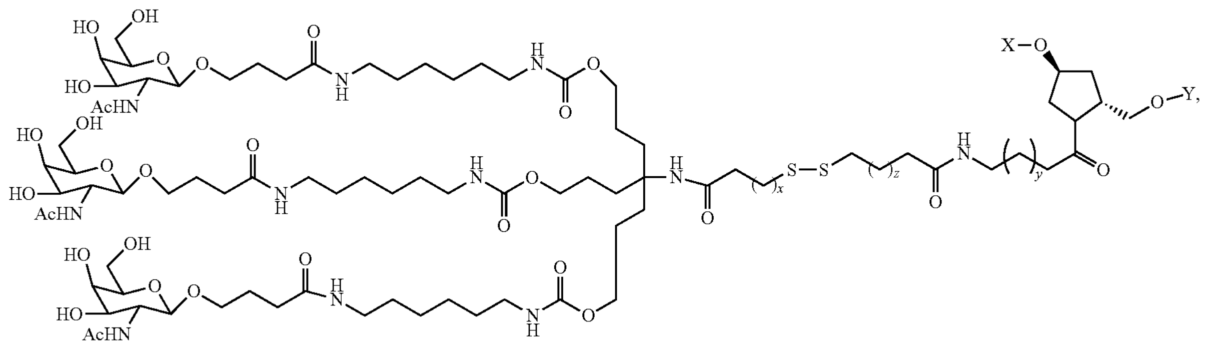
x = 0-30
y = 1-15
z = 1-20
(Formula XLIII)
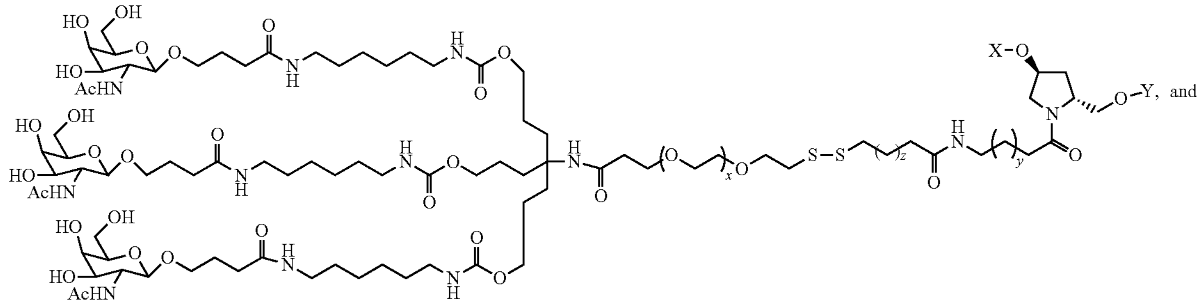
x = 1-30
y = 1-15
z = 1-20
(Formula XLIV)
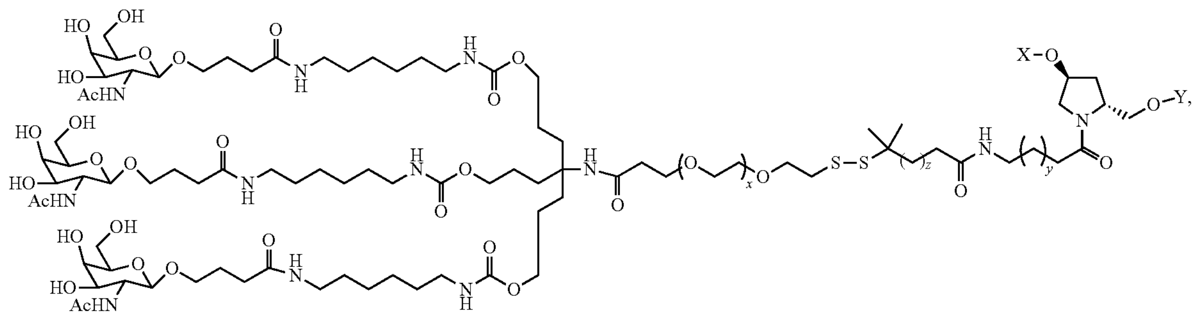
x = 1-30
y = 1-15
z = 1-20 when one of X or Y is an oligonucleotide, the other is a hydrogen.

In certain embodiments of the compositions and methods of the invention, a ligand is one or more "GalNAc" (N-acetylgalactosamine) derivatives attached through a bivalent or trivalent branched linker.

In certain embodiments, a dsRNA of the invention is conjugated to a bivalent or trivalent branched linker selected from the group of structures shown in any of formula (XLV)-(XLVI):

(IV)

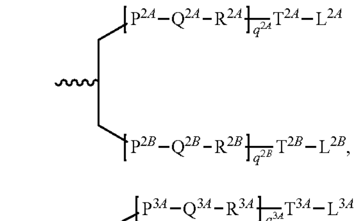

(V)

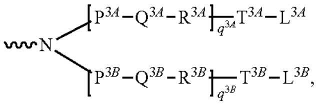

Formula XLVII

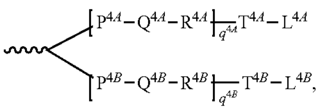

Formula XLVIII

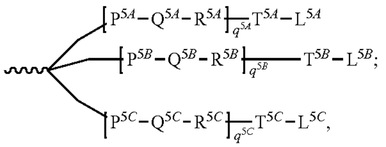

wherein:

q2A, q2B, q3A, q3B, q4A, q4B, q5A, q5B and q5C represent independently for each occurrence 0-20 and wherein the repeating unit can be the same or different;

$P^{2A}$, $p^{2B}$, $p^{3A}$, $p^{3B}$, $p^{4A}$, $P^{4B}$, $p^{5A}$, $P^{5B}$, $P^{5C}$, $T^{2A}$, $T^{2B}$, $T^{3A}$, $T^{3B}$, $T^{4A}$, $T^{4B}$, $T^{1A}$, $T^{5B}$, $T^{5C}$, are each independently for each occurrence absent, CO, NH, O, S, OC(O), NHC (O), $CH_2$, $CH_2NH$ or $CH_2O$;

$Q^{2A}$ $Q^{2B}$ $Q^{3A}$ $Q^{3B}$, $Q^{4A}$, $Q^{4B}$, $Q^{5A}$, $Q^{5B}$, $Q^{5C}$ are independently for each occurrence absent, alkylene, substituted alkylene wherein one or more methylenes can be interrupted or terminated by one or more of O, S, S(O), $SO_2$, $N(R^N)$, C(R')=C(R"), C≡C or C(O);

$R^{2A}$, $R^{2B}$, $R^{3A}$, $R^{3B}$, $R^{4A}$, $R^{4B}$, $R^{5A}$, $R^{5B}$, $R^{5C}$ are each independently for each occurrence absent, NH, O, S, $CH_2$, C(O)O, C(O)NH, $NHCH(R^a)C(O)$, $—C(O)—CH(R^a)—NH—$, CO, CH=N—O,

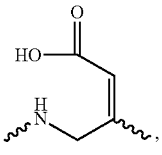,
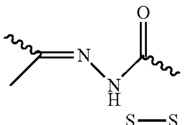,
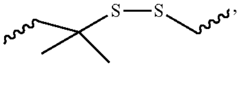,
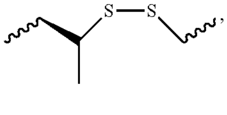,

-continued

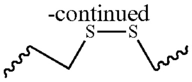

or heterocyclyl;

$L^{2A}$, $L^{2B}$ $L^{3A}$, $L^{3B}$, $L^{4A}$, $L^{4B}$, $L^5A$, $L^{5B}$ and $L^{5C}$ represent the ligand; i.e. each independently for each occurrence a monosaccharide (such as GalNAc), disaccharide, trisaccharide, tetrasaccharide, oligosaccharide, or polysaccharide; and $R^a$ is H or amino acid side chain. Trivalent conjugating GalNAc derivatives are particularly useful for use with RNAi agents for inhibiting the expression of a target gene, such as those of formula (XLIX):

Formula XLIX

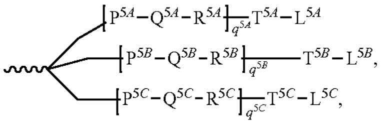

wherein $L^5A$, $L^{5B}$ and $L^{5C}$ represent a monosaccharide, such as GalNAc derivative.

Examples of suitable bivalent and trivalent branched linker groups conjugating GalNAc derivatives include, but are not limited to, the structures recited above as formulas II, VII, XI, X, and XIII.

Representative U.S. Patents that teach the preparation of RNA conjugates include, but are not limited to, U.S. Pat. Nos. 4,828,979; 4,948,882; 5,218,105; 5,525,465; 5,541,313; 5,545,730; 5,552,538; 5,578,717, 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928; 5,688,941; 6,294,664; 6,320,017; 6,576,752; 6,783,931; 6,900,297; 7,037,646; and 8,106,022, the entire contents of each of which are hereby incorporated herein by reference.

It is not necessary for all positions in a given compound to be uniformly modified, and in fact more than one of the aforementioned modifications can be incorporated in a single compound or even at a single nucleoside within an iRNA. The present invention also includes iRNA compounds that are chimeric compounds.

"Chimeric" iRNA compounds or "chimeras," in the context of this invention, are iRNA compounds, preferably dsRNA agents, that contain two or more chemically distinct regions, each made up of at least one monomer unit, i.e., a nucleotide in the case of a dsRNA compound. These iRNAs typically contain at least one region wherein the RNA is modified so as to confer upon the iRNA increased resistance to nuclease degradation, increased cellular uptake, or increased binding affinity for the target nucleic acid. An additional region of the iRNA can serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of iRNA inhibition of gene expression. Consequently, comparable results can often be obtained with shorter iRNAs when chimeric dsRNAs are used, compared to phosphorothioate deoxy dsRNAs hybridizing to the same target region. Cleavage of the RNA target can be routinely detected by gel electrophoresis and, if necessary, associated nucleic acid hybridization techniques known in the art.

In certain instances, the RNA of an iRNA can be modified by a non-ligand group. A number of non-ligand molecules have been conjugated to iRNAs in order to enhance the activity, cellular distribution or cellular uptake of the iRNA, and procedures for performing such conjugations are available in the scientific literature. Such non-ligand moieties have included lipid moieties, such as cholesterol (Kubo, T. et al., *Biochem. Biophys. Res. Comm.,* 2007, 365(1):54-61; Letsinger et al., *Proc. Natl. Acad. Sci. USA,* 1989, 86:6553), cholic acid (Manoharan et al., *Bioorg. Med. Chem. Lett.,* 1994, 4:1053), a thioether, e.g., hexyl-S-tritylthiol (Manoharan et al., *Ann. N.Y. Acad. Sci.,* 1992, 660:306; Manoharan et al., *Bioorg. Med. Chem. Let.,* 1993, 3:2765), a thiocholesterol (Oberhauser et al., *Nucl. Acids Res.,* 1992, 20:533), an aliphatic chain, e.g., dodecandiol or undecyl residues (Saison-Behmoaras et al., *EMBO J.,* 1991, 10:111; Kabanov et al., *FEBS Lett.,* 1990, 259:327; Svinarchuk et al., *Biochimie,* 1993, 75:49), a phospholipid, e.g., di-hexadecyl-rac-glycerol or triethylammonium 1,2-di-O-hexadecyl-rac-glycero-3-H-phosphonate (Manoharan et al., *Tetrahedron Lett.,* 1995, 36:3651; Shea et al., *Nucl. Acids Res.,* 1990, 18:3777), a polyamine or a polyethylene glycol chain (Manoharan et al., *Nucleosides & Nucleotides,* 1995, 14:969), or adamantane acetic acid (Manoharan et al., *Tetrahedron Lett.,* 1995, 36:3651), a palmityl moiety (Mishra et al., *Biochim. Biophys. Acta,* 1995, 1264:229), or an octadecylamine or hexylamino-carbonyl-oxycholesterol moiety (Crooke et al., J. *Pharmacol. Exp. Ther.,* 1996, 277:923). Representative United States patents that teach the preparation of such RNA conjugates have been listed above. Typical conjugation protocols involve the synthesis of RNAs bearing an aminolinker at one or more positions of the sequence. The amino group is then reacted with the molecule being conjugated using appropriate coupling or activating reagents. The conjugation reaction can be performed either with the RNA still bound to the solid support or following cleavage of the RNA, in solution phase. Purification of the RNA conjugate by HPLC typically affords the pure conjugate.

V. Delivery of an RNAi Agent of the Disclosure

The delivery of an RNAi agent of the disclosure to a cell e.g., a cell within a subject, such as a human subject (e.g., a subject in need thereof, such as a subject having an HTT-associated disorder, e.g., Huntington's disease, can be achieved in a number of different ways. For example, delivery may be performed by contacting a cell with an RNAi agent of the disclosure either in vitro or in vivo. In vivo delivery may also be performed directly by administering a composition comprising an RNAi agent, e.g., a dsRNA, to a subject. Alternatively, in vivo delivery may be performed indirectly by administering one or more vectors that encode and direct the expression of the RNAi agent. These alternatives are discussed further below.

In general, any method of delivering a nucleic acid molecule (in vitro or in vivo) can be adapted for use with an RNAi agent of the disclosure (see e.g., Akhtar S. and Julian RL., (1992) *Trends Cell. Biol.* 2(5):139-144 and WO94/02595, which are incorporated herein by reference in their entireties). For in vivo delivery, factors to consider in order to deliver an RNAi agent include, for example, biological stability of the delivered agent, prevention of non-specific effects, and accumulation of the delivered agent in the target tissue. The non-specific effects of an RNAi agent can be minimized by local administration, for example, by direct injection or implantation into a tissue or topically administering the preparation. Local administration to a treatment site maximizes local concentration of the agent, limits the exposure of the agent to systemic tissues that can otherwise be harmed by the agent or that can degrade the agent, and permits a lower total dose of the RNAi agent to be administered. Several studies have shown successful knockdown of gene products when an RNAi agent is administered locally. For example, intraocular delivery of a VEGF dsRNA by intravitreal injection in cynomolgus monkeys (Tolentino, M J. et al., (2004) *Retina* 24:132-138) and subretinal injections in mice (Reich, S J. et al. (2003) *Mol. Vis.* 9:210-216) were both shown to prevent neovascularization in an experimental model of age-related macular degeneration. In addition, direct intratumoral injection of a dsRNA in mice reduces tumor volume (Pille, J. et al. (2005) *Mol. Ther.* 11:267-274) and can prolong survival of tumor-bearing mice (Kim, W J. et al., (2006) *Mol. Ther.* 14:343-350; Li, S. et al., (2007) *Mol. Ther.* 15:515-523). RNA interference has also shown success with local delivery to the CNS by direct injection (Dorn, G. et al., (2004) *Nucleic Acids* 32: e49; Tan, P H. et al. (2005) *Gene Ther.* 12:59-66; Makimura, H. et a.l (2002) *BMC Neurosci.* 3:18; Shishkina, G T., et al. (2004) *Neuroscience* 129:521-528; Thakker, E R., et al. (2004) *Proc. Natl. Acad. Sci.* U.S.A. 101:17270-17275; Akaneya, Y., et al. (2005) *J. Neurophysiol.* 93:594-602) and to the lungs by intranasal administration (Howard, K A. et al., (2006) *Mol. Ther.* 14:476-484; Zhang, X. et al., (2004) *J. Biol. Chem.* 279:10677-10684; Bitko, V. et al., (2005) *Nat. Med.* 11:50-55). For administering an RNAi agent systemically for the treatment of a disease, the RNA can be modified or alternatively delivered using a drug delivery system; both methods act to prevent the rapid degradation of the dsRNA by endo- and exo-nucleases in vivo. Modification of the RNA or the pharmaceutical carrier can also permit targeting of the RNAi agent to the target tissue and avoid undesirable off-target effects (e.g., without wishing to be bound by theory, use of GNAs as described herein has been identified to destabilize the seed region of a dsRNA, resulting in enhanced preference of such dsRNAs for on-target effectiveness, relative to off-target effects, as such off-target effects are significantly weakened by such seed region destabilization). RNAi agents can be modified by chemical conjugation to lipophilic groups such as cholesterol to enhance cellular uptake and prevent degradation. For example, an RNAi agent directed against ApoB conjugated to a lipophilic cholesterol moiety was injected systemically into mice and resulted in knockdown of apoB mRNA in both the liver and jejunum (Soutschek, J. et al., (2004) *Nature* 432:173-178). Conjugation of an RNAi agent to an aptamer has been shown to inhibit tumor growth and mediate tumor regression in a mouse model of prostate cancer (McNamara, J O. et al., (2006) *Nat. Biotechnol.* 24:1005-1015). In an alternative embodiment, the RNAi agent can be delivered using drug delivery systems such as a nanoparticle, a dendrimer, a polymer, liposomes, or a cationic delivery system. Positively charged cationic delivery systems facilitate binding of molecule RNAi agent (negatively charged) and also enhance interactions at the negatively charged cell membrane to permit efficient uptake of an RNAi agent by the cell.

Cationic lipids, dendrimers, or polymers can either be bound to an RNAi agent, or induced to form a vesicle or micelle (see e.g., Kim SH. et al., (2008) *Journal of Controlled Release* 129(2):107-116) that encases an RNAi agent. The formation of vesicles or micelles further prevents degradation of the RNAi agent when administered systemically. Methods for making and administering cationic-RNAi agent complexes are well within the abilities of one skilled in the art (see e.g., Sorensen, D R., et al. (2003) *J. Mol. Biol* 327:761-766; Verma, U N. et al., (2003) *Clin. Cancer Res.* 9:1291-1300; Arnold, A S et al. (2007) *J. Hypertens.* 25:197-205, which are incorporated herein by reference in their entirety). Some non-limiting examples of drug delivery systems useful for systemic delivery of RNAi agents include DOTAP (Sorensen, D R., et al (2003), supra; Verma, U N. et al., (2003), supra), Oligofectamine, "solid nucleic acid lipid particles" (Zimmermann, T S. et al., (2006) *Nature* 441:111-114), cardiolipin (Chien, P Y. et al., (2005) *Cancer Gene Ther.* 12:321-328; Pal, A. et al., (2005) *Int J. Oncol.* 26:1087-1091), polyethyleneimine (Bonnet ME. et al., (2008) *Pharm. Res.* August 16 Epub ahead of print; *Aigner, A.* (2006) *J. Biomed. Biotechnol.* 71659), Arg-Gly-Asp (RGD) peptides (Liu, S. (2006) *Mol. Pharm.* 3:472-487), and polyamidoamines (Tomalia, D A. et al., (2007) *Biochem. Soc. Trans.* 35:61-67; Yoo, H. et al., (1999) *Pharm. Res.* 16:1799-1804). In some embodiments, an RNAi agent forms a complex with cyclodextrin for systemic administration. Methods for administration and pharmaceutical compositions of RNAi agents and cyclodextrins can be found in U.S. Patent No. 7, 427, 605, which is herein incorporated by reference in its entirety.

Certain aspects of the instant disclosure relate to a method of reducing the expression of an HTT target gene in a cell, comprising contacting said cell with the double-stranded RNAi agent of the disclosure. In one embodiment, the cell is an extrahepatic cell, optionally a CNS cell.

Another aspect of the disclosure relates to a method of reducing the expression of an HTT target gene in a subject, comprising administering to the subject the double-stranded RNAi agent of the disclosure.

Another aspect of the disclosure relates to a method of treating a subject having a CNS disorder, comprising administering to the subject a therapeutically effective amount of the double-stranded HTT-targeting RNAi agent of the disclosure, thereby treating the subject. Exemplary CNS disorders that can be treated by the method of the disclosure include Huntington's disease.

In one embodiment, the double-stranded RNAi agent is administered intrathecally. By intrathecal administration of the double-stranded RNAi agent, the method can reduce the expression of an HTT target gene in a brain (e.g., striatum) or spine tissue, for instance, cortex, cerebellum, cervical spine, lumbar spine, and thoracic spine.

For ease of exposition the formulations, compositions and methods in this section are discussed largely with regard to modified siRNA compounds. It may be understood, however, that these formulations, compositions and methods can be practiced with other siRNA compounds, e.g., unmodified siRNA compounds, and such practice is within the disclosure. A composition that includes an RNAi agent can be delivered to a subject by a variety of routes. Exemplary routes include: intrathecal, intravenous, topical, rectal, anal, vaginal, nasal, pulmonary, and ocular.

The RNAi agents of the disclosure can be incorporated into pharmaceutical compositions suitable for administration. Such compositions typically include one or more species of RNAi agent and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The pharmaceutical compositions of the present disclosure may be administered in a number of ways depending upon whether local or systemic treatment is desired and upon the area to be treated. Administration may be topical (including ophthalmic, vaginal, rectal, intranasal, transdermal), oral, or parenteral. Parenteral administration includes intravenous drip, subcutaneous, intraperitoneal or intramuscular injection, or intrathecal or intraventricular administration.

The route and site of administration may be chosen to enhance targeting. For example, to target muscle cells, intramuscular injection into the muscles of interest would be a logical choice. Lung cells might be targeted by administering the RNAi agent in aerosol form. The vascular endothelial cells could be targeted by coating a balloon catheter with the RNAi agent and mechanically introducing the RNA.

Formulations for topical administration may include transdermal patches, ointments, lotions, creams, gels, drops, suppositories, sprays, liquids, and powders. Conventional pharmaceutical carriers, aqueous, powder or oily bases, thickeners and the like may be necessary or desirable. Coated condoms, gloves and the like may also be useful.

Compositions for oral administration include powders or granules, suspensions or solutions in water, syrups, elixirs or non-aqueous media, tablets, capsules, lozenges, or troches. In the case of tablets, carriers that can be used include lactose, sodium citrate and salts of phosphoric acid. Various disintegrants such as starch, and lubricating agents such as magnesium stearate, sodium lauryl sulfate and talc, are commonly used in tablets. For oral administration in capsule form, useful diluents are lactose and high molecular weight polyethylene glycols. When aqueous suspensions are required for oral use, the nucleic acid compositions can be combined with emulsifying and suspending agents. If desired, certain sweetening or flavoring agents can be added.

Compositions for intrathecal or intraventricular administration may include sterile aqueous solutions which may also contain buffers, diluents, and other suitable additives.

Formulations for parenteral administration may include sterile aqueous solutions which may also contain buffers, diluents, and other suitable additives. Intraventricular injection may be facilitated by an intraventricular catheter, for example, attached to a reservoir. For intravenous use, the total concentration of solutes may be controlled to render the preparation isotonic.

In one embodiment, the administration of the siRNA compound, e.g., a double-stranded siRNA compound, or ssiRNA compound, composition is parenteral, e.g., intravenous (e.g., as a bolus or as a diffusible infusion), intradermal, intraperitoneal, intramuscular, intrathecal, intraventricular, intracranial, subcutaneous, transmucosal, buccal, sublingual, endoscopic, rectal, oral, vaginal, topical, pulmonary, intranasal, urethral, or ocular. Administration can be provided by the subject or by another person, e.g., a health care provider. The medication can be provided in measured doses or in a dispenser which delivers a metered dose. Selected modes of delivery are discussed in more detail below.

A. Intrathecal Administration

In one embodiment, the double-stranded RNAi agent is delivered by intrathecal injection (i.e., injection into the spinal fluid which bathes the brain and spinal cord tissue). Intrathecal injection of RNAi agents into the spinal fluid can be performed as a bolus injection or via minipumps which can be implanted beneath the skin, providing a regular and constant delivery of siRNA into the spinal fluid. The circulation of the spinal fluid from the choroid plexus, where it is produced, down around the spinal chord and dorsal root ganglia and subsequently up past the cerebellum and over the cortex to the arachnoid granulations, where the fluid can exit the CNS, that, depending upon size, stability, and solubility of the compounds injected, molecules delivered intrathecally could hit targets throughout the entire CNS.

In some embodiments, the intrathecal administration is via a pump. The pump may be a surgically implanted osmotic pump. In one embodiment, the osmotic pump is implanted into the subarachnoid space of the spinal canal to facilitate intrathecal administration.

In some embodiments, the intrathecal administration is via an intrathecal delivery system for a pharmaceutical including a reservoir containing a volume of the pharmaceutical agent, and a pump configured to deliver a portion of the pharmaceutical agent contained in the reservoir. More details about this intrathecal delivery system may be found in WO 2015/116658, which is incorporated by reference in its entirety.

The amount of intrathecally injected RNAi agents may vary from one target gene to another target gene and the appropriate amount that has to be applied may have to be determined individually for each target gene. Typically, this amount ranges from 10 μg to 2 mg, preferably 50 μg to 1500 μg, more preferably 100 μg to 1000 μg.

B. Vector Encoded RNAi Agents of the Disclosure

RNAi agents targeting the HTT gene can be expressed from transcription units inserted into DNA or RNA vectors (see, e.g., Couture, A, et al., *TIG.* (1996), 12:5-10; WO 00/22113, WO 00/22114, and U.S. Pat. No. 6,054,299). Expression is preferablysustained (months or longer), depending upon the specific construct used and the target tissue or cell type. These transgenes can be introduced as a linear construct, a circular plasmid, or a viral vector, which can be an integrating or non-integrating vector. The transgene can also be constructed to permit it to be inherited as an extrachromosomal plasmid (Gassmann, et al., (1995) *Proc. Natl. Acad. Sci. USA* 92:1292).

The individual strand or strands of an RNAi agent can be transcribed from a promoter on an expression vector. Where two separate strands are to be expressed to generate, for example, a dsRNA, two separate expression vectors can be co-introduced (e.g., by transfection or infection) into a target cell. Alternatively, each individual strand of a dsRNA can be transcribed by promoters both of which are located on the same expression plasmid. In one embodiment, a dsRNA is expressed as inverted repeat polynucleotides joined by a linker polynucleotide sequence such that the dsRNA has a stem and loop structure.

RNAi agent expression vectors are generally DNA plasmids or viral vectors. Expression vectors compatible with eukaryotic cells, preferably those compatible with vertebrate cells, can be used to produce recombinant constructs for the expression of an RNAi agent as described herein. Delivery of RNAi agent expressing vectors can be systemic, such as by intravenous or intramuscular administration, by administration to target cells ex-planted from the patient followed by reintroduction into the patient, or by any other means that allows for introduction into a desired target cell.

Viral vector systems which can be utilized with the methods and compositions described herein include, but are not limited to, (a) adenovirus vectors; (b) retrovirus vectors, including but not limited to lentiviral vectors, moloney murine leukemia virus, etc.; (c) adeno-associated virus vectors; (d) herpes simplex virus vectors; (e) SV 40 vectors; (f) polyoma virus vectors; (g) papilloma virus vectors; (h) picornavirus vectors; (i) pox virus vectors such as an orthopox, e.g., vaccinia virus vectors or avipox, e.g. canary pox or fowl pox; and (j) a helper-dependent or gutless adenovirus. Replication-defective viruses can also be advantageous. Different vectors will or will not become incorporated into the cells' genome. The constructs can include viral sequences for transfection, if desired. Alternatively, the construct can be incorporated into vectors capable of episomal replication, e.g. EPV and EBV vectors. Constructs for the recombinant expression of an RNAi agent will generally require regulatory elements, e.g., promoters, enhancers, etc., to ensure the expression of the RNAi agent in target cells. Other aspects to consider for vectors and constructs are known in the art.

VI. Compositions of the Invention

The present disclosure also includes compositions, including pharmaceutical compositions and formulations which include the RNAi agents of the disclosure.

For example, in one embodiment, the present invention provides compositions comprising two or more, e.g., 2, 3, or 4, dsRNA agents, such as a first dsRNA agent targeting exon 1 of human HTT and a second dsRNA agent targeting full-length human HTT, e.g., dsRNA agents comprising a sense strand and an antisense strand forming a double stranded region, wherein each of the sense strands or each of the antisense strands is a sense strand or an antisense strand independently selected from the group consisting of any of the sense strands and antisense strands in any one of Table 2-5.

In another embodiment, provided herein are pharmaceutical compositions containing an RNAi agent, or a composition, as described herein, and a pharmaceutically acceptable carrier. The pharmaceutical compositions containing the RNAi agent or the composition are useful for treating a disease or disorder associated with the expression or activity of HTT, e.g., Huntington's disease.

In some embodiments, the pharmaceutical compositions of the invention are sterile. In another embodiment, the pharmaceutical compositions of the invention are pyrogen free or non-pyrogenic.

Such pharmaceutical compositions are formulated based on the mode of delivery. One example is compositions that are formulated for systemic administration via parenteral delivery, e.g., by intravenous (IV), intramuscular (IM), or for subcutaneous (subQ) delivery. Another example is compositions that are formulated for direct delivery into the CNS, e.g., by intrathecal or intravitreal routes of injection, optionally by infusion into the brain (e.g., striatum), such as by continuous pump infusion.

The pharmaceutical compositions of the disclosure may be administered in dosages sufficient to inhibit expression of an HTT gene. In general, a suitable dose of an RNAi agent of the disclosure will be in the range of about 0.001 to about 200.0 milligrams per kilogram body weight of the recipient per day, generally in the range of about 1 to 50 mg per kilogram body weight per day.

A repeat-dose regimen may include administration of a therapeutic amount of an RNAi agent on a regular basis, such as monthly to once every six months. In certain embodiments, the RNAi agent is administered about once per quarter (i.e., about once every three months) to about twice per year.

After an initial treatment regimen (e.g., loading dose), the treatments can be administered on a less frequent basis.

In other embodiments, a single dose of the pharmaceutical compositions can be long lasting, such that subsequent doses are administered at not more than 1, 2, 3, or 4 or more month intervals. In some embodiments of the disclosure, a single dose of the pharmaceutical compositions of the disclosure is administered once per month. In other embodiments of the disclosure, a single dose of the pharmaceutical compositions of the disclosure is administered once per quarter to twice per year.

The skilled artisan will appreciate that certain factors can influence the dosage and timing required to effectively treat a subject, including but not limited to the severity of the disease or disorder, previous treatments, the general health or age of the subject, and other diseases present. Moreover, treatment of a subject with a therapeutically effective amount of a composition can include a single treatment or a series of treatments.

Advances in mouse genetics have generated a number of mouse models for the study of various human diseases, such as HD that would benefit from reduction in the expression of HTT. Such models can be used for in vivo testing of RNAi agents, as well as for determining a therapeutically effective dose. Suitable rodent models are known in the art and include, for example, those described in, for example, Cepeda, et al. (*ASN Neuro* (2010) 2(2): e00033) and Pouladi, et al. (*Nat Reviews* (2013) 14:708).

The pharmaceutical compositions of the present disclosure can be administered in a number of ways depending upon whether local or systemic treatment is desired and upon the area to be treated. Administration can be topical (e.g., by a transdermal patch), pulmonary, e.g., by inhalation or insufflation of powders or aerosols, including by nebulizer; intratracheal, intranasal, epidermal and transdermal, oral or parenteral. Parenteral administration includes intravenous, intraarterial, subcutaneous, intraperitoneal or intramuscular injection or infusion; subdermal, e.g., via an implanted device; or intracranial, e.g., by intraparenchymal, intrathecal or intraventricular, administration.

The RNAi agents can be delivered in a manner to target a particular tissue, such as the CNS (e.g., neuronal, glial or vascular tissue of the brain).

Pharmaceutical compositions and formulations for topical administration can include transdermal patches, ointments, lotions, creams, gels, drops, suppositories, sprays, liquids and powders. Conventional pharmaceutical carriers, aqueous, powder or oily bases, thickeners and the like can be necessary or desirable. Coated condoms, gloves and the like can also be useful. Suitable topical formulations include those in which the RNAi agents featured in the disclosure are in admixture with a topical delivery agent such as lipids, liposomes, fatty acids, fatty acid esters, steroids, chelating agents and surfactants. Suitable lipids and liposomes include neutral (e.g., dioleoylphosphatidyl DOPE ethanolamine, dimyristoylphosphatidyl choline DMPC, distearolyphosphatidyl choline) negative (e.g., dimyristoylphosphatidyl glycerol DMPG) and cationic (e.g., dioleoyltetramethylaminopropyl DOTAP and dioleoylphosphatidyl ethanolamine DOTMA). RNAi agents featured in the disclosure can be encapsulated within liposomes or can form complexes thereto, in particular to cationic liposomes. Alternatively, RNAi agents can be complexed to lipids, in particular to cationic lipids. Suitable fatty acids and esters include but are not limited to arachidonic acid, oleic acid, eicosanoic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a $C_{1-20}$ alkyl ester (e.g., isopropylmyristate IPM), monoglyceride, diglyceride or pharmaceutically acceptable salt thereof. Topical formulations are described in detail in U.S. Pat. No. 6,747,014, which is incorporated herein by reference.

A. RNAi Agent Formulations Comprising Membranous Molecular Assemblies

An RNAi agent for use in the compositions and methods of the disclosure can be formulated for delivery in a membranous molecular assembly, e.g., a liposome or a micelle. As used herein, the term "liposome" refers to a vesicle composed of amphiphilic lipids arranged in at least one bilayer, e.g., one bilayer or a plurality of bilayers. Liposomes include unilamellar and multilamellar vesicles that have a membrane formed from a lipophilic material and an aqueous interior. The aqueous portion contains the RNAi agent composition. The lipophilic material isolates the aqueous interior from an aqueous exterior, which typically does not include the RNAi agent composition, although in some examples, it may. Liposomes are useful for the transfer and delivery of active ingredients to the site of action. Because the liposomal membrane is structurally similar to biological membranes, when liposomes are applied to a tissue, the liposomal bilayer fuses with bilayer of the cellular membranes. As the merging of the liposome and cell progresses, the internal aqueous contents that include the RNAi agent are delivered into the cell where the RNAi agent can specifically bind to a target RNA and can mediate RNAi. In some cases the liposomes are also specifically targeted, e.g., to direct the RNAi agent to particular cell types.

A liposome containing an RNAi agent can be prepared by a variety of methods. In one example, the lipid component of a liposome is dissolved in a detergent so that micelles are formed with the lipid component. For example, the lipid component can be an amphipathic cationic lipid or lipid conjugate. The detergent can have a high critical micelle concentration and may be nonionic. Exemplary detergents include cholate, CHAPS, octylglucoside, deoxycholate, and lauroyl sarcosine. The RNAi agent preparation is then added to the micelles that include the lipid component. The cationic groups on the lipid interact with the RNAi agent and condense around the RNAi agent to form a liposome. After condensation, the detergent is removed, e.g., by dialysis, to yield a liposomal preparation of RNAi agent.

If necessary a carrier compound that assists in condensation can be added during the condensation reaction, e.g., by controlled addition. For example, the carrier compound can be a polymer other than a nucleic acid (e.g., spermine or spermidine). pH can also adjusted to favor condensation.

Methods for producing stable polynucleotide delivery vehicles, which incorporate a polynucleotide/cationic lipid complex as structural components of the delivery vehicle, are further described in, e.g., WO 96/37194, the entire contents of which are incorporated herein by reference. Liposome formation can also include one or more aspects of exemplary methods described in Felgner, P. L. et al., (1987) *Proc. Natl. Acad. Sci. USA* 8:7413-7417; U.S. Pat. Nos. 4,897,355; 5,171,678; Bangham et al., (1965) *M. Mol. Biol.* 23:238; Olson et al., (1979) *Biochim. Biophys. Acta* 557:9; Szoka et al., (1978) *Proc. Natl. Acad. Sci.* 75: 4194; Mayhew et al., (1984) *Biochim. Biophys. Acta* 775:169; Kim et al., (1983) *Biochim. Biophys. Acta* 728:339; and Fukunaga et al., (1984) *Endocrinol.* 115:757. Commonly used techniques for preparing lipid aggregates of appropriate size for use as delivery vehicles include sonication and freeze-thaw plus extrusion (see, e.g., Mayer et al., (1986) *Biochim. Biophys. Acta* 858:161. Microfluidization can be used when consistently small (50 to 200 nm) and relatively uniform aggregates are desired (Mayhew et al., (1984) *Biochim. Biophys. Acta* 775:169. These methods are readily adapted to packaging RNAi agent preparations into liposomes.

Liposomes fall into two broad classes. Cationic liposomes are positively charged liposomes which interact with the negatively charged nucleic acid molecules to form a stable complex. The positively charged nucleic acid/liposome complex binds to the negatively charged cell surface and is internalized in an endosome. Due to the acidic pH within the endosome, the liposomes are ruptured, releasing their contents into the cell cytoplasm (Wang et al. (1987) *Biochem. Biophys. Res. Commun.,* 147:980-985).

Liposomes, which are pH-sensitive or negatively charged, entrap nucleic acids rather than complex with them. Since both the nucleic acid and the lipid are similarly charged, repulsion rather than complex formation occurs. Nevertheless, some nucleic acid is entrapped within the aqueous interior of these liposomes. pH sensitive liposomes have been used to deliver nucleic acids encoding the thymidine kinase gene to cell monolayers in culture. Expression of the exogenous gene was detected in the target cells (Zhou et al. (1992) *Journal of Controlled Release,* 19:269-274).

One major type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid or phosphatidylcholine or cholesterol.

Examples of other methods to introduce liposomes into cells in vitro and in vivo include U.S. Pat. Nos. 5,283,185; 5,171,678; WO 94/00569; WO 93/24640; WO 91/16024; Felgner, (1994) *J. Biol. Chem.* 269:2550; Nabel, (1993) *Proc. Natl. Acad. Sci.* 90: 11307; Nabel, (1992) *Human Gene Ther.* 3:649; Gershon, (1993) *Biochem.* 32:7143; and Strauss, (1992) *EMBO J.* 11:417.

Non-ionic liposomal systems have also been examined to determine their utility in the delivery of drugs to the skin, in particular systems comprising non-ionic surfactant and cholesterol. Non-ionic liposomal formulations comprising Novasome™ I (glyceryl dilaurate/cholesterol/polyoxyethylene-10-stearyl ether) and Novasome™ II (glyceryl distearate/cholesterol/polyoxyethylene-10-stearyl ether) were used to deliver cyclosporin-A into the dermis of mouse skin. Results indicated that such non-ionic liposomal systems were effective in facilitating the deposition of cyclosporine A into different layers of the skin (Hu et al., (1994) *S.T.P.Pharma. Sci.,* 4(6):466).

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome (A) comprises one or more glycolipids, such as monosialoganglioside $G_M1$, or (B) is derivatized with one or more hydrophilic polymers, such as a polyethylene glycol (PEG) moiety. While not wishing to be bound by any particular theory, it is thought in the art that, at least for sterically stabilized liposomes containing gangliosides, sphingomyelin, or PEG-derivatized lipids, the enhanced circulation half-life of these sterically stabilized liposomes derives from a reduced uptake into cells of the reticuloendothelial system (RES) (Allen et al., (1987) *FEBS Letters,* 223:42; Wu et al., (1993) *Cancer Research,* 53:3765).

Various liposomes comprising one or more glycolipids are known in the art. Papahadjopoulos et al. (*Ann. N.Y. Acad. Sci*., (1987), 507:64) reported the ability of monosialoganglioside $G_M1$, galactocerebroside sulfate and phosphatidylinositol to improve blood half-lives of liposomes. These findings were expounded upon by Gabizon et al. (*Proc. Natl. Acad. Sci. U.S.A*., (1988), 85: 6949). U.S. Pat. No. 4,837,028 and WO 88/04924, both to Allen et al., disclose liposomes comprising (1) sphingomyelin and (2) the ganglioside $G_M1$ or a galactocerebroside sulfate ester. U.S. Pat. No. 5,543,152 (Webb et al.) discloses liposomes comprising sphingomyelin. Liposomes comprising 1,2-sn-dimyristoylphosphatidylcholine are disclosed in WO 97/13499 (Lim et al).

In one embodiment, cationic liposomes are used. Cationic liposomes possess the advantage of being able to fuse to the cell membrane. Non-cationic liposomes, although not able to fuse as efficiently with the plasma membrane, are taken up by macrophages in vivo and can be used to deliver RNAi agents to macrophages.

Further advantages of liposomes include: liposomes obtained from natural phospholipids are biocompatible and biodegradable; liposomes can incorporate a wide range of water and lipid soluble drugs; liposomes can protect encapsulated RNAi agents in their internal compartments from metabolism and degradation (Rosoff, in "Pharmaceutical Dosage Forms," Lieberman, Rieger and Banker (Eds.), 1988, volume 1, p. 245). Important considerations in the preparation of liposome formulations are the lipid surface charge, vesicle size and the aqueous volume of the liposomes.

A positively charged synthetic cationic lipid, N-[1-(2,3-dioleyloxy)propyl]-N,N,N-trimethylammonium chloride (DOTMA) can be used to form small liposomes that interact spontaneously with nucleic acid to form lipid-nucleic acid complexes which are capable of fusing with the negatively charged lipids of the cell membranes of tissue culture cells, resulting in delivery of RNAi agent (see, e.g., Felgner, P. L. et al., (1987) *Proc. Natl. Acad. Sci. USA* 8:7413-7417, and U.S. Pat. No. 4,897,355 for a description of DOTMA and its use with DNA).

A DOTMA analogue, 1,2-bis(oleoyloxy)-3-(trimethylammonia)propane (DOTAP) can be used in combination with a phospholipid to form DNA-complexing vesicles. Lipofectin™ Bethesda Research Laboratories, Gaithersburg, Md.) is an effective agent for the delivery of highly anionic nucleic acids into living tissue culture cells that comprise positively charged DOTMA liposomes which interact spontaneously with negatively charged polynucleotides to form complexes. When enough positively charged liposomes are used, the net charge on the resulting complexes is also positive. Positively charged complexes prepared in this way spontaneously attach to negatively charged cell surfaces, fuse with the plasma membrane, and efficiently deliver functional nucleic acids into, for example, tissue culture cells. Another commercially available cationic lipid, 1,2-bis(oleoyloxy)-3,3-(trimethylammonia)propane ("DOTAP") (Boehringer Mannheim, Indianapolis, Indiana) differs from DOTMA in that the oleoyl moieties are linked by ester, rather than ether linkages.

Other reported cationic lipid compounds include those that have been conjugated to a variety of moieties including, for example, carboxyspermine which has been conjugated to one of two types of lipids and includes compounds such as 5-carboxyspermylglycine dioctaoleoylamide ("DOGS") (Transfectam™, Promega, Madison, Wisconsin) and dipalmitoylphosphatidylethanolamine 5-carboxyspermyl-amide ("DPPES") (see, e.g., U.S. Pat. No. 5,171,678).

Another cationic lipid conjugate includes derivatization of the lipid with cholesterol ("DC-Chol") which has been formulated into liposomes in combination with DOPE (See, Gao, X. and Huang, L., (1991) *Biochim. Biophys. Res. Commun.* 179:280). Lipopolylysine, made by conjugating polylysine to DOPE, has been reported to be effective for transfection in the presence of serum (Zhou, X. et al., (1991) *Biochim. Biophys. Acta* 1065:8). For certain cell lines, these liposomes containing conjugated cationic lipids, are said to exhibit lower toxicity and provide more efficient transfection than the DOTMA-containing compositions. Other commercially available cationic lipid products include DMRIE and DMRIE-HP (Vical, La Jolla, California) and Lipofectamine (DOSPA) (Life Technology, Inc., Gaithersburg, Maryland). Other cationic lipids suitable for the delivery of oligonucleotides are described in WO 98/39359 and WO 96/37194.

Liposomal formulations are particularly suited for topical administration, liposomes present several advantages over other formulations. Such advantages include reduced side effects related to high systemic absorption of the administered drug, increased accumulation of the administered drug at the desired target, and the ability to administer RNAi agent into the skin. In some implementations, liposomes are used for delivering RNAi agent to epidermal cells and also to enhance the penetration of RNAi agent into dermal tissues, e.g., into skin. For example, the liposomes can be applied topically. Topical delivery of drugs formulated as liposomes to the skin has been documented (see, e.g., Weiner et al., (1992) *Journal of Drug Targeting*, vol. 2, 405-410 and du Plessis et al., (1992) *Antiviral Research,* 18:259-265; Mannino, R. J. and Fould-Fogerite, S., (1998) *Biotechniques* 6:682-690; Itani, T. et al., (1987) *Gene* 56:267-276; Nicolau, C. et al. (1987) *Meth. Enzymol.* 149: 157-176; Straubinger, R. M. and Papahadjopoulos, D. (1983) *Meth. Enzymol.* 101:512-527; Wang, C. Y. and Huang, L., (1987) *Proc. Natl. Acad. Sci. USA* 84:7851-7855).

Non-ionic liposomal systems have also been examined to determine their utility in the delivery of drugs to the skin, in particular systems comprising non-ionic surfactant and cholesterol. Non-ionic liposomal formulations comprising Novasome I (glyceryl dilaurate/cholesterol/polyoxyethylene-10-stearyl ether) and Novasome II (glyceryl distearate/cholesterol/polyoxyethylene-10-stearyl ether) were used to deliver a drug into the dermis of mouse skin. Such formulations with RNAi agent are useful for treating a dermatological disorder.

Liposomes that include RNAi agents can be made highly deformable. Such deformability can enable the liposomes to penetrate through pore that are smaller than the average radius of the liposome. For example, transfersomes are a type of deformable liposomes. Transferosomes can be made by adding surface edge activators, usually surfactants, to a standard liposomal composition. Transfersomes that include RNAi agent can be delivered, for example, subcutaneously by infection in order to deliver RNAi agent to keratinocytes in the skin. In order to cross intact mammalian skin, lipid vesicles must pass through a series of fine pores, each with a diameter less than 50 nm, under the influence of a suitable transdermal gradient. In addition, due to the lipid properties, these transferosomes can be self-optimizing (adaptive to the shape of pores, e.g., in the skin), self-repairing, and can frequently reach their targets without fragmenting, and often self-loading.

Other formulations amenable to the present disclosure are described in U.S. provisional application Ser. No. 61/018,616, filed Jan. 2, 2008; 61/018,611, filed Jan. 2, 2008; 61/039,748, filed Mar. 26, 2008; 61/047,087, filed Apr. 22, 2008 and 61/051,528, filed May 8, 2008. PCT application number PCT/US2007/080331, filed Oct. 3, 2007, also describes formulations that are amenable to the present disclosure.

Transfersomes, yet another type of liposomes, are highly deformable lipid aggregates which are attractive candidates for drug delivery vehicles. Transfersomes can be described as lipid droplets which are so highly deformable that they are easily able to penetrate through pores which are smaller than the droplet. Transfersomes are adaptable to the environment in which they are used, e.g., they are self-optimizing (adaptive to the shape of pores in the skin), self-repairing, frequently reach their targets without fragmenting, and often self-loading. To make transfersomes it is possible to add surface edge-activators, usually surfactants, to a standard liposomal composition. Transfersomes have been used to deliver serum albumin to the skin. The transfersome-mediated delivery of serum albumin has been shown to be as effective as subcutaneous injection of a solution containing serum albumin.

Surfactants find wide application in formulations such as those described herein, particularly in emulsions (including microemulsions) and liposomes. The most common way of classifying and ranking the properties of the many different types of surfactants, both natural and synthetic, is by the use of the hydrophile/lipophile balance (HLB). The nature of the hydrophilic group (also known as the "head") provides the most useful means for categorizing the different surfactants used in formulations (Rieger, in Pharmaceutical Dosage Forms, Marcel Dekker, Inc., New York, N.Y., 1988, p. 285).

If the surfactant molecule is not ionized, it is classified as a nonionic surfactant. Nonionic surfactants find wide application in pharmaceutical and cosmetic products and are usable over a wide range of pH values. In general, their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides.

The use of surfactants in drug products, formulations and in emulsions has been reviewed (Rieger, in Pharmaceutical Dosage Forms, Marcel Dekker, Inc., New York, N.Y., 1988, p. 285).

The RNAi agent for use in the methods of the disclosure can also be provided as micellar formulations. "Micelles" are defined herein as a particular type of molecular assembly in which amphipathic molecules are arranged in a spherical structure such that all the hydrophobic portions of the molecules are directed inward, leaving the hydrophilic portions in contact with the surrounding aqueous phase. The converse arrangement exists if the environment is hydrophobic.

A mixed micellar formulation suitable for delivery through transdermal membranes may be prepared by mixing an aqueous solution of the siRNA composition, an alkali metal $C_8$ to $C_{22}$ alkyl sulphate, and a micelle forming compounds. Exemplary micelle forming compounds include lecithin, hyaluronic acid, pharmaceutically acceptable salts of hyaluronic acid, glycolic acid, lactic acid, chamomile extract, cucumber extract, oleic acid, linoleic acid, linolenic acid, monoolein, monooleates, monolaurates, borage oil, evening of primrose oil, menthol, trihydroxy oxo cholanyl glycine and pharmaceutically acceptable salts thereof, glycerin, polyglycerin, lysine, polylysine, triolein, polyoxyethylene ethers and analogues thereof, polidocanol alkyl ethers and analogues thereof, chenodeoxycholate, deoxycholate, and mixtures thereof. The micelle forming compounds may be added at the same time or after addition of the alkali metal alkyl sulphate. Mixed micelles will form with substantially any kind of mixing of the ingredients but vigorous mixing in order to provide smaller size micelles.

In one method a first micellar composition is prepared which contains the siRNA composition and at least the alkali metal alkyl sulphate. The first micellar composition is then mixed with at least three micelle forming compounds to form a mixed micellar composition. In another method, the micellar composition is prepared by mixing the siRNA composition, the alkali metal alkyl sulphate and at least one of the micelle forming compounds, followed by addition of the remaining micelle forming compounds, with vigorous mixing.

Phenol or m-cresol may be added to the mixed micellar composition to stabilize the formulation and protect against bacterial growth. Alternatively, phenol or m-cresol may be added with the micelle forming ingredients. An isotonic agent such as glycerin may also be added after formation of the mixed micellar composition.

For delivery of the micellar formulation as a spray, the formulation can be put into an aerosol dispenser and the dispenser is charged with a propellant. The propellant, which is under pressure, is in liquid form in the dispenser. The ratios of the ingredients are adjusted so that the aqueous and propellant phases become one, i.e., there is one phase. If there are two phases, it is necessary to shake the dispenser prior to dispensing a portion of the contents, e.g., through a metered valve. The dispensed dose of pharmaceutical agent is propelled from the metered valve in a fine spray.

Propellants may include hydrogen-containing chlorofluorocarbons, hydrogen-containing fluorocarbons, dimethyl ether and diethyl ether. In certain embodiments, HFA 134a (1,1,1,2 tetrafluoroethane) may be used.

The specific concentrations of the essential ingredients can be determined by relatively straightforward experimentation. For absorption through the oral cavities, it is often desirable to increase, e.g., at least double or triple, the dosage for through injection or administration through the gastrointestinal tract.

B. Lipid Particles

RNAi agents, e.g., dsRNAs of in the disclosure may be fully encapsulated in a lipid formulation, e.g., a LNP, or other nucleic acid-lipid particle.

As used herein, the term "LNP" refers to a stable nucleic acid-lipid particle. LNPs typically contain a cationic lipid, a non-cationic lipid, and a lipid that prevents aggregation of the particle (e.g., a PEG-lipid conjugate). LNPs are extremely useful for systemic applications, as they exhibit extended circulation lifetimes following intravenous (i.v.) injection and accumulate at distal sites (e.g., sites physically separated from the administration site). LNPs include "pSPLP," which include an encapsulated condensing agent-nucleic acid complex as set forth in WO 00/03683. The particles of the present disclosure typically have a mean diameter of about 50 nm to about 150 nm, more typically about 60 nm to about 130 nm, more typically about 70 nm to about 110 nm, most typically about 70 nm to about 90 nm, and are substantially nontoxic. In addition, the nucleic acids when present in the nucleic acid-lipid particles of the present disclosure are resistant in aqueous solution to degradation with a nuclease. Nucleic acid-lipid particles and their method of preparation are disclosed in, e.g., U.S. Pat. Nos. 5,976,567; 5,981,501; 6,534,484; 6,586,410; 6,815,432; United States Patent publication No. 2010/0324120 and WO 96/40964.

In one embodiment, the lipid to drug ratio (mass/mass ratio) (e.g., lipid to dsRNA ratio) will be in the range of from about 1:1 to about 50:1, from about 1:1 to about 25:1, from about 3:1 to about 15:1, from about 4:1 to about 10:1, from about 5:1 to about 9:1, or about 6:1 to about 9:1. Ranges intermediate to the above recited ranges are also contemplated to be part of the disclosure.

Certain specific LNP formulations for delivery of RNAi agents have been described in the art, including, e.g., "LNP01" formulations as described in, e.g., WO 2008/042973, which is hereby incorporated by reference.

Additional exemplary lipid-dsRNA formulations are identified in the table below

| | Ionizable/Cationic Lipid | cationic lipid/non-cationic lipid/cholesterol/PEG-lipid conjugate Lipid:siRNA ratio |
|---|---|---|
| SNALP-1 | 1,2-Dilinolenyloxy-N,N-dimethylaminopropane (DLinDMA) | DLinDMA/DPPC/Cholesterol/PEG-CDMA (57.1/7.1/34.4/1.4) lipid:siRNA~7:1 |
| 2-XTC | 2,2-Dilinoleyl-4-dimethylaminoethyl-[1,3]-dioxolane (XTC) | XTC/DPPC/Cholesterol/PEG-cDMA 57.1/7.1/34.4/1.4 lipid:siRNA~7:1 |
| LNP05 | 2,2-Dilinoleyl-4-dimethylaminoethyl-[1,3]-dioxolane (XTC) | XTC/DSPC/Cholesterol/PEG-DMG 57.5/7.5/31.5/3.5 lipid:siRNA~6:1 |
| LNP06 | 2,2-Dilinoleyl-4-dimethylaminoethyl-[1,3]-dioxolane (XTC) | XTC/DSPC/Cholesterol/PEG-DMG 57.5/7.5/31.5/3.5 lipid:siRNA~11:1 |
| LNP07 | 2,2-Dilinoleyl-4-dimethylaminoethyl-[1,3]-dioxolane (XTC) | XTC/DSPC/Cholesterol/PEG-DMG 60/7.5/31/1.5, lipid:siRNA~6:1 |
| LNP08 | 2,2-Dilinoleyl-4-dimethylaminoethyl-[1,3]-dioxolane (XTC) | XTC/DSPC/Cholesterol/PEG-DMG 60/7.5/31/1.5, lipid:siRNA~11:1 |
| LNP09 | 2,2-Dilinoleyl-4-dimethylaminoethyl-[1,3]-dioxolane (XTC) | XTC/DSPC/Cholesterol/PEG-DMG 50/10/38.5/1.5 Lipid:siRNA 10:1 |
| LNP10 | (3aR,5s,6aS)-N,N-dimethyl-2,2-di((9Z,12Z)-octadeca-9,12-dienyl)tetrahydro-3aH-cyclopenta[d][1,3]dioxol-5-amine (ALN100) | ALN100/DSPC/Cholesterol/PEG-DMG 50/10/38.5/1.5 Lipid:siRNA 10:1 |
| LNP11 | (6Z,9Z,28Z,31Z)-heptatriaconta-6,9,28,31-tetraen-19-yl 4-(dimethylamino)butanoate (MC3) | MC-3/DSPC/Cholesterol/PEG-DMG 50/10/38.5/1.5 Lipid:siRNA 10:1 |
| LNP12 | 1,1'-(2-(4-(2-((2-(bis(2-hydroxydodecyl)amino)ethyl)(2-hydroxydodecyl)amino)ethyl)piperazin-1-yl)ethylazanediyl)didodecan-2-ol (Tech G1) | Tech G1/DSPC/Cholesterol/PEG-DMG 50/10/38.5/1.5 Lipid:siRNA 10:1 |
| LNP13 | XTC | XTC/DSPC/Chol/PEG-DMG 50/10/38.5/1.5 Lipid:siRNA: 33:1 |
| LNP14 | MC3 | MC3/DSPC/Chol/PEG-DMG 40/15/40/5 Lipid:siRNA: 11:1 |
| LNP15 | MC3 | MC3/DSPC/Chol/PEG-DSG/GalNAc-PEG-DSG 50/10/35/4.5/0.5 Lipid:siRNA: 11:1 |
| LNP16 | MC3 | MC3/DSPC/Chol/PEG-DMG 50/10/38.5/1.5 Lipid:siRNA: 7:1 |
| LNP17 | MC3 | MC3/DSPC/Chol/PEG-DSG 50/10/38.5/1.5 Lipid:siRNA: 10:1 |
| LNP18 | MC3 | MC3/DSPC/Chol/PEG-DMG 50/10/38.5/1.5 Lipid:siRNA: 12:1 |
| LNP19 | MC3 | MC3/DSPC/Chol/PEG-DMG 50/10/35/5 Lipid:siRNA: 8:1 |
| LNP20 | MC3 | MC3/DSPC/Chol/PEG-DPG 50/10/38.5/1.5 Lipid:siRNA: 10:1 |
| LNP21 | C12-200 | C12-200/DSPC/Chol/PEG-DSG 50/10/38.5/1.5 Lipid:siRNA: 7:1 |

-continued

| | Ionizable/Cationic Lipid | cationic lipid/non-cationic lipid/cholesterol/PEG-lipid conjugate Lipid:siRNA ratio |
|---|---|---|
| LNP22 | XTC | XTC/DSPC/Chol/PEG-DSG 50/10/38.5/1.5 Lipid:siRNA: 10:1 |

DSPC: distearoylphosphatidylcholine

DPPC: dipalmitoylphosphatidylcholine

PEG-DMG: PEG-didimyristoyl glycerol (C14-PEG, or PEG-C14) (PEG with avg mol wt of 2000)

PEG-DSG: PEG-distyryl glycerol (C18-PEG, or PEG-C18) (PEG with avg mol wt of 2000)

PEG-CDMA: PEG-carbamoyl-1,2-dimyristyloxypropylamine (PEG with avg mol wt of 2000)

SNALP (1,2-Dilinolenyloxy-N,N-dimethylaminopropane (DLinDMA)) comprising formulations are described in WO 2009/127060, the entire contents of which are hereby incorporated herein by reference.

XTC comprising formulations are described in WO 2010/088537, the entire contents of which are hereby incorporated herein by reference.

MC3 comprising formulations are described, e.g., in United States Patent Publication No. 2010/0324120, the entire contents of which are hereby incorporated by reference.

ALNY-100 comprising formulations are described in WO 2010/054406, the entire contents of which are hereby incorporated herein by reference.

C12-200 comprising formulations are described in WO 2010/129709, the entire contents of which are hereby incorporated herein by reference.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders can be desirable. In some embodiments, oral formulations are those in which dsRNAs featured in the disclosure are administered in conjunction with one or more penetration enhancer surfactants and chelators. Suitable surfactants include fatty acids or esters or salts thereof, bile acids or salts thereof. Suitable bile acids/salts include chenodeoxycholic acid (CDCA) and ursodeoxychenodeoxycholic acid (UDCA), cholic acid, dehydrocholic acid, deoxycholic acid, glucholic acid, glycholic acid, glycodeoxycholic acid, taurocholic acid, taurodeoxycholic acid, sodium tauro-24,25-dihydro-fusidate and sodium glycodihydrofusidate. Suitable fatty acids include arachidonic acid, undecanoic acid, oleic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a monoglyceride, a diglyceride or a pharmaceutically acceptable salt thereof (e.g., sodium). In some embodiments, combinations of penetration enhancers are used, for example, fatty acids/salts in combination with bile acids/salts. One exemplary combination is the sodium salt of lauric acid, capric acid and UDCA. Further penetration enhancers include polyoxyethylene-9-lauryl ether, polyoxyethylene-20-cetyl ether. DsRNAs featured in the disclosure can be delivered orally, in granular form including sprayed dried particles, or complexed to form micro or nanoparticles. DsRNA complexing agents include poly-amino acids; polyimines; polyacrylates; polyalkylacrylates, polyoxethanes, polyalkylcyanoacrylates; cationized gelatins, albumins, starches, acrylates, polyethyleneglycols (PEG) and starches; polyalkylcyanoacrylates; DEAE-derivatized polyimines, pollulans, celluloses and starches. Suitable complexing agents include chitosan, N-trimethylchitosan, poly-L-lysine, polyhistidine, polyornithine, polyspermines, protamine, polyvinylpyridine, polythiodiethylaminomethylethylene P(TDAE), polyaminostyrene (e.g., p-amino), poly(methylcyanoacrylate), poly (ethylcyanoacrylate), poly(butylcyanoacrylate), poly (isobutylcyanoacrylate), poly(isohexylcynaoacrylate), DEAE-methacrylate, DEAE-hexylacrylate, DEAE-acrylamide, DEAE-albumin and DEAE-dextran, polymethylacrylate, polyhexylacrylate, poly(D,L-lactic acid), poly(DL-lactic-co-glycolic acid (PLGA), alginate, and polyethyleneglycol (PEG). Oral formulations for dsRNAs and their preparation are described in detail in U.S. Pat. No. 6,887,906, U.S. 2003/0027780, and U.S. Pat. No. 6,747,014, each of which is incorporated herein by reference.

Compositions and formulations for parenteral, intraparenchymal (into the brain), intrathecal, intraventricular or intrahepatic administration can include sterile aqueous solutions which can also contain buffers, diluents and other suitable additives such as, but not limited to, penetration enhancers, carrier compounds and other pharmaceutically acceptable carriers or excipients.

Pharmaceutical compositions of the present disclosure include, but are not limited to, solutions, emulsions, and liposome-containing formulations. These compositions can be generated from a variety of components that include, but are not limited to, preformed liquids, self-emulsifying solids and self-emulsifying semisolids. Particularly preferred are formulations that target the brain when treating HTT-associated diseases or disorders.

The pharmaceutical formulations of the present disclosure, which can conveniently be presented in unit dosage form, can be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present disclosure can be formulated into any of many possible dosage forms such as, but not limited to, tablets, capsules, gel capsules, liquid syrups, soft gels, suppositories, and enemas. The compositions of the present disclosure can also be formulated as suspensions in aqueous, non-aqueous or mixed media. Aqueous suspensions can further contain substances which increase the viscosity of the suspension including, for example, sodium carboxymethylcellulose, sorbitol or dextran. The suspension can also contain stabilizers.

C. Additional Formulations i. Emulsions

The compositions of the present disclosure can be prepared and formulated as emulsions. Emulsions are typically heterogeneous systems of one liquid dispersed in another in the form of droplets usually exceeding 0.1 μm in diameter (see e.g., Ansel's Pharmaceutical Dosage Forms and Drug Delivery Systems, Allen, LV., Popovich NG., and Ansel HC., 2004, Lippincott Williams & Wilkins (8th ed.), New York, NY; Idson, in Pharmaceutical Dosage Forms, Lieberman, Rieger and Banker (Eds.), 1988, Marcel Dekker, Inc., New York, N.Y., volume 1, p. 199; Rosoff, in Pharmaceutical Dosage Forms, Lieberman, Rieger and Banker (Eds.), 1988, Marcel Dekker, Inc., New York, N.Y., Volume 1, p. 245; Block in Pharmaceutical Dosage Forms, Lieberman, Rieger and Banker (Eds.), 1988, Marcel Dekker, Inc., New York, N.Y., volume 2, p. 335; Higuchi et al., in *Remington's Pharmaceutical Sciences*, Mack Publishing Co., Easton, Pa., 1985, p. 301). Emulsions are often biphasic systems comprising two immiscible liquid phases intimately mixed and dispersed with each other. In general, emulsions can be of either the water-in-oil (w/o) or the oil-in-water (o/w) variety. When an aqueous phase is finely divided into and dispersed as minute droplets into a bulk oily phase, the resulting composition is called a water-in-oil (w/o) emulsion. Alternatively, when an oily phase is finely divided into and dispersed as minute droplets into a bulk aqueous phase, the resulting composition is called an oil-in-water (o/w) emulsion. Emulsions can contain additional components in addition to the dispersed phases, and the active drug which can be present as a solution in either aqueous phase, oily phase or itself as a separate phase. Pharmaceutical excipients such as emulsifiers, stabilizers, dyes, and anti-oxidants can also be present in emulsions as needed. Pharmaceutical emulsions can also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not. Multiple emulsions in which individual oil droplets of an o/w emulsion enclose small water droplets constitute a w/o/w emulsion. Likewise, a system of oil droplets enclosed in globules of water stabilized in an oily continuous phase provides an o/w/o emulsion.

Emulsions are characterized by little or no thermodynamic stability. Often, the dispersed or discontinuous phase of the emulsion is well dispersed into the external or continuous phase and maintained in this form through the means of emulsifiers or the viscosity of the formulation. Either of the phases of the emulsion can be a semisolid or a solid, as is the case of emulsion-style ointment bases and creams. Other means of stabilizing emulsions entail the use of emulsifiers that can be incorporated into either phase of the emulsion. Emulsifiers can broadly be classified into four categories: synthetic surfactants, naturally occurring emulsifiers, absorption bases, and finely dispersed solids (see e.g., Ansel's Pharmaceutical Dosage Forms and Drug Delivery Systems, Allen, LV., Popovich NG., and Ansel HC., 2004, Lippincott Williams & Wilkins (8th ed.), New York, NY; Idson, in Pharmaceutical Dosage Forms, Lieberman, Rieger and Banker (Eds.), 1988, Marcel Dekker, Inc., New York, N.Y., volume 1, p. 199).

Synthetic surfactants, also known as surface active agents, have found wide applicability in the formulation of emulsions and have been reviewed in the literature (see e.g., Ansel's Pharmaceutical Dosage Forms and Drug Delivery Systems, Allen, LV., Popovich NG., and Ansel HC., 2004, Lippincott Williams & Wilkins (8th ed.), New York, NY; Rieger, in Pharmaceutical Dosage Forms, Lieberman, Rieger and Banker (Eds.), 1988, Marcel Dekker, Inc., New York, N.Y., volume 1, p. 285; Idson, in Pharmaceutical Dosage Forms, Lieberman, Rieger and Banker (Eds.), Marcel Dekker, Inc., New York, N.Y., 1988, volume 1, p. 199). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants in the preparation of formulations. Surfactants can be classified into different classes based on the nature of the hydrophilic group: nonionic, anionic, cationic and amphoteric (see e.g., Ansel's Pharmaceutical Dosage Forms and Drug Delivery Systems, Allen, LV., Popovich NG., and Ansel HC., 2004, Lippincott Williams & Wilkins (8th ed.), New York, NY Rieger, in Pharmaceutical Dosage Forms, Lieberman, Rieger and Banker (Eds.), 1988, Marcel Dekker, Inc., New York, N.Y., volume 1, p. 285).

Naturally occurring emulsifiers used in emulsion formulations include lanolin, beeswax, phosphatides, lecithin and acacia. Absorption bases possess hydrophilic properties such that they can soak up water to form w/o emulsions yet retain their semisolid consistencies, such as anhydrous lanolin and hydrophilic petrolatum. Finely divided solids have also been used as good emulsifiers especially in combination with surfactants and in viscous preparations. These include polar inorganic solids, such as heavy metal hydroxides, nonswelling clays such as bentonite, attapulgite, hectorite, kaolin, montmorillonite, colloidal aluminum silicate and colloidal magnesium aluminum silicate, pigments and nonpolar solids such as carbon or glyceryl tristearate.

A large variety of non-emulsifying materials are also included in emulsion formulations and contribute to the properties of emulsions. These include fats, oils, waxes, fatty acids, fatty alcohols, fatty esters, humectants, hydrophilic colloids, preservatives and antioxidants (Block, in Pharmaceutical Dosage Forms, Lieberman, Rieger and Banker (Eds.), 1988, Marcel Dekker, Inc., New York, N.Y., volume 1, p. 335; Idson, in Pharmaceutical Dosage Forms, Lieberman, Rieger and Banker (Eds.), 1988, Marcel Dekker, Inc., New York, N.Y., volume 1, p. 199).

Hydrophilic colloids or hydrocolloids include naturally occurring gums and synthetic polymers such as polysaccharides (for example, acacia, agar, alginic acid, carrageenan, guar gum, karaya gum, and tragacanth), cellulose derivatives (for example, carboxymethylcellulose and carboxypropylcellulose), and synthetic polymers (for example, carbomers, cellulose ethers, and carboxyvinyl polymers). These disperse or swell in water to form colloidal solutions that stabilize emulsions by forming strong interfacial films around the dispersed-phase droplets and by increasing the viscosity of the external phase.

Since emulsions often contain a number of ingredients such as carbohydrates, proteins, sterols and phosphatides that can readily support the growth of microbes, these formulations often incorporate preservatives. Commonly used preservatives included in emulsion formulations include methyl paraben, propyl paraben, quaternary ammonium salts, benzalkonium chloride, esters of p-hydroxybenzoic acid, and boric acid. Antioxidants are also commonly added to emulsion formulations to prevent deterioration of the formulation. Antioxidants used can be free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

The application of emulsion formulations via dermatological, oral and parenteral routes and methods for their manufacture have been reviewed in the literature (see e.g., Ansel's Pharmaceutical Dosage Forms and Drug Delivery Systems, Allen, LV., Popovich NG., and Ansel HC., 2004, Lippincott Williams & Wilkins (8th ed.), New York, NY; Idson, in Pharmaceutical Dosage Forms, Lieberman, Rieger and Banker (Eds.), 1988, Marcel Dekker, Inc., New York, N.Y., volume 1, p. 199). Emulsion formulations for oral delivery have been very widely used because of ease of formulation, as well as efficacy from an absorption and bioavailability standpoint (see e.g., Ansel's Pharmaceutical Dosage Forms and Drug Delivery Systems, Allen, LV., Popovich NG., and Ansel HC., 2004, Lippincott Williams & Wilkins (8th ed.), New York, NY; Rosoff, in Pharmaceutical Dosage Forms, Lieberman, Rieger and Banker (Eds.), 1988, Marcel Dekker, Inc., New York, N.Y., volume 1, p. 245; Idson, in Pharmaceutical Dosage Forms, Lieberman, Rieger and Banker (Eds.), 1988, Marcel Dekker, Inc., New York, N.Y., volume 1, p. 199). Mineral-oil base laxatives, oil-soluble vitamins and high fat nutritive preparations are among the materials that have commonly been administered orally as o/w emulsions.

ii. Microemulsions

In one embodiment of the present disclosure, the compositions of RNAi agents and nucleic acids are formulated as microemulsions. A microemulsion can be defined as a system of water, oil and amphiphile which is a single optically isotropic and thermodynamically stable liquid solution (see e.g., Ansel's Pharmaceutical Dosage Forms and Drug Delivery Systems, Allen, LV., Popovich NG., and Ansel HC., 2004, Lippincott Williams & Wilkins (8th ed.), New York, NY; Rosoff, in Pharmaceutical Dosage Forms, Lieberman, Rieger and Banker (Eds.), 1988, Marcel Dekker, Inc., New York, N.Y., volume 1, p. 245). Typically, microemulsions are systems that are prepared by first dispersing an oil in an aqueous surfactant solution and then adding a sufficient amount of a fourth component, generally an intermediate chain-length alcohol to form a transparent system. Therefore, microemulsions have also been described as thermodynamically stable, isotropically clear dispersions of two immiscible liquids that are stabilized by interfacial films of surface-active molecules (Leung and Shah, in: Controlled Release of Drugs: Polymers and Aggregate Systems, Rosoff, M., Ed., 1989, VCH Publishers, New York, pages 185-215). Microemulsions commonly are prepared via a combination of three to five components that include oil, water, surfactant, cosurfactant and electrolyte. Whether the microemulsion is of the water-in-oil (w/o) or an oil-in-water (o/w) type is dependent on the properties of the oil and surfactant used, and on the structure and geometric packing of the polar heads and hydrocarbon tails of the surfactant molecules (Schott, in Remington's Pharmaceutical Sciences, Mack Publishing Co., Easton, Pa., 1985, p. 271).

The phenomenological approach utilizing phase diagrams has been extensively studied and has yielded a comprehensive knowledge, to one skilled in the art, of how to formulate microemulsions (see e.g., Ansel's Pharmaceutical Dosage Forms and Drug Delivery Systems, Allen, LV., Popovich NG., and Ansel HC., 2004, Lippincott Williams & Wilkins (8th ed.), New York, NY; Rosoff, in Pharmaceutical Dosage Forms, Lieberman, Rieger and Banker (Eds.), 1988, Marcel Dekker, Inc., New York, N.Y., volume 1, p. 245; Block, in Pharmaceutical Dosage Forms, Lieberman, Rieger and Banker (Eds.), 1988, Marcel Dekker, Inc., New York, N.Y., volume 1, p. 335). Compared to conventional emulsions, microemulsions offer the advantage of solubilizing water-insoluble drugs in a formulation of thermodynamically stable droplets that are formed spontaneously.

Surfactants used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate (SO750), decaglycerol decaoleate (DAO750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules. Microemulsions can, however, be prepared without the use of cosurfactants and alcohol-free self-emulsifying microemulsion systems are known in the art. The aqueous phase can typically be, but is not limited to, water, an aqueous solution of the drug, glycerol, PEG300, PEG400, polyglycerols, propylene glycols, and derivatives of ethylene glycol. The oil phase can include, but is not limited to, materials such as Captex 300, Captex 355, Capmul MCM, fatty acid esters, medium chain (C8-C12) mono, di, and tri-glycerides, polyoxyethylated glyceryl fatty acid esters, fatty alcohols, polyglycolized glycerides, saturated polyglycolized C8-C10 glycerides, vegetable oils and silicone oil.

Microemulsions are particularly of interest from the standpoint of drug solubilization and the enhanced absorption of drugs. Lipid based microemulsions (both o/w and w/o) have been proposed to enhance the oral bioavailability of drugs, including peptides (see e.g., U.S. Pat. Nos. 6,191,105; 7,063,860; 7,070,802; 7,157,099; Constantinides et al., *Pharmaceutical Research,* 1994, 11, 1385-1390; Ritschel, *Meth. Find. Exp. Clin. Pharmacol.,* 1993, 13, 205). Microemulsions afford advantages of improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (see e.g., U.S. Pat. Nos. 6,191,105; 7,063,860; 7,070,802; 7,157,099; Constantinides et al., *Pharmaceutical Research,* 1994, 11, 1385; Ho et al., *J. Pharm. Sci.,* 1996, 85, 138-143). Often microemulsions can form spontaneously when their components are brought together at ambient temperature. This can be particularly advantageous when formulating thermolabile drugs, peptides or RNAi agents. Microemulsions have also been effective in the transdermal delivery of active components in both cosmetic and pharmaceutical applications. It is expected that the microemulsion compositions and formulations of the present disclosure will facilitate the increased systemic absorption of RNAi agents and nucleic acids from the gastrointestinal tract, as well as improve the local cellular uptake of RNAi agents and nucleic acids.

Microemulsions of the present disclosure can also contain additional components and additives such as sorbitan monostearate (Grill 3), Labrasol, and penetration enhancers to improve the properties of the formulation and to enhance the absorption of the RNAi agents and nucleic acids of the present disclosure. Penetration enhancers used in the microemulsions of the present disclosure can be classified as belonging to one of five broad categories—surfactants, fatty acids, bile salts, chelating agents, and non-chelating non-surfactants (Lee et al., *Critical Reviews in Therapeutic Drug Carrier Systems,* 1991, p. 92). Each of these classes has been discussed above.

iii. Microparticles

An RNAi agent of the disclosure may be incorporated into a particle, e.g., a microparticle. Microparticles can be produced by spray-drying, but may also be produced by other methods including lyophilization, evaporation, fluid bed drying, vacuum drying, or a combination of these techniques.

iv. Penetration Enhancers

In one embodiment, the present disclosure employs various penetration enhancers to effect the efficient delivery of nucleic acids, particularly RNAi agents, to the skin of animals. Most drugs are present in solution in both ionized and nonionized forms. However, usually only lipid soluble or lipophilic drugs readily cross cell membranes. It has been discovered that even non-lipophilic drugs can cross cell membranes if the membrane to be crossed is treated with a penetration enhancer. In addition to aiding the diffusion of non-lipophilic drugs across cell membranes, penetration enhancers also enhance the permeability of lipophilic drugs.

Penetration enhancers can be classified as belonging to one of five broad categories, i.e., surfactants, fatty acids, bile salts, chelating agents, and non-chelating non-surfactants (see e.g., Malmsten, M. Surfactants and polymers in drug delivery, Informa Health Care, New York, NY, 2002; Lee et al., Critical Reviews in Therapeutic Drug Carrier Systems, 1991, p. 92). Each of the above mentioned classes of penetration enhancers are described below in greater detail.

Surfactants (or "surface-active agents") are chemical entities which, when dissolved in an aqueous solution, reduce the surface tension of the solution or the interfacial tension between the aqueous solution and another liquid, with the result that absorption of RNAi agents through the mucosa is enhanced. In addition to bile salts and fatty acids, these penetration enhancers include, for example, sodium lauryl sulfate, polyoxyethylene-9-lauryl ether and polyoxyethylene-20-cetyl ether) (see e.g., Malmsten, M. Surfactants and polymers in drug delivery, Informa Health Care, New York, NY, 2002; Lee et al., Critical Reviews in Therapeutic Drug Carrier Systems, 1991, p. 92); and perfluorochemical emulsions, such as FC-43. Takahashi et al., J. Pharm. Pharmacol., 1988, 40, 252).

Various fatty acids and their derivatives which act as penetration enhancers include, for example, oleic acid, lauric acid, capric acid (n-decanoic acid), myristic acid, palmitic acid, stearic acid, linoleic acid, linolenic acid, dicaprate, tricaprate, monoolein (1-monooleoyl-rac-glycerol), dilaurin, caprylic acid, arachidonic acid, glycerol 1-monocaprate, 1-dodecylazacycloheptan-2-one, acylcarnitines, acylcholines, $C_{1-20}$ alkyl esters thereof (e.g., methyl, isopropyl and t-butyl), and mono- and di-glycerides thereof (i.e., oleate, laurate, caprate, myristate, palmitate, stearate, linoleate, etc.) (see e.g., Touitou, E., et al. Enhancement in Drug Delivery, CRC Press, Danvers, M A, 2006; Lee et al., Critical Reviews in Therapeutic Drug Carrier Systems, 1991, p. 92; Muranishi, Critical Reviews in Therapeutic Drug Carrier Systems, 1990, 7, 1-33; El Hariri et al., *J. Pharm. Pharmacol.,* 1992, 44, 651-654).

The physiological role of bile includes the facilitation of dispersion and absorption of lipids and fat-soluble vitamins (see e.g., Malmsten, M. Surfactants and polymers in drug delivery, Informa Health Care, New York, NY, 2002; Brunton, Chapter 38 in: Goodman & Gilman's The Pharmacological Basis of Therapeutics, 9th Ed., Hardman et al. Eds., McGraw-Hill, New York, 1996, pp. 934-935). Various natural bile salts, and their synthetic derivatives, act as penetration enhancers. Thus the term "bile salts" includes any of the naturally occurring components of bile as well as any of their synthetic derivatives. Suitable bile salts include, for example, cholic acid (or its pharmaceutically acceptable sodium salt, sodium cholate), dehydrocholic acid (sodium dehydrocholate), deoxycholic acid (sodium deoxycholate), glucholic acid (sodium glucholate), glycholic acid (sodium glycocholate), glycodeoxycholic acid (sodium glycodeoxycholate), taurocholic acid (sodium taurocholate), taurodeoxycholic acid (sodium taurodeoxycholate), chenodeoxycholic acid (sodium chenodeoxycholate), ursodeoxycholic acid (UDCA), sodium tauro-24,25-dihydro-fusidate (STDHF), sodium glycodihydrofusidate and polyoxyethylene-9-lauryl ether (POE) (see e.g., Malmsten, M. Surfactants and polymers in drug delivery, Informa Health Care, New York, NY, 2002; Lee et al., Critical Reviews in Therapeutic Drug Carrier Systems, 1991, page 92; Swinyard, Chapter 39 In: Remington's Pharmaceutical Sciences, 18th Ed., Gennaro, ed., Mack Publishing Co., Easton, Pa., 1990, pages 782-783; Muranishi, Critical Reviews in Therapeutic Drug Carrier Systems, 1990, 7, 1-33; Yamamoto et al., J. Pharm. Exp. Ther., 1992, 263, 25; Yamashita et al., J. Pharm. Sci., 1990, 79, 579-583).

Chelating agents, as used in connection with the present disclosure, can be defined as compounds that remove metallic ions from solution by forming complexes therewith, with the result that absorption of RNAi agents through the mucosa is enhanced. With regards to their use as penetration enhancers in the present disclosure, chelating agents have the added advantage of also serving as DNase inhibitors, as most characterized DNA nucleases require a divalent metal ion for catalysis and are thus inhibited by chelating agents (Jarrett, J. Chromatogr., 1993, 618, 315-339). Suitable chelating agents include but are not limited to disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines)(see e.g., Katdare, A. et al., Excipient development for pharmaceutical, biotechnology, and drug delivery, CRC Press, Danvers, M A, 2006; Lee et al., Critical Reviews in Therapeutic Drug Carrier Systems, 1991, page 92; Muranishi, Critical Reviews in Therapeutic Drug Carrier Systems, 1990, 7, 1-33; Buur et al., J. Control Rel., 1990, 14, 43-51).

As used herein, non-chelating non-surfactant penetration enhancing compounds can be defined as compounds that demonstrate insignificant activity as chelating agents or as surfactants but that nonetheless enhance absorption of RNAi agents through the alimentary mucosa (see e.g., Muranishi, Critical Reviews in Therapeutic Drug Carrier Systems, 1990, 7, 1-33). This class of penetration enhancers includes, for example, unsaturated cyclic ureas, 1-alkyl- and 1-alkenylazacyclo-alkanone derivatives (Lee et al., Critical Reviews in Therapeutic Drug Carrier Systems, 1991, page 92); and non-steroidal anti-inflammatory agents such as diclofenac sodium, indomethacin and phenylbutazone (Yamashita et al., J. Pharm. Pharmacol., 1987, 39, 621-626).

Agents that enhance uptake of RNAi agents at the cellular level can also be added to the pharmaceutical and other compositions of the present disclosure. For example, cationic lipids, such as lipofectin (Junichi et al, U.S. Pat. No. 5,705,188), cationic glycerol derivatives, and polycationic molecules, such as polylysine (WO 97/30731), are also known to enhance the cellular uptake of dsRNAs.

Other agents can be utilized to enhance the penetration of the administered nucleic acids, including glycols such as ethylene glycol and propylene glycol, pyrrols such as 2-pyrrol, azones, and terpenes such as limonene and menthone.

vi. Excipients

In contrast to a carrier compound, a "pharmaceutical carrier" or "excipient" is a pharmaceutically acceptable solvent, suspending agent or any other pharmacologically inert vehicle for delivering one or more nucleic acids to an animal. The excipient can be liquid or solid and is selected, with the planned manner of administration in mind, so as to provide for the desired bulk, consistency, etc., when combined with a nucleic acid and the other components of a given pharmaceutical composition. Typical pharmaceutical carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); and wetting agents (e.g., sodium lauryl sulphate, etc).

Pharmaceutically acceptable organic or inorganic excipients suitable for non-parenteral administration which do not deleteriously react with nucleic acids can also be used to formulate the compositions of the present disclosure. Suitable pharmaceutically acceptable carriers include, but are not limited to, water, salt solutions, alcohols, polyethylene glycols, gelatin, lactose, amylose, magnesium stearate, talc, silicic acid, viscous paraffin, hydroxymethylcellulose, polyvinylpyrrolidone and the like.

Formulations for topical administration of nucleic acids can include sterile and non-sterile aqueous solutions, non-aqueous solutions in common solvents such as alcohols, or solutions of the nucleic acids in liquid or solid oil bases. The solutions can also contain buffers, diluents and other suitable additives. Pharmaceutically acceptable organic or inorganic excipients suitable for non-parenteral administration which do not deleteriously react with nucleic acids can be used.

Suitable pharmaceutically acceptable excipients include, but are not limited to, water, salt solutions, alcohol, polyethylene glycols, gelatin, lactose, amylose, magnesium stearate, talc, silicic acid, viscous paraffin, hydroxymethylcellulose, polyvinylpyrrolidone and the like.

vii. Other Components

The compositions of the present disclosure can additionally contain other adjunct components conventionally found in pharmaceutical compositions, at their art-established usage levels. Thus, for example, the compositions can contain additional, compatible, pharmaceutically-active materials such as, for example, antipruritics, astringents, local anesthetics or anti-inflammatory agents, or can contain additional materials useful in physically formulating various dosage forms of the compositions of the present disclosure, such as dyes, flavoring agents, preservatives, antioxidants, opacifiers, thickening agents and stabilizers. However, such materials, when added, should not unduly interfere with the biological activities of the components of the compositions of the present disclosure. The formulations can be sterilized and, if desired, mixed with auxiliary agents, e.g., lubricants, preservatives, stabilizers, wetting agents, emulsifiers, salts for influencing osmotic pressure, buffers, colorings, flavorings or aromatic substances and the like which do not deleteriously interact with the nucleic acid(s) of the formulation.

Aqueous suspensions can contain substances which increase the viscosity of the suspension including, for example, sodium carboxymethylcellulose, sorbitol or dextran. The suspension can also contain stabilizers.

In some embodiments, pharmaceutical compositions featured in the disclosure include (a) one or more RNAi agents and (b) one or more agents which function by a non-RNAi mechanism and which are useful in treating an HTT-associated disorder. Examples of such agents include, but are not limited to, monoamine inhibitors, reserpine, anticonvulsants, antipsychotic agents, and antidepressants.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit high therapeutic indices are preferred.

The data obtained from cell culture assays and animal studies can be used in formulating a range of dosage for use in humans. The dosage of compositions featured herein in the disclosure lies generally within a range of circulating concentrations that include the $ED_{50}$ with little or no toxicity. The dosage can vary within this range depending upon the dosage form employed and the route of administration utilized. For any compound used in the methods featured in the disclosure, the therapeutically effective dose can be estimated initially from cell culture assays. A dose can be formulated in animal models to achieve a circulating plasma concentration range of the compound or, when appropriate, of the polypeptide product of a target sequence (e.g., achieving a decreased concentration of the polypeptide) that includes the $IC_{50}$ (i.e., the concentration of the test compound which achieves a half-maximal inhibition of symptoms) as determined in cell culture. Such information can be used to more accurately determine useful doses in humans. Levels in plasma can be measured, for example, by high performance liquid chromatography.

In addition to their administration, as discussed above, the RNAi agents featured in the disclosure can be administered in combination with other known agents effective in treatment of pathological processes mediated by nucleotide repeat expression. In any event, the administering physician can adjust the amount and timing of RNAi agent administration on the basis of results observed using standard measures of efficacy known in the art or described herein.

VII. Kits

In certain aspects, the instant disclosure provides kits that include a suitable container containing a pharmaceutical formulation of a siRNA compound, e.g., a double-stranded siRNA compound, or ssiRNA compound, (e.g., a precursor, e.g., a larger siRNA compound which can be processed into a ssiRNA compound, or a DNA which encodes an siRNA compound, e.g., a double-stranded siRNA compound, or ssiRNA compound, or precursor thereof).

Such kits include one or more dsRNA agent(s) and instructions for use, e.g., instructions for administering a prophylactically or therapeutically effective amount of a dsRNA agent(s). The dsRNA agent may be in a vial or a pre-filled syringe. The kits may optionally further comprise means for administering the dsRNA agent (e.g., an injection device, such as a pre-filled syringe), or means for measuring the inhibition of C3 (e.g., means for measuring the inhibition of HTT mRNA, HTT protein, and/or HTT activity). Such means for measuring the inhibition of HTT may comprise a means for obtaining a sample from a subject, such as, e.g., a CSF and/or plasma sample. The kits of the invention may optionally further comprise means for determining the therapeutically effective or prophylactically effective amount.

In certain embodiments the individual components of the pharmaceutical formulation may be provided in one container, e.g., a vial or a pre-filled syringe. Alternatively, it may be desirable to provide the components of the pharmaceutical formulation separately in two or more containers, e.g., one container for a siRNA compound preparation, and at least another for a carrier compound. The kit may be packaged in a number of different configurations such as one or more containers in a single box. The different components can be combined, e.g., according to instructions provided with the kit.

The components can be combined according to a method described herein, e.g., to prepare and administer a pharmaceutical composition. The kit can also include a delivery device.

VII. Methods for Inhibiting HTT Expression

The present disclosure also provides methods of inhibiting expression of an HTT gene in a cell. The methods include contacting a cell with an RNAi agent, e.g., double stranded RNAi agent, a composition comprising a dsRNA agent of the invention, or a pharmaceutical composition comprising a dsRNA agent of the invention, in an amount effective to inhibit expression of HTT in the cell, thereby inhibiting expression of HTT in the cell. In some embodiments, the methods include contacting a cell with two or more double stranded RNAi agents, as described herein, e.g., a first dsRNA agent targeting exon 1 of human HTT and a second dsRNA agent targeting full-length human HTT, e.g., any two or more, e.g., 2, 3, or 4, of the dsRNA agents selected from the group of dsRNA agents in Tables 2-5. In certain embodiments of the methods including two or more dsRNA agents, the two or more dsRNA agents may be present in the same composition, in separate compositions, or any combination thereof. In some embodiments, the methods of the invention include contacting a cell with a composition comprising two or more, e.g., 2, 3, or 4, dsRNA agents of the invention, e.g., a first dsRNA agent targeting exon 1 of human HTT and a second dsRNA agent targeting full-length human HTT, e.g., any two or more of the dsRNA agents selected from the group of dsRNA agents in Tables 2-5. In certain embodiments of the disclosure, HTT is inhibited preferentially in CNS (e.g., brain) cells.

In some embodiments of the methods of the invention which include contacting a cell with two or more dsRNA agents, as described herein, e.g., any two or more, e.g., 2, 3, or 4, of the dsRNA agents selected from the group of dsRNA agents in Tables 2-5, the cell may be contacted with a first agent (or a composition comprising a first agent) at a first time, a second agent (or a composition comprising a second agent) at a second time, a third agent (or a composition comprising a third agent) at a third time, and a fourth agent (or a composition comprising a fourth agent) at a fourth time; or the cell may be contacted with all of the agents (or a composition comprising all of the agents) at the same time, Alternatively, the cell may be contacted with a first agent (or a composition comprising a first agent) at a first time and a second, third, and/or fourth agent (or a composition comprising a second, third, and/or fourth agent) at a second time. Other combinations of contacting the cell with two or more agents (or compositions comprising two or more dsRNA agents) of the invention are also contemplated.

Contacting of a cell with an RNAi agent, e.g., a double stranded RNAi agent, may be done in vitro or in vivo. Contacting a cell in vivo with the RNAi agent includes contacting a cell or group of cells within a subject, e.g., a human subject, with the RNAi agent. Combinations of in vitro and in vivo methods of contacting a cell are also possible.

Contacting a cell may be direct or indirect, as discussed above. Furthermore, contacting a cell may be accomplished via a targeting ligand, including any ligand described herein or known in the art. In some embodiments, the targeting ligand is a carbohydrate moiety, e.g., a GalNAc ligand, or any other ligand that directs the RNAi agent to a site of interest.

The term "inhibiting," as used herein, is used interchangeably with "reducing," "silencing," "downregulating," "suppressing" and other similar terms, and includes any level of inhibition. In certain embodiments, a level of inhibition, e.g., for an RNAi agent of the instant disclosure, can be assessed in cell culture conditions, e.g., wherein cells in cell culture are transfected via Lipofectamine™-mediated transfection at a concentration in the vicinity of a cell of 10 nM or less, 1 nM or less, etc. Knockdown of a given RNAi agent can be determined via comparison of pre-treated levels in cell culture versus post-treated levels in cell culture, optionally also comparing against cells treated in parallel with a scrambled or other form of control RNAi agent. Knockdown in cell culture of, e.g., preferably 50% or more, can thereby be identified as indicative of "inhibiting" or "reducing", "downregulating" or "suppressing", etc. having occurred. It is expressly contemplated that assessment of targeted mRNA or encoded protein levels (and therefore an extent of "inhibiting", etc. caused by an RNAi agent of the disclosure) can also be assessed in in vivo systems for the RNAi agents of the instant disclosure, under properly controlled conditions as described in the art.

The phrase "inhibiting expression of an HTT gene" or "inhibiting expression of HTT," as used herein, includes inhibition of expression of any HTT gene (such as, e.g., a mouse HTT gene, a rat HTT gene, a monkey HTT gene, or a human HTT gene) as well as variants or mutants of an HTT gene that encode an HTT protein. Thus, the HTT gene may be a wild-type HTT gene, a mutant HTT gene, or a transgenic HTT gene in the context of a genetically manipulated cell, group of cells, or organism.

"Inhibiting expression of an HTT gene" includes any level of inhibition of an HTT gene, e.g., at least partial suppression of the expression of an HTT gene, such as an inhibition by at least 20%. In certain embodiments, inhibition is by at least 30%, at least 40%, preferably at least 50%, at least about 60%, at least 70%, at least about 80%, at least 85%, at least 90%, at least 95%, at least 96%, at least 97%, at least 98%, or at least 99%; or to below the level of detection of the assay method.

The expression of an HTT gene may be assessed based on the level of any variable associated with HTT gene expression, e.g., HTT mRNA level or HTT protein level, or, for example, the level of HTT mutant protein.

Inhibition may be assessed by a decrease in an absolute or relative level of one or more of these variables compared with a control level. The control level may be any type of control level that is utilized in the art, e.g., a pre-dose baseline level, or a level determined from a similar subject, cell, or sample that is untreated or treated with a control (such as, e.g., buffer only control or inactive agent control).

In some embodiments of the methods of the disclosure, expression of an HTT gene is inhibited by at least 20%, 30%, 40%, preferably at least 50%, 60%, 70%, 80%, 85%, 90%, or 95%, or to below the level of detection of the assay. In certain embodiments, the methods include a clinically relevant inhibition of expression of HTT, e.g. as demonstrated by a clinically relevant outcome after treatment of a subject with an agent to reduce the expression of HTT.

Inhibition of the expression of an HTT gene may be manifested by a reduction of the amount of mRNA expressed by a first cell or group of cells (such cells may be present, for example, in a sample derived from a subject) in which an HTT gene is transcribed and which has or have been treated (e.g., by contacting the cell or cells with an RNAi agent of the disclosure, or by administering an RNAi agent of the disclosure to a subject in which the cells are or were present) such that the expression of an HTT gene is inhibited, as compared to a second cell or group of cells substantially identical to the first cell or group of cells but which has not or have not been so treated (control cell(s) not treated with an RNAi agent or not treated with an RNAi agent targeted to the gene of interest). The degree of inhibition may be expressed in terms of:

$$\frac{(\text{mRNA in control cells}) - (\text{mRNA in treated cells})}{(\text{mRNA in control cells})} \cdot 100\%$$

In other embodiments, inhibition of the expression of an HTT gene may be assessed in terms of a reduction of a parameter that is functionally linked to an HTT gene expression, e.g., HTT protein expression. HTT gene silencing may be determined in any cell expressing HTT, either endogenous or heterologous from an expression construct, and by any assay known in the art.

Inhibition of the expression of an HTT protein may be manifested by a reduction in the level of the HTT protein that is expressed by a cell or group of cells (e.g., the level of protein expressed in a sample derived from a subject). As explained above, for the assessment of mRNA suppression, the inhibiton of protein expression levels in a treated cell or group of cells may similarly be expressed as a percentage of the level of protein in a control cell or group of cells.

A control cell or group of cells that may be used to assess the inhibition of the expression of an HTT gene includes a cell or group of cells that has not yet been contacted with an RNAi agent of the disclosure. For example, the control cell or group of cells may be derived from an individual subject (e.g., a human or animal subject) prior to treatment of the subject with an RNAi agent.

The level of HTT mRNA that is expressed by a cell or group of cells may be determined using any method known in the art for assessing mRNA expression. In one embodiment, the level of expression of HTT in a sample is determined by detecting a transcribed polynucleotide, or portion thereof, e.g., mRNA of the HTT gene. RNA may be extracted from cells using RNA extraction techniques including, for example, using acid phenol/guanidine isothiocyanate extraction (RNAzol B; Biogenesis), RNeasy™ RNA preparation kits (Qiagen®) or PAXgene (PreAnalytix, Switzerland). Typical assay formats utilizing ribonucleic acid hybridization include nuclear run-on assays, RT-PCR, RNase protection assays, northern blotting, in situ hybridization, and microarray analysis. Circulating HTT mRNA may be detected using methods the described in WO2012/177906, the entire contents of which are hereby incorporated herein by reference.

In some embodiments, the level of expression of HTT is determined using a nucleic acid probe. The term "probe", as used herein, refers to any molecule that is capable of selectively binding to a specific HTT nucleic acid or protein, or fragment thereof. Probes can be synthesized by one of skill in the art, or derived from appropriate biological preparations. Probes may be specifically designed to be labeled. Examples of molecules that can be utilized as probes include, but are not limited to, RNA, DNA, proteins, antibodies, and organic molecules.

Isolated mRNA can be used in hybridization or amplification assays that include, but are not limited to, Southern or northern analyses, polymerase chain reaction (PCR) analyses and probe arrays. One method for the determination of mRNA levels involves contacting the isolated mRNA with a nucleic acid molecule (probe) that can hybridize to HTT mRNA. In one embodiment, the mRNA is immobilized on a solid surface and contacted with a probe, for example by running the isolated mRNA on an agarose gel and transferring the mRNA from the gel to a membrane, such as nitrocellulose. In an alternative embodiment, the probe(s) are immobilized on a solid surface and the mRNA is contacted with the probe(s), for example, in an Affymetrix® gene chip array. A skilled artisan can readily adapt known mRNA detection methods for use in determining the level of HTT mRNA.

An alternative method for determining the level of expression of HTT in a sample involves the process of nucleic acid amplification or reverse transcriptase (to prepare cDNA) of for example mRNA in the sample, e.g., by RT-PCR (the experimental embodiment set forth in Mullis, 1987, U.S. Pat. No. 4,683,202), ligase chain reaction (Barany (1991) *Proc. Natl. Acad. Sci. USA* 88:189-193), self sustained sequence replication (Guatelli et al. (1990) *Proc. Natl. Acad. Sci. USA* 87:1874-1878), transcriptional amplification system (Kwoh et al. (1989) *Proc. Natl. Acad. Sci. USA* 86:1173-1177), Q-Beta Replicase (Lizardi et al. (1988) *Bio/Technology* 6:1197), rolling circle replication (Lizardi et al., U.S. Pat. No. 5,854,033) or any other nucleic acid amplification method, followed by the detection of the amplified molecules using techniques well known to those of skill in the art. These detection schemes are especially useful for the detection of nucleic acid molecules if such molecules are present in very low numbers. In particular aspects of the disclosure, the level of expression of HTT is determined by quantitative fluorogenic RT-PCR (i.e., the TaqMan™ System), by a Dual-Glo® Luciferase assay, or by other art-recognized method for measurement of HTT expression or mRNA level.

The expression level of HTT mRNA may be monitored using a membrane blot (such as used in hybridization analysis such as northern, Southern, dot, and the like), or microwells, sample tubes, gels, beads or fibers (or any solid support comprising bound nucleic acids). See U.S. Pat. Nos. 5,770,722, 5,874,219, 5,744,305, 5,677,195 and 5,445,934, which are incorporated herein by reference. The determination of HTT expression level may also comprise using nucleic acid probes in solution.

In some embodiments, the level of mRNA expression is assessed using branched DNA (bDNA) assays or real time PCR (qPCR). The use of this PCR method is described and exemplified in the Examples presented herein. Such methods can also be used for the detection of HTT nucleic acids.

The level of HTT protein expression may be determined using any method known in the art for the measurement of protein levels. Such methods include, for example, electrophoresis, capillary electrophoresis, high performance liquid chromatography (HPLC), thin layer chromatography (TLC), hyperdiffusion chromatography, fluid or gel precipitin reactions, absorption spectroscopy, a colorimetric assays, spectrophotometric assays, flow cytometry, immunodiffusion (single or double), immunoelectrophoresis, western blotting, radioimmunoassay (RIA), enzyme-linked immunosorbent assays (ELISAs), immunofluorescent assays, electrochemiluminescence assays, and the like. Such assays can also be used for the detection of proteins indicative of the presence or replication of HTT proteins.

In some embodiments, the efficacy of the methods of the disclosure in the treatment of an HTT-related disease is assessed by a decrease in HTT mRNA level (e.g, by assessment of a CSF sample and/or plasma sample for HTT level, by brain biopsy, or otherwise).

In some embodiments of the methods of the disclosure, the RNAi agent is administered to a subject such that the RNAi agent is delivered to a specific site within the subject. The inhibition of expression of HTT may be assessed using measurements of the level or change in the level of HTT mRNA or HTT protein in a sample derived from a specific site within the subject, e.g., CNS cells. In certain embodiments, the methods include a clinically relevant inhibition of expression of HTT, e.g. as demonstrated by a clinically relevant outcome after treatment of a subject with an agent to reduce the expression of HTT, such as, for example, stabilization or inhibition of caudate atrophy (e.g., as assessed by volumetric MRI (vMRI)), a stabilization or reduction in neurofilament light chain (Nfl) levels in a CSF sample from a subject, a reduction in mutant HTT mRNA or a cleaved mutant HTT protein, e.g., one or both of full-length mutant HTT mRNA or protein and a cleaved mutant HTT mRNA or protein, and a stabilization or improvement in Unified Huntington's Disease Rating Scale (UHDRS) score.

As used herein, the terms detecting or determining a level of an analyte are understood to mean performing the steps to determine if a material, e.g., protein, RNA, is present. As used herein, methods of detecting or determining include detection or determination of an analyte level that is below the level of detection for the method used.

IX. Methods of Treating or Preventing HTT-Associated Diseases

The present disclosure also provides methods of using an RNAi agent of the disclosure, two or more, e.g., 2, 3, or 4, double stranded RNAi agents of the disclosure (e.g., each agent independently targeting a portion of a human HTT gene, such as a first dsRNA agent targeting exon 1 of human HTT and a second dsRNa agent targeting full-length human HTT), a composition (such as a pharmaceutical composition) containing a RNAi agent of the disclosure, two or more, e.g., 2, 3, or 4, compositions (such as pharmaceutical compositions), each independently comprising a dsRNA agent of the invention, or a composition comprising two or more, e.g., 2, 3, or 4, dsRNA agents of the disclosure to reduce or inhibit HTT expression in a cell. The methods include contacting the cell with a dsRNA of the disclosure, a composition of the disclosure, or a pharmaceutical composition of the disclosure, and maintaining the cell for a time sufficient to obtain degradation of the mRNA transcript of an HTT gene, thereby inhibiting expression of the HTT gene in the cell. Reduction in gene expression can be assessed by any methods known in the art. For example, a reduction in the expression of HTT may be determined by determining the mRNA expression level of HTT using methods routine to one of ordinary skill in the art, e.g., northern blotting, qRT-PCR; by determining the protein level of HTT using methods routine to one of ordinary skill in the art, such as western blotting, immunological techniques.

In the methods of the disclosure the cell may be contacted in vitro or in vivo, i.e., the cell may be within a subject.

A cell suitable for treatment using the methods of the disclosure may be any cell that expresses an HTT gene. A cell suitable for use in the methods of the disclosure may be a mammalian cell, e.g., a primate cell (such as a human cell or a non-human primate cell, e.g., a monkey cell or a chimpanzee cell), a non-primate cell (such as a rat cell, or a mouse cell). In one embodiment, the cell is a human cell, e.g., a human CNS cell.

HTT expression is inhibited in the cell by at least about 30, 40, 50, 55, 60, 65, 70, 75, 80, 85, 90, 95, 96, 97, 98, 99, or about 100%, i.e., to below the level of detection. In preferred embodiments, HTT expression is inhibited by at least 50%.

The in vivo methods of the disclosure may include administering to a subject a composition containing an RNAi agent, where the RNAi agent includes a nucleotide sequence that is complementary to at least a part of an RNA transcript of the HTT gene of the mammal to be treated. In some embodiments, the subject is administered two or more, e.g., 2, 3, or 4, compositions, each independently comprising an RNAi agent of the invention. The compositions may be the same or different. In other embodiments, the subject is administered a composition comprising two or more, e.g., 2, 3, or 4, dsRNA agents, each independently targeting a portion of an HTT gene.

When the organism to be treated is a mammal such as a human, the composition can be administered by any means known in the art including, but not limited to, oral, intraperitoneal, or parenteral routes, including intracranial (e.g., intraventricular, intraparenchymal, and intrathecal), intravenous, intramuscular, intravitreal, subcutaneous, transdermal, airway (aerosol), nasal, rectal, and topical (including buccal and sublingual) administration. In certain embodiments, the compositions are administered by intravenous infusion or injection. In certain embodiments, the compositions are administered by subcutaneous injection. In certain embodiments, the compositions are administered by intrathecal injection.

In some embodiments, the administration is via a depot injection. A depot injection may release the RNAi agent in a consistent way over a prolonged time period. Thus, a depot injection may reduce the frequency of dosing needed to obtain a desired effect, e.g., a desired inhibition of HTT, or a therapeutic or prophylactic effect. A depot injection may also provide more consistent serum concentrations. Depot injections may include subcutaneous injections or intramuscular injections. In preferred embodiments, the depot injection is a subcutaneous injection.

In some embodiments, the administration is via a pump. The pump may be an external pump or a surgically implanted pump. In certain embodiments, the pump is a subcutaneously implanted osmotic pump. In other embodiments, the pump is an infusion pump. An infusion pump may be used for intracranial, intravenous, subcutaneous, arterial, or epidural infusions. In preferred embodiments, the infusion pump is a subcutaneous infusion pump. In other embodiments, the pump is a surgically implanted pump that delivers the RNAi agent to the CNS.

The mode of administration may be chosen based upon whether local or systemic treatment is desired and based upon the area to be treated. The route and site of administration may be chosen to enhance targeting.

In one aspect, the present disclosure also provides methods for inhibiting the expression of an HTT gene in a mammal. The methods include administering to the mammal a composition comprising a dsRNA that targets an HTT gene in a cell of the mammal and maintaining the mammal for a time sufficient to obtain degradation of the mRNA transcript of the HTT gene, thereby inhibiting expression of the HTT gene in the cell. Reduction in gene expression can be assessed by any methods known it the art and by methods, e.g. qRT-PCR, described herein. In some embodiments, the dsRNA is present in a composition, such as a pharmaceutical composition. In some embodiments, the mammal is administered two or more, e.g., 2, 3, or 4, dsRNA agents of the invention. In some embodiments, each dsRNA agent administered to the subject is independently present in a composition. In other embodiments, the mammal is administered a composition comprising two or more, e.g., 2, 3, or 4, dsRNAs of the invention.

Reduction in protein production can be assessed by any methods known it the art and by methods, e.g. ELISA, described herein. In one embodiment, a CNS biopsy sample or a cerebrospinal fluid (CSF) sample serves as the tissue material for monitoring the reduction in HTT gene or protein expression (or of a proxy therefore).

The present disclosure further provides methods of treatment of a subject in need thereof. The treatment methods of the disclosure include administering an RNAi agent of the disclosure to a subject, e.g., a subject that would benefit from inhibition of HTT expression, in a therapeutically effective amount of an RNAi agent targeting an HTT gene or a pharmaceutical composition comprising an RNAi agent targeting aHTT gene. In some embodiments, the subject is administered a therapeutically effective amount of two or more, e.g., 2, 3, or 4, dsRNA agents of the invention. In some embodiments, each dsRNA agent administered to the subject is independently present in a composition. In other embodiments, the subject is administered a composition comprising two or more, e.g., 2, 3, or 4, dsRNAs of the invention.

In addition, the present disclosure provides methods of preventing, treating or inhibiting the progression of an HTT-associated disease or disorder (e.g., Huntington's disease), in a subject, such as the progression of an HTT-associated disease or disorder. The methods include administering to the subject a therapeutically effective amount of any of the RNAi agent, e.g., dsRNA agents, or the pharmaceutical composition provided herein, thereby preventing, treating or inhibiting the progression of an HTT-associated disease or disorder in the subject. In some embodiments, the subject is administered a therapeutically effective amount of two or more, e.g., 2, 3, or 4, dsRNA agents of the invention. In some embodiments, each dsRNA agent administered to the subject is independently present in a composition. In other embodiments, the subject is administered a composition comprising two or more, e.g., 2, 3, or 4, dsRNAs of the invention.

In some embodiments of the methods of the invention which include administering two or more dsRNA agents, as described herein, e.g., any two or more, e.g., 2, 3, or 4, of the dsRNA agents selected from the group of dsRNA agents in Tables 2-5, the subject may be administered a first agent (or a composition comprising a first agent) at a first time, a second agent (or a composition comprising a second agent) at a second time, a third agent (or a compositions comprising a third agent) at a third time, and a fourth agent (or a composition comprising a fourth agent) at a fourth time; or the the subject may be administered all of the agents (or a composition comprising all of the agents at the same time, Alternatively, the subject may be administered a first agent (or a composition comprising a first agent) at a first time and a second, third, and/or fourth agent (or a composition comprising a second, third and. or fourth agent) at a second time. Other combinations of contacting the cell with two or more agents of the invention are also contemplated.

An RNAi agent of the disclosure may be administered as a "free RNAi agent." A free RNAi agent is administered in the absence of a pharmaceutical composition. The naked RNAi agent may be in a suitable buffer solution. The buffer solution may comprise acetate, citrate, prolamine, carbonate, or phosphate, or any combination thereof. In one embodiment, the buffer solution is phosphate buffered saline (PBS). The pH and osmolarity of the buffer solution containing the RNAi agent can be adjusted such that it is suitable for administering to a subject.

Alternatively, an RNAi agent of the disclosure may be administered as a pharmaceutical composition, such as a dsRNA liposomal formulation.

Subjects that would benefit from a reduction or inhibition of HTT gene expression are those having an HTT-associated disease, e.g., Huntington's disease.

The disclosure further provides methods for the use of an RNAi agent or a pharmaceutical composition thereof, e.g., for treating a subject that would benefit from reduction or inhibition of HTT expression, e.g., a subject having an HTT-associated disorder, in combination with other pharmaceuticals or other therapeutic methods, e.g., with known pharmaceuticals or known therapeutic methods, such as, for example, those which are currently employed for treating these disorders. For example, in certain embodiments, an RNAi agent targeting HTT is administered in combination with, e.g., an agent useful in treating an HTT-associated disorder as described elsewhere herein or as otherwise known in the art. For example, additional agents suitable for treating a subject that would benefit from reduction in HTT expression, e.g., a subject having an HTT-associated disorder, may include agents currently used to treat symptoms of HTT. The RNAi agent and additional therapeutic agents may be administered at the same time or in the same combination, e.g., intrathecally, or the additional therapeutic agent can be administered as part of a separate composition or at separate times or by another method known in the art or described herein.

Exemplary additional therapeutics include, for example, a monoamine inhibitor, e.g., tetrabenazine (Xenazine), deutetrabenazine (Austedo), and reserpine, an anticonvulsant, e.g., valproic acid (Depakote, Depakene, Depacon), and clonazepam (Klonopin), an antipsychotic agent, e.g., risperidone (Risperdal), and haloperidol (Haldol), and an antidepressant, e.g., paroxetine (Paxil).

In one embodiment, the method includes administering a composition featured herein such that expression of the target HTT gene is decreased, for at least one month. In preferred embodiments, expression is decreased for at least 2 months, 3 months, or 6 months.

Preferably, the RNAi agents useful for the methods and compositions featured herein specifically target RNAs (primary or processed) of the target HTT gene. Compositions and methods for inhibiting the expression of these genes using RNAi agents can be prepared and performed as described herein.

Administration of the dsRNA according to the methods of the disclosure may result in a reduction of the severity, signs, symptoms, or markers of such diseases or disorders in a patient with an HTT-associated disorder. By "reduction" in this context is meant a statistically significant or clinically significant decrease in such level. The reduction can be, for example, at least 5%, 10%, 15%, 20%, 25%, 30%, 35%, 40%, 45%, 50%, 55%, 60%, 65%, 70%, 75%, 80%, 85%, 90%, 95%, or about 100%.

Efficacy of treatment or prevention of disease can be assessed, for example by measuring disease progression, disease remission, symptom severity, reduction in pain, quality of life, dose of a medication required to sustain a treatment effect, level of a disease marker or any other measurable parameter appropriate for a given disease being treated or targeted for prevention. It is well within the ability of one skilled in the art to monitor efficacy of treatment or prevention by measuring any one of such parameters, or any combination of parameters. For example, efficacy of treatment of an HTT-associated disorder may be assessed, for example, by periodic monitoring of a subject's. Comparisons of the later readings with the initial readings provide a physician an indication of whether the treatment is effective. It is well within the ability of one skilled in the art to monitor efficacy of treatment or prevention by measuring any one of such parameters, or any combination of parameters. In connection with the administration of an RNAi agent targeting HTT or pharmaceutical composition thereof, "effective against" an HTT-associated disorder indicates that administration in a clinically appropriate manner results in a beneficial effect for at least a statistically significant fraction of patients, such as an improvement of symptoms, a cure, a reduction in disease, extension of life, improvement in quality of life, or other effect generally recognized as positive by medical doctors familiar with treating HTT-associated disorders and the related causes.

A treatment or preventive effect is evident when there is a statistically significant improvement in one or more parameters of disease status, or by a failure to worsen or to develop symptoms where they would otherwise be anticipated. As an example, a favorable change of at least 10% in a measurable parameter of disease, and preferably at least 20%, 30%, 40%, 50% or more can be indicative of effective treatment. Efficacy for a given RNAi agent drug or formulation of that drug can also be judged using an experimental animal model for the given disease as known in the art. When using an experimental animal model, efficacy of treatment is evidenced when a statistically significant reduction in a marker or symptom is observed.

Alternatively, the efficacy can be measured by a reduction in the severity of disease as determined by one skilled in the art of diagnosis based on a clinically accepted disease severity grading scale. Any positive change resulting in e.g., lessening of severity of disease measured using the appropriate scale, represents adequate treatment using an RNAi agent or RNAi agent formulation as described herein.

Subjects can be administered a therapeutic amount of dsRNA, such as about 0.01 mg/kg to about 200 mg/kg.

The RNAi agent can be administered intrathecally, via intravitreal injection, or by intravenous infusion over a period of time, on a regular basis. In certain embodiments, after an initial treatment regimen, the treatments can be administered on a less frequent basis. Administration of the RNAi agent can reduce HTT levels, e.g., in a cell, tissue, blood, CSF sample or other compartment of the patient by at least 20%, 30%, 40%, 50%, 55%, 60%, 65%, 70,% 75%, 80%, 85%, 90%, 95%, 96%, 97%, 98%, or at least about 99% or more. In a preferred embodiment, administration of the RNAi agent can reduce HTT levels, e.g., in a cell, tissue, blood, CSF sample or other compartment of the patient by at least 50%.

Before administration of a full dose of the RNAi agent, patients can be administered a smaller dose, such as a 5% infusion reaction, and monitored for adverse effects, such as an allergic reaction. In another example, the patient can be monitored for unwanted immunostimulatory effects, such as increased cytokine (e.g., TNF-alpha or INF-alpha) levels.

Alternatively, the RNAi agent can be administered subcutaneously, i.e., by subcutaneous injection. One or more injections may be used to deliver the desired, e.g., monthly dose of RNAi agent to a subject. The injections may be repeated over a period of time. The administration may be repeated on a regular basis. In certain embodiments, after an initial treatment regimen, the treatments can be administered on a less frequent basis. A repeat-dose regimine may include administration of a therapeutic amount of RNAi agent on a regular basis, such as monthly or extending to once a quarter, twice per year, once per year. In certain embodiments, the RNAi agent is administered about once per month to about once per quarter (i.e., about once every three months).

Unless otherwise defined, all technical and scientific terms used herein have the same meaning as commonly understood by one of ordinary skill in the art to which this invention belongs. Although methods and materials similar or equivalent to those described herein can be used in the practice or testing of the RNAi agents and methods featured in the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

EXAMPLES

Example 1. RNAi Agent Design, Synthesis, Selection, and In Vitro Evaluation

This Example describes methods for the design, synthesis, selection, and in vitro evaluation of HTT_RNAi agents.

Source of Reagents

Where the source of a reagent is not specifically given herein, such reagent can be obtained from any supplier of reagents for molecular biology at a quality/purity standard for application in molecular biology.

Bioinformatics siRNAs targeting the human huntingtin transcript (HTT; human NCBI refseqID NM_002111.8; NCBI GeneID: 3064) were designed using custom R and Python scripts. The human NM_002111 REFSEQ mRNA, version 8, has a length of 13,498 bases.

A detailed list of the unmodified HTT sense and antisense strand nucleotide sequences are shown in Table 2. A detailed list of the modified HTT sense and antisense strand nucleotide sequences are shown in Table 3.

It is to be understood that, throughout the application, a duplex name without a decimal is equivalent to a duplex name with a decimal which merely references the batch number of the duplex. For example, AD-564727 is equivalent to AD-564727.1.

Total RNA Isolation Using DYNABEADS mRNA Isolation Kit

RNA was isolated using an automated protocol on a BioTek-EL406 platform using DYNABEADs (Invitrogen, cat #61012). Briefly, 70 μL of Lysis/Binding Buffer and 10 μL of lysis buffer containing 3 μL of magnetic beads were added to the plate with cells. Plates were incubated on an electromagnetic shaker for 10 minutes at room temperature and then magnetic beads were captured and the supernatant was removed. Bead-bound RNA was then washed 2 times with 150 μL Wash Buffer A and once with Wash Buffer B. Beads were then washed with 150 μL Elution Buffer, re-captured and supernatant removed.

cDNA synthesis using ABI High capacity cDNA reverse transcription kit (Applied Biosystems, Foster City, CA, Cat #4368813)

Ten μL of a master mix containing 1 μL 10× Buffer, 0.4 μL 25× dNTPs, 1 μL 10× Random primers, 0.5 μL Reverse Transcriptase, 0.5 μL RNase inhibitor and 6.6 μL of $H_2O$ per reaction was added to RNA isolated above. Plates were sealed, mixed, and incubated on an electromagnetic shaker for 10 minutes at room temperature, followed by 2 hour incubation at 37° C.

Real time PCR

Two μL of cDNA were added to a master mix containing 0.5 μL of human or mouse GAPDH TaqMan Probe (ThermoFisher cat 4352934E or 4351309) and 0.5 μL of appropriate HTT probe (commercially available, e.g., from Thermo Fisher) and 5 μL Lightcycler 480 probe master mix (Roche Cat #04887301001) per well in a 384 well plates (Roche cat #04887301001). Real time PCR was done in a LightCycler480 Real Time PCR system (Roche). Each duplex was tested with N=4 and data were normalized to cells transfected with a non-targeting control siRNA. To calculate relative fold change, real time data were analyzed using the ΔΔCt method and normalized to assays performed with an appropriate control.

TABLE 1

Abbreviations of nucleotide monomers used in nucleic acid sequence representation. It will be understood that these monomers, when present in an oligonucleotide, are mutually linked by 5'-3'-phosphodiester bonds; and it is understood that when the nucleotide contains a 2'-fluoro modification, then the fluoro replaces the hydroxy at that position in the parent nucleotide (i.e., it is a 2'-deoxy-2'-fluoronucleotide).

| Abbreviation | Nucleotide(s) |
|---|---|
| A | Adenosine-3'-phosphate |
| Ab | beta-L-adenosine-3'-phosphate |
| Abs | beta-L-adenosine-3'-phosphorothioate |
| Af | 2'-fluoroadenosine-3'-phosphate |
| Afs | 2'-fluoroadenosine-3'-phosphorothioate |
| As | adenosine-3'-phosphorothioate |
| C | cytidine-3'-phosphate |
| Cb | beta-L-cytidine-3'-phosphate |
| Cbs | beta-L-cytidine-3'-phosphorothioate |
| Cf | 2'-fluorocytidine-3'-phosphate |
| Cfs | 2'-fluorocytidine-3'-phosphorothioate |
| Cs | cytidine-3'-phosphorothioate |
| G | guanosine-3'-phosphate |
| Gb | beta-L-guanosine-3'-phosphate |
| Gbs | beta-L-guanosine-3'-phosphorothioate |
| Gf | 2'-fluoroguanosine-3'-phosphate |
| Gfs | 2'-fluoroguanosine-3'-phosphorothioate |
| Gs | guanosine-3'-phosphorothioate |
| T | 5'-methyluridine-3'-phosphate |
| Tf | 2'-fluoro-5-methyluridine-3'-phosphate |
| Tfs | 2'-fluoro-5-methyluridine-3'-phosphorothioate |
| Ts | 5-methyluridine-3'-phosphorothioate |
| U | Uridine-3'-phosphate |
| Uf | 2'-fluorouridine-3'-phosphate |
| Ufs | 2'-fluorouridine -3'-phosphorothioate |
| Us | uridine -3'-phosphorothioate |
| N | any nucleotide, modified or unmodified |
| a | 2'-O-methyladenosine-3'-phosphate |
| as | 2'-O-methyladenosine-3'- phosphorothioate |
| c | 2'-O-methylcytidine-3'-phosphate |
| cs | 2'-O-methylcytidine-3'- phosphorothioate |
| g | 2'-O-methylguanosine-3'-phosphate |
| gs | 2'-O-methylguanosine-3'- phosphorothioate |
| t | 2'-O-methyl-5-methyluridine-3'-phosphate |
| ts | 2'-O-methyl-5-methyluridine-3'-phosphorothioate |
| u | 2'-O-methyluridine-3'-phosphate |
| us | 2'-O-methyluridine-3'-phosphorothioate |
| s | phosphorothioate linkage |
| L96 | N-[tris(GalNAc-alkyl)-amidodecanoyl)]-4-hydroxyprolinol Hyp-(GalNAc-alkyl)3 |

TABLE 1-continued

| Abbreviations of nucleotide monomers used in nucleic acid sequence representation. It will be understood that these monomers, when present in an oligonucleotide, are mutually linked by 5'-3'-phosphodiester bonds; and it is understood that when the nucleotide contains a 2'-fluoro modification, then the fluoro replaces the hydroxy at that position in the parent nucleotide (i.e., it is a 2'-deoxy-2'-fluoronucleotide). | |
|---|---|
| Abbreviation | Nucleotide(s) |
| | 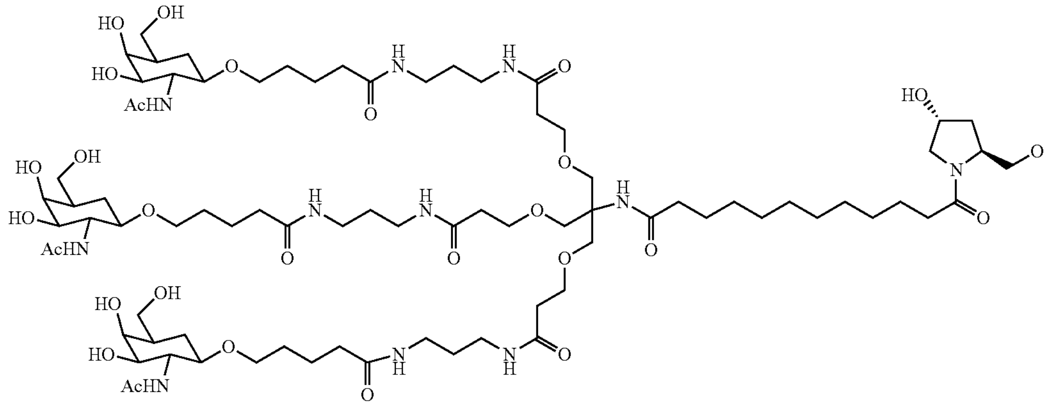 [SMILES: CC(=O)NC1C(OCCCCC(=O)NCCCNC(=O)CCOCC(COCCC(=O)NCCCNC(=O)CCCCOC2CC(CO)C(O)C(O)C2NC(C)=O)(COCCC(=O)NCCCNC(=O)CCCCOC2CC(CO)C(O)C(O)C2NC(C)=O)NC(=O)CCCCCCCCCCC(=O)N2C[C@H](O)C[C@H]2CO)CC(CO)C(O)C1O] |
| Y34 | 2-hydroxymethyl-tetrahydrofurane-4-methoxy-3-phosphate (abasic 2'-OMe furanose) |
| | 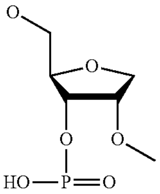 |
| Y44 | inverted abasic DNA (2-hydroxymethyl-tetrahydrofurane-5-phosphate) |
| | 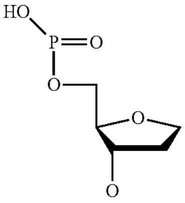 |
| L10 | N-(cholesterylcarboxamidocaproyl)-4-hydroxyprolinol (Hyp-C6-Chol) |
| | 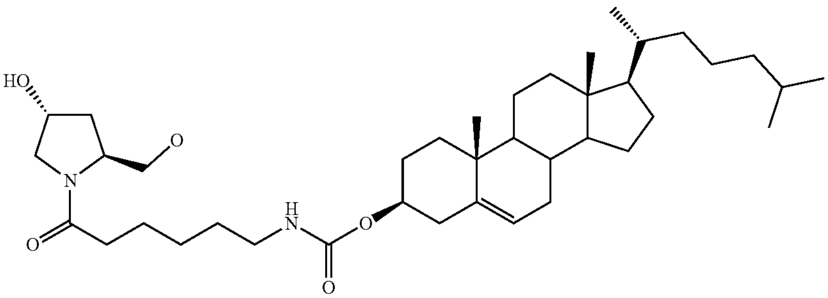 [SMILES: CC(C)CCC[C@@H](C)[C@H]1CCC2C3CC=C4C[C@@H](OC(=O)NCCCCCC(=O)N5C[C@H](O)C[C@H]5CO)CC[C@]4(C)C3CC[C@@]21C] |
| (Agn) | Adenosine-glycol nucleic acid (GNA) S-Isomer |
| (Cgn) | Cytidine-glycol nucleic acid (GNA) S-Isomer |
| (Ggn) | Guanosine-glycol nucleic acid (GNA) S-Isomer |
| (Tgn) | Thymidine-glycol nucleic acid (GNA) S-Isomer |
| P | Phosphate |
| VP | Vinyl-phosphonate |
| dA | 2'-deoxyadenosine-3'-phosphate |
| dAs | 2'-deoxyadenosine-3'-phosphorothioate |
| dC | 2'-deoxycytidine-3'-phosphate |
| dCs | 2'-deoxycytidine-3'-phosphorothioate |
| dG | 2'-deoxyguanosine-3'-phosphate |

TABLE 1-continued

Abbreviations of nucleotide monomers used in nucleic acid sequence representation. It will be understood that these monomers, when present in an oligonucleotide, are mutually linked by 5'-3'-phosphodiester bonds; and it is understood that when the nucleotide contains a 2'-fluoro modification, then the fluoro replaces the hydroxy at that position in the parent nucleotide (i.e., it is a 2'-deoxy-2'-fluoronucleotide).

| Abbreviation | Nucleotide(s) |
|---|---|
| dGs | 2'-deoxyguanosine-3'-phosphorothioate |
| dT | 2'-deoxythymidine-3'-phosphate |
| dTs | 2'-deoxythymidine-3'-phosphorothioate |
| dU | 2'-deoxyuridine |
| dUs | 2'-deoxyuridine-3'-phosphorothioate |
| (Ahd) | 2'-O-hexadecyl-adenosine-3'-phosphate |
| (Ahds) | 2'-O-hexadecyl-adenosine-3'-phosphorothioate |
| (Chd) | 2'-O-hexadecyl-cytidine-3'-phosphate |
| (Chds) | 2'-O-hexadecyl-cytidine-3'-phosphorothioate |
| (Ghd) | 2'-O-hexadecyl-guanosine-3'-phosphate |
| (Ghds) | 2'-O-hexadecyl-guanosine-3'-phosphorothioate |
| (Uhd) | 2'-O-hexadecyl-uridine-3'-phosphate |
| (Uhds) | 2'-O-hexadecyl-uridine-3'-phosphorothioate |
| (C2p) | cytidine-2'-phosphate |
| (G2p) | guanosine-2'-phosphate |
| (U2p) | uridine-2'-phosphate |
| (A2p) | adenosine-2'-phosphate |

TABLE 2

Unmodified Sense and Antisense Strand Sequences of HTT dsRNA Agents

| Duplex ID | Sense Sequence 5' to 3' | SEQ ID NO: | Antisense Sequence 5' to 3' | SEQ ID NO: | Antisense Range in NM_ 002111.8 |
|---|---|---|---|---|---|
| AD-1271085 (FL) | GCUAUUCAUAAUCACAUUCGA | 15 | UCGAAUGUGAUUAUGAAUAGCAU | 16 | 4398-4420 |
| AD-1271083 (FL) | UCAUAAUCACAUUCGUUUGUA | 25 | UACAAACGAAUGUGAUUAUGAAU | 29 | 4403-4425 |
| AD-1271084 (FL) | GCUGGUGAAUCGGAUUCCUGA | 26 | UCAGGAAUCCGAUUCACCAGCUC | 30 | 6512-6534 |
| AD-1271082 (Exon 1) | UGGAAAAGCUGAUGAAGGCCA | 27 | UGGCCUUCAUCAGCUUUUCCAGG | 31 | 154-176 |
| AD-1019465 (Exon 1) | CCAUGGCGACCCUGGAAAAGA | 28 | UCUUUUCCAGGGUCGCCAUGGCG | 32 | 142-164 |

TABLE 3

Modified Sense and Antisense Strand Sequences of HTT dsRNA Agents

| Duplex ID | Sense Sequence 5' to 3' | SEQ ID NO: | Antisense Sequence 5' to 3' | SEQ ID NO: |
|---|---|---|---|---|
| AD-1271085 (FL) | gscsuau(Uhd)CfaUfAfAfucacauucsgsa | 17 | VPusCfsgaaUfgUfGfauuaUfgAfauagcsasu | 18 |
| AD-1271083 (FL) | uscsaua(Ahd)UfcAfCfAfuucguuugsusa | 19 | VPusAfscaaAfcGfAfauguGfaUfuaugasasu | 20 |

TABLE 3-continued

Modified Sense and Antisense Strand Sequences of HTT dsRNA Agents

| Duplex ID | Sense Sequence 5' to 3' | SEQ ID NO: | Antisense Sequence 5' to 3' | SEQ ID NO: |
|---|---|---|---|---|
| AD-1271084 (FL) | gscsugg(Uhd)GfaAfUfCfggauuccusgsa | 21 | VPusCfsaggAfaUfCfcgauUfcAfccagcsusc | 22 |
| AD-1271082 (Exon 1) | usgsgaa(Ahd)AfgCfUfGfaugaaggcscsa | 23 | VPusGfsgccu(Tgn)caucagCfuUfuuccasgsg | 24 |

Example 2. In Vivo Assessment of RNAi Agents Targeting HTT

Duplexes of interest targeting either full-length (FL) human HTT or human HTT exon 1 were evaluated in vivo in non-human primates. Duplexes were synthesized and prepared using methods known in the art.

The unmodified nucleotide sequences of the sense and antisense strands of the duplexes of interest are provided in Table 2 above. The modified nucleotide sequences of the sense and antisense strands of the duplexes of interest are provided in Table 3 above.

Male non-human primates, 3-4 kg in weight, were, intrathecally administered a single 60 mg dose in a volume of 2 mls of AD-1019465 (targeting exon 1 of human HTT; see, PCT application No.: PCT/US2020/057849, the entire contents of which are incorporated herein by reference), AD-1271082 (targeting exon 1 of human HTT), or AD-1271085 (targeting full-length human HTT) (n=5 per duplex) over approximately 3 minutes by manual bolus followed by a 0.3 mL flush of artificial CSF (aCSF), or artificial aCSF on Day 1. Plasma samples were collected at pre-dose Day −7 and at and 0.5 hours, 2 hours, 8 hours, 24 hours post-dose, and Days 8, 15, 36, and 43 post dose. Cerebrospinal fluid (CSF) samples were collected at pre-dose Day −7 and Days 2, 8, 15, 36, 43 post-dose from the cisterna magna, and at Day 1 pre-dose from the lumbar intrathecal space. At Day 43 post-dose, animals were sacrificed, perfused with saline and tissues were collected. The tissues were formalin fixed and flash frozen for siRNA levels, immunohostochemical (IHC) analyses, and in situ hybridization (ISH) analyses. The collected tissues included brain (prefrontal cortex, temporal cortex, hippocampus, brain stem, cerebellum, striatum (caudate and putamen/globus pallidus), spinal cord (cervical, thoracic, lumbar), liver, kidney, and heart.

Figure 1:
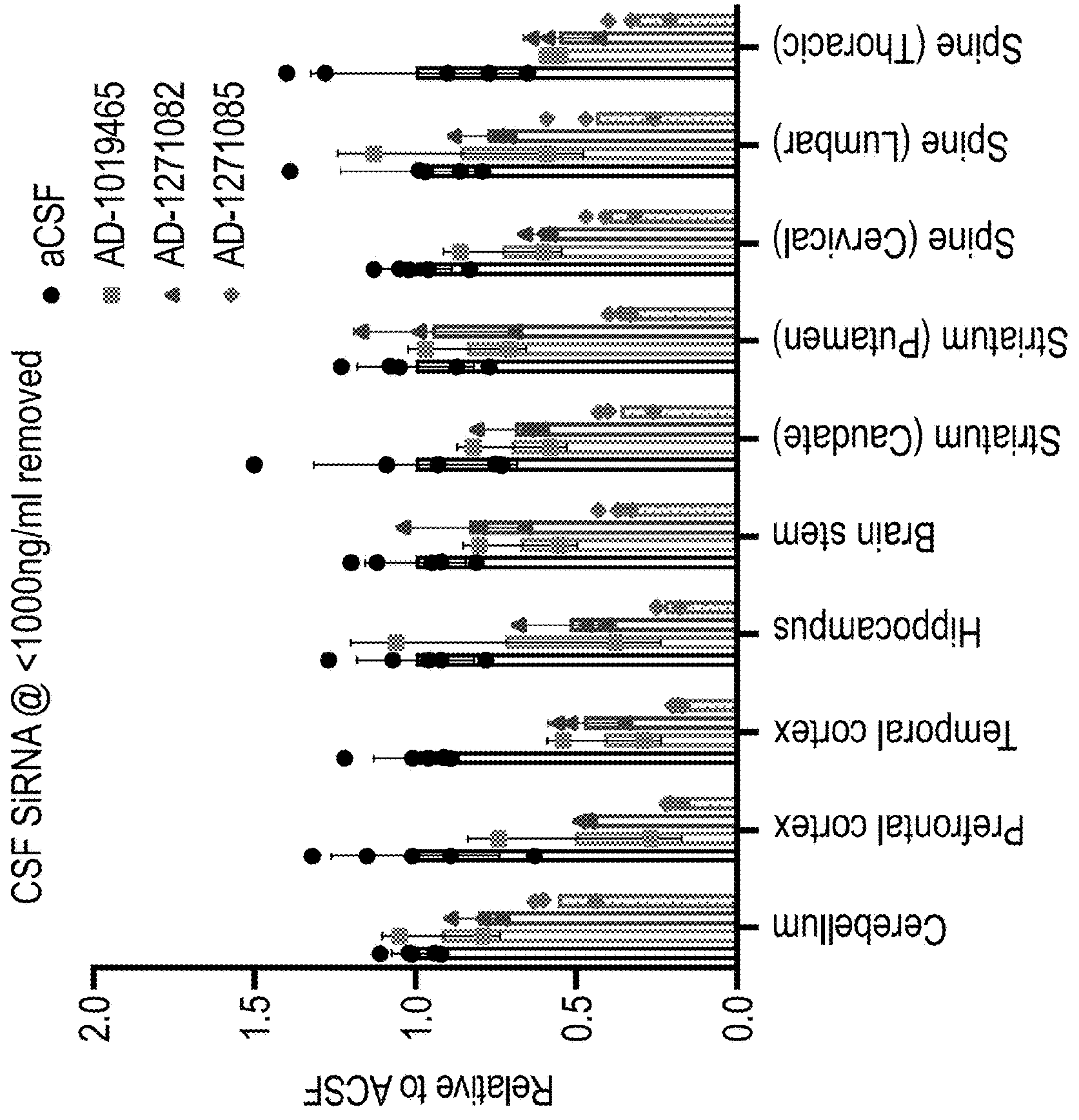
FIG. 1 is a graph depicting HTT knockdown in the indicated regions of the brain and spine of non-human primates having greater than 1000 ng/mL siRNA in CSF at 24 hours post intrathecal administration of a single 60 mg dose of the indicated duplexes.

As depicted in FIG. 1, in animals having >1000 ng/mL siRNA in CSF at 24 hours post dosing, there was potent knockdown of HTT mRNA throughout the brain and spine indicative of successful intrathecal administration. Administration of duplexes targeting full-length HTT (AD-1271085) knocked down HTT mRNA about 80% in cortex and hippocampus and about 60% in striatum and administration of duplexes targeting exon 1 of HTT (AD-1271082 and AD-1019465) knocked down HTT mRNA about 60-70% in cortex and hippocampus and about 30% in striatum.

FIG. 2 is the tabulated values of the graph depicted in FIG. 1. Due to the inherent technical variability of intrathecal dosing, siRNA levels in CSF 24 hours post dosing was used as an indicator of successful dosing. Animals with <1000 ng/ml siRNA levels were removed from the analysis.

Figure 3A:
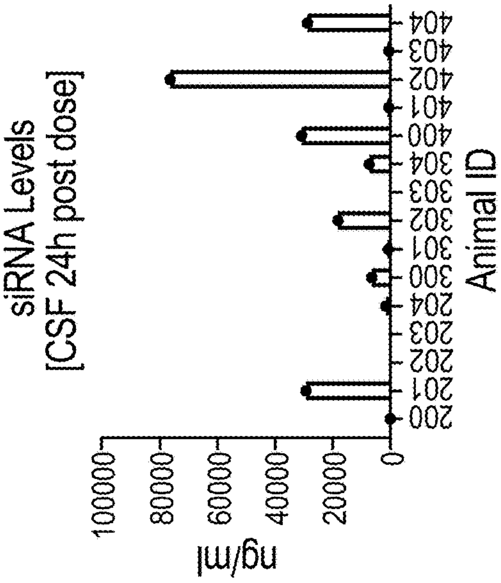
FIG. 3A is a graph depicting the concentration of siRNA in the CSF of the indicated non-human primates (see FIG. 2) at 24 hours post intrathecal administration of a single 60 mg dose of duplex.
Figure 3B:
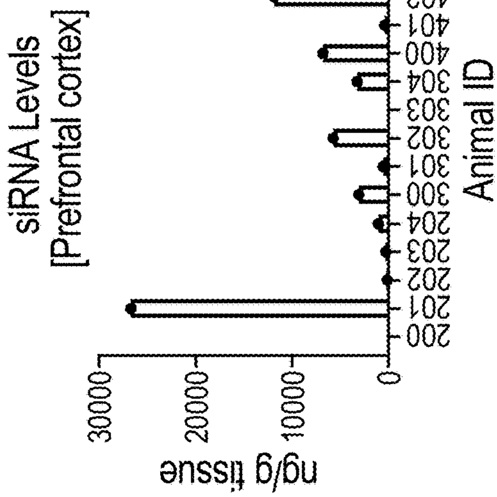
FIG. 3B is a graph depicting the concentration of siRNA in the prefrontal cortex of the indicated non-human primates (see FIG. 2) at 45 days post intrathecal administration of a single 60 mg dose of duplex.
Figure 3C:
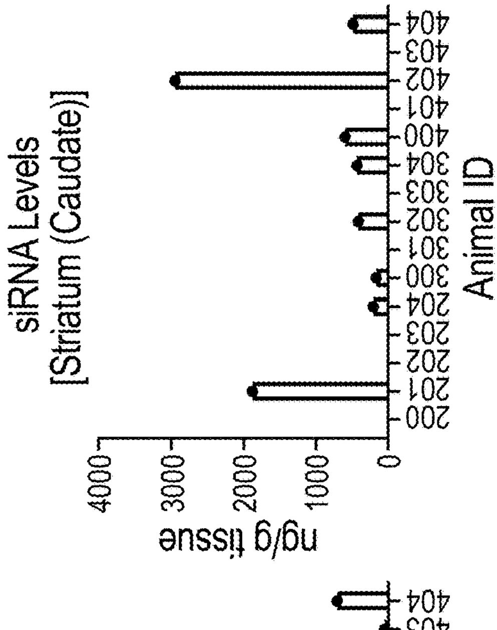
FIG. 3C is a graph depicting the concentration of siRNA in the straitum (caudate) of the indicated non-human primates (see FIG. 2) at 45 days post intrathecal administration of a single 60 mg dose of duplex.
Figure 3D:
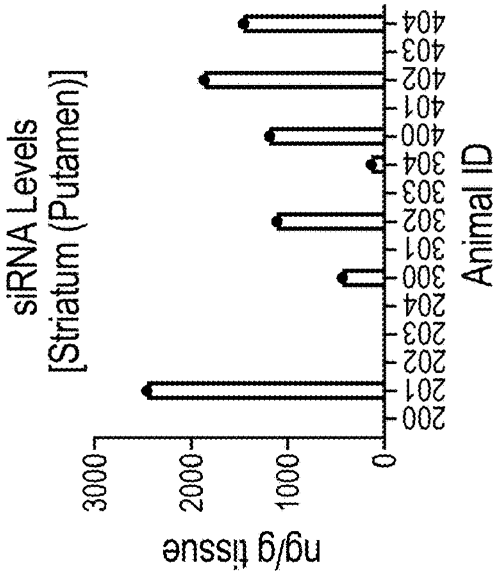
FIG. 3D is a graph depicting the concentration of siRNA in the striatum (putamen) of the indicated non-human primates (see FIG. 2) at 45 days post intrathecal administration of a single 60 mg dose of duplex.
Figure 3E:
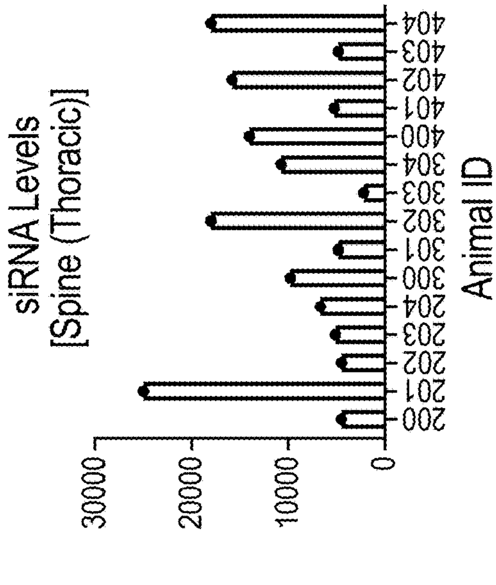
FIG. 3E is a graph depicting the concentration of siRNA in the thoracic spine of the indicated non-human primates (see FIG. 2) at 45 days post intrathecal administration of a single 60 mg dose of duplex.
Figure 4A:
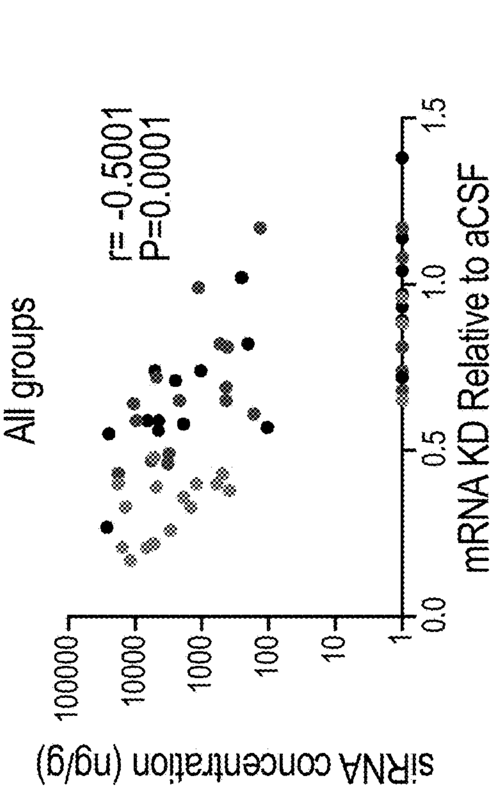
FIG. 4A is a graph depicting the correlation of siRNA concentration in brain and spinal tissues to the level of knock down of HTT in non-human primates intrathecaly administered a single 60 mg dose of all duplexes tested.
Figure 4B:
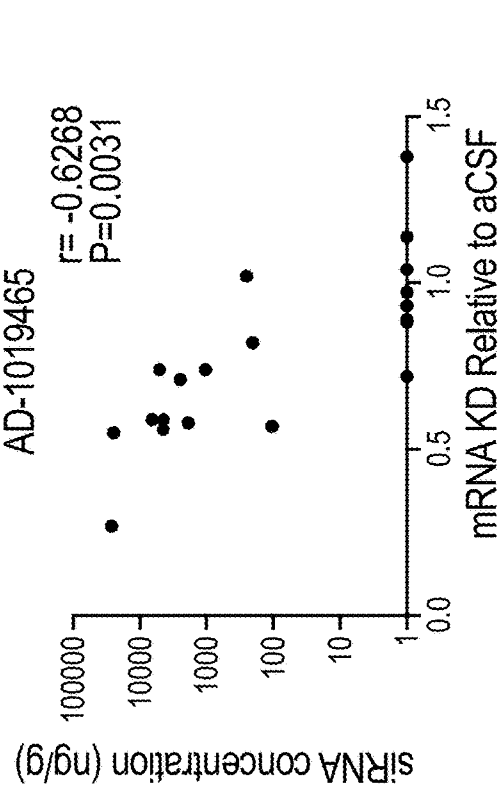
FIG. 4B is a graph depicting the correlation of siRNA concentration in brain and spinal tissues to the level of knock down of HTT in non-human primates intrathecaly administered a single 60 mg dose of duplex AD-1019465.
Figure 4C:
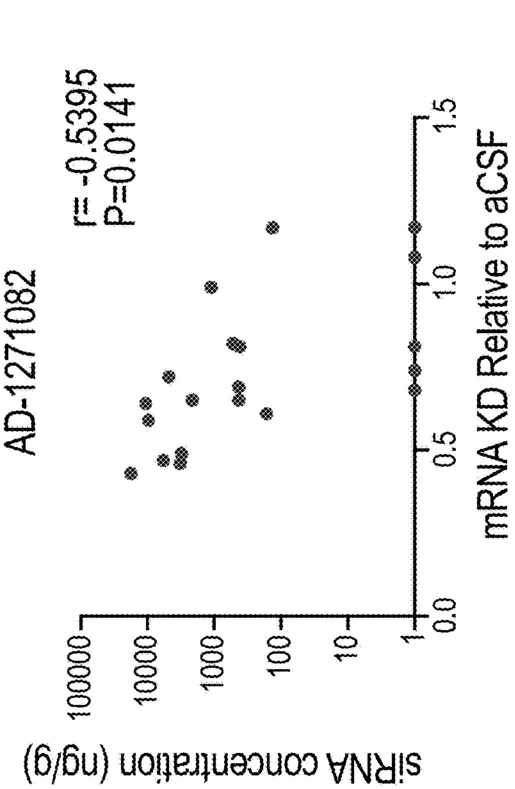
FIG. 4C is a graph depicting the correlation of siRNA concentration in brain and spinal tissues to the level of knock down of HTT in non-human primates intrathecaly administered a single 60 mg dose of duplex AD-1271082.
Figure 4D:
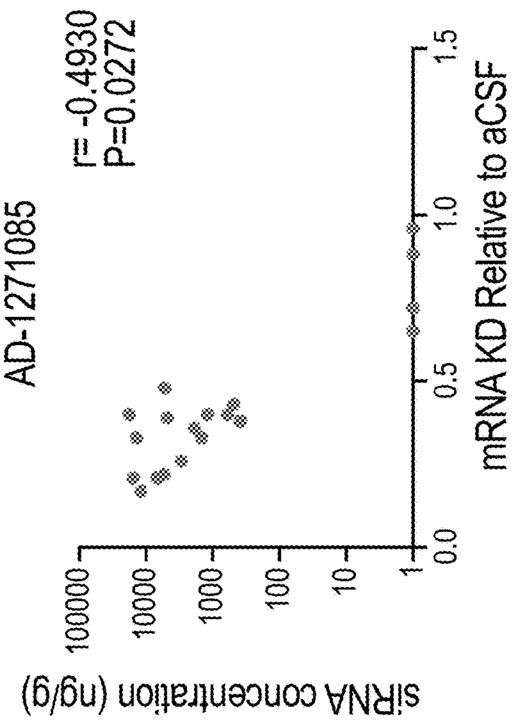
FIG. 4D is a graph depicting the correlation of siRNA concentration in brain and spinal tissues to the level of knock down of HTT in non-human primates intrathecaly administered a single 60 mg dose of duplex AD-1271085.

FIGS. 3A-3E demonstrate that, in addition to CSF from the cisterna *magna* (FIG. 3A), siRNA can be detected in regions throughout the brain following intrathecal administration. In particular, the highest concentration of siRNA was detected in thoracic spine samples from all animals following intrathecal administration of the duplexes, in a range of 2154-25030 ng/g (FIG. 3E). The next highest concentration of siRNA was detected in prefrontal cortex samples, in a range of 104-26681 ng/g, with 2 of the samples having siRNA concentrations less than the lower limit of quantification (LLOQ) (FIG. 3B). The concentration of siRNA in the caudate was in the range of 204-2953 ng/g, with 7 of the samples having siRNA levels LLOQ (FIG. 3C) and, finally, in the putamen, the range of concentration of siRNA was 134-2463 ng/g, with 8 of the samples having siRNA concentrations LLOQ (FIG. 3D).

Figure 5A:
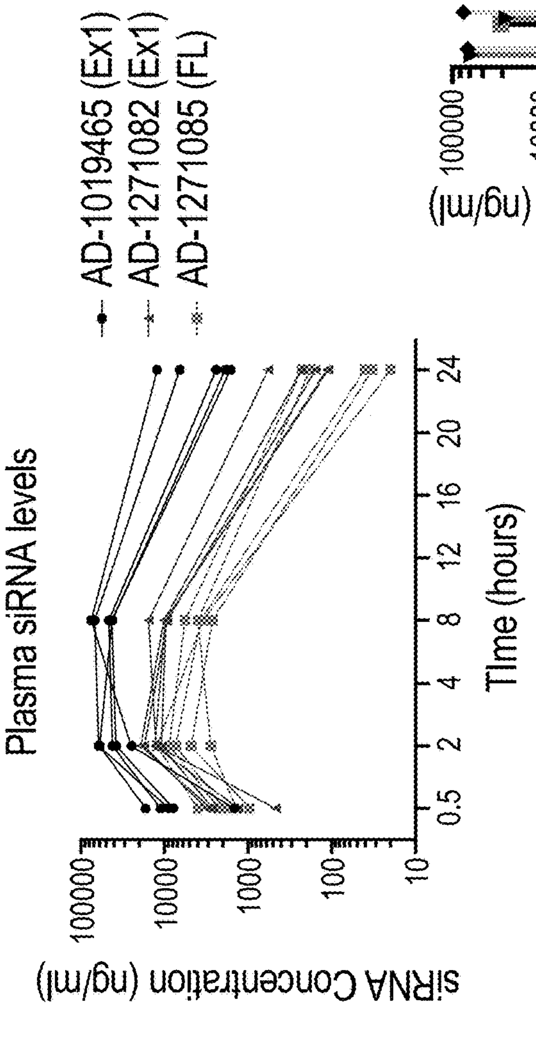
FIG. 5A is a graph depicting the concentration of siRNA in plasma samples over time following a single intrathecal 60 mg dose of duplex.
Figure 5B:
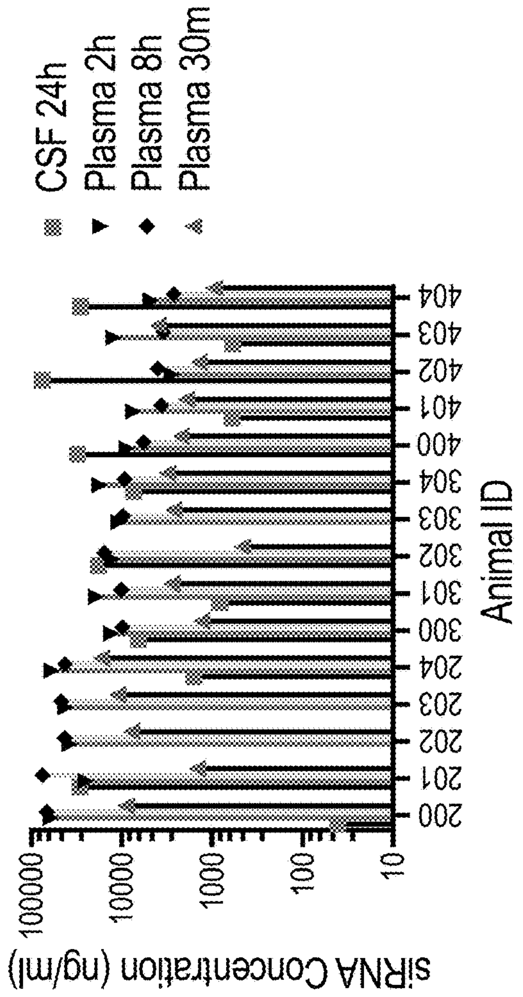
FIG. 5B is a graph depicting the concentration of siRNA in CSF and plasma at the indicated times following a single intrathecal administration of 60 mg of all tested duplexes (see FIG. 2).

In addition, and as demonstrated in FIGS. 4A-4D, tissue siRNA levels correlated with HTT transcript knockdown for all of the duplexes tested. Furthermore, as demonstrated in FIG. 5A, in addition to affecting brain and spinal tissues, intrathecal administration of duplexes resulted in increased levels of siRNA in plasma samples from non-human primates administered a single 60 mg dose of duplex. In addition, as demonstrated in FIG. 5B, low CSF levels correlated with higher plasma levels as soon as at 30 minutes post-intrathecal dosing and vice versa. These data demonstrate that it may be possible, as soon as 30 minutes post-intrathecal dosing, to collect plasma samples in order to determine the quality of IT administration as an alternative to 24 hour CSF testing.

Example 3. In Vivo Assessment of RNAi Agents Targeting Full-Length HTT

Duplexes of interest targeting full-length human HTT (AD-1271085, AD-1271084, and AD-1271083) or an antisense oligonucleotide agent, Tominersen, were evaluated in an art-recognized mouse model of Huntington disease (HD), the YAC128 mouse model of HD. YAC128 mice harbor a yeast artificial chromosome (YAC) containing the entire human HD gene containing 128 CAG repeats in their genomes. YAC128 mice develop motor abnormalities and age-dependent brain atrophy including cortical and striatal atrophy associated with striatalneuronal loss. YAC128 mice exhibit initial hyperactivity, followed by the onset of a motor deficit and finally hypokinesis (see, e.g., Slow, et al. (2003) *Human Molecular Genetics* 12(13):1555; Van Raamsdonk, et al. (2005), *Human Molecular Genetics* 14(24):3823; and Carroll, et al. (2011) *Neurobiology of Disease* 43:257-265).

At Day 0, YAC128 mice (7-13 weeks of age, 27.7±3.4 grams, n=36) were administered a single 300 μg/kg dose of the agents of interest or artificial CSF (aCSF) control by intracerebroventricular injection (ICV). At day 14 post-dose, animals were sacrificed, frontal cortex samples were collected and snap-frozen in liquid nitrogen, and mRNA was extracted and analyzed by the RT-QPCR method.

Figure 6A:
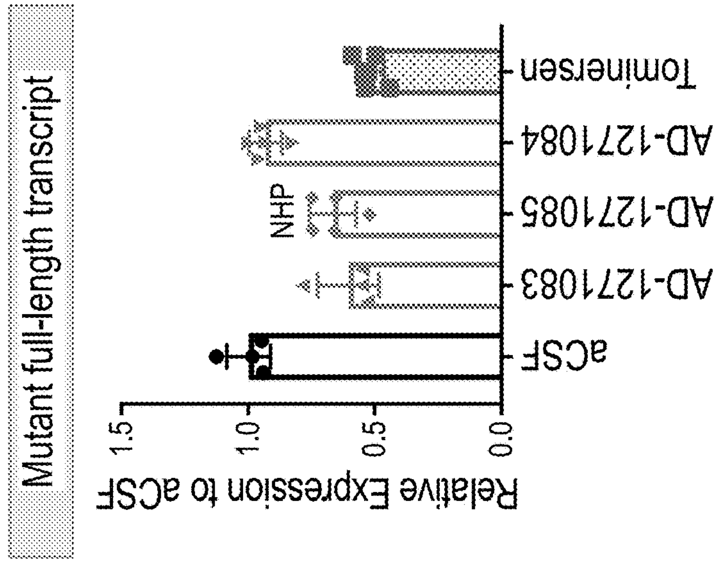

The effect of these agents on full-length mutant human HTT mRNA is shown in FIG. 6A. These data demonstrate that the exemplary duplexes tested effectively reduce the level of the mutant human HTT messenger RNA in vivo.

Human full-length mutant HTT protein levels were determined using Western Blot analysis.

Briefly, frontal cortex samples were homogenized in RIPA buffer along with protease inhibitors. Total protein was quantified using Pierce BCA kit following the manufacturer's instructions. Eighty g of total cell lysates were denatured by boiling in 4×LDS buffer and were subjected to SDS-PAGE in a 3-8% tris acetate gradient gel and transferred to PVDF membranes. The blots were blocked with Odyssey blocking buffer for 1 hour at room temperature and hybridized to specific antibodies overnight at 4° C. The following antibodies were used: HTT (Millipore, Catalog #MAB2166), Calnexin (Millipore-Sigma, catalog #C4731, Fluorescence conjugated secondary antibodies (Licor, Goat anti-rabbit, Catalog #926-32211 and Donkey anti-mouse, Catalog #926-680721:5000). Detection of protein bands was carried out using the Biorad Chemidoc MP Imaging system. The density of each HTT band was normalized to Calnexin loading control and the normalized intensities were used to quantify HTT knockdown in siRNA treated samples relative to vehicle (1×PBS) treated controls.

The effect of these agents on mutant human HTT protein levels is shown in FIG. 6B. These data demonstrate that the exemplary duplex agents tested effectively reduce the level of the full-length mutant human HTT messenger RNA in vivo.

Example 4. In Vivo Assessment of RNAi Agents Targeting Full-Length HTT or Exon 1 HTT Duplexes of interest targeting full-length human HTT (AD-1271085) or exon 1 of human HTT (AD-1271082 or AD-1019465) were evaluated in an art-recognized mouse model of Huntington disease (HD), the Q175DN heterozygous mouse model of HD (see, e.g., Menalled, et al. (2012) *PLoS One* 7(12): e49838. doi: 10.1371/journal.pone.0049838). In Q175DN mice, mouse HTT exon 1 is replaced by a knock-in of human exon 1 HTT sequence having approximately 180-220 CAG tract repeats. This mouse model of HD exhibits motor, cognitive, molecular, and electrophysiological abnormalities, including in vivo decrease in several striatal markers and HD hallmarks similarly to patients with HD. For example, homozygous mice display motor and grip strength abnormalities with an early onset (8 and 4 weeks of age, respectively), which were followed by deficits in rotarod and climbing activity at 30 weeks of age and by cognitive deficits at around 1 year of age. There are also clear behavioral deficits in heterozygous mice from around 4.5 months of age, especially in the dark phase of the diurnal cycle. Decreased body weight is observed in both heterozygotes and homozygotes, along with significantly reduced survival in the homozygotes. In addition, there is an early and significant decrease of striatal gene markers from 12 weeks of age.

At Day 0, approximately five-week old heterozygous Q175DN mice (also referred to as Q175 KI mice) (mixed sex) were administered a single 300 μg dose of the agents of interest, artificial CSF (aCSF) control, or a non-HTT targeting dsRNA agent (control) by intracerebroventricular injection (ICV). Wild-type mice were also included in the study group to control for the baseline Htt transcript expression. The study design is summarized in the Table below.

| Group ID | Treatment | Test article, ICV | Genotype | Group Size (n) | Target |
|---|---|---|---|---|---|
| 1 | Si-control | aCSF | Q175 KI | n = 5 | Control |
| 2 | Si1 | AD-1271085 | Q175 KI | n = 5 | HTT-FL |
| 3 | Si2 | AD-1271082 | Q175 KI | n = 5 | HTT-Ex1 |
| 4 | Si3 | AD-1019465 | Q175 KI | n = 6 | HTT-Ex1 |
| 5 | Si4 | AD-1025211 | Q175 KI | n = 3 | SNCA (non targeting control) |
| 6 | none | none | WT | n = 3 | Control |

At 4 weeks post-injection, the mice were subjected to sample collection of brain and spinal cord. One spinal cord sample (lumbar region) and one striatum sample from each mouse were used for QuantiGene analysis of Htt variant RNA levels. Three non-treated WT mice were used as reference controls for the QuantiGene analyses. One further sample of spinal cord sample (lumbar region) and one striatum sample from each mouse were used for Meso Scale Discovery (MSD) analysis to determine Htt wild-type and mutant protein levels The QuantiGene panel for Htt transcript assessment is provided in the Table below. Expression levels of Atp5b, Eif4a2, and Gapdh served as reference gene controls. A schematic of the portion of the Htt transcript assessed by each assay of the QuantiGene panel is depicted in FIG. 7.

| Target symbol | Name | GenBank Accession |
|---|---|---|
| Htt-11-pA1 | Htt (mouse endogenous), intron 1 with the polyA-site 1 (the 680 bp variant) | |
| Htt-11-pA2 | Htt (mouse endogenous), intron 1 with the polyA-site 2 (the 1145 bp variant) | |
| Htt-11-3' | Htt (mouse endogenous), intron 1 at its 3' end | |
| Htt-13 | Htt (mouse endogenous), intron 3 | |
| Htt-FL-(Exons_50-53) | Huntingtin, full-length (total) | NM_010414 |
| Atp5b | ATP synthase, H+ transporting mitochondrial F1 complex, beta subunit | NM_016774 |
| Eif4a2 | Eukaryotic translation initiation factor 4A2 | NM_013506 |
| Gapdh | Glyceraldehyde-3-phosphate dehydrogenase | NM_001289726 |

The statistical comparisons performed in this study were (1) Treatment groups 2-5 vs. Si-Control treated Q175 KI mice (ANOVA with Dunnett's multiple comparisons test); and (2) Treatment group 1 (Si-Control) vs. group 6 (the WT untreated mice): unpaired t-test. This comparison served as a control for the model (genotype) effect to verify that the Htt intronic transcripts (Htt-J1-pA1 and Htt-I1-pA2) increase in the Q175 animals as expected (at the given age).

FIGS. 8A-8E depict the results of the QuantiGene analysis.

As depicted in FIGS. 8A and 8B, administration of all of the agents AD-1271085, AD-1271082, or AD-1019465 inhibits the expression of endogenous mouse Htt intron 1 with the polyA-site 1 (the 680 bp variant) and endogenous mouse Htt intron 1 with the polyA-site 2 (the 1145 bp variant) in the striatum and spinal cord. As compared to aCSF control, intracerebroventricular injection of AD-1271082 (targeting Exon 1 of human HTT) inhibits endogenous mouse Htt intron 1 with the polyA-site 1 (the 680 bp variant) expression in the striatum by about 30% and endogenous mouse Htt intron 1 with the polyA-site 2 (the 1145 bp variant) expression in the striatum by about 18%. FIG. 8C, similarly demonstrates that administration of all of the agents inhibits the expression of full-length Htt in the spinal cord and striatum. As compared to control aCSF, administration of AD-1271085 inhibited full-length Htt expression by about 52% in the striatum, administration of AD-1271082 inhibited full-length Htt expression by about 39% in the striatum, and administration of AD-1019465 inhibited full-length Htt expression by about 18% in the striatum. In addition, and as expected, none of the agents inhibited Htt expression using assays on downstream introns (see FIGS. 8D and 8E).

The results of the MSD analysis to detect mutant HTT protein are depicted in FIG. 8F and the results of the MSD analysis to detect wild-type HTT exon 1 protein are depicted in FIG. 8G.

As depicted in FIGS. 8F and 8G, all duplexes tested showed some level of Htt protein knockdown as expected based their varying potency effect on transcript and targeting specificity. In particular, a knockdown of the wildtype Htt protein is only observed with AD-1271085 as this duplex only targets the mouse wildtype gene (FIG. 8G). AD-1019465 and AD-102521 both only target human HTT exon 1 and it appears that they had no effect on the full-length mouse protein (FIG. 8G). However, a carful review of the data, in particular, for groups 3 and 4 in FIG. 8G shows that there is one outlier that is skewing the average and, thus, there is protein KD (reflected by the transcript KD in FIG. 8C). Furthermore, as depicted in FIG. 8F, both AD-1019465 and AD-102521 potently knockdown mutant Htt in the spinal cord and striatum.

These data further demonstrate that the exemplary duplex agents tested, effectively reduce the level of Htt messenger RNA and Htt protein in vivo.

Example 5. HTT Protein Knockdown in Vivo Using RNAi Agents Targeting Full-Length HTT or Exon 1 HTT The ability of duplexes of interest targeting full-length human HTT (AD-1271085) or exon 1 of human HTT (AD-1271082 or AD-1019465) to knockdown wild-type HTT protein in various neural tissues of non-human primates was assessed. Specifically, male non-human primates, 3-4 kg in weight, were, intrathecally administered a single 60 mg dose in a volume of 2 mls of AD-1019465 (n=5), AD-1271082 (n=5), or AD-1271085 (n=5) over approximately 3 minutes by manual bolus followed by a 0.3 mL flush of artificial CSF (aCSF), or artificial aCSF (n=5) on Day 1. At Day 45 post-dose, animals were sacrificed, perfused with saline and tissues were collected. The tissues were flash frozen for Meso Scale Discovery (MSD) analysis. The collected tissues included prefrontal cortex, hippocampus, striatum caudate, lumbar spine, and thoracic spine.

As depicted in FIG. 9, following the suppression of the HTT transcript, HTT protein was also reduced to varying levels likely reflecting the varying potency of the siRNA duplexes tested. Maximal inhibition was observed in the prefrontal cortex and hippocampal tissues in animals administered AD-1271085.

These data further demonstrate that the exemplary duplex agents tested effectively reduce the level of HTT protein in vivo.

In another study to assess the ability of a single intrathecally administered 60 mg dose of AD-1271085 to knockdown wild-type HTT protein in various neural tissues of non-human primates over a 168 Day period, starting at Day 49 post-dose, three of 15 animals administered the duplex had late-onset 'adverse' clinical signs (prolonged tremors, seizures, loss of coordination, and decreased activity) that were not observed in previous studies. The animals were euthanized and the study halted. It was noted subsequently that dose reduction mediated an apparent adverse effect seen in this study. See, for example, Example 10, below.

Example 6. Structure-Activity Analyses of Duplexes Targeting Human HTT Exon 1

A structure-activity analysis of duplexes targeting human HTT exon 1 was performed and the efficacy of these agents was assessed in YAC128 mice.

A detailed list of the unmodified HTT sense and antisense strand nucleotide sequences designed and synthesized based on this analysis are shown in Table 4. A detailed list of the modified HTT sense and antisense strand nucleotide sequences designed and synthesized based on this analysis is shown in Table 5.

At Day 0 and at Day 14, YAC128 mice (7-13 weeks of age, 27.7±3.4 grams, n=36) were administered a 300 μg/kg dose of AD-1019476, a 600 μg/kg dose of AD-1019476, a 300 μg/kg dose of AD-1443080, a 600 μg/kg dose of AD-1443080, a 600 μg/kg dose of AD-1443079, a 300 μg/kg dose of A-1800326 (the antisense oligonucleotide, Tominersen), or artificial CSF (aCSF) control by intracerebroventricular injection (ICV).

At day 28 post-dose, animals were sacrificed, and whole hemisphere samples were collected and snap-frozen in liquid nitrogen. mRNA and protein was extracted from the samples and analyzed by the RT-QPCR method or Western blot method as described above.

The effect of these agents on mutant full-length human HTT mRNA is shown in FIG. 10A and the effect of these agents on wild-type full-length mouse HTT mRNA is shown in FIG. 10B and shows that the agents do not knockdown the human mutant transcript. However, as depicted in FIGS. 10C and 10D, using the antibody MAB2166 (Millipore, Catalog #MAB2166; binds to a 15-aa region spanning from amino acids 445 to 459 of the human HTT protein) for all agents and doses tested, both wild-type full-length mouse and mutant full-length human HTT protein is almost undetectable demonstrating remarkable efficacy of the agents on lowering protein levels.

To confirm the effect of the agents on the level of wild-type full-length mouse HTT protein and mutant full-length human HTT protein, Western blot analysis was repeated using a second antibody D7F7 (Cell Signaling Technology) and, as depicted in FIGS. 10E and 10F, the agents and doses tested demonstrated again remarkable efficacy in lowering wild-type full-length mouse HTT protein and mutant full-length human HTT protein.

Example 7. Dose Response Analyses of Duplexes Targeting Human HTT Exon 1

A dose response analysis was performed to identify the best dose of the agents to differentiate the potency of the agents.

At Day 0, YAC128 mice (male and female, 6 weeks of age, n=3, except for the 300 μg dose where n=2) were administered a single 37.5 μg, 75 μg, 150 μg or 300 μg dose of AD-1019476, or artificial CSF (aCSF) control by intracerebroventricular injection (ICV). At day 14 post-dose, animals were sacrificed, both hemispheres of the nrain were collected and snap-frozen in liquid nitrogen. Protein was extracted and analyzed by Western blot using the antibodies, MAB2166 or D7F7.

The results of this analysis are provided in FIGS. 11A and 11B and demonstrate that a single 75 μg dose of AD-1019476 provides the maximum knockdown efficacy.

Example 8. In Vivo Assessment of RNAi Agents Targeting Full-Length HTT or Exon 1 HTT Duplexes of interest targeting full-length human HTT (AD-1271085) or exon 1 of human HTT (AD-1498524 or AD-1019448) were evaluated in the Q175DN heterozygous mouse model of HD. Q175DN mice carry a knock-in of human exon 1 HTT sequence having approximately 180-220 CAG tract repeats which replaces mouse HTT exon 1.

At Day 0, approximately 9-month old heterozygous Q175DN mice (also referred to as Q175 HET mice) (mixed sex) were administered a single 300 μg dose of the agents of interest, or artificial CSF (aCSF) control, by intracerebroventricular injection (ICV). Wild-type mice were also included in the study group to control for baseline Htt transcript expression. The study design is summarized in the Table below.

| Group ID | Treatment | Test article, ICV | Genotype | Group Size (n) for 10 mo | Group Size (n) for 12 mo | Target |
|---|---|---|---|---|---|---|
| 1 | Si-control | aCSF | Q175 WT | n = 3 | n = 4 | Control |
| 2 | Si-control | aCSF | Q175 HET | n = 6 | n = 5 | Control |
| 3 | Si1 | AD-1271085 | Q175 HET | n = 4 | n = 10 | HTT-FL |
| 4 | Si2 | AD-1498524 | Q175 HET | n = 5 | n = 10 | HTT-Ex1 |
| 5 | Si3 | AD-1019448 | Q175 HET | n = 5 | | HTT-Ex1 |

At 1 month or 3 months post-dose (mice 10- or 12-months of age, respectively), the mice were subjected to tissue collection, which included spinal cord and striatum tissue samples. One spinal cord sample and one striatum sample from each mouse were used for QuantiGene analysis of Htt variant RNA levels. The Si-control-treated WT mice were used as reference controls for the QuantiGene analyses.

The QuantiGene panel for Htt transcript assessment is provided in the Table below. Expression levels of Atp5b, Eif4a2, and Gapdh served as reference gene controls. A schematic of the portion of the Htt transcript assessed by each assay of the QuantiGene panel is depicted in FIG. 7.

| Target symbol | Name | GenBank Accession |
|---|---|---|
| Htt-11-pA1 | Htt (mouse endogenous), intron 1 with the polyA-site 1 (the 680 bp variant) | |
| Htt-11-pA2 | Htt (mouse endogenous), intron 1 with the polyA-site 2 (the 1145 bp variant) | |
| Htt-11-3' | Htt (mouse endogenous), intron 1 at its 3' end | |
| Htt-13 | Htt (mouse endogenous), intron 3 | |
| Htt-FL-(Exons_50-53) | Huntingtin, full-length (total) | NM_010414 |
| Atp5b | ATP synthase, H+ transporting mitochondrial F1 complex, beta subunit | NM_016774 |
| Eif4a2 | Eukaryotic translation initiation factor 4A2 | NM_013506 |
| Gapdh | Glyceraldehyde-3-phosphate dehydrogenase | NM_001289726 |

FIGS. 12A-12J depict the results of the QuantiGene analysis.

As shown in FIGS. 12A, 12B, 12F and 12G, significantly higher expression of intronic sequence containing HTT (using the Htt-I1-pA1 and Htt-I1-pA2) was observed in the Si-Control-treated Q175 HET mice as compared to the Si-Control-treated WT mice, confirming the presence of mutant HTT fragment generated by the expanded CAG repeat insert in the heterozygote animals. This effect was seen in both spinal cord and striatum tissues, and at both endpoints (10 months and 12 months of age). Conversely, expression of the full length Htt (using Htt-FL-(Exons 50-53)) was higher in the Si-Control-treated WT mice in both tissues and at both endpoints (FIGS. 12E and 12J).

The tested agents demonstrated variable tendencies towards decreasing both the expression of transcripts detected by the intronic/splice variant (the Htt-I1-pA1 and Htt-I1-pA2) probes as well as the expression of full-length HTT transcripts, in particular, administration of AD-1498524 resulted in a pronounced effect in the 12 month old (3 month post-dose) cohort.

All of the agents demonstrated a decreasing effect on the expression of the full-length HTT transcript (Htt-FL-(Exons_50-53) relative to the Si-Control-treated Q175 HET in both tissues and both age cohorts. This resulted in even further lowering of the full-length form as compared to the WT animals.

The statistically significant effects observed in some comparisons for Htt-I1-3' (representing incompletely spliced intron 1 sequences that have not terminated at the cryptic poly(A) signals) may indicate some effects of the agents. However, the net fluorescence and normalized expression levels (as compared to the other targets) of Htt-I1-3' are overall low, suggesting that the low levels of this target may not be very biological significant.

Additional tissue samples (54 right cortex tissue samples and 54 cervical spinal cord tissue samples) that were collected from Q175DN mice administered a single 300 μg dose of the duplexes of interest targeting full-length human HTT (AD-1271085) or exon 1 of human HTT (AD-1498524 or AD-1019448), or artificial CSF (aCSF) control, by intracerebroventricular injection (ICV) at 1 month and 3 months post-injection were subjected to Meso Scale Discovery (MSD) analysis to determine mutant, wild type and total HTT protein levels.

All cortex and spinal cord tissue samples were homogenized according to standard procedures. Cortex samples were homogenized in 300 μl MSD lysis buffer 1 in 2-mL Lysing matrix D tubes from MP biomedicals (Cat #6913). Spinal cord samples were homogenized in 250 μl MSD lysis buffer 1 in 2-mL Lysing matrix Z tubes from MP biomedicals (cat #6961). Tissue was transferred to tissue homogenizing tubes containing MSD lysis buffer 1. Tissue was homogenized in three rounds of 30 seconds, at 6 m/s (cortex) or 6.5 m/s (spinal cord), using the FastPrep-24 High-speed benchtop homogenizer. Tubes were centrifuged for 20 minutes at 20,800 g at 4° C. Supernatant was transferred to 1.5-mL Eppendorf tubes and centrifuged again for 20 minutes at 20,800 g at 4° C. Lysates were aliquoted and stored at −80° C. for subsequent protein determination and MSD analysis.

BCA analysis was performed to determine total protein concentration of all samples. BCA results from each individual sample were used after MSD analysis, during data analysis, to correct for the actual amount of protein loaded.

The MSD assay for mutant HTT and total HTT determination is provided in the Table below. All cortex and spinal cord samples were loaded onto coated/blocked MSD plates and tested in inter-plate technical replicates. After sequential incubations with detection antibodies and streptavidin-SulfoTag (MSD), plates were read on an MSD S600 imager. MSD software was used to calculate HTT concentrations from the standard curves. Loaded protein concentrations were used to back-calculate to fmol/mg total HTT protein

| MSD Assay | Antibody concentration (capture/ detection; μg/mL) | Protein loaded (μg/well) Cortex | Spinal cord | Standard reference protein | Standard reference concentration range (5-fold serial) |
|---|---|---|---|---|---|
| Human HTT with expanded polyQ track (mutant HTT (mHTT)) | 1.5/0.625 | 2 | 1 | HTT-Q73 (1-3144) | 0.05-4000 pM |
| Total (expanded and WT) mouse HTT | 8.0/0.4 | 10 | 10 | HTT-Q7 (1-3120) | 0.05-4000 pM |

The results of the MSD analysis detecting mutant HTT and total HTT protein in the cortex samples are depicted in FIG. 12K and the results of the MSD analysis to detect mutant HTT and total HTT protein in the spinal cord sample are depicted in FIG. 12L.

As depicted in FIG. 12K, mutant HTT levels were significantly lowered in Q175 HET mice treated with the agents (AD-1271085, AD-1498524, or AD-1019448) as compared to the Q175 HET Si-Control group. As expected, mutant HTT was not detectable in any of the WT samples. Similarly, total mouse HTT levels were significantly lowered in Q175 HET mice treated with the agents (AD-1271085, AD-1498524, or AD-1019448) as compared to the Q175 Het Si-Control group. The total mouse HTT levels of the WT group was approximately double that of the Q175 Het group as expected. No statistical differences between the 10- and 12-month end points in mutant HTT or total mouse HTT levels were observed (two-tailed unpaired t-test), except for mutant HTT (**) and total mouse HTT (*) levels of Q175 Het Si-Ctrl groups.

Similar results were shown in the spinal cord tissue. As depicted in FIG. 12L, mutant HTT levels were significantly lowered in Q175 HET mice treated with the agents (AD-1271085, AD-1498524, or AD-1019448) as compared to the Q175 Het Si-Control group. As expected, mutant HTT was not detectable in any of the WT samples. Total mouse HTT levels were significantly lowered in Q175 HET mice treated with the agents ((AD-1271085, AD-1498524, or AD-1019448) as compared to the Q175 Het Si-Control group. The total mouse HTT levels of the WT group was approximately double that of the Q175 Het group. No statistical differences between the 10- and 12-month end points in mutant HTT or total mouse HTT levels were observed (two-tailed unpaired t-test), except for mHTT (****) levels of Q175 Het AD-1498524 groups.

Thus, all duplexes tested showed a significant reduction in mutant HTT and total mouse HTT protein levels as compared to the Si-Control group. In particular, the strongest inhibition of both mutant HTT and total HTT protein levels was observed following administration of AD-1271085 or AD-1498524, followed by AD-1019448.

In conclusion, these data further demonstrate that the exemplary duplex agents tested effectively reduce the level of mutant HTT messenger RNA and mutant HTT protein in vivo.

Example 9. HTT Protein Knockdown In Vivo Using RNAi Agents Targeting Full-Length HTT The ability of duplexes of interest targeting full-length human HTT (AD-1271085) administered to non-human primates at a low dose (e.g., 3 mg and 10 mg) to knockdown wild-type HTT transcript and protein in various neural tissues was assessed.

Specifically, female non-human primates were intrathecally administered a single 3 mg dose or a single 10 mg dose in a volume of 2 mls of AD-1271085 (n=8) over approximately 3 minutes by manual bolus followed by a 0.3 mL flush of artificial CSF (aCSF), or artificial aCSF (n=3) on Day 1. At Day 33 post-dose, animals were sacrificed, perfused with saline and tissues were collected. The tissues were flash frozen for Meso Scale Discovery (MSD) analysis. The collected tissues included prefrontal cortex, hippocampus, striatum putamen, striatum caudate, and spine L1-L3 (lumbar spine). The experimental design is provided in Table below:

| Group No. | Test Material | Dose Level (mg/dose) | Dose Volume (mL/dose) | Dose Concentration (mg/mL) | No. of main study females |
|---|---|---|---|---|---|
| 1 | aCSF | 0 | 2 | 0 | 3 |
| 2 | AD-1271085 | 3 | 2 | 1.5 | 8 |
| 3 | AD-1271085 | 10 | 2 | 5 | 8 |

As depicted in FIG. 13A, administration of a 3 mg dose of AD-1271085 resulted in about 55% reduction in HTT transcript levels in the prefrontal cortex and hippocampus. Administration of a 10 mg dose of AD-1271085 resulted in about 70% reduction in HTT transcript levels in the prefrontal cortex and hippocampus, and about 20% decrease in striatum caudate. The HTT transcript levels in the prefrontal cortex, hippocampus, striatum putamen and striatum caudate samples for each animal, at each dose is shown in FIG. 13B.

Following the suppression of the HTT transcript, HTT protein was also reduced (FIG. 13C). About 65% inhibition was observed in the prefrontal cortex and hippocampus and about 40-50% inhibition was observed in striatum caudate in animals administered 3 mg dose of AD-1271085. Administration of a 10 mg dose of AD-1271085 resulted in about 80% reduction in HTT protein levels in the prefrontal cortex and hippocampus, and about 50-60% loss in striatum caudate. The HTT protein levels in the prefrontal cortex, hippocampus, striatum putamen and striatum caudate samples for each animal at each dose is shown in FIG. 13D.

FIG. 13E depicts the correlation of effect of AD-1271085 on HTT transcript and protein lowering in prefrontal cortex, hippocampus, striatum caudate, striatum putamen, lumbar spine tissue samples.

In addition, histopathological analysis of H&E; and IBA-1 stained cortex or hippocampus sections from the examined brains and spinal cords at Day 33 terminal sacrifice demonstrated that there was no microscopic evidence of AD-1271085-related necrosis of neuronal/glial cells following administration of either the 3 mg/kg or 10 mg/dose.

These data further demonstrate that the exemplary duplex agent, AD-1271085, effectively reduced the level of HTT transcript and protein in vivo, even at a lower dose of 3 mg and 10 mg.

Example 10. HTT Protein Knockdown In Vivo of RNAi Agents Targeting Exon 1 of HTT The ability of selected duplexes of interest targeting exon 1 of human HTT (AD-1498524, AD-1498526 and AD-1498528) to knockdown wild-type HTT transcript and protein in various neural tissues of non-human primates was assessed. Specifically, female non-human primates were intrathecally administered a single 60 mg dose in a volume of 2 mls of the agents (n=5) over approximately 3 minutes by manual bolus followed by a 0.3 mL flush of artificial CSF (aCSF), or artificial aCSF (n=3) on Day 1. At Day 59 post-dose, animals were sacrificed, perfused with saline and tissues were collected. The collected tissues included prefrontal cortex, hippocampus, striatum putamen, striatum caudate, and lumbar spine. The transcript levels were determined by RT-PCR analysis, and the protein levels were quantified by liquid chromatography mass spectrometry (LC/MS).

The experimental design is provided in Table below:

| Group No. | Test Material | Dose Level (mg/dose) | Dose Volume (mL/dose) | Dose Concentration (mg/mL) | No. of main study females |
|---|---|---|---|---|---|
| 1 | aCSF | 0 | 2 | 0 | 5 |
| 2 | AD-1498524 | 60 | 2 | 30 | 5 |
| 3 | AD-1498526 | 60 | 2 | 30 | 5 |
| 4 | AD-1498526 | 60 | 2 | 30 | 5 |

As depicted in FIG. 14A, HTT protein was reduced following administration of the agents tested. A significant inhibition was observed in animals administered AD-1498524, especially in the prefrontal cortex and striatum caudate tissues. Similar inhibitory effects were observed on the transcript level for all agents tested, and animals administered AD-1498524 displayed the most significant lowering of HTT transcript levels across all tissue samples (FIG. 14B). The HTT mRNA levels in each tissue sample are also depicted in FIG. 14C. FIG. 14D shows the correlation of effect of inhibition on HTT transcript and protein levels in the tissue samples.

These data further demonstrate that the exemplary duplex agents tested effectively reduce the level of HTT messenger RNA and HTT protein in vivo.

TABLE 4

Unmodified Sense and Antisense Strand Sequences of HTT Exon 1 dsRNA Agents

| Duplex Name | Sense Sequence 5' to 3' | SEQ ID NO: | Range in NM_00 2111.8 | Antisense Sequence 5' to 3' | SEQ ID NO: | Range in NM_00 2111.8 |
|---|---|---|---|---|---|---|
| AD-1498532 | CUUCGAGUCC CUCAAGUCA | 35 | 175-193 | UGACUGAGG GACUCGAAGG C | 47 | 173-193 |
| AD-1019465 | CCAUGGCGAC CCUGGAAAAG A | 28 | 144-164 | UCUUUUCCAG GGUCGCCAUG GCG | 32 | 142-164 |
| AD-1498529 | ACCCUGGAAA AGCUGAUGAA A | 36 | 152-172 | UUUCAUCAGC UUUUCCAGGG UCG | 48 | 150-172 |
| AD-1498531 | CCUGGAAAAG CUGAUGAAA | 37 | 154-172 | UUUCAUCAGC UUUUCCAGGG U | 49 | 152-172 |
| AD-1019476 | CUGAUGAAGG CCUUCGAGUC A | 38 | 164-184 | UGACUCGAAG GCCUUCAUCA GCU | 50 | 162-184 |
| AD-1443079 | CUGAAGAAGG CCUUCGAGUC A | 39 | 164-184 | UGACTCGAAG GCCUUCUUCA GCU | 51 | 162-184 |
| AD-1443080 | GCGACCCUGG AAAAGCUGAU A | 40 | 149-169 | UAUCAGCUUU UCCAGGGUCG CCA | 52 | 147-169 |
| AD-1498521 | GCGACCCUGG AAAAGCUGAU A | 40 | 149-169 | UAUCAGCUUU UCCAGGGUCG CCG | 53 | 147-169 |
| AD-1498522 | UCCCUCAAGU CCUUCCAGCA A | 41 | 182-202 | UUGCUGGAAG GACUUGAGGG ACU | 54 | 180-202 |

TABLE 4-continued

| Unmodified Sense and Antisense Strand Sequences of HTT Exon 1 dsRNA Agents | | | | | | |
|---|---|---|---|---|---|---|
| Duplex Name | Sense Sequence 5' to 3' | SEQ ID NO: | Range in NM_002111.8 | Antisense Sequence 5' to 3' | SEQ ID NO: | Range in NM_002111.8 |
| AD-1498523 | UCCCACAAGUCCUUCCAGCAA | 42 | 182-202 | UUGCUGGAAGGACUUGUGGGACU | 55 | 180-202 |
| AD-1498524 | GCGACCCUGGAAAAGCUGAUA | 40 | 149-169 | UAUCAGCUUUUCCAGGGUCGCCG | 53 | 147-169 |
| AD-1498525 | UCAGGUUCUGCUUUUACCA | 43 | 33-51 | UGGUAAAAGCAGAACCUGAGC | 56 | 31-51 |
| AD-1498526 | CUUCGAGUCCCUCAAGUCCUA | 44 | 175-195 | UAGGACUUGAGGGACUCGAAGGC | 57 | 173-195 |
| AD-1498527 | GCCGCUCAGGUUCUGCUUUUA | 45 | 28-48 | UAAAAGCAGAACCUGAGCGGCCG | 58 | 26-48 |
| AD-1498528 | CCGGUCAGGUUCUGCUUUUAA | 46 | 29-49 | UUAAAAGCAGAACCUGACCGGCC | 59 | 27-49 |
| AD-1019448 | CCAGAGCCCCAUUCAUUGCCA | 97 | 57-77 | UGGCAAUGAAUGGGGCUCUGGGC | 98 | 55-77 |

TABLE 5

| Modified Sense and Antisense Strand Sequences of HTT Exon 1 dsRNA Agents | | | | | | |
|---|---|---|---|---|---|---|
| Duplex Name | Sense Sequence 5' to 3' | SEQ ID NO: | Antisense Sequence 5' to 3' | SEQ ID NO: | mRNA Target Sequence | SEQ ID NO: |
| AD-1498532 | csusu(Chd)GfaGfUfCfccucaaguscsa | 60 | VPusdGsacdTu(G2p)agggacUfcGfaagsgsc | 73 | GCCUUCGAGUCCCUCAAGUCC | |
| AD-1019465 | cscsaug(Ghd)CfgAfCfCfcuggaaaasgsa | 33 | VPusCfsuuuUfcCfAfggguCfgCfcauggscsg | 34 | CGCCAUGGCGACCCUGGAAAAGC | |
| AD-1498529 | ascsccu(Ghd)GfaAfAfAfgcugaugasasa | 61 | VPusUfsucau(C2p)agcuuuUfcCfaggguscsg | 74 | CGACCCUGGAAAAGCUGAUGAAG | |
| AD-1498531 | cscsuggaAfAfAfgcuga(Uhd)gasasa | 62 | VPusUfsucdAu(C2p)agcuuuUfcCfaggsgsu | 75 | ACCCUGGAAAAGCUGAUGAAG | |

TABLE 5-continued

| Modified Sense and Antisense Strand Sequences of HTT Exon 1 dsRNA Agents | | | | | | |
|---|---|---|---|---|---|---|
| Duplex Name | Sense Sequence 5' to 3' | SEQ ID NO: | Antisense Sequence 5' to 3' | SEQ ID NO: | mRNA Target Sequence | SEQ ID NO: |
| AD-1019476 | csusgau(Ghd)AfaGfGfCfcuucgaguscsa | 63 | VPusGfsacuCfgAfAfggccUfuCfaucagscsu | 76 | AGCUGAUGAAGGCCUUCGAGUCC | |
| AD-1443079 | csusga(Ahd)gAfaGfGfCfcuucgaguscsa | 64 | VPusdGsacdTc(G2p)aaggccUfuCfuucagscsu | 77 | AGCUGAUGAAGGCCUUCGAGUCC | |
| AD-1443080 | gscsgac(Chd)CfuGfGfAfaaagcugasusa | 65 | VPusAfsucag(C2p)uuuuccAfgGfgucgcscsa | 78 | UGGCGACCCUGGAAAAGCUGAUG | |
| AD-1498521 | gscsgac(Chd)CfudGgAfaaagcugasusa | 66 | VPusAfsucdAg(C2p)uuuudCcAfgdGgucgescsg | 79 | UGGCGACCCUGGAAAAGCUGAUG | |
| AD-1498522 | uscsccu(Chd) AfaGfUfCfcuuccagcsasa | 67 | VPusUfsgcug(G2p)aaggacUfuGfagggascsu | 80 | AGUCCCUCAAGUCCUUCCAGCAG | |
| AD-1498523 | uscscca(Chd)AfagUfCfcuuccagcsasa | 68 | VPusUfsgcdTg(G2p)aaggacUfudGugggascsu | 81 | AGUCCCUCAAGUCCUUCCAGCAG | |
| AD-1498524 | gscsgac(Chd)CfuGfGfAfaaagcugasusa | 65 | VPusAfsucdAg(C2p)uuuudCcAfgdGgucgcscsg | 79 | UGGCGACCCUGGAAAAGCUGAUG | |
| AD-1498525 | uscsagguUfCfUfgcuu(Uhd)uacscsa | 69 | VPusdGsgudAa(A2p)agcagaAfcCfugasgsc | 82 | GCUCAGGUUCUGCUUUUACCU | |
| AD-1498526 | csusucg(Ahd)GfuCfCfCfucaaguccsusa | 70 | VPusAfsggac(Tgn)ugaggAfcUfcgaagsgsc | 83 | GCCUUCGAGUCCCUCAAGUCCUU | |
| AD-1498527 | gscscgc(Uhd)CfadGgUfucugcuuususa | 71 | VPusAfsaadAg(C2p)agaadCcUfgAfgcggcscsg | 84 | CGGCCGCUCAGGUUCUGCUUUUA | |
| AD-1498528 | cscsggu(Chd)AfgGfUfUfcugcuuuusasa | 72 | VPusUfsaadAadGcagaacCfudGaceggscsc | 85 | GGCCGCUCAGGUUCUGCUUUUAC | |
| AD-1019448 | cscsaga(Ghd)CfcCfCfAfuucauugcscsa | 99 | VPusGfsgcaAfuGfAfauggGfgCfucuggsgsc | 100 | GCCCAGAGCCCCAUUCAUUGCCC | |

We claim:

1. A double stranded ribonucleic acid (dsRNA) agent, or a pharmaceutically acceptable salt thereof, for inhibiting expression of Huntingtin (HTT) in a cell, comprising a sense strand and an antisense strand forming a double stranded region, wherein the sense strand comprises at least 15 contiguous nucleotides differing by no more than 4 nucleotides from the nucleotide sequence 5'-gscsgac(Chd)CfuGfGfAfaaagcugasusa-3' of SEQ ID NO:65 (SEQ ID NO:65) and the antisense strand comprises at least 15 contiguous nucleotides differing by no more than 4 nucleotides from the nucleotide sequence 5'-VPusAfsucdAg(C2p)uuuudCcAfgdGgucgcscsg-3' of SEQ ID NO:79, wherein a, g, c and u are 2'-O-methyl (2'-OMe) A, G, C, and U, respectively; s is a phosphorothioate linkage; Af, Cf, and Gf are 2'-fluoro A, C, and G, respectively; (Chd) is 2'-O-hexadecyl-cytosine-3'-phosphate; C2p is cytidine-2'-phosphate; dA, dG, and dC are 2'-deoxy A, G, and C, respectively; and VP is 5'-vinyl phosphonate.

2. The dsRNA agent, or a pharmaceutically acceptable salt thereof, of claim 1, wherein the sense strand comprises at least 15 contiguous nucleotides differing by no more than 3 nucleotides from the nucleotide sequence 5'-gscsgac(Chd)CfuGfGfAfaaagcugasusa-3' of SEQ ID NO:65 and the antisense strand comprises at least 15 contiguous nucleotides differing by no more than 3 nucleotides from the nucleotide sequence 5'-VPusAfsucdAg(C2p)uuuudCcAfgdGgucgcscsg-3' of SEQ ID NO:79.

3. The dsRNA agent, or a pharmaceutically acceptable salt thereof, of claim 1, wherein the sense strand comprises at least 15 contiguous nucleotides differing by no more than 2 nucleotides from the nucleotide sequence 5'-gscsgac(Chd)CfuGfGfAfaaagcugasusa-3' of SEQ ID NO:65 and the antisense strand comprises at least 15 contiguous nucleotides differing by no more than 2 nucleotides from the nucleotide sequence 5'-VPusAfsucdAg(C2p)uuuudCcAfgdGgucgcscsg-3' of SEQ ID NO:79.

4. The dsRNA agent, or a pharmaceutically acceptable salt thereof, of claim 1, wherein the sense strand comprises at least 15 contiguous nucleotides differing by no more than 1 nucleotide from the nucleotide sequence 5'-gscsgac(Chd)CfuGfGfAfaaagcugasusa-3' of SEQ ID NO:65 and the antisense strand comprises at least 15 contiguous nucleotides differing by no more than 1 nucleotide from the nucleotide sequence 5'-VPusAfsucdAg(C2p)uuuudCcAfgdGgucgcscsg-3' of SEQ ID NO:79.

5. The dsRNA agent, or a pharmaceutically acceptable salt thereof, of claim 1, wherein the sense strand comprises the nucleotide sequence 5'-gscsgac(Chd)CfuGfGfAfaaagcugasusa-3' of SEQ ID NO:65 and the antisense strand comprises the nucleotide sequence 5'-VPusAfsucdAg(C2p)uuuudCcAfgdGgucgcscsg-3' of SEQ ID NO:79.

6. The dsRNA agent, or a pharmaceutically acceptable salt thereof, of claim 1, wherein the sense strand consists of the nucleotide sequence 5'-gscsgac(Chd)CfuGfGfAfaaagcugasusa-3' of SEQ ID NO:65 and the antisense strand consists of the nucleotide sequence 5'-VPusAfsucdAg(C2p)uuuudCcAfgdGgucgcscsg-3' of SEQ ID NO:79.

7. The dsRNA agent, or a pharmaceutically acceptable salt thereof, of claim 1, wherein the sense strand comprises at least 17 contiguous nucleotides differing by no more than 4 nucleotides from the nucleotide sequence 5'-gscsgac(Chd)CfuGfGfAfaaagcugasusa-3' of SEQ ID NO:65 and the antisense strand comprises at least 17 contiguous nucleotides differing by no more than 4 nucleotides from the nucleotide sequence 5'-VPusAfsucdAg(C2p)uuuudCcAfgdGgucgcscsg-3' of SEQ ID NO:79.

8. The dsRNA agent, or a pharmaceutically acceptable salt thereof, of claim 1, wherein the sense strand comprises at least 18 contiguous nucleotides differing by no more than 4 nucleotides from the nucleotide sequence 5'-gscsgac(Chd)CfuGfGfAfaaagcugasusa-3' of SEQ ID NO:65 and the antisense strand comprises at least 18 contiguous nucleotides differing by no more than 4 nucleotides from the nucleotide sequence 5'-VPusAfsucdAg(C2p)uuuudCcAfgdGgucgcscsg-3' of SEQ ID NO:79.

9. The dsRNA agent, or a pharmaceutically acceptable salt thereof, of claim 1, wherein the sense strand comprises at least 19 contiguous nucleotides differing by no more than 4 nucleotides from the nucleotide sequence 5'-gscsgac(Chd)CfuGfGfAfaaagcugasusa-3' of SEQ ID NO:65 and the antisense strand comprises at least 19 contiguous nucleotides differing by no more than 4 nucleotides from the nucleotide sequence 5'-VPusAfsucdAg(C2p)uuuudCcAfgdGgucgcscsg-3' of SEQ ID NO:79.

10. An isolated cell containing the dsRNA agent, or a pharmaceutically acceptable salt thereof, of any one of claims 1-9.

11. A pharmaceutical composition for inhibiting expression of a gene encoding HTT, comprising the dsRNA agent, or a pharmaceutically acceptable salt thereof, of any one of claims 1-9.

12. The pharmaceutical composition of claim 11, wherein the dsRNA agent, or a pharmaceutically acceptable salt thereof, is present in an unbuffered solution.

13. The pharmaceutical composition of claim 11, wherein the dsRNA agent, or a pharmaceutically acceptable salt thereof, is present in a buffer solution.

14. A double stranded ribonucleic acid (dsRNA) agent, or a pharmaceutically acceptable salt thereof, for inhibiting expression of Huntingtin (HTT) in a cell, comprising a sense strand and an antisense strand forming a double stranded region, wherein the sense strand comprises the nucleotide sequence 5'-gscsgac(Chd)CfuGfGfAfaaagcugasusa-3' of SEQ ID NO:65 and the antisense strand comprises the nucleotide sequence 5'-VPusAfsucdAg(C2p)uuuudCcAfgdGgucgcscsg-3' of SEQ ID NO:79, wherein a, g, c and u are 2'-O-methyl (2'-OMe) A, G, C, and U, respectively; s is a phosphorothioate linkage; Af, Cf, and Gf are 2'-fluoro A, C, and G, respectively; (Chd) is 2'-O-hexadecyl-cytosine-3'-phosphate; C2p is cytidine-2'-phosphate; dA, dG and dC are 2'-deoxy A, G, and C, respectively; and VP is 5'-vinyl phosphonate.

15. An isolated cell containing the dsRNA agent, or a pharmaceutically acceptable salt thereof, of claim 14.

16. A pharmaceutical composition for inhibiting expression of a gene encoding HTT, comprising the dsRNA agent, or a pharmaceutically acceptable salt thereof, of claim 15.

17. The pharmaceutical composition of claim 16, wherein the dsRNA agent, or a pharmaceutically acceptable salt thereof, is present in an unbuffered solution.

18. The pharmaceutical composition of claim 17, wherein the unbuffered solution is saline or water.

19. The pharmaceutical composition of claim 16, wherein the dsRNA agent, or a pharmaceutically acceptable salt thereof, is present in a buffer solution.

20. The pharmaceutical composition of claim 19, wherein the buffer solution comprises acetate, citrate, prolamine, carbonate, or phosphate or any combination thereof.

21. The pharmaceutical composition of claim 19, wherein the buffer solution is phosphate buffered saline (PBS).

22. A double stranded ribonucleic acid (dsRNA) agent, or a pharmaceutically acceptable salt thereof, for inhibiting expression of Huntingtin (HTT) in a cell, wherein the dsRNA agent, or a pharmaceutically acceptable salt thereof, comprises a sense strand and an antisense strand forming a double stranded region, wherein the sense strand consists of the nucleotide sequence 5'-gscsgac(Chd)CfuGfGfAfaaagcugasusa-3' of SEQ ID NO:65 and the antisense strand consists of the nucleotide sequence 5'-VPusAfsucdAg(C2p)uuuudCcAfgdGgucgcscsg-3' of SEQ ID NO:79, wherein a, g, c and u are 2'-O-methyl (2'-OMe) A, G, C, and U, respectively; s is a phosphorothioate linkage; Af, Cf, and Gf are 2'-fluoro A, C, and G, respectively; (Chd) is 2'-O-hexadecyl-cytosine-3'-phosphate; C2p is cytidine-2'-phosphate; dA, dG and dC are 2'-deoxy A, G, and C, respectively; and VP is 5'-vinyl phosphonate.

23. An isolated cell containing the dsRNA agent, or a pharmaceutically acceptable salt thereof, of claim 22.

24. A pharmaceutical composition for inhibiting expression of a gene encoding HTT, comprising the dsRNA agent, or a pharmaceutically acceptable salt thereof, of claim 22.

25. The pharmaceutical composition of claim 24, wherein the dsRNA agent, or a pharmaceutically acceptable salt thereof, is present in an unbuffered solution.

26. The pharmaceutical composition of claim 25, wherein the unbuffered solution is saline or water.

27. The pharmaceutical composition of claim 24, wherein the dsRNA agent, or a pharmaceutically acceptable salt thereof, is present in a buffer solution.

28. The pharmaceutical composition of claim 27, wherein the buffer solution comprises acetate, citrate, prolamine, carbonate, or phosphate or any combination thereof.

29. The pharmaceutical composition of claim 27, wherein the buffer solution is phosphate buffered saline (PBS).

30. A sodium salt of a double stranded ribonucleic acid (dsRNA) agent for inhibiting expression of Huntingtin (HTT) in a cell, wherein the dsRNA agent comprises a sense strand and an antisense strand forming a double stranded region, wherein the sense strand consists of the nucleotide sequence 5'-gscsgac(Chd)CfuGfGfAfaaagcugasusa-3' of SEQ ID NO:65 and the antisense strand consists of the nucleotide sequence 5'-VPusAfsucdAg(C2p)uuuudCcAfgdGgucgcscsg-3' of SEQ ID NO:79, wherein a, g, c and u are 2'-O-methyl (2'-OMe) A, G, C, and U, respectively; s is a phosphorothioate linkage; Af, Cf, and Gf are 2'-fluoro A, C, and G, respectively; (Chd) is 2'-O-hexadecyl-cytosine-3'-phosphate; C2p is cytidine-2'-phosphate; dA, dG and dC are 2'-deoxy A, G, and C, respectively; and VP is 5'-vinyl phosphonate.

* * * * *

SEQUENCE LISTING

Sequence total quantity: 101
SEQ ID NO: 1 moltype = DNA length = 13498
FEATURE Location/Qualifiers
source 1..13498
mol_type = genomic DNA -continued organism = Homo sapiens

SEQUENCE: 1

```
gctgccggga cgggtccaag atggacggcc gctcaggttc tgcttttacc tgcggcccag  60
agccccattc attgccccgg tgctgagcgg cgccgcgagt cggcccgagg cctccgggga  120
ctgccgtgcc gggcgggaga ccgccatggc gaccctggaa aagctgatga aggccttcga  180
gtccctcaag tccttccagc agcagcagca gcagcagcag cagcagcagc agcagcagca  240
gcagcagcag cagcagcagc aacagccgcc accgccgccg ccgccgccgc cgcctcctca  300
gcttcctcag ccgccgccgc aggcacagcc gctgctgcct cagccgcagc cgcccccgcc  360
gccgcccccg ccgccacccg gcccggctgt ggctgaggag ccgctgcacc gaccaaagaa  420
agaactttca gctaccaaga aagaccgtgt gaatcattgt ctgacaatat gtgaaaacat  480
agtggcacag tctgtcagaa attctccaga atttcagaaa cttctgggca tcgctatgga  540
actttttctg ctgtgcagtg atgacgcaga gtcagatgtc aggatggtgg ctgacgaatg  600
cctcaacaaa gttatcaaag ctttgatgga ttctaatctt ccaaggttac agctcgagct  660
ctataaggaa attaaaaaga atggtgcccc tcggagtttg cgtgctgccc tgtggaggtt  720
tgctgagctg gctcacctgg ttcggcctca gaaatgcagg ccttacctgg tgaaccttct  780
gccgtgcctg actcgaacaa gcaagagacc cgaagaatca gtccaggaga ccttggctgc  840
agctgttccc aaaattatgg cttcttttgg caattttgca aatgacaatg aaattaaggt  900
tttgttaaag gccttcatag cgaacctgaa gtcaagctcc cccaccattc ggcggacagc  960
ggctggatca gcagtgagca tctgccagca ctcaagaagg acacaatatt tctatagttg  1020
gctactaaat gtgctcttag gcttactcgt tcctgtcgag gatgaacact ccactctgct  1080
gattcttggc gtgctgctca ccctgaggta tttggtgccc ttgctgcagc agcaggtcaa  1140
ggacacaagc ctgaaaggca gcttcggagt gacaaggaaa gaaatggaag tctctccttc  1200
tgcagagcag cttgtccagg tttatgaact gacgttacat catacacagc accaagacca  1260
caatgttgtg accggagccc tggagctgtt gcagcagctc ttcagaacgc ctccacccga  1320
gcttctgcaa accctgaccg cagtcggggg cattgggcag ctcaccgctg ctaaggagga  1380
gtctggtggc cgaagccgta gtgggagtat tgtggaactt atagctggag gggttcctc  1440
atgcagccct gtcctttcaa gaaaacaaaa aggcaaagtg ctcttaggag aagaagaagc  1500
cttggaggat gactctgaat cgagatcgga tgtcagcagc tctgccttaa cagcctcagt  1560
gaaggatgag atcagtggag agctggctgc ttcttcaggg gtttccactc cagggtcagc  1620
aggtcatgac atcatcacag aacagccacg gtcacagcac acactgcagg cggactcagt  1680
ggatctggcc agctgtgact tgacaagctc tgccactgat ggggatgagg aggatatctt  1740
gagccacagc tccagccagg tcagcgccgt cccatctgac cctgccatgg acctgaatga  1800
tgggacccag gcctcgtcgc ccatcagcga cagctcccag accaccaccg aagggcctga  1860
ttcagctgtt accccttcag acagttctga aattgtgtta gacggtaccg acaaccagta  1920
tttgggcctg cagattggac agccccagga tgaagatgag gaagccacag gtattcttcc  1980
tgatgaagcc tcggaggcct tcaggaactc ttccatggcc cttcaacagg cacatttatt  2040
gaaaaacatg agtcactgca ggcagccttc tgacagcagt gttgataaat ttgtgttgag  2100
agatgaagct actgaaccgg gtgatcaaga aaacaagcct tgccgcatca aaggtgacat  2160
tggacagtcc actgatgatg actctgcacc tcttgtccat tgtgtccgcc ttttatctgc  2220
ttcgtttttg ctaacagggg gaaaaaatgt gctggttccg gacagggatg tgagggtcag  2280
cgtgaaggcc ctggccctca gctgtgtggg agcagctgtg gccctccacc cggaatcttt  2340
cttcagcaaa ctctataaag ttcctcttga caccacggaa taccctgagg aacagtatgt  2400
ctcagacatc ttgaactaca tcgatcatgg agacccacag gttcgaggag ccactgccat  2460
tctctgtggg accctcatct gctccatcct cagcaggtcc cgcttccacg tgggagattg  2520
gatgggcacc attagaaccc tcacaggaaa tacattttct ttggcggatt gcattccttt  2580
gctgcggaaa acactgaagg atgagtcttc tgttacttgc aagttagctt gtacagctgt  2640
gaggaactgt gtcatgagtc tctgcagcag cagctacagt gagttaggac tgcagctgat  2700
catcgatgtg ctgactctga ggaacagttc ctattggctg gtgaggacag agcttctgga  2760
aacccttgca gagattgact tcaggctggt gagctttttg gaggcaaaag cagaaaactt  2820
acacagaggg gctcatcatt atacagggct tttaaaactg caagaacgag tgctcaataa  2880
tgttgtcatc catttgcttg gagatgaaga ccccagggtg cgacatgttg ccgcagcatc  2940
actaattagg cttgtcccaa agctgtttta taaatgtgac caaggacaag ctgatccagt  3000
agtggccgtg gcaagagatc aaagcagtgt ttacctgaaa cttctcatgc atgagacgca  3060
gcctccatct catttctccg tcagcacaat aaccagaata tatagaggct ataacctact  3120
accaagcata acagacgtca ctatggaaaa taacctttca agagttattg cagcagtttc  3180
tcatgaacta atcacatcaa ccaccagagc actcacattt ggatgctgtg aagctttgtg  3240
tcttctttcc actgccttcc cagtttgcat ttggagttta ggttggcact gtggagtgcc  3300
tccactgagt gcctcagatg agtctaggaa gagctgtacc gttgggatgg ccacaatgat  3360
tctgaccctg ctctcgtcag cttggttccc attggatctc tcagcccatc aagatgcttt  3420
gattttggcc ggaaacttgc ttgcagccag tgctcccaaa tctctgagaa gttcatgggc  3480
ctctgaagaa gaagccaacc cagcagccac caagcaagag gaggtctggc cagccctggg  3540
ggaccgggcc ctggtgccca tggtggagca gctcttctct cacctgctga aggtgattaa  3600
catttgtgcc cacgtcctgg atgacgtggc tcctggaccc gcaataaagg cagccttgcc  3660
ttctctaaca aaccccccttt ctctaagtcc catccgacga aaggggaagg agaaagaacc  3720
aggagaacaa gcatctgtac cgttgagtcc caagaaaggc agtgaggcca gtgcagcttc  3780
tagacaatct gatacctcag gtcctgttac aacaagtaaa tcctcatcac tggggagttt  3840
ctatcatctt ccttcatacc tcaaactgca tgatgtcctg aaagctacac acgctaacta  3900
caaggtcacg ctggatcttc agaacagcac ggaaaagttt ggagggtttc tccgctcagc  3960
cttggatgtt ctttctcaga tactagagct ggccacactg caggacattg ggaagtgtgt  4020
tgaagagatc ctaggatacc tgaaatcctg ctttagtcga gaaccaatga tggcaactgt  4080
ttgtgttcaa caattgttga agactctctt tggcacaaac ttggcctccc agtttgatgg  4140
cttatcttcc aaccccagca agtcacaagg ccgagcacag cgccttggct cctccagtgt  4200
gaggccaggc ttgtaccact actgcttcat ggccccgtac acccacttca cccaggccct  4260
cgctgacgcc agcctgagga acatggtgca ggcggagcag gagaacgaca cctcgggatg  4320
gtttgatgtc ctccagaaag tgtctaccca gttgaagaca aacctcacga gtgtcacaaa  4380
gaaccgtgca gataagaatg ctattcataa tcacattcgt ttgtttgaac ctcttgttat  4440
aaaagcttta aaacagtaca cgactacaac atgtgtgcag ttacagaagc aggttttaga  4500
tttgctggcg cagctggttc agttacgggt taattactgt cttctggatt cagatcaggt  4560
gtttattggc tttgtattga aacagtttga atacattgaa gtgggccagt tcagggaatc  4620
```

```
agaggcaatc attccaaaca tctttttctt cttggtatta ctatcttatg aacgctatca  4680
ttcaaaacag atcattggaa ttcctaaaat cattcagctc tgtgatggca tcatggccag  4740
tggaaggaag gctgtgacac atgccatacc ggctctgcag cccatagtcc acgacctctt  4800
tgtattaaga ggaacaaata aagctgatgc aggaaaagag cttgaaaccc aaaaagaggt  4860
ggtggtgtca atgttactga gactcatcca gtaccatcag gtgttggaga tgttcattct  4920
tgtcctgcag cagtgccaca aggagaatga agacaagtgg aagcgactgt ctcgacagat  4980
agctgacatc atcctcccaa tgttagccaa acagcagatg cacattgact ctcatgaagc  5040
ccttggagtg ttaaatacat tatttgagat tttggcccct tcctccctcc gtccggtaga  5100
catgctttta cggagtatgt tcgtcactcc aaacacaatg gcgtccgtga gcactgttca  5160
actgtggata tcgggaattc tggccatttt gagggttctg atttcccagt caactgaaga  5220
tattgttctt tctcgtattc aggagctctc cttctctccg tatttaatct cctgtacagt  5280
aattaatagg ttaagagatg gggacagtac ttcaacgcta gaagaacaca gtgaagggaa  5340
acaaataaag aatttgccag aagaaacatt ttcaaggttt ctattacaac tggttggtat  5400
tcttttagaa gacattgtta caaaacagct gaaggtggaa atgagtgagc agcaacatac  5460
tttctattgc caggaactag gcacactgct aatgtgtctg atccacatct tcaagtctgg  5520
aatgttccgg agaatcacag cagctgccac taggctgttc cgcagtgatg gctgtggcgg  5580
cagtttctac accctggaca gcttgaactt gcgggctcgt tccatgatca ccacccaccc  5640
ggccctggtg ctgctctggt gtcagatact gctgcttgtc aaccacaccg actaccgctg  5700
gtgggcagaa gtgcagcaga ccccgaaaag acacagtctg tccagcacaa agttacttag  5760
tccccagatg tctggagaag aggaggattc tgacttggca gccaaacttg gaatgtgcaa  5820
tagagaaata gtacgaagag ggctctcat tctcttctgt gattatgtct gtcagaacct  5880
ccatgactcc gagcacttaa cgtggctcat tgtaaatcac attcaagatc tgatcagcct  5940
ttcccacgag cctccagtac aggacttcat cagtgccgtt catcggaact ctgctgccag  6000
cggcctgttc atccaggcaa ttcagtctcg ttgtgaaaac ctttcaactc caaccatgct  6060
gaagaaaact cttcagtgct tggaggggat ccatctcagc cagtcgggag ctgtgctcac  6120
gctgtatgtg gacaggcttc tgtgcacccc tttccgtgtg ctggctcgca tggtcgacat  6180
ccttgcttgt cgccgggtag aaatgcttct ggctgcaaat ttacagagca gcatggccca  6240
gttgccaatg gaagaactca acagaatcca ggaatacctt cagagcagcg ggctcgctca  6300
gagacaccaa aggctctatt ccctgctgga caggtttcgt ctctccacca tgcaagactc  6360
acttagtccc tctcctccag tctcttccca cccgctggac ggggatgggc acgtgtcact  6420
ggaaacagtg agtccggaca aagactggta cgttcatctt gtcaaatccc agtgttggac  6480
caggtcagat tctgcactgc tggaaggtgc agagctggtg aatcggattc ctgctgaaga  6540
tatgaatgcc ttcatgatga actcggagtt caacctaagc ctgctagctc catgcttaag  6600
cctagggatg agtgaaattt ctggtggcca gaagagtgcc ctttttgaag cagcccgtga  6660
ggtgactctg gcccgtgtga gcggcaccgt gcagcagctc cctgctgtcc atcatgtctt  6720
ccagcccgag ctgcctgcag agccggcggc ctactggagc aagttgaatg atctgtttgg  6780
ggatgctgca ctgtatcagt ccctgcccac tctggcccgg gccctggcac agtacctggt  6840
ggtggtctcc aaactgccca gtcatttgca ccttcctcct gagaaagaga aggacattgt  6900
gaaattcgtg gtggcaaccc ttgaggccct gtcctggcat ttgatccatg agcagatccc  6960
gctgagtctg gatctccagg cagggctgga ctgctgctgc ctggccctgc agctgcctgg  7020
cctctggagc gtggtctcct ccacagagtt tgtgacccac gcctgctccc tcatctactg  7080
tgtgcacttc atcctggagg ccgttgcagt gcagcctgga gagcagcttc ttagtccaga  7140
aagaaggaca aataccccaa aagccatcag cgaggaggag gaggaagtag atccaaacac  7200
acagaatcct aagtatatca ctgcagcctg tgagatggtg gcagaaatgg tggagtctct  7260
gcagtcggtg ttggccttgg gtcataaaag gaatagcggc gtgccggcgt ttctcacgcc  7320
attgctaagg aacatcatca tcagcctggc ccgcctgccc cttgtcaaca gctacacacg  7380
tgtgccccca ctggtgtgga agcttggatg gtcacccaaa ccgggagggg attttggcac  7440
agcattccct gagatccccg tggagttcct ccaggaaaag gaagtcttta aggagttcat  7500
ctaccgcatc aacacactag gctggaccag tcgtactcag tttgaagaaa cttgggccac  7560
cctccttggt gtcctggtga cgcagcccct cgtgatggag caggaggaga gcccaccaga  7620
agaagacaca gagaggaccc agatcaacgt cctggccgtg caggccatca cctcactggt  7680
gctcagtgca atgactgtgc ctgtggccgg caacccagct gtaagctgct tggagcagca  7740
gccccggaac aagcctctga aagctctcga caccaggttt gggaggaagc tgagcattat  7800
cagagggatt gtggagcaag agattcaagc aatggtttca aagagagaga atattgccac  7860
ccatcattta tatcaggcat gggatcctgt cccttctctg tctccggcta ctacaggtgc  7920
cctcatcagc cacgagaagc tgctgctaca gatcaacccc gagcgggagc tggggagcat  7980
gagctacaaa ctcggccagg tgtccataca ctccgtgtgg ctggggaaca gcatcacacc  8040
cctgagggag gaggaatggg acgaggaaga ggaggaggag gccgacgccc ctgcaccttc  8100
gtcaccaccc acgtctccag tcaactccag gaaacaccgg gctggagttg acatccactc  8160
ctgttcgcag tttttgcttg agttgtacag ccgctggatc ctgccgtcca gctcagccag  8220
gaggaccccg gccatcctga tcagtgaggt ggtcagatcc cttctagtgg tctcagactt  8280
gttcaccgag cgcaaccagt ttgagctgat gtatgtgacg ctgacagaac tgcgaagggt  8340
gcacccttca gaagacgaga tcctcgctca gtacctggtg cctgccacct gcaaggcagc  8400
tgccgtcctt gggatggaca aggccgtggc ggagcctgtc agccgcctgc tggagagcac  8460
gctcaggagc agccacctgc ccagcagggt tggagccctg cacggcgtcc tctatgtgct  8520
ggagtgcgac ctgctggacg acactgccaa gcagctcatc ccggtcatca gcgactatct  8580
cctctccaac ctgaaaggga tcgcccactg cgtgaacatt cacagccagc agcacgtact  8640
ggtcatgtgt gccactgcgt tttacctcat tgagaactat cctctggacg tagggccgga  8700
attttcagca tcaataatac agatgtgtgg ggtgatgctg tctggaagtg aggagtccac  8760
cccctccatc atttaccact gtgccctcag aggcctggag cgcctcctgc tctctgagca  8820
gctctcccgc ctggatgcag aatcgctggt caagctgagt gtggacagag tgaacgtgca  8880
cagcccgcac cgggccatgg cggctctggg cctgatgctc acctgcatgt acacaggaaa  8940
ggagaaagtc agtccgggta gaacttcaga ccctaatcct gcagcccccg acagcgagtc  9000
agtgattgtt gctatggagc gggtatctgt tctttttgat aggatcagga aaggctttcc  9060
ttgtgaagcc agagtggtgg ccaggatcct gccccagttt ctagacgact tcttcccacc  9120
ccaggacatc atgaacaaag tcatcggaga gtttctgtcc aaccagcagc catacccccca  9180
gttcatggcc accgtggtgt ataaggtgtt tcagactctg cacagcaccg ggcagtcgtc  9240
catggtccgg gactgggtca tgctgtccct ctccaacttc acgcagaggg ccccggtcgc  9300
catggccacg tggagcctct cctgcttctt tgtcagcgcg tccaccagcc cgtgggtcgc  9360
```

-continued

```
ggcgatcctc ccacatgtca tcagcaggat gggcaagctg gagcaggtgg acgtgaacct  9420
tttctgcctg gtcgccacag acttctacag acaccagata gaggaggagc tcgaccgcag  9480
ggccttccag tctgtgcttg aggtggttgc agccccagga agcccatatc accggctgct  9540
gacttgttta cgaaatgtcc acaaggtcac cacctgctga gcgccatggt gggagagact  9600
gtgaggcggc agctggggcc ggagcctttg gaagtctgcg cccttgtgcc ctgcctccac  9660
cgagccagct tggtccctat gggcttccgc acatgccgcg ggcggccagg caacgtgcgt  9720
gtctctgcca tgtggcagaa gtgctctttg tggcagtggc caggcaggga gtgtctgcag  9780
tcctggtggg gctgagcctg aggccttcca gaaagcagga gcagctgtgc tgcaccccat  9840
gtgggtgacc aggtcctttc tcctgatagt cacctgctgg ttgttgccag gttgcagctg  9900
ctcttgcatc tgggccagaa gtcctccctc ctgcaggctg gctgttggcc cctctgctgt  9960
cctgcagtag aaggtgccgt gagcaggctt tgggaacact ggcctgggtc tccctggtgg  10020
ggtgtgcatg ccacgccccg tgtctggatg cacagatgcc atggcctgtg ctgggccagt  10080
ggctgggggt gctagacacc cggcaccatt ctcccttctc tcttttcttc tcaggattta  10140
aaatttaatt atatcagtaa agagattaat tttaacgtaa ctctttctat gcccgtgtaa  10200
agtatgtgaa tcgcaaggcc tgtgctgcat gcgacagcgt ccggggtggt ggacagggcc  10260
cccggccacg ctccctctcc tgtagccact ggcatagccc tcctgagcac ccgctgacat  10320
ttccgttgta catgttcctg tttatgcatt cacaaggtga ctgggatgta gagaggcgtt  10380
agtgggcagg tggccacagc aggactgagg acaggccccc attatcctag gggtgcgctc  10440
acctgcagcc cctcctcctc gggcacagac gactgtcgtt ctccacccac cagtcaggga  10500
cagcagcctc cctgtcactc agctgagaag gccagccctc cctggctgtg agcagcctcc  10560
actgtgtcca gagacatggg cctcccactc ctgttccttg ctagccctgg ggtggcgtct  10620
gcctaggagc tggctggcag gtgttgggac ctgctgctcc atggatgcat gccctaagag  10680
tgtcactgag ctgtgttttg tctgagcctc tctcggtcaa cagcaaagct tggtgtcttg  10740
gcactgttag tgacagagcc cagcatccct tctgccccg ttccagctga catcttgcac  10800
ggtgacccct tttagtcagg agagtgcaga tctgtgctca tcggagactg ccccacggcc  10860
ctgtcagagc cgccactcct atccccaggc caggtccctg gaccagcctc ctgtttgcag  10920
gcccagagga gccaagtcat taaaatggaa gtggattctg gatggccggg ctgctgctga  10980
tgtaggagct ggatttggga gctctgcttg ccgactggct gtgagacgag gcaggggctc  11040
tgcttcctca gccctagagg cgagccaggc aaggttggcg actgtcatgt ggcttggttt  11100
ggtcatgccc gtcgatgttt tgggtattga atgtggtaag tggaggaaat gttggaactc  11160
tgtgcaggtg ctgccttgag acccccaagc ttccacctgt ccctctccta tgtggcagct  11220
ggggagcagc tgagatgtgg acttgtatgc tgcccacata cgtgaggggg agctgaaagg  11280
gagcccctcc tctgagcagc ctctgccagg cctgtatgag gcttttccca ccagctccca  11340
acagaggcct cccccagcca ggaccacctc gtcctcgtgg cggggcagca ggagcggtag  11400
aaaggggtcc gatgtttgag gaggccctta agggaagcta ctgaattata acacgtaaga  11460
aaatcaccat tccgtattgg ttgggggctc ctgtttctca tcctagcttt ttcctggaaa  11520
gcccgctaga aggtttggga acgaggggaa agttctcaga actgttggct gctccccacc  11580
cgcctcccgc ctcccccgca ggttatgtca gcagctctga gacagcagta tcacaggcca  11640
gatgttgttc ctggctagat gtttacattt gtaagaaata acactgtgaa tgtaaaacag  11700
agccattccc ttggaatgca tatcgctggg ctcaacatag agtttgtctt cctcttgttt  11760
acgacgtgat ctaaaccagt ccttagcaag gggctcagaa caccccgctc tggcagtagg  11820
tgtcccccac ccccaaagac ctgcctgtgt gctccggaga tgaatatgag ctcattagta  11880
aaaatgactt cacccacgca tatacataaa gtatccatgc atgtgcatat agacacatct  11940
ataattttac acacacacct ctcaagacgg agatgcatgg cctctaagag tgcccgtgtc  12000
ggttcttcct ggaagttgac tttccttaga cccgccaggt caagttagcc gcgtgacgga  12060
catccaggcg tgggacgtgg tcagggcagg gctcattcat tgcccactag gatcccactg  12120
gcgaagatgg tctccatatc agctctctgc agaagggagg aagactttat catgttccta  12180
aaaatctgtg gcaagcaccc atcgtattat ccaaattttg ttgcaaatgt gattaatttg  12240
gttgtcaagt tttgggggtg ggctgtgggg agattgcttt tgttttcctg ctggtaatat  12300
cgggaaagat tttaatgaaa ccagggtaga attgtttggc aatgcactga agcgtgtttc  12360
tttcccaaaa tgtgcctccc ttccgctgcg ggcccagctg agtctatgta ggtgatgttt  12420
ccagctgcca agtgctcttt gttactgtcc accctcattt ctgccagcgc atgtgtcctt  12480
tcaaggggaa aatgtgaagc tgaacccccct ccagacaccc agaatgtagc atctgagaag  12540
gccctgtgcc ctaaaggaca cccctcgccc ccatcttcat ggagggggtc atttcagagc  12600
cctcggagcc aatgaacagc tcctcctctt ggagctgaga tgagccccac gtggagctcg  12660
ggacggatag tagacagcaa taactcggtg tgtggccgcc tggcaggtgg aacttcctcc  12720
cgttgcgggg tggagtgagg ttagttctgt gtgtctggtg ggtggagtca ggcttctctt  12780
gctacctgtg agcatccttc ccagcagaca tcctcatcgg gctttgtccc tcccccgctt  12840
cctccctctg cggggaggac ccgggaccac agctgctggc cagggtagac ttggagctgt  12900
cctccagagg ggtcacgtgt aggagtgaga agaaggaaga tcttgagagc tgctgaggga  12960
ccttggagag ctcaggatgg ctcagacgag gacactcgct tgccgggcct gggcctcctg  13020
ggaaggaggg agctgctcag aatgccgcat gacaactgaa ggcaacctgg aaggttcagg  13080
ggccgctctt cccccatgtg cctgtcacgc tctggtgcag tcaaaggaac gccttcccct  13140
cagttgtttc taagagcaga gtctcccgct gcaatctggg tggtaactgc cagccttgga  13200
ggatcgtggc caacgtggac ctgcctacgg agggtgggct ctgacccaag tggggcctcc  13260
ttgtccaggt ctcactgctt tgcaccgtgg tcagagggac tgtcagctga gcttgagctc  13320
ccctggagcc agcagggctg tgatgggcga gtcccggagc ccccacccaga cctgaatgct  13380
tctgagagca aagggaagga ctgacgagag atgtatattt aattttttaa ctgctgcaaa  13440
cattgtacat ccaaattaaa ggaaaaaaat ggaaaccatc aaaaaaaaaa aaaaaaa    13498
```

```
SEQ ID NO: 2           moltype = DNA  length = 13237
FEATURE                Location/Qualifiers
source                 1..13237
                       mol_type = genomic DNA
                       organism = Mus musculus
SEQUENCE: 2
gcactcgccg cgagggttgc cgggacgggc ccaagatggc tgagcgcctt ggttccgctt  60
ctgcctgccg cgcagagccc cattcattgc cttgctgcta agtggcgccg cgtagtgcca  120
gtaggctcca agtcttcagg gtctgtccca tcgggcagga agccgtcatg gcaaccctgg  180
```

-continued aaaagctgat gaaggctttc gagtcgctca agtcgtttca gcagcaacag cagcagcagc 240
caccgccgca ggcgccgccg ccaccgccgc cgccgcctcc gcctcaaccc cctcagccgc 300
cgcctcaggg gcagccgccg ccgccaccac cgccgctgcc aggtccggca gaggaaccgc 360
tgcaccgacc aaagaaggaa ctctcagcca ccaagaaaga ccgtgtgaat cattgtctaa 420
caatatgtga aaacattgtg gcacagtctc tcagaaattc tccagaattt cagaaactct 480
tgggcatcgc tatggaactg tttctgctgt gcagtgacga tgcggagtca gatgtcagaa 540
tggtggctga tgagtgcctc aacaaagtca tcaaagcttt gatggattct aatcttccaa 600
ggctacagtt agaactctat aaggaaatta aaaagaatgg tgctcctcga agtttgcgtg 660
ctgccctgtg gaggtttgct gagctggctc acctggttcg acctcagaag tgcaggcctt 720
acctggtgaa tcttcttcca tgcctgaccc gaacaagcaa aagaccggag gaatcagttc 780
aggagacctt ggctgcagct gttcctaaaa ttatggcttc ttttggcaat ttcgcaaatg 840
acaatgaaat taaggttctg ttgaaagctt tcatagcaaa tctgaagtca agctctccca 900
ccgtgcggcg gacagcagcc ggctcagccg tgagcatctg ccaacattct aggaggacac 960
agtacttcta caactggctc cttaatgtcc tcctaggtct gctggttccc atggaagaag 1020
agcactccac tctcctgatc ctcggtgtgt tgctcacatt gaggtgtcta gtgcccttgc 1080
tccagcagca ggtcaaggac acaagtctaa aaggcagctt tggggtgaca cggaaagaaa 1140
tggaagtctc tccttctaca gagcagcttg tccaggttta tgaactgact ttgcatcata 1200
ctcagcacca agaccacaat gtggtgacag gggcactgga gctcctgcag cagctcttcc 1260
gtacccctcc acctgaactc ctgcaagcac tgaccacacc aggagggctt gggcagctca 1320
ctctggttca agaagaggcc cggggccgag gccgcagcgg gagcatcgtg gagcttttag 1380
ctggaggggg ttcctcgtgc agccctgtcc tctcaagaaa gcagaaaggc aaagtgctct 1440
taggagagga agaagccttg gaagatgact cggagtccag gtcagatgtc agcagctcag 1500
cctttgcagc ctctgtgaag agtgagattg gtggagagct cgctgcttct tcaggtgttt 1560
ccactcctgg ttctgttggt cacgacatca tcactgagca gcctagatcc cagcacacac 1620
ttcaagcaga ctctgtggat ttgtccggct gtgacctgac cagtgctgct actgatgggg 1680
atgaggagga catcttgagc cacagctcca gccagttcag tgctgtccca tccgaccctg 1740
ccatggacct gaatgatggg acccaggcct cctcacccat cagtgacagt tctcagacca 1800
ccactgaagg acctgattca gctgtgactc cttcggacag ttctgaaatt gtgttagatg 1860
gtgccgatag ccagtattta ggcatgcaga taggacagcc acaggaggac gatgaggagg 1920
gagctgcagg tgttctttct ggtgaagtct cagatgtttt cagaaactct tctctggccc 1980
ttcaacaggc acacttgttg gaaagaatgg gccatagcag gcagccttcc gacagcagta 2040
tagataagta tgtaacaaga gatgaggttg ctgaagccag tgatccagaa agcaagcctt 2100
gccgaatcaa aggtgacata ggacagccta atgatgatga ttctgctcct ctggtacatt 2160
gtgtccgtct tttatctgct tcctttttgt taactggtga aaagaaagca ctggttccag 2220
acagagacgt gagagtcagt gtgaaggccc tggccctcag ctgcattggt gcggctgtgg 2280
cccttcatcc agagtcgttc ttcagcagac tgtacaaagt acctcttaat accacggaaa 2340
gtactgagga acagtatgtt tctgacatct tgaactacat cgatcatgga gacccacagg 2400
tccgaggagc tactgccatt ctctgtggga cccttgtcta ctccatcctc agtaggtccc 2460
gtctccgtgt tggtgactgg ctgggcaaca tcagaaccct gacaggaaat acattttctc 2520
tggtggactg cattccttta ctgcagaaaa cgttgaagga tgaatcttct gttacttgca 2580
agttggcttg tacagctgtg aggcactgtg tcctgagtct ttgcagcagc agctacagtg 2640
acttgggatt acaactgctt attgatatgc tgcctctgaa gaacagctcc tactggctgg 2700
tgaggaccga actgctggac actctggcag agattgactt caggctcgtg agtttttttgg 2760
aggcaaaagc agaaagttta caccgagggg ctcatcatta tacagggttt ctaaaactac 2820
aagaacgagt actcaataat gtggtcattt atttgcttgg agatgaagac cccagggttc 2880
gacatgttgc tgcaacatca ttaacaaggc ttgtcccaaa gctgttttac aagtgtgacc 2940
aaggacaagc tgatccagtt gtggctgtag cgagggatca gagcagtgtc tacctgaagc 3000
tcctcatgca tgagacccag ccaccatcac acttttctgt cagcaccatc accagaatct 3060
atagaggcta tagcttactg ccaagtataa cagatgtcac catggaaaac aatctctcaa 3120
gagttgttgc cgcagtttct catgaactca ttacgtcaac aacacgggca ctcacatttg 3180
gatgctgtga agccttgtgt cttctctcag cagcctttcc agtttgcact tggagtttag 3240
gatggcactg tggagtgccc ccactgagtg cctctgatga gtccaggaag agctgcactg 3300
ttgggatggc ctccatgatt ctcaccttgc tttcatcagc ttggttccca ctggatctct 3360
cagcccatca ggatgccttg attttggctg gaaacttgct agcagcgagt gcccccaagt 3420
ctctgagaag ttcatggacc tctgaagaag aagccaactc agcagccacc agacaggagg 3480
aaatctggcc tgctctgggg gatcggactc tagtgccctt ggtggagcag cttttctccc 3540
acctgctgaa ggtgatcaat atctgtgctc atgtcttgga cgatgtgact cctggaccag 3600
caatcaaggc agccttgcct tctctaacaa acccccccttc tctaagtcct attcgacgga 3660
aagggaagga gaaagaacct ggagaacaag cttctactcc aatgagtccc aagaaagttg 3720
gtgaggccag tgcagcctct cgacaatcag acacctcagg acctgtcaca gcaagtaaat 3780
catcctcact ggggagtttc taccatctcc cctcctacct caaactgcat gatgtcctga 3840
aagccactca cgccaactat aaggtcacct tagatcttca gaacagcact gaaaagtttg 3900
gggggttcct gcgctctgcc ttggacgtcc tttctcagat tctagagctg gcgacactgc 3960
aggacattgg aaagtgtgtt gaagaggtcc ttggatacct gaaatcctgc tttagtcgag 4020
aaccaatgat ggcaactgtc tgtgtgcagc agctattgaa gactctcttt gggacaaact 4080
tagcctcaca gtttgatggc ttatcttcca accccagcaa gtctcagtgc cgagctcagc 4140
gccttggctc ttcaagtgtg aggcccggct tatatcacta ctgcttcatg gcaccataca 4200
cgcacttcac acaggccttg gctgacgcaa gcctgaggaa catggtgcag gcggagcagg 4260
agcgtgatgc ctcggggtgg tttgatgtac tccagaaagt gtctgcccaa ttgaagacga 4320
acctaacaag cgtcacaaag aaccgtgcag ataagaatgc tattcataat cacattaggt 4380
tatttgagcc tcttgttata aaagcattga agcagtacac cacgacaaca tctgtacaat 4440
tgcagaagca ggttttggat ttgctggcac agctggttca gctacgggtc aattactgtc 4500
tactggattc agaccaggtg ttcatcgggt ttgtgctgaa gcagtttgag tacattgaag 4560
tgggccagtt cagggaatca gaggcaatta ttccaaatat atttttcttc ctggtattac 4620
tgtcttatga gcgctaccat tcaaaacaga tcattggaat tcctaaaatc atccagctgt 4680
gtgatggcat catggccagt ggaaggaagg ccgttacaca tgctatacct gctctgcagc 4740
ccattgtcca tgacctcttt gtgttacgag gaacaaataa agctgatgca gggaaagagc 4800
ttgagacaca gaaggaggtg gtggtctcca tgctgttacg actcatccag taccatcagg 4860
tgctggagat gttcatcctt gtcctgcagc agtgccacaa ggagaatgag gacaagtgga 4920

```
aacggctctc tcggcaggtc gcagacatca tcctgcccat gttggccaag cagcagatgc  4980
atattgactc tcatgaagcc cttggagtgt taaatacctt gtttgagatt ttggctcctt  5040
cctccctacg tcctgtggac atgcttttgc ggagtatgtt catcactcca agcacaatgg  5100
catctgtaag cactgtgcag ctgtggatat ctggaatcct cgccattctg agggttctca  5160
tttcccagtc aaccgaggac attgttcttt gtcgtattca ggagctctcc ttctctccac  5220
acttgctctc ctgtccagtg attaacaggt taaggggtgg aggcggtaat gtaacactag  5280
gagaatgcag cgaagggaaa caaaagagtt tgccagaaga tacattctca aggtttcttt  5340
tacagctggt tggtattctt ctagaagaca tcgttacaaa acagctcaaa gtggacatga  5400
gtgaacagca gcatacgttc tactgccaag agctaggcac actgctcatg tgtctgatcc  5460
acatattcaa atctggaatg ttccggagaa tcacagcagc tgccactaga ctcttcacca  5520
gtgatggctg tgaaggcagc ttctatactc tagagagcct gaatgcacgg gtccgatcca  5580
tggtgcccac gcacccagcc ctggtactgc tctggtgtca gatcctactt ctcatcaacc  5640
acactgacca ccggtggtgg gcagaggtgc agcagacacc caagagacac agtctgtcct  5700
gcacgaagtc acttaacccc cagaagtctg gcgaagagga ggattctggc tcggcagctc  5760
agctgggaat gtgcaataga gaaatagtgc gaagaggggc ccttattctc ttctgtgatt  5820
atgtctgtca gaatctccat gactcagaac acttaacatg gctcattgtg aatcacattc  5880
aagatctgat cagcttgtct catgagcctc cagtacaaga ctttattagt gccattcatc  5940
gtaattctgc agctagtggt ctttttatcc aggcaattca gtctcgctgt gaaaatcttt  6000
caacgccaac cactctgaag aaaacacttc agtgcttgga aggcatccat ctcagccagt  6060
ctggtgctgt gctcacacta tatgtggaca ggctcctggg cacccccttc cgtgcgctgg  6120
ctcgcatggt cgacaccctg gcctgtcgcc gggtagaaat gcttttggct gcaaatttac  6180
agagcagcat ggcccagttg ccagaggagg aactaaacag aatccaagaa cacctccaga  6240
acagtgggct tgcacaaaga caccaaaggc tctattcact gctggacaga ttccgactct  6300
ctactgtgca ggactcactt agccccttgc ccccagtcac ttcccaccca ctggatgggg  6360
atgggcacac atctctggaa acagtgagtc cagacaaaga ctggtacctc cagcttgtca  6420
gatcccagtg ttggaccaga tcagattctg cactgctgga aggtgcagag ctggtcaacc  6480
gtatccctgc tgaagatatg aatgacttca tgatgagctc ggagttcaac ctaagccttt  6540
tggctccctg tttaagcctt ggcatgagcg agattgctaa tggccaaaag agtcccctct  6600
ttgaagcagc ccgtggggtg attctgaacc gggtgaccag tgttgttcag cagcttcctg  6660
ctgtccatca agtcttccag cccttcctgc ctatagagcc cacggcctac tggaacaagt  6720
tgaatgatct gcttggtgat accacatcat accagtctct gaccatactt gcccgtgccc  6780
tggcacagta cctggtggtg ctctccaaag tgcctgctca tttgcacctt cctcctgaga  6840
aggaggggga cacggtgaag tttgtggtaa tgacagttga ggccctgtca tggcatttga  6900
tccatgagca gatcccactg agtctggacc tccaagccgg gctagactgc tgctgcctgg  6960
cactacaggt gcctggcctc tggggggtgc tgtcctcccc agagtacgtg actcatgcct  7020
gctccctcat ccattgtgtg cgattcatcc tggaagccat tgcagtacaa cctggagacc  7080
agcttctcgg tcctgaaagc aggtcacata ctccaagagc tgtcagaaag gaggaagtag  7140
actcagatat acaaaaacctc agtcatgtca cttcggcctg cgagatggtg gcagacatgg  7200
tggaatccct gcagtcagtg ctggccttgg gccacaagag gaacagcacc ctgccttcat  7260
ttctcacagc tgtgctgaag aacattgtta tcagtctggc ccgactcccc ctagttaaca  7320
gctatactcg tgtgcctcct ctggtatgga aactcgggtg gtcacccaag cctggagggg  7380
attttggcac agtgtttcct gagatccctg tagagttcct ccaggagaag gagatcctca  7440
aggagttcat ctaccgcatc aacaccctag ggtggaccaa tcgtacccag ttcgaagaaa  7500
cttgggccac cctccttggt gtcctggtga ctcagcccct ggtgatggaa caggaagaga  7560
gcccaccaga ggaagacaca gaaagaaccc agatccatgt cctggctgtg caggccatca  7620
cctctctagt gctcagtgca atgaccgtgc ctgtggctgg caatccagct gtaagctgct  7680
tggagcaaca gccccggaac aagccactga aggctctcga taccagattt ggaagaaagc  7740
tgagcatgat cagagggatt gtagaacaag aaatccaaga gatggtttcc cagagagaga  7800
atactgccac tcaccattct caccaggcgt gggatcctgt cccttctctg ttaccagcta  7860
ctacaggtgc tcttatcagc catgacaagc tgctgctgca gatcaaccca gagcgggagc  7920
caggcaacat gagctacaag ctgggccagg tgtccataca ctccgtgtgg ctgggaaata  7980
acatcacacc cctgagagag gaggaatggg atgaggaaga agaggaagaa agtgatgtcc  8040
ctgcaccaac gtcaccacct gtgtctccag tcaattccag aaaacaccgt gccggggttg  8100
atattcactc ctgttcgcag tttctgcttg aattgtacag ccgatggatc ctgccatcca  8160
gtgcagccag aaggaccccc gtcatcctga tcagtgaagt ggttcgatct cttcttgtag  8220
tgtcagactt attcaccgaa cgtacccagt ttgaaatgat gtatctgacg ctgacagaac  8280
tacggagagt gcaccccttca gaagatgaga tcctcattca gtacctggtg cctgccacct  8340
gtaaggcagc tgctgtcctt ggaatggaca aaactgtggc agagccagtc agccgcctac  8400
tggagagcac actgaggagc agccacctgc ccagccagat cggagccctg cacggcatcc  8460
tctatgtgtt ggagtgtgac ctcttggatg acactgcaaa gcagctcatt ccagttgtta  8520
gtgactatct gctgtccaac ctcaaaggaa tagcccactg cgtgaacatt cacagccagc  8580
agcatgtgct ggtaatgtgt gccactgctt tctacctgat ggaaaactac cctctggatg  8640
tgggaccaga attttcagca tctgtgatac agatgtgtgg agtaatgctg tctggaagtg  8700
aggagtccac cccctccatc atttaccact gtgccctccg gggtctggag cggctcctgc  8760
tgtctgagca gctatctcgg ctagacacag agtccttggt caagctaagt gtggacagag  8820
tgaatgtaca aagcccacac agggccatgg cagccctagg cctgatgctc acctgcatgt  8880
acacaggaaa ggaaaaagcc agtccaggca gagcttctga ccccagccct gctacacctg  8940
acagcgagtc tgtgattgta gctatggagc gagtgtctgt tctctttgat aggatccgca  9000
agggatttcc ctgtgaagcc agggttgtgg caaggatcct gcctcagttc ctagatgact  9060
tctttccacc tcaagatgtc atgaacaaag tcattggaga gttcctgtcc aatcagcagc  9120
catacccaca gttcatggcc actgtagttt acaaggtttt tcagactctg cacagtgctg  9180
ggcagtcatc catggtccgg gactgggtca tgctgtccct gtccaacttc acacaaagaa  9240
ctccagttgc catggccatg tggagcctct cctgcttcct tgttagcgca tctaccagcc  9300
catgggtttc tgcgatcctt ccacatgtca tcagcaggat gggcaaactg gaacaggtgg  9360
atgtgaacct tttctgcctg gttgccacag acttctacag acaccagata gaggaggaat  9420
tcgaccgcag ggctttccag tctgtgtttg aggtggtggc tgcaccagga agtccatacc  9480
acaggctgct tgcttgtttg caaaatgttc acaaggtcac cacctgctga gtagtgcctg  9540
tgggacaaaa ggctgaaaga aggcagctgc tggggcctga gcctccagga gcctgctcca  9600
agcttctgct ggggctgcct tggccgtgca ggcttccact tgtgtcaagt ggacagccag  9660
```

```
gcaatggcag gagtgctttg caatgagggc tatgcaggga acatgcacta tgttggggtt  9720
gagcctgagt cctgggtcct ggcctcgctg cagctggtga cagtgctagg ttgaccaggt  9780
gtttgtcttt ttcctagtgt tcccctggcc atagtcgcca ggttgcagct gccctggtat  9840
gtggatcaga agtcctagct cttgccagat ggttctgagc ccgcctgctc cactgggctg  9900
gagagctccc tcccacattt acccagtagg catacctgcc acaccagtgt ctggacacaa  9960
aatgaatggt gtgtggggct gggaactggg gctgccaggt gtccagcacc attttccttt  10020
ctgtgttttc ttctcaggag ttaaaattta attatatcag taaagagatt aattttaatg  10080
taacttttcc tatgcccgtg taaagtgtgt gacttggcaa ggcctgtgct gcatgtgaca  10140
aagtttatgg aagtggaggg gccttctggc cgccactccc tctcctgtag ctactcagtc  10200
tagtcgggca ggtccctcct gtagccctcc caacaccctg tggcacttgc acttcataca  10260
gctccctttt cttatgcatt ccattaagcc agcacagaga gaggtgttgg tattgactgc  10320
ctgtgtgaga atcctgcctg tggcctaact gaggaactga aaaactgact tccactgtta  10380
gagttataag aggcttgccc tgtggcagct gccctcctct ccccttccca ggcatgactg  10440
tcaagctatc tcctccctgg tgttgatgca ctctcctagt ctctcagcct gggtagaaac  10500
agcatctgct ggacccaaag tggctatccc aataacctca tccctggttg tggctgacct  10560
gcactgtagc ctgcccacac accagctgac cattgtggat gctgtctgtc cctttgtatc  10620
ttctgcatgg ttgggacctg agaagtgctg acctgattac cccaaaggtg tctctgagct  10680
atggtttgtt ggtttgtctc agtttctcat agtcaaggga aagcttggtg tcctagcaac  10740
agttaagaat ggacccagag cctcttttgc cccttcccat cttgccttct gtcagcccag  10800
tagagtacag acctatgcct gtcagagccc agggaggact cagctgacaa gatgaggcac  10860
caaagggaag gttcaaaatc aggtcagcct ctggcctcag acagcttccc atgctggtca  10920
gagccacctc ttcccaaagc ccaagcccag agtaaccagg tcatgttaat gaaaatgagc  10980
taccttcatt tcctggcttg gtttgggaac tctgtttgct gtttgactat atgaccaagc  11040
agatttctg ctgttccgct aagtcatatc tgtatttctc agctgtagag taggggagtg  11100
gaatagtttg gagatgtttc taggctacac aggaggaaag agcttgcagc ctgtgattaa  11160
ctaactgtgc ttcagtccat ggattgcttt cttgagaccc ttgaatttcc ctctatcttt  11220
ccatcatgac aagtagcctt gctgctggga tgcaaggttc cctaccaaac acaggttgtg  11280
gggagcctca cacttggcct gactctcctc ctatctgccc tggcaaaaac caccccaagg  11340
cgtggtaaca ggaacagtgg acatggatta ggtctttcaa gaggacgtta agggaagcta  11400
ctgaatttta atgaaagaaa ttcaccaatg cccctttgct gatttagggc ttcttcttgt  11460
caccctcaat ttcccgccta gaagtgctcg gggaccatgt gaaagttctt acagtgctgc  11520
tgccacactc tgaggttggt ccaaccgctc tgagatgagc atggtgcagg cctgattact  11580
cctcatggta gatgttcata aggaaactca atataaaatc tagagccatt caccagggga  11640
ttatatcagt gagctcaacc tcaagtttag ttggcctctt gtttagtgtg atcagaaaca  11700
attcttagta tggggcaagg acagcctctg ccacaaagtt gttgtctgct catgggtgcc  11760
acaacctaga gatgcacctg ggtacaggca ggtatgtatt tgtgtacaca cataaacaca  11820
cacacaatcc tcaaagacat atgcaaggcc tctaaaaatg cctgcctgtt ttttctgaaa  11880
gcagactttt cttgcaactg ccacatacag tcagctttgt gagtctagca tctgagaatg  11940
ggactcaatt tttaaaagtc catagctcat taaagtctca ctggagacat tgccccacct  12000
gtctaactgc aggagggact aaaacttttt atcaaattcc tcaaaaatct aaagatttcc  12060
aagctttatt taaaaacaaa agttattttg actatgaggt tttaggggta ggaggtggga  12120
tgttgtttct gtttccatgg tggtactgtc aggaaagatt ttaataaaac cagggtagaa  12180
cttttggcaa tgcacttcag catgtttctt ctccaaaatg tgcctccctc cctcccactg  12240
atggccccct tgacatgtag gtgacttagc cactgccaag tgccctttat ggttctctca  12300
ttttgtctgc acatgtaccc ttcaggaggg aagaactgga gtggaaccac ctcctgccct  12360
gtagaatgca gtgccaggga agggaccaat cctaacaggt gccttccctg gcaggaagta  12420
ccttcccgtg agtgagtgaa gcagctctgc ttccggctca tgggacaggt tttatacagc  12480
aatagcttgt ctcacagcca cgtcacaagg agtcttgcct cccattgtgg ggctgcagaa  12540
ttggtctcct tgccacctgt gagcatcctt ccccacacag tctccttccc tccctccttc  12600
cctccctccc tccctccctc cctccgtccc tccctccctc cctcagcatt gagcactagg  12660
atcatggctg ctaccaggac aggcatgaag ctgtcctcca gggattggta tgtgggagtc  12720
gaagacactg agctgctgat gctgggtgtg ggctcaggat atcatggttg ggaaaagaat  12780
tgttcctcag tgggtctgga gcctccagga aagaagaacc aatgctgagc agtgtgacaa  12840
ctaaagatga tatcaaggtt cagggccacc ctccatgtgt gcttgtcaca ctctagagcc  12900
atcgaaggaa ctgctcccct caagtgtctc tggaaacacc ctctgccgca agctgggtgt  12960
aagataatag gtggcagaga cctatctgca gagatttggc tgcattctag gggctcctg  13020
tccaagcctt gctgctgtat gccatgggct tcactgggaa ctaggagggc tgtgatgggt  13080
gtgccccgga gcccagccta gacctggctg tccatttcca aaaggaagga ctgacatgaa  13140
atgtatattt aaaattttta aattgcagat attgtacagt tgaattaaag aagcgattaa  13200
accacctgtt gttgctgtta aaaaaaaaaa aaaaaaa                          13237

SEQ ID NO: 3            moltype = DNA  length = 13189
FEATURE                 Location/Qualifiers
source                  1..13189
                        mol_type = genomic DNA
                        organism = Rattus norvegicus
SEQUENCE: 3
gcactcgccg cgagggttgc cgggacgggc ccaagatggc tgggagcttt ggttccgctt  60
cggtctacct cgtagagccc cattcattac cttgctgcta agtggcgctg cgtagtgcga  120
ataggctcca agccttcagg gtctgtcctg tcgggcagga ggccgtcatg gcaaccctgg  180
aaaaactgat gaaggctttc gagtcgctca agtcgttcca gcagcaacag cagcagcagc  240
agccgccgcc gcaggcgccg ccaccaccgc cgccgccgcc gcctcaaccc cctcagccgc  300
cgcctcaggg gcagccgccg ccaccaccgc cgctgccagg tccggccgag gagccgctgc  360
accgaccaaa gaaggaactc tcagccacca agaaggaccg tgtgaatcac tgtctaacaa  420
tatgtgaaaa cattgtggca cagtctctca gaaattctcc agaatttcag aaactcttgg  480
gcattgctat ggaactgttt ctgctgtgca gcgacgatgc ggagtcagac gtcagaatgg  540
tggctgatga gtgcctcaac aaagtcatca aagctttgat ggactctaat cttccaaggc  600
tacagttaga actctataag gaaattaaaa agaatggtgc tcctcgaagt ttgcgtgcag  660
ctctgtggag gtttgctgag ctggctcacc tggttcgacc tcagaagtgc aggccttatc  720
```

-continued

```
tggtgaatct tcttccatgt ttgacccgaa caagcaaacg accggaggag tcagttcagg  780
agactttggc tgcagctgtt cctaaaatta tggcctcttt tggcaatttc gcgaatgaca  840
atgaaattaa ggttctattg aaagctttca tagcaaatct gaagtcaagc tctcccactg  900
tgcggcggac agcagctggg tcagcagtga gtatctgcca gcactctagg aggacacagt  960
acttctacaa ctggctcctg aatgtgctcc taggtttgct ggttcccatg gaggaagacc  1020
accccactct cctgatcctt ggtgtgttgc tcacactgag gtgtctagtg cccttgctcc  1080
agcagcaggt caaggacaca agtctaaagg gcagctttgg ggtaacacgg aaagaaatgg  1140
aagtctctcc ttctgcagag cagcttgtcc aggtttatga actgactttg catcacacac  1200
agcaccaaga ccataatgtg gtgacagggg cattggagct cctgcagcag ctcttccgta  1260
cccctccacc tgagctgctg caagcactga ccacaccagg agggctcggg cagctcactc  1320
tggttcgaga ggaagccggg ggccgaggcc gcagcgggag tatcgtggag cttttagctg  1380
gagggggttc ctcatgcagc cctgttctct caagaaagca aaaaggcaaa gtgctcttag  1440
gagaggaaga agccttggag gatgactcgg agtccaggtc agatgtcagc agctcagcct  1500
ttgcagcctc tgtgaagagt gagattggtg gagagctcgc tgcttcttct tcgggtgtct  1560
ccactcccgg ttctgtaggt cacgacatca tcactgagca gcctcgatcc cagcacacac  1620
ttcaagcaga ctctgtggat ttgtcaggct gtgacttgac cagtgctgct actgatggag  1680
atgaggaaga catcttgagc cacagctcca gccagttcag tgctgttcca tccgaccctg  1740
ccatggacct gaatgatggg acccaggcct cctcacccat cagtgacagt tctcagacca  1800
ccactgaagg acctgattca gctgtgactc cttctgacag ttctgaaatt gtcttagatg  1860
gtgctgacag ccagtattta ggcgtgcaga taggacagcc acaggaggaa gacgaggagg  1920
aagctgcagg tgttctttct ggtgaagtct cagacgtttt cagaaactct tctctggccc  1980
ttcagcaggc acacttgttg gaaagaatgg gtcatagccg gcagccttct gacagcagtg  2040
ttgataagtt tgtttcaaaa gatgaggttg ctgaagctgg ggacccagaa agcaagcctt  2100
gccgaatcaa aggtgacata ggacagccta atgatgatga ttctgctcct ctggtacatt  2160
gtgtccgtct tttatccgct tccttttttgt taactggcga aaagaaagca ctggttccag  2220
acagagatgt gagagtcagt gtgaaggccc tggccctcag ctgtattggt gcagctgtgg  2280
cccttcatcc agagtcgttc ttcagcaaac tctacaaagt acctctcagt accatggaaa  2340
gtactgagga acagtatgtc tctgacatcc tgaactacat cgatcatgga gaccctcagg  2400
tgcgaggagc tactgccatt ctctgtggga cccttgtcta ctccatcctc agcaggtccc  2460
gtctccgtgt tggtgactgg ctgggcacca tcagggccct gacaggaaat acattttctc  2520
tggtggactg cattccttta ctgcagaaaa ctttgaagga tgaatcttct gttacttgca  2580
agttggcttg tacagctgtg aggcactgtg tcctgagtct ttgcagcagc agctacagtg  2640
acttgggatt acaactgctt attgacatgc tgcctctgaa gaacagctcc tactggctgg  2700
tgaggactga actgctggaa actcttgcag agattgattt caggctggtg agttttttgg  2760
aggcaaaagc agaaagttta caccgagggg ctcatcatta tacagggttt ctaaaactac  2820
aagaacgagt actcaataat gtggtcattt atttgcttgg agatgaagac cccagggttc  2880
gacatgttgc tgcgacgaca ttgacaagac ttgtcccaaa gctgttttat aagtgtgacc  2940
aaggacaggc tgacccagtc gtggctgtag caagagatca aagtagtgtt tacctgaagc  3000
tcctcatgca tgagacccag ccaccatccc acttctccgt cagcaccata accagaatct  3060
atagaggcta cagcttacta ccaagtgtaa cagatgtcac catggaaaac aacctctcaa  3120
gagtcgttgc cgcagtttct catgaactca ttacgtcaac tacacgggca ctcacatttg  3180
ggtgctgtga agccttgtgt gttctttcag ccgcctttcc agtttgcact tggagtctag  3240
gatggcactg tggagtgccc ccactgagtg cctctgatga gtccaggaag agctgcactg  3300
ttgggatggc ctccatgatt ctcaccttgc tttcatcagc ttggttccca ctggatctct  3360
cagcccatca ggatgccttg attttggctg gaaacttgct agcagcgagt gcccccaagt  3420
ctctgagaag ctcatgggcc tcggaagaag aaggcagctc agcagccacc agacaggagg  3480
agatctggcc tgccctgggg gatcggactc tggtgcccat ggtggagcag cttttctccc  3540
acctgctgaa ggtgatcaat atctgtgctc atgtcttgga tgacgtgact cctggaccag  3600
caatcaaggc agctttgcct tctctcacaa accccccttc tctaagtcct attcgacgga  3660
aagggaagga gaaagagccc ggagaacaaa catccactcc gatgagtccc aagaaaggtg  3720
gagaggccag tacagcctct cgacagtcag acacctcagg acctgtcaca gcgagtaaat  3780
catcttcact tgggagtttc taccatctcc cttcctacct cagactgcat gatgtcctga  3840
aagccactca cgccaactat aaggtcacct tagatcttca gaacagcact gaaaagtttg  3900
gggggttcct gcgctctgcc ttggacgtcc tttctcagat tctagagctg gcgacactgc  3960
aggacattgg aaagtgtgtt gaagaggtcc ttggatactt gaaatcctgc tttagtcgag  4020
aaccaatgat ggcgactgtc tgtgttcagc agctattgaa gactctcttt gggacaaact  4080
tagcctcaca gtttgatggc ttatcttcca accccagcaa gtctcagtgc cgagcacagc  4140
gccttggctc ttccagtgtg aggcccggct tatatcacta ctgcttcatg gcaccataca  4200
cgcacttcac gcaggctttg gctgatgcca gcctgaggaa catggtacag gcggaccagg  4260
agcacgatgc ctcagggtgg tttgatgtac tccagaaagt gtctgctcag ttgaagacga  4320
accttacaag tgtcacaaag aaccgtgcag ataagaacgc tattcataac cacattaggt  4380
tatttgagcc tcttgttata aaagcattga agcagtacac cacgacaaca tcagtacaac  4440
tgcagaagca ggttttggat ttgctggcac agctggttca gctacgggtc aattactgtc  4500
tactggattc agatcaggtg ttcatcgggt ttgtgctgaa gcagtttgag tacattgaag  4560
tgggccagtt cagggaatca gaggcaatta ttccaaatat atttttcttc ctggtactat  4620
tatcttatga gcgctaccat tcaaaacaga tcattggaat tcctaaaatc atccagctgt  4680
gtgatggcat catggccagt ggaaggaagg ctgtcacaca tgctattcct gcgctgcagc  4740
ccattgtcca tgacctcttt gtgttaagag gaacaaataa agctgatgca gggaaagagc  4800
ttgaaaccca gaaggaggtg gtggtctcaa tgctgttacg actcatccag taccatcagg  4860
tgctagagat gttcatcctc gtcctgcagc agtgccacaa agagaatgag gacaagtgga  4920
aacggctctc tcggcaggtc gcagacatca tcctgcccat gttagccaag cagcagatgc  4980
atattgactc tcatgaagcc cttggagtat taaatacctt gtttgagatt ttggctcctt  5040
cctccctacg tcctgtggac atgcttttgc ggagtatgtt catcactcca agcacaatgg  5100
catctgtaag cactgtgcag ctgtggatat ctggaatcct agccattctg agggttctca  5160
tttcccagtc aaccgaagac attgttcttt ctcgtattca ggagctctcc ttctctccat  5220
atttaatttc ctgtccagta attaacaggt taagggatgg agacagtaat ccaacactag  5280
gagaacgcag tgaagggaaa caagtaaaga atttgccaga agatacattc tcaaggtttc  5340
tcttacagct ggttggtatt cttctggaag acattgttac aaaacagctc aaagtggaca  5400
tgagtgaaca gcagcataca ttctattgcc aagagctcgg cacactgctc atgtgtctga  5460
```

-continued

```
tccacatatt caaatctgga atgttccgga gaatcacagc cgctgccact agactcttca  5520
ccagtgatgg ctgtgaaggc agcttctata ctctagatag cctgaatgca cgggtgcgag  5580
ccatggtgcc cacacaccca gctctggtac tgctctggtg tcagatccta ctgctcatca  5640
accacactga ccaccgatgg tgggccgagg tgcagcagac gcccaagaga cacagtctgt  5700
cctgcacgaa gtcactaaac ccccagatat ctgctgaaga ggattctggc tcagcagctc  5760
agcttggaat gtgcaataga gaaatagtac gaagaggggc ccttattctc ttctgtgatt  5820
atgtctgtca gaatctccat gactcagaac acttaacatg gctcattgtg aatcacattc  5880
aagatctgat cagcttgtcc cacgagcctc cagttcaaga ctttattagt gccattcatc  5940
gtaattctgc agctagtggt ctttttatcc aggcaattca gtctcgctgt gaaaatcttt  6000
caactccaac cactctgaag aaaacacttc agtgcttgga aggcatccat ctcagccagt  6060
ctggtgctgt gctcacactg tatgtggaca ggctactggg caccccctttc cgtgcgctgg  6120
ctcgcatggt cgacaccctg gcctgtcgcc gagtagaaat gcttttggct gcaaatttac  6180
agagcagcat ggcccagttg ccagaggagg aactgaacag aatccaggaa cacctccaga  6240
acactgggct tgcacaaaga caccaaaggc tctattcact gctggacaga ttccgactct  6300
ctactgtgca ggactcactt agccccttgc ccccagtcac ttcccaccct ctggatgggg  6360
atgggcacac atccctggaa acagtgaatc cggacaaaga ctggtacctc cagcttgtca  6420
gatcccagtg ttggaccagg tcagattctg cactgctgga aggtgcagag ctggtgaacc  6480
gtatccctgc tgaagatatg agtgacttca tgatgagctc ggagttcaac ctaagccttt  6540
tggctccctg cttaagcctt ggcatgagcg agattgctaa tggccaaaag agtccccttt  6600
ttgaagcggc tcgtagggtg actctggacc gggtgaccaa tgtggttcag cagctgcctg  6660
cagtccatca agtcttccag cctttcctgc ctacagaacc cacagcctac tggagcaagc  6720
tgaatgatct ctttggtgat accacatcat accagtctct gaccacactt gcccgtgccc  6780
tggcacagta cctggtggtg ctctccaaag tgcctgctcc tttgcacctt cctcctgaga  6840
aggaggggca cacggtgaag tttgtggtaa tgacacttga ggccctgtca tggcatttga  6900
tccatgagca gatcccactg agtctggacc tccaagccgg cctagactgc tgctgcctgg  6960
cactgcaggt gcctggcctc tggggggtgc tgtcctcccc agagtacgtg actcatactt  7020
gctcccttat ccactgtgtg cgattcatcc tggaagccat tgcagtacaa cctggagacc  7080
aacttcttgg tccggaaagc aggtcacata ctccaagggc tgtcagaaag gaggaagtag  7140
actcagatat acaaaacctc agtcacatca cttcggcctg cgagatggtg gcagacatgg  7200
tggaatccct gcagtcggtg ctggccctgg gccacaagag gaacagcacc ctaccttcat  7260
ttctcacagc tgtgctgaag aacattgttg tcagtctggc ccgcctcccc ctcgttaaca  7320
gctatactcg tgtgcctcct ctggtatgga aactcgggtg gtcacccaag cctggagggg  7380
atttcggcac agtgtttcct gagatccctg tagagttcct ccaggagaag gaggtcctca  7440
aggagttcat ctaccgcatc aacaccctag ggtggaccag tcgtactcaa ttcgaagaaa  7500
cttgggccac cctccttggt gtcctggtga ctcagccctt ggtgatggaa caggaagaga  7560
gcccaccaga ggaagacacc gaaaggaccc agatccacgt cctggctgta caggccatca  7620
cctctctagt gctcagcgca atggctgtgc ctgtggctgg caatccagct gtaagctgct  7680
tggagcaaca gccccggaac aagccactga aggctctcga taccagattt ggaagaaagt  7740
tgagcatgat cagagggatt gtagaacaag aaatccaaga gatggtttcc caaagagaga  7800
atactgccac tcatcattct caccaggcat gggatcctgt cccttctctg ttaccagcta  7860
ctacaggtgc tcttatcagc catgacaagc tgctgctgca gatcaactca gagcgggagc  7920
caggcaacat gagctacaag ctgggccagg tgtccataca ctccgtgtgg ctggggaaca  7980
acatcacacc cctgagagag gaggaatggg atgaggagga ggaggaagaa gcggatgccc  8040
ctgcgccaac atcaccacct gtgtctccag tcaattccag aaaacaccgt gctggggttg  8100
atattcactc ctgttcgcag tttctgcttg aattatacag ccgttggatc ctgccatcca  8160
gtgcagccag aaggacccct gtcatcctga tcagtgaagt ggttcgatct cttcttgtgg  8220
tgtcagactt attcactgaa cgtacccagt ttgaaatgat gtatctgacg ctgacagaac  8280
tacggagagt gcacccttca gaagatgaga tcctcattca atacctggtg cctgccacct  8340
gtaaggcagc tgctgttctt ggaatggaca aaactgtggc agagccggtc agccgcctac  8400
tggagagcac actcaggagc acccacctgc ccagccagat cggagccctg catggcatcc  8460
tctatgtgtt ggagtgtgac ctcttggatg acactgtaaa gcagctcatt ccagttgtta  8520
gtgactatct gctgtccaac ctcaaaggaa tagcccactg cgtgaacatt cacagccagc  8580
agcatgtgct ggtgatgtgt gccactgcat tctacctgat ggaaaactac cctctggatg  8640
tggggccaga attctcagca tctgtgatac agatgtgtgg agtaatgctg tctggaagtg  8700
aggagtccac cccctccatc atttaccact gtgccctccg gggtctggaa cggctcctgc  8760
tgtctgagca gctctctcgg ctagacacgg agtccttggt caagctaagt gtggacagag  8820
tgaatgtaca aagcccacac aggggcatgg cagccctagg cctgatgctt acctgcatgt  8880
acacaggaaa ggaaaaagcc agtccaggca gagcttctga ccccagccct gctacccctg  8940
acagcgagtc tgtgattgta gctatggagc gagtgtctgt gctctttgac aggatccgca  9000
agggatttcc ctgtgaagcc agggtcgtgg caaggatcct gcctcagttt ctagatgact  9060
tctttccacc tcaagatgtc atgaacaaag tcattggaga gttcctgtcc aaccagcagc  9120
catacccaca gttcatggcc actgtagtat acaaggtttt tcagactctg cacagtgctg  9180
ggcagtcatc catggtccgg gactgggtta tgctgtctct gtccaacttc acacaaagaa  9240
ctccagttgc catggccatg tggagcctct cctgcttcct tgtcagtgca tctaccagcc  9300
catgggtttc tgcaatcctt ccacacgtca tcagcaggat gggcaaactg gagcaggtgg  9360
atgtgaacct tttctgcctg gttgccacag acttctacag acaccagata gaggaggaat  9420
tcgaccgcag ggctttccag tctgtgtttg aggtggtggc agcaccagga agtccatacc  9480
acaggctgct tgcttgtttg caaaatgttc acaaggtcac cgcctgctga gtagtacctg  9540
tggaacaaga ggctgagagg aggcaactgc tgtggctaca gcctccaggg gcctgcacca  9600
agcttctgct aaggctgcct tggacgtgca ggcttccact tgtgtcaagt ggacagccag  9660
gcaatggcag gagtgctttg caatgagagc tatgcaggga acatgcacta tgttggggtt  9720
gagcctgagt cctgggtcct ggcatcactg cagctggtgg cagtgctagg ttgaccaggt  9780
gtttgtcttt ttcttagtgt tgccctggcc atagttgcca ggttgcagct gccctggtat  9840
gtggaacaga atccgagctc ttgtaagatg gttctgagcc cccctgtccc actgggctgg  9900
agagctccct cccacattta cccagcaggt gtacctgcca caccagtgtc tggacacaaa  9960
gtgaatggtg tgggggctgg gaactgggac tgccaggtgt ccagcatcat tttccctttc  10020
tctgttttct tctcaggagt taaaatttaa ttatatcagt aaagagatta attttaatgt  10080
aactcttcct atgcccgtgt aaagtgtgtg acttggcaag gcctgtgctg catgtgacaa  10140
agtttatgga agtggatgcg ccttctggcc accactctct ctcctgtagc tactcagtct  10200
```

-continued

```
agtcgggcag gtccctcatg tagccctccc aacaccctat ggcacttgca cttcacacgg  10260
ctcctttttc ttatgcattc catttgacta gcacagagtg gtgttggtgt taactgccct  10320
atgtgagaat cctgcttgtg gcccagctta tgagactgac ttccacttag gattaagaga  10380
ggcttgccct gcggcagacc cccaccccta ccccaggcat gactatcaag ctgtctactc  10440
actagtgttg atgcactctc ctagtctctc agcctgggca gagacagcat ctgctggacc  10500
caaagaggct atttcaataa tctcatccct ggtcgtggct gacctgggct gtagcctgcc  10560
cagacaccgg ctgaccattg tggatgctct ctgtcccttt gtatcttctg catggttggg  10620
acctgaggaa tgctagcccg atcaccccaa aggtgtctct gagctatggc ttgttggttg  10680
tctccgtttc tcttggtcaa gggaaagctc aatgtcctag caacaattaa gaatggaacc  10740
agagcctctt ttgccccttc ccatcttgcc ttctgtcagc ccttacagta cagacctatg  10800
cctttcagag ccaagggagg actcggcctg acaagatgag gcaccaaagg gaaggttcaa  10860
aatcaggtca gcctatggcc tcagacagct tcccgtgctg ctggtcagag ccgcctcttc  10920
ccaaggccca agcccagagt agccaggaca tgttgatgag aatgagccct ggacacaggc  10980
tgccttcgtc ccctggcttg gtccaggagc tctgctggct gtgtgactga gcgggctctc  11040
tgctgcccac tcagtcctgt ctgtaccaat cgactgcaga gtggggagag gagtaatttg  11100
gagctgtttc taggctacac gggaggaaag agcttgcagc ctatgactaa ttaactgtgc  11160
ttcagtctgt ggactgcttt cttaagaatt tccttctgtt ttcccatcat gatgattaaa  11220
aggctgccgg gatgcaaggt tccctaccaa acacaggtac acaggttgtg gggagcctca  11280
cacttggcct gattctattc ctatctgccc tggcaaaggc cactgcaagc cagcccagcc  11340
catcctggtg tcatggtaac aggaacagtg gacatggatc aggtctttca agaggacctt  11400
aaaggaagct actgaatttt aatgaaagaa agtcaccaat gcccctttgc tgatttaggg  11460
tttctacttg ttaccctaga tatccctcct agaagtgctt ggagaccaca tgaaagttct  11520
cacaatgctg ctgccacact ctaaagttgg tccaacagct ctgagatgag catgttgcag  11580
gcctgattac cgattactcc tcatggtaga tgttcataag aaaacagaat ataaaatcta  11640
gagccattca cctggggttt atatcagtga cttccagttt agttggtctc ttgttcagtg  11700
tggtcagaaa taactcttag tatgggacaa gaacagcctc tgctacaaag ctgttgtctg  11760
ctcatgggtg ctgcaaccta gagatgcacc tgggcacagg cacacacgca cacacgcaca  11820
cacacacaca cacacacaca cacacacctc aaagacatat gcaagacctc taaaaatgcc  11880
tgtccattct tcctgaaagc agacttttct tgtaactgcc acatacagtc agctttgtga  11940
gtctagcatc tgagaatggg actcaatttt taaaagtcca tagtcattaa agtcccactg  12000
aagacattgc cccacctgtc taactgtagg aagaactaaa actttttatc aaattcctca  12060
aaaatctatg gatttccaaa ctttatttaa aaaaaaaaaa gtaattttga ctgtgaggtt  12120
ttgggggtag gaggtgggat gttgtttctg ttttcctgct ggtattatca ggaaagattt  12180
tagtaaaacc agggtagaac tatttggcaa tgcacttaag tatgtttctt ctccaaaatg  12240
tgcctccctc ccactgatgg ccccttgaca ttaggtgact ttgccactgc caagtgccct  12300
ttactattct ctcattttgt ctgcacatgt acccttcagg agggaaggac tagagtggaa  12360
ccacctcctg ccctgtagac tgcggtgcca gggaaggcac tgaccctaac gggtgccctc  12420
cctggcagga agtaccttcc tgtgagtgag gcagctctgc tttcagctca tgggacaggg  12480
tttatacagc aatagcttgg ctcacagcca cctggcaagg agtcctgcct cccattgtag  12540
ggctgcagaa ttagtctcct cctgcctctc gtgagcatcc ttccccactg cctgcctgcc  12600
tccctccctc cctccctccc tcaacggtga gcactaggat catggctgct gccaggacag  12660
gcacgaagct gtcttccagg gattggtatg tgggagtaga agaccctgag agctgctgag  12720
gctgggtggg ggctcaggat atcacggttt ggaagagaac tgttcctcag tgggtctgga  12780
gcctccagga aagaagaacc aatgccgagc agtgtgacaa ctgaagatga catgaaggtt  12840
cagggccacc tccatgtgtg cttgtcacac tttagagcca tcgaaggaac tgctcccctc  12900
aagtgtccgg aaacaccctc tgccacaagc tgggtgtaag gtgacagaca cctatctgca  12960
gagatttgcc tgcattctag ggggctcctg tccaggcctt gctgctgtat gccatgggct  13020
tcactgggaa ctaggagggc tgtgatgggt atgccccgga gcccagccta gacctggccg  13080
tccatttcca agaggaagga ctgacatgaa atgtatattt aaaattttta aattgcagat  13140
attgtacatt tgaattaaag aagcaattaa actacccgtt gttgctgtt             13189

SEQ ID NO: 4           moltype = DNA  length = 13328
FEATURE                Location/Qualifiers
source                 1..13328
                       mol_type = genomic DNA
                       organism = Macaca fascicularis
SEQUENCE: 4
aggcgccgcg ggggctgccg ggacgggtcc aagatggacg gccgcttcgg ttccgctttt  60
acccgcggcc cagagcccca ttcattgccc cggtgctgag cggcgctgcg agtcggcccg  120
aggcctccgg ggactgccca gccgggcggg agaccgccat ggcgaccctg gaaaagctga  180
tgaaggcctt cgagtctctc aagtccttcc agcagcagca gcagcagcag ccacccggcc  240
cggctgtggc tgaggagccg ctgcaccgac caaagaaaga actttcagct accaagaaag  300
accgtgtgaa tcattgtctg acaatatgtg aaaacatagt ggcacagtct gtcagaaatt  360
ctccagaatt tcagaaactt ctgggcatcg ctatggaact tttctgctg tgcagtgatg  420
acgcagagtc ggatgtcaga atggtggctg atgaatgcct caacaaagtt atcaaagctt  480
tgatggattc taatcttcca aggttacagc tcgagctcta taaagaaatt aaaaagaatg  540
gtgcccctcg gagtttgcgt gctgccctgt ggaggtttgc cgagctggct cacctggttc  600
ggcctcagaa atgcaggcct tacctggtga accttctgcc gtgcctaagt cgaacaagca  660
agagacccga ggaatcagtc caggagacct tggctgcagc tgttcccaaa attatggctt  720
ctttcggcaa ttttgcaaat gacaatgaaa ttaaggtttt gttaaaggcc ttcatagcga  780
acctgaagtc aagctccccc accattcggc ggacagctgc tggatcagca gtgagcatct  840
gccagcactc aagaaggaca cagtatttct atagctggct actaaatgtg ctcttaggct  900
tactggttcc tgtcgaggag gagcactcca ccctgctgat tcttggcgtg ctgctcaccc  960
tgaggtattt ggtgcccttg ctgcagcagc aggtcaagga tacaagcctg aaaggcagct  1020
tcggagtgac acggaaagaa atggaggtct gtccttctgc ggagcagctt gtccaggttt  1080
atgaactgac gttacatcat acacagcacc aagaccacaa tgttgtgacc ggagccctgg  1140
agctgttgca gcagctcttc agaacgcctc cccccgagct tctgcaagcc ctgaccacag  1200
tgggggcat tgggcagctc accgccgcta aggaggagtc tggtggccga agccgtagtg  1260
ggagtattgt ggaacttata gctggagggg gttcctcatg cagccctgtc ctttcaagaa  1320
```

-continued

```
aacaaaaagg caaagtgctc ttaggagaag aagaagcctt ggaggatgac tctgaatcga  1380
gatcggatgt cagcagctct gcctttgcag cctcagtgaa ggatgatatc agtggagagc  1440
tggctacttc ttcaggggtt tccactccag ggtcagcagg tcacgacatc atcacggagc  1500
agccacggtc acagcacacg ctgcaggcgg actcagtgga tctggccagc tgtgacttga  1560
caagctctgc cacggatggg gatgaggagg atatcttgag ccacagctcc agccaggtca  1620
gcgccgtccc atctgaccct gccatggacc tgaatgatgg gacccaggcc tcctcgccca  1680
tcagcgacag ctcccagacc accaccgaag ggcctgattc agctgtcacc ccttcagaca  1740
gttctgaaat tgtgttagac ggtaccgaca accagtattt gggcctgcag attggacagc  1800
cccaggatga agatgaggaa gccacaggtg ttcttcctga cgaagcctcg gaggccttca  1860
ggaactcttc catggccctt caacaagcac atttattgaa aaacatgagt cacagcaggc  1920
agccttctga cagcagtgtt gataaatttg tgttgagaga tgaagctact gaaccgggtg  1980
atcaagaaaa caagccttgc cgcatcaaag gtgacatcgg acagtccact gatgatgatt  2040
ctgcacctct tgtccattgt gtccgccttt tatctgcttc gtttttgcta acaggggggaa  2100
aaaatgtgct ggttccggac cgggatgtga gggtcagcgt gaaggccctg gccctcagct  2160
gtgtgggagc agctgtggct ctccacccag aatctttctt cagcaaactc tataaagttc  2220
ctcttgacac cacagaatac cctgaggaac aatatgtctc agatatcttg aactacatcg  2280
atcatggaga cccacaggtt cgaggagcca ctgccattct ctgtgggacc ctcatctgct  2340
ccatcctcag caggtcccgc ttccacgtgg gagattggat gggcgccatt agaaccctga  2400
caggaaacac attttctttg gcggattgca ttcctttgct gcggaaaaca ctgaaggacg  2460
agtcttctgt cacttgcaag ctggcttgta cagctgtgag gcattgtgtc atgagtctct  2520
gcagcagcag ctacagtgag ttaggactgc agctgatcat cgacgtgctg actctgagga  2580
acagttccta ttggctggtg aggacagagc ttctggaaac ccttgcggag attgacttca  2640
ggctggtgag ctttttggag gcaaaagcag aaaacttaca cagaggggct catcattata  2700
cagggctttt aaagctgcaa gaacgagtgc tcaataatgt tgtcatccat ttgcttgggg  2760
atgaagaccc cagggtgcga catgttgctg cagcatcatt aattaggctt gtcccaaagc  2820
tgtttttataa atgtgaccaa ggacaagctg acccagtagt ggccgtggca agagatcaaa  2880
gcagtgttta cctgaaactt ctcatgcatg agacgcagcc tccatctcat ttctccgtca  2940
gcacaataac cagaatatac agaggctata acctactacc aagcataaca gatgtcacta  3000
tggaaaataa cctttcaaga gttattgcag cagtttctca tgaactgatc acatcaacca  3060
cgagagcact cacttttgga tgctgtgaag ctttgtgtct tctttccact gccttcccag  3120
tttgcatttg gagtttaggt tggcactgtg gagtgcctcc actgagcgcc tccgatgagt  3180
ctaggaagag ctgtaccgtt gggatggcca cgatgattct gaccctgctc tcgtcagctt  3240
ggttcccatt ggatctctca gcccatcaag atgctttgat tttggccgga aacttgcttg  3300
cagccagtgc tcctaaatct ctgagaagtt catgggcctc tgaagaagaa gccaacccag  3360
cagccaccaa gcaagaggag gtctggccag ccctagggga ccgggccttg gtgcccatgg  3420
tggagcagct cttctcccac ctgctgaagg tgatcaacat ttgtgcacat gtcctggacg  3480
acgtggctcc tggaccggca ataaaggcag ccttgccttc tctaacaaac cccccttctc  3540
taagtcccat ccgacgaaag gggaaggaga aagaaccagg agaacaagca tctgtaccgt  3600
tgagtcccaa gaaaggcagt gaggccagtg cagcttctag acaatctgat acctcaggtc  3660
ctgttacaac aagtaaatcc tcatcactgg ggagtttcta tcatcttcct tcatacctca  3720
aactgcatga tgtcctgaaa gctacgcacg ctaactacaa ggtcaccttg gatcttcaga  3780
acagcacgga aaaatttgga gggtttcttc gctcagcctt ggacgttctc tctcagattc  3840
tagagctggc cacactgcag gacattggga agtgtgttga ggagatccta ggatacctga  3900
aatcctgctt tagtcgagaa ccaatgatgg caactgtttg tgttcaacaa ttgttgaaga  3960
ctctctttgg gacaaacttg gcctcccagt ttgacggctt atcatccaac cccagcaagt  4020
cacaaggccg agcacagcgc cttggctcct ccagtgtgag gccaggcttg taccactact  4080
gcttcatggc cccgtacacc cacttcaccc aggccctcgc tgacgccagc ttgaggaaca  4140
tggtgcaggc ggagcaggag cacgacacct cgggatggtt tgatgtcctc cagaaagtgt  4200
ctacccagtt gaagacgaac ctcacaagtg tcacaaagaa ccgtgcagat aagaatgcta  4260
ttcataatca cattcgtttg tttgaacctc ttgttataaa agctttaaaa cagtacacga  4320
caacaacatc tgtgcagtta cagaagcagg ttttagattt gctggcgcag ctggttcagt  4380
tacgggttaa ttactgtctt ctggattcag atcaggtgtt tattggcttt gtattgaaac  4440
agttcgaata cattgaagtg ggccagttca gggaatcaga ggcaatcatt ccaaacatct  4500
ttttcttctt ggtattactg tcttatgaac gctatcattc aaaacagatc attggaattc  4560
ctaaaatcat tcagctctgt gatggcatca tggccagtgg aaggaaggct gtgacacacg  4620
ccataccggc tctgcagccc atagtccatg accttttttgt attaagagga acaaataaag  4680
ctgatgcagg aaaagagctt gaaacccaaa aagaagtggt ggtatcaatg ttactgagac  4740
tcatccagta ccatcaggtg ttggagatgt tcattctcgt cctgcagcag tgccacaagg  4800
agaatgaaga caagtggaag cgactgtctc gacagatagc tgacatcatc ctcccaatgt  4860
tagccaaaca gcagatgcac attgactctc atgaagccct tggagtgtta aatacattat  4920
ttgagatttt ggccccttcc tccctccgtc cggtggacat gcttttacgg agtatgttcg  4980
tcactccaaa cacaatggca tctgtgagca ctgttcaact gtggatatca ggaattctgg  5040
ccattttgag ggttctgatt tcccagtcaa ctgaagatat tgttctttct cgtattcagg  5100
agctctcttt ctctccatat ttaatctcct gtccagtaat taataggcta agagatgggg  5160
acagtaattc agcactagaa gaacacagtg aagggaaaca aataaagaat ttgccggaag  5220
aaacatttc aaggtttcta ttacaactgg tgggtattct tttagaagac attgttacaa  5280
aacagctgaa ggtggaaatg agtgagcagc aacatacttt ctattgccaa gaactaggca  5340
ctctgctaat gtgtctgatc cacatcttca agtctggaat gttccggaga atcacagcag  5400
ctgccactag actgttccgc agtgatggct gtggcggcag tttctacacc ctggacagct  5460
tgaatttgcg ggctcgttcc atgatcacca cccacccggc cctggtgctg ctctggtgtc  5520
agatcctgct gcttgtcaac cacaccgact accgctggtg ggcagaagtg cagcagaccc  5580
cgaaaagaca cagtctgtcc agcacaaagt tacttagtcc ccagatgtct ggagaagagg  5640
aggattctga cttggcagcc aaacttggaa tgtgcaatag agaaatagta cgaagagggg  5700
ctctcattct cttctgtgat tatgtctgtc agaacctcca tgactccgag cacttaacgt  5760
ggctcattgt aaatcacatt caagatctga tcagcctttc ccacgagcct ccagtacagg  5820
acttcatcag tgctgttcat cggaactccg ctgccagcgg cctcttcatc caggcaattc  5880
agtctcgttg tgaaaacctt tcaactccaa ccactctgaa gaaaactctt cagtgcttgg  5940
aggggatcca tctcagccag tcgggagctg tgctcacgtt gtatgtggac aggctgctgt  6000
gcacccttt ccgtgtgctg gctcgcatgg tcgacatcct tgcttgtcgc cgggtagaaa  6060
```

-continued

```
tgcttctggc tgcaaattta cagagcagca tggcccagtt gccaatggaa gaactcaaca  6120
gaatccagga ataccttcag agcagcgggc tcgctcagag acaccagagg ctctattccc  6180
tgctggacag gtttcgtctc tccaccatgc aagactcact tagtccctct cccccagtct  6240
cttcccaccc gctggacggg gacgggcacg tgtcactgga aacagtgagt ccggacaaag  6300
actggtacat tcatcttgtc aaatcccagt gttggaccag gtcagattct gcgctgctgg  6360
aaggtgcaga gctggtgaat cggattcctg ctgaagatat gagtgccttc atgatgaact  6420
cggagttcaa cctaagcctg ctagctccat gcttaagcct agggatgagt gaaatttctg  6480
gtggccagag gagtccgctt tttgaagcag cccgtgaggt gactctggcc cgcgtgagca  6540
gcaccgtgca gcagctccct gctgtccacc acgtcttcca gtccgacctg cctgcagagc  6600
cggcggccta ctggagcaag ttgaatgatc tatttgggga tgctgcgctg tatcagtccc  6660
tgaccactct ggcccgggcc ctggcacagt acctggtggc ggtctccaaa ctgcccagtc  6720
acttgcacct tcctcctgag aaagagaagg acaccatgaa attcgtggtg gcaacccttg  6780
aggccctgtc ctggcatttg atccatgagc agattccgct gagtctggat ctccaggcag  6840
ggctggactg ctgctgcctg gccctgcagc tgcctggcct ctggagcgtg gtctcctccg  6900
cagagtttgt gacccacgcc tgctccctca tccactgtgt gcacttcatc ctggaggccg  6960
ttgcagtgca gcctggagag cagcttctta gtccagaaag aaggacaaat accccaaaag  7020
ccatcagaga ggaggaggag gaaatagatc ctaacacaca gaatccgaag tatatcaccg  7080
cagcctgtga gatggtggca gaaatggtgg agtctctgca gtcggtgttg gctttgggtc  7140
ataaaaggaa tagtggcgtg ccggcgtttc tcacgtcagt gctcaggaac atcgtcgtca  7200
gcctggcccg cctgcccctt gtcaacagct acacacgtgt gcccccactg gtgtggaagc  7260
ttggatggtc acccaaaccg ggagggggatt ttggcacagc attccctgag atccccgtgg  7320
agttcctcca ggaaaaggaa gtctttaagg agttcatcta ccgcatcaac acgctaggct  7380
ggaccagtcg tactcagttt gaagaaactt gggccactct ccttggtgtc ctggtgacgc  7440
agcccctcgt gatggagcag gaggagagcc caccagaaga agacacagag aggacgcaga  7500
tcaacgtcct ggccgtgcag gccatcacct cactggtgct cagtgcaatg accgtgcctg  7560
tggccggcaa cccagctgtg agctgcttgg agcagcagcc tcggaacaag cctctgaaag  7620
ctctggacac caggtttggg aggaagctga gcattatcag agggattgta gagcaagaga  7680
ttcaagcaat ggtttcaaag agagagaaca tcgccaccca tcatttatac caggcgtggg  7740
atcctgtccc ttctctgtcc ccggctacca caggtgccct catcagccac gagaagctgc  7800
tgctgcagat caaccccgag cgggagctgg ggagcgtgag ctacaaactc ggccaggtgt  7860
ccatacactc tgtgtggctg gggaacagca tcacacccct aagggaggag gaatgggacg  7920
aggaggagga ggaggaggcc gacgcccctg caccttcatc accacccacg tctccagtca  7980
actccaggaa acaccgggct ggagttgaca tccattcctg ttcgcagttt ttactcgagt  8040
tgtacagccg ctggatcctg ccatccaact cagccaggag gaccccggcc atcctgatca  8100
gtgaggtggt tcgatccctt ctggtggtct cagacttgtt cactgagcgc aaccagtttg  8160
agctgatgta tgtgacgctg acagaactgc gaagggtgca tccttcagaa gacgagatcc  8220
tcgctcagta cctggtgccc gccacctgca aggcagctgc cgtccttggg atggacaagg  8280
tcgtggcgga gcctgtcagc cgcctgctgg agagcacact caggagcagc cacctgccca  8340
gcagggtcgg agccctgcac ggcatcctct atgtgctgga gtgcgacctg ctggacgata  8400
ctgccaagca gctcatccca gtcatcagtg actatctcct ctccaacctg aaagggatcg  8460
cccactgcgt gaacattcac agccagcagc acgtactggt catgtgtgcc actgcgtttt  8520
acctgattga gaactatcct ctggacgtag ggccagaatt ttcagcatca ataatacaga  8580
tgtgtggggt gatgctgtcc ggaagtgagg agtccacccc ctctatcatt taccactgtg  8640
ccctcagagg cctggagcgc ctcctgctct ctgagcagct ctcccgcctg gatgcagaat  8700
ccctggtcaa gctgagtgtg gacagagtga acgtgcacag cccgcaccgg gccatggcgg  8760
ctctgggctt gatgctcacc tgcatgtaca caggaaagga gaaagtcagt ccgggtagaa  8820
cttcagaccc taatcctgca gccccagaca gcgagtcggt gattgttgct atggagcggg  8880
tgtctgttct ttttgatagg atcaggaaag gctttccttg tgaagccaga gtggtggcga  8940
ggatcctgcc ccagtttcta gatgacttct tcccacccca ggacatcatg aacaaagtca  9000
tcggagagtt tctgtccaac cagcagccat acccccagtt catggccacg gtggtgtata  9060
aggtgtttca gactctgcac agcaccgggc agtcatccat ggtccgggac tgggtcatgc  9120
tgtccctctc caacttcacg cagaggaccc cagtcgccat ggccacatgg agcctctcct  9180
gcttcttcgt cagcgcgtcc accagcccat gggttgcggc gatcctccca catgtcatca  9240
gcaggatggg aaagctggag caggtggacg tcaacctttt ctgcctggtt gccacagact  9300
tttacagaca ccagatagag gaggagctcg accgcagggc cttccagtct gtgtttgagg  9360
tggttgcagc tccaggaagc ccatatcacc ggctgctgac ttgtttacga aatgtccaca  9420
aggtcaccac ctgctgagcg ccatggtggg agagactgtg aggcggcagc tggggctgga  9480
gcctccagaa atctgcgccc tgtgccctgc ctccaccgag ccagcttggt ccctgtgggc  9540
ttccgcacat gccgcgggcg gccaggcaac gtgcgtgtct ctgccatatg gcagaagtgc  9600
tctttgtggt acagtggcca ggcaaggagt atctgcagtc ccggtggggc tgagcctgag  9660
gccttccgga gagcaggagc agctgtgctg cacgccatgt gggtgaccag gtcctttctc  9720
ctgatgctca cctgttgggt gttgccaggc tgcagctgct cttgcatctg ggccggaagt  9780
cctccctcct gcaggctggc tgtgggcccc tctgctgtcc tgcagtagaa ggtgccgtga  9840
gcaggctttg ggaacactgg cctgtgtctt cctggtgggg tgtgcatgcc acgccctgtg  9900
tctgtatgca cagatgccat ggcatgtgct gggccagtgg ctgggggtgc tagacaccca  9960
gcaccattct cccttctctc ttttcttctc aggatttaaa atttaattat atcagtaaag  10020
agattaattt taacgtaact ctttctatgc ccgtgtaaag tatgtgaatt gcaaggcctg  10080
tgctgcatgc gacagtgttc ggggaggtgg gcagggcccc tggccacgct ccctctcctg  10140
tagccactgg catagccttc ctgagcaccc gctgacattt ccgttgtaca tgttcctgtt  10200
tatgcattca caaggtgact gggatgtaga gaggcgctag tgtgcaggtg gccacagcag  10260
gactaaggac aggcccccac tgtcctaggg gcatgctcgc ctgcagcccc tccttcttgg  10320
gcacagacaa ctgttgttct ccacccacat tagggacagc agcctcccta tcagctgaga  10380
aggccagccc tccctggctg tgagcagcct ccgctgtgtc cagagacatg ggcctcccac  10440
tcctgttcct tgctagccct ggggcggtgt ctgcccagga gctggctggc cggtgttggg  10500
atctgccgtt ccatggatgc atgccccaag ggtgtcactg agctgtgttt tgtctgagcc  10560
tctcttggtc aacagcaaag cttggcgtct tggcactgtt agtgacagag cctggcatcc  10620
cttctgcccc cgttccagct gacatcttgc acggggaccc cttttagtca ggagagtgca  10680
gatctgtgct cattggagac tgccccactg ccctgtcaga gccgccactc ctatccccag  10740
gccaggtccc tggaccagcc tcttgtttgc aggcccagag gagccaagtc attaaaatgg  10800
```

```
aagtggattc tggatggccg gctgctgctg acataggagc tggatttggg agctctgaga  10860
tggggcagga gctctgcttc ctcagccctt gaggcgagcc aggcgaggtt ggcgactgtc  10920
atgtggcttg gtttgctcat gcctgttgat gttttgggta ttgaatatgg taagtggagg  10980
aaatgctttt ctggagtctg tgcaggtgct gccttgagac cctcaagctt ccacctgtcc  11040
ctctcctatg tggcagctga ggagcagctg acatgtggac ttgtgtgctg cccacataca  11100
tgaggggcg ctgaaaggga gcccctgctc aaagggagcc cctcctctga gcagcctttg  11160
acaggcctgt atgaggcttt tcccaccagc tcccaacaga ggcctccccc agccaggacc  11220
acctcgtcct cgtggcaggg cagcaggagc ggtagaaagg ggtctgatgt ttgaggaggc  11280
ccttaaggga agctactgaa ttttaacaag aaaaccaccg ttcttccgta ttggttgggg  11340
gctcctgttt ctcatcctag cttcttcctg gaaagcctgc tagaagcttt gggaatgagg  11400
ggaaagttct cagaaccgtt gctgctcccc acccacctcc cctgcagtaa gttatgtcaa  11460
cagctcggag acagaagtat cacaggccag atgttgttct gctagatgtt tacatttgta  11520
agaaataaca ctgtgaatgt aaaacggagc cattcccctt ggaatgcata tcgctgggct  11580
caacacagag tttgtcttcc ttttgtttac gacgtgatct aaaacagtcc ttagcaaggg  11640
gctcagaaca ccccgctctg gcagtgggtg tcccccactc ccaaaggcct gcctgtgtgc  11700
tccagagatg aatatgagct cattagtaaa atgactttac ccatgcgtaa gtcaagtaca  11760
cgtgcacgtg catatggaca catctgtagt tttatacacg cacatctcaa gacagagatg  11820
catggcctcc aagagtgccc gtgtcggttc ttcctggaag ttgactttcc tcagacctgc  11880
caggtaaagt tagctgtgtg acgggcgtcc aggcgcgggg cttggtcaga gcagggctca  11940
ttcatggctc actaggatcc caccggagaa aacggtctcc atatcaactc tgccgaaggg  12000
aggaagactt tgtcgcgttc ctaaaaaacc tatggcaagc accaatcata ttatccaaat  12060
tttgttgaaa atgtgattaa tttggttgtc aagttttggg ggtgagctgt ggggagactg  12120
cttttgtttt gctgctggta atatcaggaa agactttaat gaaaccaggg tagaattgtt  12180
tggcaatgca ctgaagcgcg tttctttccc aaaacgtgcc tcccttccgc tgcgggccca  12240
gctgagtctg tgtaggtgac gtttccggct gccaagcgct ctttgttact gtccaccccc  12300
atttctgcca gcacacgtgt cctttcagga ggaaaatgtg aagctgaaac ccctccagac  12360
acccagaatg tagcatctga gaaggccctg tgccctaaag gacaccccg cccccacctt  12420
catggagggg tcattccaga gccctcggag ccgatgaaca gctcgtcctc ttggagctga  12480
gctgagcccc ccacggagct cgggacggat agtaaacagc aataactcgg tctgtggctg  12540
cctggcaggt ggaagttcct ccccctgagg ggcggagtga ggttagttct gtgtgtctgt  12600
ggggtggagt cagcctgctc ctgctacctg tgagcatcct gcccagcaga catcctcacc  12660
cggctttgtc cctccccact tcctccctct gcggggagga cccaggacca cagctgctgg  12720
ccagggtagg cttggagctg tgctccggag gggccacctg agggagcgag aagaaggaag  12780
atcttgagag ctgccgaggc accctggaga gctcaggatg gtccaggcga gaagaggaca  12840
ctcgctcgcc aggcctgggc ctcctgggaa ggagggagcc gctcagagcg ccgcatgaca  12900
actgaaggca acctggaagg ttcagaggcc actcttcccc cgtgtgcctg tcacgctctg  12960
gtgcagtcca aggaacgcct tcccctcagt tgtttccaaa agcagagtct cccgctgcaa  13020
tctgggtggt gattgccagc cttggaggat tgtggccaac gtggacctgc ctacggaggg  13080
tgggctctga cccacgtggg gcctccttgt ccaggtctca ttgctttgcg ctgtggtcag  13140
agggactgtc agctgagcct gagctcccct ggagccagca gggctgtgat gggtgagtcc  13200
cggagcccca cccagacctg actgcttctg agagcaaagg gaaggactga cgagagatgt  13260
atatttaatt tttttaactg ctgcaaacat tgtacatcca aattaaagga aaaacattga  13320
aaccatca                                                           13328
```

```
SEQ ID NO: 5            moltype = DNA  length = 13447
FEATURE                 Location/Qualifiers
source                  1..13447
                        mol_type = genomic DNA
                        organism = Macaca mulatta
SEQUENCE: 5
gcaaggcgcc gcgggggctg ccgggacggg tccaagatgg acggccgctt cggttccgct  60
tttacccgcg gcccagagcc ccattcattg ccccggtgct gagcggcgct gcgagtcggc  120
ccgaggcctc cggggactgc ctagccgggc gggagaccgc catggcgacc ctggaaaagc  180
tgatgaaggc cttcgagtct ctcaagtcct tccagcagca gcagcagcag cagcagcagc  240
aacagccgcc gccgccgccg ccgccgccgc ctcctcctcc tcagcttcct cagccgccgc  300
aggcacagcc gatgctgcct cagccgcagc cgcccccgcc gccgccccg ccaccacccg  360
gcccggctgt ggctgaggag ccgctgcacc gaccaaagaa agaactttca gctaccaaga  420
aagaccgtgt gaatcattgt ctgacaatat gtgaaaacat agtggcacag tctgtcagaa  480
attctccaga atttcagaaa cttctgggca tcgctatgga actttttctg ctgtgcagtg  540
atgacgcaga gtcggatgtc agaatggtgg ctgatgaatg cctcaacaaa gttatcaaag  600
ctttgatgga ttctaatctt ccaaggttac agctcgagct ctataaagaa attaaaaaga  660
atggtgcccc tcggagtttg cgtgctgccc tgtggaggtt tgccgagctg gctcacctgg  720
ttcggcctca gaaatgcagg ccttacctgg tgaaccttct gccgtgccta agtcgaacaa  780
gcaagagacc cgaggaatca gtccaggaga ccttggctgc agctgttccc aaaattatgg  840
cttctttcgg caattttgca aatgacaatg aaattaaggt tttgttaaag gccttcatag  900
cgaacctgaa gtcaagctcc cccactattc ggcggacagc tgctggatca gcagtgagca  960
tctgccagca ctcaagaagg acacagtatt tctatagctg gctactaaat gtgctcttag  1020
gcttactggt tcctgtcgag gaggagcact ccaccctgct gattcttggc gtgctgctca  1080
ccctgaggta tttggtgccc ttgctgcagc agcaggtcaa ggatacaagc ctgaaaggca  1140
gcttcggagt gacacggaaa gaaatggagg tctctccttc tgcagagcag cttgtccagg  1200
tttatgaact gacgttacat catacacagc accaagacca caatgttgtg accggagccc  1260
tggagctgtt gcagcagctc ttcagaacgc ctcccccga gcttctgcaa gccctgacca  1320
cagtggggg cattgggcag cttaccgccg ctaaggagga gtctggtggc cgaagccgta  1380
gtgggagtat tgtggaactt atagctggag gggttcctc atgcagccct gtcctttcaa  1440
gaaaacaaaa aggcaaagtg ctcttaggag aagaagaagc cttggaggat gactctgaat  1500
cgagatcgga tgtcagcagc tctgcctttg cagcctcagt gaaggatgat atcagtggag  1560
agctggctac ttcttcaggg gtttccactc cagggtcagc aggtcacgac atcatcacgg  1620
agcagccacg gtcacagcac acgctgcagg cggactcagt ggatctggcc agctgtgact  1680
tgacaagctc tgccacggat ggggatgagg aggatatctt gagccacagc tccagccagg  1740
```

-continued tcagcgccgt cccatctgac cctgccatgg acctgaatga tgggacccag gcctcctcgc 1800
ccatcagcga cagctcccag accaccaccg aagggcctga ttcagctgtc acccccttcag 1860
acagttctga aattgtgtta gacggtaccg acaaccagta tttgggcctg cagattggac 1920
agccccagga tgaagatgag gaagccacag gtgttcttcc tgacgaagcc tcggaggcct 1980
tcaggaactc ttccatggcc cttcaacaag cacatttatt gaaaaacatg agtcacagca 2040
ggcagccttc tgacagcagt gttgataaat ttgtgttgag agatgaagct actgaaccgg 2100
gtgatcaaga aaacaagcct tgccgcatca aaggtgacat tggacagtcc actgatgatg 2160
attctgcacc tcttgtccat tgtgtccgcc ttttatctgc ttcatttttg ctaacagggg 2220
gaaaaaatgt gctggttccg gaccgggatg tgagggtcag cgtgaaggcc ctggccctca 2280
gctgtgtggg agcagctgtg gctctccacc cagaatcttt cttcagcaaa ctctataaag 2340
ttcctcttga caccacagaa taccctgagg aacaatatgt ctcagatatc ttgaactaca 2400
tcgatcatgg agacccacag gttcgaggag ccactgccat tctctgtggg accctcatct 2460
gctccatcct cagcaggtcc cgcttccacg tgggagattg gatgggcgcc attagaaccc 2520
tgacaggaaa cacatttttct ttggcggatt gcattccttt gctgcggaaa acactgaagg 2580
acgagtcttc tgtcacttgc aagctggcct gtacagctgt gaggcattgt gtcatgagtc 2640
tctgcagcag cagctacagt gagttaggac tgcagctgat catcgacgtg ctgactctga 2700
ggaacagttc ctattggctg gtgaggacag agcttctgga aacccttgcg gagattgact 2760
tcaggctggt gagctttttg gaggcaaaag cagaaaactt acacagaggg gctcatcatt 2820
atacagggct tttaaagctg caagaacgag tgctcaataa tgttgtcatc catttgcttg 2880
gggatgaaga ccccagggtg cgacatgttg ctgcagcatc attaattagg cttgtcccaa 2940
agctgtttta taaatgtgac caaggacaag ctgacccagt agtggccgtg gcaagagatc 3000
aaagcagtgt ttacctgaaa cttctcatgc atgagacgca gcctccatct catttctccg 3060
tcagcacaat aaccagaata tacagaggct ataacctact gccaagcata acagatgtca 3120
ctatggaaaa taacctttca agagttattg cagcagtttc tcatgaactg atcacatcaa 3180
ccacgagagc actcactttt ggatgctgtg aagctttgtg tcttctttcc actgccttcc 3240
cagtttgcat ttggagttta ggttggcact gtggagtgcc tccactgagc gcctccgatg 3300
agtctaggaa gagctgtacc gttgggatgg ccacgatgat tctgaccctg ctctcgtcag 3360
cttggttccc attggatctc tcagcccatc aagatgcttt gattttggcc ggaaacttgc 3420
ttgcagccag tgctcctaaa tctctgagaa gttcatgggc ctctgaagaa gaagccaacc 3480
cagcagccac caagcaagag gaggtctggc cagccctggg ggaccgggcc ttggtgccca 3540
tggtggagca gctcttctcc cacctgctga aggtgatcaa catttgtgca catgtcctgg 3600
acgacgtggc tcctggaccg gcaataaagg cagccttgcc ttctctaaca aacccccctt 3660
ctctaagtcc catccgacga aaggggaagg agaaagaacc aggagaacaa gcatctgtac 3720
cgttgagtcc caagaaaggc agtgaggcca gtgcagcttc tagacaatct gatacctcag 3780
gtcctgttac aacaagtaaa tcctcatcac tggggagttt ctatcatctt ccttcatacc 3840
tcaaactgca tgatgtcctg aaagctacgc acgctaacta caaggtcacc ttggatcttc 3900
agaacagcac ggaaaaattt ggagggtttc ttcgctcagc cttggacgtt ctctctcaga 3960
ttctagagct ggccacactg caggacattg ggaagtgtgt tgaggagatc ctaggatacc 4020
tgaaatcctg ctttagtcga gaaccaatga tggcaactgt ttgtgttcaa caattgttga 4080
agactctctt tgggacaaac ttggcctccc agtttgacgg cttatcatcc aaccccagca 4140
agtcacaagg ccgagcacag cgccttggct cctccagtgt gaggccaggc ttgtaccact 4200
actgcttcat ggcccgtac acccacttca cccaggccct cgctgacgcc agcctgagga 4260
acatggtgca ggcggagcag gagcacgaca cctcgggatg gtttgatgtc ctccagaaag 4320
tgtctaccca gttgaagacg aacctcacaa gtgtcacaaa gaaccgtgca gataagaatg 4380
ctattcataa tcacattcgt ttgtttgaac ctcttgttat aaaagcttta aaacagtaca 4440
cgacaacaac atctgtgcag ttacagaagc aggttttaga tttgctggcg cagctggttc 4500
agttacgggt taattactgt cttctggatt cagatcaggt gtttattggc tttgtattga 4560
aacagttcga atacattgaa gtgggccagt tcagggaatc agaggcaatc attccaaaca 4620
tctttttctt cttggtatta ctgtcttatg aacgctatca ttcaaaacag atcattggaa 4680
ttcctaaaat cattcagctc tgtgatggca tcatggccag tggaaggaag gctgtgacac 4740
acgccatacc ggctctgcag cccatagtcc atgacctttt tgtattaaga ggaacaaata 4800
aagctgatgc aggaaaagag cttgaaaccc aaaaagaagt ggtggtatca atgttactga 4860
gactcatcca gtaccatcag gtgttggaga tgttcattct cgtcctgcag cagtgccaca 4920
aggagaatga agacaagtgg aagcgactgt ctcgacagat agctgacatc atcctcccaa 4980
tgttagccaa acagcagatg cacattgact ctcatgaagc ccttggagtg ttaaatacat 5040
tatttgagat tttggcccct tcctccctcc gtccggtgga catgctttta cggagtatgt 5100
tcgtcactcc aaacacaatg gcatctgtga gcactgttca actgtggata tcaggaattc 5160
tggccatttt gagggttctg atttcccagt caactgaaga tattgttctt tctcgtattc 5220
aggagctctc tttctctcca tatttaatct cctgtccagt aattaatagg ctaagagatg 5280
gggacagtaa ttcagcacta gaagaacaca gtgaagggaa acaaataaag aatttgccag 5340
aagaaacatt ttcaaggttt ctattacaac tggtgggtat tcttttagaa gacattgtta 5400
caaaacagct gaaggtggaa atgagtgagc agcaacatac tttctattgc caagaactag 5460
gcactctgct aatgtgtctg atccacatct tcaagtctgg aatgttccgg agaatcacag 5520
cagctgccac tagactgttc cgcagtgatg gctgtggcgg cagtttctac accctggaca 5580
gcttgaattt gcgggctcgt tccatgatca ccacccaccc ggccctggtg ctgctctggt 5640
gtcagatcct gctgcttgtc aaccacaccg actaccgctg gtgggcagaa gtgcagcaga 5700
ccccgaaaag acacagtctg tccagcacaa agttacttag tccccagatg tctggagaag 5760
aggaggattc tgacttggca gccaaacttg gagtgtgcaa tagagaaata gtacgaagag 5820
gggctctcat tctcttctgt gattatgtct gtcagaacct ccatgactcc gagcacttaa 5880
cgtggctcat tgtaaatcac attcaagatc tgatcagcct ttcccacgag cctccagtac 5940
aggacttcat cagtgctgtt catcggaact ccgctgccag cggcctcttc atccaggcaa 6000
ttcagtctcg ttgtgaaaac ctttcaactc caaccactct gaagaaaact cttcagtgct 6060
tggaggggat ccatctcagc cagtcgggag ctgtgctcac gttgtatgtg gacaggctgc 6120
tgtgcacccc tttccgtgtg ctggctcgca tggtcgacat ccttgcttgt cgccgggtag 6180
aaatgcttct ggctgcaaat ttacagagca gcatggccca gttgccaatg gaagaactca 6240
acagaatcca ggaatacctt cagagcagcg ggctcgctca gagacaccag aggctctatt 6300
ccctgctgga caggtttcgt ctctccacca tgcaagactc acttagtccc tctcccccag 6360
tctcttccca cccgctggac ggggatgggc acgtgtcact ggaaacagtg agtccggaca 6420
aagactggta cattcatctt gtcaaatccc agtgttggac caggtcagat tctgcactgc 6480

```
tggaaggtgc agagctggtg aatcggattc ctgctgaaga tatgagtgcc ttcatgatga  6540
actcggagtt caacctaagc ctgctagctc catgcttaag cctagggatg agtgaaattt  6600
ctggtggcca gaagagtccg ctttttgaag cagcctgtga ggtgactctg gcccgcgtga  6660
gcagcaccgt gcagcagctc cctgctgtcc accacgtctt ccagtccgac ctgcctgcag  6720
agccggcggc ctactggagc aagttgaatg atctatttgg ggatgctgcg ctgtatcagt  6780
ccctgaccac tctggcccgg gccctggcac agtacctggt ggcggtctcc aaactgccca  6840
gtcacttgca ccttcctcct gagaaagaga aggacaccat gaaattcgtg gtggcaaccc  6900
ttgaggccct gtcctggcat ttgatccatg agcagattcc gctgagtctg gatctccagg  6960
cagggctgga ctgctgctgc ctggccctgc agctgcctgg cctctggagc gtggtctcct  7020
ccgcagagtt tgtgacccac gcctgctccc tcatccactg tgtgcacttc atcctggagg  7080
ccgttgcagt gcagcctgga gagcagcttc ttagtccaga aagaaggaca aataccccaa  7140
aagtcatcag agaggaggag gaggaaatag atcctaacac acagaatccg aagtatatca  7200
ccgcagcctg tgagatggtg gcagaaatgg tggagtctct gcagtcggtg ttggctttgg  7260
gtcataaaag gaatagtggc gtgccggcgt ttctcacgtc agtgctcagg aacatcgtcg  7320
tcagcctggc ccgcctgccc cttgtcaaca gctacacacg tgtgccccca ctggtgtgga  7380
agcttggatg gtcacccaaa ccgggagggg attttggcac agcattccct gagatccccg  7440
tggagttcct ccaggaaaag gaagtcttta aggagttcat ctaccgcatc aacacgctag  7500
gctggaccag tcgtactcag tttgaagaaa cttgggccac tctccttggt gtcctggtga  7560
cgcagcccct cgtgatggag caggaggaga gcccaccaga agaagacaca gagaggacgc  7620
agatcaacgt cctggccgtg caggccatca cctcactggt gctcagtgca atgaccgtgc  7680
ctgtggccgg caacccagct gtgagctgct tggagcagca gcctcggaac aagcctctga  7740
aagctctgga caccaggttt gggaggaagc tgagcattat cagagggatt gtagagcaag  7800
agattcaagc aatggtttca aagagagaga acatcgccac ccatcattta taccaggcgt  7860
gggatcctgt cccttctctg tccccggcta ccacaggtgc cctcatcagc cacgagaagc  7920
tgctgctgca gatcaacccc gagcgggagc tggggagcgt gagctacaaa ctcggccagg  7980
tgtccataca ctctgtgtgg ctggggaaca gcatcacacc cctaagggag gaggaatggg  8040
acgaggagga ggaggaggag gccgacgccc ctgcaccttc atcaccaccc acgtctccag  8100
tcaactccag gaaacaccgg gctggagttg acatccattc ctgttcgcag tttttactcg  8160
agttgtacag ccgctggatc ctgccatcca actcagccag gaggaccccg gccatcctga  8220
tcagtgaggt ggttcgatcc cttctggtgg tctcagactt gttcactgag cgcaaccagt  8280
ttgagctgat gtatgtgacg ctgacagaac tgcgaagggt gcatccttca gaagacgaga  8340
tcctcgctca gtacctggtg cccgccacct gcaaggcagc tgccgtcctt gggatggaca  8400
aggtcgtggc ggagcctgtc agccgcctgc tggagagcac actcaggagc agccacctgc  8460
ccagcagggt cggagccctg cacggcatcc tctatgtgct ggagtgcgac ctgctggacg  8520
atactgccaa gcagctcatc ccagtcatca gtgactatct cctctccaac ctgaaaggga  8580
tcgcccactg cgtgaacatt cacagccagc agcacgtact ggtcatgtgt gccactgcgt  8640
tttacctgat tgagaactat cctctggacg tagggccaga attttcagca tcaataatac  8700
agatgtgtgg ggtgatgctg tccggaagtg aggagtccac cccctctatc atttaccact  8760
gtgccctcag aggcctggag cgcctcctgc tctctgagca gctctcccgc ctggatgcag  8820
aatccctggt caagctgagt gtggacagag tgaacgtgca cagcccgcac cgggccatgg  8880
cggctctggg cttgatgctc acctgcatgt acacaggaaa ggagagaaagtc agtccgggta  8940
gaacttcaga ccctaatcct gcagccccag acagcgagtc ggtgattgtt gctatggagc  9000
gggtgtctgt tctttttgat aggatcagga aaggctttcc ttgtgaagcc agagtggtgg  9060
cgaggatcct gccccagttt ctagacgact tcttcccacc ccaggacatc atgaacaaag  9120
tcatcggaga gtttctgtcc aaccagcagc cataccccca gttcatggcc accgtggtgt  9180
ataaggtgtt tcagactctg cacagcaccg ggcagtcatc catggtccgg gactgggtca  9240
tgctgtccct ctccaacttc acacagagga ccccagtcgc catggccaca tggagcctct  9300
cctgcttctt cgtcagcgcg tccaccagcc catgggttgc ggcgatcctc ccacatgtca  9360
tcagcaggat gggaaagctg gagcaggtgg acgtcaacct tttctgcctg gttgccacag  9420
acttttacag acaccagata gaggaggagc tcgaccgcag ggccttccag tctgtgtttg  9480
aggtggttgc agctccagga agcccatatc accggctgct gacttgttta cgaaatgtcc  9540
acaaggtcac cacctgctga gcgccatggt gggagagact gtgaggcggc agctggggct  9600
ggagcctcca gaaatctgcg ccctgtgccc tgcctccacc gagccagctt ggtccctgtg  9660
ggcttccgca catgccgcgg gcggccagcc aacgtgcgtg tctctgccat atggcagaag  9720
tgctctttgt ggtacagtgg ccaggcaagg agtatctgca gtcccggtgg ggctgagcct  9780
gaggccttcc ggagagcagg agcagctgtg ctgcacgcca tgtgggtgac caggtccttt  9840
ctcctgatgc tcacctgttg ggtgttgcca ggctgcagct gctcttgcat ctgggccgga  9900
agtcctccct cctgcaggct ggctgtgggc ccctctgctg tcctgcagta gaaggtgccg  9960
tgagcaggct ttgggaacac tggcctgtgt cttcctggtg gggtgtgcat gccacgccct  10020
gtgtctgtat gcacagatgc catggcatgt gctgggccag tggctggggg tgctagacac  10080
ccagcaccat tctcccttct ctcttttctt ctcaggattt aaaatttaat tatatcagta  10140
aagagattaa ttttaacgta actctttcta tgcccgtgta aagtatgtga attgcaaggc  10200
ctgtgctgca tgcgacagtg ttcggggagg tgggcagggc ccctggccac gctccctctc  10260
ctgtagccac tggcatagcc ttcctgagca cccgctgaca tttccgttgt acatgttcct  10320
gtttatgcat tcacaaggtg actgggatgt agagaggcgc tagtgtgcag gtggccacag  10380
caggactaag gacaggcccc cactgtccta ggggcatgct cgcctgcagc ccctccttct  10440
tgggcacaga caactgttgt tctccaccca cattagggac agcagcctcc ctatcagctg  10500
agaaggccag ccctccctgg ctgtgagcag cctccgctgt gtccagagac atgggcctcc  10560
cactcctgtt ccttgctagc cctggggcgg tgtctgccca ggagctggct ggccggtgat  10620
gggatctgcc gttccatgga tgcatgcccc aagggtgtca ctgagctgtg ttttgtctga  10680
gcctctcttg gtcaacagca aagcttggcg tcttggcact gttagtgaca gagcctggca  10740
tcccttctgc ccccgttcca gctgacatct tgcacgggga cccctttag tcaggagagt  10800
gcagatctgt gctcattgga gactgcccca ctgccctgtc agagccgcca ctcctatccc  10860
caggccaggt ccctggacca gcctcttgtt tgcaggccca gaggagccaa gtcattaaaa  10920
tggaagtgga ttctggatgg ccggctgctg ctgacatagg agctggattt gggagctctg  10980
agatggggca ggagctctgc ttcctcagcc cttgaggcga gccaggcgag gttggcgact  11040
gtcatgtggc ttggtttgct catgcctgtt gatgttttgg gtattgaata tggtaagtgg  11100
aggaaatgct tttctggagt ctgtgcaggt gctgccttga gaccctcaag cttccacctg  11160
tccctctcct atgtggcagc tgaggagcag ctgacatgtg gacttgtgtg ctgcccacat  11220
```

```
acatgagggg gcgctgaaag ggagcccctg ctcaaaggga gcccctcctc tgagcagcct  11280
ttgacaggcc tgtatgaggc ttttcccacc agctcccaac agaggcctcc cccagccagg  11340
accacctcgt cctcgtggca gggcagcagg agcggtagaa aggggtctga tgtttgagga  11400
ggcccttaag ggaagctact gaattttaac aagaaagcca ccattcttcc gtattggttg  11460
ggggctcctg tttctcatcc tagcttcttc ctggaaagcc tgctagaagc tttgggaatg  11520
aggggaaagt tctcagaacc gttgctgctc cccacccacc tcccctgcag taagttatgt  11580
caacagctcg gagacagaag tatcacaggc cagatgttgt tctgctagat gtttacattt  11640
gtaagaaata acactgtgaa tgtaaaacgg agccattccc cttggaatgc atatcgctgg  11700
gctcaacaca gagtttgtct tccttttgtt tacgacgtga tctaaaacag tccttagcaa  11760
ggggctcaga acaccccgct ctggcagtgg gtgtccccca ctcccaaagg cctgcctgtg  11820
tgctccagag atgaatatga gctcattagt aaaatgactt tacccatgcg taagtcaagt  11880
acacgtgcac gtgcatatgg acacatctgt agttttatac acgcacatct caagacagag  11940
atgcatggcc tccaagagtg cccgtgtcgg ttcttcctgg aagttgactt tcctcagacc  12000
tgccaggtaa agttagctgt gtgacgggcg tccaggcgcg gggcttggtc agagcagggc  12060
tcattcatgg ctcactagga tcccaccgga gaaaacggtc tccatatcaa ctctgccgaa  12120
gggaggaaga ctttgtcgcg ttcctaaaaa acctatggca agcaccaatc atattatcca  12180
aattgtgttg aaaatgtgat taatttggtt gtcaagtttt gggggtgagc tgcggggaga  12240
ctgcttttgt tttgctgctg gtaatatcag gaaagacttt aatgaaacca gggtagaatt  12300
gtttggcaat gcactgaagc gcgtttctgt cccaaaacgt gcctcccttc cgctgcgggc  12360
ccagctgagt ctgtgtaggt gacgtttccg gctgccaagc gctctttgtt actgtccacc  12420
cccatttctg ccagcacacg tgtcctttca ggaggaaaat gtgaagcgga aacccctcca  12480
gacacccaga atgtagcatc tgagaaggcc ctgtgcccta aaggacaccc ccgcccccac  12540
cttcatggag gggtcattcc agagccctcg gagccgatga acagctcgtc ctcttggagc  12600
tgagctgagc cccccacgga gctcgggacg gatagtaaac agcaataact cggtctgtgg  12660
ctgcctggca ggtggaagtt cctccccctg aggggcggag tgaggttagt tctgtgtgtc  12720
tgtggggtgg agtcagcctg ctcctgctac ctgtgagcat cctgcccagc agacatcctc  12780
acccggcttt gtccctcccc acttcctccc tctgcgggga ggacccagga ccacagctgc  12840
tggccagggt aggcttggag ctgtgctccg gaggggccac ctgagggagc gagaagaagg  12900
aagatcttga gagctgccga ggcaccctgg agagctcagg atggtccagg cgagaagagg  12960
acactcgctc gccaggcctg ggcctcctgg gaaggaggga gccgctcaga gcgctgcatg  13020
acaactgaag gcaacctgga aggttcagag gccactcttc ccccgtgtgc ctgtcacgct  13080
ctggtgcagt ccaaggaacg ccttccctca gttgtttcca aaagcagagt ctcccgctgc  13140
aatctgggtg gtgattgcca gccttggagg attgtggcca acgtggacct gcctacggag  13200
ggtgggctct gacccacgtg gggcctcctt gtccaggtct cattgctttg cgctgtggtc  13260
agagggactg tcagctgagc ctgagctccc ctggagccag cagggctgtg atgggcgagt  13320
cccggagccc cacccagacc tgactgcttc tgagagcaaa gggaaggact gacgagagat  13380
gtatatttaa ttttttaac  tgctgcaaac attgtacatc caaattaaag gaaaaacatt  13440
gaaacca                                                            13447
```

```
SEQ ID NO: 6            moltype = DNA  length = 13498
FEATURE                 Location/Qualifiers
source                  1..13498
                        mol_type = genomic DNA
                        organism = Homo sapiens
SEQUENCE: 6
ttttttttt ttttttttga tggtttccat ttttttcctt taatttggat gtacaatgtt  60
tgcagcagtt aaaaaattaa atatacatct ctcgtcagtc cttccctttg ctctcagaag  120
cattcaggtc tgggtggggc tccgggactc gcccatcaca gccctgctgg ctccagggga  180
gctcaagctc agctgacagt ccctctgacc acggtgcaaa gcagtgagac ctggacaagg  240
aggccccact tgggtcagag cccaccctcc gtaggcaggt ccacgttggc cacgatcctc  300
caaggctggc agttaccacc cagattgcag cgggagactc tgctcttaga aacaactgag  360
gggaaggcgt tcctttgact gcaccagagc gtgacaggca catgggggaa gagcggcccc  420
tgaaccttcc aggttgcctt cagttgtcat gcggcattct gagcagctcc ctccttccca  480
ggaggcccag gcccggcaag cgagtgtcct cgtctgagcc atcctgagct ctccaaggtc  540
cctcagcagc tctcaagatc ttccttcttc tcactcctac acgtgacccc tctggaggac  600
agctccaagt ctaccctggc cagcagctgt ggtcccgggt cctccccgca gagggaggaa  660
gcgggggagg gacaaagccc gatgaggatg tctgctggga aggatgctca caggtagcaa  720
gagaagcctg actccaccca ccagacacac agaactaacc tcactccacc ccgcaacggg  780
aggaagttcc acctgccagg cggccacaca ccgagttatt gctgtctact atccgtcccg  840
agctccacgt ggggctcatc tcagctccaa gaggaggagc tgttcattgg ctccgagggc  900
tctgaaatga cccccctcat gaagatgggg gcgaggggtg tcctttaggg cacagggcct  960
tctcagatgc tacattctgg gtgtctggag ggggttcagc ttcacatttt ccccttgaaa  1020
ggacacatgc gctggcagaa atgagggtgg acagtaacaa agagcacttg gcagctggaa  1080
acatcaccta catagactca gctgggcccg cagcggaagg gaggcacatt ttgggaaaga  1140
aacacgcttc agtgcattgc caaacaattc taccctggtt tcattaaaat ctttcccgat  1200
attaccagca ggaaaacaaa agcaatctcc ccacagccca cccccaaaac ttgacaacca  1260
aattaatcac atttgcaaca aaatttggat aatacgatgg gtgcttgcca cagattttta  1320
ggaacatgat aaagtcttcc tcccttctgc agagagctga tatggagacc atcttcgcca  1380
gtgggatcct agtgggcaat gaatgagccc tgccctgacc acgtcccacg cctggatgtc  1440
cgtcacgcgg ctaacttgac ctggcgggtc taaggaaagt caacttccag gaagaaccga  1500
cacgggcact cttagaggcc atgcatctcc gtcttgagag gtgtgtgtgt aaaattatag  1560
atgtgtctat atgcacatgc atggatactt tatgtatatg cgtgggtgaa gtcattttta  1620
ctaatgagct catattcatc tccggagcac acaggcaggt ctttgggggt gggggacacc  1680
tactgccaga gcggggtgtt ctgagcccct tgctaaggac tggtttagat cacgtcgtaa  1740
acaagaggaa gacaaactct atgttgagcc cagcgatatg cattccaagg gaatggctct  1800
gttttacatt cacagtgtta tttcttacaa atgtaaacat ctagccagga acaacatctg  1860
gcctgtgata ctgctgtctc agagctgctg acataacctg cgggggaggc gggaggcggg  1920
tggggagcag ccaacagttc tgagaacttt cccctcgttc ccaaaccttc tagcgggctt  1980
tccaggaaaa agctaggatg agaaacagga gcccccaacc aatacggaat ggtgattttc  2040
```

-continued

```
ttacgtgtta taattcagta gcttccctta agggcctcct caaacatcgg accccttcct  2100
accgctcctg ctgccccgcc acgaggacga ggtggtcctg gctgggggag gcctctgttg  2160
ggagctggtg ggaaaagcct catacaggcc tggcagaggc tgctcagagg aggggctccc  2220
tttcagctcc ccctcacgta tgtgggcagc atacaagtcc acatctcagc tgctccccag  2280
ctgccacata ggagagggac aggtggaagc ttgggggtct caaggcagca cctgcacaga  2340
gttccaacat ttcctccact taccacattc aatacccaaa acatcgacgg gcatgaccaa  2400
accaagccac atgacagtcg ccaaccttgc ctggctcgcc tctagggctg aggaagcaga  2460
gcccctgcct cgtctcacag ccagtcggca agcagagctc ccaaatccag ctcctacatc  2520
agcagcagcc cggccatcca gaatccactt ccattttaat gacttggctc ctctgggcct  2580
gcaaacagga ggctggtcca gggacctggc ctggggatag gagtggcggc tctgacaggg  2640
ccgtggggca gtctccgatg agcacagatc tgcactctcc tgactaaaag gggtcaccgt  2700
gcaagatgtc agctggaacg ggggcagaag ggatgctggg ctctgtcact aacagtgcca  2760
agacaccaag ctttgctgtt gaccgagaga ggctcagaca aaacacagct cagtgacact  2820
cttagggcat gcatccatgg agcagcaggt cccaacacct gccagccagc tcctaggcag  2880
acgccacccc agggctagca aggaacagga gtgggaggcc catgtctctg gacacagtgg  2940
aggctgctca cagccaggga gggctggcct tctcagctga gtgacaggga ggctgctgtc  3000
cctgactggt gggtggagaa cgacagtcgt ctgtgcccga ggaggagggg ctgcaggtga  3060
gcgcacccct aggataatgg gggcctgtcc tcagtcctgc tgtggccacc tgcccactaa  3120
cgcctctcta catcccagtc accttgtgaa tgcataaaca ggaacatgta caacggaaat  3180
gtcagcgggt gctcaggagg gctatgccag tggctacagg agagggagcg tggccggggg  3240
ccctgtccac caccccggac gctgtcgcat gcagcacagg ccttgcgatt cacatacttt  3300
acacgggcat agaaagagtt acgttaaaat taatctcttt actgatataa ttaaatttta  3360
aatcctgaga agaaaagaga gaagggagaa tggtgccggg tgtctagcac ccccagccac  3420
tggcccagca caggccatgg catctgtgca tccagacacg gggcgtggca tgcacacccc  3480
accagggaga cccaggccag tgttcccaaa gcctgctcac ggcaccttct actgcaggac  3540
agcagagggg ccaacagcca gcctgcagga gggaggactt ctggcccaga tgcaagagca  3600
gctgcaacct ggcaacaacc agcaggtgac tatcaggaga aaggacctgg tcacccacat  3660
ggggtgcagc acagctgctc ctgctttctg gaaggcctca ggctcagccc caccaggact  3720
gcagacactc cctgcctggc cactgccaca aagagcactt ctgccacatg gcagagacac  3780
gcacgttgcc tggccgcccg cggcatgtgc ggaagcccat agggaccaag ctggctcggt  3840
ggaggcaggg cacaagggcg cagacttcca aaggctccgg ccccagctgc cgcctcacag  3900
tctctcccac catggcgctc agcaggtggt gaccttgtgg acatttcgta aacaagtcag  3960
cagccggtga tatgggcttc ctggggctgc aaccacctca agcacagact ggaaggccct  4020
gcggtcgagc tcctcctcta tctggtgtct gtagaagtct gtggcgacca ggcagaaaag  4080
gttcacgtcc acctgctcca gcttgcccat cctgctgatg acatgtggga ggatcgccgc  4140
gacccacggg ctggtggacg cgctgacaaa gaagcaggag aggctccacg tggccatggc  4200
gaccggggcc ctctgcgtga agttggagag ggacagcatg acccagtccc ggaccatgga  4260
cgactgcccg gtgctgtgca gagtctgaaa caccttatac accacggtgg ccatgaactg  4320
ggggtatggc tgctggttgg acagaaactc tccgatgact ttgttcatga tgtcctgggg  4380
tgggaagaag tcgtctagaa actggggcag gatcctggcc accactctgg cttcacaagg  4440
aaagcctttc ctgatcctat caaaaagaac agatacccgc tccatagcaa caatcactga  4500
ctcgctgtcg gggctgcag gattagggtc tgaagttcta cccggactga ctttctcctt  4560
tcctgtgtac atgcaggtga gcatcaggcc cagagccgcc atggcccggt gcgggctgtg  4620
cacgttcact ctgtccacac tcagcttgac cagcgattct gcatccaggc gggagagctg  4680
ctcagagagc aggaggcgct ccaggcctct gagggcacag tggtaaatga tggagggggt  4740
ggactcctca cttccagaca gcatcacccc acacatctgt attattgatg ctgaaaattc  4800
cggccctacg tccagaggat agttctcaat gaggtaaaac gcagtggcac acatgaccag  4860
tacgtgctgc tggctgtgaa tgttcacgca gtgggcgatc cctttcaggt tggagaggag  4920
atagtcgctg atgaccggga tgagctgctt ggcagtgtcg tccagcaggt cgcactccag  4980
cacatagagg acgccgtgca gggctccaac cctgctgggc aggtggctgc tcctgagcgt  5040
gctctccagc aggcggctga caggctccgc cacggccttg tccatcccaa ggacggcagc  5100
tgccttgcag gtggcaggca ccaggtactg agcgaggatc tcgtcttctg aagggtgcac  5160
ccttcgcagt tctgtcagcg tcacatacat cagctcaaac tggttgcgct cggtgaacaa  5220
gtctgagacc actagaaggg atctgaccac ctcactgatc aggatggccg gggtcctcct  5280
ggctgagctg gacggcagga tccagcggct gtacaactca agcaaaaact gcgaacagga  5340
gtggatgtca actccagccc ggtgtttcct ggagttgact ggagacgtgg gtggtgacga  5400
aggtgcaggg gcgtcggcct cctcctcctc ttcctcgtcc cattcctcct ccctcagggg  5460
tgtgatgctg ttccccagcc acacggagtg tatggacacc tggccgagtt tgtagctcat  5520
gctccccagc tcccgctcgg ggttgatctg tagcagcagc ttctcgtggc tgatgagggc  5580
acctgtagta gccggagaca gagaagggac aggatcccat gcctgatata aatgatgggt  5640
ggcaatattc tctctctttg aaaccattgc ttgaatctct tgctccacaa tccctctgat  5700
aatgctcagc ttcctcccaa acctggtgtc gagagctttc agaggcttgt tccggggctg  5760
ctgctccaag cagcttacag ctgggttgcc ggccacaggc acagtcattg cactgagcac  5820
cagtgaggtg atggcctgca cggccaggac gttgatctgg gtcctctctg tgtcttcttc  5880
tggtgggctc tcctcctgct ccatcacgag gggctgcgtc accaggacac caaggagggt  5940
ggcccaagtt tcttcaaact gagtacgact ggtccagcct agtgtgttga tgcggtagat  6000
gaactcctta aagacttcct tttcctggag gaactccacg gggatctcag ggaatgctgt  6060
gccaaaatcc cctcccggtt tgggtgacca tccaagcttc cacaccagtg ggggcacacg  6120
tgtgtagctg ttgacaaggg gcaggcgggc caggctgatg atgatgttcc ttagcaatgg  6180
cgtgagaaac gccggcacgc cgctattcct tttatgaccc aaggccaaca ccgactgcag  6240
agactccacc atttctgcca ccatctcaca ggctgcagtg atatacttag gattctgtgt  6300
gtttggatct acttcctcct cctcctcgct gatggctttt ggggtatttg tccttctttc  6360
tggactaaga agctgctctc caggctgcac tgcaacggcc tccaggatga agtgcacaca  6420
gtagatgagg gagcaggcgt gggtcacaaa ctctgtggag gagaccacgc tccagaggcc  6480
aggcagctgc agggccaggc agcagcagtc cagccctgcc tggagatcca gactcagcgg  6540
gatctgctca tggatcaaat gccaggacag ggcctcaagg gttgccacca cgaatttcac  6600
aatgtccttc tctttctcag gaggaaggtg caaatgactg ggcagtttgg agaccaccac  6660
caggtactgt gccagggccc gggccagagt gggcagggac tgatacagtg cagcatcccc  6720
aaacagatca ttcaacttgc tccagtaggc cgccggctct gcaggcagct cgggctggaa  6780
```

-continued

```
gacatgatgg acagcaggga gctgctgcac ggtgccgctc acacgggcca gagtcacctc  6840
acgggctgct tcaaaaaggg cactcttctg gccaccagaa atttcactca tccctaggct  6900
taagcatgga gctagcaggc ttaggttgaa ctccgagttc atcatgaagg cattcatatc  6960
ttcagcagga atccgattca ccagctctgc accttccagc agtgcagaat ctgacctggt  7020
ccaacactgg gatttgacaa gatgaacgta ccagtcttg tccggactca ctgtttccag  7080
tgacacgtgc ccatccccgt ccagcgggtg ggaagagact ggaggagagg gactaagtga  7140
gtcttgcatg gtggagagac gaaacctgtc cagcagggaa tagagccttt ggtgtctctg  7200
agcgagcccg ctgctctgaa ggtattcctg gattctgttg agttcttcca ttggcaactg  7260
ggccatgctg ctctgtaaat ttgcagccag aagcatttct acccggcgac aagcaaggat  7320
gtcgaccatg cgagccagca cacggaaagg ggtgcacaga agcctgtcca catacagcgt  7380
gagcacagct cccgactggc tgagatggat cccctccaag cactgaagag ttttcttcag  7440
catggttgga gttgaaaggt tttcacaacg agactgaatt gcctggatga acaggccgct  7500
ggcagcagag ttccgatgaa cggcactgat gaagtcctgt actggaggct cgtgggaaag  7560
gctgatcaga tcttgaatgt gatttacaat gagccacgtt aagtgctcgg agtcatggag  7620
gttctgacag acataatcac agaagagaat gagagcccct cttcgtacta tttctctatt  7680
gcacattcca agtttggctg ccaagtcaga atcctcctct tctccagaca tctggggact  7740
aagtaacttt gtgctggaca gactgtgtct tttcggggtc tgctgcactt ctgcccacca  7800
gcggtagtcg gtgtggttga caagcagcag tatctgacac cagagcagca ccagggccgg  7860
gtgggtggtg atcatggaac gagcccgcaa gttcaagctg tccagggtgt agaaactgcc  7920
gccacagcca tcactgcgga acagcctagt ggcagctgct gtgattctcc ggaacattcc  7980
agacttgaag atgtggatca gacacattag cagtgtgcct agttcctggc aatagaaagt  8040
atgttgctgc tcactcattt ccaccttcag ctgttttgta acaatgtctt ctaaaagaat  8100
accaaccagt tgtaatagaa accttgaaaa tgtttcttct ggcaaattct ttatttgttt  8160
cccttcactg tgttcttcta gcgttgaagt actgtcccca tctcttaacc tattaattac  8220
tgtacaggag attaaatacg gagagaagga gagctcctga atacgagaaa gaacaatatc  8280
ttcagttgac tgggaaatca gaaccctcaa aatggccaga attcccgata tccacagttg  8340
aacagtgctc acggacgcca ttgtgtttgg agtgacgaac atactccgta aaagcatgtc  8400
taccggacgg agggaggaag gggccaaaat ctcaaataat gtatttaaca ctccaagggc  8460
ttcatgagag tcaatgtgca tctgctgttt ggctaacatt gggaggatga tgtcagctat  8520
ctgtcgagac agtcgcttcc acttgtcttc attctccttg tggcactgct gcaggacaag  8580
aatgaacatc tccaacacct gatggtactg gatgagtctc agtaacattg acaccaccac  8640
ctctttttgg gtttcaagct cttttcctgc atcagcttta tttgttcctc ttaatacaaa  8700
gaggtcgtgg actatgggct gcagagccgg tatggcatgt gtcacagcct tccttccact  8760
ggccatgatg ccatcacaga gctgaatgat tttaggaatt ccaatgatct gttttgaatg  8820
atagcgttca taagatagta ataccaagaa gaaaaagatg tttggaatga ttgcctctga  8880
ttccctgaac tggcccactt caatgtattc aaactgtttc aatacaaagc caataaacac  8940
ctgatctgaa tccagaagac agtaattaac ccgtaactga accagctgcg ccagcaaatc  9000
taaaacctgc ttctgtaact gcacacatgt tgtagtcgtg tactgtttta aagcttttat  9060
aacaagaggt tcaaacaaac gaatgtgatt atgaatagca ttcttatctg cacggttctt  9120
tgtgacactc gtgaggtttg tcttcaactg ggtagacact ttctggagga catcaaacca  9180
tcccgaggtg tcgttctcct gctccgcctg caccatgttc ctcaggctgg cgtcagcgag  9240
ggcctgggtg aagtgggtgt acggggccat gaagcagtag tggtacaagc ctggcctcac  9300
actggaggag ccaaggcgct gtgctcggcc ttgtgacttg ctggggttgg aagataagcc  9360
atcaaactgg gaggccaagt ttgtgccaaa gagagtcttc aacaattgtt gaacacaaac  9420
agttgccatc attggttctc gactaaagca ggatttcagg tatcctagga tctcttcaac  9480
acacttccca atgtcctgca gtgtggccag ctctagtatc tgagaaagaa catccaaggc  9540
tgagcggaga aaccctccaa acttttccgt gctgttctga agatccagcg tgaccttgta  9600
gttagcgtgt gtagctttca ggacatcatg cagtttgagg tatgaaggaa gatgatagaa  9660
actccccagt gatgaggatt tacttgttgt aacaggacct gaggtatcag attgtctaga  9720
agctgcactg gcctcactgc ctttcttggg actcaacggt acagatgctt gttctcctgg  9780
ttctttctcc ttccccttcc gtcggatggg acttagagaa ggggggtttg ttagagaagg  9840
caaggctgcc tttattgcgg gtccaggagc cacgtcatcc aggacgtggg cacaaatgtt  9900
aatcaccttc agcaggtgag agaagagctg ctccaccatg ggcaccaggg cccggtcccc  9960
cagggctggc cagacctcct cttgcttggt ggctgctggg ttggcttctt cttcagaggc  10020
ccatgaactt ctcagagatt tgggagcact ggctgcaagc aagtttccgg ccaaaatcaa  10080
agcatcttga tgggctgaga gatccaatgg gaaccaagct gacgagagca gggtcagaat  10140
cattgtggcc atcccaacgg tacagctctt cctagactca tctgaggcac tcagtggagg  10200
cactccacag tgccaaccta aactccaaat gcaaactggg aaggcagtgg aaagaagaca  10260
caaagcttca cagcatccaa atgtgagtgc tctggtggtt gatgtgatta gttcatgaga  10320
aactgctgca ataactcttg aaaggttatt ttccatagtg acgtctgtta tgcttggtag  10380
taggttatag cctctatata ttctggttat tgtgctgacg gagaaatgag atggaggctg  10440
cgtctcatgc atgagaagtt tcaggtaaac actgctttga tctcttgcca cggccactac  10500
tggatcagct tgtccttggt cacatttata aaacagcttt gggacaagcc taattagtga  10560
tgctgcggca acatgtcgca ccctggggtc ttcatctcca agcaaatgga tgacaacatt  10620
attgagcact cgttcttgca gttttaaaag ccctgtataa tgatgagccc ctctgtgtaa  10680
gttttctgct tttgcctcca aaaagctcac cagcctgaag tcaatctctg caagggtttc  10740
cagaagctct gtcctcacca gccaatagga actgttcctc agagtcagca catcgatgat  10800
cagctgcagt cctaactcac tgtagctgct gctgcagaga ctcatgacac agttcctcac  10860
agctgtacaa gctaacttgc aagtaacaga agactcatcc ttcagtgttt tccgcagcaa  10920
aggaatgcaa tccgccaaag aaaatgtatt tcctgtgagg gttctaatgg tgcccatcca  10980
atctcccacg tggaagcggg acctgctgag gatggagcag atgagggtcc cacagagaat  11040
ggcagtggct cctcgaacct gtgggtctcc atgatcgatg tagttcaaga tgtctgagac  11100
atactgttcc tcagggtatt ccgtggtgtc aagaggaact ttatagagtt tgctgaagaa  11160
agattccggg tggagggcca cagctgctcc cacacagctg agggccaggg ccttcacgct  11220
gaccctcaca tccctgtccg gaaccagcac atttttttccc cctgttagca aaaacgaagc  11280
agataaaagg cggacacaat ggacaagagg tgcagagtca tcatcagtgg actgtccaat  11340
gtcacctttg atgcggcaag gcttgttttc ttgatcaccc ggttcagtag cttcatctct  11400
caacacaaat ttatcaacac tgctgtcaga aggctgcctg cagtgactca tgtttttcaa  11460
taaatgtgcc tgttgaaggg ccatggaaga gttcctgaag gcctccgagg cttcatcagg  11520
```

```
aagaatacct gtggcttcct catcttcatc ctggggctgt ccaatctgca ggcccaaata  11580
ctggttgtcg gtaccgtcta acacaatttc agaactgtct gaaggggtaa cagctgaatc  11640
aggcccttcg gtggtggtct gggagctgtc gctgatgggc gacgaggcct gggtcccatc  11700
attcaggtcc atggcagggt cagatgggac ggcgctgacc tggctggagc tgtggctcaa  11760
gatatcctcc tcatccccat cagtggcaga gcttgtcaag tcacagctgg ccagatccac  11820
tgagtccgcc tgcagtgtgt gctgtgaccg tggctgttct gtgatgatgt catgacctgc  11880
tgaccctgga gtggaaaccc ctgaagaagc agccagctct ccactgatct catccttcac  11940
tgaggctgtt aaggcagagc tgctgacatc cgatctcgat tcagagtcat cctccaaggc  12000
ttcttcttct cctaagagca ctttgccttt ttgttttctt gaaaggacag ggctgcatga  12060
ggaacccccct ccagctataa gttccacaat actcccacta cggcttcggc caccagactc  12120
ctccttagca gcggtgagct gcccaatgcc cccgactgcg gtcagggttt gcagaagctc  12180
gggtggaggc gttctgaaga gctgctgcaa cagctccagg gctccggtca caacattgtg  12240
gtcttggtgc tgtgtatgat gtaacgtcag ttcataaacc tggacaagct gctctgcaga  12300
aggagagact tccatttctt tccttgtcac tccgaagctg cctttcaggc ttgtgtcctt  12360
gacctgctgc tgcagcaagg gcaccaaata cctcagggtg agcagcacgc caagaatcag  12420
cagagtggag tgttcatcct cgacaggaac gagtaagcct aagagcacat ttagtagcca  12480
actatagaaa tattgtgtcc ttcttgagtg ctggcagatg ctcactgctg atccagccgc  12540
tgtccgccga atggtggggg agcttgactt caggttcgct atgaaggcct ttaacaaaac  12600
cttaatttca ttgtcatttg caaaattgcc aaaagaagcc ataattttgg gaacagctgc  12660
agccaaggtc tcctggactg attcttcggg tctcttgctt gttcgagtca ggcacggcag  12720
aaggttcacc aggtaaggcc tgcatttctg aggccgaacc aggtgagcca gctcagcaaa  12780
cctcccacagg gcagcacgca aactccgagg ggcaccattc tttttaattt ccttatagag  12840
ctcgagctgt aaccttggaa gattagaatc catcaaagct ttgataactt tgttgaggca  12900
ttcgtcagcc accatcctga catctgactc tgcgtcatca ctgcacagca gaaaaagttc  12960
catagcgatg cccagaagtt tctgaaattc tggagaattt ctgacagact gtgccactat  13020
gttttcacat attgtcagac aatgattcac acggtcttc ttggtagctg aaagttcttt  13080
ctttggtcgg tgcagcggct cctcagccac agccgggccg ggtggcggcg ggggcggcgg  13140
cgggggcggc tgcggctgag gcagcagcgg ctgtgcctgc ggcggcggct gaggaagctg  13200
aggaggcggc ggcggcggcg gcggcggtgg cggctgttgc tgctgctgct gctgctgctg  13260
ctgctgctgc tgctgctgct gctgctgctg ctgctgctgc tggaaggact tgagggactc  13320
gaaggccttc atcagctttt ccagggtcgc catggcggtc tcccgcccgg cacggcagtc  13380
cccggaggcc tcgggccgac tcgcggcgcc gctcagcacc ggggcaatga atggggctct  13440
gggccgcagg taaaagcaga acctgagcgg ccgtccatct tggacccgtc ccggcagc    13498
```

```
SEQ ID NO: 7              moltype = DNA  length = 13237
FEATURE                   Location/Qualifiers
source                    1..13237
                          mol_type = genomic DNA
                          organism = Mus musculus
SEQUENCE: 7
ttttttttt ttttttttaa cagcaacaac aggtggttta atcgcttctt taattcaact  60
gtacaatatc tgcaatttaa aaattttaaa tatacatttc atgtcagtcc ttccttttgg  120
aaatggacag ccaggtctag gctgggctcc ggggcacacc catcacagcc ctcctagttc  180
ccagtgaagc ccatggcata cagcagcaag gcttggacag gagcccccta gaatgcagcc  240
aaatctctgc agataggtct ctgccaccta ttatcttaca cccagcttgc ggcagagggt  300
gtttccagag acacttgagg ggagcagttc cttcgatggc tctagagtgt gacaagcaca  360
catggagggt ggccctgaac cttgatatca tctttagttg tcacactgct cagcattggt  420
tcttctttcc tggaggctcc agacccactg aggaacaatt cttttcccaa ccatgatatc  480
ctgagcccac acccagcatc agcagctcag tgtcttcgac tcccacatac caatccctgg  540
aggacagctt catgcctgtc ctggtagcag ccatgatcct agtgctcaat gctgagggag  600
ggagggaggg acggagggag ggagggaggg agggagggaa ggagggaggg aaggagactg  660
tgtggggaag gatgctcaca ggtggcaagg agaccaattc tgcagcccca caatgggagg  720
caagactcct tgtgacgtgg ctgtgagaca agctattgct gtataaaacc tgtcccatga  780
gccggaagca gagctgcttc actcactcac gggaaggtac ttcctgccag ggaaggcacc  840
tgttaggatt ggtcccttcc ctggcactgc attctacagg gcaggaggtg gttccactcc  900
agttcttccc tcctgaaggg tacatgtgca gacaaaatga gagaaccata aagggcactt  960
ggcagtggct aagtcaccta catgtcaagg gggccatcag tgggagggag ggaggcacat  1020
tttggagaag aaacatgctg aagtgcattg ccaaaagttc taccctggtt ttattaaaat  1080
ctttcctgac agtaccacca tggaaacaga aacaacatcc cacctcctac ccctaaaacc  1140
tcatagtcaa aataactttt gtttttaaat aaagcttgga aatctttaga tttttgagga  1200
atttgataaa aagttttagt ccctcctgca gttagacagg tggggcaatg tctccagtga  1260
gactttaatg agctatggac ttttaaaaat tgagtcccat tctcagatgc tagactcaca  1320
aagctgactg tatgtggcag ttgcaagaaa agtctgcttt cagaaaaaac aggcaggcat  1380
ttttagaggc cttgcatatg tctttgagga ttgtgtgtgt gtttatgtgt gtacacaaat  1440
acatacctgc ctgtacccag gtgcatctct aggttgtggc acccatgagc agacaacaac  1500
tttgtggcag aggctgtcct tgccccatac taagaattgt ttctgatcac actaaacaag  1560
aggccaacta aacttgaggt tgagctcact gatataatcc cctggtgaat ggctctagat  1620
tttatattga gtttccttat gaacatctac catgaggagt aatcaggcct gcaccatgct  1680
catctcagag cggttggacc aacctcagag tgtggcagca gcactgtaag aactttcaca  1740
tggtccccga gcacttctag gcgggaaatt gagggtgaca agaagaagcc ctaaatcagc  1800
aaaggggcat tggtgaattt ctttcattaa aattcagtag cttcccttaa cgtcctcttg  1860
aaagacctaa tccatgtcca ctgttcctgt taccacgcct tggggtggtt tttgccaggg  1920
cagataggag gagagtcagg ccaagtgtga ggctccccac aacctgtgtt tggtagggaa  1980
ccttgcatcc cagcagcaag gctacttgtc atgatggaaa gatagaggga aattcaaggg  2040
tctcaagaaa gcaatccatg gactgaagca cagttagtta atcacaggct gcaagctctt  2100
tcctcctgtg tagcctagaa acatctccaa actattccac tcccctactc tacagctgag  2160
aaatacagat atgacttagc ggaacagcag aaaatctgct tggtcatata gtcaaacagc  2220
aaacagagtt cccaaaccaa gccaggaaat gaaggtagct cattttcatt aacatgacct  2280
ggttactctg ggcttgggct ttgggaagag gtggctctga ccagcatggg aagctgtctg  2340
```

-continued

```
aggccagagg ctgacctgat tttgaacctt ccctttggtg cctcatcttg tcagctgagt  2400
cctccctggg ctctgacagg cataggtctg tactctactg ggctgacaga aggcaagatg  2460
ggaaggggca aaagaggctc tgggtccatt cttaactgtt gctaggacac caagctttcc  2520
cttgactatg agaaactgag acaaaccaac aaaccatagc tcagagacac ctttggggta  2580
atcaggtcag cacttctcag gtcccaacca tgcagaagat acaaagggac agacagcatc  2640
cacaatggtc agctggtgtg tgggcaggct acagtgcagg tcagccacaa ccagggatga  2700
ggttattggg atagccactt tgggtccagc agatgctgtt tctacccagg ctgagagact  2760
aggagagtgc atcaacacca gggaggagat agcttgacag tcatgcctgg gaaggggaga  2820
ggagggcagc tgccacaggg caagcctctt ataactctaa cagtggaagt cagtttttca  2880
gttcctcagt taggccacag gcaggattct cacacaggca gtcaatacca acacctctct  2940
ctgtgctggc ttaatggaat gcataagaaa agggagctgt atgaagtgca agtgccacag  3000
ggtgttggga gggctacagg agggacctgc ccgactagac tgagtagcta caggagaggg  3060
agtggcggcc agaaggcccc tccacttcca taaactttgt cacatgcagc acaggccttg  3120
ccaagtcaca cactttacac gggcatagga aaagttacat taaaattaat ctctttactg  3180
atataattaa attttaactc ctgagaagaa aacacagaaa ggaaaatggt gctggacacc  3240
tggcagcccc agttcccagc cccacacacc attcattttg tgtccagaca ctggtgtggc  3300
aggtatgcct actgggtaaa tgtgggaggg agctctccag cccagtggag caggcgggct  3360
cagaaccatc tggcaagagc taggacttct gatccacata ccagggcagc tgcaacctgg  3420
cgactatggc caggggaaca ctaggaaaaa gacaaacacc tggtcaacct agcactgtca  3480
ccagctgcag cgaggccagg acccaggact caggctcaac cccaacatag tgcatgttcc  3540
ctgcatagcc ctcattgcaa agcactcctg ccattgcctg gctgtccact tgacacaagt  3600
ggaagcctgc acggccaagg cagccccagc agaagcttgg agcaggctcc tggaggctca  3660
ggccccagca gctgccttct ttcagccttt tgtcccacag gcactactca gcaggtggtg  3720
accttgtgaa cattttgcaa acaagcaagc agcctgtggt atggacttcc tggtgcagcc  3780
accacctcaa acacagactg gaaagccctg cggtcgaatt cctcctctat ctggtgtctg  3840
tagaagtctg tggcaaccag gcagaaaagg ttcacatcca cctgttccag tttgcccatc  3900
ctgctgatga catgtggaag gatcgcagaa acccatgggc tggtagatgc gctaacaagg  3960
aagcaggaga ggctccacat ggccatggca actggagttc tttgtgtgaa gttggacagg  4020
gacagcatga cccagtcccg gaccatggat gactgcccag cactgtgcag agtctgaaaa  4080
accttgtaaa ctacagtggc catgaactgt gggtatggct gctgattgga caggaactct  4140
ccaatgactt tgttcatgac atcttgaggt ggaaagaagt catctaggaa ctgaggcagg  4200
atccttgcca caaccctggc ttcacaggga aatcccttgc ggatcctatc aaagagaaca  4260
gacactcgct ccatagctac aatcacagac tcgctgtcag gtgtagcagg gctggggtca  4320
gaagctctgc ctggactggc tttttccttt cctgtgtaca tgcaggtgag catcaggcct  4380
agggctgcca tggccctgtg tgggctttgt acattcactc tgtccacact tagcttgacc  4440
aaggactctg tgtctagccg agatagctgc tcagacagca ggagccgctc cagaccccgg  4500
agggcacagt ggtaaatgat ggaggggggtg gactcctcac ttccagacag cattactcca  4560
cacatctgta tcacagatgc tgaaaattct ggtcccacat ccagagggta gttttccatc  4620
aggtagaaag cagtggcaca cattaccagc acatgctgct ggctgtgaat gttcacgcag  4680
tgggctattc ctttgaggtt ggacagcaga tagtcactaa caactggaat gagctgcttt  4740
gcagtgtcat ccaagaggtc acactccaac acatagagga tgccgtgcag ggctccgatc  4800
tggctgggca ggtggctgct cctcagtgtg ctctccagta ggcggctgac tggctctgcc  4860
acagttttgt ccattccaag gacagcagct gccttacagg tggcaggcac caggtactga  4920
atgaggatct catcttctga agggtgcact ctccgtagtt ctgtcagcgt cagatacatc  4980
atttcaaact gggtacgttc ggtgaataag tctgacacta caagaagaga tcgaaccact  5040
tcactgatca ggatgacggg ggtccttctg gctgcactgg atggcaggat ccatcggctg  5100
tacaattcaa gcagaaactg cgaacaggag tgaatatcaa ccccggcacg gtgttttctg  5160
gaattgactg gagacacagg tggtgacgtt ggtgcaggga catcactttc ttcctcttct  5220
tcctcatccc attcctcctc tctcaggggt gtgatgttat ttcccagcca cacggagtgt  5280
atggacacct ggcccagctt gtagctcatg ttgcctggct cccgctctgg gttgatctgc  5340
agcagcagct tgtcatggct gataagagca cctgtagtag ctggtaacag agaagggaca  5400
ggatcccacg cctggtgaga atggtgagtg gcagtattct ctctctggga aaccatctct  5460
tggatttctt gttctacaat ccctctgatc atgctcagct ttcttccaaa tctggtatcg  5520
agagccttca gtggcttgtt ccggggctgt tgctccaagc agcttacagc tggattgcca  5580
gccacaggca cggtcattgc actgagcact agagaggtga tggcctgcac agccaggaca  5640
tggatctggg ttctttctgt gtcttcctct ggtgggctct cttcctgttc catcaccagg  5700
ggctgagtca ccaggacacc aaggagggtg gcccaagttt cttcgaactg ggtacgattg  5760
gtccacccta gggtgttgat gcggtagatg aactccttga ggatctcctt ctcctggagg  5820
aactctacag ggatctcagg aaacactgtg ccaaaatccc ctccaggctt gggtgaccac  5880
ccgagtttcc ataccagagg aggcacacga gtatagctgt taactagggg gagtcgggcc  5940
agactgataa caatgttctt cagcacagct gtgagaaatg aaggcagggt gctgttcctc  6000
ttgtggccca aggccagcac tgactgcagg gattccacca tgtctgccac catctcgcag  6060
gccgaagtga catgactgag gttttgtata tctgagtcta cttcctcctt tctgacagct  6120
cttggagtat gtgacctgct ttcaggaccg agaagctggt ctccaggttg tactgcaatg  6180
gcttccagga tgaatcgcac acaatggatg agggagcagg catgagtcac gtactctggg  6240
gaggacagca ccccccagag gccaggcacc tgtagtgcca ggcagcagca gtctagcccg  6300
gcttggaggt ccagactcag tgggatctgc tcatggatca aatgccatga cagggcctca  6360
actgtcatta ccacaaactt caccgtgtcc ccctccttct caggaggaag gtgcaaatga  6420
gcaggcactt tggagagcac caccaggtac tgtgccaggg cacgggcaag tatggtcaga  6480
gactggtatg atgtggtatc accaagcaga tcattcaact tgttccagta ggccgtgggc  6540
tctataggca ggaagggctg gaagacttga tggacagcag gaagctgctg aacaacactg  6600
gtcacccggt tcagaatcac cccacgggct gcttcaaaga ggggactctt ttggccatta  6660
gcaatctcgc tcatgccaag gcttaaacag ggagccaaaa ggcttaggtt gaactccgag  6720
ctcatcatga agtcattcat atcttcagca gggatacggt tgaccagctc tgcaccttcc  6780
agcagtgcag aatctgatct ggtccaacac tgggatctga caagctggag gtaccagtct  6840
ttgtctggac tcactgtttc cagagatgtg tgcccatccc catccagtgg gtgggaagtg  6900
actgggggca aggggctaag tgagtcctgc acagtagaga gtcggaatct gtccagcagt  6960
gaatagagcc tttggtgtct ttgtgcaagc ccactgttct ggaggtgttc ttggattctg  7020
tttagttcct cctctggcaa ctgggccatg ctgctctgta aatttgcagc caaaagcatt  7080
```

```
tctacccggc gacaggccag ggtgtcgacc atgcgagcca gcgcacggaa gggggtgccc  7140
aggagcctgt ccacatatag tgtgagcaca gcaccagact ggctgagatg gatgccttcc  7200
aagcactgaa gtgttttctt cagagtggtt ggcgttgaaa gattttcaca gcgagactga  7260
attgcctgga taaaaagacc actagctgca gaattacgat gaatggcact aataaagtct  7320
tgtactggag gctcatgaga caagctgatc agatcttgaa tgtgattcac aatgagccat  7380
gttaagtgtt ctgagtcatg gagattctga cagacataat cacagaagag aataagggcc  7440
cctcttcgca ctatttctct attgcacatt cccagctgag ctgccgagcc agaatcctcc  7500
tcttcgccag acttctgggg gttaagtgac ttcgtgcagg acagactgtg tctcttgggt  7560
gtctgctgca cctctgccca ccaccggtgg tcagtgtggt tgatgagaag taggatctga  7620
caccagagca gtaccagggc tgggtgcgtg ggcaccatgg atcggacccg tgcattcagg  7680
ctctctagag tatagaagct gccttcacag ccatcactgg tgaagagtct agtggcagct  7740
gctgtgattc tccggaacat tccagatttg aatatgtgga tcagacacat gagcagtgtg  7800
cctagctctt ggcagtagaa cgtatgctgc tgttcactca tgtccacttt gagctgtttt  7860
gtaacgatgt cttctagaag aataccaacc agctgtaaaa gaaaccttga gaatgtatct  7920
tctggcaaac tcttttgttt cccttcgctg cattctccta gtgttacatt accgcctcca  7980
ccccttaacc tgttaatcac tggacaggag agcaagtgtg gagagaagga gagctcctga  8040
atacgacaaa gaacaatgtc ctcggttgac tgggaaatga gaaccctcag aatggcgagg  8100
attccagata tccacagctg cacagtgctt acagatgcca ttgtgcttgg agtgatgaac  8160
atactccgca aaagcatgtc cacaggacgt agggaggaag gagccaaaat ctcaaacaag  8220
gtatttaaca ctccaagggc ttcatgagag tcaatatgca tctgctgctt ggccaacatg  8280
ggcaggatga tgtctgcgac ctgccgagag agccgtttcc acttgtcctc attctccttg  8340
tggcactgct gcaggacaag gatgaacatc tccagcacct gatggtactg gatgagtcgt  8400
aacagcatgg agaccaccac ctccttctgt gtctcaagct ctttccctgc atcagcttta  8460
tttgttcctc gtaacacaaa gaggtcatgg acaatgggct gcagagcagg tatagcatgt  8520
gtaacggcct tccttccact ggccatgatg ccatcacaca gctggatgat tttaggaatt  8580
ccaatgatct gttttgaatg gtagcgctca taagacagta ataccaggaa gaaaaatata  8640
tttggaataa ttgcctctga ttccctgaac tggcccactt caatgtactc aaactgcttc  8700
agcacaaacc cgatgaacac ctggtctgaa tccagtagac agtaattgac ccgtagctga  8760
accagctgtg ccagcaaatc caaaacctgc ttctgcaatt gtacagatgt tgtcgtggtg  8820
tactgcttca atgcttttat aacaagaggc tcaaataacc taatgtgatt atgaatagca  8880
ttcttatctg cacggttctt tgtgacgctt gttaggttcg tcttcaattg ggcagacact  8940
ttctggagta catcaaacca ccccgaggca tcacgctcct gctccgcctg caccatgttc  9000
ctcaggcttg cgtcagccaa ggcctgtgtg aagtgcgtgt atggtgccat gaagcagtag  9060
tgatataagc cgggcctcac acttgaagag ccaaggcgct gagctcggca ctgagacttg  9120
ctggggttgg aagataagcc atcaaactgt gaggctaagt ttgtcccaaa gagagtcttc  9180
aatagctgct gcacacagac agttgccatc attggttctc gactaaagca ggatttcagg  9240
tatccaagga cctcttcaac acactttcca atgtcctgca gtgtcgccag ctctagaatc  9300
tgagaaagga cgtccaaggc agagcgcagg aacccccaa acttttcagt gctgttctga  9360
agatctaagg tgaccttata gttggcgtga gtggctttca ggacatcatg cagtttgagg  9420
taggagggga gatggtagaa actccccagt gaggatgatt tacttgctgt gacaggtcct  9480
gaggtgtctg attgtcgaga ggctgcactg gcctcaccaa ctttcttggg actcattgga  9540
gtagaagctt gttctccagg ttctttctcc ttccctttcc gtcgaatagg acttagagaa  9600
ggggggtttg ttagagaagg caaggctgcc ttgattgctg gtccaggagt cacatcgtcc  9660
aagacatgag cacagatatt gatcaccttc agcaggtggg agaaaagctg ctccaccaag  9720
ggcactagag tccgatcccc cagagcaggc cagatttcct cctgtctggt ggctgctgag  9780
ttggcttctt cttcagaggt ccatgaactt ctcagagact tgggggcact cgctgctagc  9840
aagtttccag ccaaaatcaa ggcatcctga tgggctgaga gatccagtgg gaaccaagct  9900
gatgaaagca aggtgagaat catggaggcc atcccaacag tgcagctctt cctggactca  9960
tcagaggcac tcagtggggg cactcccacag tgccatccta aactccaagt gcaaactgga  10020
aaggctgctg agagaagaca caaggcttca cagcatccaa atgtgagtgc ccgtgttgtt  10080
gacgtaatga gttcatgaga aactgcggca acaactcttg agagattgtt ttccatggtg  10140
acatctgtta tacttggcag taagctatag cctctataga ttctggtgat ggtgctgaca  10200
gaaaagtgtg atggtggctg ggtctcatgc atgaggagct tcaggtagac actgctctga  10260
tccctcgcta cagccacaac tggatcagct tgtccttggt cacacttgta aaacagcttt  10320
gggacaagcc ttgttaatga tgttgcagca acatgtcgaa ccctggggtc ttcatctcca  10380
agcaaataaa tgaccacatt attgagtact cgttcttgta gttttagaaa ccctgtataa  10440
tgatgagccc ctcggtgtaa actttctgct tttgcctcca aaaaactcac gagcctgaag  10500
tcaatctctg ccagagtgtc cagcagttcg gtcctcacca gccagtagga gctgttcttc  10560
agaggcagca tatcaataag cagttgtaat cccaagtcac tgtagctgct gctgcaaaga  10620
ctcaggacac agtgcctcac agctgtacaa gccaacttgc aagtaacaga agattcatcc  10680
ttcaacgttt tctgcagtaa aggaatgcag tccaccagag aaaatgtatt tcctgtcagg  10740
gttctgatgt tgcccagcca gtcaccaaca cggagacggg acctactgag gatggagtag  10800
acaagggtcc cacagagaat ggcagtagct cctcggacct gtgggtctcc atgatcgatg  10860
tagttcaaga tgtcagaaac atactgttcc tcagtacttt ccgtggtatt aagaggtact  10920
ttgtacagtc tgctgaagaa cgactctgga tgaagggcca cagccgcacc aatgcagctg  10980
agggccaggg ccttcacact gactctcacg tctctgtctg gaaccagtgc tttcttttca  11040
ccagttaaca aaaaggaagc agataaaaga cggacacaat gtaccagagg agcagaatca  11100
tcatcattag gctgtcctat gtcacctttg attcggcaag gcttgctttc tggatcactg  11160
gcttcagcaa cctcatctct tgttacatac ttatctatac tgctgtcgga aggctgcctg  11220
ctatggccca ttctttccaa caagtgtgcc tgttgaaggg ccagagaaga gtttctgaaa  11280
acatctgaga cttcaccaga aagaacacct gcagctccct cctcatcgtc ctcctgtggc  11340
tgtcctatct gcatgcctaa atactggcta tcggcaccat ctaacacaat ttcagaactg  11400
tccgaaggag tcacagctga atcaggtcct tcagtggtgg tctgagaact gtcactgatg  11460
ggtgaggagg cctgggtccc atcattcagg tccatggcag ggtcggatgg gacagcactg  11520
aactggctgg agctgtggct caagatgtcc tcctcatccc catcagtagc agcactggtc  11580
aggtcacagc cggacaaatc cacagagtct gcttgaagtg tgtgctggga tctaggctgc  11640
tcagtgatga tgtcgtgacc aacagaacca ggagtggaaa cacctgaaga agcagcgagc  11700
tctccaccaa tctcactctt cacagaggct gcaaaggctg agctgctgac atctgacctg  11760
gactccgagt catcttccaa ggcttcttcc tctcctaaga gcactttgcc tttctgcttt  11820
```

```
cttgagagga cagggctgca cgaggaaccc cctccagcta aaagctccac gatgctcccg  11880
ctgcggcctc ggccccgggc ctcttcttga accagagtga gctgcccaag ccctcctggt  11940
gtggtcagtg cttgcaggag ttcaggtgga ggggtacgga agagctgctg caggagctcc  12000
agtgcccctg tcaccacatt gtggtcttgg tgctgagtat gatgcaaagt cagttcataa  12060
acctggacaa gctgctctgt agaaggagag acttccattt ctttccgtgt caccccaaag  12120
ctgcctttta gacttgtgtc cttgacctgc tgctggagca agggcactag acacctcaat  12180
gtgagcaaca caccgaggat caggagagtg gagtgctctt cttccatggg aaccagcaga  12240
cctaggagga cattaaggag ccagttgtag aagtactgtg tcctcctaga atgttggcag  12300
atgctcacgg ctgagccggc tgctgtccgc cgcacggtgg gagagcttga cttcagattt  12360
gctatgaaag ctttcaacag aaccttaatt tcattgtcat ttgcgaaatt gccaaaagaa  12420
gccataattt taggaacagc tgcagccaag gtctcctgaa ctgattcctc cggtcttttg  12480
cttgttcggg tcaggcatgg aagaagattc accaggtaag gcctgcactt ctgaggtcga  12540
accaggtgag ccagctcagc aaacctccac agggcagcac gcaaacttcg aggagcacca  12600
ttctttttaa tttccttata gagttctaac tgtagccttg gaagattaga atccatcaaa  12660
gctttgatga ctttgttgag gcactcatca gccaccattc tgacatctga ctccgcatcg  12720
tcactgcaca gcagaaacag ttccatagcg atgcccaaga gtttctgaaa ttctggagaa  12780
tttctgagag actgtgccac aatgttttca catattgtta gacaatgatt cacacggtct  12840
ttcttggtgg ctgagagttc cttctttggt cggtgcagcg gttcctctgc cggacctggc  12900
agcggcggtg gtggcggcgg cggctgcccc tgaggcggcg gctgaggggg ttgaggcgga  12960
ggcggcggcg gcggtggcgg cggcgcctgc ggcggtggct gctgctgctg ttgctgctga  13020
aacgacttga gcgactcgaa agccttcatc agcttttcca gggttgccat gacggcttcc  13080
tgcccgatgg gacagaccct gaagacttgg agcctactgg cactacgcgg cgccacttag  13140
cagcaaggca atgaatgggg ctctgcgcgg caggcagaag cggaaccaag gcgctcagcc  13200
atcttgggcc cgtcccggca accctcgcgg cgagtgc                          13237

SEQ ID NO: 8            moltype = DNA  length = 13189
FEATURE                 Location/Qualifiers
source                  1..13189
                        mol_type = genomic DNA
                        organism = Rattus norvegicus
SEQUENCE: 8
aacagcaaca acgggtagtt taattgcttc tttaattcaa atgtacaata tctgcaattt  60
aaaaatttta aatatacatt tcatgtcagt ccttcctctt ggaaatggac ggccaggtct  120
aggctgggct ccggggcata cccatcacag ccctcctagt tcccagtgaa gcccatggca  180
tacagcagca aggcctggac aggagccccc tagaatgcag gcaaatctct gcagataggt  240
gtctgtcacc ttacacccag cttgtggcag agggtgtttc cggacacttg aggggagcag  300
ttccttcgat ggctctaaag tgtgacaagc acacatggag gtggccctga accttcatgt  360
catcttcagt tgtcacactg ctcggcattg gttcttcttt cctggaggct ccagacccac  420
tgaggaacag ttctcttcca aaccgtgata tcctgagccc ccacccagcc tcagcagctc  480
tcagggtctt ctactcccac ataccaatcc ctggaagaca gcttcgtgcc tgtcctggca  540
gcagccatga tcctagtgct caccgttgag ggagggaggg agggagggag gcaggcaggc  600
agtggggaag gatgctcacg agaggcagga ggagactaat tctgcagccc tacaatggga  660
ggcaggactc cttgccaggt ggctgtgagc caagctattg ctgtataaac cctgtcccat  720
gagctgaaag cagagctgcc tcactcacag gaaggtactt cctgccaggg agggcacccg  780
ttagggtcag tgccttccct ggcaccgcag tctacagggc aggaggtggt tccactctag  840
tccttccctc ctgaagggta catgtgcaga caaaatgaga gaatagtaaa gggcacttgg  900
cagtggcaaa gtcacctaat gtcaaggggc catcagtggg agggaggcac attttggaga  960
agaaacatac ttaagtgcat tgccaaatag ttctaccctg gttttactaa aatctttcct  1020
gataatacca gcaggaaaac agaaacaaca tcccacctcc tacccccaaa acctcacagt  1080
caaaattact tttttttttt taaataaagt ttggaaatcc atagattttt gaggaatttg  1140
ataaaaagtt ttagttcttc ctacagttag acaggtgggg caatgtcttc agtgggactt  1200
taatgactat ggacttttaa aaattgagtc ccattctcag atgctagact cacaaagctg  1260
actgtatgtg gcagttacaa gaaaagtctg ctttcaggaa gaatggacag gcatttttag  1320
aggtcttgca tatgtctttg aggtgtgtgt gtgtgtgtgt gtgtgtgtgt gtgcgtgtgt  1380
gcgtgtgtgc ctgtgcccag gtgcatctct aggttgcagc acccatgagc agacaacagc  1440
tttgtagcag aggctgttct tgtcccatac taagagttat ttctgaccac actgaacaag  1500
agaccaacta aactggaagt cactgatata aaccccaggt gaatggctct agattttata  1560
ttctgttttc ttatgaacat ctaccatgag gagtaatcgg taatcaggcc tgcaacatgc  1620
tcatctcaga gctgttggac caactttaga gtgtggcagc agcattgtga gaactttcat  1680
gtggtctcca agcacttcta ggagggatat ctagggtaac aagtagaaac cctaaatcag  1740
caaaggggca ttggtgactt tctttcatta aaattcagta gcttccttta aggtcctctt  1800
gaaagacctg atccatgtcc actgttcctg ttaccatgac accaggatgg gctgggctgg  1860
cttgcagtgg cctttgccag ggcagatagg aatagaatca ggccaagtgt gaggctcccc  1920
acaacctgtg tacctgtgtt tggtagggaa ccttgcatcc cggcagcctt ttaatcatca  1980
tgatgggaaa acagaaggaa attcttaaga aagcagtcca cagactgaag cacagttaat  2040
tagtcatagg ctgcaagctc tttcctcccg tgtagcctag aaacagctcc aaattactcc  2100
tctccccact ctgcagtcga ttggtacaga caggactgag tgggcagcag agagcccgct  2160
cagtcacaca gccagcagag ctcctggacc aagccagggg acgaaggcag cctgtgtcca  2220
gggctcattc tcatcaacat gtcctggcta ctctgggctt gggccttggg aagaggcggc  2280
tctgaccagc agcacgggaa gctgtctgag gccataggct gacctgattt tgaaccttcc  2340
ctttggtgcc tcatcttgtc aggccgagtc ctcccttggc tctgaaaggc ataggtctgt  2400
actgtaaggg ctgacagaag gcaagatggg aaggggcaaa agaggctctg gttccattct  2460
taattgttgc taggacattg agctttccct tgaccaagag aaacggagac aaccaacaag  2520
ccatagctca gagacacctt tggggtgatc gggctagcat tcctcaggtc ccaaccatgc  2580
agaagataca aagggacaga gagcatccac aatggtcagc cggtgtctgg gcaggctaca  2640
gcccaggtca gccacgacca gggatgagat tattgaaata gcctctttgg gtccagcaga  2700
tgctgtctct gcccaggctg agagactagg agagtgcatc aacactagtg agtagacagc  2760
ttgatagtca tgcctggggt aggggtgggg gtctgccgca gggcaagcct ctcttaatcc  2820
taagtggaag tcagtctcat aagctgggcc acaagcagga ttctcacata gggcagttaa  2880
```

-continued

```
caccaacacc actctgtgct agtcaaatgg aatgcataag aaaaaggagc cgtgtgaagt  2940
gcaagtgcca tagggtgttg ggagggctac atgagggacc tgcccgacta gactgagtag  3000
ctacaggaga gagagtggtg gccagaaggc gcatccactt ccataaactt tgtcacatgc  3060
agcacaggcc ttgccaagtc acacacttta cacgggcata ggaagagtta cattaaaatt  3120
aatctcttta ctgatataat taaattttaa ctcctgagaa gaaaacagag aaagggaaaa  3180
tgatgctgga cacctggcag tcccagttcc cagcccccac accattcact ttgtgtccag  3240
acactggtgt ggcaggtaca cctgctgggt aaatgtggga gggagctctc cagcccagtg  3300
ggacaggggg gctcagaacc atcttacaag agctcggatt ctgttccaca taccagggca  3360
gctgcaacct ggcaactatg gccagggcaa cactaagaaa aagacaaaca cctggtcaac  3420
ctagcactgc caccagctgc agtgatgcca ggacccagga ctcaggctca accccaacat  3480
agtgcatgtt ccctgcatag ctctcattgc aaagcactcc tgccattgcc tggctgtcca  3540
cttgacacaa gtggaagcct gcacgtccaa ggcagcctta gcagaagctt ggtgcaggcc  3600
cctggaggct gtagccacag cagttgcctc ctctcagcct cttgttccac aggtactact  3660
cagcaggcgg tgaccttgtg aacattttgc aaacaagcaa gcagcctgtg gtatggactt  3720
cctggtgctg ccaccacctc aaacacagac tggaaagccc tgcggtcgaa ttcctcctct  3780
atctggtgtc tgtagaagtc tgtggcaacc aggcagaaaa ggttcacatc cacctgctcc  3840
agtttgccca tcctgctgat gacgtgtgga aggattgcag aaacccatgg gctggtagat  3900
gcactgacaa ggaagcagga gaggctccac atggccatgg caactggagt tctttgtgtg  3960
aagttggaca gagacagcat aacccagtcc cggaccatgg atgactgccc agcactgtgc  4020
agagtctgaa aaaccttgta tactacagtg gccatgaact gtgggtatgg ctgctggttg  4080
gacaggaact ctccaatgac tttgttcatg acatcttgag gtggaaagaa gtcatctaga  4140
aactgaggca ggatccttgc cacgaccctg gcttcacagg gaaatccctt gcggatcctg  4200
tcaaagagca cagacactcg ctccatagct acaatcacag actcgctgtc aggggtagca  4260
gggctggggt cagaagctct gcctggactg gctttttcct ttcctgtgta catgcaggta  4320
agcatcaggc ctagggctgc catggccctg tgtgggcttt gtacattcac tctgtccaca  4380
cttagcttga ccaaggactc cgtgtctagc cgagagagct gctcagacag caggagccgt  4440
tccagacccc ggagggcaca gtggtaaatg atggaggggg tggactcctc acttccagac  4500
agcattactc cacacatctg tatcacagat gctgagaatt ctggccccac atccagaggg  4560
tagttttcca tcaggtagaa tgcagtggca cacatcacca gcacatgctg ctggctgtga  4620
atgttcacgc agtgggctat tcctttgagg ttggacagca gatagtcact aacaactgga  4680
atgagctgct ttacagtgtc atccaagagg tcacactcca acacatagag gatgccatgc  4740
agggctccga tctggctggg caggtgggtg ctcctgagtg tgctctccag taggcggctg  4800
accggctctg ccacagtttt gtccattcca agaacagcag ctgccttaca ggtggcaggc  4860
accaggtatt gaatgaggat ctcatcttct gaagggtgca ctctccgtag ttctgtcagc  4920
gtcagataca tcatttcaaa ctgggtacgt tcagtgaata agtctgacac cacaagaaga  4980
gatcgaacca cttcactgat caggatgaca ggggtccttc tggctgcact ggatggcagg  5040
atccaacggc tgtataattc aagcagaaac tgcgaacagg agtgaatatc aaccccagca  5100
cggtgttttc tggaattgac tggagacaca ggtggtgatg ttggcgcagg ggcatccgct  5160
tcttcctcct cctcctcatc ccattcctcc tctctcaggg gtgtgatgtt gttccccagc  5220
cacacggagt gtatggacac ctggcccagc ttgtagctca tgttgcctgg ctcccgctct  5280
gagttgatct gcagcagcag cttgtcatgg ctgataagag cacctgtagt agctggtaac  5340
agagaaggga caggatccca tgcctggtga gaatgatgag tggcagtatt ctctctttgg  5400
gaaaccatct cttggatttc ttgttctaca atccctctga tcatgctcaa ctttcttcca  5460
aatctggtat cgagagcctt cagtggcttg ttccggggct gttgctccaa gcagcttaca  5520
gctggattgc cagccacagg cacagccatt gcgctgagca ctagagaggt gatggcctgt  5580
acagccagga cgtggatctg ggtcctttcg gtgtcttcct ctggtgggct ctcttcctgt  5640
tccatcacca agggctgagt caccaggaca ccaaggaggg tggcccaagt ttcttcgaat  5700
tgagtacgac tggtccaccc tagggtgttg atgcggtaga tgaactcctt gaggacctcc  5760
ttctcctgga ggaactctac agggatctca ggaaacactg tgccgaaatc ccctccaggc  5820
ttgggtgacc acccgagttt ccataccaga ggaggcacac gagtatagct gttaacgagg  5880
gggaggcggg ccagactgac aacaatgttc ttcagcacag ctgtgagaaa tgaaggtagg  5940
gtgctgttcc tcttgtggcc cagggccagc accgactgca gggattccac catgtctgcc  6000
accatctcgc aggccgaagt gatgtgactg aggttttgta tatctgagtc tacttcctcc  6060
tttctgacag cccttggagt atgtgacctg ctttccggac caagaagttg gtctccaggt  6120
tgtactgcaa tggcttccag gatgaatcgc acacagtgga taagggagca agtatgagtc  6180
acgtactctg gggaggacag caccccccag aggccaggca cctgcagtgc caggcagcag  6240
cagtctaggc cggcttggag gtccagactc agtgggatct gctcatggat caaatgccat  6300
gacagggcct caagtgtcat taccacaaac ttcaccgtgt gcccctcctt ctcaggagga  6360
aggtgcaaag gagcaggcac tttggagagc accaccaggt actgtgccag ggcacgggca  6420
agtgtggtca gagactggta tgatgtggta tcaccaaaga gatcattcag cttgctccag  6480
taggctgtgg gttctgtagg caggaaaggc tggaagactt gatggactgc aggcagctgc  6540
tgaaccacat tggtcacccg gtccagagtc accctacgag ccgcttcaaa aaggggactc  6600
ttttggccat tagcaatctc gctcatgcca aggcttaagc agggagccaa aaggcttagg  6660
ttgaactccg agctcatcat gaagtcactc atatcttcag cagggatacg gttcaccagc  6720
tctgcacctt ccagcagtgc agaatctgac ctggtccaac actgggatct gacaagctgg  6780
aggtaccagt ctttgtccgg attcactgtt tccagggatg tgtgcccatc cccatccaga  6840
gggtgggaag tgactggggg caaggggcta agtgagtcct gcacagtaga gagtcggaat  6900
ctgtccagca gtgaatagag cctttggtgt ctttgtgcaa gcccagtgtt ctggaggtgt  6960
tcctggattc tgttcagttc ctcctctggc aactgggcca tgctgctctg taaatttgca  7020
gccaaaagca tttctactcg gcgacaggcc agggtgtcga ccatgcgagc cagcgcacgg  7080
aaaggggtgc ccagtagcct gtccacatac agtgtgagca cagcaccaga ctggctgaga  7140
tggatgcctt ccaagcactg aagtgttttc ttcagagtgg ttggagttga aagattttca  7200
cagcgagact gaattgcctg gataaaaaga ccactagctg cagaattacg atgaatggca  7260
ctaataaagt cttgaactgg aggctcgtgg gacaagctga tcagatcttg aatgtgattc  7320
acaatgagcc atgttaagtg ttctgagtca tggagattct gacagacata atcacagaag  7380
agaataaggg cccctcttcg tactatttct ctattgcaca ttccaagctg agctgctgag  7440
ccagaatcct cttcagcaga tatctggggg tttagtgact tcgtgcagga cagactgtgt  7500
ctcttgggcg tctgctgcac ctcggcccac catcggtggt cagtgtggtt gatgagcagt  7560
aggatctgac accagagcag taccagagct gggtgtgtgg gcaccatggc tcgcacccgt  7620
```

```
gcattcaggc tatctagagt atagaagctg ccttcacagc catcactggt gaagagtcta  7680
gtggcagcgg ctgtgattct ccggaacatt ccagatttga atatgtggat cagacacatg  7740
agcagtgtgc cgagctcttg gcaatagaat gtatgctgct gttcactcat gtccactttg  7800
agctgttttg taacaatgtc ttccagaaga ataccaacca gctgtaagag aaaccttgag  7860
aatgtatctt ctggcaaatt ctttacttgt ttcccttcac tgcgttctcc tagtgttgga  7920
ttactgtctc catcccttaa cctgttaatt actggacagg aaattaaata tggagagaag  7980
gagagctcct gaatacgaga aagaacaatg tcttcggttg actgggaaat gagaaccctc  8040
agaatggcta ggattccaga tatccacagc tgcacagtgc ttacagatgc cattgtgctt  8100
ggagtgatga acatactccg caaaagcatg tccacaggac gtagggagga aggagccaaa  8160
atctcaaaca aggtatttaa tactccaagg gcttcatgag agtcaatatg catctgctgc  8220
ttggctaaca tgggcaggat gatgtctgcg acctgccgag agagccgttt ccacttgtcc  8280
tcattctctt tgtggcactg ctgcaggacg aggatgaaca tctctagcac ctgatggtac  8340
tggatgagtc gtaacagcat tgagaccacc acctccttct gggtttcaag ctctttccct  8400
gcatcagctt tatttgttcc tcttaacaca aagaggtcat ggacaatggg ctgcagcgca  8460
ggaatagcat gtgtgacagc cttccttcca ctggccatga tgccatcaca cagctggatg  8520
attttaggaa ttccaatgat ctgttttgaa tggtagcgct cataagataa tagtaccagg  8580
aagaaaaata tatttggaat aattgcctct gattccctga actggcccac ttcaatgtac  8640
tcaaactgct tcagcacaaa cccgatgaac acctgatctg aatccagtag acagtaattg  8700
acccgtagct gaaccagctg tgccagcaaa tccaaaacct gcttctgcag ttgtactgat  8760
gttgtcgtgg tgtactgctt caatgctttt ataacaagag gctcaaataa cctaatgtgg  8820
ttatgaatag cgttcttatc tgcacggttc tttgtgacac ttgtaaggtt cgtcttcaac  8880
tgagcagaca ctttctggag tacatcaaac caccctgagg catcgtgctc ctggtccgcc  8940
tgtaccatgt tcctcaggct ggcatcagcc aaagcctgcg tgaagtgcgt gtatggtgcc  9000
atgaagcagt agtgatataa gccgggcctc acactggaag agccaaggcg ctgtgctcgg  9060
cactgagact tgctggggtt ggaagataag ccatcaaact gtgaggctaa gtttgtccca  9120
aagagagtct tcaatagctg ctgaacacag acagtcgcca tcattggttc tcgactaaag  9180
caggatttca agtatccaag gacctcttca acacactttc caatgtcctg cagtgtcgcc  9240
agctctagaa tctgagaaag gacgtccaag gcagagcgca ggaacccccc aaacttttca  9300
gtgctgttct gaagatctaa ggtgacctta tagttggcgt gagtggcttt caggacatca  9360
tgcagtctga ggtaggaagg gagatggtag aaactcccaa gtgaagatga tttactcgct  9420
gtgacaggtc ctgaggtgtc tgactgtcga gaggctgtac tggcctctcc acctttcttg  9480
ggactcatcg gagtggatgt ttgttctccg ggctctttct ccttcccttt ccgtcgaata  9540
ggacttagag aagggggggtt tgtgagagaa ggcaaagctg ccttgattgc tggtccagga  9600
gtcacgtcat ccaagacatg agcacagata ttgatcacct tcagcaggtg ggagaaaagc  9660
tgctccacca tgggcaccag agtccgatcc cccagggcag gccagatctc ctcctgtctg  9720
gtggctgctg agctgccttc ttcttccgag gcccatgagc ttctcagaga cttgggggca  9780
ctcgctgcta gcaagtttcc agccaaaatc aaggcatcct gatgggctga gagatccagt  9840
gggaaccaag ctgatgaaag caaggtgaga atcatggagg ccatcccaac agtgcagctc  9900
ttcctggact catcagaggc actcagtggg ggcactccac agtgccatcc tagactccaa  9960
gtgcaaactg gaaaggcggc tgaaagaaca cacaaggctt cacagcaccc aaatgtgagt  10020
gcccgtgtag ttgacgtaat gagttcatga gaaactgcgg caacgactct tgagaggttg  10080
ttttccatgg tgacatctgt tacacttggt agtaagctgt agcctctata gattctggtt  10140
atggtgctga cggagaagtg ggatggtggc tgggtctcat gcatgaggag cttcaggtaa  10200
acactacttt gatctcttgc tacagccacg actgggtcag cctgtccttg gtcacactta  10260
taaaacagct ttgggacaag tcttgtcaat gtcgtcgcag caacatgtcg aaccctgggg  10320
tcttcatctc caagcaaata aatgaccaca ttattgagta ctcgttcttg tagttttaga  10380
aaccctgtat aatgatgagc ccctcggtgt aaactttctg cttttgcctc caaaaaactc  10440
accagcctga aatcaatctc tgcaagagtt tccagcagtt cagtcctcac cagccagtag  10500
gagctgttct tcagaggcag catgtcaata agcagttgta atcccaagtc actgtagctg  10560
ctgctgcaaa gactcaggac acagtgcctc acagctgtac aagccaactt gcaagtaaca  10620
gaagattcat ccttcaaagt tttctgcagt aaaggaatgc agtccaccag agaaaatgta  10680
tttcctgtca gggccctgat ggtgcccagc cagtcaccaa cacggagacg ggacctgctg  10740
aggatggagt agacaagggt cccacagaga atggcagtag ctcctcgcac ctgagggtct  10800
ccatgatcga tgtagttcag gatgtcagag acatactgtt cctcagtact ttccatggta  10860
ctgagaggta ctttgtagag tttgctgaag aacgactctg gatgaagggc cacagctgca  10920
ccaatacagc tgagggccag ggccttcaca ctgactctca catctctgtc tggaaccagt  10980
gctttctttt cgccagttaa caaaaaggaa gcggataaaa gacggacaca atgtaccaga  11040
ggagcagaat catcatcatt aggctgtcct atgtcacctt tgattcggca aggcttgctt  11100
tctgggtccc cagcttcagc aacctcatct tttgaaacaa acttatcaac actgctgtca  11160
gaaggctgcc ggctatgacc cattctttcc aacaagtgtg cctgctgaag ggccagagaa  11220
gagtttctga aaacgtctga gacttcacca gaaagaacac ctgcagcttc ctcctcgtct  11280
tcctcctgtg gctgtcctat ctgcacgcct aaatactggc tgtcagcacc atctaagaca  11340
atttcagaac tgtcagaagg agtcacagct gaatcaggtc cttcagtggt ggtctgagaa  11400
ctgtcactga tgggtgagga ggcctgggtc ccatcattca ggtccatggc agggtcggat  11460
ggaacagcac tgaactggct ggagctgtgg ctcaagatgt cttcctcatc tccatcagta  11520
gcagcactgg tcaagtcaca gcctgacaaa tccacagagt ctgcttgaag tgtgtgctgg  11580
gatcgaggct gctcagtgat gatgtcgtga cctacagaac cgggagtgga gacacccgaa  11640
gaagaagcag cgagctctcc accaatctca ctcttcacag aggctgcaaa ggctgagctg  11700
ctgacatctg acctggactc cgagtcatcc tccaaggctt cttcctctcc taagagcact  11760
ttgccttttt gctttcttga gagaacaggg ctgcatgagg aaccccctcc agctaaaagc  11820
tccacgatac tcccgctgcg gcctcggccc ccggcttcct ctcgaaccag agtgagctgc  11880
ccgagccctc ctggtgtggt cagtgcttgc agcagctcag gtggaggggt acggaagagc  11940
tgctgcagga gctccaatgc ccctgtcacc acattatggt cttggtgctg tgtgtgatgc  12000
aaagtcagtt cataaacctg gacaagctgc tctgcagaag gagagacttc catttctttc  12060
cgtgttaccc caaagctgcc ctttagactt gtgtccttga cctgctgctg gagcaagggc  12120
actagacacc tcagtgtgag caacacacca aggatcagga gagtggggtg gtcttcctcc  12180
atgggaacca gcaaacctag gagcacattc aggagccagt tgtagaagta ctgtgtcctc  12240
ctagagtgct ggcagatact cactgctgac ccagctgctg tccgccgcac agtgggagag  12300
cttgacttca gatttgctat gaaagctttc aatagaacct taatttcatt gtcattcgcg  12360
```

-continued

```
aaattgccaa aagaggccat aattttagga acagctgcag ccaaagtctc ctgaactgac  12420
tcctccggtc gtttgcttgt tcgggtcaaa catggaagaa gattcaccag ataaggcctg  12480
cacttctgag gtcgaaccag gtgagccagc tcagcaaacc tccacagagc tgcacgcaaa  12540
cttcgaggag caccattctt tttaatttcc ttatagagtt ctaactgtag ccttggaaga  12600
ttagagtcca tcaaagcttt gatgactttg ttgaggcact catcagccac cattctgacg  12660
tctgactccg catcgtcgct gcacagcaga aacagttcca tagcaatgcc caagagtttc  12720
tgaaattctg gagaatttct gagagactgt gccacaatgt tttcacatat tgttagacag  12780
tgattcacac ggtccttctt ggtggctgag agttccttct ttggtcggtg cagcggctcc  12840
tcggccggac ctggcagcgg cggtggtggc ggcggctgcc cctgaggcgg cggctgaggg  12900
ggttgaggcg gcggcggcgg cggtggtggc ggcgcctgcg gcggcggctg ctgctgctgc  12960
tgttgctgct ggaacgactt gagcgactcg aaagccttca tcagtttttc cagggttgcc  13020
atgacggcct cctgcccgac aggacagacc ctgaaggctt ggagcctatt cgcactacgc  13080
agcgccactt agcagcaagg taatgaatgg ggctctacga ggtagaccga agcggaacca  13140
aagctcccag ccatcttggg cccgtcccgg caaccctcgc ggcgagtgc              13189
```

```
SEQ ID NO: 9            moltype = DNA  length = 13328
FEATURE                 Location/Qualifiers
source                  1..13328
                        mol_type = genomic DNA
                        organism = Macaca fascicularis
SEQUENCE: 9
tgatggtttc aatgtttttc ctttaatttg gatgtacaat gtttgcagca gttaaaaaaa  60
ttaaatatac atctctcgtc agtccttccc tttgctctca gaagcagtca ggtctgggtg  120
gggctccggg actcacccat cacagccctg ctggctccag gggagctcag gctcagctga  180
cagtccctct gaccacagcg caaagcaatg agacctggac aaggaggccc cacgtgggtc  240
agagcccacc ctccgtaggc aggtccacgt tggccacaat cctccaaggc tggcaatcac  300
cacccagatt gcagcgggag actctgcttt tggaaacaac tgaggggaag gcgttccttg  360
gactgcacca gagcgtgaca ggcacacggg ggaagagtgg cctctgaacc ttccaggttg  420
ccttcagttg tcatgcggcg ctctgagcgg ctccctcctt cccaggaggc ccaggcctgg  480
cgagcgagtg tcctcttctc gcctggacca tcctgagctc tccagggtgc ctcggcagct  540
ctcaagatct tccttcttct cgctccctca ggtggcccct ccggagcaca gctccaagcc  600
taccctggcc agcagctgtg gtcctgggtc ctccccgcag agggaggaag tggggaggga  660
caaagccggg tgaggatgtc tgctgggcag gatgctcaca ggtagcagga gcaggctgac  720
tccaccccac agacacacag aactaacctc actccgcccc tcagggggag gaacttccac  780
ctgccaggca gccacagacc gagttattgc tgtttactat ccgtcccgag ctccgtgggg  840
ggctcagctc agctccaaga ggacgagctg ttcatcggct ccgagggctc tggaatgacc  900
cctccatgaa ggtgggggcg ggggtgtcct ttagggcaca gggccttctc agatgctaca  960
ttctgggtgt ctggaggggt ttcagcttca cattttcctc ctgaaaggac acgtgtgctg  1020
gcagaaatgg gggtggacag taacaaagag cgcttggcag ccggaaacgt cacctacaca  1080
gactcagctg ggcccgcagc ggaagggagg cacgttttgg gaaagaaacg cgcttcagtg  1140
cattgccaaa caattctacc ctggtttcat taaagtcttt cctgatatta ccagcagcaa  1200
aacaaaagca gtctccccac agctcacccc caaaacttga caaccaaatt aatcacattt  1260
tcaacaaaat ttggataata tgattggtgc ttgccatagg ttttttagga acgcgacaaa  1320
gtcttcctcc cttcggcaga gttgatatgg agaccgtttt ctccggtggg atcctagtga  1380
gccatgaatg agccctgctc tgaccaagcc ccgcgcctgg acgcccgtca cacagctaac  1440
tttacctggc aggtctgagg aaagtcaact tccaggaaga accgacacgg gcactcttgg  1500
aggccatgca tctctgtctt gagatgtgcg tgtataaaac tacagatgtg tccatatgca  1560
cgtgcacgtg tacttgactt acgcatgggt aaagtcattt tactaatgag ctcatattca  1620
tctctggagc acacaggcag gcctttggga gtgggggaca cccactgcca gagcggggtg  1680
ttctgagccc cttgctaagg actgttttag atcacgtcgt aaacaaaagg aagacaaact  1740
ctgtgttgag cccagcgata tgcattccaa ggggaatggc tccgttttac attcacagtg  1800
ttatttctta caaatgtaaa catctagcag aacaacatct ggcctgtgat acttctgtct  1860
ccgagctgtt gacataactt actgcagggg aggtgggtgg ggagcagcaa cggttctgag  1920
aactttcccc tcattcccaa agcttctagc aggctttcca ggaagaagct aggatgagaa  1980
acaggagccc ccaaccaata cggaagaacg gtggttttct tgttaaaatt cagtagcttc  2040
ccttaagggc ctcctcaaac atcagacccc tttctaccgc tcctgctgcc ctgccacgag  2100
gacgaggtgg tcctggctgg gggaggcctc tgttgggagc tggtgggaaa agcctcatac  2160
aggcctgtca aaggctgctc agaggagggg ctccctttga gcaggggctc cctttcagcg  2220
ccccctcatg tatgtgggca gcacacaagt ccacatgtca gctgctcctc agctgccaca  2280
taggagaggg acaggtggaa gcttgagggt ctcaaggcag cacctgcaca gactccagaa  2340
aagcatttcc tccacttacc atattcaata cccaaaacat caacaggcat gagcaaacca  2400
agccacatga cagtcgccaa cctcgcctgg ctcgcctcaa gggctgagga agcagagctc  2460
ctgccccatc tcagagctcc caaatccagc tcctatgtca gcagcagccg gccatccaga  2520
atccacttcc attttaatga cttggctcct ctgggcctgc aaacaagagg ctggtccagg  2580
gacctggcct ggggatagga gtggcggctc tgacagggca gtggggcagt ctccaatgag  2640
cacagatctg cactctcctg actaaaaggg gtccccgtgc aagatgtcag ctggaacggg  2700
ggcagaaggg atgccaggct ctgtcactaa cagtgccaag acgccaagct ttgctgttga  2760
ccaagagagg ctcagacaaa acacagctca gtgacaccct tggggcatgc atccatggaa  2820
cggcagatcc caacaccggc cagccagctc ctggcagcac accgccccag ggctagcaag  2880
gaacaggagt gggaggccca tgtctctgga cacagcggag gctgctcaca gccagggagg  2940
gctggccttc tcagctgata gggaggctgc tgtccctaat gtgggtggag aacaacagtt  3000
gtctgtgccc aagaaggagg ggctgcaggc gagcatgccc ctaggacagt gggggcctgt  3060
ccttagtcct gctgtggcca cctgcacact agcgcctctc tacatcccag tcaccttgtg  3120
aatgcataaa caggaacatg tacaacggaa atgtcagcgg gtgctcagga aggctatgcc  3180
agtggctaca ggagagggag cgtggccagg ggccctgccc acctccccga acactgtcgc  3240
atgcagcaca ggccttgcaa ttcacatact ttacacgggc atagaaagag ttacgttaaa  3300
attaatctct ttactgatat aattaaattt taaatcctga gaagaaaaga gagaagggag  3360
aatggtgctg ggtgtctagc acccccagcc actggcccag cacatgccat ggcatctgtg  3420
catacagaca cagggcgtgg catgcacacc ccaccaggaa gacacaggcc agtgttccca  3480
```

-continued

```
aagcctgctc acggcacctt ctactgcagg acagcagagg ggcccacagc cagcctgcag  3540
gagggaggac ttccggccca gatgcaagag cagctgcagc ctggcaacac ccaacaggtg  3600
agcatcagga gaaaggacct ggtcacccac atggcgtgca gcacagctgc tcctgctctc  3660
cggaaggcct caggctcagc cccaccggga ctgcagatac tccttgcctg gccactgtac  3720
cacaaagagc acttctgcca tatggcagag acacgcacgt tgcctggccg cccgcggcat  3780
gtgcggaagc ccacagggac caagctggct cggtggaggc agggcacagg gcgcagattt  3840
ctggaggctc cagccccagc tgccgcctca cagtctctcc caccatggcg ctcagcaggt  3900
ggtgaccttg tggacatttc gtaaacaagt cagcagccgg tgatatgggc ttcctggagc  3960
tgcaaccacc tcaaacacag actggaaggc cctgcggtcg agctcctcct ctatctggtg  4020
tctgtaaaag tctgtggcaa ccaggcagaa aaggttgacg tccacctgct ccagctttcc  4080
catcctgctg atgacatgtg ggaggatcgc cgcaacccat gggctggtgg acgcgctgac  4140
gaagaagcag gagaggctcc atgtggccat ggcgactggg gtcctctgcg tgaagttgga  4200
gagggacagc atgacccagt cccggaccat ggatgactgc ccggtgctgt gcagagtctg  4260
aaacacctta tacaccaccg tggccatgaa ctgggggtat ggctgctggt tggacagaaa  4320
ctctccgatg actttgttca tgatgtcctg gggtgggaag aagtcatcta gaaactgggg  4380
caggatcctc gccaccactc tggcttcaca aggaaagcct ttcctgatcc tatcaaaaag  4440
aacagacacc cgctccatag caacaatcac cgactcgctg tctggggctg caggattagg  4500
gtctgaagtt ctacccggac tgactttctc ctttcctgtg tacatgcagg tgagcatcaa  4560
gcccagagcc gccatggccc ggtgcgggct gtgcacgttc actctgtcca cactcagctt  4620
gaccagggat tctgcatcca ggcgggagag ctgctcagag agcaggaggc gctccaggcc  4680
tctgagggca cagtggtaaa tgatagaggg ggtggactcc tcacttccgg acagcatcac  4740
cccacacatc tgtattattg atgctgaaaa ttctggccct acgtccagag gatagttctc  4800
aatcaggtaa aacgcagtgg cacacatgac cagtacgtgc tgctggctgt gaatgttcac  4860
gcagtgggcg atccctttca ggttggagag gagatagtca ctgatgactg ggatgagctg  4920
cttggcagta tcgtccagca ggtcgcactc cagcacatag aggatgccgt gcagggctcc  4980
gaccctgctg ggcaggtggc tgctcctgag tgtgctctcc agcaggcggc tgacaggctc  5040
cgccacgacc ttgtccatcc caaggacggc agctgccttg caggtggcgg gcaccaggta  5100
ctgagcgagg atctcgtctt ctgaaggatg caccccttcgc agttctgtca gcgtcacata  5160
catcagctca aactggttgc gctcagtgaa caagtctgag accaccagaa gggatcgaac  5220
cacctcactg atcaggatgg ccggggtcct cctggctgag ttggatggca ggatccagcg  5280
gctgtacaac tcgagtaaaa actgcgaaca ggaatggatg tcaactccag cccggtgttt  5340
cctggagttg actggagacg tgggtggtga tgaaggtgca ggggcgtcgg cctcctcctc  5400
ctcctcctcg tcccattcct cctcccttag gggtgtgatg ctgttcccca gccacacaga  5460
gtgtatggac acctggccga gtttgtagct cacgctcccc agctcccgct cggggttgat  5520
ctgcagcagc agcttctcgt ggctgatgag ggcacctgtg gtagccgggg acagagaagg  5580
gacaggatcc cacgcctggt ataaatgatg ggtggcgatg ttctctctct ttgaaaccat  5640
tgcttgaatc tcttgctcta caatccctct gataatgctc agcttcctcc caaacctggt  5700
gtccagagct ttcagaggct tgttccgagg ctgctgctcc aagcagctca cagctgggtt  5760
gccggccaca ggcacggtca ttgcactgag caccagtgag gtgatggcct gcacggccag  5820
gacgttgatc tgcgtcctct ctgtgtcttc ttctggtggg ctctcctcct gctccatcac  5880
gaggggctgc gtcaccagga caccaaggag agtggcccaa gtttcttcaa actgagtacg  5940
actggtccag cctagcgtgt tgatgcggta gatgaactcc ttaaagactt ccttttcctg  6000
gaggaactcc acggggatct cagggaatgc tgtgccaaaa tcccctcccg gtttgggtga  6060
ccatccaagc ttccacacca gtgggggcac acgtgtgtag ctgttgacaa ggggcaggcg  6120
ggccaggctg acgacgatgt tcctgagcac tgacgtgaga aacgccggca cgccactatt  6180
ccttttatga cccaaagcca acaccgactg cagagactcc accatttctg ccaccatctc  6240
acaggctgcg gtgatatact tcggattctg tgtgttagga tctatttcct cctcctcctc  6300
tctgatggct tttggggtat ttgtccttct ttctggacta agaagctgct ctccaggctg  6360
cactgcaacg gcctccagga tgaagtgcac acagtggatg agggagcagg cgtgggtcac  6420
aaactctgcg gaggagacca cgctccagag gccaggcagc tgcagggcca ggcagcagca  6480
gtccagccct gcctggagat ccagactcag cggaatctgc tcatggatca aatgccagga  6540
cagggcctca agggttgcca ccacgaattt catggtgtcc ttctctttct caggaggaag  6600
gtgcaagtga ctgggcagtt tggagaccgc caccaggtac tgtgccaggg cccgggccag  6660
agtggtcagg gactgataca gcgcagcatc cccaaataga tcattcaact tgctccagta  6720
ggccgccggc tctgcaggca ggtcggactg gaagacgtgg tggacagcag ggagctgctg  6780
cacggtgctg ctcacgcggg ccagagtcac ctcacgggct gcttcaaaaa gcggactcct  6840
ctggccacca gaaatttcac tcatccctag gcttaagcat ggagctagca ggcttaggtt  6900
gaactccgag ttcatcatga aggcactcat atcttcagca ggaatccgat tcaccagctc  6960
tgcaccttcc agcagcgcag aatctgacct ggtccaacac tgggatttga caagatgaat  7020
gtaccagtct ttgtccggac tcactgtttc cagtgacacg tgcccgtccc cgtccagcgg  7080
gtgggaagag actgggggag agggactaag tgagtcttgc atggtggaga gacgaaacct  7140
gtccagcagg gaatagagcc tctggtgtct ctgagcgagc ccgctgctct gaaggtattc  7200
ctggattctg ttgagttctt ccattggcaa ctgggccatg ctgctctgta aatttgcagc  7260
cagaagcatt tctacccggc gacaagcaag gatgtcgacc atgcgagcca gcacacggaa  7320
aggggtgcac agcagcctgt ccacatacaa cgtgagcaca gctcccgact ggctgagatg  7380
gatcccctcc aagcactgaa gagttttctt cagagtggtt ggagttgaaa ggttttcaca  7440
acgagactga attgcctgga tgaagaggcc gctggcagcg gagttccgat gaacagcact  7500
gatgaagtcc tgtactggag gctcgtggga aaggctgatc agatcttgaa tgtgatttac  7560
aatgagccac gttaagtgct cggagtcatg gaggttctga cagacataat cacagaagag  7620
aatgagagcc cctcttcgta ctatttctct attgcacatt ccaagtttgg ctgccaagtc  7680
agaatcctcc tcttctccag acatctgggg actaagtaac tttgtgctgg acagactgtg  7740
tcttttcggg gtctgctgca cttctgccca ccagcggtag tcggtgtggt tgacaagcag  7800
caggatctga caccagagca gcaccagggc cgggtgggtg gtgatcatgg aacgagcccg  7860
caaattcaag ctgtccaggg tgtagaaact gccgccacag ccatcactgc ggaacagtct  7920
agtggcagct gctgtgattc tccggaacat tccagacttg aagatgtgga tcagacacat  7980
tagcagagtg cctagttctt ggcaatagaa agtatgttgc tgctcactca tttccacctt  8040
cagctgtttt gtaacaatgt cttctaaaag aatacccacc agttgtaata gaaaccttga  8100
aaatgtttct tccggcaaat tctttatttg tttcccttca ctgtgttctt ctagtgctga  8160
attactgtcc ccatctctta gcctattaat tactggacag gagattaaat atggagagaa  8220
```

-continued

```
agagagctcc tgaatacgag aaagaacaat atcttcagtt gactgggaaa tcagaaccct  8280
caaaatggcc agaattcctg atatccacag ttgaacagtg ctcacagatg ccattgtgtt  8340
tggagtgacg aacatactcc gtaaaagcat gtccaccgga cggagggagg aaggggccaa  8400
aatctcaaat aatgtattta acactccaag ggcttcatga gagtcaatgt gcatctgctg  8460
tttggctaac attgggagga tgatgtcagc tatctgtcga gacagtcgct tccacttgtc  8520
ttcattctcc ttgtggcact gctgcaggac gagaatgaac atctccaaca cctgatggta  8580
ctggatgagt ctcagtaaca ttgataccac cacttctttt tgggtttcaa gctcttttcc  8640
tgcatcagct ttatttgttc ctcttaatac aaaaaggtca tggactatgg gctgcagagc  8700
cggtatggcg tgtgtcacag ccttccttcc actggccatg atgccatcac agagctgaat  8760
gattttagga attccaatga tctgttttga atgatagcgt tcataagaca gtaataccaa  8820
gaagaaaaag atgtttggaa tgattgcctc tgattccctg aactggccca cttcaatgta  8880
ttcgaactgt ttcaatacaa agccaataaa cacctgatct gaatccagaa gacagtaatt  8940
aacccgtaac tgaaccagct gcgccagcaa atctaaaacc tgcttctgta actgcacaga  9000
tgttgttgtc gtgtactgtt ttaaagcttt tataacaaga ggttcaaaca aacgaatgtg  9060
attatgaata gcattcttat ctgcacggtt ctttgtgaca cttgtgaggt tcgtcttcaa  9120
ctgggtagac actttctgga ggacatcaaa ccatcccgag gtgtcgtgct cctgctccgc  9180
ctgcaccatg ttcctcaagc tggcgtcagc gagggcctgg gtgaagtggg tgtacggggc  9240
catgaagcag tagtggtaca agcctggcct cacactggag gagccaaggc gctgtgctcg  9300
gccttgtgac ttgctggggt tggatgataa gccgtcaaac tgggaggcca agtttgtccc  9360
aaagagagtc ttcaacaatt gttgaacaca aacagttgcc atcattggtt ctcgactaaa  9420
gcaggatttc aggtatccta ggatctcctc aacacacttc ccaatgtcct gcagtgtggc  9480
cagctctaga atctgagaga gaacgtccaa ggctgagcga agaaaccctc caaatttttc  9540
cgtgctgttc tgaagatcca aggtgacctt gtagttagcg tgcgtagctt tcaggacatc  9600
atgcagtttg aggtatgaag gaagatgata gaaactcccc agtgatgagg atttacttgt  9660
tgtaacagga cctgaggtat cagattgtct agaagctgca ctggcctcac tgcctttctt  9720
gggactcaac ggtacagatg cttgttctcc tggttcttc tccttcccct ttcgtcggat  9780
gggacttaga gaagggggt ttgttagaga aggcaaggct gcctttattg ccggtccagg  9840
agccacgtcg tccaggacat gtgcacaaat gttgatcacc ttcagcaggt gggagaagag  9900
ctgctccacc atgggcacca aggcccggtc ccctagggct ggccagacct cctcttgctt  9960
ggtggctgct gggttggctt cttcttcaga ggcccatgaa cttctcagag atttaggagc  10020
actggctgca agcaagtttc cggccaaaat caaagcatct tgatgggctg agagatccaa  10080
tgggaaccaa gctgacgaga gcagggtcag aatcatcgtg gccatcccaa cggtacagct  10140
cttcctagac tcatcggagg cgctcagtgg aggcactcca cagtgccaac ctaaactcca  10200
aatgcaaact gggaaggcag tggaaagaag acacaaagct tcacagcatc caaaagtgag  10260
tgctctcgtg gttgatgtga tcagttcatg agaaactgct gcaataactc ttgaaaggtt  10320
attttccata gtgacatctg ttatgcttgg tagtaggtta tagcctctgt atattctggt  10380
tattgtgctg acggagaaat gagatggagg ctgcgtctca tgcatgagaa gtttcaggta  10440
aacactgctt tgatctcttg ccacggccac tactgggtca gcttgtcctt ggtcacattt  10500
ataaaacagc tttgggacaa gcctaattaa tgatgctgca gcaacatgtc gcaccctggg  10560
gtcttcatcc ccaagcaaat ggatgacaac attattgagc actcgttctt gcagctttaa  10620
aagccctgta taatgatgag cccctctgtg taagttttct gcttttgcct ccaaaaagct  10680
caccagcctg aagtcaatct ccgcaagggt ttccagaagc tctgtcctca ccagccaata  10740
ggaactgttc ctcagagtca gcacgtcgat gatcagctgc agtcctaact cactgtagct  10800
gctgctgcag agactcatga cacaatgcct cacagctgta caagccagct tgcaagtgac  10860
agaagactcg tccttcagtg ttttccgcag caaaggaatg caatccgcca aagaaaatgt  10920
gtttcctgtc agggttctaa tggcgcccat ccaatctccc acgtggaagc gggacctgct  10980
gaggatggag cagatgaggg tcccacagag aatggcagtg gctcctcgaa cctgtgggtc  11040
tccatgatcg atgtagttca agatatctga gacatattgt tcctcagggt attctgtggt  11100
gtcaagagga actttataga gtttgctgaa gaaagattct gggtggagag ccacagctgc  11160
tcccacacag ctgagggcca gggccttcac gctgaccctc acatcccggt ccggaaccag  11220
cacatttttt ccccctgtta gcaaaaacga agcagataaa aggcggacac aatggacaag  11280
aggtgcagaa tcatcatcag tggactgtcc gatgtcacct ttgatgcggc aaggcttgtt  11340
ttcttgatca cccggttcag tagcttcatc tctcaacaca aatttatcaa cactgctgtc  11400
agaaggctgc ctgctgtgac tcatgttttt caataaatgt gcttgttgaa gggccatgga  11460
agagttcctg aaggcctccg aggcttcgtc aggaagaaca cctgtggctt cctcatcttc  11520
atcctggggc tgtccaatct gcaggcccaa atactggttg tcggtaccgt ctaacacaat  11580
ttcagaactg tctgaagggg tgacagctga atcaggccct tcggtggtgg tctgggagct  11640
gtcgctgatg ggcgaggagg cctgggtccc atcattcagg tccatggcag ggtcagatgg  11700
gacggcgctg acctggctgg agctgtggct caagatatcc tcctcatccc catccgtggc  11760
agagcttgtc aagtcacagc tggccagatc cactgagtcc gcctgcagcg tgtgctgtga  11820
ccgtggctgc tccgtgatga tgtcgtgacc tgctgaccct ggagtggaaa cccctgaaga  11880
agtagccagc tctccactga tatcatcctt cactgaggct gcaaaggcag agctgctgac  11940
atccgatctc gattcagagt catcctccaa ggcttcttct tctcctaaga gcactttgcc  12000
tttttgtttt cttgaaagga cagggctgca tgaggaaccc cctccagcta taagttccac  12060
aatactccca ctacggcttc ggccaccaga ctcctcctta gcggcggtga gctgcccaat  12120
gccccccact gtggtcaggg cttgcagaag ctcgggggga ggcgttctga agagctgctg  12180
caacagctcc agggctccgg tcacaacatt gtggtcttgg tgctgtgtat gatgtaacgt  12240
cagttcataa acctggacaa gctgctccgc agaaggacag acctccattt ctttccgtgt  12300
cactccgaag ctgcctttca ggcttgtatc cttgacctgc tgctgcagca agggcaccaa  12360
atacctcagg gtgagcagca cgccaagaat cagcagggtg gagtgctcct cctcgacagg  12420
aaccagtaag cctaagagca catttagtag ccagctatag aaatactgtg tccttcttga  12480
gtgctggcag atgctcactg ctgatccagc agctgtccgc cgaatggtgg gggagcttga  12540
cttcaggttc gctatgaagg cctttaacaa aaccttaatt tcattgtcat ttgcaaaatt  12600
gccgaaagaa gccataattt tgggaacagc tgcagccaag gtctcctgga ctgattcctc  12660
gggtctcttg cttgttcgac ttaggcacgg cagaaggttc accaggtaag gcctgcattt  12720
ctgaggccga accaggtgag ccagctcggc aaacctccac agggcagcac gcaaactccg  12780
aggggcacca ttctttttaa tttctttata gagctcgagc tgtaaccttg gaagattaga  12840
atccatcaaa gctttgataa ctttgttgag gcattcatca gccaccattc tgacatccga  12900
ctctgcgtca tcactgcaca gcagaaaaag ttccatagcg atgcccagaa gtttctgaaa  12960
```

```
ttctggagaa tttctgacag actgtgccac tatgttttca catattgtca gacaatgatt  13020
cacacggtct ttcttggtag ctgaaagttc tttctttggt cggtgcagcg gctcctcagc  13080
cacagccggg ccgggtggct gctgctgctg ctgctgctgg aaggacttga gagactcgaa  13140
ggccttcatc agcttttcca gggtcgccat ggcggtctcc cgcccggctg ggcagtcccc  13200
ggaggcctcg ggccgactcg cagcgccgct cagcaccggg gcaatgaatg gggctctggg  13260
ccgcgggtaa aagcggaacc gaagcggccg tccatcttgg acccgtcccg gcagcccccg  13320
cggcgcct                                                           13328

SEQ ID NO: 10          moltype = DNA  length = 13447
FEATURE                Location/Qualifiers
source                 1..13447
                       mol_type = genomic DNA
                       organism = Macaca mulatta
SEQUENCE: 10
tggtttcaat gtttttcctt taatttggat gtacaatgtt tgcagcagtt aaaaaaatta  60
aatatacatc tctcgtcagt ccttcccttt gctctcagaa gcagtcaggt ctgggtgggg  120
ctccgggact cgcccatcac agccctgctg gctccagggg agctcaggct cagctgacag  180
tccctctgac cacagcgcaa agcaatgaga cctggacaag gaggccccac gtgggtcaga  240
gcccaccctc cgtaggcagg tccacgttgg ccacaatcct ccaaggctgg caatcaccac  300
ccagattgca gcgggagact ctgcttttgg aaacaactga gggaaggcgt tccttggact  360
gcaccagagc gtgacaggca cacgggggaa gagtggcctc tgaaccttcc aggttgcctt  420
cagttgtcat gcagcgctct gagcggctcc ctccttccca ggaggcccag gcctggcgag  480
cgagtgtcct cttctcgcct ggaccatcct gagctctcca gggtgcctcg gcagctctca  540
agatcttcct tcttctcgct ccctcaggtg gcccctccgg agcacagctc caagcctacc  600
ctggccagca gctgtggtcc tgggtcctcc ccgcagaggg aggaagtggg gagggacaaa  660
gccgggtgag gatgtctgct gggcaggatg ctcacaggta gcaggagcag gctgactcca  720
ccccacagac acacagaact aacctcactc cgcccctcag ggggaggaac ttccacctgc  780
caggcagcca cagaccgagt tattgctgtt tactatccgt cccgagctcc gtggggggct  840
cagctcagct ccaagaggac gagctgttca tcggctccga gggctctgga atgacccctc  900
catgaaggtg ggggcggggg tgtcctttag ggcacagggc cttctcagat gctacattct  960
gggtgtctgg aggggtttcc gcttcacatt ttcctcctga aaggacacgt gtgctggcag  1020
aaatgggggt ggacagtaac aaagagcgct tggcagccgg aaacgtcacc tacacagact  1080
cagctgggcc cgcagcggaa gggaggcacg ttttgggaca gaaacgcgct tcagtgcatt  1140
gccaaacaat tctaccctgg tttcattaaa gtctttcctg atattaccag cagcaaaaca  1200
aaagcagtct ccccgcagct cacccccaaa acttgacaac caaattaatc acattttcaa  1260
cacaatttgg ataatatgat tggtgcttgc cataggtttt ttaggaacgc gacaaagtct  1320
tcctcccttc ggcagagttg atatggagac cgttttctcc ggtgggatcc tagtgagcca  1380
tgaatgagcc ctgctctgac caagccccgc gcctggacgc ccgtcacaca gctaacttta  1440
cctggcaggt ctgaggaaag tcaacttcca ggaagaaccg acacgggcac tcttggaggc  1500
catgcatctc tgtcttgaga tgtgcgtgta taaaactaca gatgtgtcca tatgcacgtg  1560
cacgtgtact tgacttacgc atgggtaaag tcattttact aatgagctca tattcatctc  1620
tggagcacac aggcaggcct ttgggagtgg gggacaccca ctgccagagc ggggtgttct  1680
gagccccttg ctaaggactg ttttagatca cgtcgtaaac aaaaggaaga caaactctgt  1740
gttgagccca gcgatatgca ttccaagggg aatggctccg ttttacattc acagtgttat  1800
ttcttacaaa tgtaaacatc tagcagaaca acatctggcc tgtgatactt ctgtctccga  1860
gctgttgaca taacttactg caggggaggt gggtggggag cagcaacggt tctgagaact  1920
ttcccctcat tcccaaagct tctagcaggc tttccaggaa gaagctagga tgagaaacag  1980
gagcccccaa ccaatacgga agaatggtgg ctttcttgtt aaaattcagt agcttccctt  2040
aagggcctcc tcaaacatca gaccccttc taccgctcct gctgccctgc cacgaggacg  2100
aggtggtcct ggctgggga ggcctctgtt gggagctggt gggaaaagcc tcatacaggc  2160
ctgtcaaagg ctgctcagag gaggggctcc ctttgagcag gggctccctt tcagcgcccc  2220
ctcatgtatg tgggcagcac acaagtccac atgtcagctg ctcctcagct gccacatagg  2280
agagggacag gtggaagctt gagggtctca aggcagcacc tgcacagact ccagaaaagc  2340
atttcctcca cttaccatat tcaataccca aaacatcaac aggcatgagc aaaccaagcc  2400
acatgacagt cgccaacctc gcctggctcg cctcaagggc tgaggaagca gagctcctgc  2460
cccatctcag agctcccaaa tccagctcct atgtcagcag cagccggcca tccagaatcc  2520
acttccattt taatgacttg gctcctctgg gcctgcaaac aagaggctgg tccagggacc  2580
tggcctgggg ataggagtgg cggctctgac agggcagtgg ggcagtctcc aatgagcaca  2640
gatctgcact ctcctgacta aaaggggtcc ccgtgcaaga tgtcagctgg aacgggggca  2700
gaagggatgc caggctctgt cactaacagt gccaagacgc caagctttgc tgttgaccaa  2760
gagaggctca gacaaaacac agctcagtga cacccttggg gcatgcatcc atggaacggc  2820
agatcccatc accggccagc cagctcctgg gcagacaccg ccccagggct agcaaggaac  2880
aggagtggga ggcccatgtc tctggacaca gcggaggctg ctcacagcca gggagggctg  2940
gccttctcag ctgataggga ggctgctgtc cctaatgtgg gtggagaaca acagttgtct  3000
gtgcccaaga aggaggggct gcaggcgagc atgcccctag gacagtgggg gcctgtcctt  3060
agtcctgctg tggccacctg cacactagcg cctctctaca tcccagtcac cttgtgaatg  3120
cataaacagg aacatgtaca acggaaatgt cagcgggtgc tcaggaaggc tatgccagtg  3180
gctacaggag agggagcgtg gccaggggcc ctgcccacct ccccgaacac tgtcgcatgc  3240
agcacaggcc ttgcaattca catactttac acgggcatag aaagagttac gttaaaatta  3300
atctctttac tgatataatt aaattttaaa tcctgagaag aaaagagaga agggagaatg  3360
gtgctgggtg tctagcaccc ccagccactg gcccagcaca tgccatggca tctgtgcata  3420
cagacacagg gcgtggcatg cacaccccac caggaagaca caggccagtg ttcccaaagc  3480
ctgctcacgg caccttctac tgcaggacag cagaggggcc cacagccagc ctgcaggagg  3540
gaggacttcc ggcccagatg caagagcagc tgcagcctgg caacacccaa caggtgagca  3600
tcaggagaaa ggacctggtc acccacatgg cgtgcagcac agctgctcct gctctccgga  3660
aggcctcagg ctcagcccca ccgggactgc agatactcct tgcctggcca ctgtaccaca  3720
aagagcactt ctgccatatg gcagagacac gcacgttgcc tggccgcccg cggcatgtgc  3780
ggaagcccac agggaccaag ctggctcggt ggaggcaggg cacagggcgc agatttctgg  3840
aggctccagc cccagctgcc gcctcacagt ctctcccacc atggcgctca gcaggtggtg  3900
```

```
accttgtgga catttcgtaa acaagtcagc agccggtgat atgggcttcc tggagctgca  3960
accacctcaa acacagactg gaaggccctg cggtcgagct cctcctctat ctggtgtctg  4020
taaaagtctg tggcaaccag gcagaaaagg ttgacgtcca cctgctccag ctttcccatc  4080
ctgctgatga catgtgggag gatcgccgca acccatgggc tggtggacgc gctgacgaag  4140
aagcaggaga ggctccatgt ggccatggcg actggggtcc tctgtgtgaa gttggagagg  4200
gacagcatga cccagtcccg gaccatggat gactgcccgg tgctgtgcag agtctgaaac  4260
accttataca ccacggtggc catgaactgg gggtatggct gctggttgga cagaaactct  4320
ccgatgactt tgttcatgat gtcctggggt gggaagaagt cgtctagaaa ctggggcagg  4380
atcctcgcca ccactctggc ttcacaagga aagcctttcc tgatcctatc aaaaagaaca  4440
gacacccgct ccatagcaac aatcaccgac tcgctgtctg gggctgcagg attagggtct  4500
gaagttctac ccggactgac tttctccttt cctgtgtaca tgcaggtgag catcaagccc  4560
agagccgcca tggcccggtg cgggctgtgc acgttcactc tgtccacact cagcttgacc  4620
agggattctg catccaggcg ggagagctgc tcagagagca ggaggcgctc caggcctctg  4680
agggcacagt ggtaaatgat agagggggtg gactcctcac ttccggacag catcacccca  4740
cacatctgta ttattgatgc tgaaaattct ggccctacgt ccagaggata gttctcaatc  4800
aggtaaaacg cagtggcaca catgaccagt acgtgctgct ggctgtgaat gttcacgcag  4860
tgggcgatcc ctttcaggtt ggagaggaga tagtcactga tgactgggat gagctgcttg  4920
gcagtatcgt ccagcaggtc gcactccagc acatagagga tgccgtgcag ggctccgacc  4980
ctgctgggca ggtggctgct cctgagtgtg ctctccagca ggcggctgac aggctccgcc  5040
acgaccttgt ccatcccaag gacggcagct gccttgcagg tggcgggcac caggtactga  5100
gcgaggatct cgtcttctga aggatgcacc cttcgcagtt ctgtcagcgt cacatacatc  5160
agctcaaact ggttgcgctc agtgaacaag tctgagacca ccagaaggga tcgaaccacc  5220
tcactgatca ggatggccgg ggtcctcctg gctgagttgg atggcaggat ccagcggctg  5280
tacaactcga gtaaaaactg cgaacaggaa tggatgtcaa ctccagcccg gtgtttcctg  5340
gagttgactg gagacgtggg tggtgatgaa ggtgcagggg cgtcggcctc ctcctcctcc  5400
tcctcgtccc attcctcctc ccttaggggt gtgatgctgt tccccagcca cacagagtgt  5460
atggacacct ggccgagttt gtagctcacg ctccccagct cccgctcggg gttgatctgc  5520
agcagcagct tctcgtggct gatgagggca cctgtggtag ccggggacag agaagggaca  5580
ggatcccacg cctggtataa atgatgggtg gcgatgttct ctctctttga aaccattgct  5640
tgaatctctt gctctacaat ccctctgata atgctcagct tcctcccaaa cctggtgtcc  5700
agagctttca gaggcttgtt ccgaggctgc tgctccaagc agctcacagc tgggttgccg  5760
gccacaggca cggtcattgc actgagcacc agtgaggtga tggcctgcac ggccaggacg  5820
ttgatctgcg tcctctctgt gtcttcttct ggtgggctct cctcctgctc catcacgagg  5880
ggctgcgtca ccaggacacc aaggagagtg gcccaagttt cttcaaactg agtacgactg  5940
gtccagccta gcgtgttgat gcggtagatg aactccttaa agacttcctt ttcctggagg  6000
aactccacgg ggatctcagg gaatgctgtg ccaaaatccc ctcccggttt gggtgaccat  6060
ccaagcttcc acaccagtgg gggcacacgt gtgtagctgt tgacaagggg caggcgggcc  6120
aggctgacga cgatgttcct gagcactgac gtgagaaacg ccggcacgcc actattcctt  6180
ttatgaccca aagccaacac cgactgcaga gactccacca tttctgccac catctcacag  6240
gctgcggtga tatacttcgg attctgtgtg ttaggatcta tttcctcctc ctcctctctg  6300
atgacttttg gggtatttgt ccttctttct ggactaagaa gctgctctcc aggctgcact  6360
gcaacggcct ccaggatgaa gtgcacacag tggatgaggg agcaggcgtg ggtcacaaac  6420
tctgcggagg agaccacgct ccagaggcca ggcagctgca gggccaggca gcagcagtcc  6480
agccctgcct ggagatccag actcagcgga atctgctcat ggatcaaatg ccaggacagg  6540
gcctcaaggg ttgccaccac gaatttcatg gtgtccttct ctttctcagg aggaaggtgc  6600
aagtgactgg gcagtttgga gaccgccacc aggtactgtg ccagggcccg ggccagagtg  6660
gtcagggact gatacagcgc agcatcccca aatagatcat tcaacttgct ccagtaggcc  6720
gccggctctg caggcaggtc ggactggaag acgtggtgga cagcagggag ctgctgcacg  6780
gtgctgctca cgcgggccag agtcacctca caggctgctt caaaaagcgg actcttctgg  6840
ccaccagaaa tttcactcat ccctaggctt aagcatggag ctagcaggct taggttgaac  6900
tccgagttca tcatgaaggc actcatatct tcagcaggaa tccgattcac cagctctgca  6960
ccttccagca gtgcagaatc tgacctggtc caacactggg atttgacaag atgaatgtac  7020
cagtctttgt ccggactcac tgtttccagt gacacgtgcc catccccgtc cagcgggtgg  7080
gaagagactg ggggagaggg actaagtgag tcttgcatgg tggagagacg aaacctgtcc  7140
agcagggaat agagcctctg gtgtctctga gcgagcccgc tgctctgaag gtattcctgg  7200
attctgttga gttcttccat tggcaactgg gccatgctgc tctgtaaatt tgcagccaga  7260
agcatttcta cccggcgaca agcaaggatg tcgaccatgc gagccagcac acggaaaggg  7320
gtgcacagca gcctgtccac atacaacgtg agcacagctc ccgactggct gagatggatc  7380
ccctccaagc actgaagagt tttcttcaga gtggttggag ttgaaaggtt ttcacaacga  7440
gactgaattg cctggatgaa gaggccgctg gcagcggagt tccgatgaac agcactgatg  7500
aagtcctgta ctggaggctc gtgggaaagg ctgatcagat cttgaatgtg atttacaatg  7560
agccacgtta agtgctcgga gtcatggagg ttctgacaga cataatcaca gaagagaatg  7620
agagcccctc ttcgtactat ttctctattg cacactccaa gtttggctgc caagtcagaa  7680
tcctcctctt ctccagacat ctggggacta agtaactttg tgctggacag actgtgtctt  7740
ttcggggtct gctgcacttc tgcccaccag cggtagtcgg tgtggttgac aagcagcagg  7800
atctgacacc agagcagcac cagggccggg tgggtggtga tcatggaacg agcccgcaaa  7860
ttcaagctgt ccagggtgta gaaactgccg ccacagccat cactgcggaa cagtctagtg  7920
gcagctgctg tgattctccg gaacattcca gacttgaaga tgtggatcag acacattagc  7980
agagtgccta gttcttggca atagaaagta tgttgctgct cactcatttc caccttcagc  8040
tgttttgtaa caatgtcttc taaaagaata cccaccagtt gtaatagaaa ccttgaaaat  8100
gtttcttctg gcaaattctt tatttgtttc ccttcactgt gttcttctag tgctgaatta  8160
ctgtccccat ctcttagcct attaattact ggacaggaga ttaaatatgg agagaaagag  8220
agctcctgaa tacgagaaag aacaatatct tcagttgact gggaaatcag aaccctcaaa  8280
atggccagaa ttcctgatat ccacagttga acagtgctca cagatgccat tgtgtttgga  8340
gtgacgaaca tactccgtaa aagcatgtcc accggacgga gggaggaagg ggccaaaatc  8400
tcaaataatg tatttaacac tccaagggct tcatgagagt caatgtgcat ctgctgtttg  8460
gctaacattg ggaggatgat gtcagctatc tgtcgagaca gtcgcttcca cttgtcttca  8520
ttctccttgt ggcactgctg caggacgaga atgaacatct ccaacacctg atggtactgg  8580
atgagtctca gtaacattga taccaccact tctttttggg tttcaagctc ttttcctgca  8640
```

-continued

```
tcagctttat ttgttcctct taatacaaaa aggtcatgga ctatgggctg cagagccggt  8700
atggcgtgtg tcacagcctt ccttccactg gccatgatgc catcacagag ctgaatgatt  8760
ttaggaattc caatgatctg ttttgaatga tagcgttcat aagacagtaa taccaagaag  8820
aaaaagatgt ttggaatgat tgcctctgat tccctgaact ggcccacttc aatgtattcg  8880
aactgtttca atacaaagcc aataaacacc tgatctgaat ccagaagaca gtaattaacc  8940
cgtaactgaa ccagctgcgc cagcaaatct aaaacctgct tctgtaactg cacagatgtt  9000
gttgtcgtgt actgttttaa agcttttata acaagaggtt caaacaaacg aatgtgatta  9060
tgaatagcat tcttatctgc acggttcttt gtgacacttg tgaggttcgt cttcaactgg  9120
gtagacactt tctggaggac atcaaaccat cccgaggtgt cgtgctcctg ctccgcctgc  9180
accatgttcc tcaggctggc gtcagcgagg gcctgggtga agtgggtgta cggggccatg  9240
aagcagtagt ggtacaagcc tggcctcaca ctggaggagc caaggcgctg tgctcggcct  9300
tgtgacttgc tggggttgga tgataagccg tcaaactggg aggccaagtt tgtcccaaag  9360
agagtcttca acaattgttg aacacaaaca gttgccatca ttggttctcg actaaagcag  9420
gatttcaggt atcctaggat ctcctcaaca cacttcccaa tgtcctgcag tgtggccagc  9480
tctagaatct gagagagaac gtccaaggct gagcgaagaa accctccaaa tttttccgtg  9540
ctgttctgaa gatccaaggt gaccttgtag ttagcgtgcg tagctttcag gacatcatgc  9600
agtttgaggt atgaaggaag atgatagaaa ctccccagtg atgaggattt acttgttgta  9660
acaggacctg aggtatcaga ttgtctagaa gctgcactgg cctcactgcc tttcttggga  9720
ctcaacggta cagatgcttg ttctcctggt tctttctcct tccccttttcg tcggatggga  9780
cttagagaag gggggtttgt tagagaaggc aaggctgcct ttattgccgg tccaggagcc  9840
acgtcgtcca ggacatgtgc acaaatgttg atcaccttca gcaggtggga gaagagctgc  9900
tccaccatgg gcaccaaggc ccggtccccc agggctggcc agacctcctc ttgcttggtg  9960
gctgctgggt tggcttcttc ttcagaggcc catgaacttc tcagagattt aggagcactg  10020
gctgcaagca agtttccggc caaaatcaaa gcatcttgat gggctgagag atccaatggg  10080
aaccaagctg acgagagcag ggtcagaatc atcgtggcca tcccaacggt acagctcttc  10140
ctagactcat cggaggcgct cagtggaggc actccacagt gccaacctaa actccaaatg  10200
caaactggga aggcagtgga aagaagacac aaagcttcac agcatccaaa agtgagtgct  10260
ctcgtggttg atgtgatcag ttcatgagaa actgctgcaa taactcttga aaggttattt  10320
tccatagtga catctgttat gcttggcagt aggttatagc ctctgtatat tctggttatt  10380
gtgctgacgg agaaatgaga tggaggctgc gtctcatgca tgagaagttt caggtaaaca  10440
ctgctttgat ctcttgccac ggccactact gggtcagctt gtccttggtc acatttataa  10500
aacagctttg ggacaagcct aattaatgat gctgcagcaa catgtcgcac cctggggtct  10560
tcatccccaa gcaaatggat gacaacatta ttgagcactc gttcttgcag ctttaaaagc  10620
cctgtataat gatgagcccc tctgtgtaag ttttctgctt ttgcctccaa aaagctcacc  10680
agcctgaagt caatctccgc aagggtttcc agaagctctg tcctcaccag ccaataggaa  10740
ctgttcctca gagtcagcac gtcgatgatc agctgcagtc ctaactcact gtagctgctg  10800
ctgcagagac tcatgacaca atgcctcaca gctgtacagg ccagcttgca agtgacagaa  10860
gactcgtcct tcagtgtttt ccgcagcaaa ggaatgcaat ccgccaaaga aaatgtgttt  10920
cctgtcaggg ttctaatggc gcccatccaa tctcccacgt ggaagcggga cctgctgagg  10980
atggagcaga tgagggtccc acagagaatg gcagtggctc ctcgaacctg tgggtctcca  11040
tgatcgatgt agttcaagat atctgagaca tattgttcct cagggtattc tgtggtgtca  11100
agaggaactt tatagagttt gctgaagaaa gattctgggt ggagagccac agctgctccc  11160
acacagctga gggccagggc cttcacgctg accctcacat cccggtccgg aaccagcaca  11220
ttttttcccc ctgttagcaa aaatgaagca gataaaaggc ggacacaatg gacaagaggt  11280
gcagaatcat catcagtgga ctgtccaatg tcacctttga tgcggcaagg cttgttttct  11340
tgatcacccg gttcagtagc ttcatctctc aacacaaatt tatcaacact gctgtcagaa  11400
ggctgcctgc tgtgactcat gtttttcaat aaatgtgctt gttgaagggc catggaagag  11460
ttcctgaagg cctccgaggc ttcgtcagga agaacacctg tggcttcctc atcttcatcc  11520
tggggctgtc caatctgcag gcccaaatac tggttgtcgg taccgtctaa cacaatttca  11580
gaactgtctg aaggggtgac agctgaatca ggcccttcgg tggtggtctg ggagctgtcg  11640
ctgatgggcg aggaggcctg ggtcccatca ttcaggtcca tggcagggtc agatgggacg  11700
gcgctgacct ggctggagct gtggctcaag atatcctcct catccccatc cgtggcagag  11760
cttgtcaagt cacagctggc cagatccact gagtccgcct gcagcgtgtg ctgtgaccgt  11820
ggctgctccg tgatgatgtc gtgacctgct gaccctggag tggaaacccc tgaagaagta  11880
gccagctctc cactgatatc atccttcact gaggctgcaa aggcagagct gctgacatcc  11940
gatctcgatt cagagtcatc ctccaaggct tcttcttctc ctaagagcac tttgcctttt  12000
tgttttcttg aaaggacagg gctgcatgag gaaccccctc cagctataag ttccacaata  12060
ctcccactac ggcttcggcc accagactcc tccttagcgg cggtaagctg cccaatgccc  12120
cccactgtgg tcagggcttg cagaagctcg gggggaggcg ttctgaagag ctgctgcaac  12180
agctccaggg ctccggtcac aacattgtgg tcttggtgct gtgtatgatg taacgtcagt  12240
tcataaacct ggacaagctg ctctgcagaa ggagagacct ccatttcttt ccgtgtcact  12300
ccgaagctgc ctttcaggct tgtatccttg acctgctgct gcagcaaggg caccaaatac  12360
ctcagggtga gcagcacgcc aagaatcagc agggtggagt gctcctcctc gacaggaacc  12420
agtaagccta agagcacatt tagtagccag ctatagaaat actgtgtcct tcttgagtgc  12480
tggcagatgc tcactgctga tccagcagct gtccgccgaa tagtgggggga gcttgacttc  12540
aggttcgcta tgaaggcctt taacaaaacc ttaatttcat tgtcatttgc aaaattgccg  12600
aaagaagcca taattttggg aacagctgca gccaaggtct cctggactga ttcctcgggt  12660
ctcttgcttg ttcgacttag gcacggcaga aggttcacca ggtaaggcct gcatttctga  12720
ggccgaacca ggtgagccag ctcggcaaac ctccacaggg cagcacgcaa actccgaggg  12780
gcaccattct ttttaatttc tttatagagc tcgagctgta accttggaag attagaatcc  12840
atcaaagctt tgataacttt gttgaggcat tcatcagcca ccattctgac atccgactct  12900
gcgtcatcac tgcacagcag aaaaagttcc atagcgatgc ccagaagttt ctgaaattct  12960
ggagaatttc tgacagactg tgccactatg ttttcacata ttgtcagaca atgattcaca  13020
cggtctttct tggtagctga aagttctttc tttggtcggt gcagcggctc ctcagccaca  13080
gccgggccgg gtggtggcgg gggcggcggc gggggcggct gcggctgagg cagcatcggc  13140
tgtgcctgcg gcggctgagg aagctgagga ggaggaggcg gcggcggcgg cggcggcggc  13200
ggctgttgct gctgctgctg ctgctgctgc tgctggaagg acttgagaga ctcgaaggcc  13260
ttcatcagct tttccagggt cgccatggcg gtctcccgcc cggctaggca gtccccggag  13320
gcctcgggcc gactcgcagc gccgctcagc accggggcaa tgaatggggc tctgggccgc  13380
```

-continued

```
gggtaaaagc ggaaccgaag cggccgtcca tcttggaccc gtcccggcag cccccgcggc  13440
gccttgc                                                            13447

SEQ ID NO: 11          moltype = AA  length = 16
FEATURE                Location/Qualifiers
REGION                 1..16
                       note = source = /note="Description of Unknown: RFGF peptide
                        sequence"
source                 1..16
                       mol_type = protein
                       organism = unidentified
SEQUENCE: 11
AAVALLPAVL LALLAP                                                  16

SEQ ID NO: 12          moltype = AA  length = 11
FEATURE                Location/Qualifiers
REGION                 1..11
                       note = source = /note="Description of Unknown: RFGF
                        analogue sequence"
source                 1..11
                       mol_type = protein
                       organism = unidentified
SEQUENCE: 12
AALLPVLLAA P                                                       11

SEQ ID NO: 13          moltype = AA  length = 13
FEATURE                Location/Qualifiers
source                 1..13
                       mol_type = protein
                       organism = Human immunodeficiency virus 1
SEQUENCE: 13
GRKKRRQRRR PPQ                                                     13

SEQ ID NO: 14          moltype = AA  length = 16
FEATURE                Location/Qualifiers
source                 1..16
                       mol_type = protein
                       organism = Drosophila sp.
SEQUENCE: 14
RQIKIWFQNR RMKWKK                                                  16

SEQ ID NO: 15          moltype = RNA  length = 21
FEATURE                Location/Qualifiers
source                 1..21
                       mol_type = other RNA
                       organism = synthetic construct
SEQUENCE: 15
gctattcata atcacattcg a                                            21

SEQ ID NO: 16          moltype = RNA  length = 23
FEATURE                Location/Qualifiers
source                 1..23
                       mol_type = other RNA
                       organism = synthetic construct
SEQUENCE: 16
tcgaatgtga ttatgaatag cat                                          23

SEQ ID NO: 17          moltype = RNA  length = 21
FEATURE                Location/Qualifiers
source                 1..21
                       mol_type = other RNA
                       organism = synthetic construct
modified_base          1
                       mod_base = OTHER
                       note = 2'-O-methylguanosine-3'-phosphorothioate
modified_base          2
                       mod_base = OTHER
                       note = 2'-O-methylcytidine-3'-phosphorothioate
modified_base          3
                       mod_base = OTHER
                       note = 2'-O-methyluridine-3'-phosphate
modified_base          4
                       mod_base = OTHER
                       note = 2'-O-methyladenosine-3'-phosphate
modified_base          5
                       mod_base = OTHER
                       note = 2'-O-methyluridine-3'-phosphate
modified_base          6
                       mod_base = OTHER
```

```
                        note = 2'-O-hexadecyl-uridine-3'-phosphate
modified_base           7
                        mod_base = OTHER
                        note = 2'-deoxy-2'-fluorocytidine-3'-phosphate
modified_base           8
                        mod_base = OTHER
                        note = 2'-O-methyladenosine-3'-phosphate
modified_base           9
                        mod_base = OTHER
                        note = 2'-deoxy-2'-fluorouridine-3'-phosphate
modified_base           10
                        mod_base = OTHER
                        note = 2'-deoxy-2'-fluoroadenosine-3'-phosphate
modified_base           11
                        mod_base = OTHER
                        note = 2'-deoxy-2'-fluoroadenosine-3'-phosphate
modified_base           12
                        mod_base = OTHER
                        note = 2'-O-methyluridine-3'-phosphate
modified_base           13
                        mod_base = OTHER
                        note = 2'-O-methylcytidine-3'-phosphate
modified_base           14
                        mod_base = OTHER
                        note = 2'-O-methyladenosine-3'-phosphate
modified_base           15
                        mod_base = OTHER
                        note = 2'-O-methylcytidine-3'-phosphate
modified_base           16
                        mod_base = OTHER
                        note = 2'-O-methyladenosine-3'-phosphate
modified_base           17
                        mod_base = OTHER
                        note = 2'-O-methyluridine-3'-phosphate
modified_base           18
                        mod_base = OTHER
                        note = 2'-O-methyluridine-3'-phosphate
modified_base           19
                        mod_base = OTHER
                        note = 2'-O-methylcytidine-3'-phosphorothioate
modified_base           20
                        mod_base = OTHER
                        note = 2'-O-methylguanosine-3'-phosphorothioate
modified_base           21
                        mod_base = OTHER
                        note = 2'-O-methyladenosine
SEQUENCE: 17
gctattcata atcacattcg a                                              21

SEQ ID NO: 18           moltype = RNA  length = 23
FEATURE                 Location/Qualifiers
source                  1..23
                        mol_type = other RNA
                        organism = synthetic construct
modified_base           1
                        mod_base = OTHER
                        note = 2'-O-methyluridine-3'-phosphorothioate
                         5'-(E)-Vinylphosphonate
modified_base           2
                        mod_base = OTHER
                        note = 2'-deoxy-2'-fluorocytidine-3'-phosphorothioate
modified_base           3
                        mod_base = OTHER
                        note = 2'-O-methylguanosine-3'-phosphate
modified_base           4
                        mod_base = OTHER
                        note = 2'-O-methyladenosine-3'-phosphate
modified_base           5
                        mod_base = OTHER
                        note = 2'-O-methyladenosine-3'-phosphate
modified_base           6
                        mod_base = OTHER
                        note = 2'-deoxy-2'-fluorouridine-3'-phosphate
modified_base           7
                        mod_base = OTHER
                        note = 2'-O-methylguanosine-3'-phosphate
modified_base           8
                        mod_base = OTHER
                        note = 2'-deoxy-2'-fluorouridine-3'-phosphate
```

-continued

```
modified_base          9
                       mod_base = OTHER
                       note = 2'-deoxy-2'-fluoroguanosine-3'-phosphate
modified_base          10
                       mod_base = OTHER
                       note = 2'-O-methyladenosine-3'-phosphate
modified_base          11
                       mod_base = OTHER
                       note = 2'-O-methyluridine-3'-phosphate
modified_base          12
                       mod_base = OTHER
                       note = 2'-O-methyluridine-3'-phosphate
modified_base          13
                       mod_base = OTHER
                       note = 2'-O-methyladenosine-3'-phosphate
modified_base          14
                       mod_base = OTHER
                       note = 2'-deoxy-2'-fluorouridine-3'-phosphate
modified_base          15
                       mod_base = OTHER
                       note = 2'-O-methylguanosine-3'-phosphate
modified_base          16
                       mod_base = OTHER
                       note = 2'-deoxy-2'-fluoroadenosine-3'-phosphate
modified_base          17
                       mod_base = OTHER
                       note = 2'-O-methyladenosine-3'-phosphate
modified_base          18
                       mod_base = OTHER
                       note = 2'-O-methyluridine-3'-phosphate
modified_base          19
                       mod_base = OTHER
                       note = 2'-O-methyladenosine-3'-phosphate
modified_base          20
                       mod_base = OTHER
                       note = 2'-O-methylguanosine-3'-phosphate
modified_base          21
                       mod_base = OTHER
                       note = 2'-O-methylcytidine-3'-phosphorothioate
modified_base          22
                       mod_base = OTHER
                       note = 2'-O-methyladenosine-3'-phosphorothioate
modified_base          23
                       mod_base = OTHER
                       note = 2'-O-methyluridine
SEQUENCE: 18
tcgaatgtga ttatgaatag cat                                               23

SEQ ID NO: 19          moltype = RNA  length = 21
FEATURE                Location/Qualifiers
source                 1..21
                       mol_type = other RNA
                       organism = synthetic construct
modified_base          1
                       mod_base = OTHER
                       note = 2'-O-methyluridine-3'-phosphorothioate
modified_base          2
                       mod_base = OTHER
                       note = 2'-O-methylcytidine-3'-phosphorothioate
modified_base          3
                       mod_base = OTHER
                       note = 2'-O-methyladenosine-3'-phosphate
modified_base          4
                       mod_base = OTHER
                       note = 2'-O-methyluridine-3'-phosphate
modified_base          5
                       mod_base = OTHER
                       note = 2'-O-methyladenosine-3'-phosphate
modified_base          6
                       mod_base = OTHER
                       note = 2'-O-hexadecyl-adenosine-3'-phosphate
modified_base          7
                       mod_base = OTHER
                       note = 2'-deoxy-2'-fluorouridine-3'-phosphate
modified_base          8
                       mod_base = OTHER
                       note = 2'-O-methylcytidine-3'-phosphate
modified_base          9
                       mod_base = OTHER
```

```
                        note = 2'-deoxy-2'-fluoroadenosine-3'-phosphate
modified_base           10
                        mod_base = OTHER
                        note = 2'-deoxy-2'-fluorocytidine-3'-phosphate
modified_base           11
                        mod_base = OTHER
                        note = 2'-deoxy-2'-fluoroadenosine-3'-phosphate
modified_base           12
                        mod_base = OTHER
                        note = 2'-O-methyluridine-3'-phosphate
modified_base           13
                        mod_base = OTHER
                        note = 2'-O-methyluridine-3'-phosphate
modified_base           14
                        mod_base = OTHER
                        note = 2'-O-methylcytidine-3'-phosphate
modified_base           15
                        mod_base = OTHER
                        note = 2'-O-methylguanosine-3'-phosphate
modified_base           16
                        mod_base = OTHER
                        note = 2'-O-methyluridine-3'-phosphate
modified_base           17
                        mod_base = OTHER
                        note = 2'-O-methyluridine-3'-phosphate
modified_base           18
                        mod_base = OTHER
                        note = 2'-O-methyluridine-3'-phosphate
modified_base           19
                        mod_base = OTHER
                        note = 2'-O-methylguanosine-3'-phosphorothioate
modified_base           20
                        mod_base = OTHER
                        note = 2'-O-methyluridine-3'-phosphorothioate
modified_base           21
                        mod_base = OTHER
                        note = 2'-O-methyladenosine
SEQUENCE: 19
tcataatcac attcgtttgt a                                             21

SEQ ID NO: 20           moltype = RNA  length = 23
FEATURE                 Location/Qualifiers
source                  1..23
                        mol_type = other RNA
                        organism = synthetic construct
modified_base           1
                        mod_base = OTHER
                        note = 2'-O-methyluridine-3'-phosphorothioate
                         5'-(E)-Vinylphosphonate
modified_base           2
                        mod_base = OTHER
                        note = 2'-deoxy-2'-fluoroadenosine-3'-phosphorothioate
modified_base           3
                        mod_base = OTHER
                        note = 2'-O-methylcytidine-3'-phosphate
modified_base           4
                        mod_base = OTHER
                        note = 2'-O-methyladenosine-3'-phosphate
modified_base           5
                        mod_base = OTHER
                        note = 2'-O-methyladenosine-3'-phosphate
modified_base           6
                        mod_base = OTHER
                        note = 2'-deoxy-2'-fluoroadenosine-3'-phosphate
modified_base           7
                        mod_base = OTHER
                        note = 2'-O-methylcytidine-3'-phosphate
modified_base           8
                        mod_base = OTHER
                        note = 2'-deoxy-2'-fluoroguanosine-3'-phosphate
modified_base           9
                        mod_base = OTHER
                        note = 2'-deoxy-2'-fluoroadenosine-3'-phosphate
modified_base           10
                        mod_base = OTHER
                        note = 2'-O-methyladenosine-3'-phosphate
modified_base           11
                        mod_base = OTHER
                        note = 2'-O-methyluridine-3'-phosphate
```

```
modified_base          12
                       mod_base = OTHER
                       note = 2'-O-methylguanosine-3'-phosphate
modified_base          13
                       mod_base = OTHER
                       note = 2'-O-methyluridine-3'-phosphate
modified_base          14
                       mod_base = OTHER
                       note = 2'-deoxy-2'-fluoroguanosine-3'-phosphate
modified_base          15
                       mod_base = OTHER
                       note = 2'-O-methyladenosine-3'-phosphate
modified_base          16
                       mod_base = OTHER
                       note = 2'-deoxy-2'-fluorouridine-3'-phosphate
modified_base          17
                       mod_base = OTHER
                       note = 2'-O-methyluridine-3'-phosphate
modified_base          18
                       mod_base = OTHER
                       note = 2'-O-methyladenosine-3'-phosphate
modified_base          19
                       mod_base = OTHER
                       note = 2'-O-methyluridine-3'-phosphate
modified_base          20
                       mod_base = OTHER
                       note = 2'-O-methylguanosine-3'-phosphate
modified_base          21
                       mod_base = OTHER
                       note = 2'-O-methyladenosine-3'-phosphorothioate
modified_base          22
                       mod_base = OTHER
                       note = 2'-O-methyladenosine-3'-phosphorothioate
modified_base          23
                       mod_base = OTHER
                       note = 2'-O-methyluridine
SEQUENCE: 20
tacaaacgaa tgtgattatg aat                                          23

SEQ ID NO: 21          moltype = RNA  length = 21
FEATURE                Location/Qualifiers
source                 1..21
                       mol_type = other RNA
                       organism = synthetic construct
modified_base          1
                       mod_base = OTHER
                       note = 2'-O-methylguanosine-3'-phosphorothioate
modified_base          2
                       mod_base = OTHER
                       note = 2'-O-methylcytidine-3'-phosphorothioate
modified_base          3
                       mod_base = OTHER
                       note = 2'-O-methyluridine-3'-phosphate
modified_base          4
                       mod_base = OTHER
                       note = 2'-O-methylguanosine-3'-phosphate
modified_base          5
                       mod_base = OTHER
                       note = 2'-O-methylguanosine-3'-phosphate
modified_base          6
                       mod_base = OTHER
                       note = 2'-O-hexadecyl-uridine-3'-phosphate
modified_base          7
                       mod_base = OTHER
                       note = 2'-deoxy-2'-fluoroguanosine-3'-phosphate
modified_base          8
                       mod_base = OTHER
                       note = 2'-O-methyladenosine-3'-phosphate
modified_base          9
                       mod_base = OTHER
                       note = 2'-deoxy-2'-fluoroadenosine-3'-phosphate
modified_base          10
                       mod_base = OTHER
                       note = 2'-deoxy-2'-fluorouridine-3'-phosphate
modified_base          11
                       mod_base = OTHER
                       note = 2'-deoxy-2'-fluorocytidine-3'-phosphate
modified_base          12
                       mod_base = OTHER
```

```
                         note = 2'-O-methylguanosine-3'-phosphate
modified_base            13
                         mod_base = OTHER
                         note = 2'-O-methylguanosine-3'-phosphate
modified_base            14
                         mod_base = OTHER
                         note = 2'-O-methyladenosine-3'-phosphate
modified_base            15
                         mod_base = OTHER
                         note = 2'-O-methyluridine-3'-phosphate
modified_base            16
                         mod_base = OTHER
                         note = 2'-O-methyluridine-3'-phosphate
modified_base            17
                         mod_base = OTHER
                         note = 2'-O-methylcytidine-3'-phosphate
modified_base            18
                         mod_base = OTHER
                         note = 2'-O-methylcytidine-3'-phosphate
modified_base            19
                         mod_base = OTHER
                         note = 2'-O-methyluridine-3'-phosphorothioate
modified_base            20
                         mod_base = OTHER
                         note = 2'-O-methylguanosine-3'-phosphorothioate
modified_base            21
                         mod_base = OTHER
                         note = 2'-O-methyladenosine
SEQUENCE: 21
gctggtgaat cggattcctg a                                               21

SEQ ID NO: 22            moltype = RNA  length = 23
FEATURE                  Location/Qualifiers
source                   1..23
                         mol_type = other RNA
                         organism = synthetic construct
modified_base            1
                         mod_base = OTHER
                         note = 2'-O-methyluridine-3'-phosphorothioate
                          5'-(E)-Vinylphosphonate
modified_base            2
                         mod_base = OTHER
                         note = 2'-deoxy-2'-fluorocytidine-3'-phosphorothioate
modified_base            3
                         mod_base = OTHER
                         note = 2'-O-methyladenosine-3'-phosphate
modified_base            4
                         mod_base = OTHER
                         note = 2'-O-methylguanosine-3'-phosphate
modified_base            5
                         mod_base = OTHER
                         note = 2'-O-methylguanosine-3'-phosphate
modified_base            6
                         mod_base = OTHER
                         note = 2'-deoxy-2'-fluoroadenosine-3'-phosphate
modified_base            7
                         mod_base = OTHER
                         note = 2'-O-methyladenosine-3'-phosphate
modified_base            8
                         mod_base = OTHER
                         note = 2'-deoxy-2'-fluorouridine-3'-phosphate
modified_base            9
                         mod_base = OTHER
                         note = 2'-deoxy-2'-fluorocytidine-3'-phosphate
modified_base            10
                         mod_base = OTHER
                         note = 2'-O-methylcytidine-3'-phosphate
modified_base            11
                         mod_base = OTHER
                         note = 2'-O-methylguanosine-3'-phosphate
modified_base            12
                         mod_base = OTHER
                         note = 2'-O-methyladenosine-3'-phosphate
modified_base            13
                         mod_base = OTHER
                         note = 2'-O-methyluridine-3'-phosphate
modified_base            14
                         mod_base = OTHER
                         note = 2'-deoxy-2'-fluorouridine-3'-phosphate
```

```
modified_base          15
                       mod_base = OTHER
                       note = 2'-O-methylcytidine-3'-phosphate
modified_base          16
                       mod_base = OTHER
                       note = 2'-deoxy-2'-fluoroadenosine-3'-phosphate
modified_base          17
                       mod_base = OTHER
                       note = 2'-O-methylcytidine-3'-phosphate
modified_base          18
                       mod_base = OTHER
                       note = 2'-O-methylcytidine-3'-phosphate
modified_base          19
                       mod_base = OTHER
                       note = 2'-O-methyladenosine-3'-phosphate
modified_base          20
                       mod_base = OTHER
                       note = 2'-O-methylguanosine-3'-phosphate
modified_base          21
                       mod_base = OTHER
                       note = 2'-O-methylcytidine-3'-phosphorothioate
modified_base          22
                       mod_base = OTHER
                       note = 2'-O-methyluridine-3'-phosphorothioate
modified_base          23
                       mod_base = OTHER
                       note = 2'-O-methylcytidine
SEQUENCE: 22
tcaggaatcc gattcaccag ctc                                            23

SEQ ID NO: 23          moltype = RNA  length = 21
FEATURE                Location/Qualifiers
source                 1..21
                       mol_type = other RNA
                       organism = synthetic construct
modified_base          1
                       mod_base = OTHER
                       note = 2'-O-methyluridine-3'-phosphorothioate
modified_base          2
                       mod_base = OTHER
                       note = 2'-O-methylguanosine-3'-phosphorothioate
modified_base          3
                       mod_base = OTHER
                       note = 2'-O-methylguanosine-3'-phosphate
modified_base          4
                       mod_base = OTHER
                       note = 2'-O-methyladenosine-3'-phosphate
modified_base          5
                       mod_base = OTHER
                       note = 2'-O-methyladenosine-3'-phosphate
modified_base          6
                       mod_base = OTHER
                       note = 2'-O-hexadecyl-adenosine-3'-phosphate
modified_base          7
                       mod_base = OTHER
                       note = 2'-deoxy-2'-fluoroadenosine-3'-phosphate
modified_base          8
                       mod_base = OTHER
                       note = 2'-O-methylguanosine-3'-phosphate
modified_base          9
                       mod_base = OTHER
                       note = 2'-deoxy-2'-fluorocytidine-3'-phosphate
modified_base          10
                       mod_base = OTHER
                       note = 2'-deoxy-2'-fluorouridine-3'-phosphate
modified_base          11
                       mod_base = OTHER
                       note = 2'-deoxy-2'-fluoroguanosine-3'-phosphate
modified_base          12
                       mod_base = OTHER
                       note = 2'-O-methyladenosine-3'-phosphate
modified_base          13
                       mod_base = OTHER
                       note = 2'-O-methyluridine-3'-phosphate
modified_base          14
                       mod_base = OTHER
                       note = 2'-O-methylguanosine-3'-phosphate
modified_base          15
                       mod_base = OTHER
```

```
                        note = 2'-O-methyladenosine-3'-phosphate
modified_base           16
                        mod_base = OTHER
                        note = 2'-O-methyladenosine-3'-phosphate
modified_base           17
                        mod_base = OTHER
                        note = 2'-O-methylguanosine-3'-phosphate
modified_base           18
                        mod_base = OTHER
                        note = 2'-O-methylguanosine-3'-phosphate
modified_base           19
                        mod_base = OTHER
                        note = 2'-O-methylcytidine-3'-phosphorothioate
modified_base           20
                        mod_base = OTHER
                        note = 2'-O-methylcytidine-3'-phosphorothioate
modified_base           21
                        mod_base = OTHER
                        note = 2'-O-methyladenosine
SEQUENCE: 23
tggaaaagct gatgaaggcc a                                              21

SEQ ID NO: 24           moltype = RNA  length = 23
FEATURE                 Location/Qualifiers
source                  1..23
                        mol_type = other RNA
                        organism = synthetic construct
modified_base           1
                        mod_base = OTHER
                        note = 2'-O-methyluridine-3'-phosphorothioate
                         5'-(E)-Vinylphosphonate
modified_base           2
                        mod_base = OTHER
                        note = 2'-deoxy-2'-fluoroguanosine-3'-phosphorothioate
modified_base           3
                        mod_base = OTHER
                        note = 2'-O-methylguanosine-3'-phosphate
modified_base           4
                        mod_base = OTHER
                        note = 2'-O-methylcytidine-3'-phosphate
modified_base           5
                        mod_base = OTHER
                        note = 2'-O-methylcytidine-3'-phosphate
modified_base           6
                        mod_base = OTHER
                        note = 2'-O-methyluridine-3'-phosphate
modified_base           7
                        mod_base = OTHER
                        note = Thymidine-glycol nucleic acid (GNA), S-Isomer
modified_base           8
                        mod_base = OTHER
                        note = 2'-O-methylcytidine-3'-phosphate
modified_base           9
                        mod_base = OTHER
                        note = 2'-O-methyladenosine-3'-phosphate
modified_base           10
                        mod_base = OTHER
                        note = 2'-O-methyluridine-3'-phosphate
modified_base           11
                        mod_base = OTHER
                        note = 2'-O-methylcytidine-3'-phosphate
modified_base           12
                        mod_base = OTHER
                        note = 2'-O-methyladenosine-3'-phosphate
modified_base           13
                        mod_base = OTHER
                        note = 2'-O-methylguanosine-3'-phosphate
modified_base           14
                        mod_base = OTHER
                        note = 2'-deoxy-2'-fluorocytidine-3'-phosphate
modified_base           15
                        mod_base = OTHER
                        note = 2'-O-methyluridine-3'-phosphate
modified_base           16
                        mod_base = OTHER
                        note = 2'-deoxy-2'-fluorouridine-3'-phosphate
modified_base           17
                        mod_base = OTHER
                        note = 2'-O-methyluridine-3'-phosphate
```

```
modified_base         18
                      mod_base = OTHER
                      note = 2'-O-methyluridine-3'-phosphate
modified_base         19
                      mod_base = OTHER
                      note = 2'-O-methylcytidine-3'-phosphate
modified_base         20
                      mod_base = OTHER
                      note = 2'-O-methylcytidine-3'-phosphate
modified_base         21
                      mod_base = OTHER
                      note = 2'-O-methyladenosine-3'-phosphorothioate
modified_base         22
                      mod_base = OTHER
                      note = 2'-O-methylguanosine-3'-phosphorothioate
modified_base         23
                      mod_base = OTHER
                      note = 2'-O-methylguanosine
SEQUENCE: 24
tggccttcat cagcttttcc agg                                          23

SEQ ID NO: 25         moltype = RNA  length = 21
FEATURE               Location/Qualifiers
source                1..21
                      mol_type = other RNA
                      organism = synthetic construct
SEQUENCE: 25
tcataatcac attcgtttgt a                                            21

SEQ ID NO: 26         moltype = RNA  length = 21
FEATURE               Location/Qualifiers
source                1..21
                      mol_type = other RNA
                      organism = synthetic construct
SEQUENCE: 26
gctggtgaat cggattcctg a                                            21

SEQ ID NO: 27         moltype = RNA  length = 21
FEATURE               Location/Qualifiers
source                1..21
                      mol_type = other RNA
                      organism = synthetic construct
SEQUENCE: 27
tggaaaagct gatgaaggcc a                                            21

SEQ ID NO: 28         moltype = RNA  length = 21
FEATURE               Location/Qualifiers
source                1..21
                      mol_type = other RNA
                      organism = synthetic construct
SEQUENCE: 28
ccatggcgac cctggaaaag a                                            21

SEQ ID NO: 29         moltype = RNA  length = 23
FEATURE               Location/Qualifiers
source                1..23
                      mol_type = other RNA
                      organism = synthetic construct
SEQUENCE: 29
tacaaacgaa tgtgattatg aat                                          23

SEQ ID NO: 30         moltype = RNA  length = 23
FEATURE               Location/Qualifiers
source                1..23
                      mol_type = other RNA
                      organism = synthetic construct
SEQUENCE: 30
tcaggaatcc gattcaccag ctc                                          23

SEQ ID NO: 31         moltype = RNA  length = 23
FEATURE               Location/Qualifiers
source                1..23
                      mol_type = other RNA
                      organism = synthetic construct
modified_base         7
                      mod_base = OTHER
                      note = 5'-methyluridine-3'-phosphate
SEQUENCE: 31
tggccttcat cagcttttcc agg                                          23
```

-continued

```
SEQ ID NO: 32          moltype = RNA  length = 23
FEATURE                Location/Qualifiers
source                 1..23
                       mol_type = other RNA
                       organism = synthetic construct
SEQUENCE: 32
tcttttccag ggtcgccatg gcg                                          23

SEQ ID NO: 33          moltype = RNA  length = 21
FEATURE                Location/Qualifiers
source                 1..21
                       mol_type = other RNA
                       organism = synthetic construct
modified_base          1
                       mod_base = OTHER
                       note = 2'-O-methylcytidine-3'-phosphorothioate
modified_base          2
                       mod_base = OTHER
                       note = 2'-O-methylcytidine-3'-phosphorothioate
modified_base          3
                       mod_base = OTHER
                       note = 2'-O-methyladenosine-3'-phosphate
modified_base          4
                       mod_base = OTHER
                       note = 2'-O-methyluridine-3'-phosphate
modified_base          5
                       mod_base = OTHER
                       note = 2'-O-methylguanosine-3'-phosphate
modified_base          6
                       mod_base = OTHER
                       note = 2'-O-hexadecyl-guanosine-3'-phosphate
modified_base          7
                       mod_base = OTHER
                       note = 2'-deoxy-2'-fluorocytidine-3'-phosphate
modified_base          8
                       mod_base = OTHER
                       note = 2'-O-methylguanosine-3'-phosphate
modified_base          9
                       mod_base = OTHER
                       note = 2'-deoxy-2'-fluoroadenosine-3'-phosphate
modified_base          10
                       mod_base = OTHER
                       note = 2'-deoxy-2'-fluorocytidine-3'-phosphate
modified_base          11
                       mod_base = OTHER
                       note = 2'-deoxy-2'-fluorocytidine-3'-phosphate
modified_base          12
                       mod_base = OTHER
                       note = 2'-O-methylcytidine-3'-phosphate
modified_base          13
                       mod_base = OTHER
                       note = 2'-O-methyluridine-3'-phosphate
modified_base          14
                       mod_base = OTHER
                       note = 2'-O-methylguanosine-3'-phosphate
modified_base          15
                       mod_base = OTHER
                       note = 2'-O-methylguanosine-3'-phosphate
modified_base          16
                       mod_base = OTHER
                       note = 2'-O-methyladenosine-3'-phosphate
modified_base          17
                       mod_base = OTHER
                       note = 2'-O-methyladenosine-3'-phosphate
modified_base          18
                       mod_base = OTHER
                       note = 2'-O-methyladenosine-3'-phosphate
modified_base          19
                       mod_base = OTHER
                       note = 2'-O-methyladenosine-3'-phosphorothioate
modified_base          20
                       mod_base = OTHER
                       note = 2'-O-methylguanosine-3'-phosphorothioate
modified_base          21
                       mod_base = OTHER
                       note = 2'-O-methyladenosine
SEQUENCE: 33
ccatggcgac cctggaaaag a                                            21
```

```
SEQ ID NO: 34           moltype = RNA  length = 23
FEATURE                 Location/Qualifiers
source                  1..23
                        mol_type = other RNA
                        organism = synthetic construct
modified_base           1
                        mod_base = OTHER
                        note = 2'-O-methyluridine-3'-phosphorothioate
                         5'-(E)-Vinylphosphonate
modified_base           2
                        mod_base = OTHER
                        note = 2'-deoxy-2'-fluorocytidine-3'-phosphorothioate
modified_base           3
                        mod_base = OTHER
                        note = 2'-O-methyluridine-3'-phosphate
modified_base           4
                        mod_base = OTHER
                        note = 2'-O-methyluridine-3'-phosphate
modified_base           5
                        mod_base = OTHER
                        note = 2'-O-methyluridine-3'-phosphate
modified_base           6
                        mod_base = OTHER
                        note = 2'-deoxy-2'-fluorouridine-3'-phosphate
modified_base           7
                        mod_base = OTHER
                        note = 2'-O-methylcytidine-3'-phosphate
modified_base           8
                        mod_base = OTHER
                        note = 2'-deoxy-2'-fluorocytidine-3'-phosphate
modified_base           9
                        mod_base = OTHER
                        note = 2'-deoxy-2'-fluoroadenosine-3'-phosphate
modified_base           10
                        mod_base = OTHER
                        note = 2'-O-methylguanosine-3'-phosphate
modified_base           11
                        mod_base = OTHER
                        note = 2'-O-methylguanosine-3'-phosphate
modified_base           12
                        mod_base = OTHER
                        note = 2'-O-methylguanosine-3'-phosphate
modified_base           13
                        mod_base = OTHER
                        note = 2'-O-methyluridine-3'-phosphate
modified_base           14
                        mod_base = OTHER
                        note = 2'-deoxy-2'-fluorocytidine-3'-phosphate
modified_base           15
                        mod_base = OTHER
                        note = 2'-O-methylguanosine-3'-phosphate
modified_base           16
                        mod_base = OTHER
                        note = 2'-deoxy-2'-fluorocytidine-3'-phosphate
modified_base           17
                        mod_base = OTHER
                        note = 2'-O-methylcytidine-3'-phosphate
modified_base           18
                        mod_base = OTHER
                        note = 2'-O-methyladenosine-3'-phosphate
modified_base           19
                        mod_base = OTHER
                        note = 2'-O-methyluridine-3'-phosphate
modified_base           20
                        mod_base = OTHER
                        note = 2'-O-methylguanosine-3'-phosphate
modified_base           21
                        mod_base = OTHER
                        note = 2'-O-methylguanosine-3'-phosphorothioate
modified_base           22
                        mod_base = OTHER
                        note = 2'-O-methylcytidine-3'-phosphorothioate
modified_base           23
                        mod_base = OTHER
                        note = 2'-O-methylguanosine
SEQUENCE: 34
tcttttccag ggtcgccatg gcg                                              23
```

```
SEQ ID NO: 35          moltype = RNA  length = 19
FEATURE                Location/Qualifiers
source                 1..19
                       mol_type = other RNA
                       organism = synthetic construct
SEQUENCE: 35
cttcgagtcc ctcaagtca                                                19

SEQ ID NO: 36          moltype = RNA  length = 21
FEATURE                Location/Qualifiers
source                 1..21
                       mol_type = other RNA
                       organism = synthetic construct
SEQUENCE: 36
accctggaaa agctgatgaa a                                             21

SEQ ID NO: 37          moltype = RNA  length = 19
FEATURE                Location/Qualifiers
source                 1..19
                       mol_type = other RNA
                       organism = synthetic construct
SEQUENCE: 37
cctggaaaag ctgatgaaa                                                19

SEQ ID NO: 38          moltype = RNA  length = 21
FEATURE                Location/Qualifiers
source                 1..21
                       mol_type = other RNA
                       organism = synthetic construct
SEQUENCE: 38
ctgatgaagg ccttcgagtc a                                             21

SEQ ID NO: 39          moltype = RNA  length = 21
FEATURE                Location/Qualifiers
source                 1..21
                       mol_type = other RNA
                       organism = synthetic construct
SEQUENCE: 39
ctgaagaagg ccttcgagtc a                                             21

SEQ ID NO: 40          moltype = RNA  length = 21
FEATURE                Location/Qualifiers
source                 1..21
                       mol_type = other RNA
                       organism = synthetic construct
SEQUENCE: 40
gcgaccctgg aaaagctgat a                                             21

SEQ ID NO: 41          moltype = RNA  length = 21
FEATURE                Location/Qualifiers
source                 1..21
                       mol_type = other RNA
                       organism = synthetic construct
SEQUENCE: 41
gcgaccctgg aaaagctgat a                                             21

SEQ ID NO: 42          moltype = RNA  length = 21
FEATURE                Location/Qualifiers
source                 1..21
                       mol_type = other RNA
                       organism = synthetic construct
SEQUENCE: 42
tccctcaagt ccttccagca a                                             21

SEQ ID NO: 43          moltype = RNA  length = 21
FEATURE                Location/Qualifiers
source                 1..21
                       mol_type = other RNA
                       organism = synthetic construct
SEQUENCE: 43
tcccacaagt ccttccagca a                                             21

SEQ ID NO: 44          moltype = RNA  length = 19
FEATURE                Location/Qualifiers
source                 1..19
                       mol_type = other RNA
                       organism = synthetic construct
SEQUENCE: 44
tcaggttctg cttttacca                                                19
```

```
SEQ ID NO: 45          moltype = RNA  length = 21
FEATURE                Location/Qualifiers
source                 1..21
                       mol_type = other RNA
                       organism = synthetic construct
SEQUENCE: 45
cttcgagtcc ctcaagtcct a                                           21

SEQ ID NO: 46          moltype = RNA  length = 21
FEATURE                Location/Qualifiers
source                 1..21
                       mol_type = other RNA
                       organism = synthetic construct
SEQUENCE: 46
gccgctcagg ttctgctttt a                                           21

SEQ ID NO: 47          moltype = RNA  length = 21
FEATURE                Location/Qualifiers
source                 1..21
                       mol_type = other RNA
                       organism = synthetic construct
SEQUENCE: 47
ccggtcaggt tctgctttta a                                           21

SEQ ID NO: 48          moltype = RNA  length = 21
FEATURE                Location/Qualifiers
source                 1..21
                       mol_type = other RNA
                       organism = synthetic construct
modified_base          5
                       mod_base = OTHER
                       note = 5'-methyluridine-3'-phosphate
SEQUENCE: 48
tgacttgagg gactcgaagg c                                           21

SEQ ID NO: 49          moltype = RNA  length = 23
FEATURE                Location/Qualifiers
source                 1..23
                       mol_type = other RNA
                       organism = synthetic construct
SEQUENCE: 49
tttcatcagc ttttccaggg tcg                                         23

SEQ ID NO: 50          moltype = RNA  length = 21
FEATURE                Location/Qualifiers
source                 1..21
                       mol_type = other RNA
                       organism = synthetic construct
SEQUENCE: 50
tttcatcagc ttttccaggg t                                           21

SEQ ID NO: 51          moltype = RNA  length = 23
FEATURE                Location/Qualifiers
source                 1..23
                       mol_type = other RNA
                       organism = synthetic construct
SEQUENCE: 51
tgactcgaag gccttcatca gct                                         23

SEQ ID NO: 52          moltype = RNA  length = 23
FEATURE                Location/Qualifiers
source                 1..23
                       mol_type = other RNA
                       organism = synthetic construct
modified_base          5
                       mod_base = OTHER
                       note = 5'-methyluridine-3'-phosphate
SEQUENCE: 52
tgactcgaag gccttcttca gct                                         23

SEQ ID NO: 53          moltype = RNA  length = 23
FEATURE                Location/Qualifiers
source                 1..23
                       mol_type = other RNA
                       organism = synthetic construct
SEQUENCE: 53
tatcagcttt tccagggtcg cca                                         23
```

```
SEQ ID NO: 54          moltype = RNA  length = 23
FEATURE                Location/Qualifiers
source                 1..23
                       mol_type = other RNA
                       organism = synthetic construct
SEQUENCE: 54
tatcagcttt tccagggtcg ccg                                          23

SEQ ID NO: 55          moltype = RNA  length = 23
FEATURE                Location/Qualifiers
source                 1..23
                       mol_type = other RNA
                       organism = synthetic construct
SEQUENCE: 55
ttgctggaag gacttgaggg act                                          23

SEQ ID NO: 56          moltype = RNA  length = 23
FEATURE                Location/Qualifiers
source                 1..23
                       mol_type = other RNA
                       organism = synthetic construct
modified_base          5
                       mod_base = OTHER
                       note = 5'-methyluridine-3'-phosphate
SEQUENCE: 56
ttgctggaag gacttgtggg act                                          23

SEQ ID NO: 57          moltype = RNA  length = 23
FEATURE                Location/Qualifiers
source                 1..23
                       mol_type = other RNA
                       organism = synthetic construct
modified_base          7
                       mod_base = OTHER
                       note = 5'-methyluridine-3'-phosphate
SEQUENCE: 57
taggacttga gggactcgaa ggc                                          23

SEQ ID NO: 58          moltype = RNA  length = 23
FEATURE                Location/Qualifiers
source                 1..23
                       mol_type = other RNA
                       organism = synthetic construct
SEQUENCE: 58
taaaagcaga acctgagcgg ccg                                          23

SEQ ID NO: 59          moltype = RNA  length = 23
FEATURE                Location/Qualifiers
source                 1..23
                       mol_type = other RNA
                       organism = synthetic construct
SEQUENCE: 59
ttaaaagcag aacctgaccg gcc                                          23

SEQ ID NO: 60          moltype = RNA  length = 19
FEATURE                Location/Qualifiers
source                 1..19
                       mol_type = other RNA
                       organism = synthetic construct
modified_base          1
                       mod_base = OTHER
                       note = 2'-O-methylcytidine-3'-phosphorothioate
modified_base          2
                       mod_base = OTHER
                       note = 2'-O-methyluridine-3'-phosphorothioate
modified_base          3
                       mod_base = OTHER
                       note = 2'-O-methyluridine-3'-phosphate
modified_base          4
                       mod_base = OTHER
                       note = 2'-O-hexadecyl-cytidine-3'-phosphate
modified_base          5
                       mod_base = OTHER
                       note = 2'-deoxy-2'-fluoroguanosine-3'-phosphate
modified_base          6
                       mod_base = OTHER
                       note = 2'-O-methyladenosine-3'-phosphate
modified_base          7
                       mod_base = OTHER
```

```
                        note = 2'-deoxy-2'-fluoroguanosine-3'-phosphate
modified_base           8
                        mod_base = OTHER
                        note = 2'-deoxy-2'-fluorouridine-3'-phosphate
modified_base           9
                        mod_base = OTHER
                        note = 2'-deoxy-2'-fluorocytidine-3'-phosphate
modified_base           10
                        mod_base = OTHER
                        note = 2'-O-methylcytidine-3'-phosphate
modified_base           11
                        mod_base = OTHER
                        note = 2'-O-methylcytidine-3'-phosphate
modified_base           12
                        mod_base = OTHER
                        note = 2'-O-methyluridine-3'-phosphate
modified_base           13
                        mod_base = OTHER
                        note = 2'-O-methylcytidine-3'-phosphate
modified_base           14
                        mod_base = OTHER
                        note = 2'-O-methyladenosine-3'-phosphate
modified_base           15
                        mod_base = OTHER
                        note = 2'-O-methyladenosine-3'-phosphate
modified_base           16
                        mod_base = OTHER
                        note = 2'-O-methylguanosine-3'-phosphate
modified_base           17
                        mod_base = OTHER
                        note = 2'-O-methyluridine-3'-phosphorothioate
modified_base           18
                        mod_base = OTHER
                        note = 2'-O-methylcytidine-3'-phosphorothioate
modified_base           19
                        mod_base = OTHER
                        note = 2'-O-methyladenosine
SEQUENCE: 60
cttcgagtcc ctcaagtca                                              19

SEQ ID NO: 61           moltype = RNA  length = 21
FEATURE                 Location/Qualifiers
source                  1..21
                        mol_type = other RNA
                        organism = synthetic construct
modified_base           1
                        mod_base = OTHER
                        note = 2'-O-methyladenosine-3'-phosphorothioate
modified_base           2
                        mod_base = OTHER
                        note = 2'-O-methylcytidine-3'-phosphorothioate
modified_base           3
                        mod_base = OTHER
                        note = 2'-O-methylcytidine-3'-phosphate
modified_base           4
                        mod_base = OTHER
                        note = 2'-O-methylcytidine-3'-phosphate
modified_base           5
                        mod_base = OTHER
                        note = 2'-O-methyluridine-3'-phosphate
modified_base           6
                        mod_base = OTHER
                        note = 2'-O-hexadecyl-guanosine-3'-phosphate
modified_base           7
                        mod_base = OTHER
                        note = 2'-deoxy-2'-fluoroguanosine-3'-phosphate
modified_base           8
                        mod_base = OTHER
                        note = 2'-O-methyladenosine-3'-phosphate
modified_base           9
                        mod_base = OTHER
                        note = 2'-deoxy-2'-fluoroadenosine-3'-phosphate
modified_base           10
                        mod_base = OTHER
                        note = 2'-deoxy-2'-fluoroadenosine-3'-phosphate
modified_base           11
                        mod_base = OTHER
                        note = 2'-deoxy-2'-fluoroadenosine-3'-phosphate
modified_base           12
```

```
                        mod_base = OTHER
                        note = 2'-O-methylguanosine-3'-phosphate
modified_base           13
                        mod_base = OTHER
                        note = 2'-O-methylcytidine-3'-phosphate
modified_base           14
                        mod_base = OTHER
                        note = 2'-O-methyluridine-3'-phosphate
modified_base           15
                        mod_base = OTHER
                        note = 2'-O-methylguanosine-3'-phosphate
modified_base           16
                        mod_base = OTHER
                        note = 2'-O-methyladenosine-3'-phosphate
modified_base           17
                        mod_base = OTHER
                        note = 2'-O-methyluridine-3'-phosphate
modified_base           18
                        mod_base = OTHER
                        note = 2'-O-methylguanosine-3'-phosphate
modified_base           19
                        mod_base = OTHER
                        note = 2'-O-methyladenosine-3'-phosphorothioate
modified_base           20
                        mod_base = OTHER
                        note = 2'-O-methyladenosine-3'-phosphorothioate
modified_base           21
                        mod_base = OTHER
                        note = 2'-O-methyladenosine
SEQUENCE: 61
accctggaaa agctgatgaa a                                              21

SEQ ID NO: 62           moltype = RNA  length = 19
FEATURE                 Location/Qualifiers
source                  1..19
                        mol_type = other RNA
                        organism = synthetic construct
modified_base           1
                        mod_base = OTHER
                        note = 2'-O-methylcytidine-3'-phosphorothioate
modified_base           2
                        mod_base = OTHER
                        note = 2'-O-methylcytidine-3'-phosphorothioate
modified_base           3
                        mod_base = OTHER
                        note = 2'-O-methyluridine-3'-phosphate
modified_base           4
                        mod_base = OTHER
                        note = 2'-O-methylguanosine-3'-phosphate
modified_base           5
                        mod_base = OTHER
                        note = 2'-O-methylguanosine-3'-phosphate
modified_base           6
                        mod_base = OTHER
                        note = 2'-O-methyladenosine-3'-phosphate
modified_base           7
                        mod_base = OTHER
                        note = 2'-deoxy-2'-fluoroadenosine-3'-phosphate
modified_base           8
                        mod_base = OTHER
                        note = 2'-deoxy-2'-fluoroadenosine-3'-phosphate
modified_base           9
                        mod_base = OTHER
                        note = 2'-deoxy-2'-fluoroadenosine-3'-phosphate
modified_base           10
                        mod_base = OTHER
                        note = 2'-O-methylguanosine-3'-phosphate
modified_base           11
                        mod_base = OTHER
                        note = 2'-O-methylcytidine-3'-phosphate
modified_base           12
                        mod_base = OTHER
                        note = 2'-O-methyluridine-3'-phosphate
modified_base           13
                        mod_base = OTHER
                        note = 2'-O-methylguanosine-3'-phosphate
modified_base           14
                        mod_base = OTHER
                        note = 2'-O-methyladenosine-3'-phosphate
```

```
modified_base          15
                       mod_base = OTHER
                       note = 2'-O-hexadecyl-uridine-3'-phosphate
modified_base          16
                       mod_base = OTHER
                       note = 2'-O-methylguanosine-3'-phosphate
modified_base          17
                       mod_base = OTHER
                       note = 2'-O-methyladenosine-3'-phosphorothioate
modified_base          18
                       mod_base = OTHER
                       note = 2'-O-methyladenosine-3'-phosphorothioate
modified_base          19
                       mod_base = OTHER
                       note = 2'-O-methyladenosine
SEQUENCE: 62
cctggaaaag ctgatgaaa                                               19

SEQ ID NO: 63          moltype = RNA  length = 21
FEATURE                Location/Qualifiers
source                 1..21
                       mol_type = other RNA
                       organism = synthetic construct
modified_base          1
                       mod_base = OTHER
                       note = 2'-O-methylcytidine-3'-phosphorothioate
modified_base          2
                       mod_base = OTHER
                       note = 2'-O-methyluridine-3'-phosphorothioate
modified_base          3
                       mod_base = OTHER
                       note = 2'-O-methylguanosine-3'-phosphate
modified_base          4
                       mod_base = OTHER
                       note = 2'-O-methyladenosine-3'-phosphate
modified_base          5
                       mod_base = OTHER
                       note = 2'-O-methyluridine-3'-phosphate
modified_base          6
                       mod_base = OTHER
                       note = 2'-O-hexadecyl-guanosine-3'-phosphate
modified_base          7
                       mod_base = OTHER
                       note = 2'-deoxy-2'-fluoroadenosine-3'-phosphate
modified_base          8
                       mod_base = OTHER
                       note = 2'-O-methyladenosine-3'-phosphate
modified_base          9
                       mod_base = OTHER
                       note = 2'-deoxy-2'-fluoroguanosine-3'-phosphate
modified_base          10
                       mod_base = OTHER
                       note = 2'-deoxy-2'-fluoroguanosine-3'-phosphate
modified_base          11
                       mod_base = OTHER
                       note = 2'-deoxy-2'-fluorocytidine-3'-phosphate
modified_base          12
                       mod_base = OTHER
                       note = 2'-O-methylcytidine-3'-phosphate
modified_base          13
                       mod_base = OTHER
                       note = 2'-O-methyluridine-3'-phosphate
modified_base          14
                       mod_base = OTHER
                       note = 2'-O-methyluridine-3'-phosphate
modified_base          15
                       mod_base = OTHER
                       note = 2'-O-methylcytidine-3'-phosphate
modified_base          16
                       mod_base = OTHER
                       note = 2'-O-methylguanosine-3'-phosphate
modified_base          17
                       mod_base = OTHER
                       note = 2'-O-methyladenosine-3'-phosphate
modified_base          18
                       mod_base = OTHER
                       note = 2'-O-methylguanosine-3'-phosphate
modified_base          19
                       mod_base = OTHER
```

```
                         note = 2'-O-methyluridine-3'-phosphorothioate
modified_base            20
                         mod_base = OTHER
                         note = 2'-O-methylcytidine-3'-phosphorothioate
modified_base            21
                         mod_base = OTHER
                         note = 2'-O-methyladenosine
SEQUENCE: 63
ctgatgaagg ccttcgagtc a                                                21

SEQ ID NO: 64            moltype = RNA  length = 21
FEATURE                  Location/Qualifiers
source                   1..21
                         mol_type = other RNA
                         organism = synthetic construct
modified_base            1
                         mod_base = OTHER
                         note = 2'-O-methylcytidine-3'-phosphorothioate
modified_base            2
                         mod_base = OTHER
                         note = 2'-O-methyluridine-3'-phosphorothioate
modified_base            3
                         mod_base = OTHER
                         note = 2'-O-methylguanosine-3'-phosphate
modified_base            4
                         mod_base = OTHER
                         note = 2'-O-methyladenosine-3'-phosphate
modified_base            5
                         mod_base = OTHER
                         note = 2'-O-hexadecyl-adenosine-3'-phosphate
modified_base            6
                         mod_base = OTHER
                         note = 2'-O-methylguanosine-3'-phosphate
modified_base            7
                         mod_base = OTHER
                         note = 2'-deoxy-2'-fluoroadenosine-3'-phosphate
modified_base            8
                         mod_base = OTHER
                         note = 2'-O-methyladenosine-3'-phosphate
modified_base            9
                         mod_base = OTHER
                         note = 2'-deoxy-2'-fluoroguanosine-3'-phosphate
modified_base            10
                         mod_base = OTHER
                         note = 2'-deoxy-2'-fluoroguanosine-3'-phosphate
modified_base            11
                         mod_base = OTHER
                         note = 2'-deoxy-2'-fluorocytidine-3'-phosphate
modified_base            12
                         mod_base = OTHER
                         note = 2'-O-methylcytidine-3'-phosphate
modified_base            13
                         mod_base = OTHER
                         note = 2'-O-methyluridine-3'-phosphate
modified_base            14
                         mod_base = OTHER
                         note = 2'-O-methyluridine-3'-phosphate
modified_base            15
                         mod_base = OTHER
                         note = 2'-O-methylcytidine-3'-phosphate
modified_base            16
                         mod_base = OTHER
                         note = 2'-O-methylguanosine-3'-phosphate
modified_base            17
                         mod_base = OTHER
                         note = 2'-O-methyladenosine-3'-phosphate
modified_base            18
                         mod_base = OTHER
                         note = 2'-O-methylguanosine-3'-phosphate
modified_base            19
                         mod_base = OTHER
                         note = 2'-O-methyluridine-3'-phosphorothioate
modified_base            20
                         mod_base = OTHER
                         note = 2'-O-methylcytidine-3'-phosphorothioate
modified_base            21
                         mod_base = OTHER
                         note = 2'-O-methyladenosine
SEQUENCE: 64
```

```
ctgaagaagg ccttcgagtc a                                           21

SEQ ID NO: 65          moltype = RNA  length = 21
FEATURE                Location/Qualifiers
source                 1..21
                       mol_type = other RNA
                       organism = synthetic construct
modified_base          1
                       mod_base = OTHER
                       note = 2'-O-methylguanosine-3'-phosphorothioate
modified_base          2
                       mod_base = OTHER
                       note = 2'-O-methylcytidine-3'-phosphorothioate
modified_base          3
                       mod_base = OTHER
                       note = 2'-O-methylguanosine-3'-phosphate
modified_base          4
                       mod_base = OTHER
                       note = 2'-O-methyladenosine-3'-phosphate
modified_base          5
                       mod_base = OTHER
                       note = 2'-O-methylcytidine-3'-phosphate
modified_base          6
                       mod_base = OTHER
                       note = 2'-O-hexadecyl-cytidine-3'-phosphate
modified_base          7
                       mod_base = OTHER
                       note = 2'-deoxy-2'-fluorocytidine-3'-phosphate
modified_base          8
                       mod_base = OTHER
                       note = 2'-O-methyluridine-3'-phosphate
modified_base          9
                       mod_base = OTHER
                       note = 2'-deoxy-2'-fluoroguanosine-3'-phosphate
modified_base          10
                       mod_base = OTHER
                       note = 2'-deoxy-2'-fluoroguanosine-3'-phosphate
modified_base          11
                       mod_base = OTHER
                       note = 2'-deoxy-2'-fluoroadenosine-3'-phosphate
modified_base          12
                       mod_base = OTHER
                       note = 2'-O-methyladenosine-3'-phosphate
modified_base          13
                       mod_base = OTHER
                       note = 2'-O-methyladenosine-3'-phosphate
modified_base          14
                       mod_base = OTHER
                       note = 2'-O-methyladenosine-3'-phosphate
modified_base          15
                       mod_base = OTHER
                       note = 2'-O-methylguanosine-3'-phosphate
modified_base          16
                       mod_base = OTHER
                       note = 2'-O-methylcytidine-3'-phosphate
modified_base          17
                       mod_base = OTHER
                       note = 2'-O-methyluridine-3'-phosphate
modified_base          18
                       mod_base = OTHER
                       note = 2'-O-methylguanosine-3'-phosphate
modified_base          19
                       mod_base = OTHER
                       note = 2'-O-methyladenosine-3'-phosphorothioate
modified_base          20
                       mod_base = OTHER
                       note = 2'-O-methyluridine-3'-phosphorothioate
modified_base          21
                       mod_base = OTHER
                       note = 2'-O-methyladenosine
SEQUENCE: 65
gcgaccctgg aaaagctgat a                                           21

SEQ ID NO: 66          moltype = DNA  length = 21
FEATURE                Location/Qualifiers
source                 1..21
                       mol_type = other DNA
                       organism = synthetic construct
modified_base          1
```

```
                         mod_base = OTHER
                         note = 2'-O-methylguanosine-3'-phosphorothioate
modified_base            2
                         mod_base = OTHER
                         note = 2'-O-methylcytidine-3'-phosphorothioate
modified_base            3
                         mod_base = OTHER
                         note = 2'-O-methylguanosine-3'-phosphate
modified_base            4
                         mod_base = OTHER
                         note = 2'-O-methyladenosine-3'-phosphate
modified_base            5
                         mod_base = OTHER
                         note = 2'-O-methylcytidine-3'-phosphate
modified_base            6
                         mod_base = OTHER
                         note = 2'-O-hexadecyl-cytidine-3'-phosphate
modified_base            7
                         mod_base = OTHER
                         note = 2'-deoxy-2'-fluorocytidine-3'-phosphate
modified_base            8
                         mod_base = OTHER
                         note = 2'-O-methyluridine-3'-phosphate
modified_base            10
                         mod_base = OTHER
                         note = 2'-O-methylguanosine-3'-phosphate
modified_base            11
                         mod_base = OTHER
                         note = 2'-deoxy-2'-fluoroadenosine-3'-phosphate
modified_base            12
                         mod_base = OTHER
                         note = 2'-O-methyladenosine-3'-phosphate
modified_base            13
                         mod_base = OTHER
                         note = 2'-O-methyladenosine-3'-phosphate
modified_base            14
                         mod_base = OTHER
                         note = 2'-O-methyladenosine-3'-phosphate
modified_base            15
                         mod_base = OTHER
                         note = 2'-O-methylguanosine-3'-phosphate
modified_base            16
                         mod_base = OTHER
                         note = 2'-O-methylcytidine-3'-phosphate
modified_base            17
                         mod_base = OTHER
                         note = 2'-O-methyluridine-3'-phosphate
modified_base            18
                         mod_base = OTHER
                         note = 2'-O-methylguanosine-3'-phosphate
modified_base            19
                         mod_base = OTHER
                         note = 2'-O-methyladenosine-3'-phosphorothioate
modified_base            20
                         mod_base = OTHER
                         note = 2'-O-methyluridine-3'-phosphorothioate
modified_base            21
                         mod_base = OTHER
                         note = 2'-O-methyladenosine
misc_feature             1..8
                         note = RNA
misc_feature             10..21
                         note = RNA
misc_feature             9
                         note = DNA
SEQUENCE: 66
gcgaccctgg aaaagctgat a                                            21

SEQ ID NO: 67            moltype = RNA  length = 21
FEATURE                  Location/Qualifiers
source                   1..21
                         mol_type = other RNA
                         organism = synthetic construct
modified_base            1
                         mod_base = OTHER
                         note = 2'-O-methyluridine-3'-phosphorothioate
modified_base            2
                         mod_base = OTHER
                         note = 2'-O-methylcytidine-3'-phosphorothioate
```

```
modified_base          3
                       mod_base = OTHER
                       note = 2'-O-methylcytidine-3'-phosphate
modified_base          4
                       mod_base = OTHER
                       note = 2'-O-methylcytidine-3'-phosphate
modified_base          5
                       mod_base = OTHER
                       note = 2'-O-methyluridine-3'-phosphate
modified_base          6
                       mod_base = OTHER
                       note = 2'-O-hexadecyl-cytidine-3'-phosphate
modified_base          7
                       mod_base = OTHER
                       note = 2'-deoxy-2'-fluoroadenosine-3'-phosphate
modified_base          8
                       mod_base = OTHER
                       note = 2'-O-methyladenosine-3'-phosphate
modified_base          9
                       mod_base = OTHER
                       note = 2'-deoxy-2'-fluoroguanosine-3'-phosphate
modified_base          10
                       mod_base = OTHER
                       note = 2'-deoxy-2'-fluorouridine-3'-phosphate
modified_base          11
                       mod_base = OTHER
                       note = 2'-deoxy-2'-fluorocytidine-3'-phosphate
modified_base          12
                       mod_base = OTHER
                       note = 2'-O-methylcytidine-3'-phosphate
modified_base          13
                       mod_base = OTHER
                       note = 2'-O-methyluridine-3'-phosphate
modified_base          14
                       mod_base = OTHER
                       note = 2'-O-methyluridine-3'-phosphate
modified_base          15
                       mod_base = OTHER
                       note = 2'-O-methylcytidine-3'-phosphate
modified_base          16
                       mod_base = OTHER
                       note = 2'-O-methylcytidine-3'-phosphate
modified_base          17
                       mod_base = OTHER
                       note = 2'-O-methyladenosine-3'-phosphate
modified_base          18
                       mod_base = OTHER
                       note = 2'-O-methylguanosine-3'-phosphate
modified_base          19
                       mod_base = OTHER
                       note = 2'-O-methylcytidine-3'-phosphorothioate
modified_base          20
                       mod_base = OTHER
                       note = 2'-O-methyladenosine-3'-phosphorothioate
modified_base          21
                       mod_base = OTHER
                       note = 2'-O-methyladenosine
SEQUENCE: 67
tccctcaagt ccttccagca a                                              21

SEQ ID NO: 68          moltype = RNA  length = 21
FEATURE                Location/Qualifiers
source                 1..21
                       mol_type = other RNA
                       organism = synthetic construct
modified_base          1
                       mod_base = OTHER
                       note = 2'-O-methyluridine-3'-phosphorothioate
modified_base          2
                       mod_base = OTHER
                       note = 2'-O-methylcytidine-3'-phosphorothioate
modified_base          3
                       mod_base = OTHER
                       note = 2'-O-methylcytidine-3'-phosphate
modified_base          4
                       mod_base = OTHER
                       note = 2'-O-methylcytidine-3'-phosphate
modified_base          5
                       mod_base = OTHER
```

```
                         note = 2'-O-methyladenosine-3'-phosphate
modified_base            6
                         mod_base = OTHER
                         note = 2'-O-hexadecyl-cytidine-3'-phosphate
modified_base            7
                         mod_base = OTHER
                         note = 2'-deoxy-2'-fluoroadenosine-3'-phosphate
modified_base            8
                         mod_base = OTHER
                         note = 2'-O-methyladenosine-3'-phosphate
modified_base            9
                         mod_base = OTHER
                         note = 2'-O-methylguanosine-3'-phosphate
modified_base            10
                         mod_base = OTHER
                         note = 2'-deoxy-2'-fluorouridine-3'-phosphate
modified_base            11
                         mod_base = OTHER
                         note = 2'-deoxy-2'-fluorocytidine-3'-phosphate
modified_base            12
                         mod_base = OTHER
                         note = 2'-O-methylcytidine-3'-phosphate
modified_base            13
                         mod_base = OTHER
                         note = 2'-O-methyluridine-3'-phosphate
modified_base            14
                         mod_base = OTHER
                         note = 2'-O-methyluridine-3'-phosphate
modified_base            15
                         mod_base = OTHER
                         note = 2'-O-methylcytidine-3'-phosphate
modified_base            16
                         mod_base = OTHER
                         note = 2'-O-methylcytidine-3'-phosphate
modified_base            17
                         mod_base = OTHER
                         note = 2'-O-methyladenosine-3'-phosphate
modified_base            18
                         mod_base = OTHER
                         note = 2'-O-methylguanosine-3'-phosphate
modified_base            19
                         mod_base = OTHER
                         note = 2'-O-methylcytidine-3'-phosphorothioate
modified_base            20
                         mod_base = OTHER
                         note = 2'-O-methyladenosine-3'-phosphorothioate
modified_base            21
                         mod_base = OTHER
                         note = 2'-O-methyladenosine
SEQUENCE: 68
tcccacaagt ccttccagca a                                      21

SEQ ID NO: 69            moltype = RNA  length = 19
FEATURE                  Location/Qualifiers
source                   1..19
                         mol_type = other RNA
                         organism = synthetic construct
modified_base            1
                         mod_base = OTHER
                         note = 2'-O-methyluridine-3'-phosphorothioate
modified_base            2
                         mod_base = OTHER
                         note = 2'-O-methylcytidine-3'-phosphorothioate
modified_base            3
                         mod_base = OTHER
                         note = 2'-O-methyladenosine-3'-phosphate
modified_base            4
                         mod_base = OTHER
                         note = 2'-O-methylguanosine-3'-phosphate
modified_base            5
                         mod_base = OTHER
                         note = 2'-O-methylguanosine-3'-phosphate
modified_base            6
                         mod_base = OTHER
                         note = 2'-O-methyluridine-3'-phosphate
modified_base            7
                         mod_base = OTHER
                         note = 2'-deoxy-2'-fluorouridine-3'-phosphate
modified_base            8
```

```
                         mod_base = OTHER
                         note = 2'-deoxy-2'-fluorocytidine-3'-phosphate
modified_base            9
                         mod_base = OTHER
                         note = 2'-deoxy-2'-fluorouridine-3'-phosphate
modified_base            10
                         mod_base = OTHER
                         note = 2'-O-methylguanosine-3'-phosphate
modified_base            11
                         mod_base = OTHER
                         note = 2'-O-methylcytidine-3'-phosphate
modified_base            12
                         mod_base = OTHER
                         note = 2'-O-methyluridine-3'-phosphate
modified_base            13
                         mod_base = OTHER
                         note = 2'-O-methyluridine-3'-phosphate
modified_base            14
                         mod_base = OTHER
                         note = 2'-O-hexadecyl-uridine-3'-phosphate
modified_base            15
                         mod_base = OTHER
                         note = 2'-O-methyluridine-3'-phosphate
modified_base            16
                         mod_base = OTHER
                         note = 2'-O-methyladenosine-3'-phosphate
modified_base            17
                         mod_base = OTHER
                         note = 2'-O-methylcytidine-3'-phosphorothioate
modified_base            18
                         mod_base = OTHER
                         note = 2'-O-methylcytidine-3'-phosphorothioate
modified_base            19
                         mod_base = OTHER
                         note = 2'-O-methyladenosine
SEQUENCE: 69
tcaggttctg cttttacca                                            19

SEQ ID NO: 70            moltype = RNA  length = 21
FEATURE                  Location/Qualifiers
source                   1..21
                         mol_type = other RNA
                         organism = synthetic construct
modified_base            1
                         mod_base = OTHER
                         note = 2'-O-methylcytidine-3'-phosphorothioate
modified_base            2
                         mod_base = OTHER
                         note = 2'-O-methyluridine-3'-phosphorothioate
modified_base            3
                         mod_base = OTHER
                         note = 2'-O-methyluridine-3'-phosphate
modified_base            4
                         mod_base = OTHER
                         note = 2'-O-methylcytidine-3'-phosphate
modified_base            5
                         mod_base = OTHER
                         note = 2'-O-methylguanosine-3'-phosphate
modified_base            6
                         mod_base = OTHER
                         note = 2'-O-hexadecyl-adenosine-3'-phosphate
modified_base            7
                         mod_base = OTHER
                         note = 2'-deoxy-2'-fluoroguanosine-3'-phosphate
modified_base            8
                         mod_base = OTHER
                         note = 2'-O-methyluridine-3'-phosphate
modified_base            9
                         mod_base = OTHER
                         note = 2'-deoxy-2'-fluorocytidine-3'-phosphate
modified_base            10
                         mod_base = OTHER
                         note = 2'-deoxy-2'-fluorocytidine-3'-phosphate
modified_base            11
                         mod_base = OTHER
                         note = 2'-deoxy-2'-fluorocytidine-3'-phosphate
modified_base            12
                         mod_base = OTHER
                         note = 2'-O-methyluridine-3'-phosphate
```

```
modified_base          13
                       mod_base = OTHER
                       note = 2'-O-methylcytidine-3'-phosphate
modified_base          14
                       mod_base = OTHER
                       note = 2'-O-methyladenosine-3'-phosphate
modified_base          15
                       mod_base = OTHER
                       note = 2'-O-methyladenosine-3'-phosphate
modified_base          16
                       mod_base = OTHER
                       note = 2'-O-methylguanosine-3'-phosphate
modified_base          17
                       mod_base = OTHER
                       note = 2'-O-methyluridine-3'-phosphate
modified_base          18
                       mod_base = OTHER
                       note = 2'-O-methylcytidine-3'-phosphate
modified_base          19
                       mod_base = OTHER
                       note = 2'-O-methylcytidine-3'-phosphorothioate
modified_base          20
                       mod_base = OTHER
                       note = 2'-O-methyluridine-3'-phosphorothioate
modified_base          21
                       mod_base = OTHER
                       note = 2'-O-methyladenosine
SEQUENCE: 70
cttcgagtcc ctcaagtcct a                                          21

SEQ ID NO: 71          moltype = DNA  length = 21
FEATURE                Location/Qualifiers
source                 1..21
                       mol_type = other DNA
                       organism = synthetic construct
modified_base          1
                       mod_base = OTHER
                       note = 2'-O-methylguanosine-3'-phosphorothioate
modified_base          2
                       mod_base = OTHER
                       note = 2'-O-methylcytidine-3'-phosphorothioate
modified_base          3
                       mod_base = OTHER
                       note = 2'-O-methylcytidine-3'-phosphate
modified_base          4
                       mod_base = OTHER
                       note = 2'-O-methylguanosine-3'-phosphate
modified_base          5
                       mod_base = OTHER
                       note = 2'-O-methylcytidine-3'-phosphate
modified_base          6
                       mod_base = OTHER
                       note = 2'-O-hexadecyl-uridine-3'-phosphate
modified_base          7
                       mod_base = OTHER
                       note = 2'-deoxy-2'-fluorocytidine-3'-phosphate
modified_base          8
                       mod_base = OTHER
                       note = 2'-O-methyladenosine-3'-phosphate
modified_base          10
                       mod_base = OTHER
                       note = 2'-O-methylguanosine-3'-phosphate
modified_base          11
                       mod_base = OTHER
                       note = 2'-deoxy-2'-fluorouridine-3'-phosphate
modified_base          12
                       mod_base = OTHER
                       note = 2'-O-methyluridine-3'-phosphate
modified_base          13
                       mod_base = OTHER
                       note = 2'-O-methylcytidine-3'-phosphate
modified_base          14
                       mod_base = OTHER
                       note = 2'-O-methyluridine-3'-phosphate
modified_base          15
                       mod_base = OTHER
                       note = 2'-O-methylguanosine-3'-phosphate
modified_base          16
                       mod_base = OTHER
```

```
                        note = 2'-O-methylcytidine-3'-phosphate
modified_base           17
                        mod_base = OTHER
                        note = 2'-O-methyluridine-3'-phosphate
modified_base           18
                        mod_base = OTHER
                        note = 2'-O-methyluridine-3'-phosphate
modified_base           19
                        mod_base = OTHER
                        note = 2'-O-methyluridine-3'-phosphorothioate
modified_base           20
                        mod_base = OTHER
                        note = 2'-O-methyluridine-3'-phosphorothioate
modified_base           21
                        mod_base = OTHER
                        note = 2'-O-methyladenosine
misc_feature            1..8
                        note = RNA
misc_feature            10..21
                        note = RNA
misc_feature            9
                        note = DNA
SEQUENCE: 71
gccgctcagg ttctgctttt a                                              21

SEQ ID NO: 72           moltype = RNA  length = 21
FEATURE                 Location/Qualifiers
source                  1..21
                        mol_type = other RNA
                        organism = synthetic construct
modified_base           1
                        mod_base = OTHER
                        note = 2'-O-methylcytidine-3'-phosphorothioate
modified_base           2
                        mod_base = OTHER
                        note = 2'-O-methylcytidine-3'-phosphorothioate
modified_base           3
                        mod_base = OTHER
                        note = 2'-O-methylguanosine-3'-phosphate
modified_base           4
                        mod_base = OTHER
                        note = 2'-O-methylguanosine-3'-phosphate
modified_base           5
                        mod_base = OTHER
                        note = 2'-O-methyluridine-3'-phosphate
modified_base           6
                        mod_base = OTHER
                        note = 2'-O-hexadecyl-cytidine-3'-phosphate
modified_base           7
                        mod_base = OTHER
                        note = 2'-deoxy-2'-fluoroadenosine-3'-phosphate
modified_base           8
                        mod_base = OTHER
                        note = 2'-O-methylguanosine-3'-phosphate
modified_base           9
                        mod_base = OTHER
                        note = 2'-deoxy-2'-fluoroguanosine-3'-phosphate
modified_base           10
                        mod_base = OTHER
                        note = 2'-deoxy-2'-fluorouridine-3'-phosphate
modified_base           11
                        mod_base = OTHER
                        note = 2'-deoxy-2'-fluorouridine-3'-phosphate
modified_base           12
                        mod_base = OTHER
                        note = 2'-O-methylcytidine-3'-phosphate
modified_base           13
                        mod_base = OTHER
                        note = 2'-O-methyluridine-3'-phosphate
modified_base           14
                        mod_base = OTHER
                        note = 2'-O-methylguanosine-3'-phosphate
modified_base           15
                        mod_base = OTHER
                        note = 2'-O-methylcytidine-3'-phosphate
modified_base           16
                        mod_base = OTHER
                        note = 2'-O-methyluridine-3'-phosphate
modified_base           17
```

```
                        mod_base = OTHER
                        note = 2'-O-methyluridine-3'-phosphate
modified_base           18
                        mod_base = OTHER
                        note = 2'-O-methyluridine-3'-phosphate
modified_base           19
                        mod_base = OTHER
                        note = 2'-O-methyluridine-3'-phosphorothioate
modified_base           20
                        mod_base = OTHER
                        note = 2'-O-methyladenosine-3'-phosphorothioate
modified_base           21
                        mod_base = OTHER
                        note = 2'-O-methyladenosine
SEQUENCE: 72
ccggtcaggt tctgctttta a                                          21

SEQ ID NO: 73           moltype = DNA  length = 21
FEATURE                 Location/Qualifiers
source                  1..21
                        mol_type = other DNA
                        organism = synthetic construct
modified_base           1
                        mod_base = OTHER
                        note = 2'-O-methyluridine-3'-phosphorothioate
                         5'-(E)-Vinylphosphonate
modified_base           2
                        mod_base = OTHER
                        note = 2'-deoxyguanosine-3'-phosphorothioate
modified_base           3
                        mod_base = OTHER
                        note = 2'-O-methyladenosine-3'-phosphate
modified_base           4
                        mod_base = OTHER
                        note = 2'-O-methylcytidine-3'-phosphate
modified_base           6
                        mod_base = OTHER
                        note = 2'-O-methyluridine-3'-phosphate
modified_base           7
                        mod_base = OTHER
                        note = guanosine-2'-phosphate
modified_base           8
                        mod_base = OTHER
                        note = 2'-O-methyladenosine-3'-phosphate
modified_base           9
                        mod_base = OTHER
                        note = 2'-O-methylguanosine-3'-phosphate
modified_base           10
                        mod_base = OTHER
                        note = 2'-O-methylguanosine-3'-phosphate
modified_base           11
                        mod_base = OTHER
                        note = 2'-O-methylguanosine-3'-phosphate
modified_base           12
                        mod_base = OTHER
                        note = 2'-O-methyladenosine-3'-phosphate
modified_base           13
                        mod_base = OTHER
                        note = 2'-O-methylcytidine-3'-phosphate
modified_base           14
                        mod_base = OTHER
                        note = 2'-deoxy-2'-fluorouridine-3'-phosphate
modified_base           15
                        mod_base = OTHER
                        note = 2'-O-methylcytidine-3'-phosphate
modified_base           16
                        mod_base = OTHER
                        note = 2'-deoxy-2'-fluoroguanosine-3'-phosphate
modified_base           17
                        mod_base = OTHER
                        note = 2'-O-methyladenosine-3'-phosphate
modified_base           18
                        mod_base = OTHER
                        note = 2'-O-methyladenosine-3'-phosphate
modified_base           19
                        mod_base = OTHER
                        note = 2'-O-methylguanosine-3'-phosphorothioate
modified_base           20
                        mod_base = OTHER
```

```
                        note = 2'-O-methylguanosine-3'-phosphorothioate
modified_base           21
                        mod_base = OTHER
                        note = 2'-O-methylcytidine
misc_feature            1
                        note = RNA
misc_feature            3..4
                        note = RNA
misc_feature            6..21
                        note = RNA
misc_feature            2
                        note = DNA
misc_feature            5
                        note = DNA
SEQUENCE: 73
tgacttgagg gactcgaagg c                                                21

SEQ ID NO: 74           moltype = RNA  length = 23
FEATURE                 Location/Qualifiers
source                  1..23
                        mol_type = other RNA
                        organism = synthetic construct
modified_base           1
                        mod_base = OTHER
                        note = 2'-O-methyluridine-3'-phosphorothioate
                         5'-(E)-Vinylphosphonate
modified_base           2
                        mod_base = OTHER
                        note = 2'-deoxy-2'-fluorouridine-3'-phosphorothioate
modified_base           3
                        mod_base = OTHER
                        note = 2'-O-methyluridine-3'-phosphate
modified_base           4
                        mod_base = OTHER
                        note = 2'-O-methylcytidine-3'-phosphate
modified_base           5
                        mod_base = OTHER
                        note = 2'-O-methyladenosine-3'-phosphate
modified_base           6
                        mod_base = OTHER
                        note = 2'-O-methyluridine-3'-phosphate
modified_base           7
                        mod_base = OTHER
                        note = cytidine-2'-phosphate
modified_base           8
                        mod_base = OTHER
                        note = 2'-O-methyladenosine-3'-phosphate
modified_base           9
                        mod_base = OTHER
                        note = 2'-O-methylguanosine-3'-phosphate
modified_base           10
                        mod_base = OTHER
                        note = 2'-O-methylcytidine-3'-phosphate
modified_base           11
                        mod_base = OTHER
                        note = 2'-O-methyluridine-3'-phosphate
modified_base           12
                        mod_base = OTHER
                        note = 2'-O-methyluridine-3'-phosphate
modified_base           13
                        mod_base = OTHER
                        note = 2'-O-methyluridine-3'-phosphate
modified_base           14
                        mod_base = OTHER
                        note = 2'-deoxy-2'-fluorouridine-3'-phosphate
modified_base           15
                        mod_base = OTHER
                        note = 2'-O-methylcytidine-3'-phosphate
modified_base           16
                        mod_base = OTHER
                        note = 2'-deoxy-2'-fluorocytidine-3'-phosphate
modified_base           17
                        mod_base = OTHER
                        note = 2'-O-methyladenosine-3'-phosphate
modified_base           18
                        mod_base = OTHER
                        note = 2'-O-methylguanosine-3'-phosphate
modified_base           19
                        mod_base = OTHER
```

```
                        note = 2'-O-methylguanosine-3'-phosphate
modified_base           20
                        mod_base = OTHER
                        note = 2'-O-methylguanosine-3'-phosphate
modified_base           21
                        mod_base = OTHER
                        note = 2'-O-methyluridine-3'-phosphorothioate
modified_base           22
                        mod_base = OTHER
                        note = 2'-O-methylcytidine-3'-phosphorothioate
modified_base           23
                        mod_base = OTHER
                        note = 2'-O-methylguanosine
SEQUENCE: 74
tttcatcagc ttttccaggg tcg                                           23

SEQ ID NO: 75           moltype = DNA  length = 21
FEATURE                 Location/Qualifiers
source                  1..21
                        mol_type = other DNA
                        organism = synthetic construct
modified_base           1
                        mod_base = OTHER
                        note = 2'-O-methyluridine-3'-phosphorothioate
                         5'-(E)-Vinylphosphonate
modified_base           2
                        mod_base = OTHER
                        note = 2'-deoxy-2'-fluorouridine-3'-phosphorothioate
modified_base           3
                        mod_base = OTHER
                        note = 2'-O-methyluridine-3'-phosphate
modified_base           4
                        mod_base = OTHER
                        note = 2'-O-methylcytidine-3'-phosphate
modified_base           6
                        mod_base = OTHER
                        note = 2'-O-methyluridine-3'-phosphate
modified_base           7
                        mod_base = OTHER
                        note = cytidine-2'-phosphate
modified_base           8
                        mod_base = OTHER
                        note = 2'-O-methyladenosine-3'-phosphate
modified_base           9
                        mod_base = OTHER
                        note = 2'-O-methylguanosine-3'-phosphate
modified_base           10
                        mod_base = OTHER
                        note = 2'-O-methylcytidine-3'-phosphate
modified_base           11
                        mod_base = OTHER
                        note = 2'-O-methyluridine-3'-phosphate
modified_base           12
                        mod_base = OTHER
                        note = 2'-O-methyluridine-3'-phosphate
modified_base           13
                        mod_base = OTHER
                        note = 2'-O-methyluridine-3'-phosphate
modified_base           14
                        mod_base = OTHER
                        note = 2'-deoxy-2'-fluorouridine-3'-phosphate
modified_base           15
                        mod_base = OTHER
                        note = 2'-O-methylcytidine-3'-phosphate
modified_base           16
                        mod_base = OTHER
                        note = 2'-deoxy-2'-fluorocytidine-3'-phosphate
modified_base           17
                        mod_base = OTHER
                        note = 2'-O-methyladenosine-3'-phosphate
modified_base           18
                        mod_base = OTHER
                        note = 2'-O-methylguanosine-3'-phosphate
modified_base           19
                        mod_base = OTHER
                        note = 2'-O-methylguanosine-3'-phosphorothioate
modified_base           20
                        mod_base = OTHER
                        note = 2'-O-methylguanosine-3'-phosphorothioate
```

```
modified_base          21
                       mod_base = OTHER
                       note = 2'-O-methyluridine
misc_feature           1..4
                       note = RNA
misc_feature           6..21
                       note = RNA
misc_feature           5
                       note = DNA
SEQUENCE: 75
tttcatcagc ttttccaggg t                                            21

SEQ ID NO: 76          moltype = RNA  length = 23
FEATURE                Location/Qualifiers
source                 1..23
                       mol_type = other RNA
                       organism = synthetic construct
modified_base          1
                       mod_base = OTHER
                       note = 2'-O-methyluridine-3'-phosphorothioate
                        5'-(E)-Vinylphosphonate
modified_base          2
                       mod_base = OTHER
                       note = 2'-deoxy-2'-fluoroguanosine-3'-phosphorothioate
modified_base          3
                       mod_base = OTHER
                       note = 2'-O-methyladenosine-3'-phosphate
modified_base          4
                       mod_base = OTHER
                       note = 2'-O-methylcytidine-3'-phosphate
modified_base          5
                       mod_base = OTHER
                       note = 2'-O-methyluridine-3'-phosphate
modified_base          6
                       mod_base = OTHER
                       note = 2'-deoxy-2'-fluorocytidine-3'-phosphate
modified_base          7
                       mod_base = OTHER
                       note = 2'-O-methylguanosine-3'-phosphate
modified_base          8
                       mod_base = OTHER
                       note = 2'-deoxy-2'-fluoroadenosine-3'-phosphate
modified_base          9
                       mod_base = OTHER
                       note = 2'-deoxy-2'-fluoroadenosine-3'-phosphate
modified_base          10
                       mod_base = OTHER
                       note = 2'-O-methylguanosine-3'-phosphate
modified_base          11
                       mod_base = OTHER
                       note = 2'-O-methylguanosine-3'-phosphate
modified_base          12
                       mod_base = OTHER
                       note = 2'-O-methylcytidine-3'-phosphate
modified_base          13
                       mod_base = OTHER
                       note = 2'-O-methylcytidine-3'-phosphate
modified_base          14
                       mod_base = OTHER
                       note = 2'-deoxy-2'-fluorouridine-3'-phosphate
modified_base          15
                       mod_base = OTHER
                       note = 2'-O-methyluridine-3'-phosphate
modified_base          16
                       mod_base = OTHER
                       note = 2'-deoxy-2'-fluorocytidine-3'-phosphate
modified_base          17
                       mod_base = OTHER
                       note = 2'-O-methyladenosine-3'-phosphate
modified_base          18
                       mod_base = OTHER
                       note = 2'-O-methyluridine-3'-phosphate
modified_base          19
                       mod_base = OTHER
                       note = 2'-O-methylcytidine-3'-phosphate
modified_base          20
                       mod_base = OTHER
                       note = 2'-O-methyladenosine-3'-phosphate
modified_base          21
```

```
                        mod_base = OTHER
                        note = 2'-O-methylguanosine-3'-phosphorothioate
modified_base           22
                        mod_base = OTHER
                        note = 2'-O-methylcytidine-3'-phosphorothioate
modified_base           23
                        mod_base = OTHER
                        note = 2'-O-methyluridine
SEQUENCE: 76
tgactcgaag gccttcatca gct                                              23

SEQ ID NO: 77           moltype = DNA  length = 23
FEATURE                 Location/Qualifiers
source                  1..23
                        mol_type = other DNA
                        organism = synthetic construct
modified_base           1
                        mod_base = OTHER
                        note = 2'-O-methyluridine-3'-phosphorothioate
                         5'-(E)-Vinylphosphonate
modified_base           2
                        mod_base = OTHER
                        note = 2'-deoxyguanosine-3'-phosphorothioate
modified_base           3
                        mod_base = OTHER
                        note = 2'-O-methyladenosine-3'-phosphate
modified_base           4
                        mod_base = OTHER
                        note = 2'-O-methylcytidine-3'-phosphate
modified_base           6
                        mod_base = OTHER
                        note = 2'-O-methylcytidine-3'-phosphate
modified_base           7
                        mod_base = OTHER
                        note = guanosine-2'-phosphate
modified_base           8
                        mod_base = OTHER
                        note = 2'-O-methyladenosine-3'-phosphate
modified_base           9
                        mod_base = OTHER
                        note = 2'-O-methyladenosine-3'-phosphate
modified_base           10
                        mod_base = OTHER
                        note = 2'-O-methylguanosine-3'-phosphate
modified_base           11
                        mod_base = OTHER
                        note = 2'-O-methylguanosine-3'-phosphate
modified_base           12
                        mod_base = OTHER
                        note = 2'-O-methylcytidine-3'-phosphate
modified_base           13
                        mod_base = OTHER
                        note = 2'-O-methylcytidine-3'-phosphate
modified_base           14
                        mod_base = OTHER
                        note = 2'-deoxy-2'-fluorouridine-3'-phosphate
modified_base           15
                        mod_base = OTHER
                        note = 2'-O-methyluridine-3'-phosphate
modified_base           16
                        mod_base = OTHER
                        note = 2'-deoxy-2'-fluorocytidine-3'-phosphate
modified_base           17
                        mod_base = OTHER
                        note = 2'-O-methyluridine-3'-phosphate
modified_base           18
                        mod_base = OTHER
                        note = 2'-O-methyluridine-3'-phosphate
modified_base           19
                        mod_base = OTHER
                        note = 2'-O-methylcytidine-3'-phosphate
modified_base           20
                        mod_base = OTHER
                        note = 2'-O-methyladenosine-3'-phosphate
modified_base           21
                        mod_base = OTHER
                        note = 2'-O-methylguanosine-3'-phosphorothioate
modified_base           22
                        mod_base = OTHER
```

```
                        note = 2'-O-methylcytidine-3'-phosphorothioate
modified_base           23
                        mod_base = OTHER
                        note = 2'-O-methyluridine
misc_feature            1
                        note = RNA
misc_feature            3..4
                        note = RNA
misc_feature            6..23
                        note = RNA
misc_feature            2
                        note = DNA
misc_feature            5
                        note = DNA
SEQUENCE: 77
tgactcgaag gccttcttca gct                                          23

SEQ ID NO: 78           moltype = RNA  length = 23
FEATURE                 Location/Qualifiers
source                  1..23
                        mol_type = other RNA
                        organism = synthetic construct
modified_base           1
                        mod_base = OTHER
                        note = 2'-O-methyluridine-3'-phosphorothioate
                         5'-(E)-Vinylphosphonate
modified_base           2
                        mod_base = OTHER
                        note = 2'-deoxy-2'-fluoroadenosine-3'-phosphorothioate
modified_base           3
                        mod_base = OTHER
                        note = 2'-O-methyluridine-3'-phosphate
modified_base           4
                        mod_base = OTHER
                        note = 2'-O-methylcytidine-3'-phosphate
modified_base           5
                        mod_base = OTHER
                        note = 2'-O-methyladenosine-3'-phosphate
modified_base           6
                        mod_base = OTHER
                        note = 2'-O-methylguanosine-3'-phosphate
modified_base           7
                        mod_base = OTHER
                        note = cytidine-2'-phosphate
modified_base           8
                        mod_base = OTHER
                        note = 2'-O-methyluridine-3'-phosphate
modified_base           9
                        mod_base = OTHER
                        note = 2'-O-methyluridine-3'-phosphate
modified_base           10
                        mod_base = OTHER
                        note = 2'-O-methyluridine-3'-phosphate
modified_base           11
                        mod_base = OTHER
                        note = 2'-O-methyluridine-3'-phosphate
modified_base           12
                        mod_base = OTHER
                        note = 2'-O-methylcytidine-3'-phosphate
modified_base           13
                        mod_base = OTHER
                        note = 2'-O-methylcytidine-3'-phosphate
modified_base           14
                        mod_base = OTHER
                        note = 2'-deoxy-2'-fluoroadenosine-3'-phosphate
modified_base           15
                        mod_base = OTHER
                        note = 2'-O-methylguanosine-3'-phosphate
modified_base           16
                        mod_base = OTHER
                        note = 2'-deoxy-2'-fluoroguanosine-3'-phosphate
modified_base           17
                        mod_base = OTHER
                        note = 2'-O-methylguanosine-3'-phosphate
modified_base           18
                        mod_base = OTHER
                        note = 2'-O-methyluridine-3'-phosphate
modified_base           19
                        mod_base = OTHER
```

```
                         note = 2'-O-methylcytidine-3'-phosphate
modified_base            20
                         mod_base = OTHER
                         note = 2'-O-methylguanosine-3'-phosphate
modified_base            21
                         mod_base = OTHER
                         note = 2'-O-methylcytidine-3'-phosphorothioate
modified_base            22
                         mod_base = OTHER
                         note = 2'-O-methylcytidine-3'-phosphorothioate
modified_base            23
                         mod_base = OTHER
                         note = 2'-O-methyladenosine
SEQUENCE: 78
tatcagcttt tccagggtcg cca                                          23

SEQ ID NO: 79            moltype = DNA  length = 23
FEATURE                  Location/Qualifiers
source                   1..23
                         mol_type = other DNA
                         organism = synthetic construct
modified_base            1
                         mod_base = OTHER
                         note = 2'-O-methyluridine-3'-phosphorothioate
                          5'-(E)-Vinylphosphonate
modified_base            2
                         mod_base = OTHER
                         note = 2'-deoxy-2'-fluoroadenosine-3'-phosphorothioate
modified_base            3
                         mod_base = OTHER
                         note = 2'-O-methyluridine-3'-phosphate
modified_base            4
                         mod_base = OTHER
                         note = 2'-O-methylcytidine-3'-phosphate
modified_base            6
                         mod_base = OTHER
                         note = 2'-O-methylguanosine-3'-phosphate
modified_base            7
                         mod_base = OTHER
                         note = cytidine-2'-phosphate
modified_base            8
                         mod_base = OTHER
                         note = 2'-O-methyluridine-3'-phosphate
modified_base            9
                         mod_base = OTHER
                         note = 2'-O-methyluridine-3'-phosphate
modified_base            10
                         mod_base = OTHER
                         note = 2'-O-methyluridine-3'-phosphate
modified_base            11
                         mod_base = OTHER
                         note = 2'-O-methyluridine-3'-phosphate
modified_base            13
                         mod_base = OTHER
                         note = 2'-O-methylcytidine-3'-phosphate
modified_base            14
                         mod_base = OTHER
                         note = 2'-deoxy-2'-fluoroadenosine-3'-phosphate
modified_base            15
                         mod_base = OTHER
                         note = 2'-O-methylguanosine-3'-phosphate
modified_base            17
                         mod_base = OTHER
                         note = 2'-O-methylguanosine-3'-phosphate
modified_base            18
                         mod_base = OTHER
                         note = 2'-O-methyluridine-3'-phosphate
modified_base            19
                         mod_base = OTHER
                         note = 2'-O-methylcytidine-3'-phosphate
modified_base            20
                         mod_base = OTHER
                         note = 2'-O-methylguanosine-3'-phosphate
modified_base            21
                         mod_base = OTHER
                         note = 2'-O-methylcytidine-3'-phosphorothioate
modified_base            22
                         mod_base = OTHER
                         note = 2'-O-methylcytidine-3'-phosphorothioate
```

```
modified_base          23
                       mod_base = OTHER
                       note = 2'-O-methylguanosine
misc_feature           1..4
                       note = RNA
misc_feature           6..11
                       note = RNA
misc_feature           13..15
                       note = RNA
misc_feature           17..23
                       note = RNA
misc_feature           5
                       note = DNA
misc_feature           12
                       note = DNA
misc_feature           16
                       note = DNA
SEQUENCE: 79
tatcagcttt tccagggtcg ccg                                          23

SEQ ID NO: 80          moltype = RNA  length = 23
FEATURE                Location/Qualifiers
source                 1..23
                       mol_type = other RNA
                       organism = synthetic construct
modified_base          1
                       mod_base = OTHER
                       note = 2'-O-methyluridine-3'-phosphorothioate
                        5'-(E)-Vinylphosphonate
modified_base          2
                       mod_base = OTHER
                       note = 2'-deoxy-2'-fluorouridine-3'-phosphorothioate
modified_base          3
                       mod_base = OTHER
                       note = 2'-O-methylguanosine-3'-phosphate
modified_base          4
                       mod_base = OTHER
                       note = 2'-O-methylcytidine-3'-phosphate
modified_base          5
                       mod_base = OTHER
                       note = 2'-O-methyluridine-3'-phosphate
modified_base          6
                       mod_base = OTHER
                       note = 2'-O-methylguanosine-3'-phosphate
modified_base          7
                       mod_base = OTHER
                       note = guanosine-2'-phosphate
modified_base          8
                       mod_base = OTHER
                       note = 2'-O-methyladenosine-3'-phosphate
modified_base          9
                       mod_base = OTHER
                       note = 2'-O-methyladenosine-3'-phosphate
modified_base          10
                       mod_base = OTHER
                       note = 2'-O-methylguanosine-3'-phosphate
modified_base          11
                       mod_base = OTHER
                       note = 2'-O-methylguanosine-3'-phosphate
modified_base          12
                       mod_base = OTHER
                       note = 2'-O-methyladenosine-3'-phosphate
modified_base          13
                       mod_base = OTHER
                       note = 2'-O-methylcytidine-3'-phosphate
modified_base          14
                       mod_base = OTHER
                       note = 2'-deoxy-2'-fluorouridine-3'-phosphate
modified_base          15
                       mod_base = OTHER
                       note = 2'-O-methyluridine-3'-phosphate
modified_base          16
                       mod_base = OTHER
                       note = 2'-deoxy-2'-fluoroguanosine-3'-phosphate
modified_base          17
                       mod_base = OTHER
                       note = 2'-O-methyladenosine-3'-phosphate
modified_base          18
                       mod_base = OTHER
```

```
                         note = 2'-O-methylguanosine-3'-phosphate
modified_base            19
                         mod_base = OTHER
                         note = 2'-O-methylguanosine-3'-phosphate
modified_base            20
                         mod_base = OTHER
                         note = 2'-O-methylguanosine-3'-phosphate
modified_base            21
                         mod_base = OTHER
                         note = 2'-O-methyladenosine-3'-phosphorothioate
modified_base            22
                         mod_base = OTHER
                         note = 2'-O-methylcytidine-3'-phosphorothioate
modified_base            23
                         mod_base = OTHER
                         note = 2'-O-methyluridine
SEQUENCE: 80
ttgctggaag gacttgaggg act                                              23

SEQ ID NO: 81            moltype = DNA  length = 23
FEATURE                  Location/Qualifiers
source                   1..23
                         mol_type = other DNA
                         organism = synthetic construct
modified_base            1
                         mod_base = OTHER
                         note = 2'-O-methyluridine-3'-phosphorothioate
                          5'-(E)-Vinylphosphonate
modified_base            2
                         mod_base = OTHER
                         note = 2'-deoxy-2'-fluorouridine-3'-phosphorothioate
modified_base            3
                         mod_base = OTHER
                         note = 2'-O-methylguanosine-3'-phosphate
modified_base            4
                         mod_base = OTHER
                         note = 2'-O-methylcytidine-3'-phosphate
modified_base            6
                         mod_base = OTHER
                         note = 2'-O-methylguanosine-3'-phosphate
modified_base            7
                         mod_base = OTHER
                         note = guanosine-2'-phosphate
modified_base            8
                         mod_base = OTHER
                         note = 2'-O-methyladenosine-3'-phosphate
modified_base            9
                         mod_base = OTHER
                         note = 2'-O-methyladenosine-3'-phosphate
modified_base            10
                         mod_base = OTHER
                         note = 2'-O-methylguanosine-3'-phosphate
modified_base            11
                         mod_base = OTHER
                         note = 2'-O-methylguanosine-3'-phosphate
modified_base            12
                         mod_base = OTHER
                         note = 2'-O-methyladenosine-3'-phosphate
modified_base            13
                         mod_base = OTHER
                         note = 2'-O-methylcytidine-3'-phosphate
modified_base            14
                         mod_base = OTHER
                         note = 2'-deoxy-2'-fluorouridine-3'-phosphate
modified_base            15
                         mod_base = OTHER
                         note = 2'-O-methyluridine-3'-phosphate
modified_base            17
                         mod_base = OTHER
                         note = 2'-O-methyluridine-3'-phosphate
modified_base            18
                         mod_base = OTHER
                         note = 2'-O-methylguanosine-3'-phosphate
modified_base            19
                         mod_base = OTHER
                         note = 2'-O-methylguanosine-3'-phosphate
modified_base            20
                         mod_base = OTHER
                         note = 2'-O-methylguanosine-3'-phosphate
```

```
modified_base         21
                      mod_base = OTHER
                      note = 2'-O-methyladenosine-3'-phosphorothioate
modified_base         22
                      mod_base = OTHER
                      note = 2'-O-methylcytidine-3'-phosphorothioate
modified_base         23
                      mod_base = OTHER
                      note = 2'-O-methyluridine
misc_feature          1..4
                      note = RNA
misc_feature          6..15
                      note = RNA
misc_feature          17..23
                      note = RNA
misc_feature          5
                      note = DNA
misc_feature          16
                      note = DNA
SEQUENCE: 81
ttgctggaag gacttgtggg act                                          23

SEQ ID NO: 82         moltype = DNA  length = 21
FEATURE               Location/Qualifiers
source                1..21
                      mol_type = other DNA
                      organism = synthetic construct
modified_base         1
                      mod_base = OTHER
                      note = 2'-O-methyluridine-3'-phosphorothioate
                       5'-(E)-Vinylphosphonate
modified_base         2
                      mod_base = OTHER
                      note = 2'-deoxyguanosine-3'-phosphorothioate
modified_base         3
                      mod_base = OTHER
                      note = 2'-O-methylguanosine-3'-phosphate
modified_base         4
                      mod_base = OTHER
                      note = 2'-O-methyluridine-3'-phosphate
modified_base         6
                      mod_base = OTHER
                      note = 2'-O-methyladenosine-3'-phosphate
modified_base         7
                      mod_base = OTHER
                      note = adenosine-2'-phosphate
modified_base         8
                      mod_base = OTHER
                      note = 2'-O-methyladenosine-3'-phosphate
modified_base         9
                      mod_base = OTHER
                      note = 2'-O-methylguanosine-3'-phosphate
modified_base         10
                      mod_base = OTHER
                      note = 2'-O-methylcytidine-3'-phosphate
modified_base         11
                      mod_base = OTHER
                      note = 2'-O-methyladenosine-3'-phosphate
modified_base         12
                      mod_base = OTHER
                      note = 2'-O-methylguanosine-3'-phosphate
modified_base         13
                      mod_base = OTHER
                      note = 2'-O-methyladenosine-3'-phosphate
modified_base         14
                      mod_base = OTHER
                      note = 2'-deoxy-2'-fluoroadenosine-3'-phosphate
modified_base         15
                      mod_base = OTHER
                      note = 2'-O-methylcytidine-3'-phosphate
modified_base         16
                      mod_base = OTHER
                      note = 2'-deoxy-2'-fluorocytidine-3'-phosphate
modified_base         17
                      mod_base = OTHER
                      note = 2'-O-methyluridine-3'-phosphate
modified_base         18
                      mod_base = OTHER
                      note = 2'-O-methylguanosine-3'-phosphate
```

```
modified_base          19
                       mod_base = OTHER
                       note = 2'-O-methyladenosine-3'-phosphorothioate
modified_base          20
                       mod_base = OTHER
                       note = 2'-O-methylguanosine-3'-phosphorothioate
modified_base          21
                       mod_base = OTHER
                       note = 2'-O-methylcytidine
misc_feature           1
                       note = RNA
misc_feature           3..4
                       note = RNA
misc_feature           6..21
                       note = RNA
misc_feature           2
                       note = DNA
misc_feature           5
                       note = DNA
SEQUENCE: 82
tggtaaaagc agaacctgag c                                              21

SEQ ID NO: 83          moltype = RNA  length = 23
FEATURE                Location/Qualifiers
source                 1..23
                       mol_type = other RNA
                       organism = synthetic construct
modified_base          1
                       mod_base = OTHER
                       note = 2'-O-methyluridine-3'-phosphorothioate
                        5'-(E)-Vinylphosphonate
modified_base          2
                       mod_base = OTHER
                       note = 2'-deoxy-2'-fluoroadenosine-3'-phosphorothioate
modified_base          3
                       mod_base = OTHER
                       note = 2'-O-methylguanosine-3'-phosphate
modified_base          4
                       mod_base = OTHER
                       note = 2'-O-methylguanosine-3'-phosphate
modified_base          5
                       mod_base = OTHER
                       note = 2'-O-methyladenosine-3'-phosphate
modified_base          6
                       mod_base = OTHER
                       note = 2'-O-methylcytidine-3'-phosphate
modified_base          7
                       mod_base = OTHER
                       note = Thymidine-glycol nucleic acid (GNA), S-Isomer
modified_base          8
                       mod_base = OTHER
                       note = 2'-O-methyluridine-3'-phosphate
modified_base          9
                       mod_base = OTHER
                       note = 2'-O-methylguanosine-3'-phosphate
modified_base          10
                       mod_base = OTHER
                       note = 2'-O-methyladenosine-3'-phosphate
modified_base          11
                       mod_base = OTHER
                       note = 2'-O-methylguanosine-3'-phosphate
modified_base          12
                       mod_base = OTHER
                       note = 2'-O-methylguanosine-3'-phosphate
modified_base          13
                       mod_base = OTHER
                       note = 2'-O-methylguanosine-3'-phosphate
modified_base          14
                       mod_base = OTHER
                       note = 2'-deoxy-2'-fluoroadenosine-3'-phosphate
modified_base          15
                       mod_base = OTHER
                       note = 2'-O-methylcytidine-3'-phosphate
modified_base          16
                       mod_base = OTHER
                       note = 2'-deoxy-2'-fluorouridine-3'-phosphate
modified_base          17
                       mod_base = OTHER
                       note = 2'-O-methylcytidine-3'-phosphate
```

```
modified_base          18
                       mod_base = OTHER
                       note = 2'-O-methylguanosine-3'-phosphate
modified_base          19
                       mod_base = OTHER
                       note = 2'-O-methyladenosine-3'-phosphate
modified_base          20
                       mod_base = OTHER
                       note = 2'-O-methyladenosine-3'-phosphate
modified_base          21
                       mod_base = OTHER
                       note = 2'-O-methylguanosine-3'-phosphorothioate
modified_base          22
                       mod_base = OTHER
                       note = 2'-O-methylguanosine-3'-phosphorothioate
modified_base          23
                       mod_base = OTHER
                       note = 2'-O-methylcytidine
SEQUENCE: 83
taggacttga gggactcgaa ggc                                          23

SEQ ID NO: 84          moltype = DNA  length = 23
FEATURE                Location/Qualifiers
source                 1..23
                       mol_type = other DNA
                       organism = synthetic construct
modified_base          1
                       mod_base = OTHER
                       note = 2'-O-methyluridine-3'-phosphorothioate
                        5'-(E)-Vinylphosphonate
modified_base          2
                       mod_base = OTHER
                       note = 2'-deoxy-2'-fluoroadenosine-3'-phosphorothioate
modified_base          3
                       mod_base = OTHER
                       note = 2'-O-methyladenosine-3'-phosphate
modified_base          4
                       mod_base = OTHER
                       note = 2'-O-methyladenosine-3'-phosphate
modified_base          6
                       mod_base = OTHER
                       note = 2'-O-methylguanosine-3'-phosphate
modified_base          7
                       mod_base = OTHER
                       note = cytidine-2'-phosphate
modified_base          8
                       mod_base = OTHER
                       note = 2'-O-methyladenosine-3'-phosphate
modified_base          9
                       mod_base = OTHER
                       note = 2'-O-methylguanosine-3'-phosphate
modified_base          10
                       mod_base = OTHER
                       note = 2'-O-methyladenosine-3'-phosphate
modified_base          11
                       mod_base = OTHER
                       note = 2'-O-methyladenosine-3'-phosphate
modified_base          13
                       mod_base = OTHER
                       note = 2'-O-methylcytidine-3'-phosphate
modified_base          14
                       mod_base = OTHER
                       note = 2'-deoxy-2'-fluorouridine-3'-phosphate
modified_base          15
                       mod_base = OTHER
                       note = 2'-O-methylguanosine-3'-phosphate
modified_base          16
                       mod_base = OTHER
                       note = 2'-deoxy-2'-fluoroadenosine-3'-phosphate
modified_base          17
                       mod_base = OTHER
                       note = 2'-O-methylguanosine-3'-phosphate
modified_base          18
                       mod_base = OTHER
                       note = 2'-O-methylcytidine-3'-phosphate
modified_base          19
                       mod_base = OTHER
                       note = 2'-O-methylguanosine-3'-phosphate
modified_base          20
```

```
                        mod_base = OTHER
                        note = 2'-O-methylguanosine-3'-phosphate
modified_base           21
                        mod_base = OTHER
                        note = 2'-O-methylcytidine-3'-phosphorothioate
modified_base           22
                        mod_base = OTHER
                        note = 2'-O-methylcytidine-3'-phosphorothioate
modified_base           23
                        mod_base = OTHER
                        note = 2'-O-methylguanosine
misc_feature            1..4
                        note = RNA
misc_feature            6..11
                        note = RNA
misc_feature            13..23
                        note = RNA
misc_feature            5
                        note = DNA
misc_feature            12
                        note = DNA
SEQUENCE: 84
taaaagcaga acctgagcgg ccg                                             23

SEQ ID NO: 85           moltype = DNA  length = 23
FEATURE                 Location/Qualifiers
source                  1..23
                        mol_type = other DNA
                        organism = synthetic construct
modified_base           1
                        mod_base = OTHER
                        note = 2'-O-methyluridine-3'-phosphorothioate
                         5'-(E)-Vinylphosphonate
modified_base           2
                        mod_base = OTHER
                        note = 2'-deoxy-2'-fluorouridine-3'-phosphorothioate
modified_base           3
                        mod_base = OTHER
                        note = 2'-O-methyladenosine-3'-phosphate
modified_base           4
                        mod_base = OTHER
                        note = 2'-O-methyladenosine-3'-phosphate
modified_base           6
                        mod_base = OTHER
                        note = 2'-O-methyladenosine-3'-phosphate
modified_base           8
                        mod_base = OTHER
                        note = 2'-O-methylcytidine-3'-phosphate
modified_base           9
                        mod_base = OTHER
                        note = 2'-O-methyladenosine-3'-phosphate
modified_base           10
                        mod_base = OTHER
                        note = 2'-O-methylguanosine-3'-phosphate
modified_base           11
                        mod_base = OTHER
                        note = 2'-O-methyladenosine-3'-phosphate
modified_base           12
                        mod_base = OTHER
                        note = 2'-O-methyladenosine-3'-phosphate
modified_base           13
                        mod_base = OTHER
                        note = 2'-O-methylcytidine-3'-phosphate
modified_base           14
                        mod_base = OTHER
                        note = 2'-deoxy-2'-fluorocytidine-3'-phosphate
modified_base           15
                        mod_base = OTHER
                        note = 2'-O-methyluridine-3'-phosphate
modified_base           17
                        mod_base = OTHER
                        note = 2'-O-methyladenosine-3'-phosphate
modified_base           18
                        mod_base = OTHER
                        note = 2'-O-methylcytidine-3'-phosphate
modified_base           19
                        mod_base = OTHER
                        note = 2'-O-methylcytidine-3'-phosphate
modified_base           20
```

```
                        mod_base = OTHER
                        note = 2'-O-methylguanosine-3'-phosphate
modified_base           21
                        mod_base = OTHER
                        note = 2'-O-methylguanosine-3'-phosphorothioate
modified_base           22
                        mod_base = OTHER
                        note = 2'-O-methylcytidine-3'-phosphorothioate
modified_base           23
                        mod_base = OTHER
                        note = 2'-O-methylcytidine
misc_feature            1..4
                        note = RNA
misc_feature            6
                        note = RNA
misc_feature            8..15
                        note = RNA
misc_feature            17..23
                        note = RNA
misc_feature            5
                        note = DNA
misc_feature            7
                        note = DNA
misc_feature            16
                        note = DNA
SEQUENCE: 85
ttaaaagcag aacctgaccg gcc                                         23

SEQ ID NO: 86           moltype = RNA  length = 21
FEATURE                 Location/Qualifiers
source                  1..21
                        mol_type = other RNA
                        organism = synthetic construct
modified_base           1
                        mod_base = OTHER
                        note = 2'-O-methylguanosine-3'-phosphate
modified_base           2
                        mod_base = OTHER
                        note = 2'-O-methylcytidine-3'-phosphate
modified_base           3
                        mod_base = OTHER
                        note = 2'-O-methylcytidine-3'-phosphate
modified_base           4
                        mod_base = OTHER
                        note = 2'-O-methyluridine-3'-phosphate
modified_base           5
                        mod_base = OTHER
                        note = 2'-O-methyluridine-3'-phosphate
modified_base           6
                        mod_base = OTHER
                        note = 2'-O-methylcytidine-3'-phosphate
modified_base           7
                        mod_base = OTHER
                        note = 2'-O-methylguanosine-3'-phosphate
modified_base           8
                        mod_base = OTHER
                        note = 2'-O-methyladenosine-3'-phosphate
modified_base           9
                        mod_base = OTHER
                        note = 2'-O-methylguanosine-3'-phosphate
modified_base           10
                        mod_base = OTHER
                        note = 2'-O-methyluridine-3'-phosphate
modified_base           11
                        mod_base = OTHER
                        note = 2'-O-methylcytidine-3'-phosphate
modified_base           12
                        mod_base = OTHER
                        note = 2'-O-methylcytidine-3'-phosphate
modified_base           13
                        mod_base = OTHER
                        note = 2'-O-methylcytidine-3'-phosphate
modified_base           14
                        mod_base = OTHER
                        note = 2'-O-methyluridine-3'-phosphate
modified_base           15
                        mod_base = OTHER
                        note = 2'-O-methylcytidine-3'-phosphate
modified_base           16
```

```
                         mod_base = OTHER
                         note = 2'-O-methyladenosine-3'-phosphate
modified_base            17
                         mod_base = OTHER
                         note = 2'-O-methyladenosine-3'-phosphate
modified_base            18
                         mod_base = OTHER
                         note = 2'-O-methylguanosine-3'-phosphate
modified_base            19
                         mod_base = OTHER
                         note = 2'-O-methyluridine-3'-phosphate
modified_base            20
                         mod_base = OTHER
                         note = 2'-O-methylcytidine-3'-phosphate
modified_base            21
                         mod_base = OTHER
                         note = 2'-O-methylcytidine
SEQUENCE: 86
gccttcgagt ccctcaagtc c                                                21

SEQ ID NO: 87            moltype = RNA  length = 23
FEATURE                  Location/Qualifiers
source                   1..23
                         mol_type = other RNA
                         organism = synthetic construct
modified_base            1
                         mod_base = OTHER
                         note = 2'-O-methylcytidine-3'-phosphate
modified_base            2
                         mod_base = OTHER
                         note = 2'-O-methylguanosine-3'-phosphate
modified_base            3
                         mod_base = OTHER
                         note = 2'-O-methylcytidine-3'-phosphate
modified_base            4
                         mod_base = OTHER
                         note = 2'-O-methylcytidine-3'-phosphate
modified_base            5
                         mod_base = OTHER
                         note = 2'-O-methyladenosine-3'-phosphate
modified_base            6
                         mod_base = OTHER
                         note = 2'-O-methyluridine-3'-phosphate
modified_base            7
                         mod_base = OTHER
                         note = 2'-O-methylguanosine-3'-phosphate
modified_base            8
                         mod_base = OTHER
                         note = 2'-O-methylguanosine-3'-phosphate
modified_base            9
                         mod_base = OTHER
                         note = 2'-O-methylcytidine-3'-phosphate
modified_base            10
                         mod_base = OTHER
                         note = 2'-O-methylguanosine-3'-phosphate
modified_base            11
                         mod_base = OTHER
                         note = 2'-O-methyladenosine-3'-phosphate
modified_base            12
                         mod_base = OTHER
                         note = 2'-O-methylcytidine-3'-phosphate
modified_base            13
                         mod_base = OTHER
                         note = 2'-O-methylcytidine-3'-phosphate
modified_base            14
                         mod_base = OTHER
                         note = 2'-O-methylcytidine-3'-phosphate
modified_base            15
                         mod_base = OTHER
                         note = 2'-O-methyluridine-3'-phosphate
modified_base            16
                         mod_base = OTHER
                         note = 2'-O-methylguanosine-3'-phosphate
modified_base            17
                         mod_base = OTHER
                         note = 2'-O-methylguanosine-3'-phosphate
modified_base            18
                         mod_base = OTHER
                         note = 2'-O-methyladenosine-3'-phosphate
```

```
modified_base          19
                       mod_base = OTHER
                       note = 2'-O-methyladenosine-3'-phosphate
modified_base          20
                       mod_base = OTHER
                       note = 2'-O-methyladenosine-3'-phosphate
modified_base          21
                       mod_base = OTHER
                       note = 2'-O-methyladenosine-3'-phosphate
modified_base          22
                       mod_base = OTHER
                       note = 2'-O-methylguanosine-3'-phosphate
modified_base          23
                       mod_base = OTHER
                       note = 2'-O-methylcytidine-3'-phosphate
SEQUENCE: 87
cgccatggcg accctggaaa agc                                          23

SEQ ID NO: 88          moltype = RNA  length = 23
FEATURE                Location/Qualifiers
source                 1..23
                       mol_type = other RNA
                       organism = synthetic construct
modified_base          1
                       mod_base = OTHER
                       note = 2'-O-methylcytidine-3'-phosphate
modified_base          2
                       mod_base = OTHER
                       note = 2'-O-methylguanosine-3'-phosphate
modified_base          3
                       mod_base = OTHER
                       note = 2'-O-methyladenosine-3'-phosphate
modified_base          4
                       mod_base = OTHER
                       note = 2'-O-methylcytidine-3'-phosphate
modified_base          5
                       mod_base = OTHER
                       note = 2'-O-methylcytidine-3'-phosphate
modified_base          6
                       mod_base = OTHER
                       note = 2'-O-methylcytidine-3'-phosphate
modified_base          7
                       mod_base = OTHER
                       note = 2'-O-methyluridine-3'-phosphate
modified_base          8
                       mod_base = OTHER
                       note = 2'-O-methylguanosine-3'-phosphate
modified_base          9
                       mod_base = OTHER
                       note = 2'-O-methylguanosine-3'-phosphate
modified_base          10
                       mod_base = OTHER
                       note = 2'-O-methyladenosine-3'-phosphate
modified_base          11
                       mod_base = OTHER
                       note = 2'-O-methyladenosine-3'-phosphate
modified_base          12
                       mod_base = OTHER
                       note = 2'-O-methyladenosine-3'-phosphate
modified_base          13
                       mod_base = OTHER
                       note = 2'-O-methyladenosine-3'-phosphate
modified_base          14
                       mod_base = OTHER
                       note = 2'-O-methylguanosine-3'-phosphate
modified_base          15
                       mod_base = OTHER
                       note = 2'-O-methylcytidine-3'-phosphate
modified_base          16
                       mod_base = OTHER
                       note = 2'-O-methyluridine-3'-phosphate
modified_base          17
                       mod_base = OTHER
                       note = 2'-O-methylguanosine-3'-phosphate
modified_base          18
                       mod_base = OTHER
                       note = 2'-O-methyladenosine-3'-phosphate
modified_base          19
                       mod_base = OTHER
```

```
                      note = 2'-O-methyluridine-3'-phosphate
modified_base         20
                      mod_base = OTHER
                      note = 2'-O-methylguanosine-3'-phosphate
modified_base         21
                      mod_base = OTHER
                      note = 2'-O-methyladenosine-3'-phosphate
modified_base         22
                      mod_base = OTHER
                      note = 2'-O-methyladenosine-3'-phosphate
modified_base         23
                      mod_base = OTHER
                      note = 2'-O-methylguanosine-3'-phosphate
SEQUENCE: 88
cgaccctgga aaagctgatg aag                                          23

SEQ ID NO: 89         moltype = RNA  length = 21
FEATURE               Location/Qualifiers
source                1..21
                      mol_type = other RNA
                      organism = synthetic construct
modified_base         1
                      mod_base = OTHER
                      note = 2'-O-methyladenosine-3'-phosphate
modified_base         2
                      mod_base = OTHER
                      note = 2'-O-methylcytidine-3'-phosphate
modified_base         3
                      mod_base = OTHER
                      note = 2'-O-methylcytidine-3'-phosphate
modified_base         4
                      mod_base = OTHER
                      note = 2'-O-methylcytidine-3'-phosphate
modified_base         5
                      mod_base = OTHER
                      note = 2'-O-methyluridine-3'-phosphate
modified_base         6
                      mod_base = OTHER
                      note = 2'-O-methylguanosine-3'-phosphate
modified_base         7
                      mod_base = OTHER
                      note = 2'-O-methylguanosine-3'-phosphate
modified_base         8
                      mod_base = OTHER
                      note = 2'-O-methyladenosine-3'-phosphate
modified_base         9
                      mod_base = OTHER
                      note = 2'-O-methyladenosine-3'-phosphate
modified_base         10
                      mod_base = OTHER
                      note = 2'-O-methyladenosine-3'-phosphate
modified_base         11
                      mod_base = OTHER
                      note = 2'-O-methyladenosine-3'-phosphate
modified_base         12
                      mod_base = OTHER
                      note = 2'-O-methylguanosine-3'-phosphate
modified_base         13
                      mod_base = OTHER
                      note = 2'-O-methylcytidine-3'-phosphate
modified_base         14
                      mod_base = OTHER
                      note = 2'-O-methyluridine-3'-phosphate
modified_base         15
                      mod_base = OTHER
                      note = 2'-O-methylguanosine-3'-phosphate
modified_base         16
                      mod_base = OTHER
                      note = 2'-O-methyladenosine-3'-phosphate
modified_base         17
                      mod_base = OTHER
                      note = 2'-O-methyluridine-3'-phosphate
modified_base         18
                      mod_base = OTHER
                      note = 2'-O-methylguanosine-3'-phosphate
modified_base         19
                      mod_base = OTHER
                      note = 2'-O-methyladenosine-3'-phosphate
modified_base         20
```

```
                        mod_base = OTHER
                        note = 2'-O-methyladenosine-3'-phosphate
modified_base           21
                        mod_base = OTHER
                        note = 2'-O-methylguanosine-3'-phosphate
SEQUENCE: 89
accctggaaa agctgatgaa g                                            21

SEQ ID NO: 90           moltype = RNA  length = 23
FEATURE                 Location/Qualifiers
source                  1..23
                        mol_type = other RNA
                        organism = synthetic construct
modified_base           1
                        mod_base = OTHER
                        note = 2'-O-methyladenosine-3'-phosphate
modified_base           2
                        mod_base = OTHER
                        note = 2'-O-methylguanosine-3'-phosphate
modified_base           3
                        mod_base = OTHER
                        note = 2'-O-methylcytidine-3'-phosphate
modified_base           4
                        mod_base = OTHER
                        note = 2'-O-methyluridine-3'-phosphate
modified_base           5
                        mod_base = OTHER
                        note = 2'-O-methylguanosine-3'-phosphate
modified_base           6
                        mod_base = OTHER
                        note = 2'-O-methyladenosine-3'-phosphate
modified_base           7
                        mod_base = OTHER
                        note = 2'-O-methyluridine-3'-phosphate
modified_base           8
                        mod_base = OTHER
                        note = 2'-O-methylguanosine-3'-phosphate
modified_base           9
                        mod_base = OTHER
                        note = 2'-O-methyladenosine-3'-phosphate
modified_base           10
                        mod_base = OTHER
                        note = 2'-O-methyladenosine-3'-phosphate
modified_base           11
                        mod_base = OTHER
                        note = 2'-O-methylguanosine-3'-phosphate
modified_base           12
                        mod_base = OTHER
                        note = 2'-O-methylguanosine-3'-phosphate
modified_base           13
                        mod_base = OTHER
                        note = 2'-O-methylcytidine-3'-phosphate
modified_base           14
                        mod_base = OTHER
                        note = 2'-O-methylcytidine-3'-phosphate
modified_base           15
                        mod_base = OTHER
                        note = 2'-O-methyluridine-3'-phosphate
modified_base           16
                        mod_base = OTHER
                        note = 2'-O-methyluridine-3'-phosphate
modified_base           17
                        mod_base = OTHER
                        note = 2'-O-methylcytidine-3'-phosphate
modified_base           18
                        mod_base = OTHER
                        note = 2'-O-methylguanosine-3'-phosphate
modified_base           19
                        mod_base = OTHER
                        note = 2'-O-methyladenosine-3'-phosphate
modified_base           20
                        mod_base = OTHER
                        note = 2'-O-methylguanosine-3'-phosphate
modified_base           21
                        mod_base = OTHER
                        note = 2'-O-methyluridine-3'-phosphate
modified_base           22
                        mod_base = OTHER
                        note = 2'-O-methylcytidine-3'-phosphate
```

```
modified_base          23
                       mod_base = OTHER
                       note = 2'-O-methylcytidine
SEQUENCE: 90
agctgatgaa ggccttcgag tcc                                          23

SEQ ID NO: 91          moltype = RNA  length = 23
FEATURE                Location/Qualifiers
source                 1..23
                       mol_type = other RNA
                       organism = synthetic construct
modified_base          1
                       mod_base = OTHER
                       note = 2'-O-methyluridine-3'-phosphate
modified_base          2
                       mod_base = OTHER
                       note = 2'-O-methylguanosine-3'-phosphate
modified_base          3
                       mod_base = OTHER
                       note = 2'-O-methylguanosine-3'-phosphate
modified_base          4
                       mod_base = OTHER
                       note = 2'-O-methylcytidine-3'-phosphate
modified_base          5
                       mod_base = OTHER
                       note = 2'-O-methylguanosine-3'-phosphate
modified_base          6
                       mod_base = OTHER
                       note = 2'-O-methyladenosine-3'-phosphate
modified_base          7
                       mod_base = OTHER
                       note = 2'-O-methylcytidine-3'-phosphate
modified_base          8
                       mod_base = OTHER
                       note = 2'-O-methylcytidine-3'-phosphate
modified_base          9
                       mod_base = OTHER
                       note = 2'-O-methylcytidine-3'-phosphate
modified_base          10
                       mod_base = OTHER
                       note = 2'-O-methyluridine-3'-phosphate
modified_base          11
                       mod_base = OTHER
                       note = 2'-O-methylguanosine-3'-phosphate
modified_base          12
                       mod_base = OTHER
                       note = 2'-O-methylguanosine-3'-phosphate
modified_base          13
                       mod_base = OTHER
                       note = 2'-O-methyladenosine-3'-phosphate
modified_base          14
                       mod_base = OTHER
                       note = 2'-O-methyladenosine-3'-phosphate
modified_base          15
                       mod_base = OTHER
                       note = 2'-O-methyladenosine-3'-phosphate
modified_base          16
                       mod_base = OTHER
                       note = 2'-O-methyladenosine-3'-phosphate
modified_base          17
                       mod_base = OTHER
                       note = 2'-O-methylguanosine-3'-phosphate
modified_base          18
                       mod_base = OTHER
                       note = 2'-O-methylcytidine-3'-phosphate
modified_base          19
                       mod_base = OTHER
                       note = 2'-O-methyluridine-3'-phosphate
modified_base          20
                       mod_base = OTHER
                       note = 2'-O-methylguanosine-3'-phosphate
modified_base          21
                       mod_base = OTHER
                       note = 2'-O-methyladenosine-3'-phosphate
modified_base          22
                       mod_base = OTHER
                       note = 2'-O-methyluridine-3'-phosphate
modified_base          23
                       mod_base = OTHER
```

```
                         note = 2'-O-methylguanosine-3'-phosphate
SEQUENCE: 91
tggcgaccct ggaaaagctg atg                                          23

SEQ ID NO: 92            moltype = RNA  length = 23
FEATURE                  Location/Qualifiers
source                   1..23
                         mol_type = other RNA
                         organism = synthetic construct
modified_base            1
                         mod_base = OTHER
                         note = 2'-O-methyladenosine-3'-phosphate
modified_base            2
                         mod_base = OTHER
                         note = 2'-O-methylguanosine-3'-phosphate
modified_base            3
                         mod_base = OTHER
                         note = 2'-O-methyluridine-3'-phosphate
modified_base            4
                         mod_base = OTHER
                         note = 2'-O-methylcytidine-3'-phosphate
modified_base            5
                         mod_base = OTHER
                         note = 2'-O-methylcytidine-3'-phosphate
modified_base            6
                         mod_base = OTHER
                         note = 2'-O-methylcytidine-3'-phosphate
modified_base            7
                         mod_base = OTHER
                         note = 2'-O-methyluridine-3'-phosphate
modified_base            8
                         mod_base = OTHER
                         note = 2'-O-methylcytidine-3'-phosphate
modified_base            9
                         mod_base = OTHER
                         note = 2'-O-methyladenosine-3'-phosphate
modified_base            10
                         mod_base = OTHER
                         note = 2'-O-methyladenosine-3'-phosphate
modified_base            11
                         mod_base = OTHER
                         note = 2'-O-methylguanosine-3'-phosphate
modified_base            12
                         mod_base = OTHER
                         note = 2'-O-methyluridine-3'-phosphate
modified_base            13
                         mod_base = OTHER
                         note = 2'-O-methylcytidine-3'-phosphate
modified_base            14
                         mod_base = OTHER
                         note = 2'-O-methylcytidine-3'-phosphate
modified_base            15
                         mod_base = OTHER
                         note = 2'-O-methyluridine-3'-phosphate
modified_base            16
                         mod_base = OTHER
                         note = 2'-O-methyluridine-3'-phosphate
modified_base            17
                         mod_base = OTHER
                         note = 2'-O-methylcytidine-3'-phosphate
modified_base            18
                         mod_base = OTHER
                         note = 2'-O-methylcytidine-3'-phosphate
modified_base            19
                         mod_base = OTHER
                         note = 2'-O-methyladenosine-3'-phosphate
modified_base            20
                         mod_base = OTHER
                         note = 2'-O-methylguanosine-3'-phosphate
modified_base            21
                         mod_base = OTHER
                         note = 2'-O-methylcytidine-3'-phosphate
modified_base            22
                         mod_base = OTHER
                         note = 2'-O-methyladenosine-3'-phosphate
modified_base            23
                         mod_base = OTHER
                         note = 2'-O-methylguanosine-3'-phosphate
SEQUENCE: 92
```

```
agtccctcaa gtccttccag cag                                         23

SEQ ID NO: 93           moltype = RNA  length = 21
FEATURE                 Location/Qualifiers
source                  1..21
                        mol_type = other RNA
                        organism = synthetic construct
modified_base           1
                        mod_base = OTHER
                        note = 2'-O-methylguanosine-3'-phosphate
modified_base           2
                        mod_base = OTHER
                        note = 2'-O-methylcytidine-3'-phosphate
modified_base           3
                        mod_base = OTHER
                        note = 2'-O-methyluridine-3'-phosphate
modified_base           4
                        mod_base = OTHER
                        note = 2'-O-methylcytidine-3'-phosphate
modified_base           5
                        mod_base = OTHER
                        note = 2'-O-methyladenosine-3'-phosphate
modified_base           6
                        mod_base = OTHER
                        note = 2'-O-methylguanosine-3'-phosphate
modified_base           7
                        mod_base = OTHER
                        note = 2'-O-methylguanosine-3'-phosphate
modified_base           8
                        mod_base = OTHER
                        note = 2'-O-methyluridine-3'-phosphate
modified_base           9
                        mod_base = OTHER
                        note = 2'-O-methyluridine-3'-phosphate
modified_base           10
                        mod_base = OTHER
                        note = 2'-O-methylcytidine-3'-phosphate
modified_base           11
                        mod_base = OTHER
                        note = 2'-O-methyluridine-3'-phosphate
modified_base           12
                        mod_base = OTHER
                        note = 2'-O-methylguanosine-3'-phosphate
modified_base           13
                        mod_base = OTHER
                        note = 2'-O-methylcytidine-3'-phosphate
modified_base           14
                        mod_base = OTHER
                        note = 2'-O-methyluridine-3'-phosphate
modified_base           15
                        mod_base = OTHER
                        note = 2'-O-methyluridine-3'-phosphate
modified_base           16
                        mod_base = OTHER
                        note = 2'-O-methyluridine-3'-phosphate
modified_base           17
                        mod_base = OTHER
                        note = 2'-O-methyluridine-3'-phosphate
modified_base           18
                        mod_base = OTHER
                        note = 2'-O-methyladenosine-3'-phosphate
modified_base           19
                        mod_base = OTHER
                        note = 2'-O-methylcytidine-3'-phosphate
modified_base           20
                        mod_base = OTHER
                        note = 2'-O-methylcytidine-3'-phosphate
modified_base           21
                        mod_base = OTHER
                        note = 2'-O-methyluridine-3'-phosphate
SEQUENCE: 93
gctcaggttc tgcttttacc t                                           21

SEQ ID NO: 94           moltype = RNA  length = 23
FEATURE                 Location/Qualifiers
source                  1..23
                        mol_type = other RNA
                        organism = synthetic construct
modified_base           1
```

```
                        mod_base = OTHER
                        note = 2'-O-methylguanosine-3'-phosphate
modified_base           2
                        mod_base = OTHER
                        note = 2'-O-methylcytidine-3'-phosphate
modified_base           3
                        mod_base = OTHER
                        note = 2'-O-methylcytidine-3'-phosphate
modified_base           4
                        mod_base = OTHER
                        note = 2'-O-methyluridine-3'-phosphate
modified_base           5
                        mod_base = OTHER
                        note = 2'-O-methyluridine-3'-phosphate
modified_base           6
                        mod_base = OTHER
                        note = 2'-O-methylcytidine-3'-phosphate
modified_base           7
                        mod_base = OTHER
                        note = 2'-O-methylguanosine-3'-phosphate
modified_base           8
                        mod_base = OTHER
                        note = 2'-O-methyladenosine-3'-phosphate
modified_base           9
                        mod_base = OTHER
                        note = 2'-O-methylguanosine-3'-phosphate
modified_base           10
                        mod_base = OTHER
                        note = 2'-O-methyluridine-3'-phosphate
modified_base           11
                        mod_base = OTHER
                        note = 2'-O-methylcytidine-3'-phosphate
modified_base           12
                        mod_base = OTHER
                        note = 2'-O-methylcytidine-3'-phosphate
modified_base           13
                        mod_base = OTHER
                        note = 2'-O-methylcytidine-3'-phosphate
modified_base           14
                        mod_base = OTHER
                        note = 2'-O-methyluridine-3'-phosphate
modified_base           15
                        mod_base = OTHER
                        note = 2'-O-methylcytidine-3'-phosphate
modified_base           16
                        mod_base = OTHER
                        note = 2'-O-methyladenosine-3'-phosphate
modified_base           17
                        mod_base = OTHER
                        note = 2'-O-methyladenosine-3'-phosphate
modified_base           18
                        mod_base = OTHER
                        note = 2'-O-methylguanosine-3'-phosphate
modified_base           19
                        mod_base = OTHER
                        note = 2'-O-methyluridine-3'-phosphate
modified_base           20
                        mod_base = OTHER
                        note = 2'-O-methylcytidine-3'-phosphate
modified_base           21
                        mod_base = OTHER
                        note = 2'-O-methylcytidine-3'-phosphate
modified_base           22
                        mod_base = OTHER
                        note = 2'-O-methyluridine-3'-phosphate
modified_base           23
                        mod_base = OTHER
                        note = 2'-O-methyluridine
SEQUENCE: 94
gccttcgagt ccctcaagtc ctt                                    23

SEQ ID NO: 95           moltype = RNA  length = 23
FEATURE                 Location/Qualifiers
source                  1..23
                        mol_type = other RNA
                        organism = synthetic construct
modified_base           1
                        mod_base = OTHER
                        note = 2'-O-methylcytidine-3'-phosphate
```

```
modified_base          2
                       mod_base = OTHER
                       note = 2'-O-methylguanosine-3'-phosphate
modified_base          3
                       mod_base = OTHER
                       note = 2'-O-methylguanosine-3'-phosphate
modified_base          4
                       mod_base = OTHER
                       note = 2'-O-methylcytidine-3'-phosphate
modified_base          5
                       mod_base = OTHER
                       note = 2'-O-methylcytidine-3'-phosphate
modified_base          6
                       mod_base = OTHER
                       note = 2'-O-methylguanosine-3'-phosphate
modified_base          7
                       mod_base = OTHER
                       note = 2'-O-methylcytidine-3'-phosphate
modified_base          8
                       mod_base = OTHER
                       note = 2'-O-methyluridine-3'-phosphate
modified_base          9
                       mod_base = OTHER
                       note = 2'-O-methylcytidine-3'-phosphate
modified_base          10
                       mod_base = OTHER
                       note = 2'-O-methyladenosine-3'-phosphate
modified_base          11
                       mod_base = OTHER
                       note = 2'-O-methylguanosine-3'-phosphate
modified_base          12
                       mod_base = OTHER
                       note = 2'-O-methylguanosine-3'-phosphate
modified_base          13
                       mod_base = OTHER
                       note = 2'-O-methyluridine-3'-phosphate
modified_base          14
                       mod_base = OTHER
                       note = 2'-O-methyluridine-3'-phosphate
modified_base          15
                       mod_base = OTHER
                       note = 2'-O-methylcytidine-3'-phosphate
modified_base          16
                       mod_base = OTHER
                       note = 2'-O-methyluridine-3'-phosphate
modified_base          17
                       mod_base = OTHER
                       note = 2'-O-methylguanosine-3'-phosphate
modified_base          18
                       mod_base = OTHER
                       note = 2'-O-methylcytidine-3'-phosphate
modified_base          19
                       mod_base = OTHER
                       note = 2'-O-methyluridine-3'-phosphate
modified_base          20
                       mod_base = OTHER
                       note = 2'-O-methyluridine-3'-phosphate
modified_base          21
                       mod_base = OTHER
                       note = 2'-O-methyluridine-3'-phosphate
modified_base          22
                       mod_base = OTHER
                       note = 2'-O-methyluridine-3'-phosphate
modified_base          23
                       mod_base = OTHER
                       note = 2'-O-methyladenosine-3'-phosphate
SEQUENCE: 95
cggccgctca ggttctgctt tta                                          23

SEQ ID NO: 96          moltype = RNA  length = 23
FEATURE                Location/Qualifiers
source                 1..23
                       mol_type = other RNA
                       organism = synthetic construct
modified_base          1
                       mod_base = OTHER
                       note = 2'-O-methylguanosine-3'-phosphate
modified_base          2
                       mod_base = OTHER
```

```
                        note = 2'-O-methylguanosine-3'-phosphate
modified_base           3
                        mod_base = OTHER
                        note = 2'-O-methylcytidine-3'-phosphate
modified_base           4
                        mod_base = OTHER
                        note = 2'-O-methylcytidine-3'-phosphate
modified_base           5
                        mod_base = OTHER
                        note = 2'-O-methylguanosine-3'-phosphate
modified_base           6
                        mod_base = OTHER
                        note = 2'-O-methylcytidine-3'-phosphate
modified_base           7
                        mod_base = OTHER
                        note = 2'-O-methyluridine-3'-phosphate
modified_base           8
                        mod_base = OTHER
                        note = 2'-O-methylcytidine-3'-phosphate
modified_base           9
                        mod_base = OTHER
                        note = 2'-O-methyladenosine-3'-phosphate
modified_base           10
                        mod_base = OTHER
                        note = 2'-O-methylguanosine-3'-phosphate
modified_base           11
                        mod_base = OTHER
                        note = 2'-O-methylguanosine-3'-phosphate
modified_base           12
                        mod_base = OTHER
                        note = 2'-O-methyluridine-3'-phosphate
modified_base           13
                        mod_base = OTHER
                        note = 2'-O-methyluridine-3'-phosphate
modified_base           14
                        mod_base = OTHER
                        note = 2'-O-methylcytidine-3'-phosphate
modified_base           15
                        mod_base = OTHER
                        note = 2'-O-methyluridine-3'-phosphate
modified_base           16
                        mod_base = OTHER
                        note = 2'-O-methylguanosine-3'-phosphate
modified_base           17
                        mod_base = OTHER
                        note = 2'-O-methylcytidine-3'-phosphate
modified_base           18
                        mod_base = OTHER
                        note = 2'-O-methyluridine-3'-phosphate
modified_base           19
                        mod_base = OTHER
                        note = 2'-O-methyluridine-3'-phosphate
modified_base           20
                        mod_base = OTHER
                        note = 2'-O-methyluridine-3'-phosphate
modified_base           21
                        mod_base = OTHER
                        note = 2'-O-methyluridine-3'-phosphate
modified_base           22
                        mod_base = OTHER
                        note = 2'-O-methyladenosine-3'-phosphate
modified_base           23
                        mod_base = OTHER
                        note = 2'-O-methylcytidine-3'-phosphate
SEQUENCE: 96
ggccgctcag gttctgcttt tac                                        23

SEQ ID NO: 97           moltype = RNA  length = 21
FEATURE                 Location/Qualifiers
source                  1..21
                        mol_type = other RNA
                        organism = synthetic construct
modified_base           1
                        mod_base = OTHER
                        note = 2'-O-methylcytidine-3'-phosphate
modified_base           2
                        mod_base = OTHER
                        note = 2'-O-methylcytidine-3'-phosphate
modified_base           3
```

```
                        mod_base = OTHER
                        note = 2'-O-methyladenosine-3'-phosphate
modified_base           4
                        mod_base = OTHER
                        note = 2'-O-methylguanosine-3'-phosphate
modified_base           5
                        mod_base = OTHER
                        note = 2'-O-methyladenosine-3'-phosphate
modified_base           6
                        mod_base = OTHER
                        note = 2'-O-methylguanosine-3'-phosphate
modified_base           7
                        mod_base = OTHER
                        note = 2'-O-methylcytidine-3'-phosphate
modified_base           8
                        mod_base = OTHER
                        note = 2'-O-methylcytidine-3'-phosphate
modified_base           9
                        mod_base = OTHER
                        note = 2'-O-methylcytidine-3'-phosphate
modified_base           10
                        mod_base = OTHER
                        note = 2'-O-methylcytidine-3'-phosphate
modified_base           11
                        mod_base = OTHER
                        note = 2'-O-methyladenosine-3'-phosphate
modified_base           12
                        mod_base = OTHER
                        note = 2'-O-methyluridine-3'-phosphate
modified_base           13
                        mod_base = OTHER
                        note = 2'-O-methyluridine-3'-phosphate
modified_base           14
                        mod_base = OTHER
                        note = 2'-O-methylcytidine-3'-phosphate
modified_base           15
                        mod_base = OTHER
                        note = 2'-O-methyladenosine-3'-phosphate
modified_base           16
                        mod_base = OTHER
                        note = 2'-O-methyluridine-3'-phosphate
modified_base           17
                        mod_base = OTHER
                        note = 2'-O-methyluridine-3'-phosphate
modified_base           18
                        mod_base = OTHER
                        note = 2'-O-methylguanosine-3'-phosphate
modified_base           19
                        mod_base = OTHER
                        note = 2'-O-methylcytidine-3'-phosphate
modified_base           20
                        mod_base = OTHER
                        note = 2'-O-methylcytidine-3'-phosphate
modified_base           21
                        mod_base = OTHER
                        note = 2'-O-methyladenosine
SEQUENCE: 97
ccagagcccc attcattgcc a                                             21

SEQ ID NO: 98           moltype = RNA  length = 23
FEATURE                 Location/Qualifiers
source                  1..23
                        mol_type = other RNA
                        organism = synthetic construct
modified_base           1
                        mod_base = OTHER
                        note = 2'-O-methyluridine-3'-phosphate
modified_base           2
                        mod_base = OTHER
                        note = 2'-O-methylguanosine-3'-phosphate
modified_base           3
                        mod_base = OTHER
                        note = 2'-O-methylguanosine-3'-phosphate
modified_base           4
                        mod_base = OTHER
                        note = 2'-O-methylcytidine-3'-phosphate
modified_base           5
                        mod_base = OTHER
                        note = 2'-O-methyladenosine-3'-phosphate
```

```
modified_base          6
                       mod_base = OTHER
                       note = 2'-O-methyladenosine-3'-phosphate
modified_base          7
                       mod_base = OTHER
                       note = 2'-O-methyluridine-3'-phosphate
modified_base          8
                       mod_base = OTHER
                       note = 2'-O-methylguanosine-3'-phosphate
modified_base          9
                       mod_base = OTHER
                       note = 2'-O-methyladenosine-3'-phosphate
modified_base          10
                       mod_base = OTHER
                       note = 2'-O-methyladenosine-3'-phosphate
modified_base          11
                       mod_base = OTHER
                       note = 2'-O-methyluridine-3'-phosphate
modified_base          12
                       mod_base = OTHER
                       note = 2'-O-methylguanosine-3'-phosphate
modified_base          13
                       mod_base = OTHER
                       note = 2'-O-methylguanosine-3'-phosphate
modified_base          14
                       mod_base = OTHER
                       note = 2'-O-methylguanosine-3'-phosphate
modified_base          15
                       mod_base = OTHER
                       note = 2'-O-methylguanosine-3'-phosphate
modified_base          16
                       mod_base = OTHER
                       note = 2'-O-methylcytidine-3'-phosphate
modified_base          17
                       mod_base = OTHER
                       note = 2'-O-methyluridine-3'-phosphate
modified_base          18
                       mod_base = OTHER
                       note = 2'-O-methylcytidine-3'-phosphate
modified_base          19
                       mod_base = OTHER
                       note = 2'-O-methyluridine-3'-phosphate
modified_base          20
                       mod_base = OTHER
                       note = 2'-O-methylguanosine-3'-phosphate
modified_base          21
                       mod_base = OTHER
                       note = 2'-O-methylguanosine-3'-phosphate
modified_base          22
                       mod_base = OTHER
                       note = 2'-O-methylguanosine-3'-phosphate
modified_base          23
                       mod_base = OTHER
                       note = 2'-O-methylcytidine-3'-phosphate
SEQUENCE: 98
tggcaatgaa tggggctctg ggc                                          23

SEQ ID NO: 99          moltype = RNA  length = 21
FEATURE                Location/Qualifiers
source                 1..21
                       mol_type = other RNA
                       organism = synthetic construct
modified_base          1
                       mod_base = OTHER
                       note = 2'-O-methylcytidine-3'-phosphate
modified_base          2
                       mod_base = OTHER
                       note = 2'-O-methylcytidine-3'-phosphate
modified_base          3
                       mod_base = OTHER
                       note = 2'-O-methyladenosine-3'-phosphate
modified_base          4
                       mod_base = OTHER
                       note = 2'-O-methylguanosine-3'-phosphate
modified_base          5
                       mod_base = OTHER
                       note = 2'-O-methyladenosine-3'-phosphate
modified_base          6
                       mod_base = OTHER
```

```
                        note = 2'-O-methylguanosine-3'-phosphate
modified_base           7
                        mod_base = OTHER
                        note = 2'-O-methylcytidine-3'-phosphate
modified_base           8
                        mod_base = OTHER
                        note = 2'-O-methylcytidine-3'-phosphate
modified_base           9
                        mod_base = OTHER
                        note = 2'-O-methylcytidine-3'-phosphate
modified_base           10
                        mod_base = OTHER
                        note = 2'-O-methylcytidine-3'-phosphate
modified_base           11
                        mod_base = OTHER
                        note = 2'-O-methyladenosine-3'-phosphate
modified_base           12
                        mod_base = OTHER
                        note = 2'-O-methyluridine-3'-phosphate
modified_base           13
                        mod_base = OTHER
                        note = 2'-O-methyluridine-3'-phosphate
modified_base           14
                        mod_base = OTHER
                        note = 2'-O-methylcytidine-3'-phosphate
modified_base           15
                        mod_base = OTHER
                        note = 2'-O-methyladenosine-3'-phosphate
modified_base           16
                        mod_base = OTHER
                        note = 2'-O-methyluridine-3'-phosphate
modified_base           17
                        mod_base = OTHER
                        note = 2'-O-methyluridine-3'-phosphate
modified_base           18
                        mod_base = OTHER
                        note = 2'-O-methylguanosine-3'-phosphate
modified_base           19
                        mod_base = OTHER
                        note = 2'-O-methylcytidine-3'-phosphate
modified_base           20
                        mod_base = OTHER
                        note = 2'-O-methylcytidine-3'-phosphate
modified_base           21
                        mod_base = OTHER
                        note = 2'-O-methyladenosine
SEQUENCE: 99
ccagagcccc attcattgcc a                                               21

SEQ ID NO: 100          moltype = RNA  length = 23
FEATURE                 Location/Qualifiers
source                  1..23
                        mol_type = other RNA
                        organism = synthetic construct
modified_base           1
                        mod_base = OTHER
                        note = 2'-O-methyluridine-3'-phosphate
modified_base           2
                        mod_base = OTHER
                        note = 2'-O-methylguanosine-3'-phosphate
modified_base           3
                        mod_base = OTHER
                        note = 2'-O-methylguanosine-3'-phosphate
modified_base           4
                        mod_base = OTHER
                        note = 2'-O-methylcytidine-3'-phosphate
modified_base           5
                        mod_base = OTHER
                        note = 2'-O-methyladenosine-3'-phosphate
modified_base           6
                        mod_base = OTHER
                        note = 2'-O-methyladenosine-3'-phosphate
modified_base           7
                        mod_base = OTHER
                        note = 2'-O-methyluridine-3'-phosphate
modified_base           8
                        mod_base = OTHER
                        note = 2'-O-methylguanosine-3'-phosphate
modified_base           9
```

```
                        mod_base = OTHER
                        note = 2'-O-methyladenosine-3'-phosphate
modified_base           10
                        mod_base = OTHER
                        note = 2'-O-methyladenosine-3'-phosphate
modified_base           11
                        mod_base = OTHER
                        note = 2'-O-methyluridine-3'-phosphate
modified_base           12
                        mod_base = OTHER
                        note = 2'-O-methylguanosine-3'-phosphate
modified_base           13
                        mod_base = OTHER
                        note = 2'-O-methylguanosine-3'-phosphate
modified_base           14
                        mod_base = OTHER
                        note = 2'-O-methylguanosine-3'-phosphate
modified_base           15
                        mod_base = OTHER
                        note = 2'-O-methylguanosine-3'-phosphate
modified_base           16
                        mod_base = OTHER
                        note = 2'-O-methylcytidine-3'-phosphate
modified_base           17
                        mod_base = OTHER
                        note = 2'-O-methyluridine-3'-phosphate
modified_base           18
                        mod_base = OTHER
                        note = 2'-O-methylcytidine-3'-phosphate
modified_base           19
                        mod_base = OTHER
                        note = 2'-O-methyluridine-3'-phosphate
modified_base           20
                        mod_base = OTHER
                        note = 2'-O-methylguanosine-3'-phosphate
modified_base           21
                        mod_base = OTHER
                        note = 2'-O-methylguanosine-3'-phosphate
modified_base           22
                        mod_base = OTHER
                        note = 2'-O-methylguanosine-3'-phosphate
modified_base           23
                        mod_base = OTHER
                        note = 2'-O-methylcytidine
SEQUENCE: 100
tggcaatgaa tggggctctg ggc                                      23

SEQ ID NO: 101          moltype = RNA  length = 23
FEATURE                 Location/Qualifiers
source                  1..23
                        mol_type = other RNA
                        organism = synthetic construct
modified_base           1
                        mod_base = OTHER
                        note = 2'-O-methylguanosine-3'-phosphate
modified_base           2
                        mod_base = OTHER
                        note = 2'-O-methylcytidine-3'-phosphate
modified_base           3
                        mod_base = OTHER
                        note = 2'-O-methylcytidine-3'-phosphate
modified_base           4
                        mod_base = OTHER
                        note = 2'-O-methylcytidine-3'-phosphate
modified_base           5
                        mod_base = OTHER
                        note = 2'-O-methyladenosine-3'-phosphate
modified_base           6
                        mod_base = OTHER
                        note = 2'-O-methylguanosine-3'-phosphate
modified_base           7
                        mod_base = OTHER
                        note = 2'-O-methyladenosine-3'-phosphate
modified_base           8
                        mod_base = OTHER
                        note = 2'-O-methylguanosine-3'-phosphate
modified_base           9
                        mod_base = OTHER
                        note = 2'-O-methylcytidine-3'-phosphate
```

-continued

```
modified_base          10
                       mod_base = OTHER
                       note = 2'-O-methylcytidine-3'-phosphate
modified_base          11
                       mod_base = OTHER
                       note = 2'-O-methylcytidine-3'-phosphate
modified_base          12
                       mod_base = OTHER
                       note = 2'-O-methylcytidine-3'-phosphate
modified_base          13
                       mod_base = OTHER
                       note = 2'-O-methyladenosine-3'-phosphate
modified_base          14
                       mod_base = OTHER
                       note = 2'-O-methyluridine-3'-phosphate
modified_base          15
                       mod_base = OTHER
                       note = 2'-O-methyluridine-3'-phosphate
modified_base          16
                       mod_base = OTHER
                       note = 2'-O-methylcytidine-3'-phosphate
modified_base          17
                       mod_base = OTHER
                       note = 2'-O-methyladenosine-3'-phosphate
modified_base          18
                       mod_base = OTHER
                       note = 2'-O-methyluridine-3'-phosphate
modified_base          19
                       mod_base = OTHER
                       note = 2'-O-methyluridine-3'-phosphate
modified_base          20
                       mod_base = OTHER
                       note = 2'-O-methylguanosine-3'-phosphate
modified_base          21
                       mod_base = OTHER
                       note = 2'-O-methylcytidine-3'-phosphate
modified_base          22
                       mod_base = OTHER
                       note = 2'-O-methylcytidine-3'-phosphate
modified_base          23
                       mod_base = OTHER
                       note = 2'-O-methylcytidine-3'-phosphate
SEQUENCE: 101
gcccagagcc ccattcattg ccc                                            23
```